US011530452B2

(12) United States Patent
Eloit et al.

(10) Patent No.: US 11,530,452 B2
(45) Date of Patent: Dec. 20, 2022

(54) BROAD RANGE GENE AND GENOTYPE PAPILLOMAVIRUS TRANSCRIPTOME AS A BIOMARKER OF PAPILLOMAVIRUS-ASSOCIATED CANCER STAGES

(71) Applicants: INSTITUT PASTEUR, Paris (FR); ECOLE NATIONALE VETERINAIRE D'ALFORT, Maisons-Alfort (FR); PATHOQUEST, Paris (FR); L'ASSISTANCE PUBLIQUE—HOPITAUX DE PARIS, Paris (FR)

(72) Inventors: Marc Eloit, Paris (FR); Nicolas Torno, Paris (FR); Jean Deregnaucourt, Paris (FR); Marion Mouton, Paris (FR); Isabelle Heard, Paris (FR); Philippe Perot, Saint-yrieix (FR)

(73) Assignees: INSTITUT PASTEUR, Paris (FR); ECOLE NATIONALE VETERINAIRE D'ALFORT, Maisons-Alfort (FR); PATHOQUEST, Paris (FR); L'ASSISTANCE PUBLIQUE—HOPITAUX DE PARIS, Paris (FR)

( * ) Notice: Subject to any disclaimer, the term of this patent is extended or adjusted under 35 U.S.C. 154(b) by 40 days.

(21) Appl. No.: 17/011,990

(22) Filed: Sep. 3, 2020

(65) Prior Publication Data
US 2021/0032705 A1 Feb. 4, 2021

Related U.S. Application Data

(62) Division of application No. 15/319,893, filed as application No. PCT/IB2015/055136 on Jul. 7, 2015, now Pat. No. 10,808,284.

(30) Foreign Application Priority Data

Jul. 7, 2014 (WO) ................. PCT/IB2014/062926

(51) Int. Cl.
*C12Q 1/70* (2006.01)
*C12Q 1/6844* (2018.01)
*C12Q 1/6886* (2018.01)
*G16H 50/30* (2018.01)

(52) U.S. Cl.
CPC ............ *C12Q 1/6886* (2013.01); *C12Q 1/70* (2013.01); *C12Q 1/708* (2013.01); *G16H 50/30* (2018.01); *C12Q 2600/118* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

2006/0222656 A1 10/2006 Strome

FOREIGN PATENT DOCUMENTS

| EP | 2184368 A1 | 5/2010 |
| WO | 91/08312 A1 | 6/1991 |
| WO | 99/29890 A2 | 6/1999 |
| WO | 03/057914 A2 | 7/2003 |
| WO | 2010/129941 A1 | 11/2010 |
| WO | 2011/131192 A1 | 10/2011 |
| WO | 2012/116220 A2 | 8/2012 |

OTHER PUBLICATIONS

Gheit et al. Development of a Sensitive and Specific Assay Combining Multiplex PCR and DNA Microarray Primer Extension to Detect High-Risk Mucosal Human Papillomavirus Types. Journal of Clinical Microbiology, Jun. 2006, 44(6): 2025-2031.*
Composition Definition from Dictionary.com. Downloaded from internet on Feb. 3, 2022.*
Chuang et al. Specific primer design for the polymerase chain reaction. Biotechnol Lett (2013) 35:1541-1549.*
Chaumpluk et al. Accumulation of amplified target DNAs using thiol/biotin labeling, S1 nuclease, and ferrocene-streptavidin-magnetic system and a direct detection of specific DNA signals with screen printed gold electrode. Science and Technology of Advanced Materials 8 (2007) 323-330.*
Hegner et al. Immobilizing DNA on gold via thiol modification for atomic force microscopy imaging in buffer solutions. FEBS Letters, 1993, 336:452-456.*
Binladen et al. 5'-Tailed sequencing primers improve sequencing quality of PCR products. BioTechniques, 2007, 42: 174-176.*
Von Keyserling et al. p16INK4a and p14ARF mRNA expression in Pap smears is age-related. Modern Pathology (2012) 25, 465-470.*
Wentzensen et al. Characterization of viral-cellular fusion transcripts in a large series of HPV16 and 18 positive anogenital lesions. Oncogene. Jan. 17, 2002;21(3):419-26.*
DATABASEMEDLINE [Online] US National Library of Medicine (NLM), Bethesda,MD, US; Feb. 16, 2005 (Feb. 16, 2005), Chenqing-Yun et al: "[Detection of integration status of human papillomavirus 16 in cervical precancerous lesions].", XP002733700, Database accession No. NLM15854531 abstract & Zhonghua Yi Xue Za Zhi Feb. 16, 2005, vol. 85. No. 6, Feb. 16, 2005 (Feb. 16, 2005), pp. 400-404.

(Continued)

*Primary Examiner* — Nianxiang Zou
(74) *Attorney, Agent, or Firm* — Arrigo, Lee, Guttman & Mouta-Bellum LLP

(57) ABSTRACT

The present invention provides compositions, kits, and method for determining the levels of expression of human polyoma or papillomavirus species and RNA transcripts. These levels can be used for the prognosis of risk of developing virally-induced cancers. The ratio (R) between early and late transcripts is indicative of HPV infections associated with higher risk of developing genital neoplasia and cancer.

10 Claims, 8 Drawing Sheets

Specification includes a Sequence Listing.

(56) References Cited

OTHER PUBLICATIONS

DATABASEMEDLINE [Online] US National Library of Medicine (NLM), Bethesda,MD. US; Sep. 2003 (Sep. 2003), Lukaszuk-krzysztof et al: "[Quantity estimation of the E2/E6 HPV gene products ratio can be a prognostic marker for the stage of the cervical cancer carcinogenesis].", XP002733701, Database accession No. NLM14674126 abstract &Ginekologia Polska Sep. 2003, vol. 74, No. 9, Sep. 2003 (Sep. 2003), pp. 793-798.
DATABASEMEDLINE [Online] 1-38 Usnational Library of Medicine (NLM), Bethesda,MD, US; Aug. 1990 (Aug. 1990), Nagai N: "[Molecular biologic study on the carcinogenesis of HPV in uterine cervical cancer and related lesions—analysis o f HPVtypes 16, 18 E6/E7 gene mRNA].", XP002733702, Database accession No. NLM2172419 abstract & Nihon Sanka Fujinka Gakkai Zasshi Aug. 1990, vol. 42, No. 8, Aug. 1990 (Aug. 1990), pp. 823-833.
International Search Report, Application No. PCT/IB2015/055136, dated Mar. 7, 2016.

\* cited by examiner

| R SCORE (EXAMPLES) | SAMPLE 117 | | | | | | SAMPLE 119 | |
|---|---|---|---|---|---|---|---|---|
| | HPV16 | | HPV35 | | HPV6 | | HPV16 | |
| | RAND. RT | HPV RT | RAND. RT | HPV RT | RAND. RT | HPV RT | RAND. RT | HPV RT |
| GENOME (CDS) | | | | | | | | |
| E6/L1 | 0,53 | 0,23 | 0,00 | 0,00 | +∞ | +∞ | +∞ | 2,00 |
| E7/L1 | 0,30 | 0,17 | 0,29 | 0,00 | +∞ | +∞ | +∞ | 0,00 |
| (E6+E7)/L1 | 0,83 | 0,40 | 0,29 | 0,00 | +∞ | +∞ | +∞ | 2,00 |
| E6+E7)/(L1+L2) | 0,46 | 0,28 | 0,19 | 0,00 | +∞ | +∞ | +∞ | 2,00 |
| (E6+E7)/E2 | 0,69 | 0,31 | 0,32 | +∞ | +∞ | +∞ | 15,00 | +∞ |
| (E6+E7)/(E2*(L1+L2)) | 0,00 | 0,00 | 0,01 | +∞ | +∞ | +∞ | +∞ | +∞ |
| (E6+E7)/(E2+E4) | 0,64 | 0,30 | 0,32 | +∞ | +∞ | +∞ | 15,00 | 0,67 |
| (E6+E7)/(E6+E7+L1+L2) | 0,31 | 0,22 | 0,16 | 0,00 | +∞ | 1,00 | 1,00 | 0,67 |
| (E6+E7+E2 - E4)/(L1+L2) | 1,07 | 1,16 | 0,81 | 0,00 | +∞ | +∞ | +∞ | 2,00 |
| (E6+E7+E1+E2+E4)/(L1+L2) | 2,36 | 2,49 | 1,64 | 0,12 | +∞ | +∞ | +∞ | 5,00 |
| (E6+E7)/(E6+E7+E2+L1+L2) * E2/(E6+E7+E2+L1+L2) | 0,07 | 0,05 | 0,04 | 0,00 | +∞ | 0,00 | 0,06 | 0,00 |
| TRANSCRIPTS (SPLICE JUNCTIONS) | | | | | | | | |
| E6*I/(L1+L1*) | +∞ | +∞ | | | | | | |
| E6*II/(L1+L1*) | +∞ | +∞ | | | | | | |
| E6*III, E5/(L1+L1*) | +∞ | +∞ | | | | | | |
| E6*IV/(L1+L1*) | +∞ | +∞ | | | | | | |
| E6^7/(L1+L1*) | +∞ | +∞ | | | | | | |
| (E6*I+E6*II+E6*III, E5+E6*IV+E6^7)/(L1+L1*) | +∞ | 24,00 | NO DATA | | NO DATA | | NOT APPLICABLE (NO READS) | |
| (E6*I+E6*II+E6*III, E5+E6*IV+E6^7)/(E2+E2C) | 6,08 | 8,00 | | | | | | |
| (E2+E2C)/(L1+L1*) | +∞ | +∞ | | | | | | |
| (E6*I+E6*II+E6*III, E5+E6*IV+E6^7) /(E6*I+E6*II+E6*III, E5+E6*IV+E6^7+L1+L1*) | 1,00 | 1,00 | | | | | | |
| (E6*I+E6*II+E6*III, E5+E6*IV+E6^7+E2+E2C - E1^E4) /(L1+L1*) | +∞ | +∞ | | | | | | |

*FIG. 8*

BROAD RANGE GENE AND GENOTYPE PAPILLOMAVIRUS TRANSCRIPTOME AS A BIOMARKER OF PAPILLOMAVIRUS-ASSOCIATED CANCER STAGES

SEQUENCE LISTING

The ASCII copy of the sequence listing submitted herewith is named Listing_15319893.txt, was created on Sep. 3, 2020, is 334,075 bytes in size, and is hereby incorporated herein by reference.

BACKGROUND OF THE INVENTION

HPV infections are associated with the development of cervix carcinoma and possibly other cancers like head and neck cancers. For example, cancer of the cervix is one of the most common cancers among women in all countries. Human papillomaviruses (HPV) are the etiologic agents responsible for over 99% of all cancers of the cervix. HPVs are DNA viruses commonly transmitted through sexual contact, which include more than 100 genotypes. Human Papillomaviruses are small, non-enveloped DNA viruses, approximately 55 nm in diameter, that infect basal cells and replicate in the nucleus of squamous epithelial cells. The genomic organization of each of the papillomaviruses is similar and can be divided into three functional regions. Following infection, the early HPV genes (E6, E7, E1, E2, E4 and E5) are expressed and the viral DNA replicates from the episomal form of the virus. In the upper layer of the epithelium the viral genome is replicated further, and the late genes (L1 and L2) and E4 are expressed. The shed virus can then initiate new infections.

Human papillomaviruses (HPV) are viruses displaying a high genetic diversity. About one hundred HPV types which are classified in different genus, mainly the alpha, beta and gamma genus. Within these genus, many species have been identified. HPV classification is based on the genomic sequence of the L1 gene which encodes the major capsid protein. The different HPV types are characterized by their tissue tropism, and HPV types with either cutaneous or mucosal tropism can be distinguished. They are also characterized by their oncogenic potential and one can distinguish between highly oncogenic HPV types (high-risk HPV) and weakly oncogenic HPV types (low-risk HPV).

HPV infections are very common and depending on the HPV types and host immune defense, the infection disappears in 6-12 months in 90% of women. According to a recent CDC report, there are 14 million new HPV infections each year in the USA alone, which account for 50% of sexually transmitted infections (STIs). This means that 1.4 million individuals are each year at risk of developing HPV induced cancer. Two HPV vaccines have been approved, but they are not broadly used in the total population. In addition, these vaccines only cover several types such as HPV6, 11, 16 and 18 and leave unprotected a significant part of the population.

Since HPV are common viruses that can cause usually warts and because there are more than 100 types of HPV, diagnosis and disease management are complex. It is even further complicated taken that most HPVs are deemed harmless, and so far only about 14 types have been shown to be associated with increased risk of cancer. These HPV types affect the genital tract and are transmitted through sexual contact with an infected partner. As of today, HPV types have been classified as low-risk or high-risk HPVs according to observations in clinical cohorts. Low-risk HPVs have been classified according to their association with genital warts; whereas High-risk HPVs (HR HPVs) are identified as a limited number of types which are shown to induce cancers of the cervix, vulva, vagina, and anus in women. In men, these High-risk HPVs can lead to cancers of the anus and penis.

Cancer biomarkers in HPV-related cancers are greatly needed for a better diagnostic of pre-cancer and cancer stages of the disease, prognosis and therapeutic management.

Despite the responsibility of HR HPVs in most cervix cancers, screening tests of cancer remain mainly based on the Pap cytology test and not on HPV tests. This is largely due to the limitations of current molecular tests. HPV DNA identification of HR HPVs is not fully predictive of cancer: only high loads of HPV16 and possibility persistence for months of HR-HPVs are associated with an increased risk of cancer development. Thus, the usage of DNA HPV tests, as a screening assay, shows low positive predictive value for CIN2/3 lesions. Expression of E6 and E7 mRNAs of HR HPVs has been proposed as a better marker of cancer development, but E6 and E7 are expressed during HPV acute infection, so it remains difficult to define a threshold of expression associated to persistence and cancer development.

Low-grade intraepithelial lesions are a site of productive viral replication. Progression to high-grade intraepithelial lesions and invasive carcinomas is associated with a persistent high-risk HPV infection and often integration of the HPV genome into the host chromosomes, loss or disruption of E2 and subsequent upregulation of E6 and E7 expression. E6 and E7 are the oncogenes of the virus and expression of these genes is required for malignant transformation. Among others, E6 and E7 mediate degradation of the tumor suppressors p53 and RB, respectively, and interfere with cell-cycle regulation. E6 and E7 proteins from low-risk types are less competent in interfering with p53 and pRb functions than E6/E7 proteins from high-risk types. Therefore, low-risk HPV infections are associated with benign proliferations, such as genital warts and low-grade intraepithelial lesions prone to regress.

Different techniques are available today for detecting HPV based on DNA typing. For example, the COBAS (Roche) and APTIMA (GEN-PROBE) kits are PCR tests of specific targets intended for the qualitative in vitro detection of mRNA of the L1 gene from 14 types of human papillomavirus (HPV) virus considered High risk (HPV 16, 18, 31, 33, 35, 39, 45, 51, 52, 56, 58, 59, 66 and 68). However, both of these HPV Assays do not distinguish the differences between the 14 High-risk types. In fact, only 6 different results are obtainable: HPV16 positive or negative, HPV18 positive or negative, others 12 HPVs positive or negative. LINEAR ARRAY HPV Genotyping Test (Roche) is a qualitative test that detects 37 high- and low-risk human papillomavirus genotypes, including those considered a significant risk factor for High-grade Squamous Intraepithelial (HSIL) progression to cervical cancer. This test is a qualitative in vitro test for the detection of Human Papilloma Virus in clinical specimens. The test utilizes amplification of target DNAs by PCR of the late gene L1 of HPV DNA genotypes 6, 11, 16, 18, 26, 31, 33, 35, 39, 40, 42, 45, 51, 52, 53, 54, 55, 56, 58, 59, 61, 62, 64, 66, 67, 68, 69, 70, 71, 72, 73 (MM9) (novel type related to HPV73), 81, 82 (MM4) (novel type related to HPV82), 83 (MM7) (novel type related to HPV83), 84 (MM8) (novel type related to HPV84), 1539 and CP6108. The digene HC2 HPV DNA Test, developed by Qiagen, is based on Capture Hybridization of HPV DNAs (L1 gene) for the qualitative detection of 18 types (HPV 16, 18, 26, 31, 33, 35, 39, 45, 51, 52, 53, 56, 58, 59, 66, 68 [68a], 73, 82MM4 [821S39]) in cervical specimens.

More recently, NucliSENS EasyQ HPV was made available to qualitative detection of oncogenes E6/E7 mRNAs of 5 specific High risk HPVs 16, 18, 31, 33 and 45. Detection of HPV E6 and E7 has been proposed as a better correlate of cancer development than HPV DNA.

In addition, WO2011/088573 (Her Majesty The Queen In Right of Canada as represented by The Minister of Health), describes a set of probes to detect and Identify 46 specifically targeted species of mucosal human papillomaviruses (HPV). These probes are used as a multiplex assay based on nested PCR amplification and the Luminex xMAP technology for genotyping DNA of L1 genes of HPV types 6, 11, 13, 16, 18, 26, 30, 31, 32, 33, 35, 39, 40, 42, 43, 44, 45, 51, 52, 53, 54, 56, 58, 59, 61, 62, 66, 67, 68, 69, 70, 71, 72, 73, 74, 81, 82, 83, 84, 85, 86, 87, 89, 90, 91 and 97.

All the molecular tests currently described for HPV identification use molecular techniques based on species/genus genotype specific oligonucleotides binding to specifically amplify and/or probe papillomavirus nucleic acids. In addition, these tests all share a specific qualitative detection restricted to some specific HPVs, but not a general and broad range of HPVs. Finally, the presence of HPV nucleic acid, especially DNA, does not mean the presence of cervical dysplasia or cervical cancer.

The inventors analyzed clinical data of cohorts of HPV infected individuals and considered that about 15% of patients are not positive for one of the classified High-risk HPVs but yet, they are at risk of developing HPV induced cancers. Therefore, there is a need to design a new HPV assay with a transversal and broad approach not limited to few specific HPV types. Moreover, the profile expression of the viral genes must be characterized. In fact, HPV infection during cancer development is associated with a shift from productive infection towards non-productive infection characterized by a high level of E6 and E7 and low levels of expression E2 and of late genes, often associated with an integration of HPV DNA in the host chromosomes, at least for HPV16. In connection with the present invention, the inventors investigated shared homology of sequences of all HPV types and no clear global homologies are found within features between polypeptide or nucleic acid sequences.

The inventors designed consensus primers within all intra subgroup alpha, and HPV-species specific composition of primers encompassing splice junctions, genomic and unspliced regions, and human fusion transcript regions of each HPV transcript. It is therefore provided hereafter several compositions of primers depending on the desired specificity and coverage of the test. The inventors propose here an approach for detecting cancer or risk of developing cancer not limited to the specific HPVs known today to be classified as High-risk. Thus, to bypass the limitation of the current tests above, the present invention does not rely on the above 14 HR species/genotype specific oligonucleotides binding to specifically amplify and/or probe papillomavirus few DNAs or few transcripts. It relies in one aspect on identification of the different gene transcripts based on High-Throughput sequencing, which allows for further transcripts/species/genotype identification based on sequence comparison with known alpha-papillomavirus sequences in relevant databases. This has the advantage of being capable of testing simultaneously the different transcripts of a great number of papillomavirus genotypes/species and to identify relevant biomarkers along the wide range of HR and LR HPVs.

The invention also provides generic consensus primers allowing a broad amplification or pre-amplification of relevant genes of alpha HPV, not depending on the specific transcripts of the 14 HR HPVs, which are amenable to PCR testing or enhance signal/noise ratio in connection with the High-Throughput sequencing mentioned above.

More particularly, the invention relates to identification of all E6/E7 transcripts in a given sample, and recognizing to which species/genotypes they belong to, sorting the reads corresponding to other viral transcripts of the same genotype/species so as to compute ratios defining relative molecular abundance of transcripts within this (these) given genotype(s) as biomarker of cancer development.

The inventors therefore designed a kit for HPV diagnosis based on a broad screening of the level of E6 and/or E7 mRNAs within the group alpha of HPVs. In the test described in details below, the inventors designed consensus primers allowing amplification or pre-amplification E6 and/or E7 mRNAs of genotypes of sub-group alpha to detect the level of expression of, wherein a significant expression level of E6 and/or E7 of group alpha HPVs in a single time point or over time is indicative of risk of developing HPV induced cancers. Following broad range amplification with consensus HPV primers or with HPV primers designed to perform a first step of HPV specific Reverse transcription reaction, the inventors also propose to quantitate E6 and or E7 as reads delivered by next generation sequencing techniques.

The present invention also provides a method for determining the level of expression of structural or late viral proteins such as L1 or L2. In such embodiment, a ratio R1 between E6 and/or E7 and L1 and/or L2 is determined, and compared to a ratio R found in low risk or non-persistent HPV infections, wherein a ratio R1 below a reference value R is indicative of HPV infections associated with higher risk of developing genital neoplasia and cancer.

GENERAL DESCRIPTION OF THE INVENTION

The invention provides a high through put sequencing method allowing relative quantification of reads across oncogenic viruses, such as polyoma virus or group alpha HPV, preferably group alpha HPV, comprising enrichment of the viral RNAs in a sample using random or consensus pre-amplification and/or specific reverse transcriptase reaction, determining the number of reads matching said viruses based on species discrimination, comparing the most prevalent high risk species, further determining within said most prevalent high risk species the relative number of reads matching at least one oncogenic gene, preferably two oncogenic genes, compared to at least one non oncogenic gene, preferably several non oncogenic genes. From these discrimination steps on species and interspecies read numbers, ratios are calculated to detect increase in relative level of high risk species versus low risk species and ratios within said high risk species of reads matching oncogenic genes versus structural or regulatory genes. Applied to HPV, this test encompasses determining the level of HR HPVs reads versus LR HPVs reads through group alpha HPVs, determining the ratio of early versus late genes (E6 and or E7 versus L1 and/or L2) within the most prevalent HR HPVs, and assessing risk of developing HPV induced cancer in patients which said ratio tend towards infinity. Refined ratios can be obtained using a filter applied on reads mapping specifically RNA spliced events.

In one embodiment, the method is for assessing risk of developing HPV induced cancer in patients infected with at least two different HPV species of group alpha.

In one embodiment, the method is for assessing HPV virus clearance in patient receiving HPV preventive or curative HPV vaccine.

In a first aspect, the present invention relates to a method for determining a patient risk of developing oncogenic virus induced cancer, such as polyoma virus or group alpha HPV comprising:
a) enrichment of the viral RNAs in a sample using random or consensus pre-amplification and/or specific reverse transcriptase reaction, preferably consensus pre-amplification;
b) sequencing cDNA produced in step a), and generating reads of said cDNA;
c) determining the number of reads matching said viruses based on species discrimination and determining the most prevalent high risk species present in the sample relative to other species;
d) determining within said most prevalent high risk species the relative number of reads matching least one oncogenic gene compared to at least one non oncogenic gene, preferably oncogenic genes compared to non oncogenic genes;
e) computing ratios within said high risk species of reads matching at least one oncogenic gene versus corresponding interspecies structural or regulatory gene, preferably oncogenic genes versus corresponding interspecies structural or regulatory genes;
f) determining risk of developing oncogenic virus induced cancer in patients wherein said ratio tend towards infinity, such as for example when ratio R is between 0.25, 0.4, 0.5, 1 to infinity.

This method is suitable for diagnosis or prognosis of risk to develop virus induced cancer in a human subject.

This method is particularly suited for assessing risk of developing HPV induced cancer in patients infected with at least two different HPV species of group alpha, for example multiple infected with HPV16, HPV35 and HPV6.

This method is also specifically suitable for assessing HPV virus clearance in patient receiving HPV preventive or curative HPV vaccine. It can be performed before vaccination to confirm vaccine potential for clearing existing infections or post-vaccination for follow-up.

In a preferred embodiment of step a), the enrichment of the viral RNAs is performed by a reverse transcription of the viral RNAs, and an amplification of the produced cDNA by multiplex-PCR with a group alpha HPV-specific composition of primers encompassing splice junctions, genomic and unspliced regions, and human fusion transcript regions of each HPV transcript.

In another embodiment, the reverse transcription is performed with random hexamers.

In another embodiment, the reverse transcription is performed with HPV-specific primers.

In another embodiment, the reverse transcription (RT) and the multiplex amplification are performed in the same tube (one-step RT-PCR).

In another preferred embodiment of step a) above, consensus pre-amplification comprises random reverse transcription of the viral RNAs followed by a multiplex amplification of the HPV transcripts.

Advantageously, the random reverse transcription is performed with random hexamers.

Advantageously, the multiplex amplification of the HPV transcripts is performed with HPV-specific primers.

In a preferred embodiment of step b) above, the sequencing is a High throughput sequencing method.

Ratio (R) is calculated as the number of reads of at least one early HPV16 transcript to the number of reads of at least one late HPV16 transcript, with a higher ratio (R) correlating with an increased risk of developing high-grade malignant HPV-induced cancer. This method further include correlating a higher number of reads of HPV16 transcripts relative to reads of transcripts of another HPV species with an increased risk of developing high-grade malignant HPV-induced cancer. To obtain sufficient number of reads, the cDNA is generated using random primers or using HPV-specific primers.

For example, the ratio is calculated by calculating a ratio (R1) of the number of reads of one HPV HR E6 and/or E7 transcripts to the number of reads of said one HPV HR L1 and/or L2 transcripts and the ratio is calculated by calculating a ratio (R2) of the number of reads of a second HPV HR E6 and E7 transcripts to the number of reads of said second HPV HR L1 and L2 transcripts. This method is applicable to determining the number of HPV sequence reads of at least 2 Alpha group HPV species, including for example HPV16.

In a specific embodiment but applied to oncogenic viruses in general such as polyoma or HPV, the method of the invention comprises:
a) optionally, pretreating nucleic acids to remove human genomic DNA,
b) optionally, pre-amplify viral mRNAs, wherein said viral mRNAs comprises oncogenic mRNAs and at least one other mRNA,
c) sequencing mRNAs, or cDNAs thereof, obtained after steps a) and b), in the sample of a human subject,
d) identifying the reads corresponding to said oncogenic mRNAs,
e) identifying to which species or genotypes said oncogenic mRNAs of step d) belong to,
f) sorting the reads corresponding to said at least one other viral mRNAs, or cDNAs thereof obtained after steps a) and b), of the same genotype or species identified in step e),
g) optionally, identifying fusion transcripts as a signature of viral DNA integrations events in the host chromosome and/or additional human cancer cell biomarkers,
h) optionally, deleting all other sequences including human sequences which are not sequences identified and sorted following steps d), e), f) and g),
i) computing ratios R defining molecular abundance of said oncogenic mRNAs relative to said at least one other viral mRNAs of the same genotype or species of step f), wherein an increase of ratios R correlate with an increased risk of developing viral induced cancer.

By virus induced cancer, it is more particularly contemplated herein Papova virus induced cancer, more specifically Papilloma or Polyoma virus induced cancer, preferably Papilloma virus induced cancer.

By other viral mRNAs in step f) it is meant mRNAs of viral genes selected from structural genes, for example capsid genes as well as from regulatory genes, and replication/transcription genes.

In a particular embodiment, the present invention relates to a method for diagnosis or prognosis of risk to develop HPV induced cancer in a human subject comprising:
a) optionally, pretreating nucleic acids to remove human genomic DNA,
b) optionally, pre-amplify HPVs mRNAs, wherein said mRNAs comprises E6 and/or E7 HPV RNAs and at least one other HPV mRNAs, c) sequencing nucleic acids in the sample of a human subject or obtain after steps a) and b),
d) identifying the reads corresponding to E6 and/or E7 HPV RNAs,
e) identifying to which species or genotypes E6 and/or E7 HPV mRNAs of step d) belong to,
f) sorting the reads corresponding to other viral HPV mRNAs of the same genotype or species identified in step e),
g) optionally, identifying fusion transcripts as a signature of HPV DNA integrations events in the host chromosome and/or additional human cancer cell biomarkers,
h) optionally, deleting all other sequences including human sequences which are not sequences identified and sorted following steps d), e), f) and g),
i) computing ratios defining molecular abundance of E6 and/or E7 HPV mRNAs relative to said other viral transcripts of the same genotype or species of step f), wherein an increased level of said ratios correlates with an increased risk of developing viral induced cancer.

By other viral mRNAs in step f), it is more particularly referred to selected mRNAs from genes coding for capsid proteins (L1 and L2), gene coding for the growth stimulation protein (E5), genes coding for replication or transcription proteins (E4, E2 and E1, E8). In step g), additional human cancer cell biomarkers can be selected for example from PRC1, CCNB2, SYCP2 CDKN3, NUSAP1, CDC20, p16INK4a, Ki-67.

In one specific embodiment, step f) comprises sorting the reads of L1 and/or L2 HPV mRNAs corresponding to the species or genotype of E6 and/or E7 HPV mRNAs identified in step d). In this embodiment, step h) comprises computing ratios defining relative molecular abundance of E6 and/or E7 HPV mRNAs relative to the reads of L1 and/or at least one other viral mRNAs corresponding to the species or genotype of E6 and/or E7 HPV mRNAs. In such embodiment, step b) optionally comprises pre-amplifying HPVs mRNAs, wherein said mRNAs comprises E6 and/or E7 HPV RNAs and L1 and/or at least one other viral HPV mRNAs.

In a second aspect, the present invention relates to a method for diagnosis risk to develop HPV induced cancer comprising:
(a) determining the level of at least a first marker selected from E6 mRNAs of group alpha HPVs, E7 mRNAs of group alpha HPVs, or both, in the sample of a patient or in the sample of an individual suspected to be infected by HPV,
(b) comparing the levels determined in step (a) to a reference value of E6 mRNAs of group alpha HPVs, E7 mRNAs of group alpha HPVs, or both in low risk individuals infected with HPVs,
(c) wherein an increased level as determined in step a) compared to the reference level in step b) is indicative of higher risk to develop HPV cancer induced.

It must be contemplated that these biomarkers are not restricted to E6 or E7 mRNAs of HPV16, 18, 31, 33, 35, 39, 45, 51, 52, 56, 58, 59, 66, 68 but extend to all E6 or E7 mRNAs of HPVs of several genus alpha, comprising and covering HPVs of groups α5, 6, 7, 10; optionally extending to additional alpha group HPVs as desired.

In this second aspect, the levels of E6 mRNAs of group alpha HPVs, E7 mRNAs of group alpha HPVs, or both are determined inter alia by hybridization with a labeled probe, amplification, including PCR, nucleic acid microarrays, high-throughput sequencing with or without pre-amplification. The measure may be carried out directly on an extracted messenger RNA (mRNA) sample, or on reverse transcribed complementary DNA (cDNA) prepared from extracted mRNA. From the mRNA or cDNA sample, the amount of nucleic acid transcripts is determined using nucleic acid microarrays, quantitative PCR, hybridization with a labeled probe, or directly by counting corresponding reads following high-throughput sequencing.

For both first and second aspect, amplification or pre-amplification is depicted in details below with specifically designed consensus primers allowing generic pre-amplification of all or desired HPVs belonging to group alpha, in particular pre-amplification of the specific domains of the group alpha, preferably of the HR-αHPV. According to the invention, primers depicted below are provided to amplify and detect the amount of E6 mRNAs and E7 mRNAs of all or several group alpha HPVs depending on the desired scope of the test. Therefore, the invention provides a much broader test extending beyond types such as HPV 16, 18, 31, 33, 35, 39, 45, 51, 52, 56, 58, 59, 66, 68 which are today classified as High-risk HPVs; as it allows the determination of high level expression of E6 and/E7 of several alpha subgroups of HPVs and even covering the all HPVs of the alpha group.

For example, In the above method, the quantification is performed on E6 and/or E7 mRNAs of papillomaviruses α6 comprising HPV 30, HPV 53, HPV 56 and HPV 66, papillomaviruses α7 comprising HPV 68, HPV 39, HPV 70, HPV 85, HPV 59, HPV 45, HPV 18, HPV 97, papillomaviruses α10 comprising HPV 16, HPV 35, HPV 31, HPV 52, HPV 67, HPV 33, HPV 58 and papillomaviruses α5 comprising HPV 26, HPV, 69, HPV 51, HPV 82. The combined generic consensus primers to generically amplify alpha subgroups are described herein-after.

In a specific embodiment, the method of the invention further refines the above method aiming at the quantitative determination of expression levels of a panel of biomarkers in biological samples of patients or individuals suspected to be infected with HPVs, which combined biomarkers are indicative and/or predictive, in a single time-point, of patients at risk of developing HPV induced cancers.

The panel provided by the invention comprises the following biomarkers:
  At least a first marker selected from E6 mRNAs of group alpha HPVs, E7 mRNAs of group alpha HPVs, or both,
  At least a second marker selected from L1 mRNAs of group alpha HPVs, L2 mRNAs of group alpha HPVs, or both,
  wherein said E6, E7, L1 and L2 mRNAs have corresponding intragenetic sequences,
  optionally, at least one host cellular marker indicative of neoplasia or cancer.

For example, the panel is composed of at least 5, 10, 20, 30 or 50 different mRNAs of said E6, E7, L1 and L2 mRNAs of group alpha HPVs. In one specific embodiment, the panel is composed of all group alpha HPVs mRNAs of E6 and/or E7, and L1 and/or L2. The combined generic consensus primers to generically amplify alpha subgroups depending on the desired scope of the test are provided herein-after. Alternatively, the invention is performed using sequence-independent-amplified or direct HT-sequencing for quantitative detection of individual mRNA of E6 and/or E7 HPV sequences belonging to the HPV alpha group.

Such method according to the invention is also provided for predicting the progression of HPV infection in a patient suffering from HPV infection.

In one embodiment, the invention encompasses a method for assessing a human papilloma virus (HPV) infected patient comprising: generating cDNA from a patient sample comprising RNA; sequencing the cDNA; generating reads of sequence of the cDNA; discriminating HPV sequence reads on the basis of HPV specie; discriminating HPV sequence reads on the basis of HPV gene transcript; quantitating the number of HPV sequence reads according to HPV species and HPV gene transcript, determining the number of HPV sequence reads of at least 2 HPV gene transcripts; and determining the number of HPV sequence reads of at least 2 HPV species; wherein the patient sample contains 2 or more HPV species.

In a further embodiment, the method comprises calculating a ratio (R) of the number of reads of at least one early HPV16 transcript to the number of reads of at least one late HPV16 transcript, with a higher ratio (R) correlating with an increased risk of developing high-grade malignant HPV-induced cancer.

In another embodiment, the method comprises correlating a higher number of reads of HPV16 transcripts relative to reads of transcripts of another HPV species with an increased risk of developing high-grade malignant HPV-induced cancer.

In one embodiment, the cDNA is generated using random primers. In one embodiment, the cDNA is generated using HPV-specific primers (i.e., primers specific to domains of a HPV, such as a HR-αHPV, comprising splice junctions, genomic and unspliced regions, and human fusion transcript regions of each HPV transcript).

In one embodiment, the ratio is calculated by calculating the ratio (R) of the number of reads of HPV16 E6 and/or E7 transcripts to the number of reads of HPV16 L1 and/or L2 transcripts. In one embodiment, the ratio is calculated by calculating the ratio (R) of the number of reads of HPV16 E6 and E7 transcripts to the number of reads of L1 and L2 transcripts.

In one embodiment, the method comprises determining the number of HPV sequence reads of at least 2 alpha group HPV species. In one embodiment, the method comprises generating at least $10^6$ reads of sequence of the cDNA. In one embodiment, the method comprises generating at least $10^7$ reads of sequence of the cDNA.

In one embodiment, the invention encompasses a method for assessing a human papilloma virus (HPV) infected patient comprising generating cDNA from a patient sample comprising RNA; sequencing the cDNA; generating reads of sequence of the cDNA; discriminating HPV sequence reads on the basis of HPV gene transcript; quantitating the level of HPV sequence reads according to HPV gene transcript; determining the number of HPV sequence reads of at least one HPV early gene transcript; determining the number of HPV sequence reads of at least one HPV late gene transcript; and determining the ratio of the number of HPV sequence reads of at least one HPV early gene transcript to the number of HPV sequence reads of at least one HPV late gene transcript.

In one embodiment, the method comprises calculating a ratio (R) of the number of reads of at least one early HPV16 transcript to the number of reads of at least one late HPV16 transcript, with a higher ratio (R) correlating with an increased risk of developing high-grade malignant HPV-induced cancer.

In one embodiment, the at least one early transcript is HPV E6 or E7 and the at least one late transcript is L1 or L2. In one embodiment, the at least one early transcript is HPV E6 and E7 and the at least one late transcript is L1 and L2.

In one embodiment, the cDNA is generated using random primers. In one embodiment, the cDNA is generated using HPV specific primers.

Some of the terms used throughout the specification are specifically defined here below:

Definitions

Biological samples as referred herein include, without limitation, mammalian bodily fluids, especially oral fluids or scrapings, genital scrapings, in particular cervix scrapings.

HPV alpha group: HPVs are contained within five evolutionary groups. HPV types that infect the cervix come from the Alpha group which contains over 60 members. HPV types from the Beta, Gamma, Mu and Nu groups or genus primarily infect cutaneous sites. Alpha papillomaviruses can be subdivided into three categories (high risk, low risk and cutaneous), depending on their prevalence in the general population and on the frequency with which they cause cervical cancer. High-risk types come from the Alpha 5, 6, 7, and 10 groups.

Primers encompassed by the invention are not limited to the sequences defined in the primers depicted below but they can comprise extra bases at the 5' end, for example from 1 to 5 extra bases as extension corresponding to sequences of the corresponding HPVs E6 or E7. Also, primers shall be understood as embracing shorter sequences of at least 12, 15, 20 or 25 consecutive bases of the primers featured below. In some embodiments, it shall be understood that the invention also contemplates generic probes which have the sequences of the primers depicted herein and which are directly or indirectly labeled. The probes and primers can be extended or swifted from 1 to 15 bases depending on the desired specificity of the PCR amplification step and/or on the specificity of the detection step using standard parameters such as the nucleic acid size and GC contents, stringent hybridization conditions and temperature reactions. For example, low stringency conditions are used when it is desired to obtain broad positive results on a range of homologous targets whereas high stringency conditions are preferred to obtain positive results only if the specific target nucleic is present in the sample. As used herein, the term "stringent hybridization conditions" refers to conditions under which the primer or probe will hybridize only to that exactly complementary target(s). The hybridization conditions affect the stability of hybrids, e.g., temperature, salt concentration, pH, formamide concentration and the like. These conditions are optimized to maximize specific binding and minimize non-specific binding of primer or probe to its target nucleic acid sequence. Stringent conditions are sequence dependent and will be different in different circumstances. Longer sequences hybridize specifically at higher temperatures. Generally, stringent conditions are selected to be about 5° C. lower than the thermal melting point (Tm) for the specific sequences at a defined ionic strength and pH. The Tm is the temperature (under defined ionic strength and pH) at which 50% of a complementary target sequence hybridizes to a perfectly matched probe or primer. Typically, stringent conditions will be those in which the salt concentration is less than about 1.0 M Na+, typically about 0.01 to 1.0 M Na+ concentration (or other salts) at pH 7.0 to 8.3 and the temperature is at least about 30° C. for short probes or primers (e.g. 10 to 50 nucleotides) and at least about 60° C. for long probes or primers (e.g. greater than 50 nucleotides). Stringent conditions may also be achieved with the addition of destabilizing agents such as formamide. Exemplary low stringent conditions include hybridization with a buffer solution of 20-30% formamide, 1 M NaCl, 1% SDS at 37° C. and a wash in 2*SSC at 40° C. Exemplary high stringency conditions include hybridization in 40-50% formamide, 1 M NaCl, 1% SDS at 37° C., and a wash in 0.1*SSC at 60° C. Determination of particular hybridization conditions relating to a specified nucleic acid is routine and is well known in the art, for instance, as described in J. Sambrook and D. W. Russell, Molecular Cloning: A Laboratory Manual, Cold Spring Harbor Laboratory Press; 3rd Ed., 2001; and F. M. Ausubel, Ed., Short Protocols in Molecular Biology, Current Protocols; 5th Ed., 2002.

Preferred PCR primers, which can be used separately or together as a set to amplify a HPV nucleic acid sequence comprise the primers.

α1:
E6
Forward:
(SEQ ID NO. 1)
5'-RGTACWTCTGCCTCATCACAGCC-3'

Reverse:
(SEQ ID NO. 2)
3'-CTCTGCAMTGSGTACASCGAC-5'

E7
Forward:
(SEQ ID NO. 3)
5'-GGARASRCRCCWACSCTAAAGGA-3'

Reverse:
(SEQ ID NO. 4)
3'-CACGCRGGCACACAAWGGACA-5'

L1
Forward:
(SEQ ID NO. 5)
5'-GCGGCCTAGTGACRACAAGG-3'

Reverse:
(SEQ ID NO. 6)
3'-GCACGYAACCCRGCYTGCAG-5'

α2:
E6
Forward:
(SEQ ID NO. 7)
5'-GHGHGCCMTAYGSTGCCTGTG-3'

Forward:
(SEQ ID NO. 8)
5'-CKCCSTACGGTGCWTGTGC-3'

Reverse:
(SEQ ID NO. 9)
3'-GCGGACCGTGCATCKTRWCCA-5'

Reverse:
(SEQ ID NO. 10)
3'-GGCTTTGGCCCATGCATCGT-5'

Reverse:
(SEQ ID NO. 11)
3'-GTGCATCGTGACCAGCAGTAC-5'

E7
Forward:
(SEQ ID NO. 12)
5'-TTGRDTCTTGCACCAGAGGMCGT-3'

Forward:
(SEQ ID NO. 13)
5'-TGCACGGTCCGCATCCCAC-3'

Forward:
(SEQ ID NO. 14)
5'-TGTCTATGGGTGCACAAGAACCC-3'

Reverse:
(SEQ ID NO. 15)
3'-CCCTTATATCTGCKTSGCTGCWS-5'

Reverse:
(SEQ ID NO. 16)
3'-GCAGCGAGGRCACACGASC-5'

Reverse:
(SEQ ID NO. 17)
3'-GGACCGTGCATCGTGACCA-5'

L1
Forward:
(SEQ ID NO. 18)
5'-ATGGCWYTSTGGCGCYCTAGTG-3'

Reverse:
(SEQ ID NO. 19)
3'-CCTCCARGCTAGTRGAYGGYGGY-5'

Reverse:
(SEQ ID NO. 20)
3'-GGGRACYACYGAACGMCGKCGCG-5'

α3:
E6
Forward:
(SEQ ID NO. 21)
5'-AGTGGACRGGRAAGTGCWGCAAC-3'

Forward:
(SEQ ID NO. 22)
5'-YTGTGCAAAGACTGCGASGTGG-3'

Forward:
(SEQ ID NO. 23)
5'-ACTGGCCATTTGGAGTMTGCGC-3'

Reverse:
(SEQ ID NO. 24)
3'-GGCCRYGCATGTTRCYCTACAGT-5'

Reverse:
(SEQ ID NO. 25)
3'-CACYKTCCTGTCCACTBYCCWGC-5'

Reverse:
(SEQ ID NO. 26)
3'-CCAGTGYCGTAGCTCYCGYRYC-5'

Reverse:
(SEQ ID NO. 27)
3'-CTGGCCGTGCATRSYCCTCT-5'

E7
Forward:
(SEQ ID NO. 28)
5'-VAGCAMAGCWGGCCYWTAGGGTG-3'

Forward:
(SEQ ID NO. 29)
5'-KGYWGAACRRGCACAGCAGGCC-3'

Reverse:
(SEQ ID NO. 30)
3'-GGCCACYRCKTCCACYATAAGCT-5'

Reverse:
(SEQ ID NO. 31)
3'-CAGCYGGGACACACTATRTCCAC-5'

Reverse:
(SEQ ID NO. 32)
3'-GCGCAGCSVGGACACACTAT-5'

L1
Forward:
(SEQ ID NO. 33)
5'-CTWTGTGGCGRCMTGGTGAYGGC-3'

Reverse:
(SEQ ID NO. 34)
3'-GGARGGAGGGGGCAMWACMCC-5'

-continued

Reverse:
(SEQ ID NO. 35)
3'-CCCTGBGCVCGNTGYAGCCAR-5'

α4:
E6
Forward:
(SEQ ID NO. 36)
5'-SAGTATGGTYTGGAGCTAGAGGA-3'

Reverse:
(SEQ ID NO. 37)
3'-GTCCSGTCCACYGGCCKGM-5'

E7
Forward:
(SEQ ID NO. 38)
5'-MCGMCCCAGCCTSRMGGAC-3'

Reverse:
(SEQ ID NO. 39)
3'-CCTCCATRACGCTABGCGCAG-5'

L1
Forward:
(SEQ ID NO. 40)
5'-TGGCCTAAACGACGTAAACGTGT-3'

Forward:
(SEQ ID NO. 41)
5'-TTCTTTGCAGATGGCTWTGTGGC-3'

Reverse:
(SEQ ID NO. 42)
5'-YGTGTCTCGMAARCGCRCCGC-3'::
3'-GCGGYGCGYTTKCGAGACACR-5'

Reverse:
(SEQ ID NO. 43)
5'-CGCAAGTTYTTRYTGCAGCGGGG-3'::
3'-CCCCGCTGCARYAARAACTTGCG-5'

α5:
E6
Forward:
(SEQ ID NO. 44)
5'-GRGAAAGACCACGAACGCTGC-3'

Forward:
(SEQ ID NO. 45)
5'-AATAGCAGGGYASTGGAAAGGGT-3'

Reverse:
(SEQ ID NO. 46)
3'-GCAATTWGCRCAYTGYCCCGTCC-5'

Reverse:
(SEQ ID NO. 47)
3'-TTGTGTTTCTGTTTGGCGCCTTG-5'

Reverse:
(SEQ ID NO. 48)
3'-GCCTTGGTCTCCAGCAGTTTG-5'

E7
Forward:
(SEQ ID NO. 49)
5'-YTAGATYTGGTGCCGCAACCCG-3'

Forward:
(SEQ ID NO. 50)
5'-MGCCATGCGTGGTAATGTACCAC-3'

Reverse:
(SEQ ID NO. 51)
3'-CTCCASCRCTCGRACGTTCTGT-5'

Reverse:
(SEQ ID NO. 52)
3'-CACGGGCAMACCAGGCTTAGK-5'

L1
Forward:
(SEQ ID NO. 53)
5'-KCAGATGGCYTTGYGGCGTACTA-3'

Forward:
(SEQ ID NO. 54)
5'-TGGCYTTGYGGCGTACTAGTGAC-3'

Forward:
(SEQ ID NO. 55)
5'-TGTATTTRCCACCTGCACCWGTG-3'

Reverse:
(SEQ ID NO. 56)
3'-GGGGCRTYRCGYTGACAKGTAGT-5'

Reverse:
(SEQ ID NO. 57)
3'-GGCMGGSCKTTTAAGGCCTGGT-5'

α6:
E6
Forward:
(SEQ ID NO. 58)
5'-GARCGHCCACGWASHBTGCACC-3'

Forward:
(SEQ ID NO. 59)
5'-AATACAGRMGAGCGMCCACGTAC-3'

Forward:
(SEQ ID NO. 60)
5'-RCAATMCACAGGAACGTCCACGA-3'

Reverse:
(SEQ ID NO. 61)
3'-CCTCTGGTGTCAACGGMTGTTGA-5'

Reverse:
(SEQ ID NO. 62)
3'-TCTCCARCACYSCAAACATGACC-5'

E7
Forward:
(SEQ ID NO. 63)
5'-GRACAGCTCAGAGGAWGAGGATG-3'

Forward:
(SEQ ID NO. 64)
5'-GCTCAGAGGAWGAGGATGAGG-3'

Forward:
(SEQ ID NO. 65)
5'-YTRCWGRAGCRGCCACAGCAAGC-3'

Forward:
(SEQ ID NO. 66)
5'-GRAGCRGCCACAGCAAGCTAG-3'

Forward:
(SEQ ID NO. 67)
5'-GAACAGCTCAGAGGAWGAGGATG-3'

Forward:
(SEQ ID NO. 68)
5'-ARTAGACCATTTGCWGGAGCGGC-3'

Reverse:
(SEQ ID NO. 69)
3'-GCCTTGTTGCRCASAGGGG-5'

Reverse:
(SEQ ID NO. 70)
3'-CGCAGAGTGGGCACGTTACT-5'

L1
Forward:
(SEQ ID NO. 71)
5'-TTGCAGATGGCGRYGTGGCG-3'

-continued

Reverse:
(SEQ ID NO. 72)
3'-CACCTAAAGGYTGDCCDCGGC-5'

α7:
E6
Forward:
(SEQ ID NO. 73)
5'-TASAGGACAGTGYCGMCRSTGC-3'

Forward:
(SEQ ID NO. 74)
5'-TCMCAAYCCTGMRGAACGGCCAT-3'

Forward:
(SEQ ID NO. 75)
5'-ASAGGACAGTGTCGYSGGTG-3'

Forward:
(SEQ ID NO. 76)
5'-TGCCAGAAACCRTTGAAYCCAGC-3'

Reverse:
(SEQ ID NO. 77)
3'-GTCTGCGGTCCTCYCGBTTDST-5'

Reverse:
(SEQ ID NO. 78)
3'-CTGSCCTCKRTASTGCCCAGCT-5'

Reverse:
(SEQ ID NO. 79)
3'-CACCAGTGTTTCACTACGCGC-5'

Reverse:
(SEQ ID NO. 80)
3'-GCCTTGCTGTTCTTGTGCACG-5'

Reverse:
(SEQ ID NO. 81)
3'-GTCTGGAAAGCCTTTCTTGCCGT-5'

E7
Forward:
(SEQ ID NO. 82)
5'-GACGRGMHGAACMACARCGTCAC-3'

Forward:
(SEQ ID NO. 83)
5'-GACGRGMHGAACMACAGCGTCAC-3'

Forward:
(SEQ ID NO. 84)
5'-ARCACCYTGTCCTTTGTGTGTCC-3'

Reverse:
(SEQ ID NO. 85)
3'-GTGWSTCCATAAACAGCWGCWGT-5'

Reverse:
(SEQ ID NO. 86)
3'-CACACCAMGGACACACAAAGGAC-5'

L1
Forward:
(SEQ ID NO. 87)
5'-GCGBTCTAGYGACARCAHGGTGT-3'

Forward:
(SEQ ID NO. 88)
5'-HCCTGCTATTGGKGARCAYTGGG-3'

Reverse:
(SEQ ID NO. 89)
3'-CCAGTGYTCYCCMATRGCRGGWA-5'

Reverse:
(SEQ ID NO. 90)
3'-TAGASCCACTDGGWGANGGRGAA-5'

α8:
E6
Forward:
(SEQ ID NO. 91)
5'-WATGWCTGCACGKWGCKGCTCC-3'

Reverse:
(SEQ ID NO. 92)
3'-GTAGGCARTATCCYTTCCACRCG-5'

Reverse:
(SEQ ID NO. 93)
3'-CTCCGAGCGTTGGCCTTTC-5'

E7
Forward:
(SEQ ID NO. 94)
5'-GCGTGAGCAAYCCACGCAAC-3'

Reverse:
(SEQ ID NO. 95)
3'-CAGCCATKGYAGTCACACMGCTG-5'

Reverse:
(SEQ ID NO. 96)
3'-TGCCATTGTTGTCACKCTGTAGC-5'

L1
Forward:
(SEQ ID NO. 97)
5'-CCYCCHATKGGNGAATATTGGGG-3'

Reverse:
(SEQ ID NO. 98)
3'-GGAGGATGGTGCWGMACGC-5'

Reverse:
(SEQ ID NO. 99)
3'-GGGTGACTGRCYYAGAAGAGGAA-5'

α9:
E6
Forward:
(SEQ ID NO. 100)
5'-AGTRMARATGCCTCCACGYCTGC-3'

Forward:
(SEQ ID NO. 101)
5'-CTGCACAGGACCAGATGGC-3'

Reverse:
(SEQ ID NO. 102)
3'-TCCATGCATGWTGWCCAGCARTG-5'

Reverse:
(SEQ ID NO. 103)
3'-GCAGCGMCCYTTCCAGGTRTCK-5'

Reverse:
(SEQ ID NO. 104)
3'-GGCATTTCGCCCACCATTGTTAT-5'

E7
Forward:
(SEQ ID NO. 105)
5'-GCYTACACTGCTGGACAACATGC-3'

Forward:
(SEQ ID NO. 106)
5'-AGACAGCTCAGAAGABGAGGTGG-3'

Forward:
(SEQ ID NO. 107)
5'-AACAATGGTGGGCGAAATGCCAG-3'

Reverse:
(SEQ ID NO. 108)
3'-CGTCCGCCATCSTTGTTATGKYT-5'

-continued

Reverse: (SEQ ID NO. 109)
3'-CCTGTRCACTSCACMACMAGCC-5'

Reverse: (SEQ ID NO. 110)
3'-CTGTCGCTGTAGGGTGCACA-5'

L1
Forward: (SEQ ID NO. 111)
5'-ATGTGCCTCCTCCYRMCCCWGTA-3'

Forward: (SEQ ID NO. 112)
5'-AGATGGCTGTCTGGTTACCAGC-3'

Reverse: (SEQ ID NO. 113)
3'-CCATAWGGRTCYGCAGCCATTTG-5'

Reverse: (SEQ ID NO. 114)
3'-GCCTTACGCCTGCGCTTGG-5'

α10:
E6
Forward: (SEQ ID NO. 115)
5'-CCSARSTGTAAWCATGCRTGGAG-3'

Forward: (SEQ ID NO. 116)
5'-MCGSAMCCTGCACGAATTGTGTG-3'

Forward: (SEQ ID NO. 117)
5'-CARGACRCWGAGGARAAACCACG-3'

Reverse: (SEQ ID NO. 118)
3'-CCAACACWCTGAACASCGYCC-5'

Reverse: (SEQ ID NO. 119)
3'-CCATGCATGATTACASCTSGGTT-5'

Reverse: (SEQ ID NO. 120)
3'-GTCGGGRYCTCCAACACRCYG-5'

Reverse: (SEQ ID NO. 121)
3'-CTCCACGCATGTTTACACTTGGG-5'

E7
Forward: (SEQ ID NO. 122)
5'-GCWCAYTWGGAATHGTGTGCCCC-3'

Forward: (SEQ ID NO. 123)
5'-CSTGTAAMAACGCCATGAGAGGA-3'

Forward: (SEQ ID NO. 124)
5'-CGCCATGAGAGGAMACAASCCA-3'

Reverse: (SEQ ID NO. 125)
3'-GGCACACDATTCCWARTGWGCCC-5'

Reverse: (SEQ ID NO. 126)
3'-GGTTCGTASGTCRSTTGYTGTAC-5'

Reverse: (SEQ ID NO. 127)
3'-GTGCACAGSYGGGRCACACWAYT-5'

L1
Forward: (SEQ ID NO. 128)
5'-GARGCCACWGTSTACYTGCCTC-3'

Forward: (SEQ ID NO. 129)
5'-ACAGATGTCTCTGTGGCGGC-3'

Reverse: (SEQ ID NO. 130)
3'-GGATGNCCACTWAYRCCHACDCC-5'

Reverse: (SEQ ID NO. 131)
3'-GAGGWWACCATAGARCCACTRGG-5'

Reverse: (SEQ ID NO. 132)
3'-GTGCACGYTGTAGCCAATAWGGC-5'

Reverse: (SEQ ID NO. 133)
3'-TCCTGTAAACTRGCAGAYGGAGG-5'

Reverse: (SEQ ID NO. 134)
3'-GGCCYTGTGCWCGTTGYAACCAA-5'

α11:
E6
Forward: (SEQ ID NO. 135)
5'-GAACGRCCATACAAGCTACMAGC-3'

Reverse: (SEQ ID NO. 136)
3'-GCAGATGGTCTCCAGCACYG-5'

E7
Forward: (SEQ ID NO. 137)
5'-WATTGTGTGCCCCAACTGTTCCA-3'

Reverse: (SEQ ID NO. 138)
3'-CTGGAACAGTTGGGGCACACA-5'

L1
Forward: (SEQ ID NO. 139)
5'-AGTTCTATCTTCCTCCCCAGCC-3'

Reverse: (SEQ ID NO. 140)
3'-GGACGKGCACGCATACCWAG-5'

α13:
E6
Forward: (SEQ ID NO. 141)
5'-TGTCTGCTACTGAACCCCACAC-3'

Reverse: (SEQ ID NO. 142)
3'-GGCTTCCAGCAATGTAGACACC-5'

E7
Forward: (SEQ ID NO. 143)
5'-GTTTGACCTGTACTGCAGGGAG-3'

Reverse: (SEQ ID NO. 144)
3'-GTGAAGCACAGGTGGGACACA-5'

L1
Forward: (SEQ ID NO. 145)
5'-AAAGTATACCTGCCTCCTACCCC-3'

-continued

Reverse:
(SEQ ID NO. 146)
3'-GCACGCTTGCGCGCTGTAC-5'

α14:
E6
Forward:
(SEQ ID NO. 147)
5'-TAYSAMSTGGACCTGCAGGACC-3'

Reverse:
(SEQ ID NO. 148)
3'-GGCCWYGCATGRTKTCCAACACT-5'

E7
Forward:
(SEQ ID NO. 149)
5'-CAATTWGCCAGCTCAGAMGAGGA-3'

Reverse:
(SEQ ID NO. 150)
3'-CCACCACMAGCCTWACTGYACRV-5'

L1
Forward:
(SEQ ID NO. 151)
5'-ARGTATACCTGCCTCCYGCCC-3'

Reverse:
(SEQ ID NO. 152)
3'-CCTGTGCWCGTTGYAGCCAG-5'

As used herein, G is used to designate Guanine, A is used to designate Adenine, T is used to designate a Thymine, C is used to designate a Cytosine. R is commonly used to designate a Purine (A or G), Y is commonly used to designate a Pyrimidine (T or C), W is commonly used to designate A or T, S is commonly used to designate C or G, K is commonly used to designate G or T, H is commonly used to designate A or T or C, B is commonly used to designate G or C or T, V is commonly used to designate G or A or T, D is commonly used to designate G or A or T, N is commonly used to designate any nucleotide (A or T or C or G).

Addition of indices and sequencing adapters are needed for sequencing technologies and can be added by standard procedures. For example, said primers can be used in solution or linked to a solid support. To permit its covalent coupling to the support, the primer is generally functionalized. Thus, it may be modified by a thiol, amine or carboxyl terminal group at the 5' or 3' position. In particular, the addition of a thiol, amine or carboxyl group makes it possible, for example, to couple the oligonucleotide to a support bearing disulphide, maleimide, amine, carboxyl, ester, epoxide, cyanogen bromide or aldehyde functions. These couplings form by establishment of disulphide, thioether, ester, amide or amine links between the primer and the support. Any other method known to a person skilled in the art may be used, such as bifunctional coupling reagents, for example.

Moreover, to improve the hybridization with the coupled oligonucleotide, it can be advantageous for the oligonucleotide to contain an "arm" and a "spacer" sequence of bases. The use of an arm makes it possible, in effect, to bind the primer at a chosen distance from the support, enabling its conditions of interaction with the DNA to be improved. The arm advantageously consists of a linear carbon chain, comprising 1 to 18 and preferably 6 or 12 ($CH_2$) groups, and an amine which permits binding to the column. The arm is linked to a phosphate of the oligonucleotide or of a "spacer" composed of bases which do not interfere with the hybridization. Thus, the "spacer" can comprise purine bases. As an example, the "spacer" can comprise the sequence GAGG. The arm is advantageously composed of a linear carbon chain comprising 6 or 12 carbon atoms.

For implementation of the present invention, different types of support may be used. These can be functionalized chromatographic supports, in bulk or prepacked in a column, functionalized plastic surfaces or functionalized latex beads, magnetic or otherwise. Chromatographic supports are preferably used. As an example, the chromatographic supports capable of being used are agarose, acrylamide or dextran as well as their derivatives (such as Sephadex, Sepharose, Superose, etc.), polymers such as poly(styrene/divinylbenzene), or grafted or ungrafted silica, for example. The chromatography columns can operate in the diffusion or perfusion mode.

As used herein, the term "sequencing" is used in a broad sense and refers to any technique known by the skilled person including but not limited to Sanger dideoxy termination sequencing, whole-genome sequencing, sequencing by hybridization, pyrosequencing, capillary electrophoresis, cycle sequencing, single-base extension sequencing, solid-phase sequencing, high-throughput sequencing, massively parallel signature sequencing (MPSS), sequencing by reversible dye terminator, paired-end sequencing, near-term sequencing, exonuclease sequencing, sequencing by ligation, short-read sequencing, single-molecule sequencing, sequencing-by-synthesis, real-time sequencing, reverse-terminator sequencing, nanopore sequencing, 454 sequencing, Solexa Genome Analyzer sequencing, SOLiD® sequencing, MS-PET sequencing, mass spectrometry, and a combination thereof. In specific embodiments, the method and kit of the invention is adapted to run on ABI PRISM® 377 DNA Sequencer, an ABI PRISM® 310, 3100, 3100-Avant, 3730, or 3730xl Genetic Analyzer, an ABI PRISM® 3700 DNA Analyzer, or an Applied Biosystems SOLiD™ System (all from Applied Biosystems), a Genome Sequencer 20 System (Roche Applied Science).

For all technologies described herein, although the said primers can be used in solution, in another embodiment the said primers are linked to a solid support.

To permit its covalent coupling to the support, the primer is generally functionalized. Thus, it may be modified by a thiol, amine or carboxyl terminal group at the 5' or 3' position. In particular, the addition of a thiol, amine or carboxyl group makes it possible, for example, to couple the oligonucleotide to a support bearing disulphide, maleimide, amine, carboxyl, ester, epoxide, cyanogen bromide or aldehyde functions. These couplings form by establishment of disulphide, thioether, ester, amide or amine links between the primer and the support. Any other method known to a person skilled in the art may be used, such as bifunctional coupling reagents, for example.

Moreover, to improve the hybridization with the coupled oligonucleotide, it can be advantageous for the oligonucleotide to contain an "arm" and a "spacer" sequence of bases. The use of an arm makes it possible, in effect, to bind the primer at a chosen distance from the support, enabling its conditions of interaction with the DNA to be improved. The arm advantageously consists of a linear carbon chain, comprising 1 to 18 and preferably 6 or 12 ($CH_2$) groups, and an amine which permits binding to the column. The arm is linked to a phosphate of the oligonucleotide or of a "spacer" composed of bases which do not interfere with the hybridization. Thus, the "spacer" can comprise purine bases. As an example, the "spacer" can comprise the sequence GAGG. The arm is advantageously composed of a linear carbon chain comprising 6 or 12 carbon atoms.

For implementation of the present invention, different types of support may be used. These can be functionalized chromatographic supports, in bulk or prepacked in a column, functionalized plastic surfaces or functionalized latex beads, magnetic or otherwise. Chromatographic supports are preferably used. As an example, the chromatographic supports capable of being used are agarose, acrylamide or dextran as well as their derivatives (such as Sephadex, Sepharose, Superose, etc.), polymers such as poly(styrene/divinylbenzene), or grafted or ungrafted silica, for example. The chromatography columns can operate in the diffusion or perfusion mode.

As used herein, "oncogenic genes or oncogenic mRNAs" refers to genes or mRNAs which are directly or indirectly inducing cell transformation into cancer cells development. For example, oncogenic genes are used to designated E6 genes and/or E7 genes.

As used herein, "other viral mRNAs" refers to mRNAs coding for capsid proteins (L1 and L2), mRNAs coding for the growth stimulation (E5), mRNAs coding for replication/transcription (E4 and E2) and mRNAs coding for replication (E1 and E8), which are not oncogenic genes.

R ratios as used herein are defined as the relative level of an oncogenic mRNA, for example E6, E7 or oncogenic mRNAs, for example E6+E7, compared to other viral mRNAs of the same genotype or species, more particularly compared to selected mRNAs from genes coding for capsid proteins (L1 and L2), gene coding for the growth stimulation protein (E5), genes coding for replication or transcription proteins (E4, E2 and E1, E8).

For example, a reference Ratio R can be defined as $$R = \Sigma(xE6 \text{ and/or } xE7)/\Sigma(xL1 \text{ and/or } xL2 \text{ and/or } xE2 \ldots)$$

Wherein x is a factor in the range 0-1000000,

Wherein xE6 is for example either the number of reads mapped to the gene Ex, or the number of times each nucleotide of the gene Ex is sequenced, and wherein xL1 is for example the number of reads mapped to the gene Lx, or the number of times each nucleotide of the gene Lx is sequenced.

DRAWINGS

Figure 7:
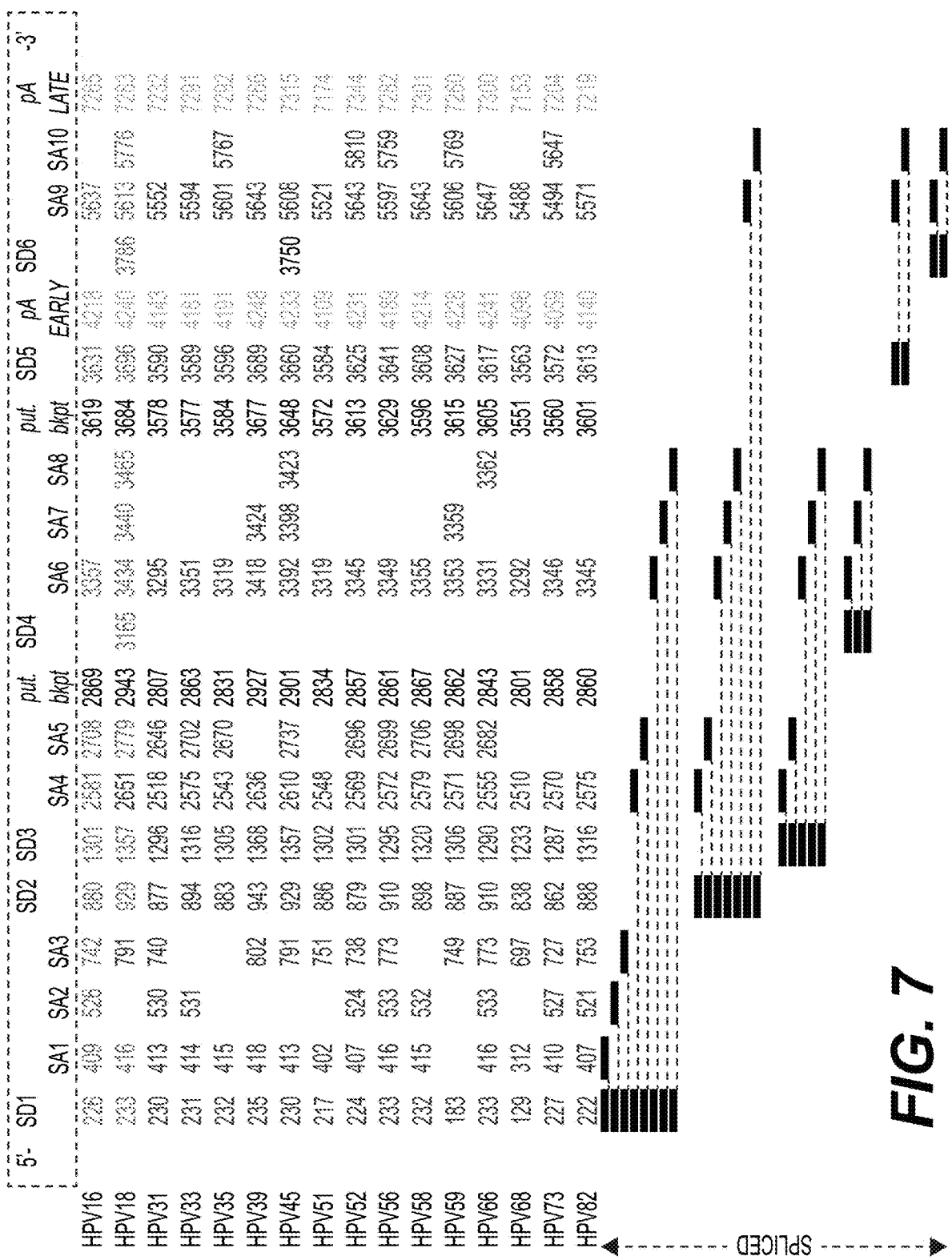

FIG. 7 represents transcription map of HR αHPV. Upper part: genomic coordinates of splice donor (SD) and acceptor (SA) sites are indicated for each HR αHPV (light grey for previously documented sites, dark grey for sites identified by analogy). Additional polyA (pA) and putative breakpoint sites (put bkpt) are added. Lower part: overview of HR αHPV splice events (black line: sequences found in mRNA; dot line: splice events) delineating splice isoforms that compose the αHPV transcripts database.

FIG. 8 presents Table 9

DETAILED DESCRIPTION

Referring to both first and second aspect, and in a first specific embodiment, the method is practiced to include at least the group consisting of papillomaviruses α6 comprising HPV 30, HPV 53, HPV 56 and HPV 66, papillomaviruses α7 comprising HPV 68, HPV 39, HPV 70, HPV 85, HPV 59, HPV 45, HPV 18, HPV 97, papillomaviruses α10 comprising HPV 16, HPV 35, HPV 31, HPV 52, HPV 67, HPV 33, HPV 58 and papillomaviruses α5 comprising HPV 26, HPV, 69, HPV 51, HPV 82.

In this regard, the invention also contemplates a composition of primers comprising for E6: α5: both SEQ ID NO. 44 and SEQ ID NO. 45, and all three SEQ ID NO. 46, SEQ ID NO. 47 and SEQ ID NO. 48 and; α6: SEQ ID NO. 58 or both SEQ ID NO. 59 and SEQ ID NO. 60, and both SEQ ID NO. 61 and SEQ ID NO. 62 and; α7: all three SEQ ID NO. 73, SEQ ID NO. 75 and SEQ ID NO. 76 or all three EQ ID NO. 74, SEQ ID NO. 75 and SEQ ID NO. 76, and all five SEQ ID NO. 77, SEQ ID NO. 78, SEQ ID NO. 79, SEQ ID NO. 80 and SEQ ID NO. 81 and; α10: all three SEQ ID NO. 115, SEQ ID NO. 116, SEQ ID NO. 117 and all four SEQ ID NO. 118, SEQ ID NO. 119, SEQ ID NO. 120, SEQ ID NO. 121, And comprising for L1 α5: SEQ ID NO. 53 or both SEQ ID NO. 54 and SEQ ID NO. 55, and both SEQ ID NO. 56 and SEQ ID NO. 57; and α6: SEQ ID NO. 71 and SEQ ID NO. 72; and α7: both SEQ ID NO. 87 and SEQ ID NO. 88, and both SEQ ID NO. 89 and SEQ ID NO. 90; and α10: both SEQ ID NO. 128, SEQ ID NO. 129 and SEQ ID NO. 130 or all four SEQ ID NO. 131, SEQ ID NO. 132, SEQ ID NO. 133, SEQ ID NO. 134.

Or, in this regard, the invention also contemplates a composition of primers comprising for E7: α5: both SEQ ID NO. 49, SEQ ID NO. 50 and both SEQ ID NO. 51, SEQ ID NO. 52; and α6: SEQ ID NO. 63 or SEQ ID NO. 64 or SEQ ID NO. 65 SEQ ID NO. 66 or both SEQ ID NO. 67 and SEQ ID NO. 68, and both SEQ ID NO. 69 and SEQ ID NO. 70; and α7: SEQ ID NO. 82 or both SEQ ID NO. 83, SEQ ID NO. 84, and both SEQ ID NO. 85, SEQ ID NO. 86; and α10: all three SEQ ID NO. 122, SEQ ID NO. 123 and SEQ ID NO. 124, and all three SEQ ID NO. 125, SEQ ID NO. 126 and SEQ ID NO. 127, And comprising for L1 α5: SEQ ID NO. 53 or both SEQ ID NO. 54 and SEQ ID NO. 55, and both SEQ ID NO. 56 and SEQ ID NO. 57; and α6: SEQ ID NO. 71 and SEQ ID NO. 72; and α7: both SEQ ID NO. 87 and SEQ ID NO. 88, and both SEQ ID NO. 89 and SEQ ID NO. 90; and α10: both SEQ ID NO. 128, SEQ ID NO. 129 and SEQ ID NO. 130 or all four SEQ ID NO. 131, SEQ ID NO. 132, SEQ ID NO. 133, SEQ ID NO. 134.

In a second specific embodiment the method is practiced to include at least the group consisting of papillomaviruses α6 comprising HPV 30, HPV 53, HPV 56 and HPV 66, papillomaviruses α7 comprising HPV 68, HPV 39, HPV 70, HPV 85, HPV 59, HPV 45, HPV 18, HPV 97, papillomaviruses α10 comprising HPV 16, HPV 35, HPV 31, HPV 52, HPV 67, HPV 33, HPV 58, papillomaviruses α5 comprising HPV 26, HPV, 69, HPV 51, HPV 82 and papillomaviruses α9 comprising HPV 6, HPV 11, HPV 13, HPV 1, HPV 74, HPV 44.

In this regard, the invention also contemplates a composition of primers comprising for E6: α5: both SEQ ID NO. 44 and SEQ ID NO. 45, and all three SEQ ID NO. 46, SEQ ID NO. 47 and SEQ ID NO. 48 and; α6: SEQ ID NO. 58 or both SEQ ID NO. 59 and SEQ ID NO. 60, and both SEQ ID NO. 61 and SEQ ID NO. 62 and; α7: all three SEQ ID NO. 73, SEQ ID NO. 75 and SEQ ID NO. 76 or all three EQ ID NO. 74, SEQ ID NO. 75 and SEQ ID NO. 76, and all five SEQ ID NO. 77, SEQ ID NO. 78, SEQ ID NO. 79, SEQ ID NO. 80 and SEQ ID NO. 81 and; α10: all three SEQ ID NO. 115, SEQ ID NO. 116, SEQ ID NO. 117 and all four SEQ ID NO. 118, SEQ ID NO. 119, SEQ ID NO. 120, SEQ ID NO. 121; and α9: both SEQ ID NO. 100 and SEQ ID NO. 101 and all three SEQ ID NO. 102, SEQ ID NO. 103 and SEQ ID NO. 104, And comprising for L1 α5: SEQ ID NO. 53 or both SEQ ID NO. 54 and SEQ ID NO. 55, and both SEQ ID NO. 56 and SEQ ID NO. 57; and α6: SEQ ID NO. 71 and SEQ ID NO. 72; and α7: both SEQ ID NO. 87 and SEQ ID NO. 88, and both SEQ ID NO. 89 and SEQ ID NO. 90; and α10: both SEQ ID NO. 128, SEQ ID NO. 129 and SEQ ID NO. 130 or all four SEQ ID NO. 131, SEQ ID NO. 132, SEQ ID NO. 133, SEQ ID NO. 134; and α9: both SEQ ID NO. 111 and SEQ ID NO. 112, and both SEQ ID NO. 113 and SEQ ID NO. 114.

Or, in this regard, the invention also contemplates a composition of primers comprising for E7: α5: both SEQ ID NO. 49, SEQ ID NO. 50 and both SEQ ID NO. 51, SEQ ID NO. 52; and α6: SEQ ID NO. 63 or SEQ ID NO. 64 or SEQ ID NO. 65 SEQ ID NO. 66 or both SEQ ID NO. 67 and SEQ ID NO. 68, and both SEQ ID NO. 69 and SEQ ID NO. 70; and α7: SEQ ID NO. 82 or both SEQ ID NO. 83, SEQ ID NO. 84, and both SEQ ID NO. 85, SEQ ID NO. 86; and α10: all three SEQ ID NO. 122, SEQ ID NO. 123 and SEQ ID NO. 124, and all three SEQ ID NO. 125, SEQ ID NO. 126 and SEQ ID NO. 127; and α9: all three SEQ ID NO. 105, SEQ ID NO. 106 and SEQ ID NO. 107, and all three SEQ ID NO. 108, SEQ ID NO. 109 and 110, And comprising for L1 α5: SEQ ID NO. 53 or both SEQ ID NO. 54 and SEQ ID NO. 55, and both SEQ ID NO. 56 and SEQ ID NO. 57; and α6: SEQ ID NO. 71 and SEQ ID NO. 72; and α7: both SEQ ID NO. 87 and SEQ ID NO. 88, and both SEQ ID NO. 89 and SEQ ID NO. 90; and α10: both SEQ ID NO. 128, SEQ ID NO. 129 and SEQ ID NO. 130 or all four SEQ ID NO. 131, SEQ ID NO. 132, SEQ ID NO. 133, SEQ ID NO. 134; and α9: both SEQ ID NO. 111 and SEQ ID NO. 112, and both SEQ ID NO. 113 and SEQ ID NO. 114.

In a third specific embodiment, the above defined invention is practiced to include at least the group consisting of papillomaviruses α6 comprising HPV 30, HPV 53, HPV 56 and HPV 66, papillomaviruses α7 comprising HPV 68, HPV 39, HPV 70, HPV 85, HPV 59, HPV 45, HPV 18, HPV 97, papillomaviruses α10 comprising HPV 16, HPV 35, HPV 31, HPV 52, HPV 67, HPV 33, HPV 58, papillomaviruses α5 comprising HPV 26, HPV, 69, HPV 51, HPV 82, papillomaviruses α9 comprising HPV 6, HPV 11, HPV 13, HPV 1, HPV 74, HPV 44 and papillomaviruses α8 comprising HPV 91, HPV 43, HPV 7, HPV 40.

In this regard, the invention also contemplates a composition of primers comprising for E6: α5: both SEQ ID NO. 44 and SEQ ID NO. 45, and all three SEQ ID NO. 46, SEQ ID NO. 47 and SEQ ID NO. 48 and; α6: SEQ ID NO. 58 or both SEQ ID NO. 59 and SEQ ID NO. 60, and both SEQ ID NO. 61 and SEQ ID NO. 62 and; α7: all three SEQ ID NO. 73, SEQ ID NO. 75 and SEQ ID NO. 76 or all three EQ ID NO. 74, SEQ ID NO. 75 and SEQ ID NO. 76, and all five SEQ ID NO. 77, SEQ ID NO. 78, SEQ ID NO. 79, SEQ ID NO. 80 and SEQ ID NO. 81 and; α10: all three SEQ ID NO. 115, SEQ ID NO. 116, SEQ ID NO. 117 and all four SEQ ID NO. 118, SEQ ID NO. 119, SEQ ID NO. 120, SEQ ID NO. 121; and α9: both SEQ ID NO. 100 and SEQ ID NO. 101 and all three SEQ ID NO. 102, SEQ ID NO. 103 and SEQ ID NO. 104; and α8: SEQ ID NO. 91, and both SEQ ID NO. 92 and SEQ ID NO. 93.

And comprising for L1 α5: SEQ ID NO. 53 or both SEQ ID NO. 54 and SEQ ID NO. 55, and both SEQ ID NO. 56 and SEQ ID NO. 57; and α6: SEQ ID NO. 71 and SEQ ID NO. 72; and α7: both SEQ ID NO. 87 and SEQ ID NO. 88, and both SEQ ID NO. 89 and SEQ ID NO. 90; and α10: both SEQ ID NO. 128, SEQ ID NO. 129 and SEQ ID NO. 130 or all four SEQ ID NO. 131, SEQ ID NO. 132, SEQ ID NO. 133, SEQ ID NO. 134; and α9: both SEQ ID NO. 111 and SEQ ID NO. 112, and both SEQ ID NO. 113 and SEQ ID NO. 114; and α8: SEQ ID NO. 97, and both SEQ ID NO. 98 and SEQ ID NO. 99.

Or, in this regard, the invention also contemplates a composition of primers comprising for E7: α5: both SEQ ID NO. 49, SEQ ID NO. 50 and both SEQ ID NO. 51, SEQ ID NO. 52; and α6: SEQ ID NO. 63 or SEQ ID NO. 64 or SEQ ID NO. 65 SEQ ID NO. 66 or both SEQ ID NO. 67 and SEQ ID NO. 68, and both SEQ ID NO. 69 and SEQ ID NO. 70; and α7: SEQ ID NO. 82 or both SEQ ID NO. 83, SEQ ID NO. 84, and both SEQ ID NO. 85, SEQ ID NO. 86; and α10: all three SEQ ID NO. 122, SEQ ID NO. 123 and SEQ ID NO. 124, and all three SEQ ID NO. 125, SEQ ID NO. 126 and SEQ ID NO. 127; and α9: all three SEQ ID NO. 105, SEQ ID NO. 106 and SEQ ID NO. 107, and all three SEQ ID NO. 108, SEQ ID NO. 109 and 110; and α8: SEQ ID NO. 94, and both SEQ ID NO. 95 and SEQ ID NO. 96

And comprising for L1 α5: SEQ ID NO. 53 or both SEQ ID NO. 54 and SEQ ID NO. 55, and both SEQ ID NO. 56 and SEQ ID NO. 57; and α6: SEQ ID NO. 71 and SEQ ID NO. 72; and α7: both SEQ ID NO. 87 and SEQ ID NO. 88, and both SEQ ID NO. 89 and SEQ ID NO. 90; and α10: both SEQ ID NO. 128, SEQ ID NO. 129 and SEQ ID NO. 130 or all four SEQ ID NO. 131, SEQ ID NO. 132, SEQ ID NO. 133, SEQ ID NO. 134; and α9: both SEQ ID NO. 111 and SEQ ID NO. 112, and both SEQ ID NO. 113 and SEQ ID NO. 114; and α8: SEQ ID NO. 97, and both SEQ ID NO. 98 and SEQ ID NO. 99.

In a forth specific embodiment, the above defined invention is practiced to include at least the group consisting of papillomaviruses α6 comprising HPV 30, HPV 53, HPV 56 and HPV 66, papillomaviruses α7 comprising HPV 68, HPV 39, HPV 70, HPV 85, HPV 59, HPV 45, HPV 18, HPV 97, papillomaviruses α10 comprising HPV 16, HPV 35, HPV 31, HPV 52, HPV 67, HPV 33, HPV 58, papillomaviruses α5 comprising HPV 26, HPV, 69, HPV 51, HPV 82, papillomaviruses α9 comprising HPV 6, HPV 11, HPV 13, HPV 1, HPV 74, HPV 44, papillomaviruses α8 comprising HPV 91, HPV 43, HPV 7, HPV 40 and papillomaviruses α1 comprising HPV 42, HPV 32.

In this regard, the invention also contemplates a composition of primers comprising for E6: α5: both SEQ ID NO. 44 and SEQ ID NO. 45, and all three SEQ ID NO. 46, SEQ ID NO. 47 and SEQ ID NO. 48 and; α6: SEQ ID NO. 58 or both SEQ ID NO. 59 and SEQ ID NO. 60, and both SEQ ID NO. 61 and SEQ ID NO. 62 and; α7: all three SEQ ID NO. 73, SEQ ID NO. 75 and SEQ ID NO. 76 or all three EQ ID NO. 74, SEQ ID NO. 75 and SEQ ID NO. 76, and all five SEQ ID NO. 77, SEQ ID NO. 78, SEQ ID NO. 79, SEQ ID NO. 80 and SEQ ID NO. 81 and; α10: all three SEQ ID NO. 115, SEQ ID NO. 116, SEQ ID NO. 117 and all four SEQ ID NO. 118, SEQ ID NO. 119, SEQ ID NO. 120, SEQ ID NO. 121; and α9: both SEQ ID NO. 100 and SEQ ID NO. 101 and all three SEQ ID NO. 102, SEQ ID NO. 103 and SEQ ID NO. 104; and α8: SEQ ID NO. 91, and both SEQ ID NO. 92 and SEQ ID NO. 93; and α1: SEQ ID NO. 1 and SEQ ID NO. 2

And comprising for L1 α5: SEQ ID NO. 53 or both SEQ ID NO. 54 and SEQ ID NO. 55, and both SEQ ID NO. 56 and SEQ ID NO. 57; and α6: SEQ ID NO. 71 and SEQ ID NO. 72; and α7: both SEQ ID NO. 87 and SEQ ID NO. 88, and both SEQ ID NO. 89 and SEQ ID NO. 90; and α10: both SEQ ID NO. 128, SEQ ID NO. 129 and SEQ ID NO. 130 or all four SEQ ID NO. 131, SEQ ID NO. 132, SEQ ID NO. 133, SEQ ID NO. 134; and α9: both SEQ ID NO. 111 and SEQ ID NO. 112, and both SEQ ID NO. 113 and SEQ ID NO. 114; and α8: SEQ ID NO. 97, and both SEQ ID NO. 98 and SEQ ID NO. 99; and α1: SEQ ID NO. 5 and SEQ ID NO. 6.

Or, in this regard, the invention also contemplates a composition of primers comprising for E7: α5: both SEQ ID NO. 49, SEQ ID NO. 50 and both SEQ ID NO. 51, SEQ ID NO. 52; and α6: SEQ ID NO. 63 or SEQ ID NO. 64 or SEQ ID NO. 65 SEQ ID NO. 66 or both SEQ ID NO. 67 and SEQ ID NO. 68, and both SEQ ID NO. 69 and SEQ ID NO. 70; and α7: SEQ ID NO. 82 or both SEQ ID NO. 83, SEQ ID NO. 84, and both SEQ ID NO. 85, SEQ ID NO. 86; and α10: all three SEQ ID NO. 122, SEQ ID NO. 123 and SEQ ID NO. 124, and all three SEQ ID NO. 125, SEQ ID NO. 126 and SEQ ID NO. 127; and α9: all three SEQ ID NO. 105, SEQ ID NO. 106 and SEQ ID NO. 107, and all three SEQ ID NO. 108, SEQ ID NO. 109 and 110; and α8: SEQ ID NO. 94, and both SEQ ID NO. 95 and SEQ ID NO. 96; and α1: SEQ ID NO. 3 and SEQ ID NO. 4

And comprising for L1 α5: SEQ ID NO. 53 or both SEQ ID NO. 54 and SEQ ID NO. 55, and both SEQ ID NO. 56 and SEQ ID NO. 57; and α6: SEQ ID NO. 71 and SEQ ID NO. 72; and α7: both SEQ ID NO. 87 and SEQ ID NO. 88, and both SEQ ID NO. 89 and SEQ ID NO. 90; and α10: both SEQ ID NO. 128, SEQ ID NO. 129 and SEQ ID NO. 130 or all four SEQ ID NO. 131, SEQ ID NO. 132, SEQ ID NO. 133, SEQ ID NO. 134; and α9: both SEQ ID NO. 111 and SEQ ID NO. 112, and both SEQ ID NO. 113 and SEQ ID NO. 114; and α8: SEQ ID NO. 97, and both SEQ ID NO. 98 and SEQ ID NO. 99; and α1: SEQ ID NO. 5 and SEQ ID NO. 6.

In a fifth specific embodiment, the above defined invention is practiced to include at least the group consisting of papillomaviruses α6 comprising HPV 30, HPV 53, HPV 56 and HPV 66, papillomaviruses α7 comprising HPV 68, HPV 39, HPV 70, HPV 85, HPV 59, HPV 45, HPV 18, HPV 97, papillomaviruses α10 comprising HPV 16, HPV 35, HPV 31, HPV 52, HPV 67, HPV 33, HPV 58, papillomaviruses α5 comprising HPV 26, HPV, 69, HPV 51, HPV 82, papillomaviruses α9 comprising HPV 6, HPV 11, HPV 13, HPV 1, HPV 74, HPV 44, papillomaviruses α8 comprising HPV 91, HPV 43, HPV 7, HPV 40 papillomaviruses α1 comprising HPV 42, HPV 32 and papillomavirus α3 comprising HPV 114, HPV 84, HPV 86, HPV87, HPV 102, HPV83, HPV89, HPV 61, HPV 72, HPV 62.

In this regard, the invention also contemplates a composition of primers comprising for E6: α5: both SEQ ID NO. 44 and SEQ ID NO. 45, and all three SEQ ID NO. 46, SEQ ID NO. 47 and SEQ ID NO. 48 and; α6: SEQ ID NO. 58 or both SEQ ID NO. 59 and SEQ ID NO. 60, and both SEQ ID NO. 61 and SEQ ID NO. 62 and; α7: all three SEQ ID NO. 73, SEQ ID NO. 75 and SEQ ID NO. 76 or all three EQ ID NO. 74, SEQ ID NO. 75 and SEQ ID NO. 76, and all five SEQ ID NO. 77, SEQ ID NO. 78, SEQ ID NO. 79, SEQ ID NO. 80 and SEQ ID NO. 81 and; α10: all three SEQ ID NO. 115, SEQ ID NO. 116, SEQ ID NO. 117 and all four SEQ ID NO. 118, SEQ ID NO. 119, SEQ ID NO. 120, SEQ ID NO. 121; and α9: both SEQ ID NO. 100 and SEQ ID NO. 101 and all three SEQ ID NO. 102, SEQ ID NO. 103 and SEQ ID NO. 104; and α8: SEQ ID NO. 91, and both SEQ ID NO. 92 and SEQ ID NO. 93; and α1: SEQ ID NO. 1 and SEQ ID NO. 2; and α3: all three SEQ ID NO. 21, SEQ ID NO. 22 and SEQ ID NO. 23, and all four SEQ ID NO. 24, SEQ ID NO. 25, SEQ ID NO. 26 and SEQ ID NO. 27

And comprising for L1 α5: SEQ ID NO. 53 or both SEQ ID NO. 54 and SEQ ID NO. 55, and both SEQ ID NO. 56 and SEQ ID NO. 57; and α6: SEQ ID NO. 71 and SEQ ID NO. 72; and α7: both SEQ ID NO. 87 and SEQ ID NO. 88, and both SEQ ID NO. 89 and SEQ ID NO. 90; and α10: both SEQ ID NO. 128, SEQ ID NO. 129 and SEQ ID NO. 130 or all four SEQ ID NO. 131, SEQ ID NO. 132, SEQ ID NO. 133, SEQ ID NO. 134; and α9: both SEQ ID NO. 111 and SEQ ID NO. 112, and both SEQ ID NO. 113 and SEQ ID NO. 114; and α8: SEQ ID NO. 97, and both SEQ ID NO. 98 and SEQ ID NO. 99; and α1: SEQ ID NO. 5 and SEQ ID NO. 6; and α3 SEQ ID NO. 33 and both SEQ ID NO. 34 and SEQ ID NO. 35.

Or, in this regard, the invention also contemplates a composition of primers comprising for E7: α5: both SEQ ID NO. 49, SEQ ID NO. 50 and both SEQ ID NO. 51, SEQ ID NO. 52; and α6: SEQ ID NO. 63 or SEQ ID NO. 64 or SEQ ID NO. 65 or SEQ ID NO. 66 or both SEQ ID NO. 67 and SEQ ID NO. 68, and both SEQ ID NO. 69 and SEQ ID NO. 70; and α7: SEQ ID NO. 82 or both SEQ ID NO. 83, SEQ ID NO. 84, and both SEQ ID NO. 85, SEQ ID NO. 86; and α10: all three SEQ ID NO. 122, SEQ ID NO. 123 and SEQ ID NO. 124, and all three SEQ ID NO. 125, SEQ ID NO. 126 and SEQ ID NO. 127; and α9: all three SEQ ID NO. 105, SEQ ID NO. 106 and SEQ ID NO. 107, and all three SEQ ID NO. 108, SEQ ID NO. 109 and 110; and α8: SEQ ID NO. 94, and both SEQ ID NO. 95 and SEQ ID NO. 96; and α1: SEQ ID NO. 3 and SEQ ID NO. 4; and α3: both SEQ ID NO. 28 and SEQ ID NO. 29, and all three SEQ ID NO. 30, SEQ ID NO. 31, SEQ ID NO. 32, And comprising for L1 α5: SEQ ID NO. 53 or both SEQ ID NO. 54 and SEQ ID NO. 55, and both SEQ ID NO. 56 and SEQ ID NO. 57; and α6: SEQ ID NO. 71 and SEQ ID NO. 72; and α7: both SEQ ID NO. 87 and SEQ ID NO. 88, and both SEQ ID NO. 89 and SEQ ID NO. 90; and α10: both SEQ ID NO. 128, SEQ ID NO. 129 and SEQ ID NO. 130 or all four SEQ ID NO. 131, SEQ ID NO. 132, SEQ ID NO. 133, SEQ ID NO. 134; and α9: both SEQ ID NO. 111 and SEQ ID NO. 112, and both SEQ ID NO. 113 and SEQ ID NO. 114; and α8: SEQ ID NO. 97, and both SEQ ID NO. 98 and SEQ ID NO. 99; and α1: SEQ ID NO. 5 and SEQ ID NO. 6; and α3 SEQ ID NO. 33 and both SEQ ID NO. 34 and SEQ ID NO. 35.

In a sixth specific embodiment, the above defined invention is practiced to include at least the group consisting of papillomaviruses α6 comprising HPV 30, HPV 53, HPV 56 and HPV 66, papillomaviruses α7 comprising HPV 68, HPV 39, HPV 70, HPV 85, HPV 59, HPV 45, HPV 18, HPV 97, papillomaviruses α10 comprising HPV 16, HPV 35, HPV 31, HPV 52, HPV 67, HPV 33, HPV 58, papillomaviruses α5 comprising HPV 26, HPV, 69, HPV 51, HPV 82, papillomaviruses α9 comprising HPV 6, HPV 11, HPV 13, HPV 1, HPV 74, HPV 44, papillomaviruses α8 comprising HPV 91, HPV 43, HPV 7, HPV 40 papillomaviruses α1 comprising HPV 42, HPV 32, papillomavirus α3 comprising HPV 114, HPV 84, HPV 86, HPV87, HPV 102, HPV83, HPV89, HPV 61, HPV 72, HPV 62 and papillomavirus α2 comprising HPV 117, HPV 10, HPV 94, HPV 28, HPV125, HPV 3, HPV 78, HPV 160, HPV 29, HPV 77.

In this regard, the invention also contemplates a composition of primers comprising for E6: α5: both SEQ ID NO. 44 and SEQ ID NO. 45, and all three SEQ ID NO. 46, SEQ ID NO. 47 and SEQ ID NO. 48 and; α6: SEQ ID NO. 58 or both SEQ ID NO. 59 and SEQ ID NO. 60, and both SEQ ID NO. 61 and SEQ ID NO. 62 and; α7: all three SEQ ID NO. 73, SEQ ID NO. 75 and SEQ ID NO. 76 or all three EQ ID NO. 74, SEQ ID NO. 75 and SEQ ID NO. 76, and all five SEQ ID NO. 77, SEQ ID NO. 78, SEQ ID NO. 79, SEQ ID NO. 80 and SEQ ID NO. 81 and; α10: all three SEQ ID NO. 115, SEQ ID NO. 116, SEQ ID NO. 117 and all four SEQ ID NO. 118, SEQ ID NO. 119, SEQ ID NO. 120, SEQ ID NO. 121; and α9: both SEQ ID NO. 100 and SEQ ID NO. 101 and all three SEQ ID NO. 102, SEQ ID NO. 103 and SEQ ID NO. 104; and α8: SEQ ID NO. 91, and both SEQ ID NO. 92 and SEQ ID NO. 93; and α1: SEQ ID NO. 1 and SEQ ID NO. 2; and α3: all three SEQ ID NO. 21, SEQ ID NO. 22 and SEQ ID NO. 23, and all four SEQ ID NO. 24, SEQ ID NO. 25, SEQ ID NO. 26 and SEQ ID NO. 27; and α2 and both SEQ ID NO. 7 and SEQ ID NO. 8, and all three SEQ ID NO. 9, SEQ ID NO. 10 and SEQ ID NO. 11

And comprising for L1 α5: SEQ ID NO. 53 or both SEQ ID NO. 54 and SEQ ID NO. 55, and both SEQ ID NO. 56 and SEQ ID NO. 57; and α6: SEQ ID NO. 71 and SEQ ID NO. 72; and α7: both SEQ ID NO. 87 and SEQ ID NO. 88, and both SEQ ID NO. 89 and SEQ ID NO. 90; and α10: both SEQ ID NO. 128, SEQ ID NO. 129 and SEQ ID NO. 130 or all four SEQ ID NO. 131, SEQ ID NO. 132, SEQ ID NO. 133, SEQ ID NO. 134; and α9: both SEQ ID NO. 111 and SEQ ID NO. 112, and both SEQ ID NO. 113 and SEQ ID NO. 114; and α8: SEQ ID NO. 97, and both SEQ ID NO. 98 and SEQ ID NO. 99; and α1: SEQ ID NO. 5 and SEQ ID NO. 6; and α3 SEQ ID NO. 33 and both SEQ ID NO. 34 and SEQ ID NO. 35; and α2 SEQ ID NO. 18, and both SEQ ID NO. 19 and SEQ ID NO. 20.

Or, in this regard, the invention also contemplates a composition of primers comprising for E7: α5: both SEQ ID NO. 49, SEQ ID NO. 50 and both SEQ ID NO. 51, SEQ ID NO. 52; and α6: SEQ ID NO. 63 or SEQ ID NO. 64 or SEQ ID NO. 65 SEQ ID NO. 66 or both SEQ ID NO. 67 and SEQ ID NO. 68, and both SEQ ID NO. 69 and SEQ ID NO. 70; and α7: SEQ ID NO. 82 or both SEQ ID NO. 83, SEQ ID NO. 84, and both SEQ ID NO. 85, SEQ ID NO. 86; and α10: all three SEQ ID NO. 122, SEQ ID NO. 123 and SEQ ID NO. 124, and all three SEQ ID NO. 125, SEQ ID NO. 126 and SEQ ID NO. 127; and α9: all three SEQ ID NO. 105, SEQ ID NO. 106 and SEQ ID NO. 107, and all three SEQ ID NO. 108, SEQ ID NO. 109 and 110; and α8: SEQ ID NO. 94, and both SEQ ID NO. 95 and SEQ ID NO. 96; and α1: SEQ ID NO. 3 and SEQ ID NO. 4; and α3: both SEQ ID NO. 28 and SEQ ID NO. 29, and all three SEQ ID NO. 30, SEQ ID NO. 31, SEQ ID NO. 32; and α2: all three SEQ ID NO. 12, SEQ ID NO. 13 and SEQ ID NO. 14, and all three SEQ ID NO. 15, SEQ ID NO. 16 and SEQ ID NO. 17, And comprising for L1 α5: SEQ ID NO. 53 or both SEQ ID NO. 54 and SEQ ID NO. 55, and both SEQ ID NO. 56 and SEQ ID NO. 57; and α6: SEQ ID NO. 71 and SEQ ID NO. 72; and α7: both SEQ ID NO. 87 and SEQ ID NO. 88, and both SEQ ID NO. 89 and SEQ ID NO. 90; and α10: both SEQ ID NO. 128, SEQ ID NO. 129 and SEQ ID NO. 130 or all four SEQ ID NO. 131, SEQ ID NO. 132, SEQ ID NO. 133, SEQ ID NO. 134; and α9: both SEQ ID NO. 111 and SEQ ID NO. 112, and both SEQ ID NO. 113 and SEQ ID NO. 114; and α8: SEQ ID NO. 97, and both SEQ ID NO. 98 and SEQ ID NO. 99; and α1: SEQ ID NO. 5 and SEQ ID NO. 6; and α3 SEQ ID NO. 33 and both SEQ ID NO. 34 and SEQ ID NO. 35; and α2 SEQ ID NO. 18, and both SEQ ID NO. 19 and SEQ ID NO. 20.

In a seventh specific embodiment, the above defined invention is practiced to include at least the group consisting of papillomaviruses α6 comprising HPV 30, HPV 53, HPV 56 and HPV 66, papillomaviruses α7 comprising HPV 68, HPV 39, HPV 70, HPV 85, HPV 59, HPV 45, HPV 18, HPV 97, papillomaviruses α10 comprising HPV 16, HPV 35, HPV 31, HPV 52, HPV 67, HPV 33, HPV 58, papillomaviruses α5 comprising HPV 26, HPV, 69, HPV 51, HPV 82, papillomaviruses α9 comprising HPV 6, HPV 11, HPV 13, HPV 1, HPV 74, HPV 44, papillomaviruses α8 comprising HPV 91, HPV 43, HPV 7, HPV 40 papillomaviruses α1 comprising HPV 42, HPV 32, papillomavirus α3 comprising HPV 114, HPV 84, HPV 86, HPV87, HPV 102, HPV83, HPV89, HPV 61, HPV 72, HPV 62, papillomavirus α2 comprising HPV 117, HPV 10, HPV 94, HPV 28, HPV125, HPV 3, HPV 78, HPV 160, HPV 29, HPV 77 and papillomaviruses α4 comprising HPV 2, HPV 27, HPV 57.

In this regard, the invention also contemplates a composition of primers comprising for E6: α5: both SEQ ID NO. 44 and SEQ ID NO. 45, and all three SEQ ID NO. 46, SEQ ID NO. 47 and SEQ ID NO. 48 and; α6: SEQ ID NO. 58 or both SEQ ID NO. 59 and SEQ ID NO. 60, and both SEQ ID NO. 61 and SEQ ID NO. 62 and; α7: all three SEQ ID NO. 73, SEQ ID NO. 75 and SEQ ID NO. 76 or all three EQ ID NO. 74, SEQ ID NO. 75 and SEQ ID NO. 76, and all five SEQ ID NO. 77, SEQ ID NO. 78, SEQ ID NO. 79, SEQ ID NO. 80 and SEQ ID NO. 81 and; α10: all three SEQ ID NO. 115, SEQ ID NO. 116, SEQ ID NO. 117 and all four SEQ ID NO. 118, SEQ ID NO. 119, SEQ ID NO. 120, SEQ ID NO. 121; and α9: both SEQ ID NO. 100 and SEQ ID NO. 101 and all three SEQ ID NO. 102, SEQ ID NO. 103 and SEQ ID NO. 104; and α8: SEQ ID NO. 91, and both SEQ ID NO. 92 and SEQ ID NO. 93; and α1: SEQ ID NO. 1 and SEQ ID NO. 2; and α3: all three SEQ ID NO. 21, SEQ ID NO. 22 and SEQ ID NO. 23, and all four SEQ ID NO. 24, SEQ ID NO. 25, SEQ ID NO. 26 and SEQ ID NO. 27; and α2 and both SEQ ID NO. 7 and SEQ ID NO. 8, and all three SEQ ID NO. 9, SEQ ID NO. 10 and SEQ ID NO. 11; and α4: SEQ ID NO. 36, and SEQ ID NO. 37

And comprising for L1 α5: SEQ ID NO. 53 or both SEQ ID NO. 54 and SEQ ID NO. 55, and both SEQ ID NO. 56 and SEQ ID NO. 57; and α6: SEQ ID NO. 71 and SEQ ID NO. 72; and α7: both SEQ ID NO. 87 and SEQ ID NO. 88, and both SEQ ID NO. 89 and SEQ ID NO. 90; and α10: both SEQ ID NO. 128, SEQ ID NO. 129 and SEQ ID NO. 130 or all four SEQ ID NO. 131, SEQ ID NO. 132, SEQ ID NO. 133, SEQ ID NO. 134; and α9: both SEQ ID NO. 111 and SEQ ID NO. 112, and both SEQ ID NO. 113 and SEQ ID NO. 114; and α8: SEQ ID NO. 97, and both SEQ ID NO. 98 and SEQ ID NO. 99; and α1: SEQ ID NO. 5 and SEQ ID NO. 6; and α3 SEQ ID NO. 33 and both SEQ ID NO. 34 and SEQ ID NO. 35; and α2 SEQ ID NO. 18, and both SEQ ID NO. 19 and SEQ ID NO. 20; and α4: SEQ ID NO. 40 or SEQ ID NO. 41, and SEQ ID NO. 42 or SEQ ID NO. 43.

Or, in this regard, the invention also contemplates a composition of primers comprising for E7: α5: both SEQ ID NO. 49, SEQ ID NO. 50 and both SEQ ID NO. 51, SEQ ID NO. 52; and α6: SEQ ID NO. 63 or SEQ ID NO. 64 or SEQ ID NO. 65 SEQ ID NO. 66 or both SEQ ID NO. 67 and SEQ ID NO. 68, and both SEQ ID NO. 69 and SEQ ID NO. 70; and α7: SEQ ID NO. 82 or both SEQ ID NO. 83, SEQ ID NO. 84, and both SEQ ID NO. 85, SEQ ID NO. 86; and α10: all three SEQ ID NO. 122, SEQ ID NO. 123 and SEQ ID NO. 124, and all three SEQ ID NO. 125, SEQ ID NO. 126 and SEQ ID NO. 127; and α9: all three SEQ ID NO. 105, SEQ ID NO. 106 and SEQ ID NO. 107, and all three SEQ ID NO. 108, SEQ ID NO. 109 and 110; and α8: SEQ ID NO. 94, and both SEQ ID NO. 95 and SEQ ID NO. 96; and α1: SEQ ID NO. 3 and SEQ ID NO. 4; and α3: both SEQ ID NO. 28 and SEQ ID NO. 29, and all three SEQ ID NO. 30, SEQ ID NO. 31, SEQ ID NO. 32; and α2: all three SEQ ID NO. 12, SEQ ID NO. 13 and SEQ ID NO. 14, and all three SEQ ID NO. 15, SEQ ID NO. 16 and SEQ ID NO. 17; and α4: SEQ ID NO. 38, and SEQ ID NO. 39

And comprising for L1 α5: SEQ ID NO. 53 or both SEQ ID NO. 54 and SEQ ID NO. 55, and both SEQ ID NO. 56 and SEQ ID NO. 57; and α6: SEQ ID NO. 71 and SEQ ID NO. 72; and α7: both SEQ ID NO. 87 and SEQ ID NO. 88, and both SEQ ID NO. 89 and SEQ ID NO. 90; and α10: both SEQ ID NO. 128, SEQ ID NO. 129 and SEQ ID NO. 130 or all four SEQ ID NO. 131, SEQ ID NO. 132, SEQ ID NO. 133, SEQ ID NO. 134; and α9: both SEQ ID NO. 111 and SEQ ID NO. 112, and both SEQ ID NO. 113 and SEQ ID NO. 114; and α8: SEQ ID NO. 97, and both SEQ ID NO. 98 and SEQ ID NO. 99; and α1: SEQ ID NO. 5 and SEQ ID NO. 6; and α3 SEQ ID NO. 33 and both SEQ ID NO. 34 and SEQ ID NO. 35; and α2 SEQ ID NO. 18, and both SEQ ID NO. 19 and SEQ ID NO. 20; and α4: SEQ ID NO. 40 or SEQ ID NO. 41, and SEQ ID NO. 42 or SEQ ID NO. 43.

In an eighth specific embodiment, the above defined invention is practiced to include at least the group consisting of papillomaviruses α6 comprising HPV 30, HPV 53, HPV 56 and HPV 66, papillomaviruses α7 comprising HPV 68, HPV 39, HPV 70, HPV 85, HPV 59, HPV 45, HPV 18, HPV 97, papillomaviruses α10 comprising HPV 16, HPV 35, HPV 31, HPV 52, HPV 67, HPV 33, HPV 58, papillomaviruses α5 comprising HPV 26, HPV, 69, HPV 51, HPV 82, papillomaviruses α9 comprising HPV 6, HPV 11, HPV 13, HPV 1, HPV 74, HPV 44, papillomaviruses α8 comprising HPV 91, HPV 43, HPV 7, HPV 40 papillomaviruses α1 comprising HPV 42, HPV 32, papillomavirus α3 comprising HPV 114, HPV 84, HPV 86, HPV87, HPV 102, HPV83, HPV89, HPV 61, HPV 72, HPV 62, papillomavirus α2 comprising HPV 117, HPV 10, HPV 94, HPV 28, HPV125, HPV 3, HPV 78, HPV 160, HPV 29, HPV 77, papillomaviruses α4 comprising HPV 2, HPV 27, HPV 57 and papillomaviruses all comprising HPV 73, HPV 34.

In this regard, the invention also contemplates a composition of primers comprising for E6: α5: both SEQ ID NO. 44 and SEQ ID NO. 45, and all three SEQ ID NO. 46, SEQ ID NO. 47 and SEQ ID NO. 48 and; α6: SEQ ID NO. 58 or both SEQ ID NO. 59 and SEQ ID NO. 60, and both SEQ ID NO. 61 and SEQ ID NO. 62 and; α7: all three SEQ ID NO. 73, SEQ ID NO. 75 and SEQ ID NO. 76 or all three EQ ID NO. 74, SEQ ID NO. 75 and SEQ ID NO. 76, and all five SEQ ID NO. 77, SEQ ID NO. 78, SEQ ID NO. 79, SEQ ID NO. 80 and SEQ ID NO. 81 and; α10: all three SEQ ID NO. 115, SEQ ID NO. 116, SEQ ID NO. 117 and all four SEQ ID NO. 118, SEQ ID NO. 119, SEQ ID NO. 120, SEQ ID NO. 121; and α9: both SEQ ID NO. 100 and SEQ ID NO. 101 and all three SEQ ID NO. 102, SEQ ID NO. 103 and SEQ ID NO. 104; and α8: SEQ ID NO. 91, and both SEQ ID NO. 92 and SEQ ID NO. 93; and α1: SEQ ID NO. 1 and SEQ ID NO. 2; and α3: all three SEQ ID NO. 21, SEQ ID NO. 22 and SEQ ID NO. 23, and all four SEQ ID NO. 24, SEQ ID NO. 25, SEQ ID NO. 26 and SEQ ID NO. 27; and α2 and both SEQ ID NO. 7 and SEQ ID NO. 8, and all three SEQ ID NO. 9, SEQ ID NO. 10 and SEQ ID NO. 11; and α4: SEQ ID NO. 36, and SEQ ID NO. 37; and all: SEQ ID NO. 135, and SEQ ID NO. 136, And comprising for L1 α5: SEQ ID NO. 53 or both SEQ ID NO. 54 and SEQ ID NO. 55, and both SEQ ID NO. 56 and SEQ ID NO. 57; and α6: SEQ ID NO. 71 and SEQ ID NO. 72; and α7: both SEQ ID NO. 87 and SEQ ID NO. 88, and both SEQ ID NO. 89 and SEQ ID NO. 90; and α10: both SEQ ID NO. 128, SEQ ID NO. 129 and SEQ ID NO. 130 or all four SEQ ID NO. 131, SEQ ID NO. 132, SEQ ID NO. 133, SEQ ID NO. 134; and α9: both SEQ ID NO. 111 and SEQ ID NO. 112, and both SEQ ID NO. 113 and SEQ ID NO. 114; and α8: SEQ ID NO. 97, and both SEQ ID NO. 98 and SEQ ID NO. 99; and α1: SEQ ID NO. 5 and SEQ ID NO. 6; and α3 SEQ ID NO. 33 and both SEQ ID NO. 34 and SEQ ID NO. 35; and α2 SEQ ID NO. 18, and both SEQ ID NO. 19 and SEQ ID NO. 20; and α4: SEQ ID NO. 40 or SEQ ID NO. 41, and SEQ ID NO. 42 or SEQ ID NO. 43; and all: SEQ ID NO. 139, and SEQ ID NO. 140.

Or, in this regard, the invention also contemplates a composition of primers comprising for E7: α5: both SEQ ID NO. 49, SEQ ID NO. 50 and both SEQ ID NO. 51, SEQ ID NO. 52; and α6: SEQ ID NO. 63 or SEQ ID NO. 64 or SEQ ID NO. 65 SEQ ID NO. 66 or both SEQ ID NO. 67 and SEQ ID NO. 68, and both SEQ ID NO. 69 and SEQ ID NO. 70; and α7: SEQ ID NO. 82 or both SEQ ID NO. 83, SEQ ID NO. 84, and both SEQ ID NO. 85, SEQ ID NO. 86; and α10: all three SEQ ID NO. 122, SEQ ID NO. 123 and SEQ ID NO. 124, and all three SEQ ID NO. 125, SEQ ID NO. 126 and SEQ ID NO. 127; and α9: all three SEQ ID NO. 105, SEQ ID NO. 106 and SEQ ID NO. 107, and all three SEQ ID NO. 108, SEQ ID NO. 109 and 110; and α8: SEQ ID NO. 94, and both SEQ ID NO. 95 and SEQ ID NO. 96; and α1: SEQ ID NO. 3 and SEQ ID NO. 4; and α3: both SEQ ID NO. 28 and SEQ ID NO. 29, and all three SEQ ID NO. 30, SEQ ID NO. 31, SEQ ID NO. 32; and α2: all three SEQ ID NO. 12, SEQ ID NO. 13 and SEQ ID NO. 14, and all three SEQ ID NO. 15, SEQ ID NO. 16 and SEQ ID NO. 17; and α4: SEQ ID NO. 38, and SEQ ID NO. 39; and all SEQ ID NO. 137, and SEQ ID NO. 138, And comprising for L1 α5: SEQ ID NO. 53 or both SEQ ID NO. 54 and SEQ ID NO. 55, and both SEQ ID NO. 56 and SEQ ID NO. 57; and α6: SEQ ID NO. 71 and SEQ ID NO. 72; and α7: both SEQ ID NO. 87 and SEQ ID NO. 88, and both SEQ ID NO. 89 and SEQ ID NO. 90; and α10: both SEQ ID NO. 128, SEQ ID NO. 129 and SEQ ID NO. 130 or all four SEQ ID NO. 131, SEQ ID NO. 132, SEQ ID NO. 133, SEQ ID NO. 134; and α9: both SEQ ID NO. 111 and SEQ ID NO. 112, and both SEQ ID NO. 113 and SEQ ID NO. 114; and α8: SEQ ID NO. 97, and both SEQ ID NO. 98 and SEQ ID NO. 99; and α1: SEQ ID NO. 5 and SEQ ID NO. 6; and α3 SEQ ID NO. 33 and both SEQ ID NO. 34 and SEQ ID NO. 35; and α2 SEQ ID NO. 18, and both SEQ ID NO. 19 and SEQ ID NO. 20; and α4: SEQ ID NO. 40 or SEQ ID NO. 41, and SEQ ID NO. 42 or SEQ ID NO. 43; and all: SEQ ID NO. 139, and SEQ ID NO. 140.

In a ninth specific embodiment, the above defined invention is practiced to include at least the group consisting of papillomaviruses α6 comprising HPV 30, HPV 53, HPV 56 and HPV 66, papillomaviruses α7 comprising HPV 68, HPV 39, HPV 70, HPV 85, HPV 59, HPV 45, HPV 18, HPV 97, papillomaviruses α10 comprising HPV 16, HPV 35, HPV 31, HPV 52, HPV 67, HPV 33, HPV 58, papillomaviruses α5 comprising HPV 26, HPV, 69, HPV 51, HPV 82, papillomaviruses α9 comprising HPV 6, HPV 11, HPV 13, HPV 1, HPV 74, HPV 44, papillomaviruses α8 comprising HPV 91, HPV 43, HPV 7, HPV 40, papillomaviruses α1 comprising HPV 42, HPV 32, papillomavirus α3 comprising HPV 114, HPV 84, HPV 86, HPV87, HPV 102, HPV83, HPV89, HPV 61, HPV 72, HPV 62, papillomavirus α2 comprising HPV 117, HPV 10, HPV 94, HPV 28, HPV125, HPV 3, HPV 78, HPV 160, HPV 29, HPV 77, papillomaviruses α4 comprising HPV 2, HPV 27, HPV 57, papillomaviruses α11 comprising HPV 73, HPV 34 and papillomaviruses α13 comprising HPV 54.

In this regard, the invention also contemplates a composition of primers comprising for E6: α5: both SEQ ID NO. 44 and SEQ ID NO. 45, and all three SEQ ID NO. 46, SEQ ID NO. 47 and SEQ ID NO. 48 and; α6: SEQ ID NO. 58 or both SEQ ID NO. 59 and SEQ ID NO. 60, and both SEQ ID NO. 61 and SEQ ID NO. 62 and; α7: all three SEQ ID NO. 73, SEQ ID NO. 75 and SEQ ID NO. 76 or all three EQ ID NO. 74, SEQ ID NO. 75 and SEQ ID NO. 76, and all five SEQ ID NO. 77, SEQ ID NO. 78, SEQ ID NO. 79, SEQ ID NO. 80 and SEQ ID NO. 81 and; α10: all three SEQ ID NO. 115, SEQ ID NO. 116, SEQ ID NO. 117 and all four SEQ ID NO. 118, SEQ ID NO. 119, SEQ ID NO. 120, SEQ ID NO. 121; and α9: both SEQ ID NO. 100 and SEQ ID NO. 101 and all three SEQ ID NO. 102, SEQ ID NO. 103 and SEQ ID NO. 104; and α8: SEQ ID NO. 91, and both SEQ ID NO. 92 and SEQ ID NO. 93; and α1: SEQ ID NO. 1 and SEQ ID NO. 2; and α3: all three SEQ ID NO. 21, SEQ ID NO. 22 and SEQ ID NO. 23, and all four SEQ ID NO. 24, SEQ ID NO. 25, SEQ ID NO. 26 and SEQ ID NO. 27; and α2 and both SEQ ID NO. 7 and SEQ ID NO. 8, and all three SEQ ID NO. 9, SEQ ID NO. 10 and SEQ ID NO. 11; and α4: SEQ ID NO. 36, and SEQ ID NO. 37; and all: SEQ ID NO. 135, and SEQ ID NO. 136; and α13 SEQ ID NO. 141, and SEQ ID NO. 142, And comprising for L1 α5: SEQ ID NO. 53 or both SEQ ID NO. 54 and SEQ ID NO. 55, and both SEQ ID NO. 56 and SEQ ID NO. 57; and α6: SEQ ID NO. 71 and SEQ ID NO. 72; and α7: both SEQ ID NO. 87 and SEQ ID NO. 88, and both SEQ ID NO. 89 and SEQ ID NO. 90; and α10: both SEQ ID NO. 128, SEQ ID NO. 129 and SEQ ID NO. 130 or all four SEQ ID NO. 131, SEQ ID NO. 132, SEQ ID NO. 133, SEQ ID NO. 134; and α9: both SEQ ID NO. 111 and SEQ ID NO. 112, and both SEQ ID NO. 113 and SEQ ID NO. 114; and α8: SEQ ID NO. 97, and both SEQ ID NO. 98 and SEQ ID NO. 99; and α1: SEQ ID NO. 5 and SEQ ID NO. 6; and α3 SEQ ID NO. 33 and both SEQ ID NO. 34 and SEQ ID NO. 35; and α2 SEQ ID NO. 18, and both SEQ ID NO. 19 and SEQ ID NO. 20; and α4: SEQ ID NO. 40 or SEQ ID NO. 41, and SEQ ID NO. 42 or SEQ ID NO. 43; and all: SEQ ID NO. 139, and SEQ ID NO. 140; and α13 SEQ ID NO. 145, and SEQ ID NO. 146.

Or, in this regard, the invention also contemplates a composition of primers comprising for E7: α5: both SEQ ID NO. 49, SEQ ID NO. 50 and both SEQ ID NO. 51, SEQ ID NO. 52; and α6: SEQ ID NO. 63 or SEQ ID NO. 64 or SEQ ID NO. 65 SEQ ID NO. 66 or both SEQ ID NO. 67 and SEQ ID NO. 68, and both SEQ ID NO. 69 and SEQ ID NO. 70; and α7: SEQ ID NO. 82 or both SEQ ID NO. 83, SEQ ID NO. 84, and both SEQ ID NO. 85 SEQ ID NO. 86; and α10: all three SEQ ID NO. 122, SEQ ID NO. 123 and SEQ ID NO. 124, and all three SEQ ID NO. 125, SEQ ID NO. 126 and SEQ ID NO. 127; and α9: all three SEQ ID NO. 105, SEQ ID NO. 106 and SEQ ID NO. 107, and all three SEQ ID NO. 108, SEQ ID NO. 109 and 110; and α8: SEQ ID NO. 94, and both SEQ ID NO. 95 and SEQ ID NO. 96; and α1: SEQ ID NO. 3 and SEQ ID NO. 4; and α3: both SEQ ID NO. 28 and SEQ ID NO. 29, and all three SEQ ID NO. 30, SEQ ID NO. 31, SEQ ID NO. 32; and α2: all three SEQ ID NO. 12, SEQ ID NO. 13 and SEQ ID NO. 14, and all three SEQ ID NO. 15, SEQ ID NO. 16 and SEQ ID NO. 17; and α4: SEQ ID NO. 38, and SEQ ID NO. 39; and all SEQ ID NO. 137, and SEQ ID NO. 138; and α13: SEQ ID NO. 143, and SEQ ID NO. 144, And comprising for L1 α5: SEQ ID NO. 53 or both SEQ ID NO. 54 and SEQ ID NO. 55, and both SEQ ID NO. 56 and SEQ ID NO. 57; and α6: SEQ ID NO. 71 and SEQ ID NO. 72; and α7: both SEQ ID NO. 87 and SEQ ID NO. 88, and both SEQ ID NO. 89 and SEQ ID NO. 90; and α10: both SEQ ID NO. 128, SEQ ID NO. 129 and SEQ ID NO. 130 or all four SEQ ID NO. 131, SEQ ID NO. 132, SEQ ID NO. 133, SEQ ID NO. 134; and α9: both SEQ ID NO. 111 and SEQ ID NO. 112, and both SEQ ID NO. 113 and SEQ ID NO. 114; and α8: SEQ ID NO. 97, and both SEQ ID NO. 98 and SEQ ID NO. 99; and α1: SEQ ID NO. 5 and SEQ ID NO. 6; and α3 SEQ ID NO. 33 and both SEQ ID NO. 34 and SEQ ID NO. 35; and α2 SEQ ID NO. 18, and both SEQ ID NO. 19 and SEQ ID NO. 20; and α4: SEQ ID NO. 40 or SEQ ID NO. 41, and SEQ ID NO. 42 or SEQ ID NO. 43; and all: SEQ ID NO. 139, and SEQ ID NO. 140; and α13 SEQ ID NO. 145, and SEQ ID NO. 146.

In a tenth specific embodiment, the above defined invention is practiced to include at least the group consisting of papillomaviruses α6 comprising HPV 30, HPV 53, HPV 56 and HPV 66, papillomaviruses α7 comprising HPV 68, HPV 39, HPV 70, HPV 85, HPV 59, HPV 45, HPV 18, HPV 97, papillomaviruses α10 comprising HPV 16, HPV 35, HPV 31, HPV 52, HPV 67, HPV 33, HPV 58, papillomaviruses α5 comprising HPV 26, HPV, 69, HPV 51, HPV 82, papillomaviruses α9 comprising HPV 6, HPV 11, HPV 13, HPV 1, HPV 74, HPV 44, papillomaviruses α8 comprising HPV 91, HPV 43, HPV 7, HPV 40, papillomaviruses α1 comprising HPV 42, HPV 32, papillomavirus α3 comprising HPV 114, HPV 84, HPV 86, HPV87, HPV 102, HPV83, HPV89, HPV 61, HPV 72, HPV 62, papillomavirus α2 comprising HPV 117, HPV 10, HPV 94, HPV 28, HPV125, HPV 3, HPV 78, HPV 160, HPV 29, HPV 77, papillomaviruses α4 comprising HPV 2, HPV 27, HPV 57, papillomaviruses α11 comprising HPV 73, HPV 34, papillomaviruses α13 comprising HPV 54 and papillomaviruses α14 comprising HPV 106, HPV 90, HPV 71.

In this regard, the invention also contemplates a composition of primers comprising for E6: α5: both SEQ ID NO. 44 and SEQ ID NO. 45, and all three SEQ ID NO. 46, SEQ ID NO. 47 and SEQ ID NO. 48 and; α6: SEQ ID NO. 58 or both SEQ ID NO. 59 and SEQ ID NO. 60, and both SEQ ID NO. 61 and SEQ ID NO. 62 and; α7: all three SEQ ID NO. 73, SEQ ID NO. 75 and SEQ ID NO. 76 or all three EQ ID NO. 74, SEQ ID NO. 75 and SEQ ID NO. 76, and all five SEQ ID NO. 77, SEQ ID NO. 78, SEQ ID NO. 79, SEQ ID NO. 80 and SEQ ID NO. 81 and; α10: all three SEQ ID NO. 115, SEQ ID NO. 116, SEQ ID NO. 117 and all four SEQ ID NO. 118, SEQ ID NO. 119, SEQ ID NO. 120, SEQ ID NO. 121; and α9: both SEQ ID NO. 100 and SEQ ID NO. 101 and all three SEQ ID NO. 102, SEQ ID NO. 103 and SEQ ID NO. 104; and α8: SEQ ID NO. 91, and both SEQ ID NO. 92 and SEQ ID NO. 93; and α1: SEQ ID NO. 1 and SEQ ID NO. 2; and α3: all three SEQ ID NO. 21, SEQ ID NO. 22 and SEQ ID NO. 23, and all four SEQ ID NO. 24, SEQ ID NO. 25, SEQ ID NO. 26 and SEQ ID NO. 27; and α2 and both SEQ ID NO. 7 and SEQ ID NO. 8, and all three SEQ ID NO. 9, SEQ ID NO. 10 and SEQ ID NO. 11; and α4: SEQ ID NO. 36, and SEQ ID NO. 37; and all: SEQ ID NO. 135, and SEQ ID NO. 136; and α13 SEQ ID NO. 141, and SEQ ID NO. 142; and α14: SEQ ID NO. 147, and SEQ ID NO. 148, And comprising for L1, α5: SEQ ID NO. 53 or both SEQ ID NO. 54 and SEQ ID NO. 55, and both SEQ ID NO. 56 and SEQ ID NO. 57; and α6: SEQ ID NO. 71 and SEQ ID NO. 72; and α7: both SEQ ID NO. 87 and SEQ ID NO. 88, and both SEQ ID NO. 89 and SEQ ID NO. 90; and α10: both SEQ ID NO. 128, SEQ ID NO. 129 and SEQ ID NO. 130 or all four SEQ ID NO. 131, SEQ ID NO. 132, SEQ ID NO. 133, SEQ ID NO. 134; and α9: both SEQ ID NO. 111 and SEQ ID NO. 112, and both SEQ ID NO. 113 and SEQ ID NO. 114; and α8: SEQ ID NO. 97, and both SEQ ID NO. 98 and SEQ ID NO. 99; and α1: SEQ ID NO. 5 and SEQ ID NO. 6; and α3 SEQ ID NO. 33 and both SEQ ID NO. 34 and SEQ ID NO. 35; and α2 SEQ ID NO. 18, and both SEQ ID NO. 19 and SEQ ID NO. 20; and α4: SEQ ID NO. 40 or SEQ ID NO. 41, and SEQ ID NO. 42 or SEQ ID NO. 43; and all: SEQ ID NO. 139, and SEQ ID NO. 140; and α13 SEQ ID NO. 145, and SEQ ID NO. 146; and α14: SEQ ID NO. 151 and SEQ ID NO. 152.

Or, in this regard, the invention also contemplates a composition of primers comprising for E7: α5: both SEQ ID NO. 49, SEQ ID NO. 50 and both SEQ ID NO. 51, SEQ ID NO. 52; and α6: SEQ ID NO. 63 or SEQ ID NO. 64 or SEQ ID NO. 65 SEQ ID NO. 66 or both SEQ ID NO. 67 and SEQ ID NO. 68, and both SEQ ID NO. 69 and SEQ ID NO. 70; and α7: SEQ ID NO. 82 or both SEQ ID NO. 83, SEQ ID NO. 84, and both SEQ ID NO. 85, SEQ ID NO. 86; and α10: all three SEQ ID NO. 122, SEQ ID NO. 123 and SEQ ID NO. 124, and all three SEQ ID NO. 125, SEQ ID NO. 126 and SEQ ID NO. 127; and α9: all three SEQ ID NO. 105, SEQ ID NO. 106 and SEQ ID NO. 107, and all three SEQ ID NO. 108, SEQ ID NO. 109 and 110; and α8: SEQ ID NO. 94, and both SEQ ID NO. 95 and SEQ ID NO. 96; and α1: SEQ ID NO. 3 and SEQ ID NO. 4; and α3: both SEQ ID NO. 28 and SEQ ID NO. 29, and all three SEQ ID NO. 30, SEQ ID NO. 31, SEQ ID NO. 32; and α2: all three SEQ ID NO. 12, SEQ ID NO. 13 and SEQ ID NO. 14, and all three SEQ ID NO. 15, SEQ ID NO. 16 and SEQ ID NO. 17; and α4: SEQ ID NO. 38, and SEQ ID NO. 39; and all SEQ ID NO. 137, and SEQ ID NO. 138; and α13: SEQ ID NO. 143, and SEQ ID NO. 144; and α14: SEQ ID NO. 149, and SEQ ID NO. 150

And comprising for L1 α5: SEQ ID NO. 53 or both SEQ ID NO. 54 and SEQ ID NO. 55, and both SEQ ID NO. 56 and SEQ ID NO. 57; and α6: SEQ ID NO. 71 and SEQ ID NO. 72; and α7: both SEQ ID NO. 87 and SEQ ID NO. 88, and both SEQ ID NO. 89 and SEQ ID NO. 90; and α10: both SEQ ID NO. 128, SEQ ID NO. 129 and SEQ ID NO. 130 or all four SEQ ID NO. 131, SEQ ID NO. 132, SEQ ID NO. 133, SEQ ID NO. 134; and α9: both SEQ ID NO. 111 and SEQ ID NO. 112, and both SEQ ID NO. 113 and SEQ ID NO. 114; and α8: SEQ ID NO. 97, and both SEQ ID NO. 98 and SEQ ID NO. 99; and α1: SEQ ID NO. 5 and SEQ ID NO. 6; and α3 SEQ ID NO. 33 and both SEQ ID NO. 34 and SEQ ID NO. 35; and α2 SEQ ID NO. 18, and both SEQ ID NO. 19 and SEQ ID NO. 20; and α4: SEQ ID NO. 40 or SEQ ID NO. 41, and SEQ ID NO. 42 or SEQ ID NO. 43; and all: SEQ ID NO. 139, and SEQ ID NO. 140; and α13 SEQ ID NO. 145, and SEQ ID NO. 146; and α14: SEQ ID NO. 151 and SEQ ID NO. 152.

In another embodiment, the present invention relates to the use of composition of primers describe above for diagnosis or prognosis of risk to develop HPV induced cancer in a human subject.

Said primers can further comprise at least one of:
a functional group for covalent coupling at the 5' or 3' end, such as a terminal group comprising a thiol, amine or carboxyl group,
a spacer molecule or sequence at the 5' or 3' end,
additional sequences as index or tag sequences to perform pre or post additional and general amplification steps not depending on the target sequences to be quantified.

In another embodiment, the present invention relates to a composition of primers comprising at least one primer selected from SEQ ID No 153 to 158. Said composition can comprise 1, 2, 3, 4, 5 or the 6 primers selected from SEQ ID No 153 to 158.

In another embodiment, the present invention relates to a kit for diagnosis or prognosis risk to develop HPV induced cancer comprising:
a) a composition of primers,
b) reagents to detect amplification products.

In a specific embodiment, the present invention relates to a kit for diagnosis or prognosis risk to develop HPV induced cancer comprising:
a) primers or probes for detecting at least a first marker selected from E6 mRNAs of group alpha HPVs, E7 mRNAs of group alpha HPVs, or both,
b) primers or probes for detecting at least a second marker selected from L1 mRNAs of group alpha HPVs, L2 mRNAs of group alpha HPVs, or both, wherein said E6, E7, L1 and L2 mRNAs have corresponding intragenetic sequences,
c) and optionally, primers or probes for detecting at least one host cellular marker indicative of neoplasia or cancer.

In various embodiments, the primers can be selected from primers comprising or consisting of the nucleic acid sequence of any of SEQ ID NOs: 1-152. Preferably the primers comprise or consist of at least 15, 16, 17, 18, 19, 20, 21, 22, 23, 24, 25, 26, 27, 28, 29, or 30 consecutive nucleotides of any of SEQ ID NOs:1-152. The kit can contain any of the compositions of primers described herein.

The kit can further contain at least 1, 2, 3, 4, or more controls for the determination of R. The controls can contain a known ratio of E6 and/or E7 to L1 and/or L2. Preferably, the controls contain a known ratio of E6 and E7 to L1 and L2.

In various embodiments, the kit contains at least 1 or at least 2 controls indicating a low risk or non-persistent HPV infection. In various embodiments, the kit contains at least 1 or at least 2 controls indicative of a high risk infection or associated with higher risk of developing genital neoplasia and cancer. In preferred embodiments, the kit contains at least 1 or at least 2 controls indicating a low risk or non-persistent HPV infection and at least 1 or at least 2 controls indicating a high risk infection or associated with higher risk of developing genital neoplasia and cancer.

In various embodiments, the invention encompasses a method for assessing a human papilloma virus (HPV) infected patient. In one embodiment, the method comprises generating cDNA from a patient sample comprising RNA and sequencing the cDNA to generate reads of sequence of the cDNA.

In various embodiments, the number of reads is at least $10^6$, $5 \times 10^6$, $10^7$, $2 \times 10^7$, or $5 \times 10^7$ reads.

In one embodiment, the cDNA is generated using random primers. In one embodiment, the cDNA is generated using HPV-specific primers. In preferred embodiments, at least one of the primers comprises or consists of the nucleic acid sequences in Table 3.

In various embodiments, the method comprises discriminating HPV sequence reads on the basis of HPV species including any of the specific species referenced herein. In various embodiments, the method comprises discriminating HPV sequence reads on the basis of HPV gene transcript, including E1, E2, E4, E5, E6, E7, E8, L1, and L2 transcripts. The transcripts can be spliced transcripts.

In various embodiments, the cDNA or the sequencing can be performed with HPV-specific or random primers, preferably HPV-specific primers.

In various embodiments, the primers comprise or consist of any of the nucleic acid sequences of SEQ ID NOs: 1-158. In various embodiments, the cDNA is generated with HPV-specific primers and the sequencing performed randomly or specifically for HPV sequences.

In various embodiments, the cDNA is generated with random primers and the sequencing performed randomly or specifically for HPV sequences.

According to a preferred embodiment, the method comprises:
a) enrichment of the viral RNAs, preferably HPV16 RNAs, in a sample,
b) random reverse transcription reaction, advantageously performed with random hexamers,
c) amplification of the cDNA produced in step a), advantageously performed by multiplex PCR with HPV-specific primers (to generate a DNA sequence library),
d) high throughput sequencing of the DNA library produced in step c) and generating reads of said cDNA,
e) determining the number of reads matching said viruses based on species discrimination and determining the most prevalent high risk species present in the sample relative to other species,
f) determining within said most prevalent high risk species the relative number of reads matching at least one oncogenic gene compared to at least one non oncogenic genes, preferably oncogenic genes compared to non oncogenic genes,
g) computing ratios within said high risk species of reads matching at least one oncogenic gene versus at least one versus corresponding at least one interspecies structural or regulatory gene, preferably oncogenic genes versus corresponding interspecies structural or regulatory genes,
h) determining risk of developing oncogenic virus induced cancer in patients in which said ratio tend towards infinity.

In advantageous embodiments, the HPV-specific primers comprise at least one of, preferably all, the following groups of pairs of primers:
the HPV16-specific primers comprising or consisting of the primers of SEQ ID NOs: 219-258 for HPV16 genomic and unspliced transcripts, SEQ ID NOs: 259-352 for HPV16 spliced transcripts and SEQ ID NOs: 353-376 for HPV16-human fusion transcripts (including the pairs of primers of SEQ ID NO: 219-220; 221-222; 223-224; 225-226; 227-228; 229-230; 231-232; 233-234; 235-236; 237-238; 239-240; 241-242; 243-244; 245-246; 247-248; 249-250; 251-252; 253-254; 255-256; 257-258; 259-260; 261-262; 263-264; 265-266; 267-268; 269-270; 271-272; 273-274; 275-276; 277-278; 279-280; 281-282; 283-284; 285-286; 287-288; 289-290; 291-292; 293-294; 295-296; 297-298; 299-300; 301-302; 303-304; 305-306; 307-308; 309-310; 311-312; 313-314; 315-316; 317-318; 319-320; 321-322; 323-324; 325-326; 327-328; 329-330; 331-332; 333-334; 335-336; 337-338; 339-340; 341-342; 343-344; 345-346; 347-348; 349-350; 351-352; 353-354; 355-356; 357-358; 359-360; 361-362; 363-364; 365-366; 367-368; 369-370; 371-372; 373-374; 375-376) or 377-470 (including the pairs of primers of SEQ ID NO. 377-378; 379-380; 381-382; 383-384; 385-386; 387-388; 389-390; 391-392; 393-394; 395-396; 397-398; 399-400; 401-402; 403-404; 405-406; 407-408; 409-410; 411-412; 413-414; 415-416; 417-418; 419-420; 421-422; 423-424; 425-426; 427-428; 429-430; 431-432; 433-434; 435-436; 437-438; 439-440; 441-442; 443-444; 445-446; 447-448; 449-450; 451-452; 453-454; 455-456; 457-458; 459-460; 461-462; 463-464; 465-466; 467-468 and; 469-470); and/or, the HPV18-specific primers comprising or consisting of the primers of SEQ ID NO. 471-574 (including the pairs of primers of SEQ ID NO.: 471-472; 473-474; 475-476; 477-478; 479-480; 481-482; 483-484; 485-486; 487-488; 489-490; 491-492; 493-494; 495-496; 497-498; 499-500; 501-502; 503-504; 505-506; 507-508; 509-510; 511-512; 513-514; 515-516; 517-518; 519-520; 521-522; 523-524; 525-526; 527-528; 529-530; 531-532; 533-534; 535-536; 537-538; 539-540; 541-542; 543-544; 545-546; 547-548; 549-550; 551-552; 553-554; 555-556; 557-558; 559-560; 561-562; 563-564; 565-566; 567-568; 569-570; 571-572; 573-574); and/or, the HPV31-specific primers comprising or consisting of the primers of SEQ ID NO. 575-668 (including the pairs of primers of SEQ ID NO.: 575-576; 577-578; 579-580; 581-582; 583-584; 585-586; 587-588; 589-590; 591-592; 593-594; 595-596; 597-598; 599-600; 601-602; 603-604; 605-606; 607-608; 609-610; 611-612; 613-614; 615-616; 617-618; 619-620; 621-622; 623-624; 625-626; 627-628; 629-630; 631-632; 633-634; 635-636; 637-638; 639-640; 641-642; 643-644; 645-646; 647-648; 649-650; 651-652; 653-654; 655-656; 657-658; 659-660; 661-662; 663-664; 665-666; 667-668); and/or, the HPV33-specific primers comprising or consisting of SEQ ID NO. 669-756 (including the pairs of primers of SEQ ID NO.: 669-670; 671-672; 673-674; 675-676; 677-678; 679-680; 681-682; 683-684; 685-686; 687-688; 689-690; 691-692; 693-694; 695-696; 697-698; 699-700; 701-702; 703-704; 705-706; 707-708; 709-710; 711-712; 713-714; 715-716; 717-718; 719-720; 721-722; 723-724; 725-726; 727-728; 729-730; 731-732; 733-734; 735-736; 737-738; 739-740; 741-742; 743-744; 745-746; 747-748; 749-750; 751-752; 753-754; 755-756); and/or, the HPV35-specific primers comprising or consisting of the primers of SEQ ID NO. 757-848 (including the pairs of primers of SEQ ID NO.: 757-758; 759-760; 761-762; 763-764; 765-766; 767-768; 769-770; 771-772; 773-774; 775-776; 777-778; 779-780; 781-782; 783-784; 785-786; 787-788; 789-790; 791-792; 793-794; 795-796; 797-798; 799-800; 801-802; 803-804; 805-806; 807-808; 809-810; 811-812; 813-814; 815-816; 817-818; 819-820; 821-822; 823-824; 825-826; 827-828; 829-830; 831-832; 833-834; 835-836; 837-838; 839-840; 841-842; 843-844; 845-846; 847-848); and/or, the HPV39-specific primers comprising or consisting of the primers of SEQ ID NO. 849-928 (including the pairs of primers of SEQ ID NO.: 849-850; 851-852; 853-854; 855-856; 857-858; 859-860; 861-862; 863-864; 865-866; 867-868; 869-870; 871-872; 873-874;

875-876; 877-878; 879-880; 881-882; 883-884; 885-886; 887-888; 889-890; 891-892; 893-894; 895-896; 897-898; 899-900; 901-902; 903-904; 905-906; 907-908; 909-910; 911-912; 913-914; 915-916; 917-918; 919-920; 921-922; 923-924; 925-926; 927-928); and/or, the HPV45-specific primers comprising or consisting of the primers of SEQ ID NO. 929-1020 (including the pairs of primers of SEQ ID NO.: 929-930; 931-932; 933-934; 935-936; 937-938; 939-940; 941-942; 943-944; 945-946; 947-948; 949-950; 951-952; 953-954; 955-956; 957-958; 959-960; 961-962; 963-964; 965-966; 967-968; 969-970; 971-972; 973-974; 975-976; 977-978; 979-980; 981-982; 983-984; 985-986; 987-988; 989-990; 991-992; 993-994; 995-996; 997-998; 999-1000; 1001-1002; 1003-1004; 1005-1006; 1007-1008; 1009-1010; 1011-1012; 1013-1014; 1015-1016; 1017-1018; 1019-1020); and/or, the HPV51-specific primers comprising or consisting of the primers of SEQ ID NO. 1021-1102 (including the pairs of primers of SEQ ID NO.: 1021-1022; 1023-1024; 1025-1026; 1027-1028; 1029-1030; 1031-1032; 1033-1034; 1035-1036; 1037-1038; 1039-1040; 1041-1042; 1043-1044; 1045-1046; 1047-1048; 1049-1050; 1051-1052; 1053-1054; 1055-1056; 1057-1058; 1059-1060; 1061-1062; 1063-1064; 1065-1066; 1067-1068; 1069-1070; 1071-1072; 1073-1074; 1075-1076; 1077-1078; 1079-1080; 1081-1082; 1083-1084; 1085-1086; 1087-1088; 1089-1090; 1091-1092; 1093-1094; 1095-1096; 1097-1098; 1099-1100; 1101-1102); and/or, the HPV52-specific primers comprising or consisting of the primers of SEQ ID NO. 1103-1200 (including the pairs of primers of SEQ ID NO.: 1103-1104; 1105-1106; 1107-1108; 1109-1110; 1111-1112; 1113-1114; 1115-1116; 1117-1118; 1119-1120; 1121-1122; 1123-1124; 1125-1126; 1127-1128; 1129-1130; 1131-1132; 1133-1134; 1135-1136; 1137-1138; 1139-1140; 1141-1142; 1143-1144; 1145-1146; 1147-1148; 1149-1150; 1151-1152; 1153-1154; 1155-1156; 1157-1158; 1159-1160; 1161-1162; 1163-1164; 1165-1166; 1167-1168; 1169-1170; 1171-1172; 1173-1174; 1175-1176; 1177-1178; 1179-1180; 1181-1182; 1183-1184; 1185-1186; 1187-1188; 1189-1190; 1191-1192; 1193-1194; 1195-1196; 1197-1198; 1199-1200); and/or, the HPV56-specific primers comprising or consisting of the primers of SEQ ID NO. 1201-1296 (including the pairs of primers of SEQ ID NO.: 1201-1202; 1203-1204; 1205-1206; 1207-1208; 1209-1210; 1211-1212; 1213-1214; 1215-1216; 1217-1218; 1219-1220; 1221-1222; 1223-1224; 1225-1226; 1227-1228; 1229-1230; 1231-1232; 1233-1234; 1235-1236; 1237-1238; 1239-1240; 1241-1242; 1243-1244; 1245-1246; 1247-1248; 1249-1250; 1251-1252; 1253-1254; 1255-1256; 1257-1258; 1259-1260; 1261-1262; 1263-1264; 1265-1266; 1267-1268; 1269-1270; 1271-1272; 1273-1274; 1275-1276; 1277-1278; 1279-1280; 1281-1282; 1283-1284; 1285-1286; 1287-1288; 1289-1290; 1291-1292; 1293-1294; 1295-1296); and/or, the HPV58-specific primers comprising or consisting of the primers of SEQ ID NO. 1297-1382 (including the pairs of primers of SEQ ID NO.: 1297-1298; 1299-1300; 1301-1302; 1303-1304; 1305-1306; 1307-1308; 1309-1310; 1311-1312; 1313-1314; 1315-1316; 1317-1318; 1319-1320; 1321-1322; 1323-1324; 1325-1326; 1327-1328; 1329-1330; 1331-1332; 1333-1334; 1335-1336; 1337-1338; 1339-1340; 1341-1342; 1343-1344; 1345-1346; 1347-1348; 1349-1350; 1351-1352; 1353-1354; 1355-1356; 1357-1358; 1359-1360; 1361-1362; 1363-1364; 1365-1366; 1367-1368; 1369-1370; 1371-1372; 1373-1374; 1375-1376; 1377-1378; 1379-1380; 1381-1382); and/or, the HPV59-specific primers comprising or consisting of the primers of SEQ ID NO. 1383-1470 (including the pairs of primers of SEQ ID NO.: 1383-1384; 1385-1386; 1387-1388; 1389-1390; 1391-1392; 1393-1394; 1395-1396; 1397-1398; 1399-1400; 1401-1402; 1403-1404; 1405-1406; 1407-1408; 1409-1410; 1411-1412; 1413-1414; 1415-1416; 1417-1418; 1419-1420; 1421-1422; 1423-1424; 1425-1426; 1427-1428; 1429-1430; 1431-1432; 1433-1434; 1435-1436; 1437-1438; 1439-1440; 1441-1442; 1443-1444; 1445-1446; 1447-1448; 1449-1450; 1451-1452; 1453-1454; 1455-1456; 1457-1458; 1459-1460; 1461-1462; 1463-1464; 1465-1466; 1467-1468; 1469-1470); and/or, the HPV66-specific primers comprising or consisting of the primers of SEQ ID NO. 1471-1560 (including the pairs of primers of SEQ ID NO.: 1471-1472; 1473-1474; 1475-1476; 1477-1478; 1479-1480; 1481-1482; 1483-1484; 1485-1486; 1487-1488; 1489-1490; 1491-1492; 1493-1494; 1495-1496; 1497-1498; 1499-1500; 1501-1502; 1503-1504; 1505-1506; 1507-1508; 1509-1510; 1511-1512; 1513-1514; 1515-1516; 1517-1518; 1519-1520; 1521-1522; 1523-1524; 1525-1526; 1527-1528; 1529-1530; 1531-1532; 1533-1534; 1535-1536; 1537-1538; 1539-1540; 1541-1542; 1543-1544; 1545-1546; 1547-1548; 1549-1550; 1551-1552; 1553-1554; 1555-1556; 1557-1558; 1559-1560; and/or, the HPV68-specific primers comprising or consisting of the primers of SEQ ID NO. 1561-1642 (including the pairs of primers of SEQ ID NO.: 1561-1562; 1563-1564; 1565-1566; 1567-1568; 1569-1570; 1571-1572; 1573-1574; 1575-1576; 1577-1578; 1579-1580; 1581-1582; 1583-1584; 1585-1586; 1587-1588; 1589-1590; 1591-1592; 1593-1594; 1595-1596; 1597-1598; 1599-1600; 1601-1602; 1603-1604; 1605-1606; 1607-1608; 1609-1610; 1611-1612; 1613-1614; 1615-1616; 1617-1618; 1619-1620; 1621-1622; 1623-1624; 1625-1626; 1627-1628; 1629-1630; 1631-1632; 1633-1634; 1635-1636; 1637-1638; 1639-1640; 1641-1642); and/or, the HPV73-specific primers comprising or consisting of the primers of SEQ ID NO. 1643-1732 (including the pairs of primers of SEQ ID NO.: 1643-1644; 1645-1646; 1647-1648; 1649-1650; 1651-1652; 1653-1654; 1655-1656; 1657-1658; 1659-1660; 1661-1662; 1663-1664; 1665-1666; 1667-1668; 1669-1670; 1671-1672; 1673-1674; 1675-1676; 1677-1678; 1679-1680; 1681-1682; 1683-1684; 1685-1686; 1687-1688; 1689-1690; 1691-1692; 1693-1694; 1695-1696; 1697-1698; 1699-1700; 1701-1702; 1703-1704; 1705-1706; 1707-1708; 1709-1710; 1711-1712; 1713-1714; 1715-1716; 1717-1718; 1719-1720; 1721-1722; 1723-1724; 1725-1726; 1727-1728; 1729-1730; 1731-1732); and/or, the HPV82-specific primers comprising or consisting of the primers of SEQ ID NO. 1733-1816 (including the pairs of primers of SEQ ID NO.: 1733-1734; 1735-1736; 1737-1738; 1739-1740; 1741-1742; 1743-1744; 1745-1746; 1747-1748; 1749-1750; 1751-1752; 1753-1754; 1755-1756; 1757-1758; 1759-1760; 1761-1762; 1763-1764; 1765-1766; 1767-1768; 1769-1770; 1771-1772; 1773-1774; 1775-1776; 1777-1778; 1779-1780; 1781-1782; 1783-1784; 1785-1786; 1787-1788; 1789-1790; 1791-1792; 1793-1794; 1795-1796; 1797-1798; 1799-1800; 1801-1802; 1803-1804; 1805-1806; 1807-1808; 1809-1810; 1811-1812; 1813-1814; 1815-1816).

In other advantageous embodiments, the HPV-specific primers comprise at least one of, preferably all, the following groups of pairs of primers:

SD1-SA1 group consisting of the pairs of primers of SEQ ID NO: 397-398; 521-522; 609-610; 695-696; 819-820; 865-866; 947-948; 1067-1068; 1119-1120; 1267-1268; 1325-1326; 1507-1508; 1597-1598; 1655-1656; 1755-1756; and/or, SD1-SA2 group consisting of the pairs of primers of SEQ ID NO: 459-460; 633-634; 687-688; 1111-1112; 1235-1236; 1341-1342; 1503-1504; 1657-1658; 1797-1798; and/or, SD1-SA3 group consisting of the pairs of primers of SEQ ID NO: 381-382; 541-542; 599-600; 903-904; 941-942; 1047-1048; 1135-1136; 1287-1288; 1459-1460; 1473-1474; 1621-1622; 1717-1718; 1745-1746; and/or, SD1-SA4 group consisting of the pairs of primers of SEQ ID NO: 413-414; 551-552; 637-638; 713-714; 793-794; 857-858; 981-982; 1093-1094; 1179-1180; 1227-1228; 1319-1320; 1413-1414; 1509-1510; 1563-1564; 1709-1710; 1791-1792; and/or, SD1-SA5 group consisting of the pairs of primers of SEQ ID NO: 453-454; 549-550; 613-614; 747-748; 761-762; 949-950; 1163-1164; 1249-1250; 1329-1330; 1453-1454; 1501-1502; and/or, SD1-SA6 group consisting of the pairs of primers of SEQ ID NO: 431-432; 595-596; 719-720; 827-828; 1089-1090; 1137-1138; 1285-1286; 1353-1354; 1561-1562; 1719-1720; 1763-1764; and/or, SD1-SA7 group consisting of the pairs of primers of SEQ ID NO: 919-920; 1449-1450; and/or, SD1-SA8 group consisting of the pairs of primers of SEQ ID NO: 489-490; 963-964; 1519-1520; and/or, SD2-SA4 group consisting of the pairs of primers of SEQ ID NO: 387-388; 473-474; 615-616; 745-746; 815-816; 849-850; 933-934; 1091-1092; 1177-1178; 1209-1210; 1367-1368; 1437-1438; 1521-1522; 1603-1604; 1651-1652; 1779-1780; and/or, SD2-SA5 group consisting of the pairs of primers of SEQ ID NO: 455-456; 529-530; 629-630; 717-718; 777-778; 975-976; 1153-1154; 1273-1274; 1347-1348; 1451-1452; 1531-1532; and/or, SD2-SA6 group consisting of the pairs of primers of SEQ ID NO: 399-400; 645-646; 727-728; 811-812; 1079-1080; 1127-1128; 1253-1254; 1369-1370; 1615-1616; 1659-1660; 1781-1782; and/or, SD2-SA7 group consisting of the pairs of primers of SEQ ID NO: 531-532; 899-900; 943-944; 1411-1412; 1495-1496; and/or, SD2-SA9 group consisting of the pairs of primers of SEQ ID NO: 437-438; 505-506; 607-608; 739-740; 785-786; 887-888; 979-980; 1063-1064; 1185-1186; 1233-1234; 1297-1298; 1423-1424; 1491-1492; 1607-1608; 1693-1694; 1775-1776; and/or, SD2-SA10 group consisting of the pairs of primers of SEQ ID NO: 545-546; 831-832; 1149-1150; 1269-1270; 1427-1428; 1671-1672; and/or, SD3-SA4 group consisting of the pairs of primers of SEQ ID NO: 379-380; 483-484; 611-612; 721-722; 833-834; 911-912; 937-938; 1053-1054; 1139-1140; 1251-1252; 1335-1336; 1435-1436; 1487-1488; 1591-1592; 1715-1716; 1785-1786; and/or, SD3-SA5 group consisting of the pairs of primers of SEQ ID NO: 415-416; 493-494; 593-594; 733-734; 817-818; 993-994; 1145-1146; 1243-1244; 1337-1338; 1401-1402; 1483-1484; and/or, SD3-SA6 group consisting of the pairs of primers of SEQ ID NO: 435-436; 655-656; 673-674; 813-814; 1045-1046; 1173-1174; 1241-1242; 1303-1304; 1557-1558; 1627-1628; 1647-1648; 1773-1774; and/or, SD3-SA7 group consisting of the pairs of primers of SEQ ID NO: 855-856; 1387-1388; and/or, SD3-SA8 group consisting of the pairs of primers of SEQ ID NO: 511-512; 957-958; 1529-1530; and/or, SD5-SA9 group consisting of the pairs of primers of SEQ ID NO: 419-420; 527-528; 567-568; 587-588; 683-684; 775-776; 891-892; 999-1000; 1041-1042; 1113-1114; 1247-1248; 1371-1372; 1403-1404; 1511-1512; 1617-1618; 1677-1678; 1733-1734; and/or, SD5-SA10 group consisting of the pairs of primers of SEQ ID NO: 495-496; 837-838; 1183-1184; 1279-1280; 1433-1434; 1723-1724.

In other embodiments, the HPV-specific primers comprise one of the following groups of pairs of primers:

the group of pairs of primers of SEQ ID NO: 397-398; 521-522; 609-610; 695-696; 819-820; 865-866; 947-948; 1067-1068; 1119-1120; 1267-1268; 1325-1326; 1507-1508; 1597-1598; 1655-1656; 1755-1756; 459-460; 633-634; 687-688; 1111-1112; 1235-1236; 1341-1342; 1503-1504; 1657-1658; 1797-1798; 381-382; 541-542; 599-600; 903-904; 941-942; 1047-1048; 1135-1136; 1287-1288; 1459-1460; 1473-1474; 1621-1622; 1717-1718; 1745-1746; 413-414; 551-552; 637-638; 713-714; 793-794; 857-858; 981-982; 1093-1094; 1179-1180; 1227-1228; 1319-1320; 1413-1414; 1509-1510; 1563-1564; 1709-1710; 1791-1792; 453-454; 549-550; 613-614; 747-748; 761-762; 949-950; 1163-1164; 1249-1250; 1329-1330; 1453-1454; 1501-1502; 431-432; 595-596; 719-720; 827-828; 1089-1090; 1137-1138; 1285-1286; 1353-1354; 1561-1562; 1719-1720; 1763-1764; 919-920; 1449-1450; 489-490; 963-964; 1519-1520; 387-388; 473-474; 615-616; 745-746; 815-816; 849-850; 933-934; 1091-1092; 1177-1178; 1209-1210; 1367-1368; 1437-1438; 1521-1522; 1603-1604; 1651-1652; 1779-1780; 455-456; 529-530; 629-630; 717-718; 777-778; 975-976; 1153-1154; 1273-1274; 1347-1348; 1451-1452; 1531-1532; 399-400; 645-646; 727-728; 811-812; 1079-1080; 1127-1128; 1253-1254; 1369-1370; 1615-1616; 1659-1660; 1781-1782; 531-532; 899-900; 943-944; 1411-1412; 1495-1496; 437-438; 505-506; 607-608; 739-740; 785-786; 887-888; 979-980; 1063-1064; 1185-1186; 1233-1234; 1297-1298; 1423-1424; 1491-1492; 1607-1608; 1693-1694; 1775-1776; 545-546; 831-832; 1149-1150; 1269-1270; 1427-1428; 1671-1672; 379-380; 483-484; 611-612; 721-722; 833-834; 911-912; 937-938; 1053-1054; 1139-1140; 1251-1252; 1335-1336; 1435-1436; 1487-1488; 1591-1592; 1715-1716; 1785-1786; 415-416; 493-494; 593-594; 733-734; 817-818; 993-994; 1145-1146; 1243-1244; 1337-1338; 1401-1402; 1483-1484; 435-436; 655-656; 673-674; 813-814; 1045-1046; 1173-1174; 1241-1242; 1303-1304; 1557-1558; 1627-1628; 1647-1648; 1773-1774; 855-856; 1387-1388; 511-512; 957-958; 1529-1530; 477-478; 419-420; 527-528; 567-568; 587-588; 683-684; 775-776; 891-892; 999-1000; 1041-1042; 1113-1114; 1247-1248; 1371-1372; 1403-1404; 1511-1512; 1617-1618; 1677-1678; 1733-1734; 495-496; 837-838; 1183-1184; 1279-1280; 1433-1434; 1723-1724; 1011-1012; 557-558; or, the group of pairs of primers of SEQ ID NO: 229-230; 233-234; 235-236; 245-246; 247-248; 249-250; 251-252; 255-256; 257-258; 265-266; 273-274; 275-276; 277-278; 279-280; 281-282; 289-290; 291-292; 295-

296; 297-298; 299-300; 301-302; 303-304; 305-306; 307-308; 309-310; 311-312; 319-320; 321-322; 323-324; 325-326; 327-328; 329-330; 331-332; 333-334; 335-336; 337-338; 341-342; 343-344; 345-346; 347-348; 349-350; 351-352; 377-378; 379-380; 381-382; 383-384; 385-386; 387-388; 389-390; 391-392; 393-394; 395-396; 397-398; 399-400; 401-402; 403-404; 405-406; 407-408; 409-410; 411-412; 413-414; 415-416; 417-418; 419-420; 421-422; 423-424; 425-426; 427-428; 429-430; 431-432; 433-434; 435-436; 437-438; 439-440; 441-442; 443-444; 445-446; 447-448; 449-450; 451-452; 453-454; 455-456; 457-458; 459-460; 461-462; 463-464; 465-466; 467-468; 469-470; 471-472; 473-474; 475-476; 477-478; 479-480; 481-482; 483-484; 485-486; 487-488; 489-490; 491-492; 493-494; 495-496; 497-498; 499-500; 501-502; 503-504; 505-506; 507-508; 509-510; 511-512; 513-514; 515-516; 517-518; 519-520; 521-522; 523-524; 525-526; 527-528; 529-530; 531-532; 533-534; 535-536; 537-538; 539-540; 541-542; 543-544; 545-546; 547-548; 549-550; 551-552; 553-554; 555-556; 557-558; 559-560; 561-562; 563-564; 565-566; 567-568; 569-570; 571-572; 573-574; 575-576; 577-578; 579-580; 581-582; 583-584; 585-586; 587-588; 589-590; 591-592; 593-594; 595-596; 597-598; 599-600; 601-602; 603-604; 605-606; 607-608; 609-610; 611-612; 613-614; 615-616; 617-618; 619-620; 621-622; 623-624; 625-626; 627-628; 629-630; 631-632; 633-634; 635-636; 637-638; 639-640; 641-642; 643-644; 645-646; 647-648; 649-650; 651-652; 653-654; 655-656; 657-658; 659-660; 661-662; 663-664; 665-666; 667-668; 669-670; 671-672; 673-674; 675-676; 677-678; 679-680; 681-682; 683-684; 685-686; 687-688; 689-690; 691-692; 693-694; 695-696; 697-698; 699-700; 701-702; 703-704; 705-706; 707-708; 709-710; 711-712; 713-714; 715-716; 717-718; 719-720; 721-722; 723-724; 725-726; 727-728; 729-730; 731-732; 733-734; 735-736; 737-738; 739-740; 741-742; 743-744; 745-746; 747-748; 749-750; 751-752; 753-754; 755-756; 757-758; 759-760; 761-762; 763-764; 765-766; 767-768; 769-770; 771-772; 773-774; 775-776; 777-778; 779-780; 781-782; 783-784; 785-786; 787-788; 789-790; 791-792; 793-794; 795-796; 797-798; 799-800; 801-802; 803-804; 805-806; 807-808; 809-810; 811-812; 813-814; 815-816; 817-818; 819-820; 821-822; 823-824; 825-826; 827-828; 829-830; 831-832; 833-834; 835-836; 837-838; 839-840; 841-842; 843-844; 845-846; 847-848; 849-850; 851-852; 853-854; 855-856; 857-858; 859-860; 861-862; 863-864; 865-866; 867-868; 869-870; 871-872; 873-874; 875-876; 877-878; 879-880; 881-882; 883-884; 885-886; 887-888; 889-890; 891-892; 893-894; 895-896; 897-898; 899-900; 901-902; 903-904; 905-906; 907-908; 909-910; 911-912; 913-914; 915-916; 917-918; 919-920; 921-922; 923-924; 925-926; 927-928; 929-930; 931-932; 933-934; 935-936; 937-938; 939-940; 941-942; 943-944; 945-946; 947-948; 949-950; 951-952; 953-954; 955-956; 957-958; 959-960; 961-962; 963-964; 965-966; 967-968; 969-970; 971-972; 973-974; 975-976; 977-978; 979-980; 981-982; 983-984; 985-986; 987-988; 989-990; 991-992; 993-994; 995-996; 997-998; 999-1000; 1001-1002; 1003-1004; 1005-1006; 1007-1008; 1009-1010; 1011-1012; 1013-1014; 1015-1016; 1017-1018; 1019-1020; 1021-1022; 1023-1024; 1025-1026; 1027-1028; 1029-1030; 1031-1032; 1033-1034; 1035-1036; 1037-1038; 1039-1040; 1041-1042; 1043-1044; 1045-1046; 1047-1048; 1049-1050; 1051-1052; 1053-1054; 1055-1056; 1057-1058; 1059-1060; 1061-1062; 1063-1064; 1065-1066; 1067-1068; 1069-1070; 1071-1072; 1073-1074; 1075-1076; 1077-1078; 1079-1080; 1081-1082; 1083-1084; 1085-1086; 1087-1088; 1089-1090; 1091-1092; 1093-1094; 1095-1096; 1097-1098; 1099-1100; 1101-1102; 1103-1104; 1105-1106; 1107-1108; 1109-1110; 1111-1112; 1113-1114; 1115-1116; 1117-1118; 1119-1120; 1121-1122; 1123-1124; 1125-1126; 1127-1128; 1129-1130; 1131-1132; 1133-1134; 1135-1136; 1137-1138; 1139-1140; 1141-1142; 1143-1144; 1145-1146; 1147-1148; 1149-1150; 1151-1152; 1153-1154; 1155-1156; 1157-1158; 1159-1160; 1161-1162; 1163-1164; 1165-1166; 1167-1168; 1169-1170; 1171-1172; 1173-1174; 1175-1176; 1177-1178; 1179-1180; 1181-1182; 1183-1184; 1185-1186; 1187-1188; 1189-1190; 1191-1192; 1193-1194; 1195-1196; 1197-1198; 1199-1200; 1201-1202; 1203-1204; 1205-1206; 1207-1208; 1209-1210; 1211-1212; 1213-1214; 1215-1216; 1217-1218; 1219-1220; 1221-1222; 1223-1224; 1225-1226; 1227-1228; 1229-1230; 1231-1232; 1233-1234; 1235-1236; 1237-1238; 1239-1240; 1241-1242; 1243-1244; 1245-1246; 1247-1248; 1249-1250; 1251-1252; 1253-1254; 1255-1256; 1257-1258; 1259-1260; 1261-1262; 1263-1264; 1265-1266; 1267-1268; 1269-1270; 1271-1272; 1273-1274; 1275-1276; 1277-1278; 1279-1280; 1281-1282; 1283-1284; 1285-1286; 1287-1288; 1289-1290; 1291-1292; 1293-1294; 1295-1296; 1297-1298; 1299-1300; 1301-1302; 1303-1304; 1305-1306; 1307-1308; 1309-1310; 1311-1312; 1313-1314; 1315-1316; 1317-1318; 1319-1320; 1321-1322; 1323-1324; 1325-1326; 1327-1328; 1329-1330; 1331-1332; 1333-1334; 1335-1336; 1337-1338; 1339-1340; 1341-1342; 1343-1344; 1345-1346; 1347-1348; 1349-1350; 1351-1352; 1353-1354; 1355-1356; 1357-1358; 1359-1360; 1361-1362; 1363-1364; 1365-1366; 1367-1368; 1369-1370; 1371-1372; 1373-1374; 1375-1376; 1377-1378; 1379-1380; 1381-1382; 1383-1384; 1385-1386; 1387-1388; 1389-1390; 1391-1392; 1393-1394; 1395-1396; 1397-1398; 1399-1400; 1401-1402; 1403-1404; 1405-1406; 1407-1408; 1409-1410; 1411-1412; 1413-1414; 1415-1416; 1417-1418; 1419-1420; 1421-1422; 1423-1424; 1425-1426; 1427-1428; 1429-1430; 1431-1432; 1433-1434; 1435-1436; 1437-1438; 1439-1440; 1441-1442; 1443-1444; 1445-1446; 1447-1448; 1449-1450; 1451-1452; 1453-1454; 1455-1456; 1457-1458; 1459-1460; 1461-1462; 1463-1464; 1465-1466; 1467-1468; 1469-1470; 1471-1472; 1473-1474; 1475-1476; 1477-1478; 1479-1480; 1481-1482; 1483-1484; 1485-1486; 1487-1488; 1489-1490; 1491-1492; 1493-1494; 1495-1496; 1497-1498; 1499-1500; 1501-1502; 1503-1504; 1505-1506; 1507-1508; 1509-1510; 1511-1512; 1513-1514; 1515-1516; 1517-1518; 1519-1520; 1521-1522; 1523-1524; 1525-1526; 1527-1528; 1529-1530; 1531-1532; 1533-1534; 1535-1536; 1537-1538; 1539-1540; 1541-1542; 1543-1544; 1545-1546; 1547-1548; 1549-1550; 1551-1552; 1553-1554; 1555-1556; 1557-1558; 1559-1560; 1561-1562; 1563-1564; 1565-1566; 1567-1568; 1569-1570; 1571-1572; 1573-1574; 1575-1576; 1577-1578; 1579-1580; 1581-1582; 1583-1584; 1585-1586; 1587-1588; 1589-1590; 1591-1592; 1593-1594; 1595-1596; 1597-1598; 1599-1600; 1601-1602; 1603-1604; 1605-1606; 1607-1608; 1609-1610; 1611-1612; 1613-1614; 1615-1616; 1617-1618; 1619-1620; 1621-1622; 1623-1624; 1625-1626; 1627-1628; 1629-1630; 1631-1632; 1633-1634; 1635-1636; 1637-1638; 1639-1640; 1641-1642; 1643-1644; 1645-1646; 1647-1648; 1649-1650; 1651-1652; 1653-1654; 1655-

1656; 1657-1658; 1659-1660; 1661-1662; 1663-1664; 1665-1666; 1667-1668; 1669-1670; 1671-1672; 1673-1674; 1675-1676; 1677-1678; 1679-1680; 1681-1682; 1683-1684; 1685-1686; 1687-1688; 1689-1690; 1691-1692; 1693-1694; 1695-1696; 1697-1698; 1699-1700; 1701-1702; 1703-1704; 1705-1706; 1707-1708; 1709-1710; 1711-1712; 1713-1714; 1715-1716; 1717-1718; 1719-1720; 1721-1722; 1723-1724; 1725-1726; 1727-1728; 1729-1730; 1731-1732; 1733-1734; 1735-1736; 1737-1738; 1739-1740; 1741-1742; 1743-1744; 1745-1746; 1747-1748; 1749-1750; 1751-1752; 1753-1754; 1755-1756; 1757-1758; 1759-1760; 1761-1762; 1763-1764; 1765-1766; 1767-1768; 1769-1770; 1771-1772; 1773-1774; 1775-1776; 1777-1778; 1779-1780; 1781-1782; 1783-1784; 1785-1786; 1787-1788; 1789-1790; 1791-1792; 1793-1794; 1795-1796; 1797-1798; 1799-1800; 1801-1802; 1803-1804; 1805-1806; 1807-1808; 1809-1810; 1811-1812; 1813-1814; 1815-1816.

In various embodiments, the number of HPV sequence reads according to HPV species and/or HPV gene transcript can be determined.

In one embodiment, the method comprises determining the number of HPV sequence reads of at least 1, 2, 3, 4, 5, 6, 7, 8, 9, or 10 HPV species. In one embodiment, the method comprises determining the number of HPV sequence reads of at least 1, 2, 3, 4, 5, 6, 7, 8, 9, or 10 Alpha group HPV species.

In a further embodiment, the method comprises calculating a ratio (R) of the number of reads of at least one early HPV transcript to the number of reads of at least one late HPV transcript. Preferably the HPV transcripts are Alpha group HPV species HPV transcripts, most preferably HPV16 or HPV18 transcripts.

R values can be determined using any of the various formulas presented in Table 9. In one embodiment, the ratio is calculated by calculating a ratio (R) of the number of reads of HPV E6 and/or E7 transcripts to the number of reads of HPV L1 and/or L2 transcripts. In one embodiment, the ratio is calculated by calculating a ratio (R) of the number of reads of HPV E6 and E7 transcripts to the number of reads of HPV L1 and L2 transcripts.

In some embodiments, a higher ratio (R) correlates with an increased risk of developing high-grade malignant HPV-induced cancer. In various embodiments, an R value tending towards high values above 0.5, 1, 25, 50, 100 and tending towards infinity, indicates that the viral cycle is integrated, non replicating viruses expressing high level of oncogenes E6 and E7; whereas, an R value below 0.25, 0.2, 0.1, 0.05, and tending towards 0, indicates that the viral lifecycle is replicative and expressing low levels of E6 and E7.

In some embodiments, a higher number of reads of transcripts of HPV16, HPV18, or another high-risk HPV relative to reads of transcripts of a lower risk HPV species correlates with an increased risk of developing high-grade malignant HPV-induced cancer.

In some embodiments, the method comprises determining the number of reads matching the viruses based on species discrimination and determining the most prevalent high risk species present in the sample relative to other species and/or determining within said most prevalent high risk species the relative number of reads matching oncogenic genes compared to non oncogenic genes.

In one embodiment, the invention encompasses methods for assessing a human papilloma virus (HPV) infected patient comprising generating cDNA from a patient sample comprising RNA; sequencing the cDNA; generating reads of sequence of the cDNA; discriminating HPV sequence reads on the basis of HPV gene transcript; quantitating the level of HPV sequence reads according to HPV gene transcript; determining the number of HPV sequence reads of at least one HPV early gene transcript; determining the number of HPV sequence reads of at least one HPV late gene transcript; and determining the ratio of the number of HPV sequence reads of at least one HPV early gene transcript to the number of HPV sequence reads of at least one HPV late gene transcript.

The invention also contemplates a composition of group alpha HPV-specific primers comprising at least one of, preferably all, the following groups of pairs of primers:

the HPV16-specific primers comprising or consisting of the primers of SEQ ID NOs: 219-258 for HPV16 genomic and unspliced transcripts, SEQ ID NOs: 259-352 for HPV16 spliced transcripts and SEQ ID NOs: 353-376 for HPV16-human fusion transcripts (including the pairs of primers of SEQ ID NO: 219-220; 221-222; 223-224; 225-226; 227-228; 229-230; 231-232; 233-234; 235-236; 237-238; 239-240; 241-242; 243-244; 245-246; 247-248; 249-250; 251-252; 253-254; 255-256; 257-258; 259-260; 261-262; 263-264; 265-266; 267-268; 269-270; 271-272; 273-274; 275-276; 277-278; 279-280; 281-282; 283-284; 285-286; 287-288; 289-290; 291-292; 293-294; 295-296; 297-298; 299-300; 301-302; 303-304; 305-306; 307-308; 309-310; 311-312; 313-314; 315-316; 317-318; 319-320; 321-322; 323-324; 325-326; 327-328; 329-330; 331-332; 333-334; 335-336; 337-338; 339-340; 341-342; 343-344; 345-346; 347-348; 349-350; 351-352; 353-354; 355-356; 357-358; 359-360; 361-362; 363-364; 365-366; 367-368; 369-370; 371-372; 373-374; 375-376) or 377-470 (including the pairs of primers of SEQ ID NO. 377-378; 379-380; 381-382; 383-384; 385-386; 387-388; 389-390; 391-392; 393-394; 395-396; 397-398; 399-400; 401-402; 403-404; 405-406; 407-408; 409-410; 411-412; 413-414; 415-416; 417-418; 419-420; 421-422; 423-424; 425-426; 427-428; 429-430; 431-432; 433-434; 435-436; 437-438; 439-440; 441-442; 443-444; 445-446; 447-448; 449-450; 451-452; 453-454; 455-456; 457-458; 459-460; 461-462; 463-464; 465-466; 467-468 and; 469-470); and/or, the HPV18-specific primers comprising or consisting of the primers of SEQ ID NO. 471-574 (including the pairs of primers of SEQ ID NO.: 471-472; 473-474; 475-476; 477-478; 479-480; 481-482; 483-484; 485-486; 487-488; 489-490; 491-492; 493-494; 495-496; 497-498; 499-500; 501-502; 503-504; 505-506; 507-508; 509-510; 511-512; 513-514; 515-516; 517-518; 519-520; 521-522; 523-524; 525-526; 527-528; 529-530; 531-532; 533-534; 535-536; 537-538; 539-540; 541-542; 543-544; 545-546; 547-548; 549-550; 551-552; 553-554; 555-556; 557-558; 559-560; 561-562; 563-564; 565-566; 567-568; 569-570; 571-572; 573-574); and/or, the HPV31-specific primers comprising or consisting of the primers of SEQ ID NO. 575-668 (including the pairs of primers of SEQ ID NO.: 575-576; 577-578; 579-580; 581-582; 583-584; 585-586; 587-588; 589-590; 591-592; 593-594; 595-596; 597-598; 599-600; 601-602; 603-604; 605-606; 607-608; 609-610; 611-612; 613-614; 615-616; 617-618; 619-620; 621-622; 623-624; 625-626; 627-628; 629-630; 631-632; 633-634; 635-636; 637-638; 639-640; 641-642; 643-644; 645-646; 647-648; 649-650; 651-652; 653-654; 655-656; 657-658; 659-660; 661-662; 663-664; 665-666; 667-668); and/or, the HPV33-specific primers comprising or consisting of SEQ ID NO. 669-756 (including the pairs of primers of SEQ ID NO.: 669-670; 671-672; 673-674; 675-676; 677-678; 679-680; 681-682; 683-684; 685-686; 687-688; 689-690; 691-692; 693-694; 695-696; 697-698; 699-700; 701-702; 703-704; 705-706; 707-708; 709-710; 711-712; 713-714; 715-716; 717-718; 719-720; 721-722; 723-724; 725-726; 727-728; 729-730; 731-732; 733-734; 735-736; 737-738; 739-740; 741-742; 743-744; 745-746; 747-748; 749-750; 751-752; 753-754; 755-756); and/or, the HPV35-specific primers comprising or consisting of the primers of SEQ ID NO. 757-848 (including the pairs of primers of SEQ ID NO.: 757-758; 759-760; 761-762; 763-764; 765-766; 767-768; 769-770; 771-772; 773-774; 775-776; 777-778; 779-780; 781-782; 783-784; 785-786; 787-788; 789-790; 791-792; 793-794; 795-796; 797-798; 799-800; 801-802; 803-804; 805-806; 807-808; 809-810; 811-812; 813-814; 815-816; 817-818; 819-820; 821-822; 823-824; 825-826; 827-828; 829-830; 831-832; 833-834; 835-836; 837-838; 839-840; 841-842; 843-844; 845-846; 847-848); and/or, the HPV39-specific primers comprising or consisting of the primers of SEQ ID NO. 849-928 (including the pairs of primers of SEQ ID NO.: 849-850; 851-852; 853-854; 855-856; 857-858; 859-860; 861-862; 863-864; 865-866; 867-868; 869-870; 871-872; 873-874; 875-876; 877-878; 879-880; 881-882; 883-884; 885-886; 887-888; 889-890; 891-892; 893-894; 895-896; 897-898; 899-900; 901-902; 903-904; 905-906; 907-908; 909-910; 911-912; 913-914; 915-916; 917-918; 919-920; 921-922; 923-924; 925-926; 927-928); and/or, the HPV45-specific primers comprising or consisting of the primers of SEQ ID NO. 929-1020 (including the pairs of primers of SEQ ID NO.: 929-930; 931-932; 933-934; 935-936; 937-938; 939-940; 941-942; 943-944; 945-946; 947-948; 949-950; 951-952; 953-954; 955-956; 957-958; 959-960; 961-962; 963-964; 965-966; 967-968; 969-970; 971-972; 973-974; 975-976; 977-978; 979-980; 981-982; 983-984; 985-986; 987-988; 989-990; 991-992; 993-994; 995-996; 997-998; 999-1000; 1001-1002; 1003-1004; 1005-1006; 1007-1008; 1009-1010; 1011-1012; 1013-1014; 1015-1016; 1017-1018; 1019-1020); and/or, the HPV51-specific primers comprising or consisting of the primers of SEQ ID NO. 1021-1102 (including the pairs of primers of SEQ ID NO.: 1021-1022; 1023-1024; 1025-1026; 1027-1028; 1029-1030; 1031-1032; 1033-1034; 1035-1036; 1037-1038; 1039-1040; 1041-1042; 1043-1044; 1045-1046; 1047-1048; 1049-1050; 1051-1052; 1053-1054; 1055-1056; 1057-1058; 1059-1060; 1061-1062; 1063-1064; 1065-1066; 1067-1068; 1069-1070; 1071-1072; 1073-1074; 1075-1076; 1077-1078; 1079-1080; 1081-1082; 1083-1084; 1085-1086; 1087-1088; 1089-1090; 1091-1092; 1093-1094; 1095-1096; 1097-1098; 1099-1100; 1101-1102); and/or, the HPV52-specific primers comprising or consisting of the primers of SEQ ID NO. 1103-1200 (including the pairs of primers of SEQ ID NO.: 1103-1104; 1105-1106; 1107-1108; 1109-1110; 1111-1112; 1113-1114; 1115-1116; 1117-1118; 1119-1120; 1121-1122; 1123-1124; 1125-1126; 1127-1128; 1129-1130; 1131-1132; 1133-1134; 1135-1136; 1137-1138; 1139-1140; 1141-1142; 1143-1144; 1145-1146; 1147-1148; 1149-1150; 1151-1152; 1153-1154; 1155-1156; 1157-1158; 1159-1160; 1161-1162; 1163-1164; 1165-1166; 1167-1168; 1169-1170; 1171-1172; 1173-1174; 1175-1176; 1177-1178; 1179-1180; 1181-1182; 1183-1184; 1185-1186; 1187-1188; 1189-1190; 1191-1192; 1193-1194; 1195-1196; 1197-1198; 1199-1200); and/or, the HPV56-specific primers comprising or consisting of the primers of SEQ ID NO. 1201-1296 (including the pairs of primers of SEQ ID NO.: 1201-1202; 1203-1204; 1205-1206; 1207-1208; 1209-1210; 1211-1212; 1213-1214; 1215-1216; 1217-1218; 1219-1220; 1221-1222; 1223-1224; 1225-1226; 1227-1228; 1229-1230; 1231-1232; 1233-1234; 1235-1236; 1237-1238; 1239-1240; 1241-1242; 1243-1244; 1245-1246; 1247-1248; 1249-1250; 1251-1252; 1253-1254; 1255-1256; 1257-1258; 1259-1260; 1261-1262; 1263-1264; 1265-1266; 1267-1268; 1269-1270; 1271-1272; 1273-1274; 1275-1276; 1277-1278; 1279-1280; 1281-1282; 1283-1284; 1285-1286; 1287-1288; 1289-1290; 1291-1292; 1293-1294; 1295-1296); and/or, the HPV58-specific primers comprising or consisting of the primers of SEQ ID NO. 1297-1382 (including the pairs of primers of SEQ ID NO.: 1297-1298; 1299-1300; 1301-1302; 1303-1304; 1305-1306; 1307-1308; 1309-1310; 1311-1312; 1313-1314; 1315-1316; 1317-1318; 1319-1320; 1321-1322; 1323-1324; 1325-1326; 1327-1328; 1329-1330; 1331-1332; 1333-1334; 1335-1336; 1337-1338; 1339-1340; 1341-1342; 1343-1344; 1345-1346; 1347-1348; 1349-1350; 1351-1352; 1353-1354; 1355-1356; 1357-1358; 1359-1360; 1361-1362; 1363-1364; 1365-1366; 1367-1368; 1369-1370; 1371-1372; 1373-1374; 1375-1376; 1377-1378; 1379-1380; 1381-1382); and/or, the HPV59-specific primers comprising or consisting of the primers of SEQ ID NO. 1383-1470 (including the pairs of primers of SEQ ID NO.: 1383-1384; 1385-1386; 1387-1388; 1389-1390; 1391-1392; 1393-1394; 1395-1396; 1397-1398; 1399-1400; 1401-1402; 1403-1404; 1405-1406; 1407-1408; 1409-1410; 1411-1412; 1413-1414; 1415-1416; 1417-1418; 1419-1420; 1421-1422; 1423-1424; 1425-1426; 1427-1428; 1429-1430; 1431-1432; 1433-1434; 1435-1436; 1437-1438; 1439-1440; 1441-1442; 1443-1444; 1445-1446; 1447-1448; 1449-1450; 1451-1452; 1453-1454; 1455-1456; 1457-1458; 1459-1460; 1461-1462; 1463-1464; 1465-1466; 1467-1468; 1469-1470); and/or, the HPV66-specific primers comprising or consisting of the primers of SEQ ID NO. 1471-1560 (including the pairs of primers of SEQ ID NO.: 1471-1472; 1473-1474; 1475-1476; 1477-1478; 1479-1480; 1481-1482; 1483-1484; 1485-1486; 1487-1488; 1489-1490; 1491-1492; 1493-1494; 1495-1496; 1497-1498; 1499-1500; 1501-1502; 1503-1504; 1505-1506; 1507-1508; 1509-1510; 1511-1512; 1513-1514; 1515-1516; 1517-1518; 1519-1520; 1521-1522; 1523-1524; 1525-1526; 1527-1528; 1529-1530; 1531-1532; 1533-1534; 1535-1536; 1537-1538; 1539-1540; 1541-1542; 1543-1544; 1545-1546; 1547-1548; 1549-1550; 1551-1552; 1553-1554; 1555-1556; 1557-1558; 1559-1560; and/or, the HPV68-specific primers comprising or consisting of the primers of SEQ ID NO. 1561-1642 (including the pairs of primers of SEQ ID NO.: 1561-1562; 1563-1564; 1565-1566; 1567-1568; 1569-1570; 1571-1572; 1573-1574; 1575-1576; 1577-1578; 1579-1580; 1581-1582; 1583-1584; 1585-1586; 1587-1588; 1589-1590; 1591-1592; 1593-1594; 1595-1596; 1597-1598; 1599-1600; 1601-1602; 1603-1604; 1605-1606; 1607-1608; 1609-1610; 1611-1612; 1613-1614; 1615-1616; 1617-

1618; 1619-1620; 1621-1622; 1623-1624; 1625-1626; 1627-1628; 1629-1630; 1631-1632; 1633-1634; 1635-1636; 1637-1638; 1639-1640; 1641-1642); and/or, the HPV73-specific primers comprising or consisting of the primers of SEQ ID NO. 1643-1732 (including the pairs of primers of SEQ ID NO.: 1643-1644; 1645-1646; 1647-1648; 1649-1650; 1651-1652; 1653-1654; 1655-1656; 1657-1658; 1659-1660; 1661-1662; 1663-1664; 1665-1666; 1667-1668; 1669-1670; 1671-1672; 1673-1674; 1675-1676; 1677-1678; 1679-1680; 1681-1682; 1683-1684; 1685-1686; 1687-1688; 1689-1690; 1691-1692; 1693-1694; 1695-1696; 1697-1698; 1699-1700; 1701-1702; 1703-1704; 1705-1706; 1707-1708; 1709-1710; 1711-1712; 1713-1714; 1715-1716; 1717-1718; 1719-1720; 1721-1722; 1723-1724; 1725-1726; 1727-1728; 1729-1730; 1731-1732); and/or, the HPV82-specific primers comprising or consisting of the primers of SEQ ID NO. 1733-1816 (including the pairs of primers of SEQ ID NO.: 1733-1734; 1735-1736; 1737-1738; 1739-1740; 1741-1742; 1743-1744; 1745-1746; 1747-1748; 1749-1750; 1751-1752; 1753-1754; 1755-1756; 1757-1758; 1759-1760; 1761-1762; 1763-1764; 1765-1766; 1767-1768; 1769-1770; 1771-1772; 1773-1774; 1775-1776; 1777-1778; 1779-1780; 1781-1782; 1783-1784; 1785-1786; 1787-1788; 1789-1790; 1791-1792; 1793-1794; 1795-1796; 1797-1798; 1799-1800; 1801-1802; 1803-1804; 1805-1806; 1807-1808; 1809-1810; 1811-1812; 1813-1814; 1815-1816).

The invention also contemplates a composition of pairs of group alpha HPV-specific primers comprising at least one of, preferably all, the following groups of pairs of primers:

SD1-SA1 group consisting of the pairs of primers of SEQ ID NO: 397-398; 521-522; 609-610; 695-696; 819-820; 865-866; 947-948; 1067-1068; 1119-1120; 1267-1268; 1325-1326; 1507-1508; 1597-1598; 1655-1656; 1755-1756; and/or, SD1-SA2 group consisting of the pairs of primers of SEQ ID NO: 459-460; 633-634; 687-688; 1111-1112; 1235-1236; 1341-1342; 1503-1504; 1657-1658; 1797-1798; and/or, SD1-SA3 group consisting of the pairs of primers of SEQ ID NO: 381-382; 541-542; 599-600; 903-904; 941-942; 1047-1048; 1135-1136; 1287-1288; 1459-1460; 1473-1474; 1621-1622; 1717-1718; 1745-1746; and/or, SD1-SA4 group consisting of the pairs of primers of SEQ ID NO: 413-414; 551-552; 637-638; 713-714; 793-794; 857-858; 981-982; 1093-1094; 1179-1180; 1227-1228; 1319-1320; 1413-1414; 1509-1510; 1563-1564; 1709-1710; 1791-1792; and/or, SD1-SA5 group consisting of the pairs of primers of SEQ ID NO: 453-454; 549-550; 613-614; 747-748; 761-762; 949-950; 1163-1164; 1249-1250; 1329-1330; 1453-1454; 1501-1502; and/or, SD1-SA6 group consisting of the pairs of primers of SEQ ID NO: 431-432; 595-596; 719-720; 827-828; 1089-1090; 1137-1138; 1285-1286; 1353-1354; 1561-1562; 1719-1720; 1763-1764; and/or, SD1-SA7 group consisting of the pairs of primers of SEQ ID NO: 919-920; 1449-1450; and/or, SD1-SA8 group consisting of the pairs of primers of SEQ ID NO: 489-490; 963-964; 1519-1520; and/or, SD2-SA4 group consisting of the pairs of primers of SEQ ID NO: 387-388; 473-474; 615-616; 745-746; 815-816; 849-850; 933-934; 1091-1092; 1177-1178; 1209-1210; 1367-1368; 1437-1438; 1521-1522; 1603-1604; 1651-1652; 1779-1780; and/or, SD2-SA5 group consisting of the pairs of primers of SEQ ID NO: 455-456; 529-530; 629-630; 717-718; 777-778; 975-976; 1153-1154; 1273-1274; 1347-1348; 1451-1452; 1531-1532; and/or, SD2-SA6 group consisting of the pairs of primers of SEQ ID NO: 399-400; 645-646; 727-728; 811-812; 1079-1080; 1127-1128; 1253-1254; 1369-1370; 1615-1616; 1659-1660; 1781-1782; and/or, SD2-SA7 group consisting of the pairs of primers of SEQ ID NO: 531-532; 899-900; 943-944; 1411-1412; 1495-1496; and/or, SD2-SA9 group consisting of the pairs of primers of SEQ ID NO: 437-438; 505-506; 607-608; 739-740; 785-786; 887-888; 979-980; 1063-1064; 1185-1186; 1233-1234; 1297-1298; 1423-1424; 1491-1492; 1607-1608; 1693-1694; 1775-1776; and/or, SD2-SA10 group consisting of the pairs of primers of SEQ ID NO: 545-546; 831-832; 1149-1150; 1269-1270; 1427-1428; 1671-1672; and/or, SD3-SA4 group consisting of the pairs of primers of SEQ ID NO: 379-380; 483-484; 611-612; 721-722; 833-834; 911-912; 937-938; 1053-1054; 1139-1140; 1251-1252; 1335-1336; 1435-1436; 1487-1488; 1591-1592; 1715-1716; 1785-1786; and/or, SD3-SA5 group consisting of the pairs of primers of SEQ ID NO: 415-416; 493-494; 593-594; 733-734; 817-818; 993-994; 1145-1146; 1243-1244; 1337-1338; 1401-1402; 1483-1484; and/or, SD3-SA6 group consisting of the pairs of primers of SEQ ID NO: 435-436; 655-656; 673-674; 813-814; 1045-1046; 1173-1174; 1241-1242; 1303-1304; 1557-1558; 1627-1628; 1647-1648; 1773-1774; and/or, SD3-SA7 group consisting of the pairs of primers of SEQ ID NO: 855-856; 1387-1388; and/or, SD3-SA8 group consisting of the pairs of primers of SEQ ID NO: 511-512; 957-958; 1529-1530; and/or, SD5-SA9 group consisting of the pairs of primers of SEQ ID NO: 419-420; 527-528; 567-568; 587-588; 683-684; 775-776; 891-892; 999-1000; 1041-1042; 1113-1114; 1247-1248; 1371-1372; 1403-1404; 1511-1512; 1617-1618; 1677-1678; 1733-1734; and/or, SD5-SA10 group consisting of the pairs of primers of SEQ ID NO: 495-496; 837-838; 1183-1184; 1279-1280; 1433-1434; 1723-1724.

The invention also contemplates a composition of group alpha HPV-specific primers comprising one of the following groups of pairs of primers:

the group of pairs of primers of SEQ ID NO: 397-398; 521-522; 609-610; 695-696; 819-820; 865-866; 947-948; 1067-1068; 1119-1120; 1267-1268; 1325-1326; 1507-1508; 1597-1598; 1655-1656; 1755-1756; 459-460; 633-634; 687-688; 1111-1112; 1235-1236; 1341-1342; 1503-1504; 1657-1658; 1797-1798; 381-382; 541-542; 599-600; 903-904; 941-942; 1047-1048; 1135-1136; 1287-1288; 1459-1460; 1473-1474; 1621-1622; 1717-1718; 1745-1746; 413-414; 551-552; 637-638; 713-714; 793-794; 857-858; 981-982; 1093-1094; 1179-1180; 1227-1228; 1319-1320; 1413-1414; 1509-1510; 1563-1564; 1709-1710; 1791-1792; 453-454; 549-550; 613-614; 747-748; 761-762; 949-950; 1163-1164; 1249-1250; 1329-1330; 1453-1454; 1501-1502; 431-432; 595-596; 719-720; 827-828; 1089-1090; 1137-1138; 1285-1286; 1353-1354; 1561-1562; 1719-1720; 1763-1764; 919-920; 1449-1450; 489-490; 963-964; 1519-1520; 387-388; 473-474; 615-616; 745-746; 815-816; 849-850; 933-934; 1091-1092; 1177-1178; 1209-1210; 1367-1368; 1437-1438; 1521-1522; 1603-

1604; 1651-1652; 1779-1780; 455-456; 529-530; 629-630; 717-718; 777-778; 975-976; 1153-1154; 1273-1274; 1347-1348; 1451-1452; 1531-1532; 399-400; 645-646; 727-728; 811-812; 1079-1080; 1127-1128; 1253-1254; 1369-1370; 1615-1616; 1659-1660; 1781-1782; 531-532; 899-900; 943-944; 1411-1412; 1495-1496; 437-438; 505-506; 607-608; 739-740; 785-786; 887-888; 979-980; 1063-1064; 1185-1186; 1233-1234; 1297-1298; 1423-1424; 1491-1492; 1607-1608; 1693-1694; 1775-1776; 545-546; 831-832; 1149-1150; 1269-1270; 1427-1428; 1671-1672; 379-380; 483-484; 611-612; 721-722; 833-834; 911-912; 937-938; 1053-1054; 1139-1140; 1251-1252; 1335-1336; 1435-1436; 1487-1488; 1591-1592; 1715-1716; 1785-1786; 415-416; 493-494; 593-594; 733-734; 817-818; 993-994; 1145-1146; 1243-1244; 1337-1338; 1401-1402; 1483-1484; 435-436; 655-656; 673-674; 813-814; 1045-1046; 1173-1174; 1241-1242; 1303-1304; 1557-1558; 1627-1628; 1647-1648; 1773-1774; 855-856; 1387-1388; 511-512; 957-958; 1529-1530; 477-478; 419-420; 527-528; 567-568; 587-588; 683-684; 775-776; 891-892; 999-1000; 1041-1042; 1113-1114; 1247-1248; 1371-1372; 1403-1404; 1511-1512; 1617-1618; 1677-1678; 1733-1734; 495-496; 837-838; 1183-1184; 1279-1280; 1433-1434; 1723-1724; 1011-1012; 557-558; or, the group of pairs of primers of SEQ ID NO: 229-230; 233-234; 235-236; 245-246; 247-248; 249-250; 251-252; 255-256; 257-258; 265-266; 273-274; 275-276; 277-278; 279-280; 281-282; 289-290; 291-292; 295-296; 297-298; 299-300; 301-302; 303-304; 305-306; 307-308; 309-310; 311-312; 319-320; 321-322; 323-324; 325-326; 327-328; 329-330; 331-332; 333-334; 335-336; 337-338; 341-342; 343-344; 345-346; 347-348; 349-350; 351-352; 377-378; 379-380; 381-382; 383-384; 385-386; 387-388; 389-390; 391-392; 393-394; 395-396; 397-398; 399-400; 401-402; 403-404; 405-406; 407-408; 409-410; 411-412; 413-414; 415-416; 417-418; 419-420; 421-422; 423-424; 425-426; 427-428; 429-430; 431-432; 433-434; 435-436; 437-438; 439-440; 441-442; 443-444; 445-446; 447-448; 449-450; 451-452; 453-454; 455-456; 457-458; 459-460; 461-462; 463-464; 465-466; 467-468; 469-470; 471-472; 473-474; 475-476; 477-478; 479-480; 481-482; 483-484; 485-486; 487-488; 489-490; 491-492; 493-494; 495-496; 497-498; 499-500; 501-502; 503-504; 505-506; 507-508; 509-510; 511-512; 513-514; 515-516; 517-518; 519-520; 521-522; 523-524; 525-526; 527-528; 529-530; 531-532; 533-534; 535-536; 537-538; 539-540; 541-542; 543-544; 545-546; 547-548; 549-550; 551-552; 553-554; 555-556; 557-558; 559-560; 561-562; 563-564; 565-566; 567-568; 569-570; 571-572; 573-574; 575-576; 577-578; 579-580; 581-582; 583-584; 585-586; 587-588; 589-590; 591-592; 593-594; 595-596; 597-598; 599-600; 601-602; 603-604; 605-606; 607-608; 609-610; 611-612; 613-614; 615-616; 617-618; 619-620; 621-622; 623-624; 625-626; 627-628; 629-630; 631-632; 633-634; 635-636; 637-638; 639-640; 641-642; 643-644; 645-646; 647-648; 649-650; 651-652; 653-654; 655-656; 657-658; 659-660; 661-662; 663-664; 665-666; 667-668; 669-670; 671-672; 673-674; 675-676; 677-678; 679-680; 681-682; 683-684; 685-686; 687-688; 689-690; 691-692; 693-694; 695-696; 697-698; 699-700; 701-702; 703-704; 705-706; 707-708; 709-710; 711-712; 713-714; 715-716; 717-718; 719-720; 721-722; 723-724; 725-726; 727-728; 729-730; 731-732; 733-734; 735-736; 737-738; 739-740; 741-742; 743-744; 745-746; 747-748; 749-750; 751-752; 753-754; 755-756; 757-758; 759-760; 761-762; 763-764; 765-766; 767-768; 769-770; 771-772; 773-774; 775-776; 777-778; 779-780; 781-782; 783-784; 785-786; 787-788; 789-790; 791-792; 793-794; 795-796; 797-798; 799-800; 801-802; 803-804; 805-806; 807-808; 809-810; 811-812; 813-814; 815-816; 817-818; 819-820; 821-822; 823-824; 825-826; 827-828; 829-830; 831-832; 833-834; 835-836; 837-838; 839-840; 841-842; 843-844; 845-846; 847-848; 849-850; 851-852; 853-854; 855-856; 857-858; 859-860; 861-862; 863-864; 865-866; 867-868; 869-870; 871-872; 873-874; 875-876; 877-878; 879-880; 881-882; 883-884; 885-886; 887-888; 889-890; 891-892; 893-894; 895-896; 897-898; 899-900; 901-902; 903-904; 905-906; 907-908; 909-910; 911-912; 913-914; 915-916; 917-918; 919-920; 921-922; 923-924; 925-926; 927-928; 929-930; 931-932; 933-934; 935-936; 937-938; 939-940; 941-942; 943-944; 945-946; 947-948; 949-950; 951-952; 953-954; 955-956; 957-958; 959-960; 961-962; 963-964; 965-966; 967-968; 969-970; 971-972; 973-974; 975-976; 977-978; 979-980; 981-982; 983-984; 985-986; 987-988; 989-990; 991-992; 993-994; 995-996; 997-998; 999-1000; 1001-1002; 1003-1004; 1005-1006; 1007-1008; 1009-1010; 1011-1012; 1013-1014; 1015-1016; 1017-1018; 1019-1020; 1021-1022; 1023-1024; 1025-1026; 1027-1028; 1029-1030; 1031-1032; 1033-1034; 1035-1036; 1037-1038; 1039-1040; 1041-1042; 1043-1044; 1045-1046; 1047-1048; 1049-1050; 1051-1052; 1053-1054; 1055-1056; 1057-1058; 1059-1060; 1061-1062; 1063-1064; 1065-1066; 1067-1068; 1069-1070; 1071-1072; 1073-1074; 1075-1076; 1077-1078; 1079-1080; 1081-1082; 1083-1084; 1085-1086; 1087-1088; 1089-1090; 1091-1092; 1093-1094; 1095-1096; 1097-1098; 1099-1100; 1101-1102; 1103-1104; 1105-1106; 1107-1108; 1109-1110; 1111-1112; 1113-1114; 1115-1116; 1117-1118; 1119-1120; 1121-1122; 1123-1124; 1125-1126; 1127-1128; 1129-1130; 1131-1132; 1133-1134; 1135-1136; 1137-1138; 1139-1140; 1141-1142; 1143-1144; 1145-1146; 1147-1148; 1149-1150; 1151-1152; 1153-1154; 1155-1156; 1157-1158; 1159-1160; 1161-1162; 1163-1164; 1165-1166; 1167-1168; 1169-1170; 1171-1172; 1173-1174; 1175-1176; 1177-1178; 1179-1180; 1181-1182; 1183-1184; 1185-1186; 1187-1188; 1189-1190; 1191-1192; 1193-1194; 1195-1196; 1197-1198; 1199-1200; 1201-1202; 1203-1204; 1205-1206; 1207-1208; 1209-1210; 1211-1212; 1213-1214; 1215-1216; 1217-1218; 1219-1220; 1221-1222; 1223-1224; 1225-1226; 1227-1228; 1229-1230; 1231-1232; 1233-1234; 1235-1236; 1237-1238; 1239-1240; 1241-1242; 1243-1244; 1245-1246; 1247-1248; 1249-1250; 1251-1252; 1253-1254; 1255-1256; 1257-1258; 1259-1260; 1261-1262; 1263-1264; 1265-1266; 1267-1268; 1269-1270; 1271-1272; 1273-1274; 1275-1276; 1277-1278; 1279-1280; 1281-1282; 1283-1284; 1285-1286; 1287-1288; 1289-1290; 1291-1292; 1293-1294; 1295-1296; 1297-1298; 1299-1300; 1301-1302; 1303-1304; 1305-1306; 1307-1308; 1309-1310; 1311-1312; 1313-1314; 1315-1316; 1317-1318; 1319-1320; 1321-1322; 1323-1324; 1325-1326; 1327-1328; 1329-1330; 1331-1332; 1333-1334; 1335-1336; 1337-1338; 1339-1340; 1341-1342; 1343-1344; 1345-1346; 1347-1348; 1349-1350; 1351-1352; 1353-1354; 1355-1356; 1357-1358; 1359-1360; 1361-1362; 1363-1364; 1365-1366; 1367-1368; 1369-1370; 1371-1372; 1373-1374; 1375-1376; 1377-1378; 1379-1380; 1381-1382; 1383-1384; 1385-1386; 1387-1388; 1389-1390; 1391-1392; 1393-1394;

1395-1396; 1397-1398; 1399-1400; 1401-1402; 1403-1404; 1405-1406; 1407-1408; 1409-1410; 1411-1412; 1413-1414; 1415-1416; 1417-1418; 1419-1420; 1421-1422; 1423-1424; 1425-1426; 1427-1428; 1429-1430; 1431-1432; 1433-1434; 1435-1436; 1437-1438; 1439-1440; 1441-1442; 1443-1444; 1445-1446; 1447-1448; 1449-1450; 1451-1452; 1453-1454; 1455-1456; 1457-1458; 1459-1460; 1461-1462; 1463-1464; 1465-1466; 1467-1468; 1469-1470; 1471-1472; 1473-1474; 1475-1476; 1477-1478; 1479-1480; 1481-1482; 1483-1484; 1485-1486; 1487-1488; 1489-1490; 1491-1492; 1493-1494; 1495-1496; 1497-1498; 1499-1500; 1501-1502; 1503-1504; 1505-1506; 1507-1508; 1509-1510; 1511-1512; 1513-1514; 1515-1516; 1517-1518; 1519-1520; 1521-1522; 1523-1524; 1525-1526; 1527-1528; 1529-1530; 1531-1532; 1533-1534; 1535-1536; 1537-1538; 1539-1540; 1541-1542; 1543-1544; 1545-1546; 1547-1548; 1549-1550; 1551-1552; 1553-1554; 1555-1556; 1557-1558; 1559-1560; 1561-1562; 1563-1564; 1565-1566; 1567-1568; 1569-1570; 1571-1572; 1573-1574; 1575-1576; 1577-1578; 1579-1580; 1581-1582; 1583-1584; 1585-1586; 1587-1588; 1589-1590; 1591-1592; 1593-1594; 1595-1596; 1597-1598; 1599-1600; 1601-1602; 1603-1604; 1605-1606; 1607-1608; 1609-1610; 1611-1612; 1613-1614; 1615-1616; 1617-1618; 1619-1620; 1621-1622; 1623-1624; 1625-1626; 1627-1628; 1629-1630; 1631-1632; 1633-1634; 1635-1636; 1637-1638; 1639-1640; 1641-1642; 1643-1644; 1645-1646; 1647-1648; 1649-1650; 1651-1652; 1653-1654; 1655-1656; 1657-1658; 1659-1660; 1661-1662; 1663-1664; 1665-1666; 1667-1668; 1669-1670; 1671-1672; 1673-1674; 1675-1676; 1677-1678; 1679-1680; 1681-1682; 1683-1684; 1685-1686; 1687-1688; 1689-1690; 1691-1692; 1693-1694; 1695-1696; 1697-1698; 1699-1700; 1701-1702; 1703-1704; 1705-1706; 1707-1708; 1709-1710; 1711-1712; 1713-1714; 1715-1716; 1717-1718; 1719-1720; 1721-1722; 1723-1724; 1725-1726; 1727-1728; 1729-1730; 1731-1732; 1733-1734; 1735-1736; 1737-1738; 1739-1740; 1741-1742; 1743-1744; 1745-1746; 1747-1748; 1749-1750; 1751-1752; 1753-1754; 1755-1756; 1757-1758; 1759-1760; 1761-1762; 1763-1764; 1765-1766; 1767-1768; 1769-1770; 1771-1772; 1773-1774; 1775-1776; 1777-1778; 1779-1780; 1781-1782; 1783-1784; 1785-1786; 1787-1788; 1789-1790; 1791-1792; 1793-1794; 1795-1796; 1797-1798; 1799-1800; 1801-1802; 1803-1804; 1805-1806; 1807-1808; 1809-1810; 1811-1812; 1813-1814; 1815-1816.

The following examples are not limitative.

Example 1: General Amplification α5, α6, α7 and α10 HPVs

We developed a NGS test for quantifying oncogenic HPV E7 mRNAs relative their respective L1 mRNAs. We searched and designed consensus primers in this regard for a quantitative pre-amplification of the oncogenic E7 HPVs mRNAs of all alpha papillomavirus (high and low risk).

We completed the test with the identification of L1 mRNA level and determine the ratio between the expression E7 (early gene) and L1 (late gene) to determine the risk of a patient developing cancer. This new test allows determining the inherent risk of any HPVs types regardless of the current classification regardless of whether the patient is infected with HPV species 16 or 18, etc. (HR) or 30 . . . etc. (BR). Furthermore, this assay allows identifications of multiple HPV infections in single individuals.

First, we analyzed the feasibility of generating consensus sequences for different HPVs type (HR and LR).

Figure 1:
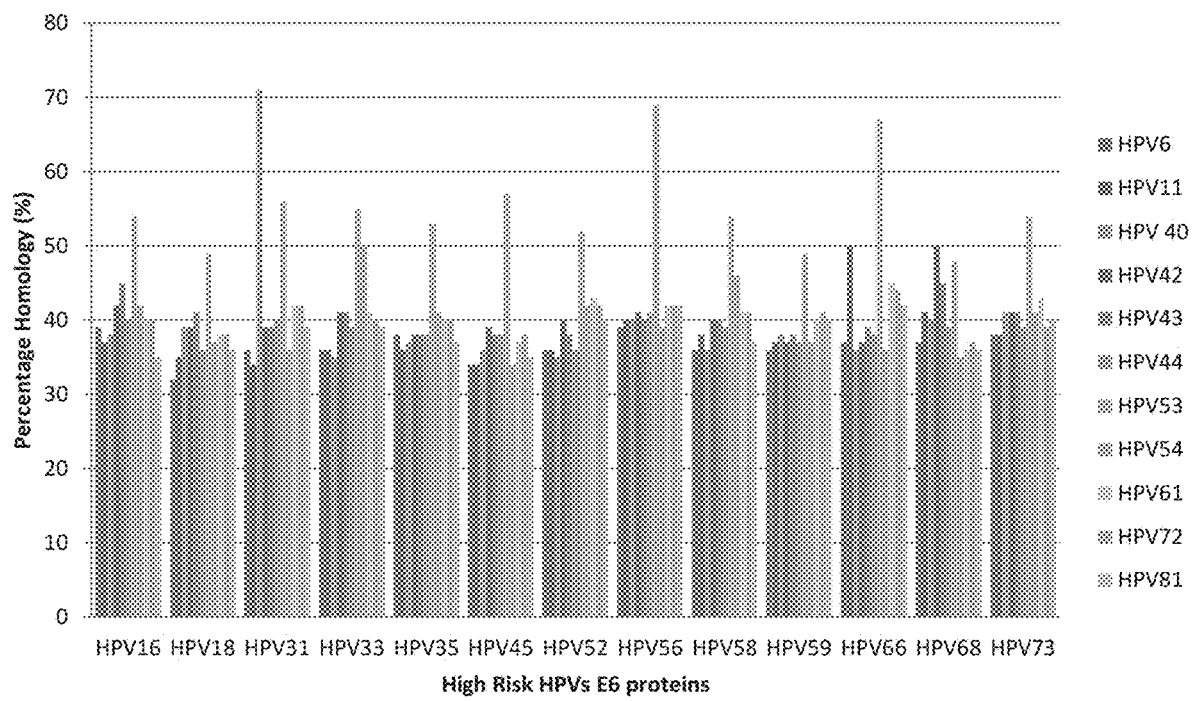
FIG. 1 represents percentage homology between oncogenic proteins E6 HPVs HR and LR. The x-axis corresponds to HR-HPVs and y-axis represents the percentage of the nucleotide sequences homology of HPVs compared to LR HR HPVs.
Figure 2:
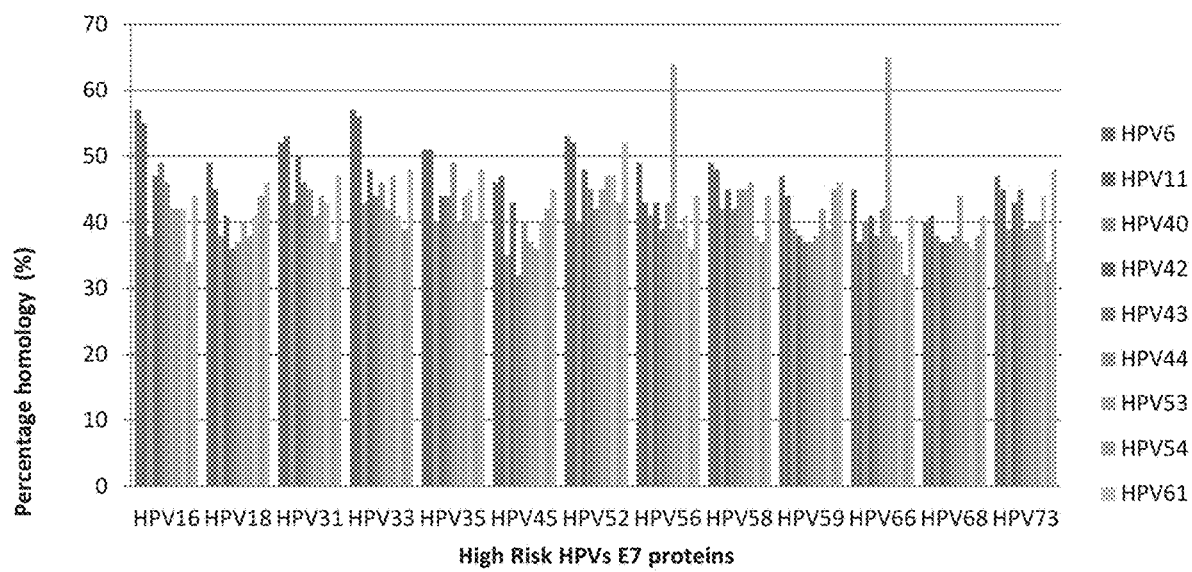
FIG. 2 represents percentage homology between oncogenic proteins E7 HPVs HR and LR. The x-axis corresponds to HR-HPVs and y-axis represents the percentage of the nucleotide sequences homology of HPVs compared to LR HR HPVs.
Figure 3:
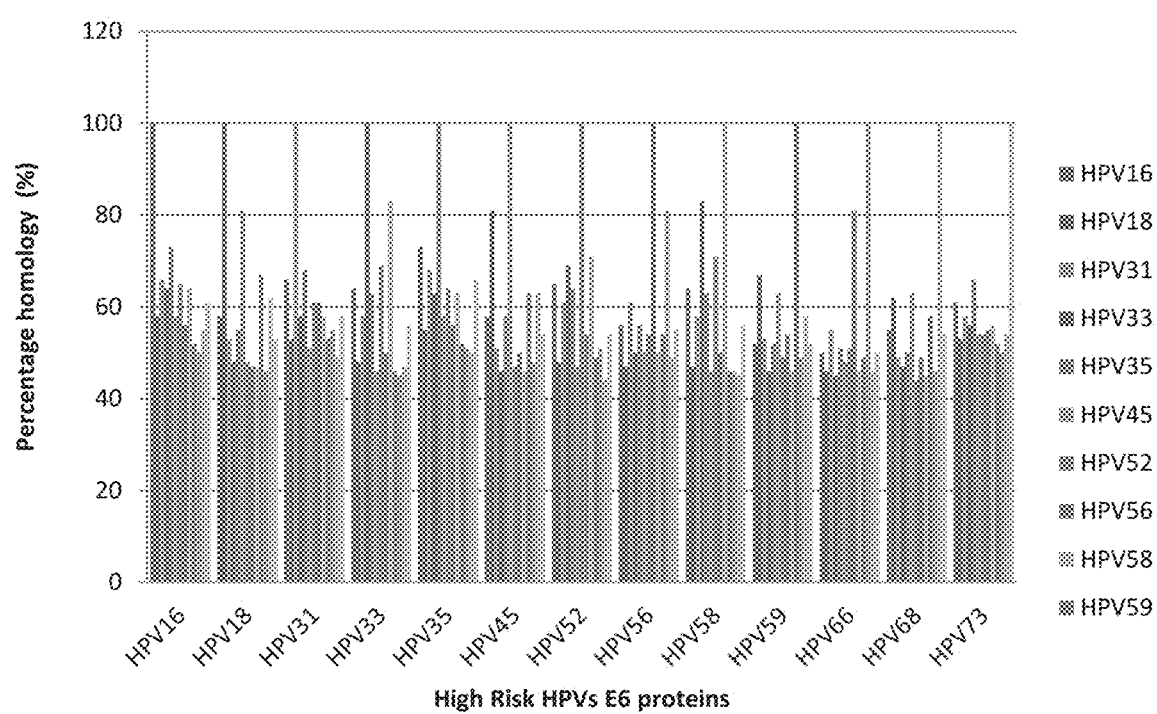
FIG. 3 represents percentage homology between oncogenic proteins E6 HPVs HR. The x-axis corresponds to HR-HPVs and y-axis represents the percentage of the nucleotide sequences homology of HR HPVs.
Figure 4:
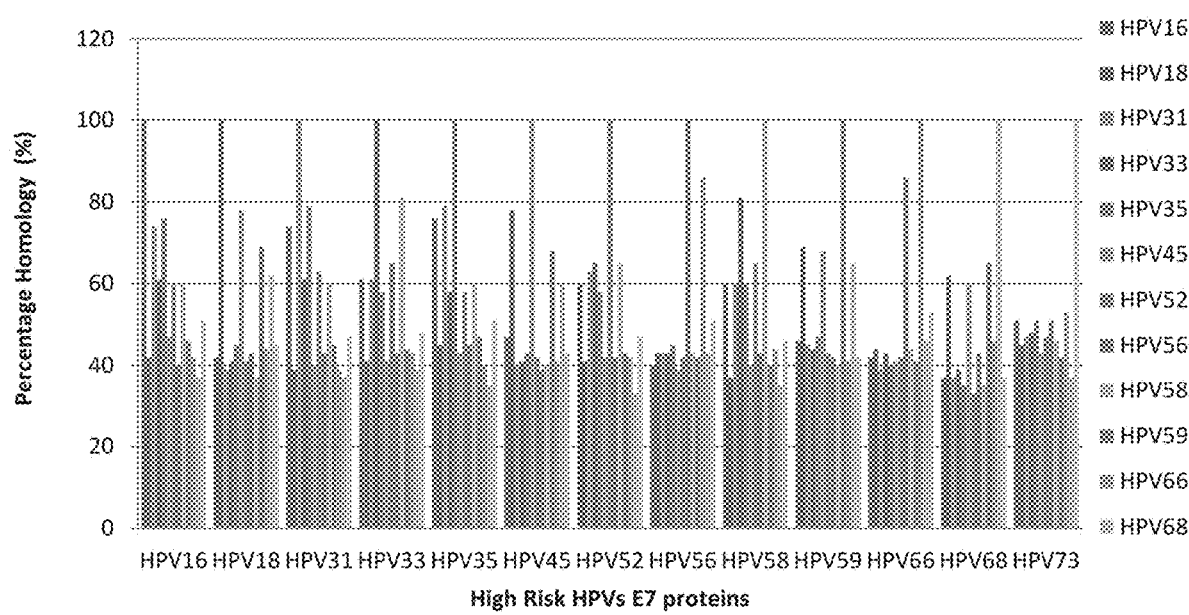
FIG. 4 represents percentage homology between oncogenic proteins E7 HPVs HR. The x-axis corresponds to HR-HPVs and y-axis represents the percentage of the nucleotide sequences homology of H HPVs.
Figure 5:
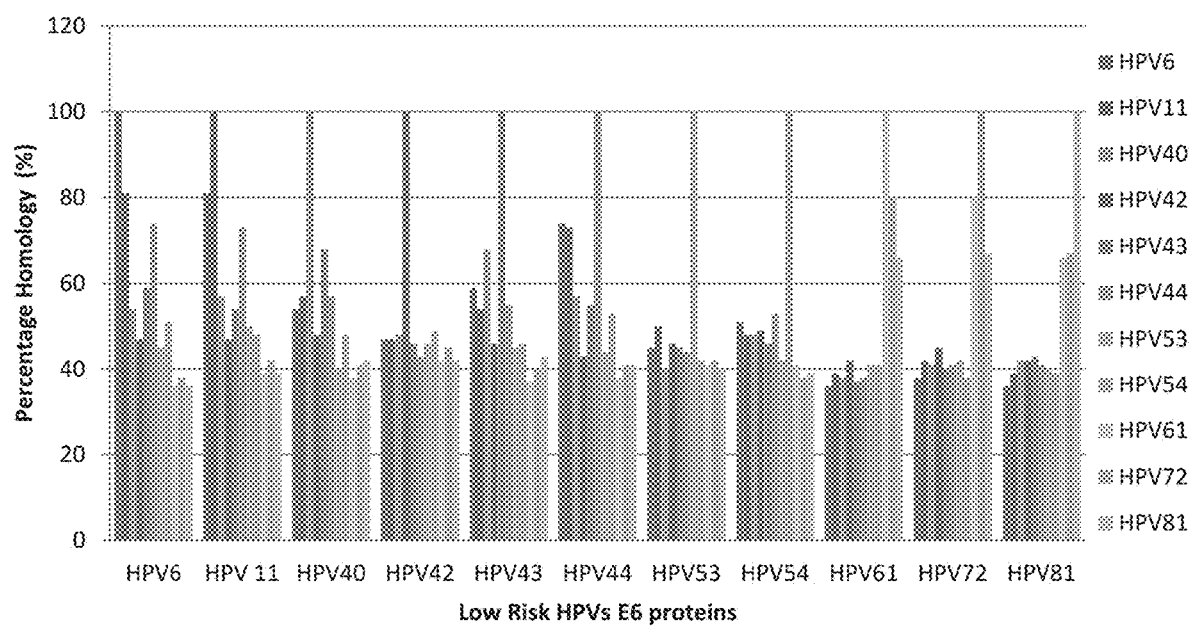
FIG. 5 represents percentage homology between oncogenic proteins E6 HPVs LR. The x-axis corresponds to HR-HPVs and y-axis represents the percentage of the nucleotide sequences homology of HR HPVs.
Figure 6:
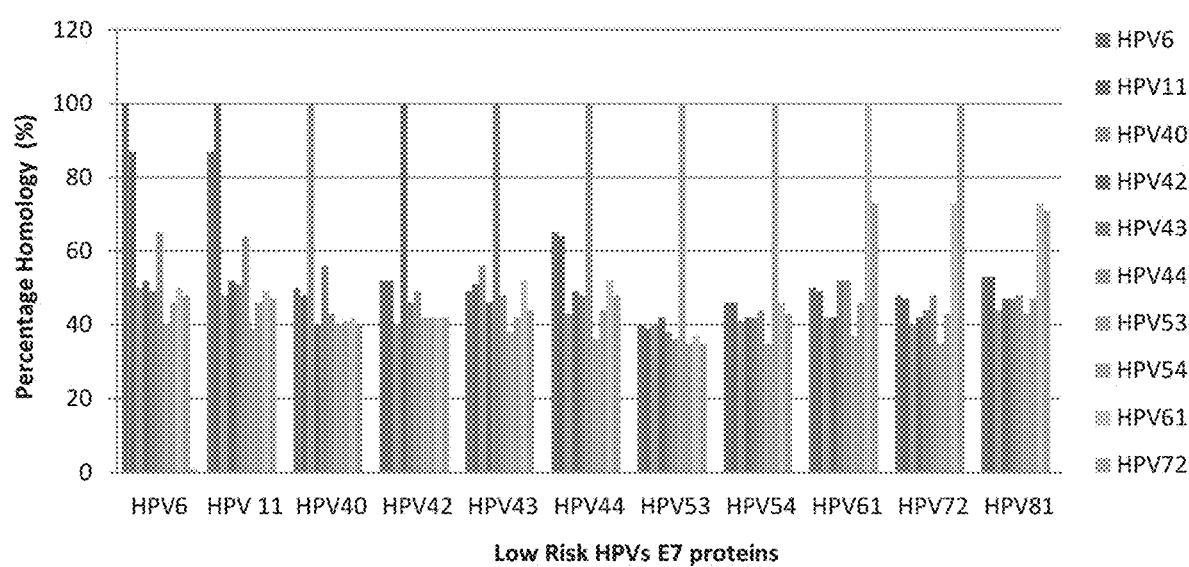
FIG. 6 represents percentage homology between oncogenic proteins E7 HPVs LR. The x-axis corresponds to HR-HPVs and y-axis represents the percentage of the nucleotide sequences homology of HR HPVs.

We started to determine the percentage protein homology of the different HPVs Type, using NCBI Blastn. We observed that a high heterogeneity exists between the gene sequence of E7 from one type of HPV to another even among HR species (FIG. 1, 2, 3, 4, 5, 6). This observation did not reveal obvious features in sequences of HPVs explaining the consensus designing partners by current classification as LR or HR. this observation reinforces the hypothesis of a lack of correlation between sequence of a whole E7 gene and the classification based on the risk: this impair a possibility to derive tests based on consensus sequence to differentiate HT=R and LR.

Then, we did a sequence alignment based on oncogenic E7 HPVs HR and LR.

We focus on global comparison of HR and LR, then only within HR and finally only within LR. We observed that no specific consensus sequence emerged from the sequence alignment of HR, HR and LR/LR overall on E7 genes species. There is very little global sequence homology, the locus of homology being very punctual.

Nonetheless, we were led to design consensus primers based on subgroup a for E7 using ClustalW for alignments. We found some homologies between HPVs types sequences contained in a subgroup.

After having generated all the FASTA files alignment, we searched to generate consensus sequences using GEMI program. Sometimes, we couldn't find any consensus sequences in all the HPV subgroup.

We divided the subgroup to generate the degenerated consensus sequences. We then selected more particularly combined primers which cover all subgroup parameters such as minimizing the number of required primers selecting primers to obtain the largest possible amplicons, further selecting primers for relative conserved 3' sequences and selecting primers which do not cross hybridize.

We did these selections for all the E7 and L1 HPVs subgroup. After analyzing all the sequences we elected the best set of primers for α5, α6, α7 and α10 E7 and α5, α6, α7 and α10 L1 to amplify all the genes.

Finally, we provide here a new diagnosis test comprising a set of probes for the pre amplification of E7 α5, α6, α7 and α10 HPVs mRNAs and L1 α5, α6, α7 and α10 HPVs mRNAs level and which allows to assess the ratio between the expression of E7 (early gene) and L1 (late gene) as a marker of the risk for a patient developing cancer.

One preferred set of primers for the pre-amplification comprises the following sequences:

```
α5:
E7
Forward:
                                  (SEQ ID NO. 49)
5'-YTAGATYTGGTGCCGCAACCCG-3'

Forward:
                                  (SEQ ID NO. 50)
5'-MGCCATGCGTGGTAATGTACCAC-3'

Reverse:
                                  (SEQ ID NO. 51)
3'-CTCCASCRCTCGRACGTTCTGT-5'

Reverse:
                                  (SEQ ID NO. 52)
3'-CACGGGCAMACCAGGCTTAGK-5'
```

-continued

L1
Forward:
                                       (SEQ ID NO. 53)
5'-KCAGATGGCYTTGYGGCGTACTA-3'

Reverse:
                                       (SEQ ID NO. 56)
3'-GGGGCRTYRCGYTGACAKGTAGT-5'

Reverse:
                                       (SEQ ID NO. 57)
3'-GGCMGGSCKTTTAAGGCCTGGT-5'

α6:
E7
Forward:
                                       (SEQ ID NO. 64)
5'-GCTCAGAGGAWGAGGATGAGG-3'

Reverse:
                                       (SEQ ID NO. 69)
3'-GCCTTGTTGCRCASAGGGG-5'

Reverse:
                                       (SEQ ID NO. 70)
3'-CGCAGAGTGGGCACGTTACT-5'

L1
Forward:
                                       (SEQ ID NO. 71)
5'-TTGCAGATGGCGRYGTGGCG-3'

Reverse:
                                       (SEQ ID NO. 72)
3'-CACCTAAAGGYTGDCCDCGGC-5'

α7:
E7
Forward:
                                       (SEQ ID NO. 82)
5'-GACGRGMHGAACMACARCGTCAC-3'

Reverse:
                                       (SEQ ID NO. 85)
3'-GTGWSTCCATAAACAGCWGCWGT-5'

Reverse:
                                       (SEQ ID NO. 86)
3'-CACACCAMGGACACACAAAGGAC-5'

L1
Forward:
                                       (SEQ ID NO. 87)
5'-GCGBTCTAGYGACARCAHGGTGT-3'

Forward:
                                       (SEQ ID NO. 88)
5'-HCCTGCTATTGGKGARCAYTGGG-3'

Reverse:
                                       (SEQ ID NO. 89)
3'-CCAGTGYTCYCCMATRGCRGGWA-5'

Reverse:
                                       (SEQ ID NO. 90)
3'-TAGASCCACTDGGWGANGGRGAA-5'

α10:
E7
Forward:
                                       (SEQ ID NO. 122)
5'-GCWCAYTWGGAATHGTGTGCCCC-3'

Forward:
                                       (SEQ ID NO. 123)
5'-CSTGTAAMAACGCCATGAGAGGA-3'

Forward:
                                       (SEQ ID NO. 124)
5'-CGCCATGAGAGGAMACAASCCA-3'

-continued

Reverse:
                                       (SEQ. ID NO. 125)
3'-GGCACACDATTCCWARTGWGCCC-5'

Reverse:
                                       (SEQ ID NO. 126)
3'-GGTTCGTASGTCRSTTGYTGTAC-5'

Reverse:
                                       (SEQ ID NO. 127)
3'-GTGCACAGSYGGGRCACACWAYT-5'

L1
Forward:
                                       (SEQ ID NO. 128)
5'-GARGCCACWGTSTACYTGCCTC-3'

Forward:
                                       (SEQ ID NO. 129)
5'-ACAGATGTCTCTGTGGCGGC-3'

Reverse:
                                       (SEQ ID NO. 130)
3'-GGATGNCCACTWAYRCCHACDCC-5'

Example 2: Quantifying E6 and E7 Reads Versus Other Viral Reads

A sample of cells is collected from the cervix using a spatula or small brush and put in a conservative solution. RNAs are extracted from the cells using standard procedure and polyA mRNAs are selected using standard procedures like using poly dT beads. Libraries are prepared using standard library preparation (RNA fragmentation and reverse transcription into double-stranded complementary DNA primed by random hexamer followed by adapter selection, or reverse transcription to single strand cDNA, ligation of cDNA and random amplification by phi 29 polymerase followed by fragmentation and adpaterligation). Alternatively RT-PCT is conducted using set of primers for E6 and E7 and at least one another late gene as described. After sequencing using several million reads of at least 100 nt, reads are mapped on a database of E6 and E7 genes: HPV genotypes expressing E6/E7 are identified. The other reads are mapped on the subset of genomes corresponding to the corresponding genotypes. Within each genotype, ratio of the number of E6/E7 reads to the reads mapped to at least one anther gene is calculated and compared to thresholds.

Example 3: Biological Samples

Two high grade lesions (HSIL) samples of the cervix from two donor women, hereinafter referred to as 117 and 119, were collected in PreservCyt medium (Hologic) and kept at room temperature for a couple of days. After homogenization, 1 mL aliquots were collected from the 20 μL total liquid medium for HPV genotyping (Papillocheck, Greiner Bio-One). Results of HPV typing are given in table 1. The remaining samples were centrifuged at 4,500×g for 10 min and the pellets were stabilized in 1 mL RNAProtect Cell (Qiagen) for storage at −80° C. before RNA extraction.

Example 4: HPV Database

Sixty four (64) reference sequences representing the entire HPV alpha genus were retrieved from the International Human Papillomavirus Reference Center (updated May 2014). Additional nine (9) sublineage sequences corresponding to HPV16, plus nine (9) sublineage sequences corresponding to HPV18 (described in Burk et al. Virology 2013) were added. The resulting eighty two (82) HPV genomes (listed in table 2) were aligned using ClustalW2 (default parameters) and the output file was analyzed using the Geneious software (Geneious 7.1.5, Biomatters Ldt).

Example 5: Design of HPV Reverse Transcription Primers

A dedicated strategy for the design of HPV reverse transcription (RT)-primers was set up with the goal to carry out a specific enrichment of HVP sequences during the reverse transcription step within a ballast of viral and non-viral RNA sequences. The overall approach consists in targeting the entire early and late populations of HPV transcripts starting from a limited number of specific RT primers. The design is achieved by taking advantage of the sequence shared by all early and late transcripts, located in the 5' vicinity of the early and late polyA signals, respectively (FIG. 1). In order to minimize the number of RT primers required to cover all kind of alpha HPV, the degree of similarity between the 82 HPV genomes was taken into account. Additional criteria for the design of RT primers were as follows: (i) an overall good specificity of the primer aligned against all existing sequences databases (BLAST NCBI) with special attention paid in considering the 3' part of the primer, (ii) a GC content around 50% (+1-12%), (iii) a melting temperature (Tm) >50° C. (assuming 0.2 µM primers and 50 mM salt), (iv) no T tracts, (v) no or low GC content in the 3' part of the primer and (vi) no or limited number of putative secondary structures. This approach was implemented manually as a proof of principle to design one (1) RT-specific primer targeting the early transcripts of the 9 HPV16 sequences, one (1) RT-specific primer targeting the late transcripts of the 9 HPV16 sequences, two (2) RT-specific primers targeting the early transcripts of the 9 HPV18 sequences and two (2) RT-specific primers targeting the late transcripts of the 9 HPV18 sequences. The resulting six (6) RT-specific primers targeting both HPV16 and HPV18 sequences and including sublineages are given in table 3. HPSF-purified primers (0.01 µmop were ordered at Eurofins genomics (http://www.eurofinsgenomics.eu).

Example 6: RNA Extraction and Characterization

Total RNA from samples 117 and 119 were extracted using the PicoPure RNA isolation kit (Life Technologies), adding a DNAse treatment step directly on column (RNAse-free DNAse set, Qiagen) as recommended by the supplier. Elution was achieved in 30 µL elution buffer. Assessment of RNA quantity and quality was done with a Nanodrop 1000 (Thermo Scientist) and a Bioanalyzer 2100 using the RNA Nano chips (Agilent).

Example 7: Random Reverse Transcription

Random reverse transcription of total RNA was carried out using the SuperScript III First-Strand cDNA Synthesis kit (Invitrogen). Briefly, 8 µL of total RNA was used for template and the reaction was performed in the presence of 50 nM random hexamers (provided by Invitrogen), incubated 10 min at 25° C., 50 min at 50° C. and 5 min at 85° C. before a final RNAse H treatment 20 min at 37° C. The resulting cDNA were stored at −20° C.

Example 8: HPV-Specific Reverse Transcription

HPV-specific reverse transcription was carried out using the SuperScript III First-Strand cDNA Synthesis kit (Invitrogen) and primed with the HPV-specific RT-primers described above. Briefly, 8 µL of total RNA was used for template and reaction was performed with a 0.2 µM mixture of the 6 HPV-specific RT primers, incubated 50 min at 50° C. and 5 min at 85° C. before a final RNAse H treatment 20 min at 37° C. The resulting cDNA were stored at −20° C.

Example 9: Control PCR

The HPV16 E7 and the human cellular beta-actin (ACTB) genes were used as controls of the random and HPV-specific reverse-transcription steps, respectively. 1 µL of reverse-transcribed cDNA was used as PCR templates in 20 µL final volume, working with LightCycler DNA Master SybrGreen I reagents (Roche Diagnostics). 45 amplification cycles were achieved on a Light Cycler 480 (Roche) as follows: 95° C. 10 sec, 56° C. 10 sec, 72° C. 30 sec. Fusion curves and electrophoresis gels served for validation. A comparison of Ct values obtained by following either the random RT or the HPV RT protocol is given in table 4.

Example 10: Whole Transcriptome Random Amplification cDNA were randomly amplified using the Multiple Displacement Amplification (MDA) protocol with phi29 polymerase and random hexamers (Whole Transcriptome Amplification, Qiagen). Phi 29 was UV-treated for one hour before use, in order to prevent any residual DNA contaminant.

Example 11: High Throughput Sequencing

Samples 117 (both random RT and HPV-specific RT) and 119 (both random RT and HPV-specific RT) were independently analyzed on two sequencing runs (300 bp paired-end sequencing, TruSeq PCR-free library prep, 600 cycle kit) on a MiSeq apparatus (Illumina). fastQ data were generated and QC tests done following standard procedures. Total numbers of sequencing reads per sample are summarized in table 5.

Example 12: Data Analysis

Quality-filtered reads were mapped to reference sequences using the following criteria: (i) alignment identity of at least 90% and (ii) Smith and Waterman score above 100. A selection of 10 human genes served as cellular controls (table 6). The analysis of the reads mapping HPV sequences relied on two strategies: first, at the genomic level, sequencing reads mapping HPV16 (NC_001526.2), HPV6 (HG793939.1) and HPV35 (JX129488.1) were count for each coding sequence (CDS), without adding any particular filter (table 7). In a second and more transcript-specific approach, reads mapping splice junctions of HPV16 were identified (table 8). This latter analysis was done for HPV16 only as a proof of principle, and relied on well-documented donor and acceptor splice sites, as described for example in Zheng et al. FrontBiosci 2006.

Example 13: Sequence Results

Following the random reverse-transcription protocol, the sequencing of patient 117 resulted in a total of 1,455 and 126 reads (over 34,977,682) that were successfully mapped to the HPV16 (NC_001526.2) and HPV35 (JX129488.1) genomes, respectively. 15 reads (over 39675490) were mapped to the HPV16 genome for the mono-infected patient 119. Following the alternative procedure with HPV-specific RT primers, the sequencing of patient 117 resulted in a total of 2033, 69 and 14 reads (over 28598603) for HPV16, HPV35 and HPV6 genomes, respectively. 6 reads (over 19383833) were mapped to the HPV16 genome for patient 119.

Two lines of analysis were conducted in order to characterize finely different populations of HPV reads. First, at the genomic level, reads mapping CDS regions were counted, giving a broad view of phenomena such as the early vs late genes equilibrium (table 7). In addition to that, we sought to characterize deeply specific HPV16 transcripts by taking advantage of well-documented donor and acceptor splice sites described for HPV16. This led us to define 11 spliced transcripts which can be associated unambiguously to one specific RNA event (table 8). Together, these two analysis showed that (i) HPV sequences are reachable using HTS, (ii) it is possible to perform a gene-by-gene reads counting at the genomic level, (iii) reads associated to specific splice junctions exist and can be characterized and counted as well, confirming essentially the detection of transcripts over possible artefacts introduced by residual HPV DNA, (iv) discrepancies exist between samples, between HPV genus and between HPV genes and transcripts patterns, which reflect probably the diversity of HPV infections.

Example 14: Examples of R Scores

These observations opened the possibly to define a score, referred to as R score, based on HPV CDS counts and/or specific transcripts within each genotype present in a given sample, to gain a fine molecular characterization of any individual HPV-positive samples. From this perspective, either one value or a combination of more than one ratio(s) could be considered. A non-restrictive list of R scores is given in table 9 in order to illustrate several possible combinations based either on CDS or specific transcripts. As an example, R scores based on a ratio E6 and/or E7 and/or E2 and/or L1 and/or L2 succeeded in generating high score values (highlighted) that should be associated of non- or lowly-productive HPV cycles typical of transformed cells. Of note, weighting coefficients such as αE6 and/or βE7 and/or γE2 and/or δL1 and/or εL2 can be added as parameters, independently, in order to better discriminate, for instance, low risk and high risk lesions.

Example 15: Random RT Vs HPV-Specific RT

As an alternative to the conventional random RT upstream of random amplification, we attempted to define and to use HPV-specific RT primers, with the ultimate goal to achieve a specific HPV enrichment over non-HPV sequences. Such targeted (semi-random) approach may prove extremely important in the perspective of reducing the depth sequencing (that is dependent on the ratio of HPV to non HPV sequences), increasing multiplexing, and reducing costs required before being able to use HTS as a screening test. Although the number of HPV reads remains roughly comparable between the random RT and the HPV-specific RT approaches, a marked difference was observed regarding cellular genes, as exemplified by both PCR (table 4, average ACTB ΔCt −3.01 for HPV RT compared to E7 ΔCt −0.56) and HTS results (table 6, average 3.3 fold reduction for HPV RT, after total reads number correction). In addition to that, HPV6 reads were detectable in the poly-infected sample 117 only when applying the HPV RT approach, thus recovering the results of the Papillocheck gold standard genotyping test. These results, albeit based on a limited number of experimental evidences, suggest a minima that our innovative HPV-specific reverse transcription approach coupled with random amplification is able to reduce the cellular and other non-HPV ballasts, without deteriorate the detection of specific HPV targets. Optimizations of the technique are now required to achieved a strong HPV enrichment and to afford linear quantification.

TABLE 1

Biological samples and associated HPV-genotyping

| Sample | Year of birth | Lesion | HPV typing (Papillocheck) |
|---|---|---|---|
| 117 | 1969 | High grade (HSIL) | 6, 16, 35 |
| 119 | 1986 | High grade (HSIL) | 16 |

TABLE 2

| Seq index | Virus name | Genus name | Species name | GenBank ID | HR αHPV (x) |
|---|---|---|---|---|---|
| 1 | HPV2 | Alpha | Alpha-4 | X55964 | |
| 2 | HPV3 | Alpha | Alpha-2 | X74462 | |
| 3 | HPV6 | Alpha | Alpha-10 | X00203 | |
| 4 | HPV7 | Alpha | Alpha-8 | X74463 | |
| 5 | HPV10 | Alpha | Alpha-2 | X74465 | |
| 6 | HPV11 | Alpha | Alpha-10 | M14119 | |
| 7 | HPV13 | Alpha | Alpha-10 | X62843 | |
| 8 | HPV16 | Alpha | Alpha-9 | K02718 | |
| 9 | HPV16 | Alpha | Alpha-9 | AF536179 | |
| 10 | HPV16 | Alpha | Alpha-9 | HQ644236 | |
| 11 | HPV16 | Alpha | Alpha-9 | AF534061 | |
| 12 | HPV16 | Alpha | Alpha-9 | AF536180 | |
| 13 | HPV16 | Alpha | Alpha-9 | HQ644298 | |
| 14 | HPV16 | Alpha | Alpha-9 | AF472509 | |
| 15 | HPV16 | Alpha | Alpha-9 | HQ644257 | |
| 16 | HPV16 | Alpha | Alpha-9 | AY686579 | x |
| 17 | HPV16 | Alpha | Alpha-9 | AF402678 | |
| 18 | HPV18 | Alpha | Alpha-7 | X05015 | x |
| 19 | HPV18 | Alpha | Alpha-7 | AY262282 | |
| 20 | HPV18 | Alpha | Alpha-7 | EF202146 | |
| 21 | HPV18 | Alpha | Alpha-7 | EF202147 | |
| 22 | HPV18 | Alpha | Alpha-7 | EF202151 | |
| 23 | HPV18 | Alpha | Alpha-7 | GQ180787 | |
| 24 | HPV18 | Alpha | Alpha-7 | EF202155 | |
| 25 | HPV18 | Alpha | Alpha-7 | KC470225 | |
| 26 | HPV18 | Alpha | Alpha-7 | EF202152 | |
| 27 | HPV18 | Alpha | Alpha-7 | KC470229 | |
| 28 | HPV26 | Alpha | Alpha-5 | X74472 | |
| 29 | HPV27 | Alpha | Alpha-4 | X74473 | |
| 30 | HPV28 | Alpha | Alpha-2 | U31783 | |
| 31 | HPV29 | Alpha | Alpha-2 | U31784 | x |
| 32 | HPV30 | Alpha | Alpha-6 | X74474 | |
| 33 | HPV31 | Alpha | Alpha-9 | J04353 | x |
| 34 | HPV32 | Alpha | Alpha-1 | X74475 | |
| 35 | HPV33 | Alpha | Alpha-9 | M12732 | X |
| 36 | HPV34 | Alpha | Alpha-11 | X74476 | |
| 37 | HPV35 | Alpha | Alpha-9 | X74477 | |
| 38 | HPV39 | Alpha | Alpha-7 | M62849 | |
| 39 | HPV40 | Alpha | Alpha-8 | X74478 | x |
| 40 | HPV42 | Alpha | Alpha-1 | M73236 | |
| 41 | HPV43 | Alpha | Alpha-8 | AJ620205 | |
| 42 | HPV44 | Alpha | Alpha-10 | U31788 | |
| 43 | HPV45 | Alpha | Alpha-7 | X74479 | |
| 44 | HPV51 | Alpha | Alpha-5 | M62877 | x |
| 45 | HPV52 | Alpha | Alpha-9 | X74481 | |
| 46 | HPV53 | Alpha | Alpha-6 | X74482 | |
| 47 | HPV54 | Alpha | Alpha-13 | U37488 | |
| 48 | HPV56 | Alpha | Alpha-6 | X74483 | |
| 49 | HPV57 | Alpha | Alpha-4 | X55965 | |
| 50 | HPV58 | Alpha | Alpha-9 | D90400 | |
| Si | HPV59 | Alpha | Alpha-7 | X77858 | x |
| 52 | HPV61 | Alpha | Alpha-3 | U31793 | x |
| 53 | HPV62 | Alpha | Alpha-3 | AY395706 | |
| 54 | HPV66 | Alpha | Alpha-6 | U31794 | |
| 55 | HPV67 | Alpha | Alpha-9 | D21208 | |
| 56 | HPV68 | Alpha | Alpha-7 | X67161 | x |

TABLE 2-continued

| Seq index | Virus name | Genus name | Species name | GenBank ID | HR αHPV (x) |
|---|---|---|---|---|---|
| 57 | HPV69 | Alpha | Alpha-5 | AB027020 | |
| 58 | HPV70 | Alpha | Alpha-7 | U21941 | x |
| 59 | HPV71 | Alpha | Alpha-14 | AB040456 | x |
| 60 | HPV72 | Alpha | Alpha-3 | X94164 | |
| 61 | HPV73 | Alpha | Alpha-11 | X94165 | |
| 62 | HPV74 | Alpha | Alpha-10 | AF436130 | |
| 63 | HPV77 | Alpha | Alpha-2 | Y15175 | |
| 64 | HPV78 | Alpha | Alpha-2 | AB793779 | |
| 65 | HPV81 | Alpha | Alpha-3 | AJ620209 | |
| 66 | HPV82 | Alpha | Alpha-5 | AB027021 | x |
| 67 | HPV83 | Alpha | Alpha-3 | AF151983 | |
| 68 | HPV84 | Alpha | Alpha-3 | AF293960 | x |
| 69 | HPV85 | Alpha | Alpha-7 | AF131950 | |
| 70 | HPV86 | Alpha | Alpha-3 | AF349909 | |
| 71 | HPV87 | Alpha | Alpha-3 | AJ400628 | |
| 72 | HPV89 | Alpha | Alpha-3 | AF436128 | |
| 73 | HPV90 | Alpha | Alpha-14 | AY057438 | x |
| 74 | HPV91 | Alpha | Alpha-8 | AF419318 | |
| 75 | HPV94 | Alpha | Alpha-2 | AJ620211 | |
| 76 | HPV97 | Alpha | Alpha-7 | DQ080080 | |
| 77 | HPV102 | Alpha | Alpha-3 | DQ080083 | |
| 78 | HPV106 | Alpha | Alpha-14 | DQ080082 | |
| 79 | HPV114 | Alpha | Alpha-3 | GQ244463 | |
| 80 | HPV117 | Alpha | Alpha-2 | GQ246950 | |
| 81 | HPV125 | Alpha | Alpha-2 | FN547152 | |
| 82 | HPV160 | Alpha | Alpha-2 | AB745694 | x |

TABLE 3

Primers used for HPV-specific reverse transcription

| Primer name | Sequence (5'->3') | Length (bp) | % GC | Tm | SEQ ID NO. |
|---|---|---|---|---|---|
| HPV16-early | CAGCGGACGT ATTAATAGG | 19 | 47 | 54.5 | SEQ ID NO.153 |
| HPV16-late | TCATATTCCT CCCCATGTC | 19 | 47 | 54.5 | SEQ ID NO.154 |
| HPV18-early-pop1 | AGGGGACGT TATTACCAC | 18 | 50 | 53.7 | SEQ ID NO.155 |
| HPV18-early-pop2 | CAGGGGACGT TATTATCAC | 19 | 47 | 54.5 | SEQ ID NO.156 |
| HPV18-late-pop1 | ATATTCCTCA ACATGTCTGC | 20 | 40 | 53.2 | SEQ ID NO.157 |
| HPV18-late-pop2 | CATATTCTTCA ACATGTCTGC | 21 | 38 | 54.0 | SEQ ID NO.158 |

TABLE 4

Comparative Ct values obtained by PCR after random or HPV-specific reverse transcription

| | Human ACTB | | | E7 HPV16 | | |
|---|---|---|---|---|---|---|
| | Random RT | HPV RT | ΔCt | Random RT | HPV RT | ΔCt |
| Sample 117 | 26.69 | 29.48 | −2.79 | 37.23 | 37.35 | −0.12 |
| Sample 119 | 23.97 | 27.20 | −3.23 | 35.25 | 36.25 | −1.00 |

TABLE 5

Total number of sequencing reads

| | Total reads # (raw) | Quality Filtering |
|---|---|---|
| Sample 117 random RT | 37,055,284 | 34,977,682 |
| Sample 117 HPV RT | 30,607,370 | 28,598,603 |
| Sample 119 random RT | 41,994,892 | 39,675,490 |
| Sample 119 HPV RT | 20,462,884 | 19,383,833 |

TABLE 6

Number of sequencing reads mapping human cellular genes (GRCh37) after random or HPV-specific reverse transcription

| | ACTB | GAPDH | G6PD | HPRT1 | RPLP0 | GUSB | PPIA | KRT19 | CDKN2A | MKI67P1 | TOTAL |
|---|---|---|---|---|---|---|---|---|---|---|---|
| Sample 117 random RT | 731 | 7 | 1 | 32 | 0 | 4 | 4 | 10 | 5 | 0 | 794 |
| Sample 117 HPV RT | 86 | 0 | 0 | 13 | 2 | 2 | 2 | 5 | 11 | 0 | 121 |
| Sample 119 random RT | 546 | 19 | 9 | 183 | 38 | 23 | 50 | 57 | 96 | 0 | 1,021 |
| Sample 119 HPV RT | 47 | 5 | 28 | 146 | 6 | 17 | 50 | 0 | 73 | 12 | 384 |

TABLE 7

Number of sequencing reads mapping HPV CDS

| | Sample 117 | | | | | | Sample 119 | |
|---|---|---|---|---|---|---|---|---|
| HPV | HPV16 | | HPV35 | | HPV6 | | HPV16 | |
| CDS | Rand. RT | HPV RT | Rand. RT | HPV RT | Rand. RT | HPV RT | Rand. RT | HPV RT |
| E6 | 162 | 121 | 0 | 0 | 0 | 0 | 6 | 2 |
| E7 | 91 | 91 | 7 | 0 | 0 | 14 | 9 | 0 |
| E1 | 585 | 862 | 30 | 7 | 0 | 13 | 3 | 3 |

TABLE 7-continued

Number of sequencing reads mapping HPV CDS

| HPV | Sample 117 | | | | | | Sample 119 | |
|---|---|---|---|---|---|---|---|---|
|  | HPV16 | | HPV35 | | HPV6 | | HPV16 | |
| CDS | Rand. RT | HPV RT | Rand. RT | HPV RT | Rand. RT | HPV RT | Rand. RT | HPV RT |
| E2 | 366 | 684 | 22 | 0 | 0 | 0 | 1 | 0 |
| E4 | 29 | 33 | 0 | 0 | 0 | 0 | 0 | 0 |
| E5 | 71 | 70 | 0 | 0 | 0 | 0 | 1 | 0 |
| L2 | 248 | 211 | 12 | 11 | 0 | 0 | 0 | 0 |
| L1 | 305 | 535 | 24 | 47 | 0 | 0 | 0 | 1 |

TABLE 8

Number of sequencing reads mapping spliced HPV16 transcripts

| HPV16 splice transcripts | Genomic coordinates of HPV16 splice sites (NC_001526.2) | | Sample 117 Number of reads at the splice junction | | Sample 119 Number of reads at the splice junction | |
|---|---|---|---|---|---|---|
|  | Spl. Donor | Spl. Accep. | Rand. RT | HPV RT | Rand. RT | HPV RT |
| E6*I | 226 | 409 | 33 | 25 | 0 | 0 |
| E6*II | 226 | 526 | 4 | 0 | 0 | 0 |
| E6*III, E5 | 226 | 3358 | 0 | 0 | 0 | 0 |
| E6*IV | 226 | 2709 | 36 | 23 | 0 | 0 |
| E6^E7 | 226 | 742 | 0 | 0 | 0 | 0 |
| E1C | 880 | 2582 | 0 | 0 | 0 | 0 |
| E1^E4 | 880 | 3358 | 12 | 4 | 0 | 0 |
| E2 | 880 | 2709 | 0 | 2 | 0 | 0 |
| E2C | 1302 | 3358 | 0 | 0 | 0 | 0 |
| L1 | 3632 | 5639 | 0 | 0 | 0 | 0 |
| L1* | 1302 | 5639 | 0 | 0 | 0 | 0 |

Example 16: Summary of Examples 1-15

The method according to the present invention described in the Examples above comprises:
1. Extraction of viral RNAs (Example 6) from a biological sample (Example 3),
2. Reverse transcription of the RNAs into cDNA with random hexamers (Example 7) or primers specific for HPV (Example 8); the design of the primers being illustrated by Example 1 (consensus primer) and Example 5 (HPV16 and HPV18 specific primers). A cDNA quality control is carried out by quantitative PCR (Example 9).
3. Amplification of cDNA by MDA technology with random hexamers (Example 10) to generate a DNA sequence bank (Example 2),
4. High throughput sequencing of the DNA bank and generation of "sequencing reads" (Example 1.1),
5. Aligning reads (Example 12) with the sequences of the HPV genomes present in the database (Example 5). Two analytical strategies are possible (Example 12, results in Example 13):
   a. counting reads aligning with each CDS of interest, or
   b. enumeration of reads aligning only the known splice junctions of each CDS of interest;
6. Computing R score (Example 14) whose the different possible computings are ratios described in Table 9. The ratio is defined as the ratio between the number of reads generated for at least 2 genes described in the present patent application.

Example 17: Detection and Quantification of HPV16 and Human Transcripts 17.1 HPV Database Sixty four (64) genomic sequences representing the HPV alpha genus were retrieved from the International Human Papillomavirus Reference Center (http://www.hpvcenter.se/index.html; updated May 2014). Additional nine (9) sublineage sequences corresponding to HPV16, plus nine (9) sublineage sequences corresponding to HPV18 (described in Burk et al. Virology 2013) were added. The resulting eighty two (82) HPV genomes are referred to as the αHPV database (Table 2 above). A subgroup of the αHPV database composed of sixteen (16) sequences (16, 18, 31, 33, 35, 39, 45, 51, 52, 56, 58, 59, 66, 68, 73 and 82), corresponding to high risk or putative high risk Papillomaviruses, is referred to as the HR αHPV group.

17.2 Delineation of Transcription Maps for HR αHPV

For each sequences of the HR αHPV group, known and putative/predicted splice donor (SD) and splice acceptor (SA) sites were annotated. First, previously documented SD and SA sites for HPV16 and HPV18 were retrieved from Zheng et al. Front Biosci. 2006, Wang et al. Journal of Virology 2011 and Toots et al. PLoS ONE 2014 (FIG. 7, light grey). Based on the idea that virtually all spliced sites are analogous to those previously described for other papillomaviruses (Wang et al. Journal of Virology 2011), the annotation of SA and SD was then expanded to the entire αHPV group by direct analogy (FIG. 7, black numbers). In addition, SA/SD predictions were supported by online splice site prediction software.

17.3 Transcripts Database and Primers Design

A database of short (150 to 500 bp) sequences reconstructed 5' from the splice donor site and 3' from the splice acceptor site was generated, gathering each transcript, part of transcript, or putative transcript for each HR αHPV, and is referred to as the αHPV transcripts database. This database served as a basis for the design of PCR primers. More precisely, a pair of primers was defined for each transcript, part of transcript or putative transcript when possible, with the objective of encompassing the splice junction, as defined in FIG. 7 (the corresponding transcripts appear with suffix 'sp_' in Table 10).

TABLE 10

Primer pairs for HPV16 and human transcripts

| | Transcript targeted | Forward primer | SEQ ID NO. | Reverse primer | SEQ ID NO. |
|---|---|---|---|---|---|
| Human Transcripts | ACTB.E4E5 | CCAGGTCATCACCATTGGCAAT | 159 | CGTACAGGTCTTTGCGGATGT | 160 |
| | AKT1.E2EB | CCATGAGCGACGTGGCTATT | 161 | CTCACGTTGGTCCACATCCT | 162 |
| | B2M.E1E2 | CTGTGCTCGCGCTACTCT | 163 | CAACTTCAATGTCGGATGGATGAAAC | 164 |
| | BCL2.E2E3 | GTGGATGACTGAGTACCTGAACC | 165 | GGCCAAACTGAGCAGAGTCTT | 166 |
| | BRAF.E11E12 | CGGGACTCGAGTGATGATTGG | 167 | CTGAGGTGTAGGTGCTGTCA | 168 |
| | CDH1.E10E11 | CTCCTGAAAAGAGAGTGGAAGTGT | 169 | CCGGATTAATCTCCAGCCAGTT | 170 |
| | CDKN2A.E1E2 | AACGCACCGAATAGTTACGGT | 171 | ACGGGTCGGGTGAGAGT | 172 |
| | CDKN2B.E1E2 | CGGATCCCAACGGAGTCAA | 173 | ACCGGTCGGGTGAGAGT | 174 |
| | ERBB2.E11E12 | TCTTCCAGAACCTGCAAGTAATCC | 175 | GGTGGGTGTTATGGTGGATGA | 176 |
| | FOS.E3E4 | AGGAGAATCCGAAGGGAAAGGAATA | 177 | TCCTTCAGCAGGTTGGCAAT | 178 |
| | GAPDH.E5E6 | AGTCCACTGGCGTCTTCAC | 179 | TGATCTTGAGGCTGTTGTCATACTTC | 180 |
| | GUSB.E10E11 | GCGAGTATGGAGCAGAAACGA | 181 | AATTCCAAATGAGCTCTCCAACCA | 182 |
| | HRAS.E2E3 | CGGAATATAAGCTGGTGGTGGT | 183 | GCACGTCTCCCCATCAATGA | 184 |
| | KRAS.E3E4 | GTGCAATGAGGGACCAGTACA | 185 | CTACTAGGACCATAGGTACATCTTCAGA | 186 |
| | KRT10.E3E4 | GATGAGCTGACCCTGACCAA | 187 | GGCAGCATTCATTTCCACATTCAC | 188 |
| | KRT14.E3E4 | AGGAGCTGGCCTACCTGAA | 189 | CTTCTCATACTGGTCACGCATCT | 190 |
| | KRT17.E1E2 | AACACTGAGCTGGAGGTGAAG | 191 | CTGTAGCAGGATGTTGGCATTG | 192 |
| | MET.E2E3 | TGTGTGCATTCCCTATCAAATATGTCAA | 193 | GCGCTTCACAGCCTGATGA | 194 |
| | MKI67.E6E7 | CGTCGTGTCTCAAGATCTAGCTT | 195 | TGAGTCATCTGCGGTACTGTCT | 196 |
| | MYC.E1E2 | GCTTCTCTGAAAGGCTCTCCTT | 197 | AAATACGGCTGCACCGAGT | 198 |
| | NOTCH1.E31E32 | CCGACGCACAAGGTGTCTT | 199 | GTCGGCGTGTGAGTTGATGA | 200 |
| | PCNA.E4E5 | GACGGAGTGAAATTTTCTGCAAGT | 201 | GAAGTTCAGGTACCTCAGTGCAAA | 202 |
| | PTEN.E8E9 | AGCGTGCAGATAATGACAAGGAA | 203 | GATTTGACGGCTCCTCTACTGT | 204 |
| | RB1.E22E23 | CGGTCTTCATGCAGAGACTGA | 205 | GTGAAATATAGATGTTCCCTCCAGGAAT | 206 |
| | RPLP0.E7E8 | GACGGATTACACCTTCCCACTT | 207 | GACTCTTCCTTGGCTTCAACCTTA | 208 |
| | STAT1.E18E19 | CGATGGGCTCAGCTTTCAGA | 209 | ACAAAACCTCGTCCACGGAAT | 210 |
| | TERT.E10E11 | TCCTGCGTTTGGTGGATGAT | 211 | CCTCGTCTTCTACAGGGAAGTTCA | 212 |
| | TOP2A.E21E22 | TGGGTGGTTCCTGCAAAATCC | 213 | ACATATTGATTTGGAGCCAGTTCTTCA | 214 |
| | TP53.E4E5 | CTGGCCCCTGTCATCTTCTG | 215 | CTTGGCCAGTTGGCAAAACAT | 216 |
| | WNT1.E2E3 | CTGGAACTGTCCCACTGCT | 217 | CAGGATTCGATGGAACCTTCTGA | 218 |
| HPV16 genomic and unspliced transcripts | unsp_226_227 | CACAGAGCTGCAAACAACTATACAT | 219 | CACATACAGCATATGGATTCCCATCTC | 220 |
| | unsp_408_409 | GGAACAACATTAGAACAGCAATACAACA | 221 | TGTCCAGATGTCTTTGCTTTTCTTCA | 222 |
| | unsp_525_526 | CGGTGGACCGGTCGATG | 223 | TCAGTTGTCTCTGGTTGCAAATCT | 224 |
| | unsp_741_742 | CTCAGAGGAGGAGGATGAAATAGATG | 225 | CCATTAACAGGTCTTCCAAAGTACGA | 226 |
| | unsp_880_881 | GGAATTGTGTGCCCCATCTGT | 227 | CATCCATTACATCCCGTACCCT | 228 |
| | unsp_p997_998 | GGTTTTATGTAGAGGCTGTAGTGGAA | 229 | TGTGCAGTAAACAACGCATGTG | 230 |
| | unsp_1301_1302 | GCGGGTATGGCAATACTGAAGT | 231 | TGGTGTTTGGCATATAGTGTGTCTTT | 232 |
| | gen_1553_2056 | ATCAACGTGTTGCGATTGGT | 233 | CTAATAGTAACACAACCATTCCCCATGA | 234 |
| | unsp_p2307_2308 | GAGGTGATTGGAAGCAAATTGTTATGT | 235 | CAGACCCTTGCAGAAATTTCATTAAACT | 236 |
| | unsp_2580_2581 | GGATGTAAAGCATAGACCATTGGTACA | 237 | GTTTTCGTCAAATGGAAACTCATTAGGA | 238 |
| | unsp_2707_2708 | CGGAAATCCAGTGTATGAGCTTAATGAT | 239 | TGACACACATTTAAACGTTGGCAAAG | 240 |
| | unsp_3356_3357 | CATGCGGGTGGTCAGGTAA | 241 | AAGGCGACGGCTTTGGTAT | 242 |
| | unsp_3631_3632 | GCTCACACAAAGGACGGATTAAC | 243 | CCAATGCCATGTAGACGACACT | 244 |
| | gen_3883_4218 | GCGTGCTTTTTGCTTTGCTTTG | 245 | CAGAGGCTGCTGTTATCCACAATA | 246 |
| | unsp_4619_p4620 | TGGGCCCTTCTGATCCTTCTAT | 247 | GGTCAGTGAAAGTGGGATTATTATGTGT | 248 |
| | unsp_p5009_5010 | CTGCTTTTGTAACCACTCCCACTA | 249 | CCTAGAGGTTAATGCTGGCCTATG | 250 |
| | unsp_5408_p5409 | CTTCACATGCAGCCTCACCTA | 251 | GGAATATTGTATGCACCACCAAAAGG | 252 |
| | unsp_5636_5637 | CCTATAGTTCCAGGGTCTCCACAA | 253 | ATCCGTGCTTACAACCTTAGATACTG | 254 |
| | gen_5889_6779 | GGATGACACAGAAAATGCTAGTGCTTA | 255 | CACCTGGATTTACTGCAACATTGG | 256 |
| | unsp_7029_p7030 | ACCTCCAGCACCTAAAGAAGATGA | 257 | GGTGTAGCTTTTCGTTTTCCTAATGAA | 258 |
| HPV16 spliced transcripts | sp_226_409 | CACAGAGCTGCAAACAACTATACAT | 259 | TGTCCAGATGTCTTTGCTTTTCTTCA | 260 |
| | sp_226_526 | CACAGAGCTGCAAACAACTATACAT | 261 | TCAGTTGTCTCTGGTTGCAAATCT | 262 |
| | sp_226_742 | CACAGAGCTGCAAACAACTATACAT | 263 | CCATTAACAGGTCTTCCAAAGTACGA | 264 |
| | sp_226_p1087 | CACAGAGCTGCAAACAACTATACAT | 265 | CACTAAGTGGACTACCAAATACTTTCGT | 266 |
| | sp_226_2581 | CACAGAGCTGCAAACAACTATACAT | 267 | GTTTTCGTCAAATGGAAACTCATTAGGA | 268 |
| | sp_226_2708 | CACAGAGCTGCAAACAACTATACAT | 269 | TGACACACATTTAAACGTTGGCAAAG | 270 |
| | sp_226_3357 | CACAGAGCTGCAAACAACTATACAT | 271 | AAGGCGACGGCTTTGGTAT | 272 |
| | sp_226_p4620 | CACAGAGCTGCAAACAACTATACAT | 273 | GGTCAGTGAAAGTGGGATTATTATGTGT | 274 |
| | sp_226_p5409 | CACAGAGCTGCAAACAACTATACAT | 275 | GGAATATTGTATGCACCACCAAAAGG | 276 |
| | sp_226_5637 | CACAGAGCTGCAAACAACTATACAT | 277 | ATCCGTGCTTACAACCTTAGATACTG | 278 |
| | sp_226_p7030 | CACAGAGCTGCAAACAACTATACAT | 279 | GGTGTAGCTTTTCGTTTTCCTAATGAA | 280 |
| | sp_880_p1087 | GGAATTGTGTGCCCCATCTGT | 281 | CACTAAGTGGACTACCAAATACTTTCGT | 282 |
| | sp_880_2581 | GGAATTGTGTGCCCCATCTGT | 283 | GTTTTCGTCAAATGGAAACTCATTAGGA | 284 |
| | sp_880_2708 | GGAATTGTGTGCCCCATCTGT | 285 | TGACACACATTTAAACGTTGGCAAAG | 286 |

TABLE 10-continued

Primer pairs for HPV16 and human transcripts

| Transcript targeted | Forward primer | SEQ ID NO. | Reverse primer | SEQ ID NO. |
|---|---|---|---|---|
| | sp_880_3357 | GGAATTGTGTGCCCCATCTGT | 287 | AAGGCGACGGCTTTGGTAT | 288 |
| | sp_880_p4620 | GGAATTGTGTGCCCCATCTGT | 289 | GTGTCTAGTGTAATAGTGTGTGATTTATTATGTGT | 290 |
| | sp_880_p5409 | GGAATTGTGTGCCCCATCTGT | 291 | GGTAATATTTGTTATTGCACCACCTAAAAGG | 292 |
| | sp_880_5637 | GGAATTGTGTGCCCCATCTGT | 293 | ATTCCGTTGTCTTTACTATACCTTTAGTATTACTTG | 294 |
| | sp_880_p7030 | GGAATTGTGTGCCCCATCTGT | 295 | GGTGTAGCTTTTTTTCGTTTTCTAATGTTTAA | 296 |
| | sp_p997_p1087 | GGTTTTATGTAGAGGCTGTAGTGGAA | 297 | CACTAAGTGGACTACCAAATACTTTCGT | 298 |
| | sp_p997_2581 | GGTTTTATGTAGAGGCTGTAGTGGAA | 299 | GTTTTCGTCAAATGGAAACTCATTAGGA | 300 |
| | sp_p997_2708 | GGTTTTATGTAGAGGCTGTAGTGGAA | 301 | TGACACACATTTAAACGTTGGCAAAG | 302 |
| | sp_p997_3357 | GGTTTTATGTAGAGGCTGTAGTGGAA | 303 | AAGGCGACGGCTTTGGTAT | 304 |
| | sp_p997_p4620 | GGTTTTATGTAGAGGCTGTAGTGGAA | 305 | GGTCAGTGAAAGTGGGATTATTATGTGT | 306 |
| | sp_p997_p5409 | GGTTTTATGTAGAGGCTGTAGTGGAA | 307 | GGTAATATTTGTTATTGCACCACCTAAAAGG | 308 |
| | sp_p997_5637 | GGTTTTATGTAGAGGCTGTAGTGGAA | 309 | ATCCGTGTCTTTACTAACTCTTAGATACTG | 310 |
| | sp_p997_p7030 | GGTTTTATGTAGAGGCTGTAGTGGAA | 311 | GGTGTAGCTTTfTTCGTTTTTTCCTTTAATTGTTTAA | 312 |
| | sp_1301_2581 | GCGGGTATGGCAATACTGAAGT | 313 | GTTTTCGTCAAATGGAAACTCATTAGGA | 314 |
| | sp_1301_2708 | GCGGGTATGGCAATACTGAAGT | 315 | TGACACACATTTAAACGTTGGCAAAG | 316 |
| | sp_1301_3357 | GCGGGTATGGCAATACTGAAGT | 317 | AAGGCGACGGCTTTGGTAT | 318 |
| | sp_1301_5637 | GCGGGTATGGCAATACTGAAGT | 319 | ATCCGTGTCTTTACTAACCTTAGTATTACTG | 320 |
| | sp_1301_p4620 | GCGGGTATGGCAATACTGAAGT | 321 | GGTCAGTGAAAGTGGGATTATTATGTGT | 322 |
| | sp_1301_p5409 | GCGGGTATGGCAATACTGAAGT | 323 | GGTAATATTTGTATTGCACCACCAAAAGG | 324 |
| | sp_1301_p7030 | GCGGGTATGGCAATACTGAAGT | 325 | GGTGTAGCTTTTTTCGTTTTTTCCTAATGTAA | 326 |
| | sp_p2307_2708 | GAGGTGATTGGAAGCAAATTGTTATGT | 327 | TGACACACATTTAAACGTTGGCAAAG | 328 |
| | sp_p2307_3357 | GAGGTGATTGGAAGCAAATTGTTATGT | 329 | AAGGCGACGGCTTTGGTAT | 330 |
| | sp_p2307_5637 | GAGGTGATTGGAAGCAAATTGTTATGT | 331 | ATTCCGTGCTTTACTATACCTTTAGTATTACTG | 332 |
| | sp_p2307_p4620 | GAGGTGATTGGAAGCAAATTGTTATGT | 333 | GGTCAGTGAAAGTGGGATTATTATGTGT | 334 |
| | sp_p2307_p5409 | GAGGTGATTGGAAGCAAATTGTTATGT | 335 | GGAATATTGTATGCACCACCAAAAGG | 336 |
| | sp_p2307_p7030 | GAGGTGATTGGAAGCAAATTGTTATGT | 337 | GGTGTAGCTTTTTCGTTTTTCCTTTAATTGTTTAA | 338 |
| | sp_3631_5637 | GCTCACACAAAGGACGGATTAAC | 339 | ATCCGTGCTTACAACCTTAGATACTG | 340 |
| | sp_3631_p4620 | GCTCACACAAAGGACGGATTAAC | 341 | GGTCAGTGAAAGTGGGATTATTATGTGT | 342 |
| | sp_3631_p5409 | GCTCACACAAAGGACGGATTAAC | 343 | GGAATATTGTATGCACCACCAAAAGG | 344 |
| | sp_3631_p7030 | GCTCACACAAAGGACGGATTAAC | 345 | GGTTGTTAGCTTTTTCGTTTTTTCCTTTAATTGTTTAA | 346 |
| | sp_p5009_p5409 | CTGCTTTTGTAACCACTCCCACTA | 347 | GGAATATTGTATGCACCACCAAAAGG | 348 |
| | sp_p5009_5637 | CTGCTTTTGTAACCACTCCCACTA | 349 | ATCCGTGCTTACAACCTTAGATACTG | 350 |
| | sp_p5009_p7030 | CTGCTTTTGTAACCACTCCCACTA | 351 | GGTGTAGCTTTTTTCGTTTTCCTAATGTAA | 352 |
| HPV16-human fusion transcripts | fus_880_MYC_001_exon1 | GGAATTGTGTGCCCCATCTGT | 353 | CTGAGAAGCCCTGCCCTTC | 354 |
| | fus_880_MYC_001_exon2 | GGAATTGTGTGCCCCATCTGT | 355 | AAATACGGCTGCACCGAGT | 356 |
| | fus_880_MYC_001_exon3 | GGAATTGTGTGCCCCATCTGT | 357 | GGTTGATTCCAGTACTTCTTGTACCTTTTG | 358 |
| | fus_880_PVT1_002_exon3 | GGAATTGTGTGCCCCATCTGT | 359 | ATCATGATGGCTGTATGTGCCA | 360 |
| | fus_880_PVT1_004_exon1 | GGAATTGTGTGCCCCATCTGT | 361 | CATTGTGTTTCCTACCTAGTCGTTTATT | 362 |
| | fUS_880_PVT1_005_exon1 | GGAATTGTGTGCCCCATCTGT | 363 | TCTTTGCTCGCAGCTCGT | 364 |
| | fus_2869_MYC_001_exon1 | AGTACAGACCTACGTGACCATATAGAC | 365 | CTGAGAAGCCCTGCCCTTC | 366 |
| | fus_2869_MYC_001_exon2 | AGTACAGACCTACGTGACCATATAGAC | 367 | AAATACGGCTGCACCGAGT | 368 |
| | fus_2869_MYC_001_exon3 | AGTACAGACCTACGTGACCATATAGAC | 369 | GGTGATCCAGALTC1GACCTTTTG | 370 |
| | fus_2869_PVT1_002_exon3 | AGTACAGACCTACGTGACCATATAGAC | 371 | ATCATGATGGCTGTATGTGCCA | 372 |
| | fus_2869_PVT1_004_exon1 | AGTACAGACCTACGTGACCATATAGAC | 373 | CATGGTTCCACCAGCGTTATT | 374 |
| | fus_2869_PVT1_005_exon1 | AGTACAGACCTACGTGACCATATAGAC | 375 | TCTTTGCTCGCAGCTCGT | 376 |

In particular, the nearest neighbor splice sites have been taken into consideration in order to minimize risks of co-amplifying several spliced isoforms with a given couple of primers. Additional primers pairs were defined, when possible, to amplify the boundaries at the 5'-SD-genomic and genomic-SA-3' positions (suffix 'unsp_') to allow for a better quantitative monitoring of concomitant spliced and/or genomic/unspliced transcription events and refine if necessary the description of transcripts equilibrium in the course of HPV infection. To complete this view and provide extra controls, primers were also designed within some HPV genomic regions lacking known SD/SA sites (suffix 'gen_'), meaning that the detection of such sequences could result only from locally unspliced transcription or DNA contamination. A selection of human transcripts has been included in the design as well for normalization purposes and/or to support or improve a combination of human and/or HPV transcripts being able to discriminate low grade vs high grade lesions of the cervix. Of note, extra fusion transcripts ('fus_') were investigated and primers were conceived following HPV breakpoint hypothesis in the context of HPV integration within the two human locus MYC and PTV1, as discussed for example in Lu et al. PLoS ONE 2014, Tang et al. Nature Communication 2013, Wentzensen et al. Oncogene 2002 or Peter et al. Oncogene 2006. In this case, forward primers were located 5' of HPV breakpoints (see FIG. 7) and reverse primers designed within the targeted human exons, thus allowing for the detection and fine characterization of hybrid HPV-human transcripts.

17.4 Biological Samples and Cell Line

Two high grade lesions (HSIL) samples of the cervix from two donor women, hereinafter referred to as 610 and 729, were collected in PreservCyt medium (Hologic) and kept at room temperature for a couple of days. After homogenization, 1 mL aliquots were collected from the 20 μL total liquid medium for HPV genotyping (Papillocheck, Greiner Bio-One). Results of HPV typing are given in Table 11.

TABLE 11

HPV16 mono-infected samples from patients

| Sample | Year of birth | Lesion | HPV typing (Papillocheck) |
|---|---|---|---|
| 610 | 1985 | High grade (HSIL) | 16 |
| 729 | 1950 | High grade (HSIL) | 16 |

The remaining samples were centrifuged at 4,500×g for 10 min and the pellets were stored at −80° C. before RNA extraction. In addition, SiHa cells (HPV16 genomic integration) were cultured and harvested, providing another source of RNA.

17.5 RNA Extraction and Characterization

Total RNA from samples 610 and 729 were extracted using the PicoPure RNA isolation kit (Life Technologies), adding a DNAse treatment step directly on column (RNAse-free DNAse set, Qiagen) as recommended by the supplier. Elution was achieved in 30 μL elution buffer. Assessment of RNA quantity and quality was done with a Nanodrop 1000 (Thermo Scientist) and a Bioanalyzer 2100 using the RNA Nano chips (Agilent).

17.6 Random Reverse Transcription

Random reverse transcription of total RNA was carried out using the SuperScript III First-Strand cDNA Synthesis kit (Invitrogen). Briefly, 2 μL of total RNA was used for template and the reaction was performed in the presence of 50 nM random hexamers (provided by Invitrogen), incubated 10 min at 25° C., 60 min at 50° C. and 5 min at 85° C. before a final RNAse H treatment 20 min at 37° C. The resulting cDNA were immediately amplified using the multiplex approach described below.

17.7 Multiplex Amplification of Specific Transcripts

Amplification of HPV along with human transcripts was performed from the cDNA of samples 610, 729 and SiHa using a mixture of primers (appropriate for AmpliSeg™ technology; Life technologies) in a multiplex-manner, by a 20 cycles of amplification reaction. Following amplification, sequencing libraries were constructed (Life technologies) and validated on a Bioanalyzer 2100 before sequencing.

17.8 High Throughput Sequencing and Data Analysis

Samples 610, 729 and SiHa were sequenced on an Ion PGM apparatus using an Ion 118 chip (Life Technologies). FastQ data were generated and QC tests done following standard procedures. For each sample, sequencing reads were trimmed according to their Phred quality score then mapped to the HPV transcripts database using Bowtie 2 (Langmead et al. Nature Methods 2012). For spliced transcripts, alignments that did not encompass the splice junction were removed from the analysis. The number of reads for each sample is detailed in Table 12.

TABLE 12

Reads number for HPV16 and human transcripts

| | Transcript targeted | 610 | 729 | SiHa |
|---|---|---|---|---|
| Human transcripts | ACTB.E4E5 | 258790 | 81325 | 53371 |
| | AKT1.E2E3 | 837 | 3517 | 1412 |
| | B2M.E1E2 | 73613 | 101287 | 14808 |
| | BCL2.E2E3 | 80 | 937 | 1 |
| | BRAF.E11E12 | n.d. | 5509 | 1447 |
| | CDH1.E10E11 | n.d. | 37368 | 2018 |
| | CDKN2A.E1E2 | 137 | 300 | 365 |
| | CDKN2B.E1E2 | n.d. | 57289 | 2958 |
| | ERBB2.E11E12 | n.d. | 73226 | 2159 |
| | FOS.E3E4 | n.d. | 8966 | 9397 |
| | GAPDH.E5E6 | 79755 | 52860 | 70892 |
| | GUSB.E10E11 | 137 | 226 | 112 |
| | HRAS.E2E3 | 65 | 700 | 181 |
| | KRAS.E3E4 | n.d. | 1006 | 474 |
| | KRT10.E3E4 | 374 | 412 | 0 |
| | KRT14.E3E4 | 38273 | 6019 | 86442 |
| | KRT17.E1E2 | n.d. | 21485 | 260630 |
| | MET.E2E3 | n.d. | 1361 | 308 |
| | MKI67.E6E7 | 1 | 4 | 1210 |
| | MYC.E1E2 | 0 | 112 | 223 |
| | NOTCH1.E31E32 | n.d. | 15301 | 1420 |
| | PCNA.E4E5 | 116 | 609 | 1262 |
| | PTEN.E8E9 | n.d. | 1568 | 1392 |
| | RB1.E22E23 | n.d. | 2807 | 2571 |
| | RPLP0.E7E8 | 32454 | 38380 | 5104 |
| | STAT1.E18E19 | n.d. | 12373 | 7993 |
| | TERT.E10E11 | n.d. | 0 | 628 |
| | TOP2A.E21E22 | 8 | 15 | 4267 |
| | TP53.E4E5 | n.d. | 11798 | 5551 |
| | WNT1.E2E3 | n.d. | 0 | 0 |
| HPV16 genomic and unspliced transcripts | unsp_226_227 | n.d. | 0 | 9180 |
| | unsp_408_409 | 61 | 0 | 18 |
| | unsp_525_526 | 1122 | 2 | 2871 |
| | unsp_741_742 | 2102 | 2 | 1651 |
| | unsp_880_881 | n.d. | 0 | 1079 |
| | unsp_p997_998 | 1610 | 0 | 383 |
| | unsp_1301_1302 | 140 | 2 | 592 |
| | gen_1553_2056 | 1740 | 1 | 297 |
| | unsp_p2307_2308 | 7923 | 1 | 608 |
| | unsp_2580_2581 | 11800 | 1 | 881 |
| | unsp_2707_2708 | 25162 | 2 | 828 |
| | unsp_3356_3357 | 2996 | 0 | 0 |
| | unsp_3631_3632 | 10497 | 2 | 0 |
| | gen_3883_4218 | 1661 | 0 | 2 |
| | unsp_4619_p4620 | 2685 | 0 | 0 |
| | unsp_p5009_5010 | 1619 | 1 | 0 |
| | unsp_5408_p5409 | 1690 | 0 | 1 |
| | unsp_5636_5637 | 3047 | 0 | 0 |
| | gen_5889_6779 | 1356 | 0 | 0 |
| | unsp_7029_p7030 | 5794 | 1 | 0 |
| HPV16 spliced transcripts | sp_226_409 | n.d. | 7 | 905 |
| | sp_226_526 | n.d. | 0 | 568 |
| | sp_226_742 | n.d. | 0 | 39 |
| | sp_226_p1087 | n.d. | 0 | 0 |
| | sp_226_2581 | n.d. | 0 | 0 |
| | sp_226_2708 | n.d. | 0 | 3 |
| | sp_226_3357 | n.d. | 0 | 0 |
| | sp_226_p4620 | n.d. | 0 | 0 |
| | sp_226_p5409 | n.d. | 0 | 0 |
| | sp_226_5637 | n.d. | 0 | 0 |
| | sp_226_p7030 | n.d. | 0 | 0 |
| | sp_880_p1087 | n.d. | 0 | 0 |
| | sp_880_2581 | 0 | 0 | 4 |
| | sp_880_2708 | 29 | 0 | 92 |
| | sp_880_3357 | 11874 | 2 | 0 |

TABLE 12-continued

Reads number for HPV16 and human transcripts

| | Transcript targeted | 610 | 729 | SiHa |
|---|---|---|---|---|
| | sp_880_p4620 | 0 | 0 | 0 |
| | sp_880_p5409 | 0 | 0 | 0 |
| | sp_880_5637 | 0 | 0 | 0 |
| | sp_880_p7030 | 0 | 0 | 0 |
| | sp_p997_p1087 | n.d. | 0 | 0 |
| | sp_p997_2581 | 0 | 0 | 0 |
| | sp_p997_2708 | 0 | 0 | 0 |
| | sp_p997_3357 | 0 | 0 | 0 |
| | sp_p997_p4620 | 0 | 0 | 0 |
| | sp_p997_p5409 | 0 | 0 | 0 |
| | sp_p997_5637 | 0 | 0 | 0 |
| | sp_p997_p7030 | 0 | 0 | 0 |
| | sp_1301_2581 | 0 | 0 | 0 |
| | sp_1301_2708 | 0 | 0 | 0 |
| | sp_1301_3357 | 0 | 0 | 0 |
| | sp_1301_5637 | 0 | 0 | 0 |
| | sp_1301_p4620 | 0 | 0 | 0 |
| | sp_1301_p5409 | 0 | 0 | 0 |
| | sp_1301_p7030 | 0 | 0 | 0 |
| | sp_p2307_2708 | 0 | 0 | 0 |
| | sp_p2307_3357 | 0 | 0 | 0 |
| | sp_p2307_5637 | 0 | 0 | 0 |
| | sp_p2307_p4620 | 0 | 0 | 0 |
| | sp_p2307_p5409 | 0 | 0 | 0 |
| | sp_p2307_p7030 | 0 | 0 | 0 |
| | sp_3631_5637 | 30 | 0 | 0 |
| | sp_3631_p4620 | 0 | 0 | 0 |
| | sp_3631_p5409 | 0 | 0 | 0 |
| | sp_3631_p7030 | 0 | 0 | 0 |
| | sp_p5009_p5409 | 0 | 0 | 0 |
| | sp_p5009_5637 | 0 | 0 | 0 |
| | sp_p5009_p7030 | 0 | 0 | 0 |
| HPV16-human fusion transcripts | fus_880_MYC_001_exon1 | 0 | 0 | 0 |
| | fus_880_MYC_001_exon2 | 0 | 0 | 0 |
| | fus_880_MYC_001_exon3 | 0 | 0 | 0 |
| | fus_880_PVT1_002_exon3 | 0 | 0 | 0 |
| | fus_880_PVT1_004_exon1 | 0 | 0 | 0 |
| | fus_880_PVT1_005_exon1 | 0 | 0 | 0 |
| | fus_2869_MYC_001_exon1 | 0 | 0 | 0 |
| | fus_2869_MYC_001_exon2 | 0 | 0 | 0 |
| | fus_2869_MYC_001_exon3 | 0 | 0 | 0 |
| | fus_2869_PVT1_002_exon3 | 0 | 0 | 0 |
| | fus_2869_PVT1_004_exon1 | 0 | 0 | 0 |
| | fus_2869_PVT1_005_exon1 | 0 | 0 | 0 |

17.9 Multiplex Amplification and Quantification of HPV16 Transcripts

As a proof of principle, it was sought to discriminate 47 spliced transcripts ('sp_'), 16 unspliced transcripts ('unsp_'), 3 genomic transcripts ('gen_'), 12 putative HPV-human fusion transcripts ('fus_'), plus additional 30 human transcripts, from mono-infected HPV16 samples (samples 610 and 729) and SiHa cells. To ensure amplification specificity, the design has been checked for its lack of cross-match against the HPV database in addition to the human genome and transcripts databases. Primers are detailed in Table 10. Reads number following QC, mapping and validation of the splice junction are detailed in Table 12.

17.10 Results: Detection and Quantification of HPV16 and Human Transcripts

The experiment showed that (i) specific human transcripts, as internal and/or normalization controls, were detected in samples 610, 729 and SiHa with expression levels varying between transcripts and from one sample to another, thus validating the integrity of starting RNA material and the effectiveness of subsequent multiplex amplification steps (ii) specific spliced ('sp_') and unspliced ('unsp_') HPV16 transcripts were successfully detected and characterized in samples 610, 729 and SiHa, albeit in a variable proportion between samples, supporting the quantitative variations of specific HPV16 transcripts or transcription events between biological samples, (iii) in particular, sample SiHa exhibited no or rare genomic ('gen_'), unspliced ('unsp_') and spliced ('sp_') transcripts reads beyond genomic position 3356, which appeared consistent with the loss of viral late genes following HPV16 integration into the genome of SiHa cells, and (iv) it thus demonstrated the capability of the method to accurately differentiate between non-replicative, integrative HPV16 infection stages often associated with higher levels of E6/E7 transcripts (in this particular case sp_226_409, sp_226_526 and sp_226_742, see Table 12), from other anterior, HPV16-induced transformation and/or proliferation steps which usually imply transcription of the E2 and/or L1 and/or L2 genes (see as an example sp_880_3357 in Table 12). Consequently, specific HPV16 spliced transcripts and/or HPV16 unspliced transcripts and/or HPV16 genomic transcripts and/or HPV16-human fusion transcripts can be weighted to compute a score, or score ratio, discriminating different stages of interaction of HPV16 with infected cells, in particular the early vs late stages of HPV16 cycle, and/or the integrative vs non integrative forms of the HPV16 genome into infected cells, which are events associated to cell transformation. More generally, these results suggest that the method can be extended and applied to all HR αHPV.

17.11 Examples of R Scores

These observations reinforce the possibly to define a score, referred to as R score, based on specific HPV transcripts counts as a molecular marker of any individual HPV-positive samples. From this perspective, either one value or a combination of more than one ratio(s) could be used as a marker of the viral-cell interactions that shapes the transformation process. A non-restrictive list of R scores is given in Table 13 in order to illustrate several possible combinations based on specific HPV16 transcripts.

TABLE 13

Examples of R scores

| R scores (examples) | 610 | 729 | SiHa |
|---|---|---|---|
| sp_226_409/sp_880_2708 | n.d. | +∞ | 9.83 |
| sp_880_2581/sp_3631_5637 | 0 | n.a. | +∞ |
| sp_880_2708/sp_3631_5637 | 0.96 | n.a. | +∞ |
| sp_880_3357/sp_3631_5637 | 395.8 | +∞ | n.a. |
| unsp_741_742/unsp_p5009_5010 | 1.29 | 2 | +∞ |

As an example, R scores based on a ratio sp_226_409/sp_880_2708 and/or sp_880_2581/sp_3631_5637 and/or sp_880_2708/sp_3631_5637 and/or sp_880_3357/sp_3631_5637 and/or unsp_741_742/unsp_p5009_5010 succeeded in generating high score values (e.g.: +∞) that are associated with non- or lowly-productive HPV cycles typical of transformed cells. Of note, weighting coefficients such as α(sp_226_409/sp_880_2708) and/or β(sp_880_2581/sp_3631_5637) and/or γ(sp_880_2708/sp_3631_5637) and/or δ(sp_880_3357/sp_3631_5637) and/or ε(unsp_741_742/unsp_p5009_5010) can be added as parameters, independently, in order to better discriminate, for instance, low risk and high risk lesions.

17.12 Extension of the Method to the HR αHPV Group

The method was extended to the entire HR αHPV group (i.e.: HPV16, 18, 31, 33, 35, 39, 45, 51, 52, 56, 58, 59, 66, 68, 73 and 82) based on the transcription map described in FIG. 7. Primers resulting from this improved design are listed in Table 14.

TABLE 14

Primer pairs for HR aHPV group and human transcripts

| Virus name | Transcript targeted | Forward primer (5'-3') | SEQ ID NO | Reverse primer (5'-3') | SEQ ID NO |
|---|---|---|---|---|---|
| HVP16 | 16_fus_2869_PVT1_005_exon1 | AGTACAGACCTACGTGACCATATAGAC | 377 | TCTTTGCTCGCAGCTCGT | 378 |
| HVP16 | 16_sp_1301_2581 | GCGGGTATGGCAATACTGAAGT | 379 | GTTTTCGTCAAATGGAAACTCATTAGGA | 380 |
| HVP16 | 16_sp_226_742 | CACAGAGCTGCAAACAACTATACAT | 381 | CCATTAACAGGTCTTCCAAAGTACGA | 382 |
| HVP16 | 16_unsp_525_526 | CGGTGGACCGGTCGATG | 383 | TCAGTTGTCTCTGGTTGCAAATCT | 384 |
| HVP16 | 16_unsp_1301_1302 | GCGGGTATGGCAATACTGAAGT | 385 | TGGTGTTTGGCATATAGTGTGTCTTT | 386 |
| HVP16 | 16_sp_880_2581 | GGAATTGTGTGCCCCATCTGT | 387 | GTTTTCGTCAAATGGAAACTCATTAGGA | 388 |
| HVP16 | 16_fus_2869_MYC_001_exon2 | AGTACAGACCTACGTGACCATATAGAC | 389 | AAATACGGCTGCACCGAGT | 390 |
| HVP16 | 16_fus_3619_PVT1_005_exon1 | GCTCACACAAAGGACGGATTAAC | 391 | TCTTTGCTCGCAGCTCGT | 392 |
| HVP16 | 16_fus_880_PVT1_005_exon1 | GGAATTGTGTGCCCCATCTGT | 393 | TCTTTGCTCGCAGCTCGT | 394 |
| HVP16 | 16_unsp_226_227 | CACAGAGCTGCAAACAACTATACAT | 395 | CACATACAGCATATGGATTCCCATCTC | 396 |
| HVP16 | 16_sp_226_409 | CACAGAGCTGCAAACAACTATACAT | 397 | TGTCCAGATGTCTTTGCTTTTCTTCA | 398 |
| HVP16 | 16_sp_880_3357 | GGAATTGTGTGCCCCATCTGT | 399 | AAGGCGACGGCTTTGGTAT | 400 |
| HVP16 | 16_unsp_2580_2581 | GGATGTAAAGCATAGACCATTGGTACA | 401 | GTTTTCGTCAAATGGAAACTCATTAGGA | 402 |
| HVP16 | 16_fus_2869_MYC_001_exon3 | AGTACAGACCTACGTGACCATATAGAC | 403 | GGTGATCCAGACTCTGACCTTTTG | 404 |
| HVP16 | 16_fus_2869_PVT1_002_exon3 | AGTACAGACCTACGTGACCATATAGAC | 405 | ATCATGATGGCTGTATGTGCCA | 406 |
| HVP16 | 16_unsp_3631_3632 | GCTCACACAAAGGACGGATTAAC | 407 | CCAATGCCATGTAGACGACACT | 408 |
| HVP16 | 16_fus_3619_PVT1_004_exon1 | GCTCACACAAAGGACGGATTAAC | 409 | CATGGTTCCACCAGCGTTATT | 410 |
| HVP16 | 16_fus_880_MYC_001_exon3 | GGAATTGTGTGCCCCATCTGT | 411 | GGTGATCCAGACTCTGACCTTTTG | 412 |
| HVP16 | 16_sp_226_2581 | CACAGAGCTGCAAACAACTATACAT | 413 | GTTTTCGTCAAATGGAAACTCATTAGGA | 414 |
| HVP16 | 16_sp_1301_2708 | GCGGGTATGGCAATACTGAAGT | 415 | TGACACACATTTAAACGTTGGCAAAG | 416 |
| HVP16 | 16_fus_880_PVT1_002_exon3 | GGAATTGTGTGCCCCATCTGT | 417 | ATCATGATGGCTGTATGTGCCA | 418 |
| HVP16 | 16_sp_3631_5637 | GCTCACACAAAGGACGGATTAAC | 419 | ATCCGTGCTTACAACCTTAGATACTG | 420 |
| HVP16 | 16_unsp_3356_3357 | CATGCGGGTGGTCAGGTAA | 421 | AAGGCGACGGCTTTGGTAT | 422 |
| HVP16 | 16_unsp_5636_5637 | CCTATAGTTCCAGGGTCTCCACAA | 423 | ATCCGTGCTTACAACCTTAGATACTG | 424 |
| HVP16 | 16_fus_880_PVT1_004_exon1 | GGAATTGTGTGCCCCATCTGT | 425 | CATGGTTCCACCAGCGTTATT | 426 |
| HVP16 | 16_fus_2869_MYC_001_exon1 | AGTACAGACCTACGTGACCATATAGAC | 427 | CTGAGAAGCCCTGCCCTTC | 428 |

TABLE 14 -continued

Primer pairs for HR aHPV group and human transcripts

| Virus name | Transcript targeted | Forward primer (5'-3') | SEQ ID NO | Reverse primer (5'-3') | SEQ ID NO |
|---|---|---|---|---|---|
| HVP16 | 16_unsp_2707_2708 | CGGAAATCCAGTGTATGAGCTTAATGAT | 429 | TGACACACATTTAAACGTTGGCAAAG | 430 |
| HVP16 | 16_sp_226_3357 | CACAGAGCTGCAAACAACTATACAT | 431 | AAGGCGACGGCTTTGGTAT | 432 |
| HVP16 | 16_fus_3619_MYC_001_exon1 | GCTCACACAAAGGACGGATTAAC | 433 | CTGAGAAGCCCTGCCCTTC | 434 |
| HVP16 | 16_sp_1301_3357 | GCGGGTATGGCAATACTGAAGT | 435 | AAGGCGACGGCTTTGGTAT | 436 |
| HVP16 | 16_sp_880_5637 | GGAATTGTGTGCCCCATCTGT | 437 | ATCCGTGCTTACAACCTTAGATACTG | 438 |
| HVP16 | 16_unsp_741_742 | CTCAGAGGAGGAGGATGAAATAGATG | 439 | CCATTAACAGGTCTTCCAAAGTACGA | 440 |
| HVP16 | 16_fus_880_MYC_001_exon2 | GGAATTGTGTGCCCCATCTGT | 441 | AAATACGGCTGCACCGAGT | 442 |
| HVP16 | 16_fus_3619_MYC_001_exon3 | GCTCACACAAAGGACGGATTAAC | 443 | GGTGATCCAGACTCTGACCTTTTG | 444 |
| HVP16 | 16_fus_880_MYC_001_exon1 | GGAATTGTGTGCCCCATCTGT | 445 | CTGAGAAGCCCTGCCCTTC | 446 |
| HVP16 | 16_unsp_408_409 | GGAACAACATTAGAACAGCAATACAACA | 447 | TGTCCAGATGTCTTTGCTTTTCTTCA | 448 |
| HVP16 | 16_unsp_880_881 | GGAATTGTGTGCCCCATCTGT | 449 | CATCCATTACATCCCGTACCCT | 450 |
| HVP16 | 16_fus_3619_PVT1_002_exon3 | GCTCACACAAAGGACGGATTAAC | 451 | ATCATGATGGCTGTATGTGCCA | 452 |
| HVP16 | 16_sp_226_2708 | CACAGAGCTGCAAACAACTATACAT | 453 | TGACACACATTTAAACGTTGGCAAAG | 454 |
| HVP16 | 16_sp_880_2708 | GGAATTGTGTGCCCCATCTGT | 455 | TGACACACATTTAAACGTTGGCAAG | 456 |
| HVP16 | 16_fus_3619_MYC_001_exon2 | GCTCACACAAAGGACGGATTAAC | 457 | AAATACGGCTGCACCGAGT | 458 |
| HVP16 | 16_sp_226_526 | CACAGAGCTGCAAACAACTATACAT | 459 | TCAGTTGTCTCTGGTTGCAAATCT | 460 |
| HVP16 | 16_fus_2869_PVT1_004_exon1 | AGTACAGACCTACGTGACCATATAGAC | 461 | CATGGTTCCACCAGCGTTATT | 462 |
| HVP16 | 16_gen_3881_4212 | CGTGCTTTTTGCTTTGCTTTGT | 463 | GAGGCTGCTGTTATCCACAATAGTAAT | 464 |
| HVP16 | 16_gen_5887_7259 | CCTGTGTAGGTGTTGAGGTAGGT | 465 | TCTATTATCCACACCTGCATTTGCT | 466 |
| HVP16 | 16_gen_1551_2331 | AACGTGTTGCGATTGGTGTATTG | 467 | CATTCCCCATGAACATGCTAAACTTTG | 468 |
| HVP16 | 16_gen_7266_7904 | CCAGGCCCATTTTGTAGCTT | 469 | AGGTCAGGAAAACAGGGATTTGG | 470 |
| HVP18 | 18_unsp_2650_2651 | CTAAAATGTCCTCCAATACTACTAACCACAA | 471 | GTCATTTATTTCATATACTGGATTGCCA | 472 |
| HVP18 | 18_sp_929_2651 | TGCATCCCAGCAGTAAGCAA | 473 | GTCATTTATTTCATATACTGGATTGCCA | 474 |
| HVP18 | 18_unsp_3165_3166 | GGATTGGACACTGCAAGACACA | 475 | CCCATGCTACATAGGTCATACAATTGTC | 476 |
| HVP18 | 18_sp_3165_3465 | GGATTGGACACTGCAAGACACA | 477 | ACGTCTGGCCGTAGGTCT | 478 |
| HVP18 | 18_unsp_790_791 | CAGAGGAAGAAAACGATGAAATAGATGG | 479 | AGAAACAGCTGCTGGAATGCT | 480 |

TABLE 14 -continued

Primer pairs for HR aHPV group and human transcripts

| Virus name | Transcript targeted | Forward primer (5'-3') | SEQ ID NO | Reverse primer (5'-3') | SEQ ID NO |
|---|---|---|---|---|---|
| HVP18 | 18_unsp_5612_5613 | TCCTAAGAAACGTAAACGTGTTCCC | 481 | GTATTTACAACTCTTGCCACAGAAGGA | 482 |
| HVP18 | 18_sp_1357_2651 | TCAGATAGTGGCTATGGCTGTTCT | 483 | GTCATTTATTTCATATACTGGATTGCCA | 484 |
| HVP18 | 18_fus_3684_MYC_001_exon3 | CAGCTACACCTACAGGCAACAA | 485 | GGTGATCCAGACTCTGACCTTTTG | 486 |
| HVP18 | 18_fus_2943_MYC_001_exon2 | AATGACAGTAAAGACATAGACAGCCAAA | 487 | AAATACGGCTGCACCGAGT | 488 |
| HVP18 | 18_sp_233_3465 | TTCACTGCAAGACATAGAAATAACCTGT | 489 | ACGTCTGGCCGTAGGTCT | 490 |
| HVP18 | 18_fus_3684_PVT1_002_exon3 | CAGCTACACCTACAGGCAACAA | 491 | ATCATGATGGCTGTATGTGCCA | 492 |
| HVP18 | 18_sp_1357_2779 | TCAGATAGTGGCTATGGCTGTTCT | 493 | GGTTTCCTTCGGTGTCTGCAT | 494 |
| HVP18 | 18_sp_3696_5776 | CAGCTACACCTACAGGCAACAA | 495 | TCAGGTAACTGCACCCTAAATACTCTAT | 496 |
| HVP18 | 18_fus_2943_PVT1_004_exon1 | AATGACAGTAAAGACATAGACAGCCAAA | 497 | CATGGTTCCACCAGCGTTATT | 498 |
| HVP18 | 18_fus_3684_MYC_001_exon2 | CAGCTACACCTACAGGCAACAA | 499 | AAATACGGCTGCACCGAGT | 500 |
| HVP18 | 18_fus_3684_PVT1_005_exon1 | CAGCTACACCTACAGGCAACAA | 501 | TCTTTGCTCGCAGCTCGT | 502 |
| HVP18 | 18_unsp_5775_5776 | GCATATTTTATCATGCTGGCAGCTCTA | 503 | TCAGGTAACTGCACCCTAAATACTCTAT | 504 |
| HVP18 | 18_sp_929_5613 | TGCATCCCAGCAGTAAGCAA | 505 | GTATTTACAACTCTTGCCACAGAAGGA | 506 |
| HVP18 | 18_fus_929_PVT1_005_exon1 | TGCATCCCAGCAGTAAGCAA | 507 | TCTTTGCTCGCAGCTCGT | 508 |
| HVP18 | 18_fus_2943_PVT1_002_exon3 | AATGACAGTAAAGACATAGACAGCCAAA | 509 | ATCATGATGGCTGTATGTGCCA | 510 |
| HVP18 | 18_sp_1357_3465 | TCAGATAGTGGCTATGGCTGTTCT | 511 | ACGTCTGGCCGTAGGTCT | 512 |
| HVP18 | 18_fus_929_MYC_001_exon2 | TGCATCCCAGCAGTAAGCAA | 513 | AAATACGGCTGCACCGAGT | 514 |
| HVP18 | 18_fus_929_MYC_001_exon1 | TGCATCCCAGCAGTAAGCAA | 515 | CTGAGAAGCCCTGCCCTTC | 516 |
| HVP18 | 18_fus_2943_PVT1_005_exon1 | AATGACAGTAAAGACATAGACAGCCAAA | 517 | TCTTTGCTCGCAGCTCGT | 518 |
| HVP18 | 18_fus_2943_MYC_001_exon3 | AATGACAGTAAAGACATAGACAGCCAAA | 519 | GGTGATCCAGACTCTGACCTTTTG | 520 |
| HVP18 | 18_sp_233_416 | TTCACTGCAAGACATAGAAATAACCTGT | 521 | CCCAGCTATGTTGTGAAATCGT | 522 |
| HVP18 | 18_fus_929_PVT1_004_exon1 | TGCATCCCAGCAGTAAGCAA | 523 | CATGGTTCCACCAGCGTTATT | 524 |
| HVP18 | 18_unsp_1357_1358 | TCAGATAGTGGCTATGGCTGTTCT | 525 | CCGTTGTCTATAGCCTCCGT | 526 |

TABLE 14 -continued

Primer pairs for HR aHPV group and human transcripts

| Virus name | Transcript targeted | Forward primer (5'-3') | SEQ ID NO | Reverse primer (5'-3') | SEQ ID NO |
|---|---|---|---|---|---|
| HVP18 | 18_sp_3696_5613 | CAGCTACACCTACAGGCAACAA | 527 | GTATTTACAACTCTTGCCACAGAAGGA | 528 |
| HVP18 | 18_sp_929_2779 | TGCATCCCAGCAGTAAGCAA | 529 | GGTTTCCTTCGGTGTCTGCAT | 530 |
| HVP18 | 18_sp_929_3465 | TGCATCCCAGCAGTAAGCAA | 531 | ACGTCTGGCCGTAGGTCT | 532 |
| HVP18 | 18_unsp_233_234 | TTCACTGCAAGACATAGAAATAACCTGT | 533 | CTATACATTTATGGCATGCAGCATGG | 534 |
| HVP18 | 18_unsp_415_416 | TCAGACTCTGTGTATGGAGACACAT | 535 | CCCAGCTATGTTGTGAAATCGT | 536 |
| HVP18 | 18_fus_2943_MYC_001_exon1 | AATGACAGTAAAGACATAGACAGCCAAA | 537 | CTGAGAAGCCCTGCCCTTC | 538 |
| HVP18 | 18_fus_929_MYC_001_exon3 | TGCATCCCAGCAGTAAGCAA | 539 | GGTGATCCAGACTCTGACCTTTTG | 540 |
| HVP18 | 18_sp_233_791 | TTCACTGCAAGACATAGAAATAACCTGT | 541 | AGAAACAGCTGCTGGAATGCT | 542 |
| HVP18 | 18_fus_3684_PVT1_004_exon1 | CAGCTACACCTACAGGCAACAA | 543 | CATGGTTCCACCAGCGTTATT | 544 |
| HVP18 | 18_sp_929_5776 | TGCATCCCAGCAGTAAGCAA | 545 | TCAGGTAACTGCACCCTAAATACTCTAT | 546 |
| HVP18 | 18_fus_929_PVT1_002_exon3 | TGCATCCCAGCAGTAAGCAA | 547 | ATCATGATGGCTGTATGTGCCA | 548 |
| HVP18 | 18_sp_233_2779 | TTCACTGCAAGACATAGAAATAACCTGT | 549 | GGTTTCCTTCGGTGTCTGCAT | 550 |
| HVP18 | 18_sp_233_2651 | TTCACTGCAAGACATAGAAATAACCTGT | 551 | GTCATTTATTTCATATACTGGATTGCCA | 552 |
| HVP18 | 18_fus_3684_MYC_001_exon1 | CAGCTACACCTACAGGCAACAA | 553 | CTGAGAAGCCCTGCCCTTC | 554 |
| HVP18 | 18_unsp_929_930 | TGCATCCCAGCAGTAAGCAA | 555 | CTCGTCATCTGATATTACATCTCCTGTT | 556 |
| HVP18 | 18_sp_3786_5776 | CGAAAACATAGCGACCACTATAGAGAT | 557 | TCAGGTAACTGCACCCTAAATACTCTAT | 558 |
| HVP18 | 18_unsp_3464_3465 | TGACGACACGGTATCCGCTA | 559 | ACGTCTGGCCGTAGGTCT | 560 |
| HVP18 | 18_unsp_3786_3787 | CGAAAACATAGCGACCACTATAGAGAT | 561 | TTGTACACTATCTGGAATTGCAACAGT | 562 |
| HVP18 | 18_unsp_3696_3697 | CAGCTACACCTACAGGCAACAA | 563 | GTCGCTATGTTTTCGCAATCTGTA | 564 |
| HVP18 | 18_gen_1607_2401 | TGGAGTAAACCCAACAATAGCAGAAG | 565 | CATTTGTAACGCAACAGGGCTAAT | 566 |
| HVP18 | 18_sp_3786_5613 | CGAAAACATAGCGACCACTATAGAGAT | 567 | GTATTTACAACTCTTGCCACAGAAGGA | 568 |
| HVP18 | 18_gen_7284_7857 | CGCCCTAGTGAGTAACAACTGTATTT | 569 | GGAGGATTGTAGGATAAAATGGATGCT | 570 |
| HVP18 | 18_gen_6026_7277 | GAGGACGTTAGGGACAATGTGT | 571 | CCCTGTGATAAAGGACGCGATTT | 572 |
| HVP18 | 18_gen_3946_4234 | CGTATGCATGGGTATTGGTATTTGTG | 573 | CATGTATATGCAATAGTAACATGGGCAA | 574 |
| HVP31 | 31_unsp_5551_5552 | GCCACAAGTGTCTATTTTTGTTGATG | 575 | TTTAGACACTGGGACAGGTGGTA | 576 |
| HVP31 | 31_unsp_739_740 | CAGATGAGGAGGATGTCATAGACAGT | 577 | CATTAACAGCTCTTGCAATATGCGAATA | 578 |

TABLE 14 -continued

Primer pairs for HR aHPV group and human transcripts

| Virus name | Transcript targeted | Forward primer (5'-3') | SEQ ID NO | Reverse primer (5'-3') | SEQ ID NO |
|---|---|---|---|---|---|
| HVP31 | 31_fus_3578_MYC_001_exon3 | CAGCTGCATGCACAAACCA | 579 | GGTGATCCAGACTCTGACCTTTTG | 580 |
| HVP31 | 31_fus_2807_MYC_001_exon2 | CAACGTTTAAATGTGTGTCAGGACAAA | 581 | AAATACGGCTGCACCGAGT | 582 |
| HVP31 | 31_fus_2807_PVT1_004_exon1 | CAACGTTTAAATGTGTGTCAGGACAAA | 583 | CATGGTTCCACCAGCGTTATT | 584 |
| HVP31 | 31_fus_3578_PVT1_004_exon1 | CAGCTGCATGCACAAACCA | 585 | CATGGTTCCACCAGCGTTATT | 586 |
| HVP31 | 31_sp_3590_5552 | CAGCTGCATGCACAAACCA | 587 | TTTAGACACTGGGACAGGTGGTA | 588 |
| HVP31 | 31_fus_2807_PVT1_002_exon3 | CAACGTTTAAATGTGTGTCAGGACAAA | 589 | ATCATGATGGCTGTATGTGCCA | 590 |
| HVP31 | 31_unsp_1296_1297 | GCGGGTATGGCAATACTGAAGT | 591 | TGGAGTTTCATTCTCTCGTTCACTATG | 592 |
| HVP31 | 31_sp_1296_2646 | GCGGGTATGGCAATACTGAAGT | 593 | CGTTGAGAAAGAGTCTCCATCGTTTT | 594 |
| HVP31 | 31_sp_230_3295 | CGGCATTGGAAATACCCTACGAT | 595 | GAATTCGATGTGGTGGTGTTGTTG | 596 |
| HVP31 | 31_fus_2807_MYC_001_exon1 | CAACGTTTAAATGTGTGTCAGGACAAA | 597 | CTGAGAAGCCCTGCCCTTC | 598 |
| HVP31 | 31_sp_230_740 | CGGCATTGGAAATACCCTACGAT | 599 | CATTAACAGCTCTTGCAATATGCGAATA | 600 |
| HVP31 | 31_fus_2807_MYC_001_exon3 | CAACGTTTAAATGTGTGTCAGGACAAA | 601 | GGTGATCCAGACTCTGACCTTTTG | 602 |
| HVP31 | 31_fus_877_PVT1_004_exon1 | AATCGTGTGCCCCAACTGT | 603 | CATGGTTCCACCAGCGTTATT | 604 |
| HVP31 | 31_unsp_2645_2646 | CTGGTGGTTTTTACATTTCCAAATCCAT | 605 | CGTTGAGAAAGAGTCTCCATCGTTTT | 606 |
| HVP31 | 31_sp_877_5552 | AATCGTGTGCCCCAACTGT | 607 | TTTAGACACTGGGACAGGTGGTA | 608 |
| HVP31 | 31_sp_230_413 | CGGCATTGGAAATACCCTACGAT | 609 | TTTTCTTCTGGACACAACGGTCTT | 610 |
| HVP31 | 31_sp_1296_2518 | GCGGGTATGGCAATACTGAAGT | 611 | AATGTAAAAACCACCAGTCTGCTATGTA | 612 |
| HVP31 | 31_sp_230_2646 | CGGCATTGGAAATACCCTACGAT | 613 | CGTTGAGAAAGAGTCTCCATCGTTTT | 614 |
| HVP31 | 31_sp_877_2518 | AATCGTGTGCCCCAACTGT | 615 | AATGTAAAAACCACCAGTCTGCTATGTA | 616 |
| HVP31 | 31_fus_3578_PVT1_005_exon1 | CAGCTGCATGCACAAACCA | 617 | TCTTTGCTCGCAGCTCGT | 618 |
| HVP31 | 31_unsp_230_231 | CGGCATTGGAAATACCCTACGAT | 619 | TCTTAAACATTTTGTACACACTCCGTGT | 620 |
| HVP31 | 31_fus_3578_MYC_001_exon2 | CAGCTGCATGCACAAACCA | 621 | AAATACGGCTGCACCGAGT | 622 |
| HVP31 | 31_fus_877_PVT1_002_exon3 | AATCGTGTGCCCCAACTGT | 623 | ATCATGATGGCTGTATGTGCCA | 624 |

TABLE 14 -continued

Primer pairs for HR aHPV group and human transcripts

| Virus name | Transcript targeted | Forward primer (5'-3') | SEQ ID NO | Reverse primer (5'-3') | SEQ ID NO |
|---|---|---|---|---|---|
| HVP31 | 31_fus_877_MYC_001_exon1 | AATCGTGTGCCCCAACTGT | 625 | CTGAGAAGCCCTGCCCTTC | 626 |
| HVP31 | 31_unsp_877_878 | AATCGTGTGCCCCAACTGT | 627 | CCCCTGTCTGTCTGTCAATTACTG | 628 |
| HVP31 | 31_sp_877_2646 | AATCGTGTGCCCCAACTGT | 629 | CGTTGAGAAAGAGTCTCCATCGTTTT | 630 |
| HVP31 | 31_unsp_3590_3591 | CAGCTGCATGCACAAACCA | 631 | GCCATGTAGATGACACTTGTTCATACAA | 632 |
| HVP31 | 31_sp_230_530 | CGGCATTGGAAATACCCTACGAT | 633 | ACATAGTCTTGCAACGTAGGTGTTT | 634 |
| HVP31 | 31_unsp_412_413 | GGAACAACATTAGAAAAATTGACAAACAAAGG | 635 | TTTTCTTCTGGACACAACGGTCTT | 636 |
| HVP31 | 31_sp_230_2518 | CGGCATTGGAAATACCCTACGAT | 637 | AATGTAAAAACCACCAGTCTGCTATGTA | 638 |
| HVP31 | 31_fus_3578_PVT1_002_exon3 | CAGCTGCATGCACAAACCA | 639 | ATCATGATGGCTGTATGTGCCA | 640 |
| HVP31 | 31_fus_877_PVT1_005_exon1 | AATCGTGTGCCCCAACTGT | 641 | TCTTTGCTCGCAGCTCGT | 642 |
| HVP31 | 31_unsp_2517_2518 | CACTAGATGGCAACCCTGTATCT | 643 | AATGTAAAAACCACCAGTCTGCTATGTA | 644 |
| HVP31 | 31_sp_877_3295 | AATCGTGTGCCCCAACTGT | 645 | GAATTCGATGTGGTGGTGTTGTTG | 646 |
| HVP31 | 31_fus_877_MYC_001_exon3 | AATCGTGTGCCCCAACTGT | 647 | GGTGATCCAGACTCTGACCTTTTG | 648 |
| HVP31 | 31_unsp_3294_3295 | CATGCGGGTGGTCAGGTAA | 649 | GAATTCGATGTGGTGGTGTTGTTG | 650 |
| HVP31 | 31_fus_877_MYC_001_exon2 | AATCGTGTGCCCCAACTGT | 651 | AAATACGGCTGCACCGAGT | 652 |
| HVP31 | 31_unsp_529_530 | GAAACGATTCCACAACATAGGAGGA | 653 | ACATAGTCTTGCAACGTAGGTGTT | 654 |
| HVP31 | 31_sp_1296_3295 | GCGGGTATGGCAATACTGAAGT | 655 | GAATTCGATGTGGTGGTGTTGTTG | 656 |
| HVP31 | 31_fus_3578_MYC_001_exon1 | CAGCTGCATGCACAAACCA | 657 | CTGAGAAGCCCTGCCCTTC | 658 |
| HVP31 | 31_fus_2807_PVT1_005_exon1 | CAACGTTTAAATGTGTGTCAGGACAAA | 659 | TCTTTGCTCGCAGCTCGT | 660 |
| HVP31 | 31_gen_7233_7912 | TGTGTGTGTTGTGTATGTTGTCCTT | 661 | CAACTTTTACTATGGCGTGACACCTA | 662 |
| HVP31 | 31_gen_5802_7226 | GCTTAGTTTGGGCCTGTGTT | 663 | ACCACCGGCATATCTATTAGAGTTTTC | 664 |
| HVP31 | 31_gen_3840_4137 | GCATTGTGCTATGCTTTTTGCTTTG | 665 | ACAACGTAATGGAGAGGTTGCAATA | 666 |
| HVP31 | 31_gen_1546_2268 | GTGAAACACCAGAATGGATAGAAAGAC | 667 | TGCACATGCATTACTATCACTGTCA | 668 |
| HVP33 | 33_fus_3577_MYC_001_exon3 | ACGTACTGCAACTAACTGCACAA | 669 | GGTGATCCAGACTCTGACCTTTTG | 670 |
| HVP33 | 33_fus_3577_PVT1_004_exon1 | ACGTACTGCAACTAACTGCACAA | 671 | CATGGTTCCACCAGCGTTATT | 672 |
| HVP33 | 33_sp_1316_3351 | GATGAGCTAGAAGACAGCGGATATG | 673 | GTGGTGGTCGGTTATCGTTGT | 674 |

TABLE 14 -continued

Primer pairs for HR aHPV group and human transcripts

| Virus name | Transcript targeted | Forward primer (5'-3') | SEQ ID NO | Reverse primer (5'-3') | SEQ ID NO |
|---|---|---|---|---|---|
| HVP33 | 33_unsp_894_895 | GTGCCCTACCTGTGCACAA | 675 | TTCTTCTCTCTATGACTGCTTCTACCT | 676 |
| HVP33 | 33_unsp_2574_2575 | TGTGAAACATAGGGCATTAGTGCAATTA | 677 | CATACACTGGGTTACCATTTTCATCAAA | 678 |
| HVP33 | 33_fus_894_PVT1_002_exon3 | GTGCCCTACCTGTGCACAA | 679 | ATCATGATGGCTGTATGTGCCA | 680 |
| HVP33 | 33_fus_894_MYC_001_exon1 | GTGCCCTACCTGTGCACAA | 681 | CTGAGAAGCCCTGCCCTTC | 682 |
| HVP33 | 33_sp_3589_5594 | ACGTACTGCAACTAACTGCACAA | 683 | ATCAGTGCTGACAACTTTAGATACAGG | 684 |
| HVP33 | 33_fus_3577_PVT1_005_exon1 | ACGTACTGCAACTAACTGCACAA | 685 | TCTTTGCTCGCAGCTCGT | 686 |
| HVP33 | 33_sp_231_531 | AGCATTGGAGACAACTATACACAACATT | 687 | CATATTCCTTTAACGTTGGCTTGTGT | 688 |
| HVP33 | 33_unsp_413_414 | ATTCTGTATATGGAAATACATTAGAACAAACAG | 689 | TCGTTTGTTTAAATCCACATGTCGTTTT | 690 |
| HVP33 | 33_fus_3577_MYC_001_exon1 | ACGTACTGCAACTAACTGCACAA | 691 | CTGAGAAGCCCTGCCCTTC | 692 |
| HVP33 | 33_fus_3577_MYC_001_exon2 | ACGTACTGCAACTAACTGCACAA | 693 | AAATACGGCTGCACCGAGT | 694 |
| HVP33 | 33_sp_231_414 | AGCATTGGAGACAACTATACACAACATT | 695 | TCGTTTGTTTAAATCCACATGTCGTTTT | 696 |
| HVP33 | 33_fus_2863_MYC_001_exon1 | GTGCAGGAGAAAATACTAGATCTTTACGA | 697 | CTGAGAAGCCCTGCCCTTC | 698 |
| HVP33 | 33_unsp_1316_1317 | GATGAGCTAGAAGACAGCGGATATG | 699 | CATCCCCCACCCCACTAGAT | 700 |
| HVP33 | 33_fus_3577_PVT1_002_exon3 | ACGTACTGCAACTAACTGCACAA | 701 | ATCATGATGGCTGTATGTGCCA | 702 |
| HVP33 | 33_fus_2863_PVT1_002_exon3 | GTGCAGGAGAAAATACTAGATCTTTACGA | 703 | ATCATGATGGCTGTATGTGCCA | 704 |
| HVP33 | 33_unsp_231_232 | AGCATTGGAGACAACTATACACAACATT | 705 | CGCAAACACAGTTTACATATTCCAAATG | 706 |
| HVP33 | 33_fus_894_PVT1_005_exon1 | GTGCCCTACCTGTGCACAA | 707 | TCTTTGCTCGCAGCTCGT | 708 |
| HVP33 | 33_fus_894_MYC_001_exon2 | GTGCCCTACCTGTGCACAA | 709 | AAATACGGCTGCACCGAGT | 710 |
| HVP33 | 33_fus_2863_MYC_001_exon3 | GTGCAGGAGAAAATACTAGATCTTTACGA | 711 | GGTGATCCAGACTCTGACCTTTTG | 712 |
| HVP33 | 33_sp_231_2575 | AGCATTGGAGACAACTATACACAACATT | 713 | CATACACTGGGTTACCATTTTCATCAAA | 714 |
| HVP33 | 33_fus_2863_PVT1_004_exon1 | GTGCAGGAGAAAATACTAGATCTTTACGA | 715 | CATGGTTCCACCAGCGTTATT | 716 |
| HVP33 | 33_sp_894_2702 | GTGCCCTACCTGTGCACAA | 717 | TGATATTTCCTCCATGGTTTTCCTTGTC | 718 |
| HVP33 | 33_sp_231_3351 | AGCATTGGAGACAACTATACACAACATT | 719 | GTGGTGGTCGGTTATCGTTGT | 720 |
| HVP33 | 33_sp_1316_2575 | GATGAGCTAGAAGACAGCGGATATG | 721 | CATACACTGGGTTACCATTTTCATCAAA | 722 |
| HVP33 | 33_fus_894_MYC_001_exon3 | GTGCCCTACCTGTGCACAA | 723 | GGTGATCCAGACTCTGACCTTTTG | 724 |

TABLE 14 -continued

Primer pairs for HR aHPV group and human transcripts

| Virus name | Transcript targeted | Forward primer (5'-3') | SEQ ID NO | Reverse primer (5'-3') | SEQ ID NO |
|---|---|---|---|---|---|
| HVP33 | 33_fus_2863_PVT1_005_exon1 | GTGCAGGAGAAAATACTAGATCTTTACGA | 725 | TCTTTGCTCGCAGCTCGT | 726 |
| HVP33 | 33_sp_894_3351 | GTGCCCTACCTGTGCACAA | 727 | GTGGTGGTCGGTTATCGTTGT | 728 |
| HVP33 | 33_fus_894_PVT1_004_exon1 | GTGCCCTACCTGTGCACAA | 729 | CATGGTTCCACCAGCGTTATT | 730 |
| HVP33 | 33_fus_2863_MYC_001_exon2 | GTGCAGGAGAAAATACTAGATCTTTACGA | 731 | AAATACGGCTGCACCGAGT | 732 |
| HVP33 | 33_sp_1316_2702 | GATGAGCTAGAAGACAGCGGATATG | 733 | TGATATTTCCTCCATGGTTTTCCTTGTC | 734 |
| HVP33 | 33_unsp_3350_3351 | GGATGCTGCAAAGTATTCTAAAACACAA | 735 | GTGGTGGTCGGTTATCGTTGT | 736 |
| HVP33 | 33_unsp_530_531 | CGATTTCATAATATTTCGGGTCGTTGG | 737 | CATATTCCTTTAACGTTGGCTTGTGT | 738 |
| HVP33 | 33_sp_894_5594 | GTGCCCTACCTGTGCACAA | 739 | ATCAGTGCTGACAACTTTAGATACAGG | 740 |
| HVP33 | 33_unsp_3589_3590 | ACGTACTGCAACTAACTGCACAA | 741 | GCCAGGTGGATGACATAGAACTATACA | 742 |
| HVP33 | 33_unsp_5593_5594 | TTGTTGTAGACGGTGCTGACTTT | 743 | ATCAGTGCTGACAACTTTAGATACAGG | 744 |
| HVP33 | 33_sp_894_2575 | GTGCCCTACCTGTGCACAA | 745 | CATACACTGGGTTACCATTTTCATCAAA | 746 |
| HVP33 | 33_sp_231_2702 | AGCATTGGAGACAACTATACACAACATT | 747 | TGATATTTCCTCCATGGTTTTCCTTGTC | 748 |
| HVP33 | 33_gen_3839_4175 | CCATTTCTACCTATGCTTGGTTGCT | 749 | GTTGTGTCATATGCTGTGCATGAAA | 750 |
| HVP33 | 33_gen_7292_7909 | CTTGCCCTACCCTGCATTG | 751 | CGGTTAGGCATACAAAATGGAGGAAAT | 752 |
| HVP33 | 33_gen_1566_2325 | CGGAGCCAAACATGTGCATTG | 753 | CGTTATCATATGCCCACTGTACCATT | 754 |
| HVP33 | 33_gen_5844_7285 | CATGTGTAGGCCTTGAAATAGGTAGAG | 755 | CCTATTATCAGCACCCGGTTGT | 756 |
| HVP35 | 35_unsp_232_233 | CGAGGTAGAAGAAAGCATCCATGAAAT | 757 | CATACTCCATATGGCTGGCCTTC | 758 |
| HVP35 | 35_unsp_3596_3597 | TCTACATCTGACTGCACAAACAAAGA | 759 | CCATCTCCATGTAGATGAAGCATCTTG | 760 |
| HVP35 | 35_sp_232_2670 | CGAGGTAGAAGAAAGCATCCATGAAAT | 761 | GGAAAGCGTCTCCATCATTTTCTTTG | 762 |
| HVP35 | 35_fus_2831_MYC_001_exon3 | ATTACGAGACTGATAGCACATGTTTGT | 763 | GGTGATCCAGACTCTGACCTTTTG | 764 |
| HVP35 | 35_fus_3584_MYC_001_exon3 | TCTACATCTGACTGCACAAACAAAGA | 765 | GGTGATCCAGACTCTGACCTTTTG | 766 |
| HVP35 | 35_fus_883_MYC_001_exon2 | CGGCTGTTCACAGAGAGCATAAT | 767 | AAATACGGCTGCACCGAGT | 768 |
| HVP35 | 35_fus_2831_PVT1_004_exon1 | ATTACGAGACTGATAGCACATGTTTGT | 769 | CATGGTTCCACCAGCGTTATT | 770 |
| HVP35 | 35_unsp_5600_5601 | GGGTGAUTTTATTTACACCCTAGTT | 771 | CATCAGTGCTAACAACCTTAGACACT | 772 |

TABLE 14 -continued

Primer pairs for HR aHPV group and human transcripts

| Virus name | Transcript targeted | Forward primer (5'-3') | SEQ ID NO | Reverse primer (5'-3') | SEQ ID NO |
|---|---|---|---|---|---|
| HVP35 | 35_fus_2831_PVT1_005_exon1 | ATTACGAGACTGATAGCACATGTTTGT | 773 | TCTTTGCTCGCAGCTCGT | 774 |
| HVP35 | 35_sp_3596_5601 | TCTACATCTGACTGCACAAACAAAGA | 775 | CATCAGTGCTAACAACCTTAGACACT | 776 |
| HVP35 | 35_sp_883_2670 | CGGCTGTTCACAGAGAGCATAAT | 777 | GGAAAGCGTCTCCATCATTTTCTTTG | 778 |
| HVP35 | 35_unsp_883_884 | CGGCTGTTCACAGAGAGCATAAT | 779 | CCCGTACGTCTACTAACTACTGCTT | 780 |
| HVP35 | 35_fus_2831_PVT1_002_exon3 | ATTACGAGACTGATAGCACATGTTTGT | 781 | ATCATGATGGCTGTATGTGCCA | 782 |
| HVP35 | 35_fus_883_MYC_001_exon3 | CGGCTGTTCACAGAGAGCATAAT | 783 | GGTGATCCAGACTCTGACCTTTTG | 784 |
| HVP35 | 35_sp_883_5601 | CGGCTGTTCACAGAGAGCATAAT | 785 | CATCAGTGCTAACAACCTTAGACACT | 786 |
| HVP35 | 35_fus_883_MYC_001_exon1 | CGGCTGTTCACAGAGAGCATAAT | 787 | CTGAGAAGCCCTGCCCTTC | 788 |
| HVP35 | 35_fus_3584_PVT1_005_exon1 | TCTACATCTGACTGCACAAACAAAGA | 789 | TCTTTGCTCGCAGCTCGT | 790 |
| HVP35 | 35_fus_2831_MYC_001_exon2 | ATTACGAGACTGATAGCACATGTTTGT | 791 | AAATACGGCTGCACCGAGT | 792 |
| HVP35 | 35_sp_232_2543 | CGAGGTAGAAGAAAGCATCCATGAAAT | 793 | TCATTGTGAAATGTAAAGACCACTACCC | 794 |
| HVP35 | 35_fus_2831_MYC_001_exon1 | ATTACGAGACTGATAGCACATGTTTGT | 795 | CTGAGAAGCCCTGCCCTTC | 796 |
| HVP35 | 35_unsp_5766_5767 | CATCTACTATCATGCAGGCAGTTCT | 797 | ACTCTGTATTGCAAACCAGATACCTTG | 798 |
| HVP35 | 35_unsp_2669_2670 | GGAAACCCAGTGTATGGGCTTAAT | 799 | GGAAAGCGTCTCCATCATTTTCTTTG | 800 |
| HVP35 | 35_fus_883_PVT1_002_exon3 | CGGCTGTTCACAGAGAGCATAAT | 801 | ATCATGATGGCTGTATGTGCCA | 802 |
| HVP35 | 35_fus_3584_PVT1_004_exon1 | TCTACATCTGACTGCACAAACAAAGA | 803 | CATGGTTCCACCAGCGTTATT | 804 |
| HVP35 | 35_fus_3584_PVT1_002_exon3 | TCTACATCTGACTGCACAAACAAAGA | 805 | ATCATGATGGCTGTATGTGCCA | 806 |
| HVP35 | 35_fus_883_PVT1_005_exon1 | CGGCTGTTCACAGAGAGCATAAT | 807 | TCTTTGCTCGCAGCTCGT | 808 |
| HVP35 | 35_fus_3584_MYC_001_exon1 | TCTACATCTGACTGCACAAACAAAGA | 809 | CTGAGAAGCCCTGCCCTTC | 810 |
| HVP35 | 35_sp_883_3319 | CGGCTGTTCACAGAGAGCATAAT | 811 | GCTTTGGTATGGGTCTCGGT | 812 |
| HVP35 | 35_sp_1305_3319 | ATTATTTGAACTACCAGACAGCGGTT | 813 | GCTTTGGTATGGGTCTCGGT | 814 |
| HVP35 | 35_sp_883_2543 | CGGCTGTTCACAGAGAGCATAAT | 815 | TCATTGTGAAATGTAAAGACCACTACCC | 816 |
| HVP35 | 35__sp_1305_2670 | ATTATTTGAACTACCAGACAGCGGTT | 817 | GGAAAGCGTCTCCATCATTTTCTTTG | 818 |
| HVP35 | 35__sp_232_415 | CGAGGTAGAAGAAAGCATCCATGAAAT | 819 | TCCACCGATGTTATGGAATCGTTTT | 820 |
| HVP35 | 35_fus_3584_MYC_001_exon2 | TCTACATCTGACTGCACAAACAAAGA | 821 | AAATACGGCTGCACCGAGT | 822 |
| HVP35 | 35_fus_883_PVT1_004_exon1 | CGGCTGTTCACAGAGAGCATAAT | 823 | CATGGTTCCACCAGCGTTATT | 824 |

TABLE 14 -continued

Primer pairs for HR aHPV group and human transcripts

| Virus name | Transcript targeted | Forward primer (5'-3') | SEQ ID NO | Reverse primer (5'-3') | SEQ ID NO |
|---|---|---|---|---|---|
| HVP35 | 35_unsp_414_415 | GGAGAAACGTTAGAAAAACAATGCAACA | 825 | TCCACCGATGTTATGGAATCGTTTT | 826 |
| HVP35 | 35_sp_232_3319 | CGAGGTAGAAGAAAGCATCCATGAAAT | 827 | GCTTTGGTATGGGTCTCGGT | 828 |
| HVP35 | 35_unsp_1305_1306 | ATTATTTGAACTACCAGACAGCGGTT | 829 | GCTACTAGAGGTTATACTATCCCCACT | 830 |
| HVP35 | 35_sp_883_5767 | CGGCTGTTCACAGAGAGCATAAT | 831 | ACTCTGTATTGCAAACCAGATACCTTG | 832 |
| HVP35 | 35_sp_1305_2543 | ATTATTTGAACTACCAGACAGCGGTT | 833 | TCATTGTGAAATGTAAAGACCACTACCC | 834 |
| HVP35 | 35_unsp_2542_2543 | CATTAGTGCAATTAAAATGCCCACCTT | 835 | TCATTGTGAAATGTAAAGACCACTACCC | 836 |
| HVP35 | 35_sp_3596_5767 | TCTACATCTGACTGCACAAACAAGA | 837 | ACTCTGTATTGCAAACCAGATACCTTG | 838 |
| HVP35 | 35_unsp_3318_3319 | AAAATATATGGGAAGTGCATGTGGGT | 839 | GCTTTGGTATGGGTCTCGGT | 840 |
| HVP35 | 35_gen_3846_4185 | CGTTCGCTATTGCTATCTGTGTCATTA | 841 | GCCAAATATTGTGCATGAGCGTTAATC | 842 |
| HVP35 | 35_gen_7293_7879 | AACATTCCTACCTCAGCAGAACAC | 843 | TGGGTGGACCACAAGTATGAAAA | 844 |
| HVP35 | 35_gen_6017_7286 | GGTACAGATAACAGGGAATGCATTTCT | 845 | GACATTCICC1GCI111ACCIGGTTA | 846 |
| HVP35 | 35_gen_1555_2293 | GCTATGTATTTCAGCTGCAAGTATGCT | 847 | CATTCTGGTGTTTCTCCATCAACCT | 848 |
| HVP39 | 39_sp_943_2636 | CGTGGTGTGCAACTGCAA | 849 | CTGTTTTGGTCAAATGGAAATGCATTAG | 850 |
| HVP39 | 39_unsp_5642_5643 | GCAATAACCATTCAGGGTTCCAATT | 851 | AGTATTGACAACCTTCGCCACA | 852 |
| HVP39 | 39_unsp_1368_1369 | GGTGTATTCCGTGCCAGACA | 853 | GTACACTGCCGCCATGTTC | 854 |
| HVP39 | 39_sp_1368_3424 | GGTGTATTCCGTGCCAGACA | 855 | GGTCGCGGTGGTGTTTGATAA | 856 |
| HVP39 | 39_sp_235_2636 | CACCACCTTGCAGGACATTACAATA | 857 | CTGTTTTGGTCAAATGGAAATGCATTAG | 858 |
| HVP39 | 39_fus_3677_PVT1_004_exon1 | CACAGTAACAGTACAGGCCACA | 859 | CATGGTTCCACCAGCGTTATT | 860 |
| HVP39 | 39_fus_3677_PVT1_002_exon3 | CACAGTAACAGTACAGGCCACA | 861 | ATCATGATGGCTGTATGTGCCA | 862 |
| HVP39 | 39_unsp_801_802 | CATGCAGTTAATCACCAACATCAACT | 863 | TGCTGTAGTTGTCGCAGAGTATC | 864 |
| HVP39 | 39_sp_235_418 | CACCACCTTGCAGGACATTACAATA | 865 | CTGTCCTGTATAGCTTCCTGCTATTTT | 866 |
| HVP39 | 39_unsp_943_944 | CGTGGTGTGCAACTGCAA | 867 | CACTGTGTCGCCTGTTTGTTTAT | 868 |
| HVP39 | 39_fus_943_MYC_001_exon2 | CGTGGTGTGCAACTGCAA | 869 | AAATACGGCTGCACCGAGT | 870 |
| HVP39 | 39_unsp_2635_2636 | ATTAGATGGGTATGCAATAAGTTTAGATAGG | 871 | CTGTTTTGGTCAAATGGAAATGCATTAG | 872 |
| HVP39 | 39_fus_2927_MYC_001_exon2 | ACAACGTTTAAATGTGTTACAGGACA | 873 | AAATACGGCTGCACCGAGT | 874 |
| HVP39 | 39_fus_2927_PVT1_002_exon3 | ACAACGTTTAAATGTGTTACAGGACA | 875 | ATCATGATGGCTGTATGTGCCA | 876 |
| HVP39 | 39_fus_943_PVT1_002_exon3 | CGTGGTGTGCAACTGCAA | 877 | ATCATGATGGCTGTATGTGCCA | 878 |

TABLE 14 -continued

Primer pairs for HR aHPV group and human transcripts

| Virus name | Transcript targeted | Forward primer (5'-3') | SEQ ID NO | Reverse primer (5'-3') | SEQ ID NO |
|---|---|---|---|---|---|
| HVP39 | 39_fus_943_PVT1_005_exon1 | CGTGGTGTGCAACTGCAA | 879 | TCTTTGCTCGCAGCTCGT | 880 |
| HVP39 | 39_fus_943_MYC_001_exon3 | CGTGGTGTGCAACTGCAA | 881 | GGTGATCCAGACTCTGACCTTTTG | 882 |
| HVP39 | 39_fus_2927_PVT1_005_exon1 | ACAACGTTTAAATGTGTTACAGGACA | 883 | TCTTTGCTCGCAGCTCGT | 884 |
| HVP39 | 39_fus_943_MYC_001_exon1 | CGTGGTGTGCAACTGCAA | 885 | CTGAGAAGCCCTGCCCTTC | 886 |
| HVP39 | 39_sp_943_5643 | CGTGGTGTGCAACTGCAA | 887 | AGTATTGACAACCTTCGCCACA | 888 |
| HVP39 | 39_unsp_3689_3690 | CACAGTAACAGTACAGGCCACA | 889 | CGTATCCAATGCCAGGTACATGAAA | 890 |
| HVP39 | 39_sp_3689_5643 | CACAGTAACAGTACAGGCCACA | 891 | AGTATTGACAACCTTCGCCACA | 892 |
| HVP39 | 39_fus_3677_PVT1_005_exon1 | CACAGTAACAGTACAGGCCACA | 893 | TCTTTGCTCGCAGCTCGT | 894 |
| HVP39 | 39_unsp_417_418 | CTCGGACTCGGTGTATGCAA | 895 | CTGTCCTGTATAGCTTCCTGCTATTTT | 896 |
| HVP39 | 39_fus_943_PVT1_004_exon1 | CGTGGTGTGCAACTGCAA | 897 | CATGGTTCCACCAGCGTTATT | 898 |
| HVP39 | 39_sp_943_3424 | CGTGGTGTGCAACTGCAA | 899 | GGTCGCGGTGGTGTTTGATAA | 900 |
| HVP39 | 39_unsp_235_236 | CACCACCTTGCAGGACATTACAATA | 901 | GATTGGCATGCAGCTAGTGG | 902 |
| HVP39 | 39_sp_235_802 | CACCACCTTGCAGGACATTACAATA | 903 | TGCTGTAGTTGTCGCAGAGTATC | 904 |
| HVP39 | 39_fus_2927_MYC_001_exon3 | ACAACGTTTAAATGTGTTACAGGACA | 905 | GGTGATCCAGACTCTGACCTTTTG | 906 |
| HVP39 | 39_fus_2927_MYC_001_exon1 | ACAACGTTTAAATGTGTTACAGGACA | 907 | CTGAGAAGCCCTGCCCTTC | 908 |
| HVP39 | 39_fus_3677_MYC_001_exon2 | CACAGTAACAGTACAGGCCACA | 909 | AAATACGGCTGCACCGAGT | 910 |
| HVP39 | 39_sp_1368_2636 | GGTGTATTCCGTGCCAGACA | 911 | CTGTTTTGGTCAAATGGAAATGCATTAG | 912 |
| HVP39 | 39_fus_3677_MYC_001_exon1 | CACAGTAACAGTACAGGCCACA | 913 | CTGAGAAGCCCTGCCCTTC | 914 |
| HVP39 | 39_fus_2927_PVT1_004_exon1 | ACAACGTTTAAATGTGTTACAGGACA | 915 | CATGGTTCCACCAGCGTTATT | 916 |
| HVP39 | 39_fus_3677_MYC_001_exon3 | CACAGTAACAGTACAGGCCACA | 917 | GGTGATCCAGACTCTGACCTTTTG | 918 |
| HVP39 | 39_sp_235_3424 | CACCACCTTGCAGGACATTACAATA | 919 | GGTCGCGGTGGTGTTTGATAA | 920 |
| HVP39 | 39_gen_3939_4242 | TTGGTGTGGTTTGGTGTGTATAT | 921 | CTCCAATGGTGTGGTACGTATAAGAA | 922 |
| HVP39 | 39_gen_7267_7833 | CATTTTGTGGCGACCGAAGT | 923 | CCTGGACAGGATGATGAGTAATAAGG | 924 |
| HVP39 | 39_gen_1618_2386 | AGGGTTACTGTAGGAAAGGGATTAAGT | 925 | CGTATCCCCTGTTACCACACTAATATTG | 926 |
| HVP39 | 39_gen_5893_7260 | CCAGCCATTGGGTGTTGGTA | 927 | GCCTATAATGCACAACTGTGTCTGTT | 928 |
| HVP45 | 45_fus_929_MYC_001_exon3 | AGCACCTTGTCCTTTGTGTGT | 929 | GGTGATCCAGACTCTGACCTTTTG | 930 |
| HVP45 | 45_fus_2901_PVT1_004_exon1 | CGTTACAGGACAAAATACTAGACCACTA | 931 | CATGGTTCCACCAGCGTTATT | 932 |

TABLE 14 -continued

Primer pairs for HR aHPV group and human transcripts

| Virus name | Transcript targeted | Forward primer (5'-3') | SEQ ID NO | Reverse primer (5'-3') | SEQ ID NO |
|---|---|---|---|---|---|
| HVP45 | 45_sp_929_2610 | AGCACCTTGTCCTTTGTGTGT | 933 | GAAATGCATGTGGAAATGTAAATACCGT | 934 |
| HVP45 | 45_fus_3648V_MYC_001_exon2 | TCCTGTGTTCAAGTACAAGTAACAACAA | 935 | AAATACGGCTGCACCGAGT | 936 |
| HVP45 | 45_sp_1357_2610 | TCAGATAGTGGCTATGGCTGTTCT | 937 | GAAATGCATGTGGAAATGTAAATACCGT | 938 |
| HVP45 | 45_fus_3648_MYC_001_exon3 | TCCTGTGTTCAAGTACAAGTAACAACAA | 939 | GGTGATCCAGACTCTGACCTTTTG | 940 |
| HVP45 | 45_sp_230_791 | CTACAAGACGTATCTATTGCCTGTGT | 941 | TCAAAAACAGCTGCTGTAGTGTTCT | 942 |
| HVP45 | 45_sp_929_3423 | AGCACCTTGTCCTTTGTGTGT | 943 | CCCACGGATGCGGTTTTG | 944 |
| HVP45 | 45_unsp_412_413 | AAACTCTGTATATGGAGAGACACTGGA | 945 | CGTTTGTCCTTAAGGTGTCTACGTTTT | 946 |
| HVP45 | 45_sp_230_413 | CTACAAGACGTATCTATTGCCTGTGT | 947 | CGTTTGTCCTTAAGGTGTCTACGTTTT | 948 |
| HVP45 | 45_sp_230_2737 | CTACAAGACGTATCTATTGCCTGTGT | 949 | GGATTCCTTCGGTGTCTGCAT | 950 |
| HVP45 | 45_fus_2901_MYC_001_exon1 | CGTTACAGGACAAAATACTAGACCACTA | 951 | CTGAGAAGCCCTGCCCTTC | 952 |
| HVP45 | 45_unsp_230_231 | CTACAAGACGTATCTATTGCCTGTGT | 953 | AAGTCTATACATTTATGGCATGCAGCATA | 954 |
| HVP45 | 45_fus_929_PVT1_004_exon1 | AGCACCTTGTCCTTTGTGTGT | 955 | CATGGTTCCACCAGCGTTATT | 956 |
| HVP45 | 45_sp_1357_3423 | TCAGATAGTGGCTATGGCTGTTCT | 957 | CCCACGGATGCGGTTTTG | 958 |
| HVP45 | 45_fus_929_MYC_001_exon2 | AGCACCTTGTCCTTTGTGTGT | 959 | AAATACGGCTGCACCGAGT | 960 |
| HVP45 | 45_fus_929_PVT1_005_exon1 | AGCACCTTGTCCTTTGTGTGT | 961 | TCTTTGCTCGCAGCTCGT | 962 |
| HVP45 | 45_sp_230_3423 | CTACAAGACGTATCTATTGCCTGTGT | 963 | CCCACGGATGCGGTTTTG | 964 |
| HVP45 | 45_unsp_2609_2610 | CATTATTACAGCTAAAATGTCCTCCAATCC | 965 | GAAATGCATGTGGAAATGTAAATACCGT | 966 |
| HVP45 | 45_fus_3648_PVT1_002_exon3 | TCCTGTGTTCAAGTACAAGTAACAACAA | 967 | ATCATGATGGCTGTATGTGCCA | 968 |
| HVP45 | 45_fus_2901_PVT1_002_exon3 | CGTTACAGGACAAAATACTAGACCACTA | 969 | ATCATGATGGCTGTATGTGCCA | 970 |
| HVP45 | 45_fus_2901_MYC_001_exon2 | CGTTACAGGACAAAATACTAGACCACTA | 971 | AAATACGGCTGCACCGAGT | 972 |
| HVP45 | 45_unsp_790_791 | GGAGTTAGTCATGCACAACTACCA | 973 | TCAAAAACAGCTGCTGTAGTGTTCT | 974 |
| HVP45 | 45_sp_929_2737 | AGCACCTTGTCCTTTGTGTGT | 975 | GGATTCCTTCGGTGTCTGCAT | 976 |
| HVP45 | 45_fus_3648_PVT1_005_exon1 | TCCTGTGTTCAAGTACAAGTAACAACAA | 977 | TCTTTGCTCGCAGCTCGT | 978 |
| HVP45 | 45_sp_929_5608 | AGCACCTTGTCCTTTGTGTGT | 979 | GCTGACAACTCTGGCCACA | 980 |
| HVP45 | 45_sp_230_2610 | CTACAAGACGTATCTATTGCCTGTGT | 981 | GAAATGCATGTGGAAATGTAAATACCGT | 982 |
| HVP45 | 45_unsp_5607_5608 | GCACACAATATTATTTATGGCCATGGTA | 983 | GCTGACAACTCTGGCCACA | 984 |
| HVP45 | 45_fus_2901_PVT1_005_exon1 | CGTTACAGGACAAAATACTAGACCACTA | 985 | TCTTTGCTCGCAGCTCGT | 986 |
| HVP45 | 45_unsp_929_930 | AGCACCTTGTCCTTTGTGTGT | 987 | CAATTGTTTCTACAAAGAACCAGCCATT | 988 |

TABLE 14-continued

Primer pairs for HR aHPV group and human transcripts

| Virus name | Transcript targeted | Forward primer (5'-3') | SEQ ID NO | Reverse primer (5'-3') | SEQ ID NO |
|---|---|---|---|---|---|
| HVP45 | 45_fus_2901_MYC_001_exon3 | CGTTACAGGACAAAATACTAGACCACTA | 989 | GGTGATCCAGACTCTGACCTTTTG | 990 |
| HVP45 | 45_fus_929_MYC_001_exon1 | AGCACCTTGTCCTTTGTGTGT | 991 | CTGAGAAGCCCTGCCCTTC | 992 |
| HVP45 | 45_sp_1357_2737 | TCAGATAGTGGCTATGGCTGTTCT | 993 | GGATTCCTTCGGTGTCTGCAT | 994 |
| HVP45 | 45_unsp_1357_1358 | TCAGATAGTGGCTATGGCTGTTCT | 995 | ACTATCCCCACCACTACTTTGTGTA | 996 |
| HVP45 | 45_fus_3648_PVT1_004_exon1 | TCCTGTGTTCAAGTACAAGTAACAACAA | 997 | CATGGTTCCACCAGCGTTATT | 998 |
| HVP45 | 45_sp_3660_5608 | TCCTGTGTTCAAGTACAAGTAACAACAA | 999 | GCTGACAACTCTGGCCACA | 1000 |
| HVP45 | 45_fus_3648_MYC_001_exon1 | TCCTGTGTTCAAGTACAAGTAACAACAA | 1001 | CTGAGAAGCCCTGCCCTTC | 1002 |
| HVP45 | 45_fus_929_PVT1_002_exon3 | AGCACCTTGTCCTTTGTGTGT | 1003 | ATCATGATGGCTGTATGTGCCA | 1004 |
| HVP45 | 45_gen_3910_4227 | TGCTTTTGCTTGGTTGTTGGT | 1005 | CATCACAGGTATGTTACACTGTACTGT | 1006 |
| HVP45 | 45_unsp_3660_3661 | TCCTGTGTTCAAGTACAAGTAACAACAA | 1007 | GGTCTGCATATTTGCGTAGCCTATA | 1008 |
| HVP45 | 45_gen_7316_7858 | ATTTCGGTTGCCTGTGGCTTATA | 1009 | CAGTTGTGCAAGCCATTGTTTTAGT | 1010 |
| HVP45 | 45_sp_3750_5608 | CGCAAATATGCAGACCATTACTCAGAA | 1011 | GCTGACAACTCTGGCCACA | 1012 |
| HVP45 | 45_gen_1607_2360 | 6CAACGTTATAC6CCCATATCCAAT | 1013 | GGTACGTGCAACAATGTGCTTAA | 1014 |
| HVP45 | 45_unsp_3750_3751 | CGCAAATATGCAGACCATTACTCAGAA | 1015 | CCCACCGAGATTTGTACACTGTTA | 1016 |
| HVP45 | 45_gen_5858_7309 | GGCATGTGTAGGTATGGAAATTGGT | 1017 | ACATCCTGCGTAATAACAGCTGTAG | 1018 |
| HVP45 | 45_unsp_3422_3423 | TGACGACACGGTATCCGCTA | 1019 | CCCACGGATGCGGTTTTG | 1020 |
| HVP51 | 51_unsp_2547_2548 | AGTATGTCCACCATTACTAATAACGTCAAAC | 1021 | TCATTCAATGTATACACAGCATTCCCAT | 1022 |
| HVP51 | 51_fus_3572_MYC_001_exon2 | CTAACACTGGAGGGCACCAAA | 1023 | AAATACGGCTGCACCGAGT | 1024 |
| HVP51 | 51_fus_886_PVT1_002_exon3 | GGGCGAACTAAGCCTGGTTT | 1025 | ATCATGATGGCTGTATGTGCCA | 1026 |
| HVP51 | 51_fus_886_MYC_001_exon2 | GGGCGAACTAAGCCTGGTTT | 1027 | AAATACGGCTGCACCGAGT | 1028 |
| HVP51 | 51_fus_3572_PVT1_005_exon1 | CTAACACTGGAGGGCACCAAA | 1029 | TCTTTGCTCGCAGCTCGT | 1030 |
| HVP51 | 51_fus_2834_MYC_001_exon1 | GTGCCAGGAGAAAATACTAGACTGTTAT | 1031 | CTGAGAAGCCCTGCCCTTC | 1032 |
| HVP51 | 51_unsp_3584_3585 | CTAACACTGGAGGGCACCAAA | 1033 | ATGCCAGGTTGAGGATACGTTTTTAT | 1034 |
| HVP51 | 51_fus_2834_PVT1_004_exon1 | GTGCCAGGAGAAAATACTAGACTGTTAT | 1035 | CATGGTTCCACCAGCGTTATT | 1036 |
| HVP51 | 51_unsp_1302_1303 | CGGACAGCGGATATGGCAATA | 1037 | TCTGTTGTTTCCACATCCATAACACT | 1038 |

TABLE 14 -continued

Primer pairs for HR aHPV group and human transcripts

| Virus name | Transcript targeted | Forward primer (5'-3') | SEQ ID NO | Reverse primer (5'-3') | SEQ ID NO |
|---|---|---|---|---|---|
| HVP51 | 51_fus_3572_PVT1_002_exon3 | CTAACACTGGAGGGCACCAAA | 1039 | ATCATGATGGCTGTATGTGCCA | 1040 |
| HVP51 | 51_sp_3584_5521 | CTAACACTGGAGGGCACCAAA | 1041 | CAATTCGAGACACAGGTGCAG | 1042 |
| HVP51 | 51_unsp_401_402 | GAGAGTATAGACGTTATAGCAGGTCTGT | 1043 | TCCCGCTATTTCATGGAACCTTTT | 1044 |
| HVP51 | 51_sp_1302_3319 | CGGACAGCGGATATGGCAATA | 1045 | CCACGCAGGTGGTAAGGG | 1046 |
| HVP51 | 51_sp_217_751 | CTGCATGAATTATGTGAAGCTTTGAAC | 1047 | CATCTGCTGTACAACGCGAAG | 1048 |
| HVP51 | 51_fus_886_MYC_001_exon3 | GGGCGAACTAAGCCTGGTTT | 1049 | GGTGATCCAGACTCTGACCTTTTG | 1050 |
| HVP51 | 51_fus_3572_PVT1_004_exon1 | CTAACACTGGAGGGCACCAAA | 1051 | CATGGTTCCACCAGCGTTATT | 1052 |
| HVP51 | 51_sp_1302_2548 | CGGACAGCGGATATGGCAATA | 1053 | TCATTCAATGTATACACAGCATTCCCAT | 1054 |
| HVP51 | 51_unsp_886_887 | GGGCGAACTAAGCCTGGTTT | 1055 | CTCATCATCCGAAACATTATCTCCTGT | 1056 |
| HVP51 | 51_fus_2834_PVT1_002_exon3 | GTGCCAGGAGAAAATACTAGACTGTTAT | 1057 | ATCATGATGGCTGTATGTGCCA | 1058 |
| HVP51 | 51_unsp_3318_3319 | GCACAACAGTGGGAGGTCTATATG | 1059 | CCACGCAGGTGGTAAGGG | 1060 |
| HVP51 | 51_fus_2834_MYC_001_exon2 | GTGCCAGGAGAAAATACTAGACTGTTAT | 1061 | AAATACGGCTGCACCGAGT | 1062 |
| HVP51 | 51_sp_886_5521 | GGGCGAACTAAGCCTGGTTT | 1063 | CAATTCGAGACACAGGTGCAG | 1064 |
| HVP51 | 51_fus_3572_MYC_001_exon3 | CTAACACTGGAGGGCACCAAA | 1065 | GGTGATCCAGACTCTGACCTTTTG | 1066 |
| HVP51 | 51_sp_217_402 | CTGCATGAATTATGTGAAGCTTTGAAC | 1067 | TCCCGCTATTTCATGGAACCTTTT | 1068 |
| HVP51 | 51_unsp_750_751 | GCGTGACCAGCTACCAGAAA | 1069 | CATCTGCTGTACAACGCGAAG | 1070 |
| HVP51 | 51_fus_886_PVT1_004_exon1 | GGGCGAACTAAGCCTGGTTT | 1071 | CATGGTTCCACCAGCGTTATT | 1072 |
| HVP51 | 51_fus_3572_MYC_001_exon1 | CTAACACTGGAGGGCACCAAA | 1073 | CTGAGAAGCCCTGCCCTTC | 1074 |
| HVP51 | 51_unsp_217_218 | CTGCATGAATTATGTGAAGCTTTGAAC | 1075 | GTAAACATTGTTTGCATACTGCATATGGA | 1076 |
| HVPS1 | 51_fus_886_MYC_001_exon1 | GGGCGAACTAAGCCTGGTTT | 1077 | CTGAGAAGCCCTGCCCTTC | 1078 |
| HVP51 | 51_sp_886_3319 | GGGCGAACTAAGCCTGGTTT | 1079 | CCACGCAGGTGGTAAGGG | 1080 |
| HVPS1 | 51_fus_2834_MYC_001_exon3 | GTGCCAGGAGAAAATACTAGACTGTTAT | 1081 | GGTGATCCAGACTCTGACCTTTTG | 1082 |
| HVP51 | 51_fus_2834_PVT1_005_exon1 | GTGCCAGGAGAAAATACTAGACTGTTAT | 1083 | TCTTTGCTCGCAGCTCGT | 1084 |
| HVP51 | 51_fus_886_PVT1_005_exon1 | GGGCGAACTAAGCCTGGTTT | 1085 | TCTTTGCTCGCAGCTCGT | 1086 |
| HVP51 | 51_unsp_5520_5521 | GGCCCTATACACATTTACTACGCAAA | 1087 | CAATTCGAGACACAGGTGCAG | 1088 |
| HVP51 | 51_sp_217_3319 | CTGCATGAATTATGTGAAGCTTTGAAC | 1089 | CCACGCAGGTGGTAAGGG | 1090 |
| HVP51 | 51_sp_886_2548 | GGGCGAACTAAGCCTGGTTT | 1091 | TCATTCAATGTATACACAGCATTCCCAT | 1092 |

TABLE 14 -continued

Primer pairs for HR aHPV group and human transcripts

| Virus name | Transcript targeted | Forward primer (5'-3') | SEQ ID NO | Reverse primer (5'-3') | SEQ ID NO |
|---|---|---|---|---|---|
| HVP51 | 51_sp_217_2548 | CTGCATGAATTATGTGAAGCTTTGAAC | 1093 | TCATTCAATGTATACACAGCATTCCCAT | 1094 |
| HVP51 | 51_gen_7175_7808 | GGGTATTACATTATCCCCGTAGGTCAA | 1095 | GCTGCAGCTGTAACAAAATGGAA | 1096 |
| HVP51 | 51_gen_3834_4103 | AGCCAATATGTGCTGCTAATTGTA | 1097 | AACACGTATTGGGACAGCAGTAG | 1098 |
| HVPS1 | 51_gen_1552_2298 | GATGGAGGCAACTGGAGAGAAATT | 1099 | GTGTTTGGTGGGCCATATATGACTAT | 1100 |
| HVP51 | 51_gen_5771_7168 | ACACCCCTCCACAGGCTAA | 1101 | TGTACGCCAACCTGCAACAA | 1102 |
| HVP52 | 52_unsp_523_524 | GACATGTTAATGCAAACAAGCGATTTC | 1103 | TCAGTTGTTTCAGGTTGCAGATCTAATA | 1104 |
| HVPS2 | 52_fus_879_MYC_001_exon1 | GCTGTTGGGCACATTACAAGTT | 1105 | CTGAGAAGCCCTGCCCTTC | 1106 |
| HVP52 | 52_fus_2857_PVT1_005_exon1 | GCTGATAGTAATGACCTAAACGCACAAA | 1107 | TCTTTGCTCGCAGCTCGT | 1108 |
| HVP52 | 52_fus_879_PVT1_004_exon1 | GCTGTTGGGCACATTACAAGTT | 1109 | CATGGTTCCACCAGCGTTATT | 1110 |
| HVP52 | 52_sp_224_524 | AGAATCGGTGCATGAAATAAGGCT | 1111 | TCAGTTGTTTCAGGTTGCAGATCTAATA | 1112 |
| HVP52 | 52_sp_3625_5643 | TCACTGCAACTGAGTGCACAA | 1113 | TGCTTACAACCTTAGAGACAGGTACA | 1114 |
| HVP52 | 52_fus_3613_PVT1_005_exon1 | TCACTGCAACTGAGTGCACAA | 1115 | TCTTTGCTCGCAGCTCGT | 1116 |
| HVP52 | 52_unsp_5642_5643 | TTTTACTACGTCGCAGGCGTAA | 1117 | TGCTTACAACCTTAGAGACAGGTACA | 1118 |
| HVP52 | 52_sp_224_407 | AGAATCGGTGCATGAAATAAGGCT | 1119 | CGCTTGTTTGCATTAACATGTCTTTCT | 1120 |
| HVP52 | 52_unsp_3625_3626 | TCACTGCAACTGAGTGCACAA | 1121 | TGCCAGGTAGATGAAATTTGAACATACA | 1122 |
| HVPS2 | 52_fus_879_MYC_001_exon3 | GCTGTTGGGCACATTACAAGTT | 1123 | GGTGATCCAGACTCTGACCTTTTG | 1124 |
| HVP52 | 52_fus_879_MYC_001_exon2 | GCTGTTGGGCACATTACAAGTT | 1125 | AAATACGGCTGCACCGAGT | 1126 |
| HVP52 | 52_sp_879_3345 | GCTGTTGGGCACATTACAAGTT | 1127 | GCGGAGGTCTTGGAGGTTT | 1128 |
| HVP52 | 52_fus_3613_PVT1_002_exon3 | TCACTGCAACTGAGTGCACAA | 1129 | ATCATGATGGCTGTATGTGCCA | 1130 |
| HVP52 | 52_fus_2857_MYC_001_exon3 | GCTGATAGTAATGACCTAAACGCACAAA | 1131 | GGTGATCCAGACTCTGACCTTTTG | 1132 |
| HVP52 | S2_fus_879_PVT1_002_exon3 | GCTGTTGGGCACATTACAAGTT | 1133 | ATCATGATGGCTGTATGTGCCA | 1134 |
| HVP52 | 52_sp_224_738 | AGAATCGGTGCATGAAATAAGGCT | 1135 | GCATTTGCTGTAGAGTACGAAGGT | 1136 |
| HVP52 | 52_sp_224_3345 | AGAATCGGTGCATGAAATAAGGCT | 1137 | GCGGAGGTCTTGGAGGTTT | 1138 |
| HVP52 | 52_sp_1301_2569 | CAAACCATGTCACGTAGAAGACAG | 1139 | GGGTTTTTGAAATGAAACACAACCAATC | 1140 |
| HVPS2 | 52_unsp_737_738 | GATGAGGAGGATACAGATGGTGTG | 1141 | GCATTTGCTGTAGAGTACGAAGGT | 1142 |

TABLE 14 -continued

Primer pairs for HR aHPV group and human transcripts

| Virus name | Transcript targeted | Forward primer (5'-3') | SEQ ID NO | Reverse primer (5'-3') | SEQ ID NO |
|---|---|---|---|---|---|
| HVP52 | 52_unsp_1301_1302 | CAAACCATGTCACGTAGAAGACAG | 1143 | CCCCACCCCACTTGATTGA | 1144 |
| HVP52 | 52_sp_1301_2696 | CAAACCATGTCACGTAGAAGACAG | 1145 | CGGTATCGACTCCATCGTTTTCC | 1146 |
| HVP52 | 52_fus_28S7_MYC_001_exon1 | GCTGATAGTAATGACCTAAACGCACAAA | 1147 | CTGAGAAGCCCTGCCCTTC | 1148 |
| HVP52 | 52_sp_879_S810 | GCTGTTGGGCACATTACAAGTT | 1149 | CCTGTATTGCAGGCCAGACA | 1150 |
| HVP52 | 52_unsp_224_225 | AGAATCGGTGCATGAAATAAGGCT | 1151 | CACACGCCATATGGATTATTGTCTCTA | 1152 |
| HVP52 | 52_sp_879_2696 | GCTGTTGGGCACATTACAAGTT | 1153 | CGGTATCGACTCCATCGTTTTCC | 1154 |
| HVP52 | 52_fus_3613_MYC_001_exon3 | TCACTGCAACTGAGTGCACAA | 1155 | GGTGATCCAGACTCTGACCTTTTG | 1156 |
| HVP52 | 52_unsp_879_880 | GCTGTTGGGCACATTACAAGTT | 1157 | TCCTCTGAAATGTTATCTCCTGTTTGTT | 1158 |
| HVP52 | 52_unsp_2568_2569 | CCTTAGTACAAATAAAATGCCCACCAT | 1159 | GGGTTTTTGAAATGAAACACAACCAATC | 1160 |
| HVP52 | 52_fus_2857_PVT1_002_exon3 | GCTGATAGTAATGACCTAAACGCACAAA | 1161 | ATCATGATGGCTGTATGTGCCA | 1162 |
| HVP52 | 52_sp_224_2696 | AGAATCGGTGCATGAAATAAGGCT | 1163 | CGGTATCGACTCCATCGTTTTCC | 1164 |
| HVP52 | 52_fus_28S7_MYC_001_exon2 | GCTGATAGTAATGACCTAAACGCACAAA | 1165 | AAATACGGCTGCACCGAGT | 1166 |
| HVP52 | 52_fus_879_PVT1_005_exon1 | GCTGTTGGGCACATTACAAGTT | 1167 | TCTTTGCTCGCAGCTCGT | 1168 |
| HVP52 | 52_unsp_3344_3345 | GTAACAGGAGTATGGGAAGTACATGTG | 1169 | GCGGAGGTCTTGGAGGTTT | 1170 |
| HVP52 | 52_unsp_406_407 | GTATGGGAAAACATTAGAAGAGAGGGT | 1171 | CGCTTGTTTGCATTAACATGTCTTTCT | 1172 |
| HVP52 | 52_sp_1301_3345 | CAAACCATGTCACGTAGAAGACAG | 1173 | GCGGAGGTCTTGGAGGTTT | 1174 |
| HVP52 | 52_fus_3613_MYC_001_exon2 | TCACTGCAACTGAGTGCACAA | 1175 | AAATACGGCTGCACCGAGT | 1176 |
| HVP52 | 52_sp_879_2569 | GCTGTTGGGCACATTACAAGTT | 1177 | GGGTTTTTGAAATGAAACACAACCAATC | 1178 |
| HVP52 | 52_sp_224_2569 | AGAATCGGTGCATGAAATAAGGCT | 1179 | GGGTTTTTGAAATGAAACACAACCAATC | 1180 |
| HVP52 | 52_fus_3613_PVT1_004_exon1 | TCACTGCAACTGAGTGCACAA | 1181 | CATGGTTCCACCAGCGTTATT | 1182 |
| HVP52 | S2_sp_3625_5810 | TCACTGCAACTGAGTGCACAA | 1183 | CCTGTATTGCAGGCCAGACA | 1184 |
| HVP52 | 52_sp_879_5643 | GCTGTTGGGCACATTACAAGTT | 1185 | TGCTTACAACCTTAGAGACAGGTACA | 1186 |
| HVP52 | 52_unsp_5809_5810 | AAGCATCTATTATTATGCAGGCAGTTCT | 1187 | CCTGTATTGCAGGCCAGACA | 1188 |
| HVP52 | 52_fus_3613_MYC_001_exon1 | TCACTGCAACTGAGTGCACAA | 1189 | CTGAGAAGCCCTGCCCTTC | 1190 |
| HVP52 | 52_fus_2857_PVT1_004_exon1 | GCTGATAGTAATGACCTAAACGCACAAA | 1191 | CATGGTTCCACCAGCGTTATT | 1192 |
| HVP52 | 52_gen_6060_7338 | GGACTATATGTTTGGGAGGTGGATTT | 1193 | GATGCAGGGCGTTTTAGTTTGG | 1194 |
| HVP52 | 52_gen_1551_2319 | CACCATCAGTTGCAGAAGGATTAAAAG | 1195 | CTGTGACATTAGTTTGGACACTGTT | 1196 |
| HVP52 | 52_gen_7345_7942 | TCGGTTGGTCTTGGCACAA | 1197 | TTTAGGCGGGACAACAAGTGT | 1198 |
| HVP52 | 52_gen_3875_4225 | CAACACAAGCCAATATTGCTGCTA | 1199 | CCTGCGCATACACCGATATAGAT | 1200 |

TABLE 14 -continued

Primer pairs for HR aHPV group and human transcripts

| Virus name | Transcript targeted | Forward primer (5'-3') | SEQ ID NO | Reverse primer (5'-3') | SEQ ID NO |
|---|---|---|---|---|---|
| HVP56 | 56_unsp_910_911 | GTTAACAGTAACGTGCCCACTCT | 1201 | TTCTACAATTGCCTCTACTTCAAACCAT | 1202 |
| HVP56 | 56_fus_3629_MYC_001_exon2 | ACAACAACCACCCTGGTGATAAG | 1203 | AAATACGGCTGCACCGAGT | 1204 |
| HVP56 | 56_fus_2861_PVT1_002_exon3 | GTGCCAGAACAAAATACTAGACTGTTT | 1205 | ATCATGATGGCTGTATGTGCCA | 1206 |
| HVP56 | S6_fus_910_MYC_001_exon3 | GTTAACAGTAACGTGCCCACTCT | 1207 | GGTGATCCAGACTCTGACCTTTTG | 1208 |
| HVP56 | 56_sp_910_2572 | GTTAACAGTAACGTGCCCACTCT | 1209 | TGAAACTGAAACACTAACATTCTACTGTGT | 1210 |
| HVP56 | 56_fus_2861_PVT1_005_exon1 | GTGCCAGAACAAAATACTAGACTGTTT | 1211 | TCTTTGCTCGCAGCTCGT | 1212 |
| HVPS6 | S6_fus_2861_PVT1_004_exon1 | GTGCCAGAACAAAATACTAGACTGTTT | 1213 | CATGGTTCCACCAGCGTTATT | 1214 |
| HVP56 | 56_fus_3629_MYC_001_exon1 | ACAACAACCACCCTGGTGATAAG | 1215 | CTGAGAAGCCCTGCCCTTC | 1216 |
| HVP56 | 56_unsp_3641_3642 | ACAACAACCACCCTGGTGATAAG | 1217 | TATTGTCTGTACTTGTCCAATGATATGT | 1218 |
| HVP56 | 56_unsp_532_533 | TGCATTGTGACAGAAAAAGACGATTTC | 1219 | ACGTCTTGCAGCGTTGGTA | 1220 |
| HVP56 | 56_unsp_26982699 | AGAATGTTAGTGTTTCAGTTTCAAAATCC | 1221 | TTTTCTTTGTCCTCGTCGTTATCCAA | 1222 |
| HVP56 | 56_fus_3629_PVT1_002_exon3 | ACAACAACCACCCTGGTGATAAG | 1223 | ATCATGATGGCTGTATGTGCCA | 1224 |
| HVP56 | 56_fus_2861_MYC_001_exon1 | GTGCCAGAACAAAATACTAGACTGTTT | 1225 | CTGAGAAGCCCTGCCCTTC | 1226 |
| HVP56 | 56_sp_233_2572 | GCACCACTTGAGTGAGGTATTAGAA | 1227 | TGAAACTGAAACACTAACATTCTACTGTGT | 1228 |
| HVP56 | 56_unsp_772_773 | ACAGCAAGCTAGACAAGCTAAACAA | 1229 | TGTACAACACGCAGGTCCTC | 1230 |
| HVP56 | 56_fus_910_MYC_001_exon1 | GTTAACAGTAACGTGCCCACTCT | 1231 | CTGAGAAGCCCTGCCCTTC | 1232 |
| HVP56 | 56_sp_910_5597 | GTTAACAGTAACGTGCCCACTCT | 1233 | ACAACCTTTGAAACAGGTGTTGA | 1234 |
| HVP56 | 56_sp_233_533 | GCACCACTTGAGTGAGGTATTAGAA | 1235 | ACGTCTTGCAGCGTTGGTA | 1236 |
| HVP56 | 56_fus_2861_MYC_001_exon3 | GTGCCAGAACAAAATACTAGACTGTTT | 1237 | GGTGATCCAGACTCTGACCTTTTG | 1238 |
| HVP56 | 56_unsp_5758_5759 | ATCATGCAGGCAGTTCACGA | 1239 | CAACCGTACCCTAAATACCCTATATTGA | 1240 |
| HVP56 | 56_sp_1295_3349 | CAAGACAGCGGGTATGGCAATA | 1241 | GGTGGTGGTGGTGGTCTT | 1242 |
| HVP56 | 56_sp_1295_2699 | CAAGACAGCGGGTATGGCAATA | 1243 | TTTTCTTTGTCCTCGTCGTTATCCAA | 1244 |
| HVP56 | 56_unsp_233_234 | GCACCACTTGAGTGAGGTATTAGAA | 1245 | ACAATAAACATACTCTGCACACTGCATA | 1246 |
| HVP56 | 56_sp_3641_5597 | ACAACAACCACCCTGGTGATAAG | 1247 | ACAACCTTTGAAACAGGTGTTGA | 1248 |
| HVP56 | 56_sp_233_2699 | GCACCACTTGAGTGAGGTATTAGAA | 1249 | TTTTCTTTGTCCTCGTCGTTATCCAA | 1250 |
| HVP56 | 56_sp_1295_2572 | CAAGACAGCGGGTATGGCAATA | 1251 | TGAAACTGAAACACTAACATTCTACTGTGT | 1252 |

TABLE 14 -continued

Primer pairs for HR aHPV group and human transcripts

| Virus name | Transcript targeted | Forward primer (5'-3') | SEQ ID NO | Reverse primer (5'-3') | SEQ ID NO |
|---|---|---|---|---|---|
| HVP56 | 56_sp_910_3349 | GTTAACAGTAACGTGCCCACTCT | 1253 | GGTGGTGGTGGTGGTCTT | 1254 |
| HVP56 | 56_unsp_1295_1296 | CAAGACAGCGGGTATGGCAATA | 1255 | GGTACTGTTTTGTGAGCCTCCATTT | 1256 |
| HVP56 | 56_fus_910_MYC_001_exon2 | GTTAACAGTAACGTGCCCACTCT | 1257 | AAATACGGCTGCACCGAGT | 1258 |
| HVP56 | 56_fus_3629_MYC_001_exon3 | ACAACAACCACCCTGGTGATAAG | 1259 | GGTGATCCAGACTCTGACCTTTTG | 1260 |
| HVP56 | 56_fus_3629_PVT1_004_exon1 | ACAACAACCACCCTGGTGATAAG | 1261 | CATGGTTCCACCAGCGTTATT | 1262 |
| HVP56 | 56_fus_2861_MYC_001_exon2 | GTGCCAGAACAAAATACTAGACTGTTT | 1263 | AAATACGGCTGCACCGAGT | 1264 |
| HVP56 | 56_unsp_5596_5597 | AGGGATCCTCCTTTGCATTATGG | 1265 | ACAACCTTTGAAACAGGTGTTGGA | 1266 |
| HVP56 | 56_sp_233_416 | GCACCACTTGAGTGAGGTATTAGAA | 1267 | CAATTGCTTTTCCTCCGGAGTTAA | 1268 |
| HVP56 | 56_sp_910_5759 | GTTAACAGTAACGTGCCCACTCT | 1269 | CAACCGTACCCTAAATACCCTATATTGA | 1270 |
| HVP56 | 56_fus_910_PVT1_002_exon3 | GTTAACAGTAACGTGCCCACTCT | 1271 | ATCATGATGGCTGTATGTGCCA | 1272 |
| HVP56 | 56_sp_910_2699 | GTTAACAGTAACGTGCCCACTCT | 1273 | TTTTCTTTGTCCTCGTCGTTATCCAA | 1274 |
| HVP56 | 56_unsp_415_416 | TCAGTGTATGGAGCTACACTAGAAAGT | 1275 | CAATTGCTTTTCCTCCGGAGTTAA | 1276 |
| HVP56 | 56_fus_910_PVT1_005_exon1 | GTTAACAGTAACGTGCCCACTCT | 1277 | TCTTTGCTCGCAGCTCGT | 1278 |
| HVP56 | 56_sp_3641_5759 | ACAACAACCACCCTGGTGATAAG | 1279 | CAACCGTACCCTAAATACCCTATATTGA | 1280 |
| HVP56 | 56_fus_910_PVT1_004_exon1 | GTTAACAGTAACGTGCCCACTCT | 1281 | CATGGTTCCACCAGCGTTATT | 1282 |
| HVP56 | 56_fus_3629_PVT1_005_exon1 | ACAACAACCACCCTGGTGATAAG | 1283 | TCTTTGCTCGCAGCTCGT | 1284 |
| HVP56 | 56_sp_233_3349 | GCACCACTTGAGTGAGGTATTAGAA | 1285 | GGTGGTGGTGGTGGTCTT | 1286 |
| HVP56 | 56_sp_233_773 | GCACCACTTGAGTGAGGTATTAGAA | 1287 | TGTACAACACGCAGGTCCTC | 1288 |
| HVP56 | 56_gen_3891_4183 | TGCTACGCATATATATTGCAACCATTGA | 1289 | GGATGTGGCTATAACAAACCAAAACAAT | 1290 |
| HVP56 | 56_gen_7283_7844 | AATTCGGTTGCATGGCCTAGT | 1291 | GGGTGCGGTACTGTACATAATTCAAG | 1292 |
| HVP56 | 56_gen_6009_7276 | TGTACTCCCGCTATGGGTGAA | 1293 | GTGTCTATCATGTCCCCATCCTCTA | 1294 |
| HVP56 | 56_gen_1545_2322 | CAGATGATAGCCAAATTGCGTTTCA | 1295 | GCTGTTGTGCCCTTTTATAATGTCTAC | 1296 |
| HVP58 | 58_sp_898_5643 | TGCTTATGGGCACATGTACCATT | 1297 | GCTTACAACCTTAGACACAGGCA | 1298 |
| HVP58 | 58_fus_3596_PVT1_002_exon3 | GAGGAGGACTACACAGTACAACTAACT | 1299 | ATCATGATGGCTGTATGTGCCA | 1300 |
| HVP58 | 58_fus_898_MYC_001_exon3 | TGCTTATGGGCACATGTACCATT | 1301 | GGTGATCCAGACTCTGACCTTTTG | 1302 |
| HVP58 | 58_sp_1320_3355 | AAAATTATTGAGCTAGAAGACAGCGGAT | 1303 | CCCTGTGTACTTTCGTTGTTGGT | 1304 |

TABLE 14 -continued

Primer pairs for HR aHPV group and human transcripts

| Virus name | Transcript targeted | Forward primer (5'-3') | SEQ ID NO | Reverse primer (5'-3') | SEQ ID NO |
|---|---|---|---|---|---|
| HVP58 | 58_unsp_1320_1321 | AAAATTATTGAGCTAGAAGACAGCGGAT | 1305 | CCCCACTAGACTCCGAGTCATTTAA | 1306 |
| HVP58 | 58_fus_3596_MYC_001_exon3 | GAGGAGGACTACACAGTACAACTAACT | 1307 | GGTGATCCAGACTCTGACCTTTTG | 1308 |
| HVP58 | 58_fus_2867_PVT1_005_exon1 | GCAGGACAAAATCCTAGACATATACGAA | 1309 | TCTTTGCTCGCAGCTCGT | 1310 |
| HVP58 | 58_fus_3596_PVT1_004_exon1 | GAGGAGGACTACACAGTACAACTAACT | 1311 | CATGGTTCCACCAGCGTTATT | 1312 |
| HVP58 | 58_unsp_898_899 | TGCTTATGGGCACATGTACCATT | 1313 | CTGTTCTTCGTTCTATTACCGCCTA | 1314 |
| HVP58 | 58_fus_898_PVT1_002_exon3 | TGCTTATGGGCACATGTACCATT | 1315 | ATCATGATGGCTGTATGTGCCA | 1316 |
| HVP58 | 58_unsp_2578_2579 | ATTAGATGGTAACGACATTTCAATAGATGT | 1317 | TGCATCAAATGGAAATGGATTGTTAAATTCA | 1318 |
| HVP58 | 58_sp_232_2579 | GTCAGGCGTTGGAGACATCT | 1319 | TGCATCAAATGGAAATGGATTGTTAAATTCA | 1320 |
| HVP58 | 58_fus_2867_MYC_001_exon3 | GCAGGACAAAATCCTAGACATATACGAA | 1321 | GGTGATCCAGACTCTGACCTTTTG | 1322 |
| HVP58 | 58_fus_898_MYC_001_exon2 | TGCTTATGGGCACATGTACCATT | 1323 | AAATACGGCTGCACCGAGT | 1324 |
| HVP58 | 58_sp_232_415 | GTCAGGCGTTGGAGACATCT | 1325 | CGACCCGAAATATTATGAAACCTTTTGT | 1326 |
| HVP58 | 58_fus_898_PVT1_005_exon1 | TGCTTATGGGCACATGTACCATT | 1327 | TCTTTGCTCGCAGCTCGT | 1328 |
| HVP58 | 58_sp_232_2706 | GTCAGGCGTTGGAGACATCT | 1329 | TGATATTTCCTCCATCGTTTTCCTTGTC | 1330 |
| HVP58 | 58_unsp_414_415 | CGCTATATGGAGACACATTAGAACAAACA | 1331 | CGACCCGAAATATTATGAAACCTTTTGT | 1332 |
| HVP58 | 58_unsp_3354_3355 | ACAATTATGGGAGGTACATGTGGGTA | 1333 | CCCTGTGTACTTTCGTTGTTGGT | 1334 |
| HVP58 | 58_sp_1320_2579 | AAAATTATTGAGCTAGAAGACAGCGGAT | 1335 | TGCATCAAATGGAAATGGATTGTTAAATTCA | 1336 |
| HVP58 | 58_sp_1320_2706 | AAAATTATTGAGCTAGAAGACAGCGGAT | 1337 | TGATATTTCCTCCATCGTTTTCCTTGTC | 1338 |
| HVP58 | 58_fus_2867_MYC_001_exon2 | GCAGGACAAAATCCTAGACATATACGAA | 1339 | AAATACGGCTGCACCGAGT | 1340 |
| HVP58 | 58_sp_232_532 | GTCAGGCGTTGGAGACATCT | 1341 | GCGTTGGGTTGTTTCCTCTCA | 1342 |
| HVP58 | 58_fus_898_PVT1_004_exon1 | TGCTTATGGGCACATGTACCATT | 1343 | CATGGTTCCACCAGCGTTATT | 1344 |
| HVP58 | 58_fus_898_MYC_001_exon1 | TGCTTATGGGCACATGTACCATT | 1345 | CTGAGAAGCCCTGCCCTTC | 1346 |
| HVP58 | 58_sp_898_2706 | TGCTTATGGGCACATGTACCATT | 1347 | TGATATTTCCTCCATCGTTTTCCTTGTC | 1348 |
| HVP58 | 58_fus_3596_PVT1_005_exon1 | GAGGAGGACTACACAGTACAACTAACT | 1349 | TCTTTGCTCGCAGCTCGT | 1350 |

TABLE 14 -continued

Primer pairs for HR aHPV group and human transcripts

| Virus name | Transcript targeted | Forward primer (5'-3') | SEQ ID NO | Reverse primer (5'-3') | SEQ ID NO |
|---|---|---|---|---|---|
| HVP58 | 58_fus_2867_PVT1_004_exon1 | GCAGGACAAAATCCTAGACATATACGAA | 1351 | CATGGTTCCACCAGCGTTATT | 1352 |
| HVP58 | 58_sp_232_3355 | GTCAGGCGTTGGAGACATCT | 1353 | CCCTGTGTACTTTCGTTGTTGGT | 1354 |
| HVP58 | 58_fus_2867_PVT1_002_exon3 | GCAGGACAAAATCCTAGACATATACGAA | 1355 | ATCATGATGGCTGTATGTGCCA | 1356 |
| HVP58 | 58_fus_3596_MYC_001_exon2 | GAGGAGGACTACACAGTACAACTAACT | 1357 | AAATACGGCTGCACCGAGT | 1358 |
| HVP58 | 58_unsp_3608_3609 | GAGGAGGACTACACAGTACAACTAACT | 1359 | CCAATGCCATGTGGATGACATATTACA | 1360 |
| HVP58 | 58_unsp_5642_5643 | CTGATTTTATGTTGCACCCTAGCTATTT | 1361 | GCTTACAACCTTAGACACAGGCA | 1362 |
| HVP58 | 58_fus_3596_MYC_001_exon1 | GAGGAGGACTACACAGTACAACTAACT | 1363 | CTGAGAAGCCCTGCCCTTC | 1364 |
| HVP58 | 58_unsp_232_233 | GTCAGGCGTTGGAGACATCT | 1365 | TCGTAAGCACACTTTACATACTGCAAA | 1366 |
| HVP58 | 58_sp_898_2579 | TGCTTATGGGCACATGTACCATT | 1367 | TGCATCAAATGGAAATGGATTGTTAAATTCA | 1368 |
| HVP58 | 58_sp_898_3355 | TGCTTATGGGCACATGTACCATT | 1369 | CCCTGTGTACTTTCGTTGTTGGT | 1370 |
| HVP58 | 58_sp_3608_5643 | GAGGAGGACTACACAGTACAACTAACT | 1371 | GCTTACAACCTTAGACACAGGCA | 1372 |
| HVP58 | 58_fus_2867_MYC_001_exon1 | GCAGGACAAAATCCTAGACATATACGAA | 1373 | CTGAGAAGCCCTGCCCTTC | 1374 |
| HVP58 | 58_gen_5893_7295 | CGTTTGGTCTGGGCATGTGTA | 1375 | GCTGTGCGGGATATCTGTTACTG | 1376 |
| HVP58 | 58_gen_38S8_4208 | TCTATATATGCTTGGTTGCTGGTGTTG | 1377 | CATGTGCAGAACCAGTATACAGTTAGT | 1378 |
| HVP58 | 58_gen_1570_2329 | CAATGGGACAATGGATACAAAGTAGGT | 1379 | GGGCCACACAGTAACATACAACT | 1380 |
| HVP58 | 58_gen_7302_7824 | TCTATGAGTAAGGTGCTGTCCCTAAAT | 1381 | GGAGGTAAAGTAAAATGGAGGCAGTA | 1382 |
| HVP59 | 59_unsp_3627_3628 | TCCGTTTGCATCCAGGCAA | 1383 | CCAATGCCAGGTAGAGGAAATATTTTCA | 1384 |
| HVP59 | 59_fus_2862_MYC_001_exon1 | GCGTTTAAGTGTGTTACAGGATCAAAT | 1385 | CTGAGAAGCCCTGCCCTTC | 1386 |
| HVP59 | 59_sp_1306_3359 | AAAGAAGGTTAATAACAGTGCCAGACA | 1387 | CCCAAGTACGTGGCTTCGG | 1388 |
| HVP59 | 59_unsp_2570_2571 | AGATAGAAAGCATAGGCACCTAGTACAA | 1389 | TCTATTTTGTCAAATGGCAATTGTTTGGA | 1390 |
| HVP59 | 59_unsp_748_749 | CAGATGGAGTTAATCATCCTTTGCTACT | 1391 | TGTAAGGCTCGCAATCCGT | 1392 |
| HVP59 | 59_fus_887_PVT1_004_exon1 | ACTATCCTTTGTGTGTCCTTTGTGT | 1393 | CATGGTTCCACCAGCGTTATT | 1394 |
| HVP59 | 59_fus_2862_PVT1_004_exon1 | GCGTTTAAGTGTGTTACAGGATCAAAT | 1395 | CATGGTTCCACCAGCGTTATT | 1396 |
| HVP59 | 59_fus_887_PVT1_002_exon3 | ACTATCCTTTGTGTGTCCTTTGTGT | 1397 | ATCATGATGGCTGTATGTGCCA | 1398 |
| HVP59 | 59_fus_3615_MYC_001_exon1 | TCCGTTTGCATCCAGGCAA | 1399 | CTGAGAAGCCCTGCCCTTC | 1400 |

TABLE 14 -continued

Primer pairs for HR aHPV group and human transcripts

| Virus name | Transcript targeted | Forward primer (5'-3') | SEQ ID NO | Reverse primer (5'-3') | SEQ ID NO |
|---|---|---|---|---|---|
| HVP59 | 59_sp_1306_2698 | AAAGAAGGTTAATAACAGTGCCAGACA | 1401 | GGTGTCCATCACTGTCTGCAT | 1402 |
| HVP59 | 59_sp_3627_5606 | TCCGTTTGCATCCAGGCAA | 1403 | TGACATACTCATCAGTGCTGACAAC | 1404 |
| HVP59 | 59_fus_3615_MYC_001_exon2 | TCCGTTTGCATCCAGGCAA | 1405 | AAATACGGCTGCACCGAGT | 1406 |
| HVP59 | 59_fus_2862_MYC_001_exon3 | GCGTTTAAGTGTGTTACAGGATCAAAT | 1407 | GGTGATCCAGACTCTGACCTTTTG | 1408 |
| HVP59 | 59_unsp_5768_5769 | GTATGTCACCCGTACCAGTATTTTCTAC | 1409 | GCCAAATTTATTGGGATCAGGTAACTT | 1410 |
| HVP59 | 59_sp_887_3359 | ACTATCCTTTGTGTGTCCTTTGTGT | 1411 | CCCAAGTACGTGGCTTCGG | 1412 |
| HVP59 | 59_sp_183_2571 | GCATCAAHGTGTGTTTTGCAAAGG | 1413 | TCTATTTTTGTCAAATGGCAATTTGTTTGGA | 1414 |
| HVP59 | 59_fus_3615_MYC_001_exon3 | TCCGTTTGCATCCAGGCAA | 1415 | GGTGATCCAGACTCTGACCTTTTG | 1416 |
| HVP59 | 59_fus_887_MYC_001_exon3 | ACTATCCTTTGTGTGTCCTTTGTGT | 1417 | GGTGATCCAGACTCTGACCTTTTG | 1418 |
| HVP59 | 59_fus_3615_PVT1_005_exon1 | TCCGTTTGCATCCAGGCAA | 1419 | TCTTTGCTCGCAGCTCGT | 1420 |
| HVP59 | 59_fus_2862_MYC_001_exon2 | GCGTTTAAGTGTGTTACAGGATCAAAT | 1421 | AAATACGGCTGCACCGAGT | 1422 |
| HVP59 | 59_sp_887_5606 | ACTATCCTTTGTGTGTCCTTTGTGT | 1423 | TGACATACTCATCAGTGCTGACAAC | 1424 |
| HVP59 | 59_fus_887_MYC_001_exon2 | ACTATCCTTTGTGTGTCCTTTGTGT | 1425 | AAATACGGCTGCACCGAGT | 1426 |
| HVP59 | 59_sp_887_5769 | ACTATCCTTTGTGTGTCCTTTGTGT | 1427 | GCCAAATTTATTGGGATCAGGTAACTT | 1428 |
| HVP59 | 59_unsp_887_888 | ACTATCCTTTGTGTGTCCTTTGTGT | 1429 | CGTCATCTGAAATTTTGTCACCTGTTTT | 1430 |
| HVP59 | 59_fus_2862_PVT1_002_exon3 | GCGrTTAAGTGTGTTACAGGATCAAAT | 1431 | ATCATGATGGCTGTATGTGCCA | 1432 |
| HVP59 | S9_sp_3627_5769 | TCCGTTTGCATCCAGGCAA | 1433 | GCCAAATTTATTGGGATCAGGTAACTT | 1434 |
| HVP59 | S9_sp_1306_2571 | AAAGAAGGTTAATAACAGTGCCAGACA | 1435 | TCTATTTTTGTCAAATGGCAATTTGTTTGGA | 1436 |
| HVP59 | 59_sp_887_2571 | ACTATCCTTTGTGTGTCCTTTGTGT | 1437 | TCTATTTTTGTCAAATGGCAATTTGTTTGGA | 1438 |
| HVP59 | 59_unsp_1306_1307 | AAAGAAGGTTAATAACAGTGCCAGACA | 1439 | GTCTATTTGACTGTCGCTACAAACAC | 1440 |
| HVPS9 | 59_unsp_5605_5606 | CCTCGTAAACGTAAACGTGTTCC | 1441 | TGACATACTCATCAGTGCTGACAAC | 1442 |
| HVP59 | 59_fus_3615_PVT1_002_exon3 | TCCGTTTGCATCCAGGCAA | 1443 | ATCATGATGGCTGTATGTGCCA | 1444 |
| HVP59 | 59_fus_3615_PVT1_004_exon1 | TCCGTTTGCATCCAGGCAA | 1445 | CATGGTTCCACCAGCGTTATT | 1446 |
| HVP59 | 59_fus_2862_PVT1_005_exon1 | GCGTTTAAGTGTGTTACAGG ATCAAAT | 1447 | TCTTTGCTCGCAGCTCGT | 1448 |
| HVP59 | 59_sp_183_3359 | GCATCAATTGTGTGTTTTGCAAAGG | 1449 | CCCAAGTACGTGGCTTCGG | 1450 |

TABLE 14 -continued

Primer pairs for HR aHPV group and human transcripts

| Virus name | Transcript targeted | Forward primer (5'-3') | SEQ ID NO | Reverse primer (5'-3') | SEQ ID NO |
|---|---|---|---|---|---|
| HVP59 | 59_sp_887_2698 | ACTATCCTTTGTGTGTCCTTTGTGT | 1451 | GGTGTCCATCACTGTCTGCAT | 1452 |
| HVP59 | 59_sp_183_2698 | GCATCAATTGTGTGTTTTGCAAAGG | 1453 | GGTGTCCATCACTGTCTGCAT | 1454 |
| HVP59 | 59_fus_887_MYC_001_exon1 | ACTATCCTTTGTGTGTCCTTTGTGT | 1455 | CTGAGAAGCCCTGCCCTTC | 1456 |
| HVP59 | 59_fus_887_PVT1_005_exon1 | ACTATCCTTTGTGTGTCCTTTGTGT | 1457 | TCTTTGCTCGCAGCTCGT | 1458 |
| HVP59 | 59_sp_183_749 | GCATCAATTGTGTGTTTTGCAAAGG | 1459 | TGTAAGGCTCGCAATCCGT | 1460 |
| HVP59 | 59_unsp_183_184 | GCATCAATTGTGTGTTTTGCAAAGG | 1461 | GCATTTCAGACACGCTGCATAC | 1462 |
| HVP59 | 59_gen_3877_4222 | GTTGCAATGTCCCGCTTCTG | 1463 | CATGGGCATATAGTAGTAACAGTGGAA | 1464 |
| HVP59 | 59_gen_7261_7896 | GGTTGCACCCAATGAGTAAGGTA | 1465 | GCAAAACTGGACATTCAGGACAAAA | 1466 |
| HVP59 | 59_gen_6019_7254 | GCTGTGTACCTGCCATTGGA | 1467 | CTGTGTCTACCATATCACCATCTTCA | 1468 |
| HVP59 | 59_gen_1556_2321 | GTGCATGTTAATTGAACCACCCAAA | 1469 | TCAAACACGCTATCATCAACTCCAT | 1470 |
| HVP66 | 66_fus_2843_PVT1_002_exon3 | CGTGCCAGAACAAAATACTAGACTGT | 1471 | ATCATGATGGCTGTATGTGCCA | 1472 |
| HVP66 | 66_sp_233_773 | CACCATCTGAGCGAGGTATTACA | 1473 | TGTACCACACGTAGCTCCTCT | 1474 |
| HVP66 | 66_fus_910_MYC_001_exon1 | GTTAACAGTAACGTGCCCACTCT | 1475 | CTGAGAAGCCCTGCCCTTC | 1476 |
| HVP66 | 66_unsp_233_234 | CACCATCTGAGCGAGGTATTACA | 1477 | ACAATAAACATACCCTACATACTGCATATGG | 1478 |
| HVP66 | 66_fus_910_MYC_001_exon3 | GTTAACAGTAACGTGCCCACTCT | 1479 | GGTGATCCAGACTCTGACCTTTTG | 1480 |
| HVP66 | 66_fus_2843_MYC_001_exon1 | CGTGCCAGAACAAAATACTAGACTGT | 1481 | CTGAGAAGCCCTGCCCTTC | 1482 |
| HVP66 | 66_sp_1290_2682 | GAAGACAGCGGGTATGGCAATA | 1483 | TTTTCTTTGTCCTCGTCGTTATCCAA | 1484 |
| HVP66 | 66_fus_2843_MYC_001_exon3 | CGTGCCAGAACAAAATACTAGACTGT | 1485 | GGTGATCCAGACTCTGACCTTTTG | 1486 |
| HVP66 | 66_sp_1290_2555 | GAAGACAGCGGGTATGGCAATA | 1487 | CATTACTTAATTCATACACAGGATTACCATT | 1488 |
| HVP66 | 66_fus_3605_PVT1_005_exon1 | GTATCAACACACAAAGCCACTGT | 1489 | TCTTTGCTCGCAGCTCGT | 1490 |
| HVP66 | 66_sp_910_5647 | GTTAACAGTAACGTGCCCACTCT | 1491 | ACAACCTTTGAAACAGGTGTTGGA | 1492 |
| HVP66 | 66_fus_3605_MYC_001_exon3 | GTATCAACACACAAAGCCACTGT | 1493 | GGTGATCCAGACTCTGACCTTTTG | 1494 |
| HVP66 | 66_sp_910_3362 | GTTAACAGTAACGTGCCCACTCT | 1495 | GGTGGTGGTGGTCCTGTG | 1496 |
| HVP66 | 66_fus_3605_PVT1_004_exon1 | GTATCAACACACAAAGCCACTGT | 1497 | CATGGTTCCACCAGCGTTATT | 1498 |
| HVP66 | 66_fus_2843_MYC_001_exon2 | CGTGCCAGAACAAAATACTAGACTGT | 1499 | AAATACGGCTGCACCGAGT | 1500 |
| HVP66 | 66_sp_233_2682 | CACCATCTGAGCGAGGTATTACA | 1501 | TTTTCTTTGTCCTCGTCGTTATCCAA | 1502 |

TABLE 14 -continued

Primer pairs for HR aHPV group and human transcripts

| Virus name | Transcript targeted | Forward primer (5'-3') | SEQ ID NO | Reverse primer (5'-3') | SEQ ID NO |
|---|---|---|---|---|---|
| HVP66 | 66_sp_233_533 | CACCATCTGAGCGAGGTATTACA | 1503 | AACCTCTTGCAACGTTGGTACT | 1504 |
| HVP66 | 66_unsp_772_773 | ACAGCAAGCTAGACAAGCTGAA | 1505 | TGTACCACACGTAGCTCCTCT | 1506 |
| HVP66 | 66_sp_233_416 | CACCATCTGAGCGAGGTATTACA | 1507 | GAAATCGTCTTTTATGTTCACAGTGCAA | 1508 |
| HVP66 | 66_sp_233_2555 | CACCATCTGAGCGAGGTATTACA | 1509 | CATTACTTAATTCATACACAGGATTACCATT | 1510 |
| HVP66 | 66_sp_3617_5647 | GTATCAACACACAAAGCCACTGT | 1511 | ACAACCTTTGAAACAGGTGTTGGA | 1512 |
| HVP66 | 66_fus_2843_PVT1_004_exon1 | CGTGCCAGAACAAAATACTAGACTGT | 1513 | CATGGTTCCACCAGCGTTATT | 1514 |
| HVP66 | 66_fus_910_PVT1_002_exon3 | GTTAACAGTAACGTGCCCACTCT | 1515 | ATCATGATGGCTGTATGTGCCA | 1516 |
| HVP66 | 66_unsp_910_911 | GTTAACAGTAACGTGCCCACTCT | 1517 | TTCTACAATTGCTTCTACCTGAAACCAT | 1518 |
| HVP66 | 66_sp_233_3362 | CACCATCTGAGCGAGGTATTACA | 1519 | GGTGGTGGTGGTCCTGTG | 1520 |
| HVP66 | 66_sp_910_2555 | GTTAACAGTAACGTGCCCACTCT | 1521 | CATTACTTAATTCATACACAGGATTACCATT | 1522 |
| HVP66 | 66_fus_3605_MYC_001_exon2 | GTATCAACACACAAAGCCACTGT | 1523 | AAATACGGCTGCACCGAGT | 1524 |
| HVP66 | 66_fus_2843_PVT1_005_exon1 | CGTGCCAGAACAAAATACTAGACTGT | 1525 | TCTTTGCTCGCAGCTCGT | 1526 |
| HVP66 | 66_fus_3605_PVT1_002_exon3 | GTATCAACACACAAAGCCACTGT | 1527 | ATCATGATGGCTGTATGTGCCA | 1528 |
| HVP66 | 66_sp_1290_3362 | GAAGACAGCGGGTATGGCAATA | 1529 | GGTGGTGGTGGTCCTGTG | 1530 |
| HVP66 | 66_sp_910_2682 | GTTAACAGTAACGTGCCCACTCT | 1531 | TTTTCTTTGTCCTCGTCGTTATCCAA | 1532 |
| HVP66 | 66_fus_910_MYC_001_exon2 | GTTAACAGTAACGTGCCCACTCT | 1533 | AAATACGGCTGCACCGAGT | 1534 |
| HVP66 | 66_fus_3605_MYC_001_exon1 | GTATCAACACACAAAGCCACTGT | 1535 | CTGAGAAGCCCTGCCCTTC | 1536 |
| HVP66 | 66_unsp_1290_1291 | GAAGACAGCGGGTATGGCAATA | 1537 | GATACCGAGTGCTCACTACAATTACTG | 1538 |
| HVP66 | 66_fus_910_PVT1_004_exon1 | GTTAACAGTAACGTGCCCACTCT | 1539 | CATGGTTCCACCAGCGTTATT | 1540 |
| HVP66 | 66_fus_910_PVT1_005_exon1 | GTTAACAGTAACGTGCCCACTCT | 1541 | TCTTTGCTCGCAGCTCGT | 1542 |
| HVP66 | 66_unsp_3617_3618 | GTATCAACACACAAAGCCACTGT | 1543 | TCTGTACTTGTCCAATGATATGTTGTTGT | 1544 |
| HVP66 | 66_unsp_5646_5647 | GCTACATTTGCACTATGGCCTGTA | 1545 | ACAACCTTTGAAACAGGTGTTGGA | 1546 |
| HVP66 | 66_unsp_415_416 | GGGCAACATTAGAAAGTATAACTAAAAAACA | 1547 | GAAATCGTCTTTTATGTTCACAGTGCAA | 1548 |
| HVP66 | 66_gen_7301_7824 | GGTTAGGTGGTGTTCCTTACTGTTTA | 1549 | CAAAAGGCTAGGCAACCGAATT | 1550 |
| HVP66 | 66_gen_1540_2305 | AGACATAGATAGCAATGCACAAGCA | 1551 | ATCACCCCCTTCATCTACTTTACTACA | 1552 |
| HVP66 | 66_gen_3867_4235 | GTTTGTCTGTGTGTGTGCCATT | 1553 | GCATGGCAATATATACACAGTGTAGGT | 1554 |

TABLE 14 -continued

Primer pairs for HR aHPV group and human transcripts

| Virus name | Transcript targeted | Forward primer (5'-3') | SEQ ID NO | Reverse primer (5'-3') | SEQ ID NO |
|---|---|---|---|---|---|
| HVP66 | 66_gen_5897_7294 | GTAGGCCGAGGTCAACCTTTA | 1555 | GTGCACATCCCACAATACATAACTG | 1556 |
| HVP66 | 66_sp_1290_3331 | GACAGGGAGACAGCTCAACAATTATT | 1557 | CTCTCGGTACACAGTTTGCTGATTA | 1558 |
| HVP66 | 66_unsp_3330_3331 | GTGGGTGGTGTAAAGTGTCATCA | 1559 | GGACAGTAAATACTCTCGGTTTCCAT | 1560 |
| HVP68 | 68_sp_129_3292 | GACATTGGACACTACATTGCATGAC | 1561 | TCGCGGTGGTGTTCTGTAG | 1562 |
| HVP68 | 68_sp_129_2510 | GACATTGGACACTACATTGCATGAC | 1563 | CTGTTTTGGTCAAATGGAAATGCATTAG | 1564 |
| HVP68 | 68_fus_2801_MYC_001_exon1 | ACAGGACAGTAAATGTATACAGGACCAT | 1565 | CTGAGAAGCCCTGCCCTTC | 1566 |
| HVP68 | 68_unsp_5487_5488 | TACAACCTTTGCCATAACTATATATGGT | 1567 | ATTGACAACCTTCGCCACTGA | 1568 |
| HVP68 | 68_fus_3551_PVT1_004_exon1 | AGTAGAAGTGCAGGCCAAAACAA | 1569 | CATGGTTCCACCAGCGTTATT | 1570 |
| HVP68 | 68_fus_838_MYC_001_exon1 | TCCGTGGTGTGCAACTGAA | 1571 | CTGAGAAGCCCTGCCCTTC | 1572 |
| HVP68 | 68_fus_3551_MYC_001_exon3 | AGTAGAAGTGCAGGCCAAAACAA | 1573 | GGTGATCCAGACTCTGACCTTTTG | 1574 |
| HVP68 | 68_fus_2801_PVT1_002_exon3 | ACAGGACAGTAAATGTATACAGGACCAT | 1575 | ATCATGATGGCTGTATGTGCCA | 1576 |
| HVP68 | 68_fus_2801_MYC_001_exon2 | ACAGGACAGTAAATGTATACAGGACCAT | 1577 | AAATACGGCTGCACCGAGT | 1578 |
| HVP68 | 68_fus_838_PVT1_004_exon1 | TCCGTGGTGTGCAACTGAA | 1579 | CATGGTTCCACCAGCGTTATT | 1580 |
| HVP68 | 68_unsp_1233_1234 | AGACAACCGGCGTATACAGTG | 1581 | CACACTACTACAGTCCTCCCGTAT | 1582 |
| HVP68 | 68_fus_3551_MYC_001_exon1 | AGTAGAAGTGCAGGCCAAAACAA | 1583 | CTGAGAAGCCCTGCCCTTC | 1584 |
| HVP68 | 68_fus_2801_PVT1_004_exon1 | ACAGGACAGTAAATGTATACAGGACCAT | 1585 | CATGGTTCCACCAGCGTTATT | 1586 |
| HVP68 | 68_unsp_129_130 | GACATTGGACACTACATTGCATGAC | 1587 | GATTGGCATGCAGCAAATGGTA | 1588 |
| HVP68 | 68_fus_2801_MYC_001_exon3 | ACAGGACAGTAAATGTATACAGGACCAT | 1589 | GGTGATCCAGACTCTGACCTTTTG | 1590 |
| HVP68 | 68_sp_1233_2510 | AGACAACCGGCGTATACAGTG | 1591 | CTGTTTTGGTCAAATGGAAATGCATTAG | 1592 |
| HVP68 | 68_unsp_696_697 | CCACCAACATCTACTACTAGCCAGA | 1593 | CTGTTGTAGTGTCCGCAGGTT | 1594 |
| HVP68 | 68_unsp_2509_2510 | CCTAATACAAATAAAGTGTCCACCAATGCT | 1595 | CTGTTTTGGTCAAATGGAAATGCATTAG | 1596 |
| HVP68 | 68_sp_129_312 | GACATTGGACACTACATTGCATGAC | 1597 | CTTCGTTTTGTTGTTAGGTGCCTTAG | 1598 |
| HVP68 | 68_fus_3551_PVT1_002_exon3 | AGTAGAAGTGCAGGCCAAAACAA | 1599 | ATCATGATGGCTGTATGTGCCA | 1600 |
| HVP68 | 68_fus_3551_PVT1_005_exon1 | AGTAGAAGTGCAGGCCAAAACAA | 1601 | TCTTTGCTCGCAGCTCGT | 1602 |
| HVP68 | 68_sp_838_2510 | TCCGTGGTGTGCAACTGAA | 1603 | CTGTTTTGGTCAAATGGAAATGCATTAG | 1604 |
| HVP68 | 68_unsp_838_839 | TCCGTGGTGTGCAACTGAA | 1605 | GACTGTGTCACCTGTTTGTTTATCTACT | 1606 |

TABLE 14 -continued

Primer pairs for HR aHPV group and human transcripts

| Virus name | Transcript targeted | Forward primer (5'-3') | SEQ ID NO | Reverse primer (5'-3') | SEQ ID NO |
|---|---|---|---|---|---|
| HVP68 | 68_sp_838_5488 | TCCGTGGTGTGCAACTGAA | 1607 | ATTGACAACCTTCGCCACTGA | 1608 |
| HVP68 | 68_fus_3551_MYC_001_exon2 | AGTAGAAGTGCAGGCCAAAACAA | 1609 | AAATACGGCTGCACCGAGT | 1610 |
| HVP68 | 68_fus_838_PVT1_002_exon3 | TCCGTGGTGTGCAACTGAA | 1611 | ATCATGATGGCTGTATGTGCCA | 1612 |
| HVP68 | 68_fus_838_PVT1_005_exon1 | TCCGTGGTGTGCAACTGAA | 1613 | TCTTTGCTCGCAGCTCGT | 1614 |
| HVP68 | 68_sp_838_3292 | TCCGTGGTGTGCAACTGAA | 1615 | TCGCGGTGGTGTTCTGTAG | 1616 |
| HVP68 | 68_sp_3563_5488 | AGTAGAAGTGCAGGCCAAAACAA | 1617 | ATTGACAACCTTCGCCACTGA | 1618 |
| HVP68 | 68_fus_838_MYC_001_exon2 | TCCGTGGTGTGCAACTGAA | 1619 | AAATACGGCTGCACCGAGT | 1620 |
| HVP68 | 68_sp_129_697 | GACATTGGACACTACATTGCATGAC | 1621 | CTGTTGTAGTGTCCGCAGGTT | 1622 |
| HVP68 | 68_unsp_3291_3292 | CTAGTGGAAAATGGGACGTGCATTATA | 1623 | TCGCGGTGGTGTTCTGTAG | 1624 |
| HVP68 | 68_unsp_3563_3564 | AGTAGAAGTGCAGGCCAAAACAA | 1625 | AAGCGTTATGTTTTGCAACCTATACC | 1626 |
| HVP68 | 68_sp_1233_3292 | AGACAACCGGCGTATACAGTG | 1627 | TCGCGGTGGTGTTCTGTAG | 1628 |
| HVP68 | 68_fus_838_MYC_001_exon3 | TCCGTGGTGTGCAACTGAA | 1629 | GGTGATCCAGACTCTGACCTTTTG | 1630 |
| HVP68 | 68_fus_2801_PVT1_005_exon1 | ACAGGACAGTAAATGTATACAGGACCAT | 1631 | TCTTTGCTCGCAGCTCGT | 1632 |
| HVP68 | 68_unsp_311_312 | GGAATCGGTGTATGCAACTACATTA6AA | 1633 | CTTCGTTTTGTTGTTAGGTGCCTTAG | 1634 |
| HVP68 | 68_gen_7154_7822 | CCCTGTGACTAACATATGTCCTTGT | 1635 | CCACACGGTATAGTTTGCAACCAT | 1636 |
| HVP68 | 68_gen_5738_7147 | GCCTGTGTTGGTGTTGAAATAGGTA | 1637 | TGCAACATTGTCCCTACTGTCTTTAG | 1638 |
| HVP68 | 68_gen_3813_4090 | GGTGTGGTTTTGTGTATGCATGT | 1639 | GGTATACAGCAAACACCTCAAATGGT | 1640 |
| HVP68 | 68_gen_1483_2260 | CGACACGCCGGAATG6ATAA | 1641 | CGCTGCAGCATTACTATTACAATCTG | 1642 |
| HVP73 | 73_unsp_5493_5494 | TGGGTCAGGTTTTATATTACACCCTAGT | 1643 | GCTTACAACCTTAGACACAGACACA | 1644 |
| HVP73 | 73_fus_2858_MYC_001_exon1 | GTATGAACGTGACAGTGTACACCTAA | 1645 | CTGAGAAGCCCTGCCCTTC | 1646 |
| HVP73 | 73_sp_1287_3346 | AAACGAAGACTGTTTGAGGAGCA | 1647 | TGGTGTTGGTGGTTGTGG | 1648 |
| HVP73 | 73_fus_3560_MYC_001_exon2 | ACCTACATCCCACCACAGAGT | 1649 | AAATACGGCTGCACCGAGT | 1650 |
| HVP73 | 73_sp_862_2570 | TGCTTATGGGTACACTAGGTATTGTGT | 1651 | GGGTTCCCATTACTGTCAAATGGA | 1652 |
| HVP73 | 73_fus_862_MYC_001_exon3 | TGCTTATGGGTACACTAGGTATTGTGT | 1653 | GGTGATCCAGACTCTGACCTTTTG | 1654 |
| HVP73 | 73_sp_227_410 | AGCGTTATGTGACGAAGTGAATATTTCT | 1655 | CTGTTCTGCTATTTGATGAAACCGTTTT | 1656 |
| HVP73 | 73_sp_227_527 | AGCGTTATGTGACGAAGTGAATATTTCT | 1657 | TTCGTTGTTGGTTTCAGGTCTAA | 1658 |
| HVP73 | 73_sp_862_3346 | TGCTTATGGGTACACTAGGTATTGTGT | 1659 | TGGTGTTGGTGGTTGTGGT | 1660 |
| HVP73 | 73_unsp_3345_3346 | GGGTAAAAGGCATATGGGAAGTACAT | 1661 | TGGTGTTGGTGGTTGTGGT | 1662 |

TABLE 14 -continued

Primer pairs for HR aHPV group and human transcripts

| Virus name | Transcript targeted | Forward primer (5'-3') | SEQ ID NO | Reverse primer (5'-3') | SEQ ID NO |
|---|---|---|---|---|---|
| HVP73 | 73_unsp_2569_2570 | CAAGTTAAATGCCCTCCATTACTGATAAC | 1663 | GGGTTCCCATTACTGTCAAATGGA | 1664 |
| HVP73 | 73_fus_862_PVT1_004_exon1 | TGCTTATGGGTACACTAGGTATTGTGT | 1665 | CATGGTTCCACCAGCGTTATT | 1666 |
| HVP73 | 73_unsp_3572_3573 | ACCTACATCCCACCACAGAGT | 1667 | GTCCAATGCCATGTTGTTGTTACA | 1668 |
| HVP73 | 73_fus_3560_PVT1_002_exon3 | ACCTACATCCCACCACAGAGT | 1669 | ATCATGATGGCTGTATGTGCCA | 1670 |
| HVP73 | 73_sp_862_5647 | TGCTTATGGGTACACTAGGTATTGTGT | 1671 | ACGAAGCCTAAACACCCTGTATTG | 1672 |
| HVP73 | 73_fus_2858_PVT1_002_exon3 | GTATGAACGTGACAGTGTACACCTAA | 1673 | ATCATGATGGCTGTATGTGCCA | 1674 |
| HVP73 | 73_unsp_726_727 | ACTCAGAGGATGAGGATGAAACAGA | 1675 | CCTAGTGTACCCATAAGCAACTCTTCTA | 1676 |
| HVP73 | 73_sp_3572_5494 | ACCTACATCCCACCACAGAGT | 1677 | GCTTACAACCTTAGACACAGACACA | 1678 |
| HVP73 | 73_unsp_1287_1288 | AAACGAAGACTGTTTGAGGAGCA | 1679 | GACACAATTTGGTTGCCTTCTTCATTAA | 1680 |
| HVP73 | 73_fus_862_MYC_001_exon2 | TGCTTATGGGTACACTAGGTATTGTGT | 1681 | AAATACGGCTGCACCGAGT | 1682 |
| HVP73 | 73_unsp_5646_5647 | TGCAGGTAGCACACGTTTGT | 1683 | ACGAAGCCTAAACACCCTGTATTG | 1684 |
| HVP73 | 73_fus_3560_PVT1_005_exon1 | ACCTACATCCCACCACAGAGT | 1685 | TCTTTGCTCGCAGCTCGT | 1686 |
| HVP73 | 73_unsp_862_863 | TGCTTATGGGTACACTAGGTATTGTGT | 1687 | TGGAATTGGATCCCCTGTTTTCTTT | 1688 |
| HVP73 | 73_fus_862_PVT1_005_exon1 | TGCTTATGGGTACACTAGGTATTGTGT | 1689 | TCTTTGCTCGCAGCTCGT | 1690 |
| HVP73 | 73_fus_862_MYC_001_exon1 | TGCTTATGGGTACACTAGGTATTGTGT | 1691 | CTGAGAAGCCCTGCCCTTC | 1692 |
| HVP73 | 73_sp_862_5494 | TGCTTATGGGTACACTAGGTATTGTGT | 1693 | GCTTACAACCTTAGACACAGACACA | 1694 |
| HVP73 | 73_fus_2858_PVT1_004_exon1 | GTATGAACGTGACAGTGTACACCTAA | 1695 | CATGGTTCCACCAGCGTTATT | 1696 |
| HVP73 | 73_unsp_227_228 | AGCGTTATGTGACGAAGTGAATATTTCT | 1697 | AAAATTTTAAACACGGTTGACATACAC | 1698 |
| HVP73 | 73_fus_28S8_MYC_001_exon2 | GTATGAACGTGACAGTGTACACCTAA | 1699 | AAATACGGCTGCACCGAGT | 1700 |
| HVP73 | 73_fus_2858_PVT1_005_exon1 | GTATGAACGTGACAGTGTACACCTAA | 1701 | TCTTTGCTCGCAGCTCGT | 1702 |
| HVP73 | 73_fus_862_PVT1_002_exon3 | TGCTTATGGGTACACTAGGTATTGTGT | 1703 | ATCATGATGGCTGTATGTGCCA | 1704 |
| HVP73 | 73_unsp_409_410 | AGACAATCAGTATATGGCACTACGTTAGA | 1705 | CTGTTCTGCTATTTGATGAAACCGTTTT | 1706 |
| HVP73 | 73_fus_3560_PVT1_004_exon1 | ACCTACATCCCACCACAGAGT | 1707 | CATGGTTCCACCAGCGTTATT | 1708 |
| HVP73 | 73_sp_227_2570 | AGCGTTATGTGACGAAGTGAATATTTCT | 1709 | GGGTTCCCATTACTGTCAAATGGA | 1710 |
| HVP73 | 73_fus_3560_MYC_001_exon1 | ACCTACATCCCACCACAGAGT | 1711 | CTGAGAAGCCCTGCCCTTC | 1712 |

TABLE 14 -continued

Primer pairs for HR aHPV group and human transcripts

| Virus name | Transcript targeted | Forward primer (5'-3') | SEQ ID NO | Reverse primer (5'-3') | SEQ ID NO |
|---|---|---|---|---|---|
| HVP73 | 73_fus_3560_MYC_001_exon3 | ACCTACATCCCACCACAGAGT | 1713 | GGTGATCCAGACTCTGACCTTTTG | 1714 |
| HVP73 | 73_sp_1287_2570 | AAACGAAGACTGTTTGAGGAGCA | 1715 | GGGTTCCCATTACTGTCAAATGGA | 1716 |
| HVP73 | 73_sp_227_727 | AGCGTTATGTGACGAAGTGAATATTTCT | 1717 | CCTAGTGTACCCATAAGCAACTCTTCTA | 1718 |
| HVP73 | 73_sp_227_3346 | AGCGTTATGTGACGAAGTGAATATTTCT | 1719 | TGGTGTTGGTGGTTGTGGT | 1720 |
| HVP73 | 73_fus_2858_MYC_001_exon3 | GTATGAACGTGACAGTGTACACCTAA | 1721 | GGTGATCCAGACTCTGACCTTTTG | 1722 |
| HVP73 | 73_sp_3572_5647 | ACCTACATCCCACCACAGAGT | 1723 | ACGAAGCCTAAACACCCTGTATTG | 1724 |
| HVP73 | 73_gen_3822_4053 | TCGCTTGCAGTGTCTGTGTATATTT | 1725 | CATGGTAATGTACAAGTGCCATAGGA | 1726 |
| HVP73 | 73_gen_1537_2320 | GAACGCATGTTAATTGAACCTCCAA | 1727 | GCTGCACTAACGTTTGTCTTTTAATCC | 1728 |
| HVP73 | 73_gen_5897_7198 | TGTATTTTAGGTTGTAGGCCTCCCTTA | 1729 | CTCCAAAGCCAACATCTATCATATCAC | 1730 |
| HVP73 | 73_gen_7205_7700 | GTCGCCATTTTACATGCATTAAGGT | 1731 | AGGAAACAAACCCTGCCAAGTT | 1732 |
| HVP82 | 82_sp_3613_5571 | TGCGACCACCAAATACACTGT | 1733 | GTGTTGACAATGCGTGACACT | 1734 |
| HVP82 | 82_fus_3601_MYC_001_exon1 | TGCGACCACCAAATACACTGT | 1735 | CTGAGAAGCCCTGCCCTTC | 1736 |
| HVP82 | 82_fus_2860_MYC_001_exon3 | GTGCCAGGAGAAAATACTAGACTGTTAT | 1737 | GGTGATCCAGACTCTGACCTTTTG | 1738 |
| HVP82 | 82_fus_2860_PVT1_005_exon1 | GTGCCAGGAGAAAATACTAGACTGTTAT | 1739 | TCTTTGCTCGCAGCTCGT | 1740 |
| HVP82 | 82_fus_2860_MYC_001_exon1 | GTGCCAGGAGAAAATACTAGACTGTTAT | 1741 | CTGAGAAGCCCTGCCCTTC | 1742 |
| HVP82 | 82_unsp_1316_1317 | CCGGACAGTGGATATGGCAATA | 1743 | GGTCTATCTCTGTACTTCTGTCGCT | 1744 |
| HVP82 | 82_sp_222_753 | CCTGCAATACGTCTATGCACAAT | 1745 | CCAGTAACATTTGCTGAAATATGCGAA | 1746 |
| HVP82 | 82_unsp_752_753 | GGAGGATGAAGTAGATAATATGCGTGAC | 1747 | CCAGTAACATTTGCTGAAATATGCGAA | 1748 |
| HVP82 | 82_unsp_3344_3345 | GGGCACAACAATGGGAGGTA | 1749 | GGGTGTTCGATAGCTGTTCAA | 1750 |
| HVP82 | 82_unsp_3613_3614 | TGCGACCACCAAATACACTGT | 1751 | CAATGCCAGGTAGATGACACTTCTTTAA | 1752 |
| HVP82 | 82_unsp_5570_5571 | GGGATTACTACTTTGTGGCCGTATA | 1753 | GTGTTGACAATGCGTGACACT | 1754 |
| HVP82 | 82_sp_222_407 | CCTGCAATACGTCTATGCACAAT | 1755 | TTTTTTGTCGTCCACCACCTTTTG | 1756 |
| HVP82 | 82_fus_3601_MYC_001_exon3 | TGCGACCACCAAATACACTGT | 1757 | GGTGATCCAGACTCTGACCTTTTG | 1758 |
| HVP82 | 82_fus_888_MYC_001_exon2 | CGTGGTGTGCGACCAACTAA | 1759 | AAATACGGCTGCACCGAGT | 1760 |
| HVP82 | 82_fus_888_MYC_001_exon1 | CGTGGTGTGCGACCAACTAA | 1761 | CTGAGAAGCCCTGCCCTTC | 1762 |
| HVP82 | 82_sp_222_3345 | CCTGCAATACGTCTATGCACAAT | 1763 | GGGTGTTCGATAGCTGTTCAA | 1764 |
| HVP82 | 82_unsp_222_223 | CCTGCAATACGTCTATGCACAAT | 1765 | CATGCTGCATATGGCGTATTGTC | 1766 |

TABLE 14 -continued

Primer pairs for HR aHPV group and human transcripts

| Virus name | Transcript targeted | Forward primer (5'-3') | SEQ ID NO | Reverse primer (5'-3') | SEQ ID NO |
|---|---|---|---|---|---|
| HVP82 | 82_unsp_406_407 | GTAGGTCTGTGTATGGTGCTACATT | 1767 | TTTTTTGTCGTCCACCACCTTTTG | 1768 |
| HVP82 | 82_fus_3601_PVT1_002_exon3 | TGCGACCACCAAATACACTGT | 1769 | ATCATGATGGCTGTATGTGCCA | 1770 |
| HVP82 | 82_fus_3601_PVT1_005_exon1 | TGCGACCACCAAATACACTGT | 1771 | TCTTTGCTCGCAGCTCGT | 1772 |
| HVP82 | 82_sp_1316_3345 | CCGGACAGTGGATATGGCAATA | 1773 | GGGTGTTCGATAGCTGTTCAA | 1774 |
| HVP82 | 82_sp_888_5571 | CGTGGTGTGCGACCAACTAA | 1775 | GTGTTGACAATGCGTGACACT | 1776 |
| HVP82 | 82_fus_888_PVT1_004_exon1 | CGTGGTGTGCGACCAACTAA | 1777 | CATGGTTCCACCAGCGTTATT | 1778 |
| HVP82 | 82_sp_888_2575 | CGTGGTGTGCGACCAACTAA | 1779 | CATCATTTAGTGCATATACAGGATTCCC | 1780 |
| HVP82 | 82_sp_888_3345 | CGTGGTGTGCGACCAACTAA | 1781 | GGGTGTTCGATAGCTGTTCAA | 1782 |
| HVP82 | 82_fus_2860_PVT1_004_exon1 | GTGCCAGGAGAAAATACTAGACTGTTAT | 1783 | CATGGTTCCACCAGCGTTATT | 1784 |
| HVP82 | 82_sp_1316_2575 | CCGGACAGTGGATATGGCAATA | 1785 | CATCATTTAGTGCATATACAGGATTCCC | 1786 |
| HVP82 | 82_fus_3601_PVT1_004_exon1 | TGCGACCACCAAATACACTGT | 1787 | CATGGTTCCACCAGCGTTATT | 1788 |
| HVP82 | 82_fus_888_PVT1_005_exon1 | CGTGGTGTGCGACCAACTAA | 1789 | TCTTTGCTCGCAGCTCGT | 1790 |
| HVP82 | 82_sp_222_2575 | CCTGCAATACGTCTATGCACAAT | 1791 | CATCATTTAGTGCATATACAGGATTCCC | 1792 |
| HVP82 | 82_fus_888_MYC_001_exon3 | CGTGGTGTGCGACCAACTAA | 1793 | GGTGATCCAGACTCTGACCTTTTG | 1794 |
| HVP82 | 82_unsp_888_889 | CGTGGTGTGCGACCAACTAA | 1795 | TTGTCAACTACTGCCTCCACATAAAA | 1796 |
| HVP82 | 82_sp_222_521 | CCTGCAATACGTCTATGCACAAT | 1797 | TCCAACACTATGTCCTTTAATTGTGGT | 1798 |
| HVP82 | 82_fus_3601_MYC_001_exon2 | TGCGACCACCAAATACACTGT | 1799 | AAATACGGCTGCACCGAGT | 1800 |
| HVP82 | 82_fus_2860_MYC_001_exon2 | GTGCCAGGAGAAAATACTAGACTGTTAT | 1801 | AAATACGGCTGCACCGAGT | 1802 |
| HVP82 | 82_fus_2860_PVT1_002_exon3 | GTGCCAGGAGAAAATACTAGACTGTTAT | 1803 | ATCATGATGGCTGTATGTGCCA | 1804 |
| HVP82 | 82_fus_888_PVT1_002_exon3 | CGTGGTGTGCGACCAACTAA | 1805 | ATCATGATGGCTGTATGTGCCA | 1806 |
| HVP82 | 82_unsp_2574_2575 | ACACAGAAGCCTGCTGCAAA | 1807 | CATCATTTAGTGCATATACAGGATTCCC | 1808 |
| HVP82 | 82_gen_7220_7871 | CCTGTAGGTTAAGGGTGGTGTT | 1809 | AAATCGGTCGCCACAAAATGG | 1810 |
| HVP82 | 82_gen_1566_2325 | CGTAGTACAGCCGTTGCATTG | 1811 | CCCATTGTACCATTTGCGATAGTT | 1812 |
| HVP82 | 82_gen_5821_7213 | GGATGTGTTGGTGTTGAAGTAGGTA | 1813 | TCCTGTTGGTCGTTGCCATT | 1814 |
| HVP82 | 82_gen_3863_4134 | GCTGCTAAGTGTATATAGTTACTCGCA | 1815 | CTGCTGCAAACACATATTGGGATT | 1816 |

17.13 Summary of Example 17

The method according to the present invention described in Example 17 comprises:
1. Extraction of the viral RNA (Example 17.5) from a biological sample (Example 17.4),
2. Reverse transcription of the RNAs into cDNA with random hexamers (Example 17.6),
3. Amplification of the cDNA by multiplex PCR (Example 7) to generate a DNA sequence database.

The multiplex amplification is performed with HPV-specific primer pairs (Example 17.3)

The primers are designed specifically for each of the HPV genomes present in the database (Example 17.2).

The primers are modified to make them compatible with the high-throughput sequencing technique that is used.
4. High throughput sequencing of the DNA library and generation of "sequencing reads" (Example 17.8),
5. Aligning reads (Example 8) with the sequences of the HPV genomes present in the database (Examples 17.3 and 17.8).
6. Computing a score R (Example 17.11) whose the different possible computing are ratios described in Table 13. In this case, the ratio is defined as the ratio between the number of reads generated by at least 2 of pairs of primers described herein.

The invention claimed is:

1. A composition of primers comprising at least one group of HPV primers, wherein the group of HPV primers comprises a pair of primers for amplifying a target from each member of a set of HPV species, wherein the set comprises HPV 16, HPV18, HPV 31, HPV33, HPV35, HPV39, HPV45, HPV51, HPV 52, HPV56, HPV58, HPV66, HPV68, HPV73, and HPV82, wherein at least one group of HPV primers is selected from:

SD1-SA1 group consisting of the pairs of primers of SEQ ID NO: 397-398; 521-522; 609-610; 695-696; 819-820; 865-866; 947-948; 1067-1068; 1119-1120; 1267-1268; 1325-1326; 1507-1508; 1597-1598; 1655-1656; and 1755-1756;

SD1-SA2 group consisting of the pairs of primers of SEQ ID NO: 459-460; 633-634; 687-688; 1111-1112; 1235-1236; 1341-1342; 1503-1504; 1657-1658; and 1797-1798;

SD1-SA3 group consisting of the pairs of primers of SEQ ID NO: 381-382; 541-542; 599-600; 903-904; 941-942; 1047-1048; 1135-1136; 1287-1288; 1459-1460; 1473-1474; 1621-1622; 1717-1718; and 1745-1746;

SD1-SA4 group consisting of the pairs of primers of SEQ ID NO: 413-414; 551-552; 637-638; 713-714; 793-794; 857-858; 981-982; 1093-1094; 1179-1180; 1227-1228; 1319-1320; 1413-1414; 1509-1510; 1563-1564; 1709-1710; and 1791-1792;

SD1-SA5 group consisting of the pairs of primers of SEQ ID NO: 453-454; 549-550; 613-614; 747-748; 761-762; 949-950; 1163-1164; 1249-1250; 1329-1330; 1453-1454; and 1501-1502;

SD1-SA6 group consisting of the pairs of primers of SEQ ID NO: 431-432; 595-596; 719-720; 827-828; 1089-1090; 1137-1138; 1285-1286; 1353-1354; 1561-1562; 1719-1720; and 1763-1764;

SD1-SA7 group consisting of the pairs of primers of SEQ ID NO: 919-920; and 1449-1450;

SD1-SA8 group consisting of the pairs of primers of SEQ ID NO: 489-490; 963-964; and 1519-1520;

SD2-SA4 group consisting of the pairs of primers of SEQ ID NO: 387-388; 473-474; 615-616; 745-746; 815-816; 849-850; 933-934; 1091-1092; 1177-1178; 1209-1210; 1367-1368; 1437-1438; 1521-1522; 1603-1604; 1651-1652; and 1779-1780;

SD2-SA5 group consisting of the pairs of primers of SEQ ID NO: 455-456; 529-530; 629-630; 717-718; 777-778; 975-976; 1153-1154; 1273-1274; 1347-1348; 1451-1452; and 1531-1532;

SD2-SA6 group consisting of the pairs of primers of SEQ ID NO: 399-400; 645-646; 727-728; 811-812; 1079-1080; 1127-1128; 1253-1254; 1369-1370; 1615-1616; 1659-1660; and 1781-1782;

SD2-SA7 group consisting of the pairs of primers of SEQ ID NO: 531-532; 899-900; 943-944; 1411-1412; and 1495-1496;

SD2-SA9 group consisting of the pairs of primers of SEQ ID NO: 437-438; 505-506; 607-608; 739-740; 785-786; 887-888; 979-980; 1063-1064; 1185-1186; 1233-1234; 1297-1298; 1423-1424; 1491-1492; 1607-1608; 1693-1694; and 1775-1776;

SD2-SA10 group consisting of the pairs of primers of SEQ ID NO: 545-546; 831-832; 1149-1150; 1269-1270; 1427-1428; and 1671-1672;

SD3-SA4 group consisting of the pairs of primers of SEQ ID NO: 379-380; 483-484; 611-612; 721-722; 833-834; 911-912; 937-938; 1053-1054; 1139-1140; 1251-1252; 1335-1336; 1435-1436; 1487-1488; 1591-1592; 1715-1716; and 1785-1786;

SD3-SA5 group consisting of the pairs of primers of SEQ ID NO: 415-416; 493-494; 593-594; 733-734; 817-818; 993-994; 1145-1146; 1243-1244; 1337-1338; 1401-1402; and 1483-1484;

SD3-SA6 group consisting of the pairs of primers of SEQ ID NO: 435-436; 655-656; 673-674; 813-814; 1045-1046; 1173-1174; 1241-1242; 1303-1304; 1557-1558; 1627-1628; 1647-1648; and 1773-1774;

SD3-SA7 group consisting of the pairs of primers of SEQ ID NO: 855-856; and 1387-1388;

SD3-SA8 group consisting of the pairs of primers of SEQ ID NO: 511-512; 957-958; and 1529-1530;

SD5-SA9 group consisting of the pairs of primers of SEQ ID NO: 419-420; 527-528; 567-568; 587-588; 683-684; 775-776; 891-892; 999-1000; 1041-1042; 1113-1114; 1247-1248; 1371-1372; 1403-1404; 1511-1512; 1617-1618; 1677-1678; and 1733-1734; and SD5-SA10 group consisting of the pairs of primers of SEQ ID NO: 495-496; 837-838; 1183-1184; 1279-1280; and 1433-1434.

2. The composition of primers according to claim 1, wherein said primers further comprise a functional group for covalent coupling at the 5' and/or 3' end.

3. The composition of primers according to claim 2, wherein said functional group comprises a thiol, amine or carboxyl group.

4. The composition of primers according to claim 1, wherein said primers further comprise an arm consisting of from 6 to 12 $CH_2$ groups.

5. The composition of primers according to claim 1, wherein said primers further comprise a spacer composed of bases that do not interfere with hybridization.

6. The composition of primers according to claim 4, wherein said primers further comprise a spacer composed of bases that do not interfere with hybridization.

7. A kit for diagnosis or prognosis of risk to develop HPV induced cancer comprising:
   a) a composition of primers according to claim 1, and
   b) reagents to detect or sequence amplification products.

8. A kit for diagnosis or prognosis of risk to develop HPV induced cancer comprising:
   a) a composition of primers according to claim 1, and
   b) primers or probes for detecting at least one host cellular marker indicative of neoplasia or cancer.

9. The kit of claim 8, further comprising at least 1 control containing a known ratio of E6 and/or E7 to L1 and/or L2.

10. The composition of primers according to claim 1, wherein the composition further comprises HPV primers that amplify genomic regions and unspliced regions.

* * * * *

SEQUENCE LISTING

```
<160> NUMBER OF SEQ ID NOS: 1816

<210> SEQ ID NO 1
<211> LENGTH: 23
<212> TYPE: DNA
<213> ORGANISM: Artificial Sequence
<220> FEATURE:
<223> OTHER INFORMATION: Primer Forward E6 alpha1

<400> SEQUENCE: 1
rgtacwtctg cctcatcaca gcc                                          23

<210> SEQ ID NO 2
<211> LENGTH: 21
<212> TYPE: DNA
<213> ORGANISM: Artificial Sequence
<220> FEATURE:
<223> OTHER INFORMATION: Primer Reverse E6 alpha1

<400> SEQUENCE: 2
ctctgcamtg sgtacascga c                                            21

<210> SEQ ID NO 3
<211> LENGTH: 23
<212> TYPE: DNA
<213> ORGANISM: Artificial Sequence
<220> FEATURE:
<223> OTHER INFORMATION: Primer Forward E7 alpha1

<400> SEQUENCE: 3
ggarasrcrc cwacsctaaa gga                                          23

<210> SEQ ID NO 4
<211> LENGTH: 21
<212> TYPE: DNA
<213> ORGANISM: Artificial Sequence
<220> FEATURE:
<223> OTHER INFORMATION: Primer Reverse E7 alpha 1

<400> SEQUENCE: 4
cacgcrggca cacaawggac a                                            21

<210> SEQ ID NO 5
<211> LENGTH: 20
<212> TYPE: DNA
<213> ORGANISM: Artificial Sequence
<220> FEATURE:
<223> OTHER INFORMATION: Primer Forward L1 alpha1

<400> SEQUENCE: 5
gcggcctagt gacracaagg                                              20
```

<210> SEQ ID NO 6
<211> LENGTH: 20
<212> TYPE: DNA
<213> ORGANISM: Artificial Sequence
<220> FEATURE:
<223> OTHER INFORMATION: Primer Reverse L1 alpha1

<400> SEQUENCE: 6
gcacgyaacc crgcytgcag                                                   20

<210> SEQ ID NO 7
<211> LENGTH: 21
<212> TYPE: DNA
<213> ORGANISM: Artificial Sequence
<220> FEATURE:
<223> OTHER INFORMATION: Primer Forward 1 E6 alpha 2

<400> SEQUENCE: 7
ghghgccmta ygstgcctgt g                                                 21

<210> SEQ ID NO 8
<211> LENGTH: 19
<212> TYPE: DNA
<213> ORGANISM: Artificial Sequence
<220> FEATURE:
<223> OTHER INFORMATION: Primer Forward 2 E6 alpha 2

<400> SEQUENCE: 8
ckccstacgg tgcwtgtgc                                                    19

<210> SEQ ID NO 9
<211> LENGTH: 21
<212> TYPE: DNA
<213> ORGANISM: Artificial Sequence
<220> FEATURE:
<223> OTHER INFORMATION: Primer Reverse 1 E6 alpha2

<400> SEQUENCE: 9
gcggaccgtg catcktrwcc a                                                 21

<210> SEQ ID NO 10
<211> LENGTH: 20
<212> TYPE: DNA
<213> ORGANISM: Artificial Sequence
<220> FEATURE:
<223> OTHER INFORMATION: Primer Reverse 2 E6 alpha2

<400> SEQUENCE: 10
ggctttggcc catgcatcgt                                                   20

<210> SEQ ID NO 11
<211> LENGTH: 21
<212> TYPE: DNA
<213> ORGANISM: Artificial Sequence
<220> FEATURE:
<223> OTHER INFORMATION: Primer Reverse 3 E6 alpha2

<400> SEQUENCE: 11
gtgcatcgtg accagcagta c                                                 21

<210> SEQ ID NO 12
<211> LENGTH: 23
<212> TYPE: DNA
<213> ORGANISM: Artificial Sequence
<220> FEATURE:
<223> OTHER INFORMATION: Primer Forward 1 E7 alpha2

<400> SEQUENCE: 12
ttgrdtcttg caccagaggm cgt                                              23

<210> SEQ ID NO 13
<211> LENGTH: 19
<212> TYPE: DNA
<213> ORGANISM: Artificial Sequence
<220> FEATURE:
<223> OTHER INFORMATION: Primer Forward 2 E7 alpha2

<400> SEQUENCE: 13
tgcacggtcc gcatcccac                                                   19

<210> SEQ ID NO 14
<211> LENGTH: 23
<212> TYPE: DNA
<213> ORGANISM: Artificial Sequence
<220> FEATURE:
<223> OTHER INFORMATION: Primer Forward 3 E7 alpha2

<400> SEQUENCE: 14
tgtctatggg tgcacaagaa ccc                                              23

<210> SEQ ID NO 15
<211> LENGTH: 23
<212> TYPE: DNA
<213> ORGANISM: Artificial Sequence
<220> FEATURE:
<223> OTHER INFORMATION: Primer Reverse 1 E7 alpha2

<400> SEQUENCE: 15
cccttatatc tgcktsgctg cws                                              23

<210> SEQ ID NO 16
<211> LENGTH: 19
<212> TYPE: DNA
<213> ORGANISM: Artificial Sequence
<220> FEATURE:
<223> OTHER INFORMATION: Primer Reverse 2 E7 alpha2

<400> SEQUENCE: 16
gcagcgaggr cacacgasc                                                   19

<210> SEQ ID NO 17
<211> LENGTH: 19
<212> TYPE: DNA
<213> ORGANISM: Artificial Sequence
<220> FEATURE:
<223> OTHER INFORMATION: Primer Reverse 3 E7 alpha2

<400> SEQUENCE: 17
ggaccgtgca tcgtgacca                                                   19

<210> SEQ ID NO 18
<211> LENGTH: 22
<212> TYPE: DNA
<213> ORGANISM: Artificial Sequence
<220> FEATURE:
<223> OTHER INFORMATION: Primer Forward L1 alpha2

<400> SEQUENCE: 18
atggcwytst ggcgcyctag tg                                               22

<210> SEQ ID NO 19

```
<211> LENGTH: 23
<212> TYPE: DNA
<213> ORGANISM: Artificial Sequence
<220> FEATURE:
<223> OTHER INFORMATION: Primer Reverse 1 L1 alpha2

<400> SEQUENCE: 19
cctccargct agtrgayggy ggy                                              23

<210> SEQ ID NO 20
<211> LENGTH: 23
<212> TYPE: DNA
<213> ORGANISM: Artificial Sequence
<220> FEATURE:
<223> OTHER INFORMATION: Primer Reverse 2 L1 alpha2

<400> SEQUENCE: 20
gggracyacy gaacgmcgkc gcg                                              23

<210> SEQ ID NO 21
<211> LENGTH: 23
<212> TYPE: DNA
<213> ORGANISM: Artificial Sequence
<220> FEATURE:
<223> OTHER INFORMATION: Primer Forward 1 E6 alpha3

<400> SEQUENCE: 21
agtggacrgg raagtgcwgc aac                                              23

<210> SEQ ID NO 22
<211> LENGTH: 22
<212> TYPE: DNA
<213> ORGANISM: Artificial Sequence
<220> FEATURE:
<223> OTHER INFORMATION: Primer Forward 2 E6 alpha3

<400> SEQUENCE: 22
ytgtgcaaag actgcgasgt gg                                               22

<210> SEQ ID NO 23
<211> LENGTH: 22
<212> TYPE: DNA
<213> ORGANISM: Artificial Sequence
<220> FEATURE:
<223> OTHER INFORMATION: Primer Forward 3 E6 alpha3

<400> SEQUENCE: 23
actggccatt tggagtmtgc gc                                               22

<210> SEQ ID NO 24
<211> LENGTH: 23
<212> TYPE: DNA
<213> ORGANISM: Artificial Sequence
<220> FEATURE:
<223> OTHER INFORMATION: Primer Reverse 1 E6 alpha3

<400> SEQUENCE: 24
ggccrygcat gttrcyctac agt                                              23

<210> SEQ ID NO 25
<211> LENGTH: 23
<212> TYPE: DNA
<213> ORGANISM: Artificial Sequence
<220> FEATURE:
<223> OTHER INFORMATION: Primer Reverse 2 E6 alpha3

<400> SEQUENCE: 25
```
cacyktcctg tccactbycc wgc                                          23

<210> SEQ ID NO 26
<211> LENGTH: 22
<212> TYPE: DNA
<213> ORGANISM: Artificial Sequence
<220> FEATURE:
<223> OTHER INFORMATION: Primer Reverse 3 E6 alpha3

<400> SEQUENCE: 26
ccagtgycgt agctcycgyr yc                                           22

<210> SEQ ID NO 27
<211> LENGTH: 20
<212> TYPE: DNA
<213> ORGANISM: Artificial Sequence
<220> FEATURE:
<223> OTHER INFORMATION: Primer Reverse 4 E6 alpha3

<400> SEQUENCE: 27
ctggccgtgc atrsycctct                                              20

<210> SEQ ID NO 28
<211> LENGTH: 23
<212> TYPE: DNA
<213> ORGANISM: Artificial Sequence
<220> FEATURE:
<223> OTHER INFORMATION: Primer Forward 1 E7 alpha3

<400> SEQUENCE: 28
vagcamagcw ggccywtagg gtg                                          23

<210> SEQ ID NO 29
<211> LENGTH: 22
<212> TYPE: DNA
<213> ORGANISM: Artificial Sequence
<220> FEATURE:
<223> OTHER INFORMATION: Primer Forward 2 E7 alpha3

<400> SEQUENCE: 29
kgywgaacrr gcacagcagg cc                                           22

<210> SEQ ID NO 30
<211> LENGTH: 23
<212> TYPE: DNA
<213> ORGANISM: Artificial Sequence
<220> FEATURE:
<223> OTHER INFORMATION: Primer Reverse 1 E7 alpha3

<400> SEQUENCE: 30
ggccacyrck tccacyataa gct                                          23

<210> SEQ ID NO 31
<211> LENGTH: 23
<212> TYPE: DNA
<213> ORGANISM: Artificial Sequence
<220> FEATURE:
<223> OTHER INFORMATION: Primer Reverse 2 E7 alpha3

<400> SEQUENCE: 31
cagcygggac acactatrtc cac                                          23

<210> SEQ ID NO 32
<211> LENGTH: 20
<212> TYPE: DNA

<213> ORGANISM: Artificial Sequence
<220> FEATURE:
<223> OTHER INFORMATION: Primer Reverse 3 E7 alpha3

<400> SEQUENCE: 32
gcgcagcsvg gacacactat          20

<210> SEQ ID NO 33
<211> LENGTH: 23
<212> TYPE: DNA
<213> ORGANISM: Artificial Sequence
<220> FEATURE:
<223> OTHER INFORMATION: Primer Forward L1 alpha3

<400> SEQUENCE: 33
ctwtgtggcg rcmtggtgay ggc          23

<210> SEQ ID NO 34
<211> LENGTH: 21
<212> TYPE: DNA
<213> ORGANISM: Artificial Sequence
<220> FEATURE:
<223> OTHER INFORMATION: Primer Reverse 1 L1 alpha3

<400> SEQUENCE: 34
ggarggaggg ggcamwacmc c          21

<210> SEQ ID NO 35
<211> LENGTH: 21
<212> TYPE: DNA
<213> ORGANISM: Artificial Sequence
<220> FEATURE:
<223> OTHER INFORMATION: Primer Reverse 2 L1 alpha3
<220> FEATURE:
<221> NAME/KEY: misc_feature
<222> LOCATION: (12)..(12)
<223> OTHER INFORMATION: n is a, c, g, or t

<400> SEQUENCE: 35
ccctgbgcvc gntgyagcca r          21

<210> SEQ ID NO 36
<211> LENGTH: 23
<212> TYPE: DNA
<213> ORGANISM: Artificial Sequence
<220> FEATURE:
<223> OTHER INFORMATION: Primer Forward E6 alpha4

<400> SEQUENCE: 36
sagtatggty tggagctaga gga          23

<210> SEQ ID NO 37
<211> LENGTH: 19
<212> TYPE: DNA
<213> ORGANISM: Artificial Sequence
<220> FEATURE:
<223> OTHER INFORMATION: Primer Reverse E6 alpha4

<400> SEQUENCE: 37
gtccsgtcca cyggcckgm          19

<210> SEQ ID NO 38
<211> LENGTH: 19
<212> TYPE: DNA
<213> ORGANISM: Artificial Sequence
<220> FEATURE:
<223> OTHER INFORMATION: Primer Forward E7 alpha4

```
<400> SEQUENCE: 38
mcgmcccagc ctsrmggac                                              19

<210> SEQ ID NO 39
<211> LENGTH: 21
<212> TYPE: DNA
<213> ORGANISM: Artificial Sequence
<220> FEATURE:
<223> OTHER INFORMATION: Primer Reverse E7 alpha4

<400> SEQUENCE: 39
cctccatrac gctabgcgca g                                           21

<210> SEQ ID NO 40
<211> LENGTH: 23
<212> TYPE: DNA
<213> ORGANISM: Artificial Sequence
<220> FEATURE:
<223> OTHER INFORMATION: Primer Forward 1 L1 alpha4

<400> SEQUENCE: 40
tggcctaaac gacgtaaacg tgt                                         23

<210> SEQ ID NO 41
<211> LENGTH: 23
<212> TYPE: DNA
<213> ORGANISM: Artificial Sequence
<220> FEATURE:
<223> OTHER INFORMATION: Primer Forward 2 L1 alpha4

<400> SEQUENCE: 41
ttctttgcag atggctwtgt ggc                                         23

<210> SEQ ID NO 42
<211> LENGTH: 21
<212> TYPE: DNA
<213> ORGANISM: Artificial Sequence
<220> FEATURE:
<223> OTHER INFORMATION: Primer Reverse 1 L1 alpha4

<400> SEQUENCE: 42
gcggygcgyt tkcgagacac r                                           21

<210> SEQ ID NO 43
<211> LENGTH: 23
<212> TYPE: DNA
<213> ORGANISM: Artificial Sequence
<220> FEATURE:
<223> OTHER INFORMATION: Primer Reverse 2 L1 alpha4

<400> SEQUENCE: 43
ccccgctgca ryaaraactt gcg                                         23

<210> SEQ ID NO 44
<211> LENGTH: 21
<212> TYPE: DNA
<213> ORGANISM: Artificial Sequence
<220> FEATURE:
<223> OTHER INFORMATION: Primer Forward 1 E6 alpha5

<400> SEQUENCE: 44
grgaaagacc acgaacgctg c                                           21

<210> SEQ ID NO 45
```

```
<211> LENGTH: 23
<212> TYPE: DNA
<213> ORGANISM: Artificial Sequence
<220> FEATURE:
<223> OTHER INFORMATION: Primer Forward 2 E6 alpha5

<400> SEQUENCE: 45
aatagcaggg yastggaaag ggt                                            23

<210> SEQ ID NO 46
<211> LENGTH: 23
<212> TYPE: DNA
<213> ORGANISM: Artificial Sequence
<220> FEATURE:
<223> OTHER INFORMATION: Primer Reverse 1 E6 alpha5

<400> SEQUENCE: 46
gcaattwgcr caytgycccg tcc                                            23

<210> SEQ ID NO 47
<211> LENGTH: 23
<212> TYPE: DNA
<213> ORGANISM: Artificial Sequence
<220> FEATURE:
<223> OTHER INFORMATION: Primer Reverse 2 E6 alpha5

<400> SEQUENCE: 47
ttgtgtttct gtttggcgcc ttg                                            23

<210> SEQ ID NO 48
<211> LENGTH: 21
<212> TYPE: DNA
<213> ORGANISM: Artificial Sequence
<220> FEATURE:
<223> OTHER INFORMATION: Primer Reverse 3 E6 alpha5

<400> SEQUENCE: 48
gccttggtct ccagcagttt g                                              21

<210> SEQ ID NO 49
<211> LENGTH: 22
<212> TYPE: DNA
<213> ORGANISM: Artificial Sequence
<220> FEATURE:
<223> OTHER INFORMATION: Primer Forwward 1 E7 alpha5

<400> SEQUENCE: 49
ytagatytgg tgccgcaacc cg                                             22

<210> SEQ ID NO 50
<211> LENGTH: 23
<212> TYPE: DNA
<213> ORGANISM: Artificial Sequence
<220> FEATURE:
<223> OTHER INFORMATION: Primer Forward 2 E7 alpha5

<400> SEQUENCE: 50
mgccatgcgt ggtaatgtac cac                                            23

<210> SEQ ID NO 51
<211> LENGTH: 22
<212> TYPE: DNA
<213> ORGANISM: Artificial Sequence
<220> FEATURE:
<223> OTHER INFORMATION: Primer Reverse 1 E7 alpha5

<400> SEQUENCE: 51
```

```
ctccascrct cgracgttct gt                                              22
```

<210> SEQ ID NO 52
<211> LENGTH: 21
<212> TYPE: DNA
<213> ORGANISM: Artificial Sequence
<220> FEATURE:
<223> OTHER INFORMATION: Primer Reverse 2 E7 alpha5

<400> SEQUENCE: 52

```
cacgggcama ccaggcttag k                                               21
```

<210> SEQ ID NO 53
<211> LENGTH: 23
<212> TYPE: DNA
<213> ORGANISM: Artificial Sequence
<220> FEATURE:
<223> OTHER INFORMATION: Primer Forward 1 L1 alpha5

<400> SEQUENCE: 53

```
kcagatggcy ttgyggcgta cta                                             23
```

<210> SEQ ID NO 54
<211> LENGTH: 23
<212> TYPE: DNA
<213> ORGANISM: Artificial Sequence
<220> FEATURE:
<223> OTHER INFORMATION: Primer Forward 2 L1 alpha5

<400> SEQUENCE: 54

```
tggcyttgyg gcgtactagt gac                                             23
```

<210> SEQ ID NO 55
<211> LENGTH: 23
<212> TYPE: DNA
<213> ORGANISM: Artificial Sequence
<220> FEATURE:
<223> OTHER INFORMATION: Primer Forward 3 L1 alpha5

<400> SEQUENCE: 55

```
tgtatttrcc acctgcaccw gtg                                             23
```

<210> SEQ ID NO 56
<211> LENGTH: 23
<212> TYPE: DNA
<213> ORGANISM: Artificial Sequence
<220> FEATURE:
<223> OTHER INFORMATION: Primer Reverse 1 L1 alpha5

<400> SEQUENCE: 56

```
ggggcrtyrc gytgacakgt agt                                             23
```

<210> SEQ ID NO 57
<211> LENGTH: 22
<212> TYPE: DNA
<213> ORGANISM: Artificial Sequence
<220> FEATURE:
<223> OTHER INFORMATION: Primer Reverse 2 L1 alpha5

<400> SEQUENCE: 57

```
ggcmggsckt ttaaggcctg gt                                              22
```

<210> SEQ ID NO 58
<211> LENGTH: 22
<212> TYPE: DNA

```
<213> ORGANISM: Artificial Sequence
<220> FEATURE:
<223> OTHER INFORMATION: Primer Forward 1 E6 alpha6

<400> SEQUENCE: 58
garcghccac gwashbtgca cc                                      22

<210> SEQ ID NO 59
<211> LENGTH: 23
<212> TYPE: DNA
<213> ORGANISM: Artificial Sequence
<220> FEATURE:
<223> OTHER INFORMATION: Primer Forward 2 E6 alpha6

<400> SEQUENCE: 59
aatacagrmg agcgmccacg tac                                     23

<210> SEQ ID NO 60
<211> LENGTH: 23
<212> TYPE: DNA
<213> ORGANISM: Artificial Sequence
<220> FEATURE:
<223> OTHER INFORMATION: Primer Forward 3 E6 alpha6

<400> SEQUENCE: 60
rcaatmcaca ggaacgtcca cga                                     23

<210> SEQ ID NO 61
<211> LENGTH: 23
<212> TYPE: DNA
<213> ORGANISM: Artificial Sequence
<220> FEATURE:
<223> OTHER INFORMATION: Primer Reverse 1 E6 alpha6

<400> SEQUENCE: 61
cctctggtgt caacggmtgt tga                                     23

<210> SEQ ID NO 62
<211> LENGTH: 23
<212> TYPE: DNA
<213> ORGANISM: Artificial Sequence
<220> FEATURE:
<223> OTHER INFORMATION: Primer Reverse 2 E6 alpha6

<400> SEQUENCE: 62
tctccarcac yscaaacatg acc                                     23

<210> SEQ ID NO 63
<211> LENGTH: 23
<212> TYPE: DNA
<213> ORGANISM: Artificial Sequence
<220> FEATURE:
<223> OTHER INFORMATION: Primer Forward 1 E7 alpha6

<400> SEQUENCE: 63
gracagctca gaggawgagg atg                                     23

<210> SEQ ID NO 64
<211> LENGTH: 21
<212> TYPE: DNA
<213> ORGANISM: Artificial Sequence
<220> FEATURE:
<223> OTHER INFORMATION: Primer Forward 2 E7 alpha6

<400> SEQUENCE: 64
gctcagagga wgaggatgag g                                       21
```

<210> SEQ ID NO 65
<211> LENGTH: 23
<212> TYPE: DNA
<213> ORGANISM: Artificial Sequence
<220> FEATURE:
<223> OTHER INFORMATION: Primer Forward 3 E7 alpha6

<400> SEQUENCE: 65
ytrcwgragc rgccacagca agc                                             23

<210> SEQ ID NO 66
<211> LENGTH: 21
<212> TYPE: DNA
<213> ORGANISM: Artificial Sequence
<220> FEATURE:
<223> OTHER INFORMATION: Primer Forward 4 E7 alpha6

<400> SEQUENCE: 66
gragcrgcca cagcaagcta g                                               21

<210> SEQ ID NO 67
<211> LENGTH: 23
<212> TYPE: DNA
<213> ORGANISM: Artificial Sequence
<220> FEATURE:
<223> OTHER INFORMATION: Primer Forward 5 E7 alpha6

<400> SEQUENCE: 67
gaacagctca gaggawgagg atg                                             23

<210> SEQ ID NO 68
<211> LENGTH: 23
<212> TYPE: DNA
<213> ORGANISM: Artificial Sequence
<220> FEATURE:
<223> OTHER INFORMATION: Primer Forward 6 E7 alpha6

<400> SEQUENCE: 68
artagaccat ttgcwggagc ggc                                             23

<210> SEQ ID NO 69
<211> LENGTH: 19
<212> TYPE: DNA
<213> ORGANISM: Artificial Sequence
<220> FEATURE:
<223> OTHER INFORMATION: Primer Reverse 1 E7 alpha6

<400> SEQUENCE: 69
gccttgttgc rcasagggg                                                  19

<210> SEQ ID NO 70
<211> LENGTH: 20
<212> TYPE: DNA
<213> ORGANISM: Artificial Sequence
<220> FEATURE:
<223> OTHER INFORMATION: Primer Reverse 2 E7 alpha6

<400> SEQUENCE: 70
cgcagagtgg gcacgttact                                                 20

<210> SEQ ID NO 71
<211> LENGTH: 20
<212> TYPE: DNA
<213> ORGANISM: Artificial Sequence
<220> FEATURE:

<223> OTHER INFORMATION: Primer Forward L1 alpha6

<400> SEQUENCE: 71
ttgcagatgg cgrygtggcg                                                   20

<210> SEQ ID NO 72
<211> LENGTH: 21
<212> TYPE: DNA
<213> ORGANISM: Artificial Sequence
<220> FEATURE:
<223> OTHER INFORMATION: Primer Reverse L1 alpha6

<400> SEQUENCE: 72
cacctaaagg ytgdccdcgg c                                                 21

<210> SEQ ID NO 73
<211> LENGTH: 22
<212> TYPE: DNA
<213> ORGANISM: Artificial Sequence
<220> FEATURE:
<223> OTHER INFORMATION: Primer Forward 1 E6 alpha7

<400> SEQUENCE: 73
tasaggacag tgycgmcrst gc                                                22

<210> SEQ ID NO 74
<211> LENGTH: 23
<212> TYPE: DNA
<213> ORGANISM: Artificial Sequence
<220> FEATURE:
<223> OTHER INFORMATION: Primer Forward 2 E6 alpha7

<400> SEQUENCE: 74
tcmcaaycct gmrgaacggc cat                                               23

<210> SEQ ID NO 75
<211> LENGTH: 20
<212> TYPE: DNA
<213> ORGANISM: Artificial Sequence
<220> FEATURE:
<223> OTHER INFORMATION: Primer Forward 3 E6 alpha7

<400> SEQUENCE: 75
asaggacagt gtcgysggtg                                                   20

<210> SEQ ID NO 76
<211> LENGTH: 23
<212> TYPE: DNA
<213> ORGANISM: Artificial Sequence
<220> FEATURE:
<223> OTHER INFORMATION: Primer Forward 4 E6 alpha7

<400> SEQUENCE: 76
tgccagaaac crttgaaycc agc                                               23

<210> SEQ ID NO 77
<211> LENGTH: 22
<212> TYPE: DNA
<213> ORGANISM: Artificial Sequence
<220> FEATURE:
<223> OTHER INFORMATION: Primer Reverse 1 E6 alpha7

<400> SEQUENCE: 77
gtctgcggtc ctcycgbttd st                                                22

```
<210> SEQ ID NO 78
<211> LENGTH: 22
<212> TYPE: DNA
<213> ORGANISM: Artificial Sequence
<220> FEATURE:
<223> OTHER INFORMATION: Primer Reverse 2 E6 alpha7

<400> SEQUENCE: 78
ctgscctckr tastgcccag ct                                              22

<210> SEQ ID NO 79
<211> LENGTH: 21
<212> TYPE: DNA
<213> ORGANISM: Artificial Sequence
<220> FEATURE:
<223> OTHER INFORMATION: Primer Reverse 3 E6 alpha7

<400> SEQUENCE: 79
caccagtgtt tcactacgcg c                                               21

<210> SEQ ID NO 80
<211> LENGTH: 21
<212> TYPE: DNA
<213> ORGANISM: Artificial Sequence
<220> FEATURE:
<223> OTHER INFORMATION: Primer Reverse 4 E6 alpha7

<400> SEQUENCE: 80
gccttgctgt tcttgtgcac g                                               21

<210> SEQ ID NO 81
<211> LENGTH: 23
<212> TYPE: DNA
<213> ORGANISM: Artificial Sequence
<220> FEATURE:
<223> OTHER INFORMATION: Primer Reverse 5 E6 alpha7

<400> SEQUENCE: 81
gtctggaaag cctttcttgc cgt                                             23

<210> SEQ ID NO 82
<211> LENGTH: 23
<212> TYPE: DNA
<213> ORGANISM: Artificial Sequence
<220> FEATURE:
<223> OTHER INFORMATION: Primer Forward 1 E7 alpha7

<400> SEQUENCE: 82
gacgrgmhga acmacarcgt cac                                             23

<210> SEQ ID NO 83
<211> LENGTH: 23
<212> TYPE: DNA
<213> ORGANISM: Artificial Sequence
<220> FEATURE:
<223> OTHER INFORMATION: Primer Forward 2 E7 alpha7

<400> SEQUENCE: 83
gacgrgmhga acmacagcgt cac                                             23

<210> SEQ ID NO 84
<211> LENGTH: 23
<212> TYPE: DNA
<213> ORGANISM: Artificial Sequence
<220> FEATURE:
<223> OTHER INFORMATION: Primer Forward 3 E7 alpha7
```

```
<400> SEQUENCE: 84
arcaccytgt cctttgtgtg tcc                                              23

<210> SEQ ID NO 85
<211> LENGTH: 23
<212> TYPE: DNA
<213> ORGANISM: Artificial Sequence
<220> FEATURE:
<223> OTHER INFORMATION: Primer Reverse 1 E7 alpha7

<400> SEQUENCE: 85
gtgwstccat aaacagcwgc wgt                                              23

<210> SEQ ID NO 86
<211> LENGTH: 23
<212> TYPE: DNA
<213> ORGANISM: Artificial Sequence
<220> FEATURE:
<223> OTHER INFORMATION: Primer Reverse 2 E7 alpha7

<400> SEQUENCE: 86
cacaccamgg acacacaaag gac                                              23

<210> SEQ ID NO 87
<211> LENGTH: 23
<212> TYPE: DNA
<213> ORGANISM: Artificial Sequence
<220> FEATURE:
<223> OTHER INFORMATION: Primer Forward 1 L1 alpha7

<400> SEQUENCE: 87
gcgbtctagy gacarcahgg tgt                                              23

<210> SEQ ID NO 88
<211> LENGTH: 23
<212> TYPE: DNA
<213> ORGANISM: Artificial Sequence
<220> FEATURE:
<223> OTHER INFORMATION: Primer Forward 2 L1 alpha7

<400> SEQUENCE: 88
hcctgctatt ggkgarcayt ggg                                              23

<210> SEQ ID NO 89
<211> LENGTH: 23
<212> TYPE: DNA
<213> ORGANISM: Artificial Sequence
<220> FEATURE:
<223> OTHER INFORMATION: Primer Reverse 1 L1 alpha7

<400> SEQUENCE: 89
ccagtgytcy ccmatrgcrg gwa                                              23

<210> SEQ ID NO 90
<211> LENGTH: 23
<212> TYPE: DNA
<213> ORGANISM: Artificial Sequence
<220> FEATURE:
<223> OTHER INFORMATION: Primer Reverse 2 L1 alpha7
<220> FEATURE:
<221> NAME/KEY: misc_feature
<222> LOCATION: (17)..(17)
<223> OTHER INFORMATION: n is a, c, g, or t

<400> SEQUENCE: 90
tagasccact dggwganggr gaa                                              23
```

<210> SEQ ID NO 91
<211> LENGTH: 22
<212> TYPE: DNA
<213> ORGANISM: Artificial Sequence
<220> FEATURE:
<223> OTHER INFORMATION: Primer Forward E6 alpha8

<400> SEQUENCE: 91
watgwctgca cgkwgckgct cc                                             22

<210> SEQ ID NO 92
<211> LENGTH: 23
<212> TYPE: DNA
<213> ORGANISM: Artificial Sequence
<220> FEATURE:
<223> OTHER INFORMATION: Primer Reverse 1 E6 alpha8

<400> SEQUENCE: 92
gtaggcarta tccyttccac rcg                                            23

<210> SEQ ID NO 93
<211> LENGTH: 19
<212> TYPE: DNA
<213> ORGANISM: Artificial Sequence
<220> FEATURE:
<223> OTHER INFORMATION: Primer Reverse 2 E6 alpha8

<400> SEQUENCE: 93
ctccgagcgt tggcctttc                                                 19

<210> SEQ ID NO 94
<211> LENGTH: 20
<212> TYPE: DNA
<213> ORGANISM: Artificial Sequence
<220> FEATURE:
<223> OTHER INFORMATION: Primer Forward E7 alpha8

<400> SEQUENCE: 94
gcgtgagcaa yccacgcaac                                                20

<210> SEQ ID NO 95
<211> LENGTH: 23
<212> TYPE: DNA
<213> ORGANISM: Artificial Sequence
<220> FEATURE:
<223> OTHER INFORMATION: Primer Reverse 1 E7  alpha8

<400> SEQUENCE: 95
cagccatkgy agtcacacmg ctg                                            23

<210> SEQ ID NO 96
<211> LENGTH: 23
<212> TYPE: DNA
<213> ORGANISM: Artificial Sequence
<220> FEATURE:
<223> OTHER INFORMATION: Primer Reverse 2 E7 alpha8

<400> SEQUENCE: 96
tgccattgtt gtcackctgt agc                                            23

<210> SEQ ID NO 97
<211> LENGTH: 23
<212> TYPE: DNA
<213> ORGANISM: Artificial Sequence
<220> FEATURE:

-continued

```
<223> OTHER INFORMATION: Primer Forward L1 alpha8
<220> FEATURE:
<221> NAME/KEY: misc_feature
<222> LOCATION: (12)..(12)
<223> OTHER INFORMATION: n is a, c, g, or t

<400> SEQUENCE: 97
ccycchatkg gngaatattg ggg                                          23

<210> SEQ ID NO 98
<211> LENGTH: 19
<212> TYPE: DNA
<213> ORGANISM: Artificial Sequence
<220> FEATURE:
<223> OTHER INFORMATION: Primer Reverse 1 L1 alpha8

<400> SEQUENCE: 98
ggaggatggt gcwgmacgc                                               19

<210> SEQ ID NO 99
<211> LENGTH: 23
<212> TYPE: DNA
<213> ORGANISM: Artificial Sequence
<220> FEATURE:
<223> OTHER INFORMATION: Primer Reverse 2 L1 alpha8

<400> SEQUENCE: 99
gggtgactgr cyyagaagag gaa                                          23

<210> SEQ ID NO 100
<211> LENGTH: 23
<212> TYPE: DNA
<213> ORGANISM: Artificial Sequence
<220> FEATURE:
<223> OTHER INFORMATION: Primer Forward 1 E6 alpha9

<400> SEQUENCE: 100
agtrmaratg cctccacgyc tgc                                          23

<210> SEQ ID NO 101
<211> LENGTH: 19
<212> TYPE: DNA
<213> ORGANISM: Artificial Sequence
<220> FEATURE:
<223> OTHER INFORMATION: Primer Forward 2 E6 alpha9

<400> SEQUENCE: 101
ctgcacagga ccagatggc                                               19

<210> SEQ ID NO 102
<211> LENGTH: 23
<212> TYPE: DNA
<213> ORGANISM: Artificial Sequence
<220> FEATURE:
<223> OTHER INFORMATION: Primer Reverse 1 E6 alpha9

<400> SEQUENCE: 102
tccatgcatg wtgwccagca rtg                                          23

<210> SEQ ID NO 103
<211> LENGTH: 22
<212> TYPE: DNA
<213> ORGANISM: Artificial Sequence
<220> FEATURE:
<223> OTHER INFORMATION: Primer Reverse 2 E6 alpha9

<400> SEQUENCE: 103
```

```
gcagcgmccy ttccaggtrt ck                                           22

<210> SEQ ID NO 104
<211> LENGTH: 23
<212> TYPE: DNA
<213> ORGANISM: Artificial Sequence
<220> FEATURE:
<223> OTHER INFORMATION: Primer Reverse 3 E6 alpha9

<400> SEQUENCE: 104
ggcatttcgc ccaccattgt tat                                          23

<210> SEQ ID NO 105
<211> LENGTH: 23
<212> TYPE: DNA
<213> ORGANISM: Artificial Sequence
<220> FEATURE:
<223> OTHER INFORMATION: Primer Forward 1 E7 alpha9

<400> SEQUENCE: 105
gcytacactg ctggacaaca tgc                                          23

<210> SEQ ID NO 106
<211> LENGTH: 23
<212> TYPE: DNA
<213> ORGANISM: Artificial Sequence
<220> FEATURE:
<223> OTHER INFORMATION: Primer Forward 2 E7 alpha9

<400> SEQUENCE: 106
agacagctca gaagabgagg tgg                                          23

<210> SEQ ID NO 107
<211> LENGTH: 23
<212> TYPE: DNA
<213> ORGANISM: Artificial Sequence
<220> FEATURE:
<223> OTHER INFORMATION: Primer Forward 3 E7 alpha9

<400> SEQUENCE: 107
aacaatggtg ggcgaaatgc cag                                          23

<210> SEQ ID NO 108
<211> LENGTH: 23
<212> TYPE: DNA
<213> ORGANISM: Artificial Sequence
<220> FEATURE:
<223> OTHER INFORMATION: Primer Reverse 1 E7 alpha9

<400> SEQUENCE: 108
cgtccgccat csttgttatg kyt                                          23

<210> SEQ ID NO 109
<211> LENGTH: 22
<212> TYPE: DNA
<213> ORGANISM: Artificial Sequence
<220> FEATURE:
<223> OTHER INFORMATION: Primer Reverse 2 E7 alpha9

<400> SEQUENCE: 109
cctgtrcact scacmacmag cc                                           22

<210> SEQ ID NO 110
<211> LENGTH: 20
<212> TYPE: DNA
```

```
<213> ORGANISM: Artificial Sequence
<220> FEATURE:
<223> OTHER INFORMATION: Primer Reverse 3 E7 alpha9

<400> SEQUENCE: 110
ctgtcgctgt agggtgcaca                                            20

<210> SEQ ID NO 111
<211> LENGTH: 23
<212> TYPE: DNA
<213> ORGANISM: Artificial Sequence
<220> FEATURE:
<223> OTHER INFORMATION: Primer Forward 1 L1 alpha9

<400> SEQUENCE: 111
atgtgcctcc tccyrmcccw gta                                        23

<210> SEQ ID NO 112
<211> LENGTH: 22
<212> TYPE: DNA
<213> ORGANISM: Artificial Sequence
<220> FEATURE:
<223> OTHER INFORMATION: Primer Forward 2 L1 alpha9

<400> SEQUENCE: 112
agatggctgt ctggttacca gc                                         22

<210> SEQ ID NO 113
<211> LENGTH: 23
<212> TYPE: DNA
<213> ORGANISM: Artificial Sequence
<220> FEATURE:
<223> OTHER INFORMATION: Primer Reverse 1 L1 alpha9

<400> SEQUENCE: 113
ccatawggrt cygcagccat ttg                                        23

<210> SEQ ID NO 114
<211> LENGTH: 19
<212> TYPE: DNA
<213> ORGANISM: Artificial Sequence
<220> FEATURE:
<223> OTHER INFORMATION: Primer Reverse 2 L1 alpha9

<400> SEQUENCE: 114
gccttacgcc tgcgcttgg                                             19

<210> SEQ ID NO 115
<211> LENGTH: 23
<212> TYPE: DNA
<213> ORGANISM: Artificial Sequence
<220> FEATURE:
<223> OTHER INFORMATION: Primer Forward 1 E6 alpha10

<400> SEQUENCE: 115
ccsarstgta awcatgcrtg gag                                        23

<210> SEQ ID NO 116
<211> LENGTH: 23
<212> TYPE: DNA
<213> ORGANISM: Artificial Sequence
<220> FEATURE:
<223> OTHER INFORMATION: Primer Forward 2 E6 alpha10

<400> SEQUENCE: 116
mcgsamcctg cacgaattgt gtg                                        23
```

<210> SEQ ID NO 117
<211> LENGTH: 23
<212> TYPE: DNA
<213> ORGANISM: Artificial Sequence
<220> FEATURE:
<223> OTHER INFORMATION: Primer Forward 3 E6 alpha10

<400> SEQUENCE: 117
cargacrcwg aggaraaacc acg                                          23

<210> SEQ ID NO 118
<211> LENGTH: 21
<212> TYPE: DNA
<213> ORGANISM: Artificial Sequence
<220> FEATURE:
<223> OTHER INFORMATION: Primer Reverse 1 E6 alpha10

<400> SEQUENCE: 118
ccaacacwct gaacascgyc c                                            21

<210> SEQ ID NO 119
<211> LENGTH: 23
<212> TYPE: DNA
<213> ORGANISM: Artificial Sequence
<220> FEATURE:
<223> OTHER INFORMATION: Primer Reverse 2 E6 alpha10

<400> SEQUENCE: 119
ccatgcatga ttacasctsg gtt                                          23

<210> SEQ ID NO 120
<211> LENGTH: 21
<212> TYPE: DNA
<213> ORGANISM: Artificial Sequence
<220> FEATURE:
<223> OTHER INFORMATION: Primer Reverse 3 E6 alpha10

<400> SEQUENCE: 120
gtcgggryct ccaacacrcy g                                            21

<210> SEQ ID NO 121
<211> LENGTH: 23
<212> TYPE: DNA
<213> ORGANISM: Artificial Sequence
<220> FEATURE:
<223> OTHER INFORMATION: Primer Reverse 4 E6 alpha10

<400> SEQUENCE: 121
ctccacgcat gtttacactt ggg                                          23

<210> SEQ ID NO 122
<211> LENGTH: 23
<212> TYPE: DNA
<213> ORGANISM: Artificial Sequence
<220> FEATURE:
<223> OTHER INFORMATION: Primer Forward E7 alpha10

<400> SEQUENCE: 122
gcwcaytwgg aathgtgtgc ccc                                          23

<210> SEQ ID NO 123
<211> LENGTH: 23
<212> TYPE: DNA
<213> ORGANISM: Artificial Sequence
<220> FEATURE:

<223> OTHER INFORMATION: Primer Forward 2 E7 alpha10

<400> SEQUENCE: 123
cstgtaamaa cgccatgaga gga                                          23

<210> SEQ ID NO 124
<211> LENGTH: 22
<212> TYPE: DNA
<213> ORGANISM: Artificial Sequence
<220> FEATURE:
<223> OTHER INFORMATION: Primer Forward 3 E7 alpha10

<400> SEQUENCE: 124
cgccatgaga ggamacaasc ca                                           22

<210> SEQ ID NO 125
<211> LENGTH: 23
<212> TYPE: DNA
<213> ORGANISM: Artificial Sequence
<220> FEATURE:
<223> OTHER INFORMATION: Primer Reverse 1 E7 alpha10

<400> SEQUENCE: 125
ggcacacdat tccwartgwg ccc                                          23

<210> SEQ ID NO 126
<211> LENGTH: 23
<212> TYPE: DNA
<213> ORGANISM: Artificial Sequence
<220> FEATURE:
<223> OTHER INFORMATION: Primer Reverse 2 E7 alpha10

<400> SEQUENCE: 126
ggttcgtasg tcrsttgytg tac                                          23

<210> SEQ ID NO 127
<211> LENGTH: 23
<212> TYPE: DNA
<213> ORGANISM: Artificial Sequence
<220> FEATURE:
<223> OTHER INFORMATION: Primer Reverse 3 E7 alpha10

<400> SEQUENCE: 127
gtgcacagsy gggrcacacw ayt                                          23

<210> SEQ ID NO 128
<211> LENGTH: 22
<212> TYPE: DNA
<213> ORGANISM: Artificial Sequence
<220> FEATURE:
<223> OTHER INFORMATION: Primer Forward 1 L1 alpha10

<400> SEQUENCE: 128
gargccacwg tstacytgcc tc                                           22

<210> SEQ ID NO 129
<211> LENGTH: 20
<212> TYPE: DNA
<213> ORGANISM: Artificial Sequence
<220> FEATURE:
<223> OTHER INFORMATION: Primer Forward 2 L1 alpha10

<400> SEQUENCE: 129
acagatgtct ctgtggcggc                                              20

```
<210> SEQ ID NO 130
<211> LENGTH: 23
<212> TYPE: DNA
<213> ORGANISM: Artificial Sequence
<220> FEATURE:
<223> OTHER INFORMATION: Primer Reverse 1 L1 alpha10
<220> FEATURE:
<221> NAME/KEY: misc_feature
<222> LOCATION: (6)..(6)
<223> OTHER INFORMATION: n is a, c, g, or t

<400> SEQUENCE: 130
ggatgnccac twayrcchac dcc                                      23

<210> SEQ ID NO 131
<211> LENGTH: 23
<212> TYPE: DNA
<213> ORGANISM: Artificial Sequence
<220> FEATURE:
<223> OTHER INFORMATION: Primer Reverse 2 L1 alpha10

<400> SEQUENCE: 131
gaggwwacca tagarccact rgg                                      23

<210> SEQ ID NO 132
<211> LENGTH: 23
<212> TYPE: DNA
<213> ORGANISM: Artificial Sequence
<220> FEATURE:
<223> OTHER INFORMATION: Primer Reverse 3 L1 alpha10

<400> SEQUENCE: 132
gtgcacgytg tagccaataw ggc                                      23

<210> SEQ ID NO 133
<211> LENGTH: 23
<212> TYPE: DNA
<213> ORGANISM: Artificial Sequence
<220> FEATURE:
<223> OTHER INFORMATION: Primer Reverse 4 L1 alpha10

<400> SEQUENCE: 133
tcctgtaaac trgcagaygg agg                                      23

<210> SEQ ID NO 134
<211> LENGTH: 23
<212> TYPE: DNA
<213> ORGANISM: Artificial Sequence
<220> FEATURE:
<223> OTHER INFORMATION: Primer Reverse 5 L1 alpha10

<400> SEQUENCE: 134
ggccytgtgc wcgttgyaac caa                                      23

<210> SEQ ID NO 135
<211> LENGTH: 23
<212> TYPE: DNA
<213> ORGANISM: Artificial Sequence
<220> FEATURE:
<223> OTHER INFORMATION: Primer Forward E6 alpha11

<400> SEQUENCE: 135
gaacgrccat acaagctacm agc                                      23

<210> SEQ ID NO 136
<211> LENGTH: 20
<212> TYPE: DNA
```

<213> ORGANISM: Artificial Sequence
<220> FEATURE:
<223> OTHER INFORMATION: Primer Reverse E6 alpha11

<400> SEQUENCE: 136
gcagatggtc tccagcacyg                                        20

<210> SEQ ID NO 137
<211> LENGTH: 23
<212> TYPE: DNA
<213> ORGANISM: Artificial Sequence
<220> FEATURE:
<223> OTHER INFORMATION: Primer Forward E7 alpha11

<400> SEQUENCE: 137
wattgtgtgc cccaactgtt cca                                    23

<210> SEQ ID NO 138
<211> LENGTH: 21
<212> TYPE: DNA
<213> ORGANISM: Artificial Sequence
<220> FEATURE:
<223> OTHER INFORMATION: Primer Reverse E7 alpha11

<400> SEQUENCE: 138
ctggaacagt tggggcacac a                                      21

<210> SEQ ID NO 139
<211> LENGTH: 22
<212> TYPE: DNA
<213> ORGANISM: Artificial Sequence
<220> FEATURE:
<223> OTHER INFORMATION: Primer Forward L1 alpha11

<400> SEQUENCE: 139
agttctatct tcctccccag cc                                     22

<210> SEQ ID NO 140
<211> LENGTH: 20
<212> TYPE: DNA
<213> ORGANISM: Artificial Sequence
<220> FEATURE:
<223> OTHER INFORMATION: Primer Reverse L1 alpha11

<400> SEQUENCE: 140
ggacgkgcac gcataccwag                                        20

<210> SEQ ID NO 141
<211> LENGTH: 22
<212> TYPE: DNA
<213> ORGANISM: Artificial Sequence
<220> FEATURE:
<223> OTHER INFORMATION: Primer Forward E6 alpha13

<400> SEQUENCE: 141
tgtctgctac tgaaccccac ac                                     22

<210> SEQ ID NO 142
<211> LENGTH: 22
<212> TYPE: DNA
<213> ORGANISM: Artificial Sequence
<220> FEATURE:
<223> OTHER INFORMATION: Primer Reverse E6 alpha13

<400> SEQUENCE: 142
ggcttccagc aatgtagaca cc                                     22

-continued

<210> SEQ ID NO 143
<211> LENGTH: 22
<212> TYPE: DNA
<213> ORGANISM: Artificial Sequence
<220> FEATURE:
<223> OTHER INFORMATION: Primer Forward E7 alpha13

<400> SEQUENCE: 143
gtttgacctg tactgcaggg ag                                        22

<210> SEQ ID NO 144
<211> LENGTH: 21
<212> TYPE: DNA
<213> ORGANISM: Artificial Sequence
<220> FEATURE:
<223> OTHER INFORMATION: Primer Reverse E7 alpha13

<400> SEQUENCE: 144
gtgaagcaca ggtgggacac a                                         21

<210> SEQ ID NO 145
<211> LENGTH: 23
<212> TYPE: DNA
<213> ORGANISM: Artificial Sequence
<220> FEATURE:
<223> OTHER INFORMATION: Primer Forward L1 alpha13

<400> SEQUENCE: 145
aaagtatacc tgcctcctac ccc                                       23

<210> SEQ ID NO 146
<211> LENGTH: 19
<212> TYPE: DNA
<213> ORGANISM: Artificial Sequence
<220> FEATURE:
<223> OTHER INFORMATION: Primer Reverse L1 alpha13

<400> SEQUENCE: 146
gcacgcttgc gcgctgtac                                            19

<210> SEQ ID NO 147
<211> LENGTH: 22
<212> TYPE: DNA
<213> ORGANISM: Artificial Sequence
<220> FEATURE:
<223> OTHER INFORMATION: Primer Forward E6 alpha14

<400> SEQUENCE: 147
taysamstgg acctgcagga cc                                        22

<210> SEQ ID NO 148
<211> LENGTH: 23
<212> TYPE: DNA
<213> ORGANISM: Artificial Sequence
<220> FEATURE:
<223> OTHER INFORMATION: Primer Reverse E6 alpha14

<400> SEQUENCE: 148
ggccwygcat grtktccaac act                                       23

<210> SEQ ID NO 149
<211> LENGTH: 23
<212> TYPE: DNA
<213> ORGANISM: Artificial Sequence
<220> FEATURE:

<223> OTHER INFORMATION: Primer Forward E7 alpha14

<400> SEQUENCE: 149
caattwgcca gctcagamga gga                                       23

<210> SEQ ID NO 150
<211> LENGTH: 23
<212> TYPE: DNA
<213> ORGANISM: Artificial Sequence
<220> FEATURE:
<223> OTHER INFORMATION: Primer Reverse E7 alpha14

<400> SEQUENCE: 150
ccaccacmag cctwactgya crv                                       23

<210> SEQ ID NO 151
<211> LENGTH: 21
<212> TYPE: DNA
<213> ORGANISM: Artificial Sequence
<220> FEATURE:
<223> OTHER INFORMATION: Primer Forward L1 alpha14

<400> SEQUENCE: 151
argtatacct gcctccygcc c                                         21

<210> SEQ ID NO 152
<211> LENGTH: 20
<212> TYPE: DNA
<213> ORGANISM: Artificial Sequence
<220> FEATURE:
<223> OTHER INFORMATION: Primer Reverse L1 alpha14

<400> SEQUENCE: 152
cctgtgcwcg ttgyagccag                                           20

<210> SEQ ID NO 153
<211> LENGTH: 19
<212> TYPE: DNA
<213> ORGANISM: Artificial Sequence
<220> FEATURE:
<223> OTHER INFORMATION: Primer HPV16-early

<400> SEQUENCE: 153
cagcggacgt attaatagg                                            19

<210> SEQ ID NO 154
<211> LENGTH: 19
<212> TYPE: DNA
<213> ORGANISM: Artificial Sequence
<220> FEATURE:
<223> OTHER INFORMATION: Primer HPV16-late

<400> SEQUENCE: 154
tcatattcct ccccatgtc                                            19

<210> SEQ ID NO 155
<211> LENGTH: 18
<212> TYPE: DNA
<213> ORGANISM: Artificial Sequence
<220> FEATURE:
<223> OTHER INFORMATION: Primer HPV18-early-pop1

<400> SEQUENCE: 155
aggggacgtt attaccac                                             18

```
<210> SEQ ID NO 156
<211> LENGTH: 19
<212> TYPE: DNA
<213> ORGANISM: Artificial Sequence
<220> FEATURE:
<223> OTHER INFORMATION: Primer HPV18-early-pop2

<400> SEQUENCE: 156
caggggacgt tattatcac                                                    19

<210> SEQ ID NO 157
<211> LENGTH: 20
<212> TYPE: DNA
<213> ORGANISM: Artificial Sequence
<220> FEATURE:
<223> OTHER INFORMATION: Primer HPV18-late-pop1

<400> SEQUENCE: 157
atattcctca acatgtctgc                                                   20

<210> SEQ ID NO 158
<211> LENGTH: 21
<212> TYPE: DNA
<213> ORGANISM: Artificial Sequence
<220> FEATURE:
<223> OTHER INFORMATION: Primer HPV18-late-pop2

<400> SEQUENCE: 158
catattcttc aacatgtctg c                                                 21

<210> SEQ ID NO 159
<211> LENGTH: 22
<212> TYPE: DNA
<213> ORGANISM: Artificial Sequence
<220> FEATURE:
<223> OTHER INFORMATION: Primer

<400> SEQUENCE: 159
ccaggtcatc accattggca at                                                22

<210> SEQ ID NO 160
<211> LENGTH: 21
<212> TYPE: DNA
<213> ORGANISM: Artificial Sequence
<220> FEATURE:
<223> OTHER INFORMATION: Primer

<400> SEQUENCE: 160
cgtacaggtc tttgcggatg t                                                 21

<210> SEQ ID NO 161
<211> LENGTH: 20
<212> TYPE: DNA
<213> ORGANISM: Artificial Sequence
<220> FEATURE:
<223> OTHER INFORMATION: Primer

<400> SEQUENCE: 161
ccatgagcga cgtggctatt                                                   20

<210> SEQ ID NO 162
<211> LENGTH: 20
<212> TYPE: DNA
<213> ORGANISM: Artificial Sequence
<220> FEATURE:
<223> OTHER INFORMATION: Primer
```

```
<400> SEQUENCE: 162
ctcacgttgg tccacatcct                                             20

<210> SEQ ID NO 163
<211> LENGTH: 18
<212> TYPE: DNA
<213> ORGANISM: Artificial Sequence
<220> FEATURE:
<223> OTHER INFORMATION: Primer

<400> SEQUENCE: 163
ctgtgctcgc gctactct                                               18

<210> SEQ ID NO 164
<211> LENGTH: 26
<212> TYPE: DNA
<213> ORGANISM: Artificial Sequence
<220> FEATURE:
<223> OTHER INFORMATION: Primer

<400> SEQUENCE: 164
caacttcaat gtcggatgga tgaaac                                      26

<210> SEQ ID NO 165
<211> LENGTH: 23
<212> TYPE: DNA
<213> ORGANISM: Artificial Sequence
<220> FEATURE:
<223> OTHER INFORMATION: Primer

<400> SEQUENCE: 165
gtggatgact gagtacctga acc                                         23

<210> SEQ ID NO 166
<211> LENGTH: 21
<212> TYPE: DNA
<213> ORGANISM: Artificial Sequence
<220> FEATURE:
<223> OTHER INFORMATION: Primer

<400> SEQUENCE: 166
ggccaaactg agcagagtct t                                           21

<210> SEQ ID NO 167
<211> LENGTH: 21
<212> TYPE: DNA
<213> ORGANISM: Artificial Sequence
<220> FEATURE:
<223> OTHER INFORMATION: Primer

<400> SEQUENCE: 167
cgggactcga gtgatgattg g                                           21

<210> SEQ ID NO 168
<211> LENGTH: 20
<212> TYPE: DNA
<213> ORGANISM: Artificial Sequence
<220> FEATURE:
<223> OTHER INFORMATION: Primer

<400> SEQUENCE: 168
ctgaggtgta ggtgctgtca                                             20

<210> SEQ ID NO 169
<211> LENGTH: 24
```

<212> TYPE: DNA
<213> ORGANISM: Artificial Sequence
<220> FEATURE:
<223> OTHER INFORMATION: Primer

<400> SEQUENCE: 169
ctcctgaaaa gagagtggaa gtgt                                          24

<210> SEQ ID NO 170
<211> LENGTH: 22
<212> TYPE: DNA
<213> ORGANISM: Artificial Sequence
<220> FEATURE:
<223> OTHER INFORMATION: Primer

<400> SEQUENCE: 170
ccggattaat ctccagccag tt                                            22

<210> SEQ ID NO 171
<211> LENGTH: 21
<212> TYPE: DNA
<213> ORGANISM: Artificial Sequence
<220> FEATURE:
<223> OTHER INFORMATION: Primer

<400> SEQUENCE: 171
aacgcaccga atagttacgg t                                             21

<210> SEQ ID NO 172
<211> LENGTH: 17
<212> TYPE: DNA
<213> ORGANISM: Artificial Sequence
<220> FEATURE:
<223> OTHER INFORMATION: Primer

<400> SEQUENCE: 172
acgggtcggg tgagagt                                                  17

<210> SEQ ID NO 173
<211> LENGTH: 19
<212> TYPE: DNA
<213> ORGANISM: Artificial Sequence
<220> FEATURE:
<223> OTHER INFORMATION: Primer

<400> SEQUENCE: 173
cggatcccaa cggagtcaa                                                19

<210> SEQ ID NO 174
<211> LENGTH: 17
<212> TYPE: DNA
<213> ORGANISM: Artificial Sequence
<220> FEATURE:
<223> OTHER INFORMATION: Primer

<400> SEQUENCE: 174
accggtcggg tgagagt                                                  17

<210> SEQ ID NO 175
<211> LENGTH: 24
<212> TYPE: DNA
<213> ORGANISM: Artificial Sequence
<220> FEATURE:
<223> OTHER INFORMATION: Primer

<400> SEQUENCE: 175
tcttccagaa cctgcaagta atcc 24

<210> SEQ ID NO 176
<211> LENGTH: 21
<212> TYPE: DNA
<213> ORGANISM: Artificial Sequence
<220> FEATURE:
<223> OTHER INFORMATION: Primer

<400> SEQUENCE: 176
ggtgggtgtt atggtggatg a 21

<210> SEQ ID NO 177
<211> LENGTH: 25
<212> TYPE: DNA
<213> ORGANISM: Artificial Sequence
<220> FEATURE:
<223> OTHER INFORMATION: Primer

<400> SEQUENCE: 177
aggagaatcc gaagggaaag gaata 25

<210> SEQ ID NO 178
<211> LENGTH: 20
<212> TYPE: DNA
<213> ORGANISM: Artificial Sequence
<220> FEATURE:
<223> OTHER INFORMATION: Primer

<400> SEQUENCE: 178
tccttcagca ggttggcaat 20

<210> SEQ ID NO 179
<211> LENGTH: 19
<212> TYPE: DNA
<213> ORGANISM: Artificial Sequence
<220> FEATURE:
<223> OTHER INFORMATION: Primer

<400> SEQUENCE: 179
agtccactgg cgtcttcac 19

<210> SEQ ID NO 180
<211> LENGTH: 26
<212> TYPE: DNA
<213> ORGANISM: Artificial Sequence
<220> FEATURE:
<223> OTHER INFORMATION: Primer

<400> SEQUENCE: 180
tgatcttgag gctgttgtca tacttc 26

<210> SEQ ID NO 181
<211> LENGTH: 21
<212> TYPE: DNA
<213> ORGANISM: Artificial Sequence
<220> FEATURE:
<223> OTHER INFORMATION: Primer

<400> SEQUENCE: 181
gcgagtatgg agcagaaacg a 21

<210> SEQ ID NO 182
<211> LENGTH: 24
<212> TYPE: DNA
<213> ORGANISM: Artificial Sequence
<220> FEATURE:
<223> OTHER INFORMATION: Primer

<400> SEQUENCE: 182
aattccaaat gagctctcca acca                                    24

<210> SEQ ID NO 183
<211> LENGTH: 22
<212> TYPE: DNA
<213> ORGANISM: Artificial Sequence
<220> FEATURE:
<223> OTHER INFORMATION: Primer

<400> SEQUENCE: 183
cggaatataa gctggtggtg gt                                      22

<210> SEQ ID NO 184
<211> LENGTH: 20
<212> TYPE: DNA
<213> ORGANISM: Artificial Sequence
<220> FEATURE:
<223> OTHER INFORMATION: Primer

<400> SEQUENCE: 184
gcacgtctcc ccatcaatga                                         20

<210> SEQ ID NO 185
<211> LENGTH: 21
<212> TYPE: DNA
<213> ORGANISM: Artificial Sequence
<220> FEATURE:
<223> OTHER INFORMATION: Primer

<400> SEQUENCE: 185
gtgcaatgag ggaccagtac a                                       21

<210> SEQ ID NO 186
<211> LENGTH: 28
<212> TYPE: DNA
<213> ORGANISM: Artificial Sequence
<220> FEATURE:
<223> OTHER INFORMATION: Primer

<400> SEQUENCE: 186
ctactaggac cataggtaca tcttcaga                                28

<210> SEQ ID NO 187
<211> LENGTH: 20
<212> TYPE: DNA
<213> ORGANISM: Artificial Sequence
<220> FEATURE:
<223> OTHER INFORMATION: Primer

<400> SEQUENCE: 187
gatgagctga ccctgaccaa                                         20

<210> SEQ ID NO 188
<211> LENGTH: 24
<212> TYPE: DNA
<213> ORGANISM: Artificial Sequence
<220> FEATURE:
<223> OTHER INFORMATION: Primer

<400> SEQUENCE: 188
ggcagcattc atttccacat tcac                                    24

<210> SEQ ID NO 189
<211> LENGTH: 19
<212> TYPE: DNA
<213> ORGANISM: Artificial Sequence
<220> FEATURE:
<223> OTHER INFORMATION: Primer

<400> SEQUENCE: 189
aggagctggc ctacctgaa                                                    19

<210> SEQ ID NO 190
<211> LENGTH: 23
<212> TYPE: DNA
<213> ORGANISM: Artificial Sequence
<220> FEATURE:
<223> OTHER INFORMATION: Primer

<400> SEQUENCE: 190
cttctcatac tggtcacgca tct                                               23

<210> SEQ ID NO 191
<211> LENGTH: 21
<212> TYPE: DNA
<213> ORGANISM: Artificial Sequence
<220> FEATURE:
<223> OTHER INFORMATION: Primer

<400> SEQUENCE: 191
aacactgagc tggaggtgaa g                                                 21

<210> SEQ ID NO 192
<211> LENGTH: 22
<212> TYPE: DNA
<213> ORGANISM: Artificial Sequence
<220> FEATURE:
<223> OTHER INFORMATION: Primer

<400> SEQUENCE: 192
ctgtagcagg atgttggcat tg                                                22

<210> SEQ ID NO 193
<211> LENGTH: 28
<212> TYPE: DNA
<213> ORGANISM: Artificial Sequence
<220> FEATURE:
<223> OTHER INFORMATION: Primer

<400> SEQUENCE: 193
tgtgtgcatt ccctatcaaa tatgtcaa                                          28

<210> SEQ ID NO 194
<211> LENGTH: 19
<212> TYPE: DNA
<213> ORGANISM: Artificial Sequence
<220> FEATURE:
<223> OTHER INFORMATION: Primer

<400> SEQUENCE: 194
gcgcttcaca gcctgatga                                                    19

<210> SEQ ID NO 195
<211> LENGTH: 23
<212> TYPE: DNA
<213> ORGANISM: Artificial Sequence
<220> FEATURE:
<223> OTHER INFORMATION: Primer

```
<400> SEQUENCE: 195
cgtcgtgtct caagatctag ctt                                    23

<210> SEQ ID NO 196
<211> LENGTH: 22
<212> TYPE: DNA
<213> ORGANISM: Artificial Sequence
<220> FEATURE:
<223> OTHER INFORMATION: Primer

<400> SEQUENCE: 196
tgagtcatct gcggtactgt ct                                     22

<210> SEQ ID NO 197
<211> LENGTH: 22
<212> TYPE: DNA
<213> ORGANISM: Artificial Sequence
<220> FEATURE:
<223> OTHER INFORMATION: Primer

<400> SEQUENCE: 197
gcttctctga aaggctctcc tt                                     22

<210> SEQ ID NO 198
<211> LENGTH: 19
<212> TYPE: DNA
<213> ORGANISM: Artificial Sequence
<220> FEATURE:
<223> OTHER INFORMATION: Primer

<400> SEQUENCE: 198
aaatacggct gcaccgagt                                         19

<210> SEQ ID NO 199
<211> LENGTH: 19
<212> TYPE: DNA
<213> ORGANISM: Artificial Sequence
<220> FEATURE:
<223> OTHER INFORMATION: Primer

<400> SEQUENCE: 199
ccgacgcaca aggtgtctt                                         19

<210> SEQ ID NO 200
<211> LENGTH: 20
<212> TYPE: DNA
<213> ORGANISM: Artificial Sequence
<220> FEATURE:
<223> OTHER INFORMATION: Primer

<400> SEQUENCE: 200
gtcggcgtgt gagttgatga                                        20

<210> SEQ ID NO 201
<211> LENGTH: 24
<212> TYPE: DNA
<213> ORGANISM: Artificial Sequence
<220> FEATURE:
<223> OTHER INFORMATION: Primer

<400> SEQUENCE: 201
gacggagtga aattttctgc aagt                                   24

<210> SEQ ID NO 202
```

```
<211> LENGTH: 24
<212> TYPE: DNA
<213> ORGANISM: Artificial Sequence
<220> FEATURE:
<223> OTHER INFORMATION: Primer

<400> SEQUENCE: 202
gaagttcagg tacctcagtg caaa                                          24

<210> SEQ ID NO 203
<211> LENGTH: 23
<212> TYPE: DNA
<213> ORGANISM: Artificial Sequence
<220> FEATURE:
<223> OTHER INFORMATION: Primer

<400> SEQUENCE: 203
agcgtgcaga taatgacaag gaa                                           23

<210> SEQ ID NO 204
<211> LENGTH: 22
<212> TYPE: DNA
<213> ORGANISM: Artificial Sequence
<220> FEATURE:
<223> OTHER INFORMATION: Primer

<400> SEQUENCE: 204
gatttgacgg ctcctctact gt                                            22

<210> SEQ ID NO 205
<211> LENGTH: 21
<212> TYPE: DNA
<213> ORGANISM: Artificial Sequence
<220> FEATURE:
<223> OTHER INFORMATION: Primer

<400> SEQUENCE: 205
cggtcttcat gcagagactg a                                             21

<210> SEQ ID NO 206
<211> LENGTH: 28
<212> TYPE: DNA
<213> ORGANISM: Artificial Sequence
<220> FEATURE:
<223> OTHER INFORMATION: Primer

<400> SEQUENCE: 206
gtgaaatata gatgttccct ccaggaat                                      28

<210> SEQ ID NO 207
<211> LENGTH: 22
<212> TYPE: DNA
<213> ORGANISM: Artificial Sequence
<220> FEATURE:
<223> OTHER INFORMATION: Primer

<400> SEQUENCE: 207
gacggattac accttcccac tt                                            22

<210> SEQ ID NO 208
<211> LENGTH: 24
<212> TYPE: DNA
<213> ORGANISM: Artificial Sequence
<220> FEATURE:
<223> OTHER INFORMATION: Primer

<400> SEQUENCE: 208
```

```
gactcttcct tggcttcaac ctta                                          24
```

<210> SEQ ID NO 209
<211> LENGTH: 20
<212> TYPE: DNA
<213> ORGANISM: Artificial Sequence
<220> FEATURE:
<223> OTHER INFORMATION: Primer

<400> SEQUENCE: 209

```
cgatgggctc agctttcaga                                               20
```

<210> SEQ ID NO 210
<211> LENGTH: 21
<212> TYPE: DNA
<213> ORGANISM: Artificial Sequence
<220> FEATURE:
<223> OTHER INFORMATION: Primer

<400> SEQUENCE: 210

```
acaaaacctc gtccacggaa t                                             21
```

<210> SEQ ID NO 211
<211> LENGTH: 20
<212> TYPE: DNA
<213> ORGANISM: Artificial Sequence
<220> FEATURE:
<223> OTHER INFORMATION: Primer

<400> SEQUENCE: 211

```
tcctgcgttt ggtggatgat                                               20
```

<210> SEQ ID NO 212
<211> LENGTH: 24
<212> TYPE: DNA
<213> ORGANISM: Artificial Sequence
<220> FEATURE:
<223> OTHER INFORMATION: Primer

<400> SEQUENCE: 212

```
cctcgtcttc tacagggaag ttca                                          24
```

<210> SEQ ID NO 213
<211> LENGTH: 20
<212> TYPE: DNA
<213> ORGANISM: Artificial Sequence
<220> FEATURE:
<223> OTHER INFORMATION: Primer

<400> SEQUENCE: 213

```
tgggtggtcc tgcaaaatcc                                               20
```

<210> SEQ ID NO 214
<211> LENGTH: 27
<212> TYPE: DNA
<213> ORGANISM: Artificial Sequence
<220> FEATURE:
<223> OTHER INFORMATION: Primer

<400> SEQUENCE: 214

```
acatattgat ttggagccag ttcttca                                       27
```

<210> SEQ ID NO 215
<211> LENGTH: 20
<212> TYPE: DNA

```
<213> ORGANISM: Artificial Sequence
<220> FEATURE:
<223> OTHER INFORMATION: Primer

<400> SEQUENCE: 215
ctggcccctg tcatcttctg                                              20

<210> SEQ ID NO 216
<211> LENGTH: 21
<212> TYPE: DNA
<213> ORGANISM: Artificial Sequence
<220> FEATURE:
<223> OTHER INFORMATION: Primer

<400> SEQUENCE: 216
cttggccagt tggcaaaaca t                                            21

<210> SEQ ID NO 217
<211> LENGTH: 19
<212> TYPE: DNA
<213> ORGANISM: Artificial Sequence
<220> FEATURE:
<223> OTHER INFORMATION: Primer

<400> SEQUENCE: 217
ctggaactgt cccactgct                                               19

<210> SEQ ID NO 218
<211> LENGTH: 23
<212> TYPE: DNA
<213> ORGANISM: Artificial Sequence
<220> FEATURE:
<223> OTHER INFORMATION: Primer

<400> SEQUENCE: 218
caggattcga tggaaccttc tga                                          23

<210> SEQ ID NO 219
<211> LENGTH: 25
<212> TYPE: DNA
<213> ORGANISM: Artificial Sequence
<220> FEATURE:
<223> OTHER INFORMATION: Primer

<400> SEQUENCE: 219
cacagagctg caaacaacta tacat                                        25

<210> SEQ ID NO 220
<211> LENGTH: 27
<212> TYPE: DNA
<213> ORGANISM: Artificial Sequence
<220> FEATURE:
<223> OTHER INFORMATION: Primer

<400> SEQUENCE: 220
cacatacagc atatggattc ccatctc                                      27

<210> SEQ ID NO 221
<211> LENGTH: 28
<212> TYPE: DNA
<213> ORGANISM: Artificial Sequence
<220> FEATURE:
<223> OTHER INFORMATION: Primer

<400> SEQUENCE: 221
ggaacaacat tagaacagca atacaaca                                     28
```

<210> SEQ ID NO 222
<211> LENGTH: 26
<212> TYPE: DNA
<213> ORGANISM: Artificial Sequence
<220> FEATURE:
<223> OTHER INFORMATION: Primer

<400> SEQUENCE: 222
tgtccagatg tctttgcttt tcttca                                    26

<210> SEQ ID NO 223
<211> LENGTH: 17
<212> TYPE: DNA
<213> ORGANISM: Artificial Sequence
<220> FEATURE:
<223> OTHER INFORMATION: Primer

<400> SEQUENCE: 223
cggtggaccg gtcgatg                                              17

<210> SEQ ID NO 224
<211> LENGTH: 24
<212> TYPE: DNA
<213> ORGANISM: Artificial Sequence
<220> FEATURE:
<223> OTHER INFORMATION: Primer

<400> SEQUENCE: 224
tcagttgtct ctggttgcaa atct                                      24

<210> SEQ ID NO 225
<211> LENGTH: 26
<212> TYPE: DNA
<213> ORGANISM: Artificial Sequence
<220> FEATURE:
<223> OTHER INFORMATION: Primer

<400> SEQUENCE: 225
ctcagaggag gaggatgaaa tagatg                                    26

<210> SEQ ID NO 226
<211> LENGTH: 26
<212> TYPE: DNA
<213> ORGANISM: Artificial Sequence
<220> FEATURE:
<223> OTHER INFORMATION: Primer

<400> SEQUENCE: 226
ccattaacag gtcttccaaa gtacga                                    26

<210> SEQ ID NO 227
<211> LENGTH: 21
<212> TYPE: DNA
<213> ORGANISM: Artificial Sequence
<220> FEATURE:
<223> OTHER INFORMATION: Primer

<400> SEQUENCE: 227
ggaattgtgt gccccatctg t                                         21

<210> SEQ ID NO 228
<211> LENGTH: 22
<212> TYPE: DNA
<213> ORGANISM: Artificial Sequence
<220> FEATURE:

<223> OTHER INFORMATION: Primer

<400> SEQUENCE: 228
catccattac atcccgtacc ct                                            22

<210> SEQ ID NO 229
<211> LENGTH: 26
<212> TYPE: DNA
<213> ORGANISM: Artificial Sequence
<220> FEATURE:
<223> OTHER INFORMATION: Primer

<400> SEQUENCE: 229
ggttttatgt agaggctgta gtggaa                                        26

<210> SEQ ID NO 230
<211> LENGTH: 22
<212> TYPE: DNA
<213> ORGANISM: Artificial Sequence
<220> FEATURE:
<223> OTHER INFORMATION: Primer

<400> SEQUENCE: 230
tgtgcagtaa acaacgcatg tg                                            22

<210> SEQ ID NO 231
<211> LENGTH: 22
<212> TYPE: DNA
<213> ORGANISM: Artificial Sequence
<220> FEATURE:
<223> OTHER INFORMATION: Primer

<400> SEQUENCE: 231
gcgggtatgg caatactgaa gt                                            22

<210> SEQ ID NO 232
<211> LENGTH: 26
<212> TYPE: DNA
<213> ORGANISM: Artificial Sequence
<220> FEATURE:
<223> OTHER INFORMATION: Primer

<400> SEQUENCE: 232
tggtgtttgg catatagtgt gtcttt                                        26

<210> SEQ ID NO 233
<211> LENGTH: 20
<212> TYPE: DNA
<213> ORGANISM: Artificial Sequence
<220> FEATURE:
<223> OTHER INFORMATION: Primer

<400> SEQUENCE: 233
atcaacgtgt tgcgattggt                                               20

<210> SEQ ID NO 234
<211> LENGTH: 28
<212> TYPE: DNA
<213> ORGANISM: Artificial Sequence
<220> FEATURE:
<223> OTHER INFORMATION: Primer

<400> SEQUENCE: 234
ctaatagtaa cacaaccatt ccccatga                                      28

```
<210> SEQ ID NO 235
<211> LENGTH: 27
<212> TYPE: DNA
<213> ORGANISM: Artificial Sequence
<220> FEATURE:
<223> OTHER INFORMATION: Primer

<400> SEQUENCE: 235
gaggtgattg gaagcaaatt gttatgt                                           27

<210> SEQ ID NO 236
<211> LENGTH: 28
<212> TYPE: DNA
<213> ORGANISM: Artificial Sequence
<220> FEATURE:
<223> OTHER INFORMATION: Primer

<400> SEQUENCE: 236
cagacccttg cagaaatttc attaaact                                          28

<210> SEQ ID NO 237
<211> LENGTH: 27
<212> TYPE: DNA
<213> ORGANISM: Artificial Sequence
<220> FEATURE:
<223> OTHER INFORMATION: Primer

<400> SEQUENCE: 237
ggatgtaaag catagaccat tggtaca                                           27

<210> SEQ ID NO 238
<211> LENGTH: 28
<212> TYPE: DNA
<213> ORGANISM: Artificial Sequence
<220> FEATURE:
<223> OTHER INFORMATION: Primer

<400> SEQUENCE: 238
gttttcgtca aatggaaact cattagga                                          28

<210> SEQ ID NO 239
<211> LENGTH: 28
<212> TYPE: DNA
<213> ORGANISM: Artificial Sequence
<220> FEATURE:
<223> OTHER INFORMATION: Primer

<400> SEQUENCE: 239
cggaaatcca gtgtatgagc ttaatgat                                          28

<210> SEQ ID NO 240
<211> LENGTH: 26
<212> TYPE: DNA
<213> ORGANISM: Artificial Sequence
<220> FEATURE:
<223> OTHER INFORMATION: Primer

<400> SEQUENCE: 240
tgacacacat ttaaacgttg gcaaag                                            26

<210> SEQ ID NO 241
<211> LENGTH: 19
<212> TYPE: DNA
<213> ORGANISM: Artificial Sequence
<220> FEATURE:
<223> OTHER INFORMATION: Primer
```

<400> SEQUENCE: 241
catgcgggtg gtcaggtaa                                          19

<210> SEQ ID NO 242
<211> LENGTH: 19
<212> TYPE: DNA
<213> ORGANISM: Artificial Sequence
<220> FEATURE:
<223> OTHER INFORMATION: Primer

<400> SEQUENCE: 242
aaggcgacgg ctttggtat                                          19

<210> SEQ ID NO 243
<211> LENGTH: 23
<212> TYPE: DNA
<213> ORGANISM: Artificial Sequence
<220> FEATURE:
<223> OTHER INFORMATION: Primer

<400> SEQUENCE: 243
gctcacacaa aggacggatt aac                                     23

<210> SEQ ID NO 244
<211> LENGTH: 22
<212> TYPE: DNA
<213> ORGANISM: Artificial Sequence
<220> FEATURE:
<223> OTHER INFORMATION: Primer

<400> SEQUENCE: 244
ccaatgccat gtagacgaca ct                                      22

<210> SEQ ID NO 245
<211> LENGTH: 22
<212> TYPE: DNA
<213> ORGANISM: Artificial Sequence
<220> FEATURE:
<223> OTHER INFORMATION: Primer

<400> SEQUENCE: 245
gcgtgctttt tgctttgctt tg                                      22

<210> SEQ ID NO 246
<211> LENGTH: 24
<212> TYPE: DNA
<213> ORGANISM: Artificial Sequence
<220> FEATURE:
<223> OTHER INFORMATION: Primer

<400> SEQUENCE: 246
cagaggctgc tgttatccac aata                                    24

<210> SEQ ID NO 247
<211> LENGTH: 22
<212> TYPE: DNA
<213> ORGANISM: Artificial Sequence
<220> FEATURE:
<223> OTHER INFORMATION: Primer

<400> SEQUENCE: 247
tgggcccttc tgatccttct at                                      22

<210> SEQ ID NO 248
<211> LENGTH: 28

```
<212> TYPE: DNA
<213> ORGANISM: Artificial Sequence
<220> FEATURE:
<223> OTHER INFORMATION: Primer

<400> SEQUENCE: 248
ggtcagtgaa agtgggatta ttatgtgt                                    28

<210> SEQ ID NO 249
<211> LENGTH: 24
<212> TYPE: DNA
<213> ORGANISM: Artificial Sequence
<220> FEATURE:
<223> OTHER INFORMATION: Primer

<400> SEQUENCE: 249
ctgcttttgt aaccactccc acta                                        24

<210> SEQ ID NO 250
<211> LENGTH: 24
<212> TYPE: DNA
<213> ORGANISM: Artificial Sequence
<220> FEATURE:
<223> OTHER INFORMATION: Primer

<400> SEQUENCE: 250
cctagaggtt aatgctggcc tatg                                        24

<210> SEQ ID NO 251
<211> LENGTH: 21
<212> TYPE: DNA
<213> ORGANISM: Artificial Sequence
<220> FEATURE:
<223> OTHER INFORMATION: Primer

<400> SEQUENCE: 251
cttcacatgc agcctcacct a                                           21

<210> SEQ ID NO 252
<211> LENGTH: 26
<212> TYPE: DNA
<213> ORGANISM: Artificial Sequence
<220> FEATURE:
<223> OTHER INFORMATION: Primer

<400> SEQUENCE: 252
ggaatattgt atgcaccacc aaaagg                                      26

<210> SEQ ID NO 253
<211> LENGTH: 24
<212> TYPE: DNA
<213> ORGANISM: Artificial Sequence
<220> FEATURE:
<223> OTHER INFORMATION: Primer

<400> SEQUENCE: 253
cctatagttc cagggtctcc acaa                                        24

<210> SEQ ID NO 254
<211> LENGTH: 26
<212> TYPE: DNA
<213> ORGANISM: Artificial Sequence
<220> FEATURE:
<223> OTHER INFORMATION: Primer

<400> SEQUENCE: 254
```

-continued atccgtgctt acaaccttag atactg 26

<210> SEQ ID NO 255
<211> LENGTH: 27
<212> TYPE: DNA
<213> ORGANISM: Artificial Sequence
<220> FEATURE:
<223> OTHER INFORMATION: Primer

<400> SEQUENCE: 255
ggatgacaca gaaaatgcta gtgctta 27

<210> SEQ ID NO 256
<211> LENGTH: 24
<212> TYPE: DNA
<213> ORGANISM: Artificial Sequence
<220> FEATURE:
<223> OTHER INFORMATION: Primer

<400> SEQUENCE: 256
cacctggatt tactgcaaca ttgg 24

<210> SEQ ID NO 257
<211> LENGTH: 24
<212> TYPE: DNA
<213> ORGANISM: Artificial Sequence
<220> FEATURE:
<223> OTHER INFORMATION: Primer

<400> SEQUENCE: 257
acctccagca cctaaagaag atga 24

<210> SEQ ID NO 258
<211> LENGTH: 28
<212> TYPE: DNA
<213> ORGANISM: Artificial Sequence
<220> FEATURE:
<223> OTHER INFORMATION: Primer

<400> SEQUENCE: 258
ggtgtagctt ttcgttttcc taatgtaa 28

<210> SEQ ID NO 259
<211> LENGTH: 25
<212> TYPE: DNA
<213> ORGANISM: Artificial Sequence
<220> FEATURE:
<223> OTHER INFORMATION: Primer

<400> SEQUENCE: 259
cacagagctg caaacaacta tacat 25

<210> SEQ ID NO 260
<211> LENGTH: 26
<212> TYPE: DNA
<213> ORGANISM: Artificial Sequence
<220> FEATURE:
<223> OTHER INFORMATION: Primer

<400> SEQUENCE: 260
tgtccagatg tctttgcttt tcttca 26

<210> SEQ ID NO 261
<211> LENGTH: 25
<212> TYPE: DNA
<213> ORGANISM: Artificial Sequence -continued

```
<220> FEATURE:
<223> OTHER INFORMATION: Primer

<400> SEQUENCE: 261
cacagagctg caaacaacta tacat                                             25

<210> SEQ ID NO 262
<211> LENGTH: 24
<212> TYPE: DNA
<213> ORGANISM: Artificial Sequence
<220> FEATURE:
<223> OTHER INFORMATION: Primer

<400> SEQUENCE: 262
tcagttgtct ctggttgcaa atct                                              24

<210> SEQ ID NO 263
<211> LENGTH: 25
<212> TYPE: DNA
<213> ORGANISM: Artificial Sequence
<220> FEATURE:
<223> OTHER INFORMATION: Primer

<400> SEQUENCE: 263
cacagagctg caaacaacta tacat                                             25

<210> SEQ ID NO 264
<211> LENGTH: 26
<212> TYPE: DNA
<213> ORGANISM: Artificial Sequence
<220> FEATURE:
<223> OTHER INFORMATION: Primer

<400> SEQUENCE: 264
ccattaacag gtcttccaaa gtacga                                            26

<210> SEQ ID NO 265
<211> LENGTH: 25
<212> TYPE: DNA
<213> ORGANISM: Artificial Sequence
<220> FEATURE:
<223> OTHER INFORMATION: Primer

<400> SEQUENCE: 265
cacagagctg caaacaacta tacat                                             25

<210> SEQ ID NO 266
<211> LENGTH: 28
<212> TYPE: DNA
<213> ORGANISM: Artificial Sequence
<220> FEATURE:
<223> OTHER INFORMATION: Primer

<400> SEQUENCE: 266
cactaagtgg actaccaaat actttcgt                                          28

<210> SEQ ID NO 267
<211> LENGTH: 25
<212> TYPE: DNA
<213> ORGANISM: Artificial Sequence
<220> FEATURE:
<223> OTHER INFORMATION: Primer

<400> SEQUENCE: 267
cacagagctg caaacaacta tacat                                             25
```

```
<210> SEQ ID NO 268
<211> LENGTH: 28
<212> TYPE: DNA
<213> ORGANISM: Artificial Sequence
<220> FEATURE:
<223> OTHER INFORMATION: Primer

<400> SEQUENCE: 268
gttttcgtca aatggaaact cattagga                                              28

<210> SEQ ID NO 269
<211> LENGTH: 25
<212> TYPE: DNA
<213> ORGANISM: Artificial Sequence
<220> FEATURE:
<223> OTHER INFORMATION: Primer

<400> SEQUENCE: 269
cacagagctg caaacaacta tacat                                                 25

<210> SEQ ID NO 270
<211> LENGTH: 26
<212> TYPE: DNA
<213> ORGANISM: Artificial Sequence
<220> FEATURE:
<223> OTHER INFORMATION: Primer

<400> SEQUENCE: 270
tgacacacat ttaaacgttg gcaaag                                                26

<210> SEQ ID NO 271
<211> LENGTH: 25
<212> TYPE: DNA
<213> ORGANISM: Artificial Sequence
<220> FEATURE:
<223> OTHER INFORMATION: Primer

<400> SEQUENCE: 271
cacagagctg caaacaacta tacat                                                 25

<210> SEQ ID NO 272
<211> LENGTH: 19
<212> TYPE: DNA
<213> ORGANISM: Artificial Sequence
<220> FEATURE:
<223> OTHER INFORMATION: Primer

<400> SEQUENCE: 272
aaggcgacgg ctttggtat                                                        19

<210> SEQ ID NO 273
<211> LENGTH: 25
<212> TYPE: DNA
<213> ORGANISM: Artificial Sequence
<220> FEATURE:
<223> OTHER INFORMATION: Primer

<400> SEQUENCE: 273
cacagagctg caaacaacta tacat                                                 25

<210> SEQ ID NO 274
<211> LENGTH: 28
<212> TYPE: DNA
<213> ORGANISM: Artificial Sequence
<220> FEATURE:
<223> OTHER INFORMATION: Primer
```

```
<400> SEQUENCE: 274
ggtcagtgaa agtgggatta ttatgtgt                                28

<210> SEQ ID NO 275
<211> LENGTH: 25
<212> TYPE: DNA
<213> ORGANISM: Artificial Sequence
<220> FEATURE:
<223> OTHER INFORMATION: Primer

<400> SEQUENCE: 275
cacagagctg caaacaacta tacat                                   25

<210> SEQ ID NO 276
<211> LENGTH: 26
<212> TYPE: DNA
<213> ORGANISM: Artificial Sequence
<220> FEATURE:
<223> OTHER INFORMATION: Primer

<400> SEQUENCE: 276
ggaatattgt atgcaccacc aaaagg                                  26

<210> SEQ ID NO 277
<211> LENGTH: 25
<212> TYPE: DNA
<213> ORGANISM: Artificial Sequence
<220> FEATURE:
<223> OTHER INFORMATION: Primer

<400> SEQUENCE: 277
cacagagctg caaacaacta tacat                                   25

<210> SEQ ID NO 278
<211> LENGTH: 26
<212> TYPE: DNA
<213> ORGANISM: Artificial Sequence
<220> FEATURE:
<223> OTHER INFORMATION: Primer

<400> SEQUENCE: 278
atccgtgctt acaaccttag atactg                                  26

<210> SEQ ID NO 279
<211> LENGTH: 25
<212> TYPE: DNA
<213> ORGANISM: Artificial Sequence
<220> FEATURE:
<223> OTHER INFORMATION: Primer

<400> SEQUENCE: 279
cacagagctg caaacaacta tacat                                   25

<210> SEQ ID NO 280
<211> LENGTH: 28
<212> TYPE: DNA
<213> ORGANISM: Artificial Sequence
<220> FEATURE:
<223> OTHER INFORMATION: Primer

<400> SEQUENCE: 280
ggtgtagctt ttcgtttcc taatgtaa                                 28

<210> SEQ ID NO 281
```

```
<211> LENGTH: 21
<212> TYPE: DNA
<213> ORGANISM: Artificial Sequence
<220> FEATURE:
<223> OTHER INFORMATION: Primer

<400> SEQUENCE: 281
ggaattgtgt gccccatctg t                                              21

<210> SEQ ID NO 282
<211> LENGTH: 28
<212> TYPE: DNA
<213> ORGANISM: Artificial Sequence
<220> FEATURE:
<223> OTHER INFORMATION: Primer

<400> SEQUENCE: 282
cactaagtgg actaccaaat actttcgt                                       28

<210> SEQ ID NO 283
<211> LENGTH: 21
<212> TYPE: DNA
<213> ORGANISM: Artificial Sequence
<220> FEATURE:
<223> OTHER INFORMATION: Primer

<400> SEQUENCE: 283
ggaattgtgt gccccatctg t                                              21

<210> SEQ ID NO 284
<211> LENGTH: 28
<212> TYPE: DNA
<213> ORGANISM: Artificial Sequence
<220> FEATURE:
<223> OTHER INFORMATION: Primer

<400> SEQUENCE: 284
gttttcgtca aatggaaact cattagga                                       28

<210> SEQ ID NO 285
<211> LENGTH: 21
<212> TYPE: DNA
<213> ORGANISM: Artificial Sequence
<220> FEATURE:
<223> OTHER INFORMATION: Primer

<400> SEQUENCE: 285
ggaattgtgt gccccatctg t                                              21

<210> SEQ ID NO 286
<211> LENGTH: 26
<212> TYPE: DNA
<213> ORGANISM: Artificial Sequence
<220> FEATURE:
<223> OTHER INFORMATION: Primer

<400> SEQUENCE: 286
tgacacacat ttaaacgttg gcaaag                                         26

<210> SEQ ID NO 287
<211> LENGTH: 21
<212> TYPE: DNA
<213> ORGANISM: Artificial Sequence
<220> FEATURE:
<223> OTHER INFORMATION: Primer

<400> SEQUENCE: 287
```
ggaattgtgt gccccatctg t    21

<210> SEQ ID NO 288
<211> LENGTH: 19
<212> TYPE: DNA
<213> ORGANISM: Artificial Sequence
<220> FEATURE:
<223> OTHER INFORMATION: Primer

<400> SEQUENCE: 288
aaggcgacgg ctttggtat    19

<210> SEQ ID NO 289
<211> LENGTH: 21
<212> TYPE: DNA
<213> ORGANISM: Artificial Sequence
<220> FEATURE:
<223> OTHER INFORMATION: Primer

<400> SEQUENCE: 289
ggaattgtgt gccccatctg t    21

<210> SEQ ID NO 290
<211> LENGTH: 28
<212> TYPE: DNA
<213> ORGANISM: Artificial Sequence
<220> FEATURE:
<223> OTHER INFORMATION: Primer

<400> SEQUENCE: 290
ggtcagtgaa agtgggatta ttatgtgt    28

<210> SEQ ID NO 291
<211> LENGTH: 21
<212> TYPE: DNA
<213> ORGANISM: Artificial Sequence
<220> FEATURE:
<223> OTHER INFORMATION: Primer

<400> SEQUENCE: 291
ggaattgtgt gccccatctg t    21

<210> SEQ ID NO 292
<211> LENGTH: 26
<212> TYPE: DNA
<213> ORGANISM: Artificial Sequence
<220> FEATURE:
<223> OTHER INFORMATION: Primer

<400> SEQUENCE: 292
ggaatattgt atgcaccacc aaaagg    26

<210> SEQ ID NO 293
<211> LENGTH: 21
<212> TYPE: DNA
<213> ORGANISM: Artificial Sequence
<220> FEATURE:
<223> OTHER INFORMATION: Primer

<400> SEQUENCE: 293
ggaattgtgt gccccatctg t    21

<210> SEQ ID NO 294
<211> LENGTH: 26
<212> TYPE: DNA

<213> ORGANISM: Artificial Sequence
<220> FEATURE:
<223> OTHER INFORMATION: Primer

<400> SEQUENCE: 294
atccgtgctt acaaccttag atactg                                          26

<210> SEQ ID NO 295
<211> LENGTH: 21
<212> TYPE: DNA
<213> ORGANISM: Artificial Sequence
<220> FEATURE:
<223> OTHER INFORMATION: Primer

<400> SEQUENCE: 295
ggaattgtgt gccccatctg t                                               21

<210> SEQ ID NO 296
<211> LENGTH: 28
<212> TYPE: DNA
<213> ORGANISM: Artificial Sequence
<220> FEATURE:
<223> OTHER INFORMATION: Primer

<400> SEQUENCE: 296
ggtgtagctt ttcgttttcc taatgtaa                                        28

<210> SEQ ID NO 297
<211> LENGTH: 26
<212> TYPE: DNA
<213> ORGANISM: Artificial Sequence
<220> FEATURE:
<223> OTHER INFORMATION: Primer

<400> SEQUENCE: 297
ggttttatgt agaggctgta gtggaa                                          26

<210> SEQ ID NO 298
<211> LENGTH: 28
<212> TYPE: DNA
<213> ORGANISM: Artificial Sequence
<220> FEATURE:
<223> OTHER INFORMATION: Primer

<400> SEQUENCE: 298
cactaagtgg actaccaaat actttcgt                                        28

<210> SEQ ID NO 299
<211> LENGTH: 26
<212> TYPE: DNA
<213> ORGANISM: Artificial Sequence
<220> FEATURE:
<223> OTHER INFORMATION: Primer

<400> SEQUENCE: 299
ggttttatgt agaggctgta gtggaa                                          26

<210> SEQ ID NO 300
<211> LENGTH: 28
<212> TYPE: DNA
<213> ORGANISM: Artificial Sequence
<220> FEATURE:
<223> OTHER INFORMATION: Primer

<400> SEQUENCE: 300
gttttcgtca aatggaaact cattagga                                        28

<210> SEQ ID NO 301
<211> LENGTH: 26
<212> TYPE: DNA
<213> ORGANISM: Artificial Sequence
<220> FEATURE:
<223> OTHER INFORMATION: Primer

<400> SEQUENCE: 301
ggttttatgt agaggctgta gtggaa                                          26

<210> SEQ ID NO 302
<211> LENGTH: 26
<212> TYPE: DNA
<213> ORGANISM: Artificial Sequence
<220> FEATURE:
<223> OTHER INFORMATION: Primer

<400> SEQUENCE: 302
tgacacacat ttaaacgttg gcaaag                                          26

<210> SEQ ID NO 303
<211> LENGTH: 26
<212> TYPE: DNA
<213> ORGANISM: Artificial Sequence
<220> FEATURE:
<223> OTHER INFORMATION: Primer

<400> SEQUENCE: 303
ggttttatgt agaggctgta gtggaa                                          26

<210> SEQ ID NO 304
<211> LENGTH: 19
<212> TYPE: DNA
<213> ORGANISM: Artificial Sequence
<220> FEATURE:
<223> OTHER INFORMATION: Primer

<400> SEQUENCE: 304
aaggcgacgg ctttggtat                                                  19

<210> SEQ ID NO 305
<211> LENGTH: 26
<212> TYPE: DNA
<213> ORGANISM: Artificial Sequence
<220> FEATURE:
<223> OTHER INFORMATION: Primer

<400> SEQUENCE: 305
ggttttatgt agaggctgta gtggaa                                          26

<210> SEQ ID NO 306
<211> LENGTH: 28
<212> TYPE: DNA
<213> ORGANISM: Artificial Sequence
<220> FEATURE:
<223> OTHER INFORMATION: Primer

<400> SEQUENCE: 306
ggtcagtgaa agtgggatta ttatgtgt                                        28

<210> SEQ ID NO 307
<211> LENGTH: 26
<212> TYPE: DNA
<213> ORGANISM: Artificial Sequence
<220> FEATURE:

<223> OTHER INFORMATION: Primer

<400> SEQUENCE: 307
ggttttatgt agaggctgta gtggaa                                          26

<210> SEQ ID NO 308
<211> LENGTH: 26
<212> TYPE: DNA
<213> ORGANISM: Artificial Sequence
<220> FEATURE:
<223> OTHER INFORMATION: Primer

<400> SEQUENCE: 308
ggaatattgt atgcaccacc aaaagg                                          26

<210> SEQ ID NO 309
<211> LENGTH: 26
<212> TYPE: DNA
<213> ORGANISM: Artificial Sequence
<220> FEATURE:
<223> OTHER INFORMATION: Primer

<400> SEQUENCE: 309
ggttttatgt agaggctgta gtggaa                                          26

<210> SEQ ID NO 310
<211> LENGTH: 26
<212> TYPE: DNA
<213> ORGANISM: Artificial Sequence
<220> FEATURE:
<223> OTHER INFORMATION: Primer

<400> SEQUENCE: 310
atccgtgctt acaaccttag atactg                                          26

<210> SEQ ID NO 311
<211> LENGTH: 26
<212> TYPE: DNA
<213> ORGANISM: Artificial Sequence
<220> FEATURE:
<223> OTHER INFORMATION: Primer

<400> SEQUENCE: 311
ggttttatgt agaggctgta gtggaa                                          26

<210> SEQ ID NO 312
<211> LENGTH: 28
<212> TYPE: DNA
<213> ORGANISM: Artificial Sequence
<220> FEATURE:
<223> OTHER INFORMATION: Primer

<400> SEQUENCE: 312
ggtgtagctt ttcgttttcc taatgtaa                                        28

<210> SEQ ID NO 313
<211> LENGTH: 22
<212> TYPE: DNA
<213> ORGANISM: Artificial Sequence
<220> FEATURE:
<223> OTHER INFORMATION: Primer

<400> SEQUENCE: 313
gcgggtatgg caatactgaa gt                                              22

```
<210> SEQ ID NO 314
<211> LENGTH: 28
<212> TYPE: DNA
<213> ORGANISM: Artificial Sequence
<220> FEATURE:
<223> OTHER INFORMATION: Primer

<400> SEQUENCE: 314
gttttcgtca aatggaaact cattagga                                        28

<210> SEQ ID NO 315
<211> LENGTH: 22
<212> TYPE: DNA
<213> ORGANISM: Artificial Sequence
<220> FEATURE:
<223> OTHER INFORMATION: Primer

<400> SEQUENCE: 315
gcgggtatgg caatactgaa gt                                              22

<210> SEQ ID NO 316
<211> LENGTH: 26
<212> TYPE: DNA
<213> ORGANISM: Artificial Sequence
<220> FEATURE:
<223> OTHER INFORMATION: Primer

<400> SEQUENCE: 316
tgacacacat ttaaacgttg gcaaag                                          26

<210> SEQ ID NO 317
<211> LENGTH: 22
<212> TYPE: DNA
<213> ORGANISM: Artificial Sequence
<220> FEATURE:
<223> OTHER INFORMATION: Primer

<400> SEQUENCE: 317
gcgggtatgg caatactgaa gt                                              22

<210> SEQ ID NO 318
<211> LENGTH: 19
<212> TYPE: DNA
<213> ORGANISM: Artificial Sequence
<220> FEATURE:
<223> OTHER INFORMATION: Primer

<400> SEQUENCE: 318
aaggcgacgg ctttggtat                                                  19

<210> SEQ ID NO 319
<211> LENGTH: 22
<212> TYPE: DNA
<213> ORGANISM: Artificial Sequence
<220> FEATURE:
<223> OTHER INFORMATION: Primer

<400> SEQUENCE: 319
gcgggtatgg caatactgaa gt                                              22

<210> SEQ ID NO 320
<211> LENGTH: 26
<212> TYPE: DNA
<213> ORGANISM: Artificial Sequence
<220> FEATURE:
<223> OTHER INFORMATION: Primer
```

<400> SEQUENCE: 320
atccgtgctt acaaccttag atactg                                    26

<210> SEQ ID NO 321
<211> LENGTH: 22
<212> TYPE: DNA
<213> ORGANISM: Artificial Sequence
<220> FEATURE:
<223> OTHER INFORMATION: Primer

<400> SEQUENCE: 321
gcgggtatgg caatactgaa gt                                        22

<210> SEQ ID NO 322
<211> LENGTH: 28
<212> TYPE: DNA
<213> ORGANISM: Artificial Sequence
<220> FEATURE:
<223> OTHER INFORMATION: Primer

<400> SEQUENCE: 322
ggtcagtgaa agtgggatta ttatgtgt                                  28

<210> SEQ ID NO 323
<211> LENGTH: 22
<212> TYPE: DNA
<213> ORGANISM: Artificial Sequence
<220> FEATURE:
<223> OTHER INFORMATION: Primer

<400> SEQUENCE: 323
gcgggtatgg caatactgaa gt                                        22

<210> SEQ ID NO 324
<211> LENGTH: 26
<212> TYPE: DNA
<213> ORGANISM: Artificial Sequence
<220> FEATURE:
<223> OTHER INFORMATION: Primer

<400> SEQUENCE: 324
ggaatattgt atgcaccacc aaaagg                                    26

<210> SEQ ID NO 325
<211> LENGTH: 22
<212> TYPE: DNA
<213> ORGANISM: Artificial Sequence
<220> FEATURE:
<223> OTHER INFORMATION: Primer

<400> SEQUENCE: 325
gcgggtatgg caatactgaa gt                                        22

<210> SEQ ID NO 326
<211> LENGTH: 28
<212> TYPE: DNA
<213> ORGANISM: Artificial Sequence
<220> FEATURE:
<223> OTHER INFORMATION: Primer

<400> SEQUENCE: 326
ggtgtagctt ttcgttttcc taatgtaa                                  28

<210> SEQ ID NO 327
<211> LENGTH: 27

```
<212> TYPE: DNA
<213> ORGANISM: Artificial Sequence
<220> FEATURE:
<223> OTHER INFORMATION: Primer

<400> SEQUENCE: 327
gaggtgattg gaagcaaatt gttatgt                                          27

<210> SEQ ID NO 328
<211> LENGTH: 26
<212> TYPE: DNA
<213> ORGANISM: Artificial Sequence
<220> FEATURE:
<223> OTHER INFORMATION: Primer

<400> SEQUENCE: 328
tgacacacat ttaaacgttg gcaaag                                           26

<210> SEQ ID NO 329
<211> LENGTH: 27
<212> TYPE: DNA
<213> ORGANISM: Artificial Sequence
<220> FEATURE:
<223> OTHER INFORMATION: Primer

<400> SEQUENCE: 329
gaggtgattg gaagcaaatt gttatgt                                          27

<210> SEQ ID NO 330
<211> LENGTH: 19
<212> TYPE: DNA
<213> ORGANISM: Artificial Sequence
<220> FEATURE:
<223> OTHER INFORMATION: Primer

<400> SEQUENCE: 330
aaggcgacgg ctttggtat                                                   19

<210> SEQ ID NO 331
<211> LENGTH: 27
<212> TYPE: DNA
<213> ORGANISM: Artificial Sequence
<220> FEATURE:
<223> OTHER INFORMATION: Primer

<400> SEQUENCE: 331
gaggtgattg gaagcaaatt gttatgt                                          27

<210> SEQ ID NO 332
<211> LENGTH: 26
<212> TYPE: DNA
<213> ORGANISM: Artificial Sequence
<220> FEATURE:
<223> OTHER INFORMATION: Primer

<400> SEQUENCE: 332
atccgtgctt acaaccttag atactg                                           26

<210> SEQ ID NO 333
<211> LENGTH: 27
<212> TYPE: DNA
<213> ORGANISM: Artificial Sequence
<220> FEATURE:
<223> OTHER INFORMATION: Primer

<400> SEQUENCE: 333
```

```
gaggtgattg gaagcaaatt gttatgt                                          27

<210> SEQ ID NO 334
<211> LENGTH: 28
<212> TYPE: DNA
<213> ORGANISM: Artificial Sequence
<220> FEATURE:
<223> OTHER INFORMATION: Primer

<400> SEQUENCE: 334
ggtcagtgaa agtgggatta ttatgtgt                                         28

<210> SEQ ID NO 335
<211> LENGTH: 27
<212> TYPE: DNA
<213> ORGANISM: Artificial Sequence
<220> FEATURE:
<223> OTHER INFORMATION: Primer

<400> SEQUENCE: 335
gaggtgattg gaagcaaatt gttatgt                                          27

<210> SEQ ID NO 336
<211> LENGTH: 26
<212> TYPE: DNA
<213> ORGANISM: Artificial Sequence
<220> FEATURE:
<223> OTHER INFORMATION: Primer

<400> SEQUENCE: 336
ggaatattgt atgcaccacc aaaagg                                           26

<210> SEQ ID NO 337
<211> LENGTH: 27
<212> TYPE: DNA
<213> ORGANISM: Artificial Sequence
<220> FEATURE:
<223> OTHER INFORMATION: Primer

<400> SEQUENCE: 337
gaggtgattg gaagcaaatt gttatgt                                          27

<210> SEQ ID NO 338
<211> LENGTH: 28
<212> TYPE: DNA
<213> ORGANISM: Artificial Sequence
<220> FEATURE:
<223> OTHER INFORMATION: Primer

<400> SEQUENCE: 338
ggtgtagctt ttcgttttcc taatgtaa                                         28

<210> SEQ ID NO 339
<211> LENGTH: 23
<212> TYPE: DNA
<213> ORGANISM: Artificial Sequence
<220> FEATURE:
<223> OTHER INFORMATION: Primer

<400> SEQUENCE: 339
gctcacacaa aggacggatt aac                                              23

<210> SEQ ID NO 340
<211> LENGTH: 26
<212> TYPE: DNA
<213> ORGANISM: Artificial Sequence
```

```
<220> FEATURE:
<223> OTHER INFORMATION: Primer

<400> SEQUENCE: 340
atccgtgctt acaaccttag atactg                                          26

<210> SEQ ID NO 341
<211> LENGTH: 23
<212> TYPE: DNA
<213> ORGANISM: Artificial Sequence
<220> FEATURE:
<223> OTHER INFORMATION: Primer

<400> SEQUENCE: 341
gctcacacaa aggacggatt aac                                             23

<210> SEQ ID NO 342
<211> LENGTH: 28
<212> TYPE: DNA
<213> ORGANISM: Artificial Sequence
<220> FEATURE:
<223> OTHER INFORMATION: Primer

<400> SEQUENCE: 342
ggtcagtgaa agtgggatta ttatgtgt                                        28

<210> SEQ ID NO 343
<211> LENGTH: 23
<212> TYPE: DNA
<213> ORGANISM: Artificial Sequence
<220> FEATURE:
<223> OTHER INFORMATION: Primer

<400> SEQUENCE: 343
gctcacacaa aggacggatt aac                                             23

<210> SEQ ID NO 344
<211> LENGTH: 26
<212> TYPE: DNA
<213> ORGANISM: Artificial Sequence
<220> FEATURE:
<223> OTHER INFORMATION: Primer

<400> SEQUENCE: 344
ggaatattgt atgcaccacc aaaagg                                          26

<210> SEQ ID NO 345
<211> LENGTH: 23
<212> TYPE: DNA
<213> ORGANISM: Artificial Sequence
<220> FEATURE:
<223> OTHER INFORMATION: Primer

<400> SEQUENCE: 345
gctcacacaa aggacggatt aac                                             23

<210> SEQ ID NO 346
<211> LENGTH: 28
<212> TYPE: DNA
<213> ORGANISM: Artificial Sequence
<220> FEATURE:
<223> OTHER INFORMATION: Primer

<400> SEQUENCE: 346
ggtgtagctt ttcgttttcc taatgtaa                                        28
```

```
<210> SEQ ID NO 347
<211> LENGTH: 24
<212> TYPE: DNA
<213> ORGANISM: Artificial Sequence
<220> FEATURE:
<223> OTHER INFORMATION: Primer

<400> SEQUENCE: 347
ctgcttttgt aaccactccc acta                                              24

<210> SEQ ID NO 348
<211> LENGTH: 26
<212> TYPE: DNA
<213> ORGANISM: Artificial Sequence
<220> FEATURE:
<223> OTHER INFORMATION: Primer

<400> SEQUENCE: 348
ggaatattgt atgcaccacc aaaagg                                            26

<210> SEQ ID NO 349
<211> LENGTH: 24
<212> TYPE: DNA
<213> ORGANISM: Artificial Sequence
<220> FEATURE:
<223> OTHER INFORMATION: Primer

<400> SEQUENCE: 349
ctgcttttgt aaccactccc acta                                              24

<210> SEQ ID NO 350
<211> LENGTH: 26
<212> TYPE: DNA
<213> ORGANISM: Artificial Sequence
<220> FEATURE:
<223> OTHER INFORMATION: Primer

<400> SEQUENCE: 350
atccgtgctt acaaccttag atactg                                            26

<210> SEQ ID NO 351
<211> LENGTH: 24
<212> TYPE: DNA
<213> ORGANISM: Artificial Sequence
<220> FEATURE:
<223> OTHER INFORMATION: Primer

<400> SEQUENCE: 351
ctgcttttgt aaccactccc acta                                              24

<210> SEQ ID NO 352
<211> LENGTH: 28
<212> TYPE: DNA
<213> ORGANISM: Artificial Sequence
<220> FEATURE:
<223> OTHER INFORMATION: Primer

<400> SEQUENCE: 352
ggtgtagctt ttcgttttcc taatgtaa                                          28

<210> SEQ ID NO 353
<211> LENGTH: 21
<212> TYPE: DNA
<213> ORGANISM: Artificial Sequence
<220> FEATURE:
<223> OTHER INFORMATION: Primer
```

```
<400> SEQUENCE: 353
ggaattgtgt gccccatctg t                                          21

<210> SEQ ID NO 354
<211> LENGTH: 19
<212> TYPE: DNA
<213> ORGANISM: Artificial Sequence
<220> FEATURE:
<223> OTHER INFORMATION: Primer

<400> SEQUENCE: 354
ctgagaagcc ctgcccttc                                             19

<210> SEQ ID NO 355
<211> LENGTH: 21
<212> TYPE: DNA
<213> ORGANISM: Artificial Sequence
<220> FEATURE:
<223> OTHER INFORMATION: Primer

<400> SEQUENCE: 355
ggaattgtgt gccccatctg t                                          21

<210> SEQ ID NO 356
<211> LENGTH: 19
<212> TYPE: DNA
<213> ORGANISM: Artificial Sequence
<220> FEATURE:
<223> OTHER INFORMATION: Primer

<400> SEQUENCE: 356
aaatacggct gcaccgagt                                             19

<210> SEQ ID NO 357
<211> LENGTH: 21
<212> TYPE: DNA
<213> ORGANISM: Artificial Sequence
<220> FEATURE:
<223> OTHER INFORMATION: Primer

<400> SEQUENCE: 357
ggaattgtgt gccccatctg t                                          21

<210> SEQ ID NO 358
<211> LENGTH: 24
<212> TYPE: DNA
<213> ORGANISM: Artificial Sequence
<220> FEATURE:
<223> OTHER INFORMATION: Primer

<400> SEQUENCE: 358
ggtgatccag actctgacct tttg                                       24

<210> SEQ ID NO 359
<211> LENGTH: 21
<212> TYPE: DNA
<213> ORGANISM: Artificial Sequence
<220> FEATURE:
<223> OTHER INFORMATION: Primer

<400> SEQUENCE: 359
ggaattgtgt gccccatctg t                                          21

<210> SEQ ID NO 360
```

```
<211> LENGTH: 22
<212> TYPE: DNA
<213> ORGANISM: Artificial Sequence
<220> FEATURE:
<223> OTHER INFORMATION: Primer

<400> SEQUENCE: 360
atcatgatgg ctgtatgtgc ca                                              22

<210> SEQ ID NO 361
<211> LENGTH: 21
<212> TYPE: DNA
<213> ORGANISM: Artificial Sequence
<220> FEATURE:
<223> OTHER INFORMATION: Primer

<400> SEQUENCE: 361
ggaattgtgt gccccatctg t                                               21

<210> SEQ ID NO 362
<211> LENGTH: 21
<212> TYPE: DNA
<213> ORGANISM: Artificial Sequence
<220> FEATURE:
<223> OTHER INFORMATION: Primer

<400> SEQUENCE: 362
catggttcca ccagcgttat t                                               21

<210> SEQ ID NO 363
<211> LENGTH: 21
<212> TYPE: DNA
<213> ORGANISM: Artificial Sequence
<220> FEATURE:
<223> OTHER INFORMATION: Primer

<400> SEQUENCE: 363
ggaattgtgt gccccatctg t                                               21

<210> SEQ ID NO 364
<211> LENGTH: 18
<212> TYPE: DNA
<213> ORGANISM: Artificial Sequence
<220> FEATURE:
<223> OTHER INFORMATION: Primer

<400> SEQUENCE: 364
tctttgctcg cagctcgt                                                   18

<210> SEQ ID NO 365
<211> LENGTH: 27
<212> TYPE: DNA
<213> ORGANISM: Artificial Sequence
<220> FEATURE:
<223> OTHER INFORMATION: Primer

<400> SEQUENCE: 365
agtacagacc tacgtgacca tatagac                                         27

<210> SEQ ID NO 366
<211> LENGTH: 19
<212> TYPE: DNA
<213> ORGANISM: Artificial Sequence
<220> FEATURE:
<223> OTHER INFORMATION: Primer

<400> SEQUENCE: 366
```
ctgagaagcc ctgcccttc                                                    19

<210> SEQ ID NO 367
<211> LENGTH: 27
<212> TYPE: DNA
<213> ORGANISM: Artificial Sequence
<220> FEATURE:
<223> OTHER INFORMATION: Primer

<400> SEQUENCE: 367
agtacagacc tacgtgacca tatagac                                           27

<210> SEQ ID NO 368
<211> LENGTH: 19
<212> TYPE: DNA
<213> ORGANISM: Artificial Sequence
<220> FEATURE:
<223> OTHER INFORMATION: Primer

<400> SEQUENCE: 368
aaatacggct gcaccgagt                                                    19

<210> SEQ ID NO 369
<211> LENGTH: 27
<212> TYPE: DNA
<213> ORGANISM: Artificial Sequence
<220> FEATURE:
<223> OTHER INFORMATION: Primer

<400> SEQUENCE: 369
agtacagacc tacgtgacca tatagac                                           27

<210> SEQ ID NO 370
<211> LENGTH: 24
<212> TYPE: DNA
<213> ORGANISM: Artificial Sequence
<220> FEATURE:
<223> OTHER INFORMATION: Primer

<400> SEQUENCE: 370
ggtgatccag actctgacct tttg                                              24

<210> SEQ ID NO 371
<211> LENGTH: 27
<212> TYPE: DNA
<213> ORGANISM: Artificial Sequence
<220> FEATURE:
<223> OTHER INFORMATION: Primer

<400> SEQUENCE: 371
agtacagacc tacgtgacca tatagac                                           27

<210> SEQ ID NO 372
<211> LENGTH: 22
<212> TYPE: DNA
<213> ORGANISM: Artificial Sequence
<220> FEATURE:
<223> OTHER INFORMATION: Primer

<400> SEQUENCE: 372
atcatgatgg ctgtatgtgc ca                                                22

<210> SEQ ID NO 373
<211> LENGTH: 27
<212> TYPE: DNA

```
<213> ORGANISM: Artificial Sequence
<220> FEATURE:
<223> OTHER INFORMATION: Primer

<400> SEQUENCE: 373
agtacagacc tacgtgacca tatagac                                              27

<210> SEQ ID NO 374
<211> LENGTH: 21
<212> TYPE: DNA
<213> ORGANISM: Artificial Sequence
<220> FEATURE:
<223> OTHER INFORMATION: Primer

<400> SEQUENCE: 374
catggttcca ccagcgttat t                                                    21

<210> SEQ ID NO 375
<211> LENGTH: 27
<212> TYPE: DNA
<213> ORGANISM: Artificial Sequence
<220> FEATURE:
<223> OTHER INFORMATION: Primer

<400> SEQUENCE: 375
agtacagacc tacgtgacca tatagac                                              27

<210> SEQ ID NO 376
<211> LENGTH: 18
<212> TYPE: DNA
<213> ORGANISM: Artificial Sequence
<220> FEATURE:
<223> OTHER INFORMATION: Primer

<400> SEQUENCE: 376
tctttgctcg cagctcgt                                                        18

<210> SEQ ID NO 377
<211> LENGTH: 27
<212> TYPE: DNA
<213> ORGANISM: Artificial Sequence
<220> FEATURE:
<223> OTHER INFORMATION: Primer

<400> SEQUENCE: 377
agtacagacc tacgtgacca tatagac                                              27

<210> SEQ ID NO 378
<211> LENGTH: 18
<212> TYPE: DNA
<213> ORGANISM: Artificial Sequence
<220> FEATURE:
<223> OTHER INFORMATION: Primer

<400> SEQUENCE: 378
tctttgctcg cagctcgt                                                        18

<210> SEQ ID NO 379
<211> LENGTH: 22
<212> TYPE: DNA
<213> ORGANISM: Artificial Sequence
<220> FEATURE:
<223> OTHER INFORMATION: Primer

<400> SEQUENCE: 379
gcgggtatgg caatactgaa gt                                                   22
```

```
<210> SEQ ID NO 380
<211> LENGTH: 28
<212> TYPE: DNA
<213> ORGANISM: Artificial Sequence
<220> FEATURE:
<223> OTHER INFORMATION: Primer

<400> SEQUENCE: 380
gttttcgtca aatggaaact cattagga                                    28

<210> SEQ ID NO 381
<211> LENGTH: 25
<212> TYPE: DNA
<213> ORGANISM: Artificial Sequence
<220> FEATURE:
<223> OTHER INFORMATION: Primer

<400> SEQUENCE: 381
cacagagctg caaacaacta tacat                                       25

<210> SEQ ID NO 382
<211> LENGTH: 26
<212> TYPE: DNA
<213> ORGANISM: Artificial Sequence
<220> FEATURE:
<223> OTHER INFORMATION: Primer

<400> SEQUENCE: 382
ccattaacag gtcttccaaa gtacga                                      26

<210> SEQ ID NO 383
<211> LENGTH: 17
<212> TYPE: DNA
<213> ORGANISM: Artificial Sequence
<220> FEATURE:
<223> OTHER INFORMATION: Primer

<400> SEQUENCE: 383
cggtggaccg gtcgatg                                                17

<210> SEQ ID NO 384
<211> LENGTH: 24
<212> TYPE: DNA
<213> ORGANISM: Artificial Sequence
<220> FEATURE:
<223> OTHER INFORMATION: Primer

<400> SEQUENCE: 384
tcagttgtct ctggttgcaa atct                                        24

<210> SEQ ID NO 385
<211> LENGTH: 22
<212> TYPE: DNA
<213> ORGANISM: Artificial Sequence
<220> FEATURE:
<223> OTHER INFORMATION: Primer

<400> SEQUENCE: 385
gcgggtatgg caatactgaa gt                                          22

<210> SEQ ID NO 386
<211> LENGTH: 26
<212> TYPE: DNA
<213> ORGANISM: Artificial Sequence
<220> FEATURE:
```

<223> OTHER INFORMATION: Primer

<400> SEQUENCE: 386
tggtgtttgg catatagtgt gtcttt                                    26

<210> SEQ ID NO 387
<211> LENGTH: 21
<212> TYPE: DNA
<213> ORGANISM: Artificial Sequence
<220> FEATURE:
<223> OTHER INFORMATION: Primer

<400> SEQUENCE: 387
ggaattgtgt gccccatctg t                                         21

<210> SEQ ID NO 388
<211> LENGTH: 28
<212> TYPE: DNA
<213> ORGANISM: Artificial Sequence
<220> FEATURE:
<223> OTHER INFORMATION: Primer

<400> SEQUENCE: 388
gttttcgtca aatggaaact cattagga                                  28

<210> SEQ ID NO 389
<211> LENGTH: 27
<212> TYPE: DNA
<213> ORGANISM: Artificial Sequence
<220> FEATURE:
<223> OTHER INFORMATION: Primer

<400> SEQUENCE: 389
agtacagacc tacgtgacca tatagac                                   27

<210> SEQ ID NO 390
<211> LENGTH: 19
<212> TYPE: DNA
<213> ORGANISM: Artificial Sequence
<220> FEATURE:
<223> OTHER INFORMATION: Primer

<400> SEQUENCE: 390
aaatacggct gcaccgagt                                            19

<210> SEQ ID NO 391
<211> LENGTH: 23
<212> TYPE: DNA
<213> ORGANISM: Artificial Sequence
<220> FEATURE:
<223> OTHER INFORMATION: Primer

<400> SEQUENCE: 391
gctcacacaa aggacggatt aac                                       23

<210> SEQ ID NO 392
<211> LENGTH: 18
<212> TYPE: DNA
<213> ORGANISM: Artificial Sequence
<220> FEATURE:
<223> OTHER INFORMATION: Primer

<400> SEQUENCE: 392
tctttgctcg cagctcgt                                             18

```
<210> SEQ ID NO 393
<211> LENGTH: 21
<212> TYPE: DNA
<213> ORGANISM: Artificial Sequence
<220> FEATURE:
<223> OTHER INFORMATION: Primer

<400> SEQUENCE: 393
ggaattgtgt gccccatctg t                                              21

<210> SEQ ID NO 394
<211> LENGTH: 18
<212> TYPE: DNA
<213> ORGANISM: Artificial Sequence
<220> FEATURE:
<223> OTHER INFORMATION: Primer

<400> SEQUENCE: 394
tctttgctcg cagctcgt                                                  18

<210> SEQ ID NO 395
<211> LENGTH: 25
<212> TYPE: DNA
<213> ORGANISM: Artificial Sequence
<220> FEATURE:
<223> OTHER INFORMATION: Primer

<400> SEQUENCE: 395
cacagagctg caaacaacta tacat                                          25

<210> SEQ ID NO 396
<211> LENGTH: 27
<212> TYPE: DNA
<213> ORGANISM: Artificial Sequence
<220> FEATURE:
<223> OTHER INFORMATION: Primer

<400> SEQUENCE: 396
cacatacagc atatggattc ccatctc                                        27

<210> SEQ ID NO 397
<211> LENGTH: 25
<212> TYPE: DNA
<213> ORGANISM: Artificial Sequence
<220> FEATURE:
<223> OTHER INFORMATION: Primer

<400> SEQUENCE: 397
cacagagctg caaacaacta tacat                                          25

<210> SEQ ID NO 398
<211> LENGTH: 26
<212> TYPE: DNA
<213> ORGANISM: Artificial Sequence
<220> FEATURE:
<223> OTHER INFORMATION: Primer

<400> SEQUENCE: 398
tgtccagatg tctttgcttt tcttca                                         26

<210> SEQ ID NO 399
<211> LENGTH: 21
<212> TYPE: DNA
<213> ORGANISM: Artificial Sequence
<220> FEATURE:
<223> OTHER INFORMATION: Primer
```

<400> SEQUENCE: 399
ggaattgtgt gccccatctg t                                          21

<210> SEQ ID NO 400
<211> LENGTH: 19
<212> TYPE: DNA
<213> ORGANISM: Artificial Sequence
<220> FEATURE:
<223> OTHER INFORMATION: Primer

<400> SEQUENCE: 400
aaggcgacgg ctttggtat                                             19

<210> SEQ ID NO 401
<211> LENGTH: 27
<212> TYPE: DNA
<213> ORGANISM: Artificial Sequence
<220> FEATURE:
<223> OTHER INFORMATION: Primer

<400> SEQUENCE: 401
ggatgtaaag catagaccat tggtaca                                    27

<210> SEQ ID NO 402
<211> LENGTH: 28
<212> TYPE: DNA
<213> ORGANISM: Artificial Sequence
<220> FEATURE:
<223> OTHER INFORMATION: Primer

<400> SEQUENCE: 402
gttttcgtca aatggaaact cattagga                                   28

<210> SEQ ID NO 403
<211> LENGTH: 27
<212> TYPE: DNA
<213> ORGANISM: Artificial Sequence
<220> FEATURE:
<223> OTHER INFORMATION: Primer

<400> SEQUENCE: 403
agtacagacc tacgtgacca tatagac                                    27

<210> SEQ ID NO 404
<211> LENGTH: 24
<212> TYPE: DNA
<213> ORGANISM: Artificial Sequence
<220> FEATURE:
<223> OTHER INFORMATION: Primer

<400> SEQUENCE: 404
ggtgatccag actctgacct tttg                                       24

<210> SEQ ID NO 405
<211> LENGTH: 27
<212> TYPE: DNA
<213> ORGANISM: Artificial Sequence
<220> FEATURE:
<223> OTHER INFORMATION: Primer

<400> SEQUENCE: 405
agtacagacc tacgtgacca tatagac                                    27

<210> SEQ ID NO 406
<211> LENGTH: 22

-continued

```
<212> TYPE: DNA
<213> ORGANISM: Artificial Sequence
<220> FEATURE:
<223> OTHER INFORMATION: Primer

<400> SEQUENCE: 406
atcatgatgg ctgtatgtgc ca                                              22

<210> SEQ ID NO 407
<211> LENGTH: 23
<212> TYPE: DNA
<213> ORGANISM: Artificial Sequence
<220> FEATURE:
<223> OTHER INFORMATION: Primer

<400> SEQUENCE: 407
gctcacacaa aggacggatt aac                                             23

<210> SEQ ID NO 408
<211> LENGTH: 22
<212> TYPE: DNA
<213> ORGANISM: Artificial Sequence
<220> FEATURE:
<223> OTHER INFORMATION: Primer

<400> SEQUENCE: 408
ccaatgccat gtagacgaca ct                                              22

<210> SEQ ID NO 409
<211> LENGTH: 23
<212> TYPE: DNA
<213> ORGANISM: Artificial Sequence
<220> FEATURE:
<223> OTHER INFORMATION: Primer

<400> SEQUENCE: 409
gctcacacaa aggacggatt aac                                             23

<210> SEQ ID NO 410
<211> LENGTH: 21
<212> TYPE: DNA
<213> ORGANISM: Artificial Sequence
<220> FEATURE:
<223> OTHER INFORMATION: Primer

<400> SEQUENCE: 410
catggttcca ccagcgttat t                                               21

<210> SEQ ID NO 411
<211> LENGTH: 21
<212> TYPE: DNA
<213> ORGANISM: Artificial Sequence
<220> FEATURE:
<223> OTHER INFORMATION: Primer

<400> SEQUENCE: 411
ggaattgtgt gccccatctg t                                               21

<210> SEQ ID NO 412
<211> LENGTH: 24
<212> TYPE: DNA
<213> ORGANISM: Artificial Sequence
<220> FEATURE:
<223> OTHER INFORMATION: Primer

<400> SEQUENCE: 412
```
ggtgatccag actctgacct tttg    24

<210> SEQ ID NO 413
<211> LENGTH: 25
<212> TYPE: DNA
<213> ORGANISM: Artificial Sequence
<220> FEATURE:
<223> OTHER INFORMATION: Primer

<400> SEQUENCE: 413
cacagagctg caaacaacta tacat    25

<210> SEQ ID NO 414
<211> LENGTH: 28
<212> TYPE: DNA
<213> ORGANISM: Artificial Sequence
<220> FEATURE:
<223> OTHER INFORMATION: Primer

<400> SEQUENCE: 414
gttttcgtca aatggaaact cattagga    28

<210> SEQ ID NO 415
<211> LENGTH: 22
<212> TYPE: DNA
<213> ORGANISM: Artificial Sequence
<220> FEATURE:
<223> OTHER INFORMATION: Primer

<400> SEQUENCE: 415
gcgggtatgg caatactgaa gt    22

<210> SEQ ID NO 416
<211> LENGTH: 26
<212> TYPE: DNA
<213> ORGANISM: Artificial Sequence
<220> FEATURE:
<223> OTHER INFORMATION: Primer

<400> SEQUENCE: 416
tgacacacat ttaaacgttg gcaaag    26

<210> SEQ ID NO 417
<211> LENGTH: 21
<212> TYPE: DNA
<213> ORGANISM: Artificial Sequence
<220> FEATURE:
<223> OTHER INFORMATION: Primer

<400> SEQUENCE: 417
ggaattgtgt gccccatctg t    21

<210> SEQ ID NO 418
<211> LENGTH: 22
<212> TYPE: DNA
<213> ORGANISM: Artificial Sequence
<220> FEATURE:
<223> OTHER INFORMATION: Primer

<400> SEQUENCE: 418
atcatgatgg ctgtatgtgc ca    22

<210> SEQ ID NO 419
<211> LENGTH: 23
<212> TYPE: DNA
<213> ORGANISM: Artificial Sequence

```
<220> FEATURE:
<223> OTHER INFORMATION: Primer

<400> SEQUENCE: 419
gctcacacaa aggacggatt aac                                         23

<210> SEQ ID NO 420
<211> LENGTH: 26
<212> TYPE: DNA
<213> ORGANISM: Artificial Sequence
<220> FEATURE:
<223> OTHER INFORMATION: Primer

<400> SEQUENCE: 420
atccgtgctt acaaccttag atactg                                      26

<210> SEQ ID NO 421
<211> LENGTH: 19
<212> TYPE: DNA
<213> ORGANISM: Artificial Sequence
<220> FEATURE:
<223> OTHER INFORMATION: Primer

<400> SEQUENCE: 421
catgcgggtg gtcaggtaa                                              19

<210> SEQ ID NO 422
<211> LENGTH: 19
<212> TYPE: DNA
<213> ORGANISM: Artificial Sequence
<220> FEATURE:
<223> OTHER INFORMATION: Primer

<400> SEQUENCE: 422
aaggcgacgg ctttggtat                                              19

<210> SEQ ID NO 423
<211> LENGTH: 24
<212> TYPE: DNA
<213> ORGANISM: Artificial Sequence
<220> FEATURE:
<223> OTHER INFORMATION: Primer

<400> SEQUENCE: 423
cctatagttc cagggtctcc acaa                                        24

<210> SEQ ID NO 424
<211> LENGTH: 26
<212> TYPE: DNA
<213> ORGANISM: Artificial Sequence
<220> FEATURE:
<223> OTHER INFORMATION: Primer

<400> SEQUENCE: 424
atccgtgctt acaaccttag atactg                                      26

<210> SEQ ID NO 425
<211> LENGTH: 21
<212> TYPE: DNA
<213> ORGANISM: Artificial Sequence
<220> FEATURE:
<223> OTHER INFORMATION: Primer

<400> SEQUENCE: 425
ggaattgtgt gccccatctg t                                           21
```

<210> SEQ ID NO 426
<211> LENGTH: 21
<212> TYPE: DNA
<213> ORGANISM: Artificial Sequence
<220> FEATURE:
<223> OTHER INFORMATION: Primer

<400> SEQUENCE: 426
catggttcca ccagcgttat t                                          21

<210> SEQ ID NO 427
<211> LENGTH: 27
<212> TYPE: DNA
<213> ORGANISM: Artificial Sequence
<220> FEATURE:
<223> OTHER INFORMATION: Primer

<400> SEQUENCE: 427
agtacagacc tacgtgacca tatagac                                    27

<210> SEQ ID NO 428
<211> LENGTH: 19
<212> TYPE: DNA
<213> ORGANISM: Artificial Sequence
<220> FEATURE:
<223> OTHER INFORMATION: Primer

<400> SEQUENCE: 428
ctgagaagcc ctgcccttc                                             19

<210> SEQ ID NO 429
<211> LENGTH: 28
<212> TYPE: DNA
<213> ORGANISM: Artificial Sequence
<220> FEATURE:
<223> OTHER INFORMATION: Primer

<400> SEQUENCE: 429
cggaaatcca gtgtatgagc ttaatgat                                   28

<210> SEQ ID NO 430
<211> LENGTH: 26
<212> TYPE: DNA
<213> ORGANISM: Artificial Sequence
<220> FEATURE:
<223> OTHER INFORMATION: Primer

<400> SEQUENCE: 430
tgacacacat ttaaacgttg gcaaag                                     26

<210> SEQ ID NO 431
<211> LENGTH: 25
<212> TYPE: DNA
<213> ORGANISM: Artificial Sequence
<220> FEATURE:
<223> OTHER INFORMATION: Primer

<400> SEQUENCE: 431
cacagagctg caaacaacta tacat                                      25

<210> SEQ ID NO 432
<211> LENGTH: 19
<212> TYPE: DNA
<213> ORGANISM: Artificial Sequence
<220> FEATURE:
<223> OTHER INFORMATION: Primer

<400> SEQUENCE: 432
aaggcgacgg ctttggtat                                                19

<210> SEQ ID NO 433
<211> LENGTH: 23
<212> TYPE: DNA
<213> ORGANISM: Artificial Sequence
<220> FEATURE:
<223> OTHER INFORMATION: Primer

<400> SEQUENCE: 433
gctcacacaa aggacggatt aac                                           23

<210> SEQ ID NO 434
<211> LENGTH: 19
<212> TYPE: DNA
<213> ORGANISM: Artificial Sequence
<220> FEATURE:
<223> OTHER INFORMATION: Primer

<400> SEQUENCE: 434
ctgagaagcc ctgcccttc                                                19

<210> SEQ ID NO 435
<211> LENGTH: 22
<212> TYPE: DNA
<213> ORGANISM: Artificial Sequence
<220> FEATURE:
<223> OTHER INFORMATION: Primer

<400> SEQUENCE: 435
gcgggtatgg caatactgaa gt                                            22

<210> SEQ ID NO 436
<211> LENGTH: 19
<212> TYPE: DNA
<213> ORGANISM: Artificial Sequence
<220> FEATURE:
<223> OTHER INFORMATION: Primer

<400> SEQUENCE: 436
aaggcgacgg ctttggtat                                                19

<210> SEQ ID NO 437
<211> LENGTH: 21
<212> TYPE: DNA
<213> ORGANISM: Artificial Sequence
<220> FEATURE:
<223> OTHER INFORMATION: Primer

<400> SEQUENCE: 437
ggaattgtgt gccccatctg t                                             21

<210> SEQ ID NO 438
<211> LENGTH: 26
<212> TYPE: DNA
<213> ORGANISM: Artificial Sequence
<220> FEATURE:
<223> OTHER INFORMATION: Primer

<400> SEQUENCE: 438
atccgtgctt acaaccttag atactg                                        26

<210> SEQ ID NO 439

```
<211> LENGTH: 26
<212> TYPE: DNA
<213> ORGANISM: Artificial Sequence
<220> FEATURE:
<223> OTHER INFORMATION: Primer

<400> SEQUENCE: 439
ctcagaggag gaggatgaaa tagatg                                          26

<210> SEQ ID NO 440
<211> LENGTH: 26
<212> TYPE: DNA
<213> ORGANISM: Artificial Sequence
<220> FEATURE:
<223> OTHER INFORMATION: Primer

<400> SEQUENCE: 440
ccattaacag gtcttccaaa gtacga                                          26

<210> SEQ ID NO 441
<211> LENGTH: 21
<212> TYPE: DNA
<213> ORGANISM: Artificial Sequence
<220> FEATURE:
<223> OTHER INFORMATION: Primer

<400> SEQUENCE: 441
ggaattgtgt gccccatctg t                                               21

<210> SEQ ID NO 442
<211> LENGTH: 19
<212> TYPE: DNA
<213> ORGANISM: Artificial Sequence
<220> FEATURE:
<223> OTHER INFORMATION: Primer

<400> SEQUENCE: 442
aaatacggct gcaccgagt                                                  19

<210> SEQ ID NO 443
<211> LENGTH: 23
<212> TYPE: DNA
<213> ORGANISM: Artificial Sequence
<220> FEATURE:
<223> OTHER INFORMATION: Primer

<400> SEQUENCE: 443
gctcacacaa aggacggatt aac                                             23

<210> SEQ ID NO 444
<211> LENGTH: 24
<212> TYPE: DNA
<213> ORGANISM: Artificial Sequence
<220> FEATURE:
<223> OTHER INFORMATION: Primer

<400> SEQUENCE: 444
ggtgatccag actctgacct tttg                                            24

<210> SEQ ID NO 445
<211> LENGTH: 21
<212> TYPE: DNA
<213> ORGANISM: Artificial Sequence
<220> FEATURE:
<223> OTHER INFORMATION: Primer

<400> SEQUENCE: 445
```
ggaattgtgt gccccatctg t    21

<210> SEQ ID NO 446
<211> LENGTH: 19
<212> TYPE: DNA
<213> ORGANISM: Artificial Sequence
<220> FEATURE:
<223> OTHER INFORMATION: Primer

<400> SEQUENCE: 446
ctgagaagcc ctgcccttc    19

<210> SEQ ID NO 447
<211> LENGTH: 28
<212> TYPE: DNA
<213> ORGANISM: Artificial Sequence
<220> FEATURE:
<223> OTHER INFORMATION: Primer

<400> SEQUENCE: 447
ggaacaacat tagaacagca atacaaca    28

<210> SEQ ID NO 448
<211> LENGTH: 26
<212> TYPE: DNA
<213> ORGANISM: Artificial Sequence
<220> FEATURE:
<223> OTHER INFORMATION: Primer

<400> SEQUENCE: 448
tgtccagatg tctttgcttt tcttca    26

<210> SEQ ID NO 449
<211> LENGTH: 21
<212> TYPE: DNA
<213> ORGANISM: Artificial Sequence
<220> FEATURE:
<223> OTHER INFORMATION: Primer

<400> SEQUENCE: 449
ggaattgtgt gccccatctg t    21

<210> SEQ ID NO 450
<211> LENGTH: 22
<212> TYPE: DNA
<213> ORGANISM: Artificial Sequence
<220> FEATURE:
<223> OTHER INFORMATION: 16_unsp_880_881

<400> SEQUENCE: 450
catccattac atcccgtacc ct    22

<210> SEQ ID NO 451
<211> LENGTH: 23
<212> TYPE: DNA
<213> ORGANISM: Artificial Sequence
<220> FEATURE:
<223> OTHER INFORMATION: Primer

<400> SEQUENCE: 451
gctcacacaa aggacggatt aac    23

<210> SEQ ID NO 452
<211> LENGTH: 22
<212> TYPE: DNA

```
<213> ORGANISM: Artificial Sequence
<220> FEATURE:
<223> OTHER INFORMATION: Primer

<400> SEQUENCE: 452
atcatgatgg ctgtatgtgc ca                                          22

<210> SEQ ID NO 453
<211> LENGTH: 25
<212> TYPE: DNA
<213> ORGANISM: Artificial Sequence
<220> FEATURE:
<223> OTHER INFORMATION: Primer

<400> SEQUENCE: 453
cacagagctg caaacaacta tacat                                       25

<210> SEQ ID NO 454
<211> LENGTH: 26
<212> TYPE: DNA
<213> ORGANISM: Artificial Sequence
<220> FEATURE:
<223> OTHER INFORMATION: Primer

<400> SEQUENCE: 454
tgacacacat ttaaacgttg gcaaag                                      26

<210> SEQ ID NO 455
<211> LENGTH: 21
<212> TYPE: DNA
<213> ORGANISM: Artificial Sequence
<220> FEATURE:
<223> OTHER INFORMATION: Primer

<400> SEQUENCE: 455
ggaattgtgt gccccatctg t                                           21

<210> SEQ ID NO 456
<211> LENGTH: 26
<212> TYPE: DNA
<213> ORGANISM: Artificial Sequence
<220> FEATURE:
<223> OTHER INFORMATION: Primer

<400> SEQUENCE: 456
tgacacacat ttaaacgttg gcaaag                                      26

<210> SEQ ID NO 457
<211> LENGTH: 23
<212> TYPE: DNA
<213> ORGANISM: Artificial Sequence
<220> FEATURE:
<223> OTHER INFORMATION: Primer

<400> SEQUENCE: 457
gctcacacaa aggacggatt aac                                         23

<210> SEQ ID NO 458
<211> LENGTH: 19
<212> TYPE: DNA
<213> ORGANISM: Artificial Sequence
<220> FEATURE:
<223> OTHER INFORMATION: Primer

<400> SEQUENCE: 458
aaatacggct gcaccgagt                                              19
```

<210> SEQ ID NO 459
<211> LENGTH: 25
<212> TYPE: DNA
<213> ORGANISM: Artificial Sequence
<220> FEATURE:
<223> OTHER INFORMATION: Primer

<400> SEQUENCE: 459
cacagagctg caaacaacta tacat                                              25

<210> SEQ ID NO 460
<211> LENGTH: 24
<212> TYPE: DNA
<213> ORGANISM: Artificial Sequence
<220> FEATURE:
<223> OTHER INFORMATION: Primer

<400> SEQUENCE: 460
tcagttgtct ctggttgcaa atct                                               24

<210> SEQ ID NO 461
<211> LENGTH: 27
<212> TYPE: DNA
<213> ORGANISM: Artificial Sequence
<220> FEATURE:
<223> OTHER INFORMATION: Primer

<400> SEQUENCE: 461
agtacagacc tacgtgacca tatagac                                            27

<210> SEQ ID NO 462
<211> LENGTH: 21
<212> TYPE: DNA
<213> ORGANISM: Artificial Sequence
<220> FEATURE:
<223> OTHER INFORMATION: Primer

<400> SEQUENCE: 462
catggttcca ccagcgttat t                                                  21

<210> SEQ ID NO 463
<211> LENGTH: 22
<212> TYPE: DNA
<213> ORGANISM: Artificial Sequence
<220> FEATURE:
<223> OTHER INFORMATION: Primer

<400> SEQUENCE: 463
cgtgcttttt gctttgcttt gt                                                 22

<210> SEQ ID NO 464
<211> LENGTH: 27
<212> TYPE: DNA
<213> ORGANISM: Artificial Sequence
<220> FEATURE:
<223> OTHER INFORMATION: Primer

<400> SEQUENCE: 464
gaggctgctg ttatccacaa tagtaat                                            27

<210> SEQ ID NO 465
<211> LENGTH: 23
<212> TYPE: DNA
<213> ORGANISM: Artificial Sequence
<220> FEATURE:

<223> OTHER INFORMATION: Primer

<400> SEQUENCE: 465
cctgtgtagg tgttgaggta ggt                                            23

<210> SEQ ID NO 466
<211> LENGTH: 25
<212> TYPE: DNA
<213> ORGANISM: Artificial Sequence
<220> FEATURE:
<223> OTHER INFORMATION: Primer

<400> SEQUENCE: 466
tctattatcc acacctgcat ttgct                                          25

<210> SEQ ID NO 467
<211> LENGTH: 23
<212> TYPE: DNA
<213> ORGANISM: Artificial Sequence
<220> FEATURE:
<223> OTHER INFORMATION: Primer

<400> SEQUENCE: 467
aacgtgttgc gattggtgta ttg                                            23

<210> SEQ ID NO 468
<211> LENGTH: 27
<212> TYPE: DNA
<213> ORGANISM: Artificial Sequence
<220> FEATURE:
<223> OTHER INFORMATION: Primer

<400> SEQUENCE: 468
cattccccat gaacatgcta aactttg                                        27

<210> SEQ ID NO 469
<211> LENGTH: 20
<212> TYPE: DNA
<213> ORGANISM: Artificial Sequence
<220> FEATURE:
<223> OTHER INFORMATION: Primer

<400> SEQUENCE: 469
ccaggcccat tttgtagctt                                                20

<210> SEQ ID NO 470
<211> LENGTH: 23
<212> TYPE: DNA
<213> ORGANISM: Artificial Sequence
<220> FEATURE:
<223> OTHER INFORMATION: Primer

<400> SEQUENCE: 470
aggtcaggaa aacagggatt tgg                                            23

<210> SEQ ID NO 471
<211> LENGTH: 31
<212> TYPE: DNA
<213> ORGANISM: Artificial Sequence
<220> FEATURE:
<223> OTHER INFORMATION: Primer

<400> SEQUENCE: 471
ctaaaatgtc ctccaatact actaaccaca a                                   31

```
<210> SEQ ID NO 472
<211> LENGTH: 28
<212> TYPE: DNA
<213> ORGANISM: Artificial Sequence
<220> FEATURE:
<223> OTHER INFORMATION: Primer

<400> SEQUENCE: 472
gtcatttatt tcatatactg gattgcca                                          28

<210> SEQ ID NO 473
<211> LENGTH: 20
<212> TYPE: DNA
<213> ORGANISM: Artificial Sequence
<220> FEATURE:
<223> OTHER INFORMATION: Primer

<400> SEQUENCE: 473
tgcatcccag cagtaagcaa                                                   20

<210> SEQ ID NO 474
<211> LENGTH: 28
<212> TYPE: DNA
<213> ORGANISM: Artificial Sequence
<220> FEATURE:
<223> OTHER INFORMATION: Primer

<400> SEQUENCE: 474
gtcatttatt tcatatactg gattgcca                                          28

<210> SEQ ID NO 475
<211> LENGTH: 22
<212> TYPE: DNA
<213> ORGANISM: Artificial Sequence
<220> FEATURE:
<223> OTHER INFORMATION: Primer

<400> SEQUENCE: 475
ggattggaca ctgcaagaca ca                                                22

<210> SEQ ID NO 476
<211> LENGTH: 28
<212> TYPE: DNA
<213> ORGANISM: Artificial Sequence
<220> FEATURE:
<223> OTHER INFORMATION: Primer

<400> SEQUENCE: 476
cccatgctac ataggtcata caattgtc                                          28

<210> SEQ ID NO 477
<211> LENGTH: 22
<212> TYPE: DNA
<213> ORGANISM: Artificial Sequence
<220> FEATURE:
<223> OTHER INFORMATION: Primer

<400> SEQUENCE: 477
ggattggaca ctgcaagaca ca                                                22

<210> SEQ ID NO 478
<211> LENGTH: 18
<212> TYPE: DNA
<213> ORGANISM: Artificial Sequence
<220> FEATURE:
<223> OTHER INFORMATION: Primer
```

<400> SEQUENCE: 478
acgtctggcc gtaggtct                                                 18

<210> SEQ ID NO 479
<211> LENGTH: 28
<212> TYPE: DNA
<213> ORGANISM: Artificial Sequence
<220> FEATURE:
<223> OTHER INFORMATION: Primer

<400> SEQUENCE: 479
cagaggaaga aaacgatgaa atagatgg                                      28

<210> SEQ ID NO 480
<211> LENGTH: 21
<212> TYPE: DNA
<213> ORGANISM: Artificial Sequence
<220> FEATURE:
<223> OTHER INFORMATION: Primer

<400> SEQUENCE: 480
agaaacagct gctggaatgc t                                             21

<210> SEQ ID NO 481
<211> LENGTH: 25
<212> TYPE: DNA
<213> ORGANISM: Artificial Sequence
<220> FEATURE:
<223> OTHER INFORMATION: Primer

<400> SEQUENCE: 481
tcctaagaaa cgtaaacgtg ttccc                                         25

<210> SEQ ID NO 482
<211> LENGTH: 27
<212> TYPE: DNA
<213> ORGANISM: Artificial Sequence
<220> FEATURE:
<223> OTHER INFORMATION: Primer

<400> SEQUENCE: 482
gtatttacaa ctcttgccac agaagga                                       27

<210> SEQ ID NO 483
<211> LENGTH: 24
<212> TYPE: DNA
<213> ORGANISM: Artificial Sequence
<220> FEATURE:
<223> OTHER INFORMATION: Primer

<400> SEQUENCE: 483
tcagatagtg gctatggctg ttct                                          24

<210> SEQ ID NO 484
<211> LENGTH: 28
<212> TYPE: DNA
<213> ORGANISM: Artificial Sequence
<220> FEATURE:
<223> OTHER INFORMATION: Primer

<400> SEQUENCE: 484
gtcatttatt tcatatactg gattgcca                                      28

<210> SEQ ID NO 485
<211> LENGTH: 22

```
<212> TYPE: DNA
<213> ORGANISM: Artificial Sequence
<220> FEATURE:
<223> OTHER INFORMATION: Primer

<400> SEQUENCE: 485
cagctacacc tacaggcaac aa                                              22

<210> SEQ ID NO 486
<211> LENGTH: 24
<212> TYPE: DNA
<213> ORGANISM: Artificial Sequence
<220> FEATURE:
<223> OTHER INFORMATION: Primer

<400> SEQUENCE: 486
ggtgatccag actctgacct tttg                                            24

<210> SEQ ID NO 487
<211> LENGTH: 28
<212> TYPE: DNA
<213> ORGANISM: Artificial Sequence
<220> FEATURE:
<223> OTHER INFORMATION: Primer

<400> SEQUENCE: 487
aatgacagta aagacataga cagccaaa                                        28

<210> SEQ ID NO 488
<211> LENGTH: 19
<212> TYPE: DNA
<213> ORGANISM: Artificial Sequence
<220> FEATURE:
<223> OTHER INFORMATION: Primer

<400> SEQUENCE: 488
aaatacggct gcaccgagt                                                  19

<210> SEQ ID NO 489
<211> LENGTH: 28
<212> TYPE: DNA
<213> ORGANISM: Artificial Sequence
<220> FEATURE:
<223> OTHER INFORMATION: Primer

<400> SEQUENCE: 489
ttcactgcaa gacatagaaa taacctgt                                        28

<210> SEQ ID NO 490
<211> LENGTH: 18
<212> TYPE: DNA
<213> ORGANISM: Artificial Sequence
<220> FEATURE:
<223> OTHER INFORMATION: Primer

<400> SEQUENCE: 490
acgtctggcc gtaggtct                                                   18

<210> SEQ ID NO 491
<211> LENGTH: 22
<212> TYPE: DNA
<213> ORGANISM: Artificial Sequence
<220> FEATURE:
<223> OTHER INFORMATION: Primer

<400> SEQUENCE: 491
```
cagctacacc tacaggcaac aa                                            22

<210> SEQ ID NO 492
<211> LENGTH: 22
<212> TYPE: DNA
<213> ORGANISM: Artificial Sequence
<220> FEATURE:
<223> OTHER INFORMATION: Primer

<400> SEQUENCE: 492
atcatgatgg ctgtatgtgc ca                                            22

<210> SEQ ID NO 493
<211> LENGTH: 24
<212> TYPE: DNA
<213> ORGANISM: Artificial Sequence
<220> FEATURE:
<223> OTHER INFORMATION: Primer

<400> SEQUENCE: 493
tcagatagtg gctatggctg ttct                                          24

<210> SEQ ID NO 494
<211> LENGTH: 21
<212> TYPE: DNA
<213> ORGANISM: Artificial Sequence
<220> FEATURE:
<223> OTHER INFORMATION: Primer

<400> SEQUENCE: 494
ggtttccttc ggtgtctgca t                                             21

<210> SEQ ID NO 495
<211> LENGTH: 22
<212> TYPE: DNA
<213> ORGANISM: Artificial Sequence
<220> FEATURE:
<223> OTHER INFORMATION: Primer

<400> SEQUENCE: 495
cagctacacc tacaggcaac aa                                            22

<210> SEQ ID NO 496
<211> LENGTH: 28
<212> TYPE: DNA
<213> ORGANISM: Artificial Sequence
<220> FEATURE:
<223> OTHER INFORMATION: Primer

<400> SEQUENCE: 496
tcaggtaact gcaccctaaa tactctat                                      28

<210> SEQ ID NO 497
<211> LENGTH: 28
<212> TYPE: DNA
<213> ORGANISM: Artificial Sequence
<220> FEATURE:
<223> OTHER INFORMATION: Primer

<400> SEQUENCE: 497
aatgacagta aagacataga cagccaaa                                      28

<210> SEQ ID NO 498
<211> LENGTH: 21
<212> TYPE: DNA
<213> ORGANISM: Artificial Sequence

```
<220> FEATURE:
<223> OTHER INFORMATION: Primer

<400> SEQUENCE: 498
catggttcca ccagcgttat t                                              21

<210> SEQ ID NO 499
<211> LENGTH: 22
<212> TYPE: DNA
<213> ORGANISM: Artificial Sequence
<220> FEATURE:
<223> OTHER INFORMATION: Primer

<400> SEQUENCE: 499
cagctacacc tacaggcaac aa                                             22

<210> SEQ ID NO 500
<211> LENGTH: 19
<212> TYPE: DNA
<213> ORGANISM: Artificial Sequence
<220> FEATURE:
<223> OTHER INFORMATION: Primer

<400> SEQUENCE: 500
aaatacggct gcaccgagt                                                 19

<210> SEQ ID NO 501
<211> LENGTH: 22
<212> TYPE: DNA
<213> ORGANISM: Artificial Sequence
<220> FEATURE:
<223> OTHER INFORMATION: Primer

<400> SEQUENCE: 501
cagctacacc tacaggcaac aa                                             22

<210> SEQ ID NO 502
<211> LENGTH: 18
<212> TYPE: DNA
<213> ORGANISM: Artificial Sequence
<220> FEATURE:
<223> OTHER INFORMATION: Primer

<400> SEQUENCE: 502
tctttgctcg cagctcgt                                                  18

<210> SEQ ID NO 503
<211> LENGTH: 27
<212> TYPE: DNA
<213> ORGANISM: Artificial Sequence
<220> FEATURE:
<223> OTHER INFORMATION: Primer

<400> SEQUENCE: 503
gcatatttta tcatgctggc agctcta                                        27

<210> SEQ ID NO 504
<211> LENGTH: 28
<212> TYPE: DNA
<213> ORGANISM: Artificial Sequence
<220> FEATURE:
<223> OTHER INFORMATION: Primer

<400> SEQUENCE: 504
tcaggtaact gcaccctaaa tactctat                                       28
```

<210> SEQ ID NO 505
<211> LENGTH: 20
<212> TYPE: DNA
<213> ORGANISM: Artificial Sequence
<220> FEATURE:
<223> OTHER INFORMATION: Primer

<400> SEQUENCE: 505
tgcatcccag cagtaagcaa                                         20

<210> SEQ ID NO 506
<211> LENGTH: 27
<212> TYPE: DNA
<213> ORGANISM: Artificial Sequence
<220> FEATURE:
<223> OTHER INFORMATION: Primer

<400> SEQUENCE: 506
gtatttacaa ctcttgccac agaagga                                 27

<210> SEQ ID NO 507
<211> LENGTH: 20
<212> TYPE: DNA
<213> ORGANISM: Artificial Sequence
<220> FEATURE:
<223> OTHER INFORMATION: Primer

<400> SEQUENCE: 507
tgcatcccag cagtaagcaa                                         20

<210> SEQ ID NO 508
<211> LENGTH: 18
<212> TYPE: DNA
<213> ORGANISM: Artificial Sequence
<220> FEATURE:
<223> OTHER INFORMATION: Primer

<400> SEQUENCE: 508
tctttgctcg cagctcgt                                           18

<210> SEQ ID NO 509
<211> LENGTH: 28
<212> TYPE: DNA
<213> ORGANISM: Artificial Sequence
<220> FEATURE:
<223> OTHER INFORMATION: Primer

<400> SEQUENCE: 509
aatgacagta aagacataga cagccaaa                                28

<210> SEQ ID NO 510
<211> LENGTH: 22
<212> TYPE: DNA
<213> ORGANISM: Artificial Sequence
<220> FEATURE:
<223> OTHER INFORMATION: Primer

<400> SEQUENCE: 510
atcatgatgg ctgtatgtgc ca                                      22

<210> SEQ ID NO 511
<211> LENGTH: 24
<212> TYPE: DNA
<213> ORGANISM: Artificial Sequence
<220> FEATURE:
<223> OTHER INFORMATION: Primer

<400> SEQUENCE: 511
tcagatagtg gctatggctg ttct					24

<210> SEQ ID NO 512
<211> LENGTH: 18
<212> TYPE: DNA
<213> ORGANISM: Artificial Sequence
<220> FEATURE:
<223> OTHER INFORMATION: Primer

<400> SEQUENCE: 512
acgtctggcc gtaggtct					18

<210> SEQ ID NO 513
<211> LENGTH: 20
<212> TYPE: DNA
<213> ORGANISM: Artificial Sequence
<220> FEATURE:
<223> OTHER INFORMATION: Primer

<400> SEQUENCE: 513
tgcatcccag cagtaagcaa					20

<210> SEQ ID NO 514
<211> LENGTH: 19
<212> TYPE: DNA
<213> ORGANISM: Artificial Sequence
<220> FEATURE:
<223> OTHER INFORMATION: Primer

<400> SEQUENCE: 514
aaatacggct gcaccgagt					19

<210> SEQ ID NO 515
<211> LENGTH: 20
<212> TYPE: DNA
<213> ORGANISM: Artificial Sequence
<220> FEATURE:
<223> OTHER INFORMATION: Primer

<400> SEQUENCE: 515
tgcatcccag cagtaagcaa					20

<210> SEQ ID NO 516
<211> LENGTH: 19
<212> TYPE: DNA
<213> ORGANISM: Artificial Sequence
<220> FEATURE:
<223> OTHER INFORMATION: Primer

<400> SEQUENCE: 516
ctgagaagcc ctgcccttc					19

<210> SEQ ID NO 517
<211> LENGTH: 28
<212> TYPE: DNA
<213> ORGANISM: Artificial Sequence
<220> FEATURE:
<223> OTHER INFORMATION: Primer

<400> SEQUENCE: 517
aatgacagta aagacataga cagccaaa					28

<210> SEQ ID NO 518

```
<211> LENGTH: 18
<212> TYPE: DNA
<213> ORGANISM: Artificial Sequence
<220> FEATURE:
<223> OTHER INFORMATION: Primer

<400> SEQUENCE: 518
tctttgctcg cagctcgt                                                       18

<210> SEQ ID NO 519
<211> LENGTH: 28
<212> TYPE: DNA
<213> ORGANISM: Artificial Sequence
<220> FEATURE:
<223> OTHER INFORMATION: Primer

<400> SEQUENCE: 519
aatgacagta aagacataga cagccaaa                                            28

<210> SEQ ID NO 520
<211> LENGTH: 24
<212> TYPE: DNA
<213> ORGANISM: Artificial Sequence
<220> FEATURE:
<223> OTHER INFORMATION: Primer

<400> SEQUENCE: 520
ggtgatccag actctgacct tttg                                                24

<210> SEQ ID NO 521
<211> LENGTH: 28
<212> TYPE: DNA
<213> ORGANISM: Artificial Sequence
<220> FEATURE:
<223> OTHER INFORMATION: Primer

<400> SEQUENCE: 521
ttcactgcaa gacatagaaa taacctgt                                            28

<210> SEQ ID NO 522
<211> LENGTH: 22
<212> TYPE: DNA
<213> ORGANISM: Artificial Sequence
<220> FEATURE:
<223> OTHER INFORMATION: Primer

<400> SEQUENCE: 522
cccagctatg ttgtgaaatc gt                                                  22

<210> SEQ ID NO 523
<211> LENGTH: 20
<212> TYPE: DNA
<213> ORGANISM: Artificial Sequence
<220> FEATURE:
<223> OTHER INFORMATION: Primer

<400> SEQUENCE: 523
tgcatcccag cagtaagcaa                                                     20

<210> SEQ ID NO 524
<211> LENGTH: 21
<212> TYPE: DNA
<213> ORGANISM: Artificial Sequence
<220> FEATURE:
<223> OTHER INFORMATION: Primer

<400> SEQUENCE: 524
```
catggttcca ccagcgttat t                                    21

<210> SEQ ID NO 525
<211> LENGTH: 24
<212> TYPE: DNA
<213> ORGANISM: Artificial Sequence
<220> FEATURE:
<223> OTHER INFORMATION: Primer

<400> SEQUENCE: 525
tcagatagtg gctatggctg ttct                                 24

<210> SEQ ID NO 526
<211> LENGTH: 20
<212> TYPE: DNA
<213> ORGANISM: Artificial Sequence
<220> FEATURE:
<223> OTHER INFORMATION: Primer

<400> SEQUENCE: 526
ccgttgtcta tagcctccgt                                      20

<210> SEQ ID NO 527
<211> LENGTH: 22
<212> TYPE: DNA
<213> ORGANISM: Artificial Sequence
<220> FEATURE:
<223> OTHER INFORMATION: Primer

<400> SEQUENCE: 527
cagctacacc tacaggcaac aa                                   22

<210> SEQ ID NO 528
<211> LENGTH: 27
<212> TYPE: DNA
<213> ORGANISM: Artificial Sequence
<220> FEATURE:
<223> OTHER INFORMATION: Primer

<400> SEQUENCE: 528
gtatttacaa ctcttgccac agaagga                              27

<210> SEQ ID NO 529
<211> LENGTH: 20
<212> TYPE: DNA
<213> ORGANISM: Artificial Sequence
<220> FEATURE:
<223> OTHER INFORMATION: Primer

<400> SEQUENCE: 529
tgcatcccag cagtaagcaa                                      20

<210> SEQ ID NO 530
<211> LENGTH: 21
<212> TYPE: DNA
<213> ORGANISM: Artificial Sequence
<220> FEATURE:
<223> OTHER INFORMATION: Primer

<400> SEQUENCE: 530
ggtttccttc ggtgtctgca t                                    21

<210> SEQ ID NO 531
<211> LENGTH: 20
<212> TYPE: DNA

```
<213> ORGANISM: Artificial Sequence
<220> FEATURE:
<223> OTHER INFORMATION: Primer

<400> SEQUENCE: 531
tgcatcccag cagtaagcaa                                              20

<210> SEQ ID NO 532
<211> LENGTH: 18
<212> TYPE: DNA
<213> ORGANISM: Artificial Sequence
<220> FEATURE:
<223> OTHER INFORMATION: Primer

<400> SEQUENCE: 532
acgtctggcc gtaggtct                                                18

<210> SEQ ID NO 533
<211> LENGTH: 28
<212> TYPE: DNA
<213> ORGANISM: Artificial Sequence
<220> FEATURE:
<223> OTHER INFORMATION: Primer

<400> SEQUENCE: 533
ttcactgcaa gacatagaaa taacctgt                                     28

<210> SEQ ID NO 534
<211> LENGTH: 26
<212> TYPE: DNA
<213> ORGANISM: Artificial Sequence
<220> FEATURE:
<223> OTHER INFORMATION: Primer

<400> SEQUENCE: 534
ctatacattt atggcatgca gcatgg                                       26

<210> SEQ ID NO 535
<211> LENGTH: 25
<212> TYPE: DNA
<213> ORGANISM: Artificial Sequence
<220> FEATURE:
<223> OTHER INFORMATION: Primer

<400> SEQUENCE: 535
tcagactctg tgtatggaga cacat                                        25

<210> SEQ ID NO 536
<211> LENGTH: 22
<212> TYPE: DNA
<213> ORGANISM: Artificial Sequence
<220> FEATURE:
<223> OTHER INFORMATION: Primer

<400> SEQUENCE: 536
cccagctatg ttgtgaaatc gt                                           22

<210> SEQ ID NO 537
<211> LENGTH: 28
<212> TYPE: DNA
<213> ORGANISM: Artificial Sequence
<220> FEATURE:
<223> OTHER INFORMATION: Primer

<400> SEQUENCE: 537
aatgacagta aagacataga cagccaaa                                     28
```

<210> SEQ ID NO 538
<211> LENGTH: 19
<212> TYPE: DNA
<213> ORGANISM: Artificial Sequence
<220> FEATURE:
<223> OTHER INFORMATION: Primer

<400> SEQUENCE: 538
ctgagaagcc ctgcccttc                                              19

<210> SEQ ID NO 539
<211> LENGTH: 20
<212> TYPE: DNA
<213> ORGANISM: Artificial Sequence
<220> FEATURE:
<223> OTHER INFORMATION: Primer

<400> SEQUENCE: 539
tgcatcccag cagtaagcaa                                             20

<210> SEQ ID NO 540
<211> LENGTH: 24
<212> TYPE: DNA
<213> ORGANISM: Artificial Sequence
<220> FEATURE:
<223> OTHER INFORMATION: Primer

<400> SEQUENCE: 540
ggtgatccag actctgacct tttg                                        24

<210> SEQ ID NO 541
<211> LENGTH: 28
<212> TYPE: DNA
<213> ORGANISM: Artificial Sequence
<220> FEATURE:
<223> OTHER INFORMATION: Primer

<400> SEQUENCE: 541
ttcactgcaa gacatagaaa taacctgt                                    28

<210> SEQ ID NO 542
<211> LENGTH: 21
<212> TYPE: DNA
<213> ORGANISM: Artificial Sequence
<220> FEATURE:
<223> OTHER INFORMATION: Primer

<400> SEQUENCE: 542
agaaacagct gctggaatgc t                                           21

<210> SEQ ID NO 543
<211> LENGTH: 22
<212> TYPE: DNA
<213> ORGANISM: Artificial Sequence
<220> FEATURE:
<223> OTHER INFORMATION: Primer

<400> SEQUENCE: 543
cagctacacc tacaggcaac aa                                          22

<210> SEQ ID NO 544
<211> LENGTH: 21
<212> TYPE: DNA
<213> ORGANISM: Artificial Sequence
<220> FEATURE:

<223> OTHER INFORMATION: Primer

<400> SEQUENCE: 544
catggttcca ccagcgttat t                                              21

<210> SEQ ID NO 545
<211> LENGTH: 20
<212> TYPE: DNA
<213> ORGANISM: Artificial Sequence
<220> FEATURE:
<223> OTHER INFORMATION: Primer

<400> SEQUENCE: 545
tgcatcccag cagtaagcaa                                                20

<210> SEQ ID NO 546
<211> LENGTH: 28
<212> TYPE: DNA
<213> ORGANISM: Artificial Sequence
<220> FEATURE:
<223> OTHER INFORMATION: Primer

<400> SEQUENCE: 546
tcaggtaact gcaccctaaa tactctat                                       28

<210> SEQ ID NO 547
<211> LENGTH: 20
<212> TYPE: DNA
<213> ORGANISM: Artificial Sequence
<220> FEATURE:
<223> OTHER INFORMATION: Primer

<400> SEQUENCE: 547
tgcatcccag cagtaagcaa                                                20

<210> SEQ ID NO 548
<211> LENGTH: 22
<212> TYPE: DNA
<213> ORGANISM: Artificial Sequence
<220> FEATURE:
<223> OTHER INFORMATION: Primer

<400> SEQUENCE: 548
atcatgatgg ctgtatgtgc ca                                             22

<210> SEQ ID NO 549
<211> LENGTH: 28
<212> TYPE: DNA
<213> ORGANISM: Artificial Sequence
<220> FEATURE:
<223> OTHER INFORMATION: Primer

<400> SEQUENCE: 549
ttcactgcaa gacatagaaa taacctgt                                       28

<210> SEQ ID NO 550
<211> LENGTH: 21
<212> TYPE: DNA
<213> ORGANISM: Artificial Sequence
<220> FEATURE:
<223> OTHER INFORMATION: Primer

<400> SEQUENCE: 550
ggtttccttc ggtgtctgca t                                              21

-continued

```
<210> SEQ ID NO 551
<211> LENGTH: 28
<212> TYPE: DNA
<213> ORGANISM: Artificial Sequence
<220> FEATURE:
<223> OTHER INFORMATION: Primer

<400> SEQUENCE: 551
ttcactgcaa gacatagaaa taacctgt                                          28

<210> SEQ ID NO 552
<211> LENGTH: 28
<212> TYPE: DNA
<213> ORGANISM: Artificial Sequence
<220> FEATURE:
<223> OTHER INFORMATION: Primer

<400> SEQUENCE: 552
gtcatttatt tcatatactg gattgcca                                          28

<210> SEQ ID NO 553
<211> LENGTH: 22
<212> TYPE: DNA
<213> ORGANISM: Artificial Sequence
<220> FEATURE:
<223> OTHER INFORMATION: Primer

<400> SEQUENCE: 553
cagctacacc tacaggcaac aa                                                22

<210> SEQ ID NO 554
<211> LENGTH: 19
<212> TYPE: DNA
<213> ORGANISM: Artificial Sequence
<220> FEATURE:
<223> OTHER INFORMATION: Primer

<400> SEQUENCE: 554
ctgagaagcc ctgcccttc                                                    19

<210> SEQ ID NO 555
<211> LENGTH: 20
<212> TYPE: DNA
<213> ORGANISM: Artificial Sequence
<220> FEATURE:
<223> OTHER INFORMATION: Primer

<400> SEQUENCE: 555
tgcatcccag cagtaagcaa                                                   20

<210> SEQ ID NO 556
<211> LENGTH: 28
<212> TYPE: DNA
<213> ORGANISM: Artificial Sequence
<220> FEATURE:
<223> OTHER INFORMATION: Primer

<400> SEQUENCE: 556
ctcgtcatct gatattacat ctcctgtt                                          28

<210> SEQ ID NO 557
<211> LENGTH: 27
<212> TYPE: DNA
<213> ORGANISM: Artificial Sequence
<220> FEATURE:
<223> OTHER INFORMATION: Primer
```

<400> SEQUENCE: 557
cgaaaacata gcgaccacta tagagat                                              27

<210> SEQ ID NO 558
<211> LENGTH: 28
<212> TYPE: DNA
<213> ORGANISM: Artificial Sequence
<220> FEATURE:
<223> OTHER INFORMATION: Primer

<400> SEQUENCE: 558
tcaggtaact gcaccctaaa tactctat                                             28

<210> SEQ ID NO 559
<211> LENGTH: 20
<212> TYPE: DNA
<213> ORGANISM: Artificial Sequence
<220> FEATURE:
<223> OTHER INFORMATION: Primer

<400> SEQUENCE: 559
tgacgacacg gtatccgcta                                                      20

<210> SEQ ID NO 560
<211> LENGTH: 18
<212> TYPE: DNA
<213> ORGANISM: Artificial Sequence
<220> FEATURE:
<223> OTHER INFORMATION: Primer

<400> SEQUENCE: 560
acgtctggcc gtaggtct                                                        18

<210> SEQ ID NO 561
<211> LENGTH: 27
<212> TYPE: DNA
<213> ORGANISM: Artificial Sequence
<220> FEATURE:
<223> OTHER INFORMATION: Primer

<400> SEQUENCE: 561
cgaaaacata gcgaccacta tagagat                                              27

<210> SEQ ID NO 562
<211> LENGTH: 27
<212> TYPE: DNA
<213> ORGANISM: Artificial Sequence
<220> FEATURE:
<223> OTHER INFORMATION: Primer

<400> SEQUENCE: 562
ttgtacacta tctggaattg caacagt                                              27

<210> SEQ ID NO 563
<211> LENGTH: 22
<212> TYPE: DNA
<213> ORGANISM: Artificial Sequence
<220> FEATURE:
<223> OTHER INFORMATION: Primer

<400> SEQUENCE: 563
cagctacacc tacaggcaac aa                                                   22

<210> SEQ ID NO 564
<211> LENGTH: 24

```
<212> TYPE: DNA
<213> ORGANISM: Artificial Sequence
<220> FEATURE:
<223> OTHER INFORMATION: Primer

<400> SEQUENCE: 564
gtcgctatgt tttcgcaatc tgta                                            24

<210> SEQ ID NO 565
<211> LENGTH: 26
<212> TYPE: DNA
<213> ORGANISM: Artificial Sequence
<220> FEATURE:
<223> OTHER INFORMATION: Primer

<400> SEQUENCE: 565
tggagtaaac ccaacaatag cagaag                                          26

<210> SEQ ID NO 566
<211> LENGTH: 24
<212> TYPE: DNA
<213> ORGANISM: Artificial Sequence
<220> FEATURE:
<223> OTHER INFORMATION: Primer

<400> SEQUENCE: 566
catttgtaac gcaacagggc taat                                            24

<210> SEQ ID NO 567
<211> LENGTH: 27
<212> TYPE: DNA
<213> ORGANISM: Artificial Sequence
<220> FEATURE:
<223> OTHER INFORMATION: Primer

<400> SEQUENCE: 567
cgaaaacata gcgaccacta tagagat                                         27

<210> SEQ ID NO 568
<211> LENGTH: 27
<212> TYPE: DNA
<213> ORGANISM: Artificial Sequence
<220> FEATURE:
<223> OTHER INFORMATION: Primer

<400> SEQUENCE: 568
gtatttacaa ctcttgccac agaagga                                         27

<210> SEQ ID NO 569
<211> LENGTH: 26
<212> TYPE: DNA
<213> ORGANISM: Artificial Sequence
<220> FEATURE:
<223> OTHER INFORMATION: Primer

<400> SEQUENCE: 569
cgccctagtg agtaacaact gtattt                                          26

<210> SEQ ID NO 570
<211> LENGTH: 27
<212> TYPE: DNA
<213> ORGANISM: Artificial Sequence
<220> FEATURE:
<223> OTHER INFORMATION: Primer

<400> SEQUENCE: 570
```
ggaggattgt aggataaaat ggatgct                               27

<210> SEQ ID NO 571
<211> LENGTH: 22
<212> TYPE: DNA
<213> ORGANISM: Artificial Sequence
<220> FEATURE:
<223> OTHER INFORMATION: Primer

<400> SEQUENCE: 571
gaggacgtta gggacaatgt gt                                   22

<210> SEQ ID NO 572
<211> LENGTH: 23
<212> TYPE: DNA
<213> ORGANISM: Artificial Sequence
<220> FEATURE:
<223> OTHER INFORMATION: Primer

<400> SEQUENCE: 572
ccctgtgata aaggacgcga ttt                                  23

<210> SEQ ID NO 573
<211> LENGTH: 26
<212> TYPE: DNA
<213> ORGANISM: Artificial Sequence
<220> FEATURE:
<223> OTHER INFORMATION: Primer

<400> SEQUENCE: 573
cgtatgcatg ggtattggta tttgtg                               26

<210> SEQ ID NO 574
<211> LENGTH: 28
<212> TYPE: DNA
<213> ORGANISM: Artificial Sequence
<220> FEATURE:
<223> OTHER INFORMATION: Primer

<400> SEQUENCE: 574
catgtatatg caatagtaac atgggcaa                             28

<210> SEQ ID NO 575
<211> LENGTH: 26
<212> TYPE: DNA
<213> ORGANISM: Artificial Sequence
<220> FEATURE:
<223> OTHER INFORMATION: Primer

<400> SEQUENCE: 575
gccacaagtg tctatttttg ttgatg                               26

<210> SEQ ID NO 576
<211> LENGTH: 23
<212> TYPE: DNA
<213> ORGANISM: Artificial Sequence
<220> FEATURE:
<223> OTHER INFORMATION: Primer

<400> SEQUENCE: 576
tttagacact gggacaggtg gta                                  23

<210> SEQ ID NO 577
<211> LENGTH: 26
<212> TYPE: DNA
<213> ORGANISM: Artificial Sequence

```
<220> FEATURE:
<223> OTHER INFORMATION: Primer

<400> SEQUENCE: 577
cagatgagga ggatgtcata gacagt                                        26

<210> SEQ ID NO 578
<211> LENGTH: 28
<212> TYPE: DNA
<213> ORGANISM: Artificial Sequence
<220> FEATURE:
<223> OTHER INFORMATION: Primer

<400> SEQUENCE: 578
cattaacagc tcttgcaata tgcgaata                                      28

<210> SEQ ID NO 579
<211> LENGTH: 19
<212> TYPE: DNA
<213> ORGANISM: Artificial Sequence
<220> FEATURE:
<223> OTHER INFORMATION: Primer

<400> SEQUENCE: 579
cagctgcatg cacaaaacca                                               19

<210> SEQ ID NO 580
<211> LENGTH: 24
<212> TYPE: DNA
<213> ORGANISM: Artificial Sequence
<220> FEATURE:
<223> OTHER INFORMATION: Primer

<400> SEQUENCE: 580
ggtgatccag actctgacct tttg                                          24

<210> SEQ ID NO 581
<211> LENGTH: 27
<212> TYPE: DNA
<213> ORGANISM: Artificial Sequence
<220> FEATURE:
<223> OTHER INFORMATION: Primer

<400> SEQUENCE: 581
caacgtttaa atgtgtgtca ggacaaa                                       27

<210> SEQ ID NO 582
<211> LENGTH: 19
<212> TYPE: DNA
<213> ORGANISM: Artificial Sequence
<220> FEATURE:
<223> OTHER INFORMATION: Primer

<400> SEQUENCE: 582
aaatacggct gcaccgagt                                                19

<210> SEQ ID NO 583
<211> LENGTH: 27
<212> TYPE: DNA
<213> ORGANISM: Artificial Sequence
<220> FEATURE:
<223> OTHER INFORMATION: Primer

<400> SEQUENCE: 583
caacgtttaa atgtgtgtca ggacaaa                                       27
```

<210> SEQ ID NO 584
<211> LENGTH: 21
<212> TYPE: DNA
<213> ORGANISM: Artificial Sequence
<220> FEATURE:
<223> OTHER INFORMATION: Primer

<400> SEQUENCE: 584
catggttcca ccagcgttat t                                    21

<210> SEQ ID NO 585
<211> LENGTH: 19
<212> TYPE: DNA
<213> ORGANISM: Artificial Sequence
<220> FEATURE:
<223> OTHER INFORMATION: Primer

<400> SEQUENCE: 585
cagctgcatg cacaaaacca                                      19

<210> SEQ ID NO 586
<211> LENGTH: 21
<212> TYPE: DNA
<213> ORGANISM: Artificial Sequence
<220> FEATURE:
<223> OTHER INFORMATION: Primer

<400> SEQUENCE: 586
catggttcca ccagcgttat t                                    21

<210> SEQ ID NO 587
<211> LENGTH: 19
<212> TYPE: DNA
<213> ORGANISM: Artificial Sequence
<220> FEATURE:
<223> OTHER INFORMATION: Primer

<400> SEQUENCE: 587
cagctgcatg cacaaaacca                                      19

<210> SEQ ID NO 588
<211> LENGTH: 23
<212> TYPE: DNA
<213> ORGANISM: Artificial Sequence
<220> FEATURE:
<223> OTHER INFORMATION: Primer

<400> SEQUENCE: 588
tttagacact gggacaggtg gta                                  23

<210> SEQ ID NO 589
<211> LENGTH: 27
<212> TYPE: DNA
<213> ORGANISM: Artificial Sequence
<220> FEATURE:
<223> OTHER INFORMATION: Primer

<400> SEQUENCE: 589
caacgtttaa atgtgtgtca ggacaaa                              27

<210> SEQ ID NO 590
<211> LENGTH: 22
<212> TYPE: DNA
<213> ORGANISM: Artificial Sequence
<220> FEATURE:
<223> OTHER INFORMATION: Primer

<400> SEQUENCE: 590
atcatgatgg ctgtatgtgc ca                                         22

<210> SEQ ID NO 591
<211> LENGTH: 22
<212> TYPE: DNA
<213> ORGANISM: Artificial Sequence
<220> FEATURE:
<223> OTHER INFORMATION: Primer

<400> SEQUENCE: 591
gcgggtatgg caatactgaa gt                                         22

<210> SEQ ID NO 592
<211> LENGTH: 27
<212> TYPE: DNA
<213> ORGANISM: Artificial Sequence
<220> FEATURE:
<223> OTHER INFORMATION: Primer

<400> SEQUENCE: 592
tggagtttca ttctctcgtt cactatg                                    27

<210> SEQ ID NO 593
<211> LENGTH: 22
<212> TYPE: DNA
<213> ORGANISM: Artificial Sequence
<220> FEATURE:
<223> OTHER INFORMATION: Primer

<400> SEQUENCE: 593
gcgggtatgg caatactgaa gt                                         22

<210> SEQ ID NO 594
<211> LENGTH: 26
<212> TYPE: DNA
<213> ORGANISM: Artificial Sequence
<220> FEATURE:
<223> OTHER INFORMATION: Primer

<400> SEQUENCE: 594
cgttgagaaa gagtctccat cgtttt                                     26

<210> SEQ ID NO 595
<211> LENGTH: 23
<212> TYPE: DNA
<213> ORGANISM: Artificial Sequence
<220> FEATURE:
<223> OTHER INFORMATION: Primer

<400> SEQUENCE: 595
cggcattgga aataccctac gat                                        23

<210> SEQ ID NO 596
<211> LENGTH: 24
<212> TYPE: DNA
<213> ORGANISM: Artificial Sequence
<220> FEATURE:
<223> OTHER INFORMATION: Primer

<400> SEQUENCE: 596
gaattcgatg tggtggtgtt gttg                                       24

<210> SEQ ID NO 597

```
<211> LENGTH: 27
<212> TYPE: DNA
<213> ORGANISM: Artificial Sequence
<220> FEATURE:
<223> OTHER INFORMATION: Primer

<400> SEQUENCE: 597
caacgtttaa atgtgtgtca ggacaaa                                          27

<210> SEQ ID NO 598
<211> LENGTH: 19
<212> TYPE: DNA
<213> ORGANISM: Artificial Sequence
<220> FEATURE:
<223> OTHER INFORMATION: Primer

<400> SEQUENCE: 598
ctgagaagcc ctgcccttc                                                   19

<210> SEQ ID NO 599
<211> LENGTH: 23
<212> TYPE: DNA
<213> ORGANISM: Artificial Sequence
<220> FEATURE:
<223> OTHER INFORMATION: Primer

<400> SEQUENCE: 599
cggcattgga aataccctac gat                                              23

<210> SEQ ID NO 600
<211> LENGTH: 28
<212> TYPE: DNA
<213> ORGANISM: Artificial Sequence
<220> FEATURE:
<223> OTHER INFORMATION: Primer

<400> SEQUENCE: 600
cattaacagc tcttgcaata tgcgaata                                         28

<210> SEQ ID NO 601
<211> LENGTH: 27
<212> TYPE: DNA
<213> ORGANISM: Artificial Sequence
<220> FEATURE:
<223> OTHER INFORMATION: Primer

<400> SEQUENCE: 601
caacgtttaa atgtgtgtca ggacaaa                                          27

<210> SEQ ID NO 602
<211> LENGTH: 24
<212> TYPE: DNA
<213> ORGANISM: Artificial Sequence
<220> FEATURE:
<223> OTHER INFORMATION: Primer

<400> SEQUENCE: 602
ggtgatccag actctgacct tttg                                             24

<210> SEQ ID NO 603
<211> LENGTH: 19
<212> TYPE: DNA
<213> ORGANISM: Artificial Sequence
<220> FEATURE:
<223> OTHER INFORMATION: Primer

<400> SEQUENCE: 603
```
aatcgtgtgc cccaactgt                    19

<210> SEQ ID NO 604
<211> LENGTH: 21
<212> TYPE: DNA
<213> ORGANISM: Artificial Sequence
<220> FEATURE:
<223> OTHER INFORMATION: Primer

<400> SEQUENCE: 604
catggttcca ccagcgttat t                 21

<210> SEQ ID NO 605
<211> LENGTH: 28
<212> TYPE: DNA
<213> ORGANISM: Artificial Sequence
<220> FEATURE:
<223> OTHER INFORMATION: Primer

<400> SEQUENCE: 605
ctggtggttt ttacatttcc aaatccat          28

<210> SEQ ID NO 606
<211> LENGTH: 26
<212> TYPE: DNA
<213> ORGANISM: Artificial Sequence
<220> FEATURE:
<223> OTHER INFORMATION: Primer

<400> SEQUENCE: 606
cgttgagaaa gagtctccat cgtttt            26

<210> SEQ ID NO 607
<211> LENGTH: 19
<212> TYPE: DNA
<213> ORGANISM: Artificial Sequence
<220> FEATURE:
<223> OTHER INFORMATION: Primer

<400> SEQUENCE: 607
aatcgtgtgc cccaactgt                    19

<210> SEQ ID NO 608
<211> LENGTH: 23
<212> TYPE: DNA
<213> ORGANISM: Artificial Sequence
<220> FEATURE:
<223> OTHER INFORMATION: Primer

<400> SEQUENCE: 608
tttagacact gggacaggtg gta               23

<210> SEQ ID NO 609
<211> LENGTH: 23
<212> TYPE: DNA
<213> ORGANISM: Artificial Sequence
<220> FEATURE:
<223> OTHER INFORMATION: Primer

<400> SEQUENCE: 609
cggcattgga aataccctac gat               23

<210> SEQ ID NO 610
<211> LENGTH: 24
<212> TYPE: DNA

```
<213> ORGANISM: Artificial Sequence
<220> FEATURE:
<223> OTHER INFORMATION: Primer

<400> SEQUENCE: 610 tttttcttctg gacacaacgg tctt                                     24

<210> SEQ ID NO 611
<211> LENGTH: 22
<212> TYPE: DNA
<213> ORGANISM: Artificial Sequence
<220> FEATURE:
<223> OTHER INFORMATION: Primer

<400> SEQUENCE: 611
gcgggtatgg caatactgaa gt                                        22

<210> SEQ ID NO 612
<211> LENGTH: 28
<212> TYPE: DNA
<213> ORGANISM: Artificial Sequence
<220> FEATURE:
<223> OTHER INFORMATION: Primer

<400> SEQUENCE: 612
aatgtaaaaa ccaccagtct gctatgta                                  28

<210> SEQ ID NO 613
<211> LENGTH: 23
<212> TYPE: DNA
<213> ORGANISM: Artificial Sequence
<220> FEATURE:
<223> OTHER INFORMATION: Primer

<400> SEQUENCE: 613
cggcattgga aataccctac gat                                       23

<210> SEQ ID NO 614
<211> LENGTH: 26
<212> TYPE: DNA
<213> ORGANISM: Artificial Sequence
<220> FEATURE:
<223> OTHER INFORMATION: Primer

<400> SEQUENCE: 614
cgttgagaaa gagtctccat cgtttt                                    26

<210> SEQ ID NO 615
<211> LENGTH: 19
<212> TYPE: DNA
<213> ORGANISM: Artificial Sequence
<220> FEATURE:
<223> OTHER INFORMATION: Primer

<400> SEQUENCE: 615
aatcgtgtgc cccaactgt                                            19

<210> SEQ ID NO 616
<211> LENGTH: 28
<212> TYPE: DNA
<213> ORGANISM: Artificial Sequence
<220> FEATURE:
<223> OTHER INFORMATION: Primer

<400> SEQUENCE: 616
aatgtaaaaa ccaccagtct gctatgta                                  28
```

<210> SEQ ID NO 617
<211> LENGTH: 19
<212> TYPE: DNA
<213> ORGANISM: Artificial Sequence
<220> FEATURE:
<223> OTHER INFORMATION: Primer

<400> SEQUENCE: 617
cagctgcatg cacaaacca                                                  19

<210> SEQ ID NO 618
<211> LENGTH: 18
<212> TYPE: DNA
<213> ORGANISM: Artificial Sequence
<220> FEATURE:
<223> OTHER INFORMATION: Primer

<400> SEQUENCE: 618
tctttgctcg cagctcgt                                                   18

<210> SEQ ID NO 619
<211> LENGTH: 23
<212> TYPE: DNA
<213> ORGANISM: Artificial Sequence
<220> FEATURE:
<223> OTHER INFORMATION: Primer

<400> SEQUENCE: 619
cggcattgga aataccctac gat                                             23

<210> SEQ ID NO 620
<211> LENGTH: 28
<212> TYPE: DNA
<213> ORGANISM: Artificial Sequence
<220> FEATURE:
<223> OTHER INFORMATION: Primer

<400> SEQUENCE: 620
tcttaaacat tttgtacaca ctccgtgt                                        28

<210> SEQ ID NO 621
<211> LENGTH: 19
<212> TYPE: DNA
<213> ORGANISM: Artificial Sequence
<220> FEATURE:
<223> OTHER INFORMATION: Primer

<400> SEQUENCE: 621
cagctgcatg cacaaacca                                                  19

<210> SEQ ID NO 622
<211> LENGTH: 19
<212> TYPE: DNA
<213> ORGANISM: Artificial Sequence
<220> FEATURE:
<223> OTHER INFORMATION: Primer

<400> SEQUENCE: 622
aaatacggct gcaccgagt                                                  19

<210> SEQ ID NO 623
<211> LENGTH: 19
<212> TYPE: DNA
<213> ORGANISM: Artificial Sequence
<220> FEATURE:

<223> OTHER INFORMATION: Primer

<400> SEQUENCE: 623
aatcgtgtgc cccaactgt                                                19

<210> SEQ ID NO 624
<211> LENGTH: 22
<212> TYPE: DNA
<213> ORGANISM: Artificial Sequence
<220> FEATURE:
<223> OTHER INFORMATION: Primer

<400> SEQUENCE: 624
atcatgatgg ctgtatgtgc ca                                            22

<210> SEQ ID NO 625
<211> LENGTH: 19
<212> TYPE: DNA
<213> ORGANISM: Artificial Sequence
<220> FEATURE:
<223> OTHER INFORMATION: Primer

<400> SEQUENCE: 625
aatcgtgtgc cccaactgt                                                19

<210> SEQ ID NO 626
<211> LENGTH: 19
<212> TYPE: DNA
<213> ORGANISM: Artificial Sequence
<220> FEATURE:
<223> OTHER INFORMATION: Primer

<400> SEQUENCE: 626
ctgagaagcc ctgcccttc                                                19

<210> SEQ ID NO 627
<211> LENGTH: 19
<212> TYPE: DNA
<213> ORGANISM: Artificial Sequence
<220> FEATURE:
<223> OTHER INFORMATION: Primer

<400> SEQUENCE: 627
aatcgtgtgc cccaactgt                                                19

<210> SEQ ID NO 628
<211> LENGTH: 24
<212> TYPE: DNA
<213> ORGANISM: Artificial Sequence
<220> FEATURE:
<223> OTHER INFORMATION: Primer

<400> SEQUENCE: 628
cccctgtctg tctgtcaatt actg                                          24

<210> SEQ ID NO 629
<211> LENGTH: 19
<212> TYPE: DNA
<213> ORGANISM: Artificial Sequence
<220> FEATURE:
<223> OTHER INFORMATION: Primer

<400> SEQUENCE: 629
aatcgtgtgc cccaactgt                                                19

```
<210> SEQ ID NO 630
<211> LENGTH: 26
<212> TYPE: DNA
<213> ORGANISM: Artificial Sequence
<220> FEATURE:
<223> OTHER INFORMATION: Primer

<400> SEQUENCE: 630
cgttgagaaa gagtctccat cgtttt                                          26

<210> SEQ ID NO 631
<211> LENGTH: 19
<212> TYPE: DNA
<213> ORGANISM: Artificial Sequence
<220> FEATURE:
<223> OTHER INFORMATION: Primer

<400> SEQUENCE: 631
cagctgcatg cacaaaacca                                                 19

<210> SEQ ID NO 632
<211> LENGTH: 28
<212> TYPE: DNA
<213> ORGANISM: Artificial Sequence
<220> FEATURE:
<223> OTHER INFORMATION: Primer

<400> SEQUENCE: 632
gccatgtaga tgacacttgt tcatacaa                                        28

<210> SEQ ID NO 633
<211> LENGTH: 23
<212> TYPE: DNA
<213> ORGANISM: Artificial Sequence
<220> FEATURE:
<223> OTHER INFORMATION: Primer

<400> SEQUENCE: 633
cggcattgga aataccctac gat                                             23

<210> SEQ ID NO 634
<211> LENGTH: 25
<212> TYPE: DNA
<213> ORGANISM: Artificial Sequence
<220> FEATURE:
<223> OTHER INFORMATION: Primer

<400> SEQUENCE: 634
acatagtctt gcaacgtagg tgttt                                           25

<210> SEQ ID NO 635
<211> LENGTH: 32
<212> TYPE: DNA
<213> ORGANISM: Artificial Sequence
<220> FEATURE:
<223> OTHER INFORMATION: Primer

<400> SEQUENCE: 635
ggaacaacat tagaaaaatt gacaaacaaa gg                                   32

<210> SEQ ID NO 636
<211> LENGTH: 24
<212> TYPE: DNA
<213> ORGANISM: Artificial Sequence
<220> FEATURE:
<223> OTHER INFORMATION: Primer
```

```
<400> SEQUENCE: 636 tttcttctg gacacaacgg tctt                                              24

<210> SEQ ID NO 637
<211> LENGTH: 23
<212> TYPE: DNA
<213> ORGANISM: Artificial Sequence
<220> FEATURE:
<223> OTHER INFORMATION: Primer

<400> SEQUENCE: 637
cggcattgga aatacccctac gat                                             23

<210> SEQ ID NO 638
<211> LENGTH: 28
<212> TYPE: DNA
<213> ORGANISM: Artificial Sequence
<220> FEATURE:
<223> OTHER INFORMATION: Primer

<400> SEQUENCE: 638
aatgtaaaaa ccaccagtct gctatgta                                         28

<210> SEQ ID NO 639
<211> LENGTH: 19
<212> TYPE: DNA
<213> ORGANISM: Artificial Sequence
<220> FEATURE:
<223> OTHER INFORMATION: Primer

<400> SEQUENCE: 639
cagctgcatg cacaaaacca                                                  19

<210> SEQ ID NO 640
<211> LENGTH: 22
<212> TYPE: DNA
<213> ORGANISM: Artificial Sequence
<220> FEATURE:
<223> OTHER INFORMATION: Primer

<400> SEQUENCE: 640
atcatgatgg ctgtatgtgc ca                                               22

<210> SEQ ID NO 641
<211> LENGTH: 19
<212> TYPE: DNA
<213> ORGANISM: Artificial Sequence
<220> FEATURE:
<223> OTHER INFORMATION: Primer

<400> SEQUENCE: 641
aatcgtgtgc cccaactgt                                                   19

<210> SEQ ID NO 642
<211> LENGTH: 18
<212> TYPE: DNA
<213> ORGANISM: Artificial Sequence
<220> FEATURE:
<223> OTHER INFORMATION: Primer

<400> SEQUENCE: 642
tctttgctcg cagctcgt                                                    18

<210> SEQ ID NO 643
<211> LENGTH: 23
```

```
<212> TYPE: DNA
<213> ORGANISM: Artificial Sequence
<220> FEATURE:
<223> OTHER INFORMATION: Primer

<400> SEQUENCE: 643
cactagatgg caaccctgta tct                                            23

<210> SEQ ID NO 644
<211> LENGTH: 28
<212> TYPE: DNA
<213> ORGANISM: Artificial Sequence
<220> FEATURE:
<223> OTHER INFORMATION: Primer

<400> SEQUENCE: 644
aatgtaaaaa ccaccagtct gctatgta                                       28

<210> SEQ ID NO 645
<211> LENGTH: 19
<212> TYPE: DNA
<213> ORGANISM: Artificial Sequence
<220> FEATURE:
<223> OTHER INFORMATION: Primer

<400> SEQUENCE: 645
aatcgtgtgc cccaactgt                                                 19

<210> SEQ ID NO 646
<211> LENGTH: 24
<212> TYPE: DNA
<213> ORGANISM: Artificial Sequence
<220> FEATURE:
<223> OTHER INFORMATION: Primer

<400> SEQUENCE: 646
gaattcgatg tggtggtgtt gttg                                           24

<210> SEQ ID NO 647
<211> LENGTH: 19
<212> TYPE: DNA
<213> ORGANISM: Artificial Sequence
<220> FEATURE:
<223> OTHER INFORMATION: Primer

<400> SEQUENCE: 647
aatcgtgtgc cccaactgt                                                 19

<210> SEQ ID NO 648
<211> LENGTH: 24
<212> TYPE: DNA
<213> ORGANISM: Artificial Sequence
<220> FEATURE:
<223> OTHER INFORMATION: Primer

<400> SEQUENCE: 648
ggtgatccag actctgacct tttg                                           24

<210> SEQ ID NO 649
<211> LENGTH: 19
<212> TYPE: DNA
<213> ORGANISM: Artificial Sequence
<220> FEATURE:
<223> OTHER INFORMATION: Primer

<400> SEQUENCE: 649
```

| | |
|---|---|
| catgcgggtg gtcaggtaa | 19 |

<210> SEQ ID NO 650
<211> LENGTH: 24
<212> TYPE: DNA
<213> ORGANISM: Artificial Sequence
<220> FEATURE:
<223> OTHER INFORMATION: Primer

<400> SEQUENCE: 650

| | |
|---|---|
| gaattcgatg tggtggtgtt gttg | 24 |

<210> SEQ ID NO 651
<211> LENGTH: 19
<212> TYPE: DNA
<213> ORGANISM: Artificial Sequence
<220> FEATURE:
<223> OTHER INFORMATION: Primer

<400> SEQUENCE: 651

| | |
|---|---|
| aatcgtgtgc cccaactgt | 19 |

<210> SEQ ID NO 652
<211> LENGTH: 19
<212> TYPE: DNA
<213> ORGANISM: Artificial Sequence
<220> FEATURE:
<223> OTHER INFORMATION: Primer

<400> SEQUENCE: 652

| | |
|---|---|
| aaatacggct gcaccgagt | 19 |

<210> SEQ ID NO 653
<211> LENGTH: 25
<212> TYPE: DNA
<213> ORGANISM: Artificial Sequence
<220> FEATURE:
<223> OTHER INFORMATION: Primer

<400> SEQUENCE: 653

| | |
|---|---|
| gaaacgattc cacaacatag gagga | 25 |

<210> SEQ ID NO 654
<211> LENGTH: 25
<212> TYPE: DNA
<213> ORGANISM: Artificial Sequence
<220> FEATURE:
<223> OTHER INFORMATION: Primer

<400> SEQUENCE: 654

| | |
|---|---|
| acatagtctt gcaacgtagg tgttt | 25 |

<210> SEQ ID NO 655
<211> LENGTH: 22
<212> TYPE: DNA
<213> ORGANISM: Artificial Sequence
<220> FEATURE:
<223> OTHER INFORMATION: Primer

<400> SEQUENCE: 655

| | |
|---|---|
| gcgggtatgg caatactgaa gt | 22 |

<210> SEQ ID NO 656
<211> LENGTH: 24
<212> TYPE: DNA
<213> ORGANISM: Artificial Sequence

```
<220> FEATURE:
<223> OTHER INFORMATION: Primer

<400> SEQUENCE: 656
gaattcgatg tggtggtgtt gttg                                          24

<210> SEQ ID NO 657
<211> LENGTH: 19
<212> TYPE: DNA
<213> ORGANISM: Artificial Sequence
<220> FEATURE:
<223> OTHER INFORMATION: Primer

<400> SEQUENCE: 657
cagctgcatg cacaaaacca                                               19

<210> SEQ ID NO 658
<211> LENGTH: 19
<212> TYPE: DNA
<213> ORGANISM: Artificial Sequence
<220> FEATURE:
<223> OTHER INFORMATION: Primer

<400> SEQUENCE: 658
ctgagaagcc ctgcccttc                                                19

<210> SEQ ID NO 659
<211> LENGTH: 27
<212> TYPE: DNA
<213> ORGANISM: Artificial Sequence
<220> FEATURE:
<223> OTHER INFORMATION: Primer

<400> SEQUENCE: 659
caacgtttaa atgtgtgtca ggacaaa                                       27

<210> SEQ ID NO 660
<211> LENGTH: 18
<212> TYPE: DNA
<213> ORGANISM: Artificial Sequence
<220> FEATURE:
<223> OTHER INFORMATION: Primer

<400> SEQUENCE: 660
tctttgctcg cagctcgt                                                 18

<210> SEQ ID NO 661
<211> LENGTH: 25
<212> TYPE: DNA
<213> ORGANISM: Artificial Sequence
<220> FEATURE:
<223> OTHER INFORMATION: Primer

<400> SEQUENCE: 661
tgtgtgtgtt gtgtatgttg tcctt                                         25

<210> SEQ ID NO 662
<211> LENGTH: 26
<212> TYPE: DNA
<213> ORGANISM: Artificial Sequence
<220> FEATURE:
<223> OTHER INFORMATION: Primer

<400> SEQUENCE: 662 caactttac tatggcgtga caccta                                         26
```

<210> SEQ ID NO 663
<211> LENGTH: 20
<212> TYPE: DNA
<213> ORGANISM: Artificial Sequence
<220> FEATURE:
<223> OTHER INFORMATION: Primer

<400> SEQUENCE: 663
gcttagtttg ggcctgtgtt                                           20

<210> SEQ ID NO 664
<211> LENGTH: 27
<212> TYPE: DNA
<213> ORGANISM: Artificial Sequence
<220> FEATURE:
<223> OTHER INFORMATION: Primer

<400> SEQUENCE: 664
accaccggca tatctattag agttttc                                   27

<210> SEQ ID NO 665
<211> LENGTH: 25
<212> TYPE: DNA
<213> ORGANISM: Artificial Sequence
<220> FEATURE:
<223> OTHER INFORMATION: Primer

<400> SEQUENCE: 665
gcattgtgct atgcttttg ctttg                                      25

<210> SEQ ID NO 666
<211> LENGTH: 25
<212> TYPE: DNA
<213> ORGANISM: Artificial Sequence
<220> FEATURE:
<223> OTHER INFORMATION: Primer

<400> SEQUENCE: 666
acaacgtaat ggagaggttg caata                                     25

<210> SEQ ID NO 667
<211> LENGTH: 27
<212> TYPE: DNA
<213> ORGANISM: Artificial Sequence
<220> FEATURE:
<223> OTHER INFORMATION: Primer

<400> SEQUENCE: 667
gtgaaacacc agaatggata gaaagac                                   27

<210> SEQ ID NO 668
<211> LENGTH: 25
<212> TYPE: DNA
<213> ORGANISM: Artificial Sequence
<220> FEATURE:
<223> OTHER INFORMATION: Primer

<400> SEQUENCE: 668
tgcacatgca ttactatcac tgtca                                     25

<210> SEQ ID NO 669
<211> LENGTH: 23
<212> TYPE: DNA
<213> ORGANISM: Artificial Sequence
<220> FEATURE:
<223> OTHER INFORMATION: Primer -continued

```
<400> SEQUENCE: 669
acgtactgca actaactgca caa                                        23

<210> SEQ ID NO 670
<211> LENGTH: 24
<212> TYPE: DNA
<213> ORGANISM: Artificial Sequence
<220> FEATURE:
<223> OTHER INFORMATION: Primer

<400> SEQUENCE: 670
ggtgatccag actctgacct tttg                                       24

<210> SEQ ID NO 671
<211> LENGTH: 23
<212> TYPE: DNA
<213> ORGANISM: Artificial Sequence
<220> FEATURE:
<223> OTHER INFORMATION: Primer

<400> SEQUENCE: 671
acgtactgca actaactgca caa                                        23

<210> SEQ ID NO 672
<211> LENGTH: 21
<212> TYPE: DNA
<213> ORGANISM: Artificial Sequence
<220> FEATURE:
<223> OTHER INFORMATION: Primer

<400> SEQUENCE: 672
catggttcca ccagcgttat t                                          21

<210> SEQ ID NO 673
<211> LENGTH: 25
<212> TYPE: DNA
<213> ORGANISM: Artificial Sequence
<220> FEATURE:
<223> OTHER INFORMATION: Primer

<400> SEQUENCE: 673
gatgagctag aagacagcgg atatg                                      25

<210> SEQ ID NO 674
<211> LENGTH: 21
<212> TYPE: DNA
<213> ORGANISM: Artificial Sequence
<220> FEATURE:
<223> OTHER INFORMATION: Primer

<400> SEQUENCE: 674
gtggtggtcg gttatcgttg t                                          21

<210> SEQ ID NO 675
<211> LENGTH: 19
<212> TYPE: DNA
<213> ORGANISM: Artificial Sequence
<220> FEATURE:
<223> OTHER INFORMATION: Primer

<400> SEQUENCE: 675
gtgccctacc tgtgcacaa                                             19

<210> SEQ ID NO 676
```

```
<211> LENGTH: 27
<212> TYPE: DNA
<213> ORGANISM: Artificial Sequence
<220> FEATURE:
<223> OTHER INFORMATION: Primer

<400> SEQUENCE: 676
ttcttctctc tatgactgct tctacct                                          27

<210> SEQ ID NO 677
<211> LENGTH: 28
<212> TYPE: DNA
<213> ORGANISM: Artificial Sequence
<220> FEATURE:
<223> OTHER INFORMATION: Primer

<400> SEQUENCE: 677
tgtgaaacat agggcattag tgcaatta                                         28

<210> SEQ ID NO 678
<211> LENGTH: 28
<212> TYPE: DNA
<213> ORGANISM: Artificial Sequence
<220> FEATURE:
<223> OTHER INFORMATION: Primer

<400> SEQUENCE: 678
catacactgg gttaccattt tcatcaaa                                         28

<210> SEQ ID NO 679
<211> LENGTH: 19
<212> TYPE: DNA
<213> ORGANISM: Artificial Sequence
<220> FEATURE:
<223> OTHER INFORMATION: Primer

<400> SEQUENCE: 679
gtgccctacc tgtgcacaa                                                   19

<210> SEQ ID NO 680
<211> LENGTH: 22
<212> TYPE: DNA
<213> ORGANISM: Artificial Sequence
<220> FEATURE:
<223> OTHER INFORMATION: Primer

<400> SEQUENCE: 680
atcatgatgg ctgtatgtgc ca                                               22

<210> SEQ ID NO 681
<211> LENGTH: 19
<212> TYPE: DNA
<213> ORGANISM: Artificial Sequence
<220> FEATURE:
<223> OTHER INFORMATION: Primer

<400> SEQUENCE: 681
gtgccctacc tgtgcacaa                                                   19

<210> SEQ ID NO 682
<211> LENGTH: 19
<212> TYPE: DNA
<213> ORGANISM: Artificial Sequence
<220> FEATURE:
<223> OTHER INFORMATION: Primer

<400> SEQUENCE: 682
```
ctgagaagcc ctgcccttc                                                   19

<210> SEQ ID NO 683
<211> LENGTH: 23
<212> TYPE: DNA
<213> ORGANISM: Artificial Sequence
<220> FEATURE:
<223> OTHER INFORMATION: Primer

<400> SEQUENCE: 683
acgtactgca actaactgca caa                                              23

<210> SEQ ID NO 684
<211> LENGTH: 27
<212> TYPE: DNA
<213> ORGANISM: Artificial Sequence
<220> FEATURE:
<223> OTHER INFORMATION: Primer

<400> SEQUENCE: 684
atcagtgctg acaactttag atacagg                                          27

<210> SEQ ID NO 685
<211> LENGTH: 23
<212> TYPE: DNA
<213> ORGANISM: Artificial Sequence
<220> FEATURE:
<223> OTHER INFORMATION: Primer

<400> SEQUENCE: 685
acgtactgca actaactgca caa                                              23

<210> SEQ ID NO 686
<211> LENGTH: 18
<212> TYPE: DNA
<213> ORGANISM: Artificial Sequence
<220> FEATURE:
<223> OTHER INFORMATION: Primer

<400> SEQUENCE: 686
tctttgctcg cagctcgt                                                    18

<210> SEQ ID NO 687
<211> LENGTH: 28
<212> TYPE: DNA
<213> ORGANISM: Artificial Sequence
<220> FEATURE:
<223> OTHER INFORMATION: Primer

<400> SEQUENCE: 687
agcattggag acaactatac acaacatt                                         28

<210> SEQ ID NO 688
<211> LENGTH: 26
<212> TYPE: DNA
<213> ORGANISM: Artificial Sequence
<220> FEATURE:
<223> OTHER INFORMATION: Primer

<400> SEQUENCE: 688
catattcctt taacgttggc ttgtgt                                           26

<210> SEQ ID NO 689
<211> LENGTH: 33
<212> TYPE: DNA

```
<213> ORGANISM: Artificial Sequence
<220> FEATURE:
<223> OTHER INFORMATION: Primer

<400> SEQUENCE: 689
attctgtata tggaaataca ttagaacaaa cag                                    33

<210> SEQ ID NO 690
<211> LENGTH: 28
<212> TYPE: DNA
<213> ORGANISM: Artificial Sequence
<220> FEATURE:
<223> OTHER INFORMATION: Primer

<400> SEQUENCE: 690
tcgtttgttt aaatccacat gtcgtttt                                          28

<210> SEQ ID NO 691
<211> LENGTH: 23
<212> TYPE: DNA
<213> ORGANISM: Artificial Sequence
<220> FEATURE:
<223> OTHER INFORMATION: Primer

<400> SEQUENCE: 691
acgtactgca actaactgca caa                                               23

<210> SEQ ID NO 692
<211> LENGTH: 19
<212> TYPE: DNA
<213> ORGANISM: Artificial Sequence
<220> FEATURE:
<223> OTHER INFORMATION: Primer

<400> SEQUENCE: 692
ctgagaagcc ctgcccttc                                                    19

<210> SEQ ID NO 693
<211> LENGTH: 23
<212> TYPE: DNA
<213> ORGANISM: Artificial Sequence
<220> FEATURE:
<223> OTHER INFORMATION: Primer

<400> SEQUENCE: 693
acgtactgca actaactgca caa                                               23

<210> SEQ ID NO 694
<211> LENGTH: 19
<212> TYPE: DNA
<213> ORGANISM: Artificial Sequence
<220> FEATURE:
<223> OTHER INFORMATION: Primer

<400> SEQUENCE: 694
aaatacggct gcaccgagt                                                    19

<210> SEQ ID NO 695
<211> LENGTH: 28
<212> TYPE: DNA
<213> ORGANISM: Artificial Sequence
<220> FEATURE:
<223> OTHER INFORMATION: Primer

<400> SEQUENCE: 695
agcattggag acaactatac acaacatt                                          28
```

<210> SEQ ID NO 696
<211> LENGTH: 28
<212> TYPE: DNA
<213> ORGANISM: Artificial Sequence
<220> FEATURE:
<223> OTHER INFORMATION: Primer

<400> SEQUENCE: 696
tcgtttgttt aaatccacat gtcgtttt                                      28

<210> SEQ ID NO 697
<211> LENGTH: 29
<212> TYPE: DNA
<213> ORGANISM: Artificial Sequence
<220> FEATURE:
<223> OTHER INFORMATION: Primer

<400> SEQUENCE: 697
gtgcaggaga aaatactaga tctttacga                                     29

<210> SEQ ID NO 698
<211> LENGTH: 19
<212> TYPE: DNA
<213> ORGANISM: Artificial Sequence
<220> FEATURE:
<223> OTHER INFORMATION: Primer

<400> SEQUENCE: 698
ctgagaagcc ctgcccttc                                                19

<210> SEQ ID NO 699
<211> LENGTH: 25
<212> TYPE: DNA
<213> ORGANISM: Artificial Sequence
<220> FEATURE:
<223> OTHER INFORMATION: Primer

<400> SEQUENCE: 699
gatgagctag aagacagcgg atatg                                         25

<210> SEQ ID NO 700
<211> LENGTH: 20
<212> TYPE: DNA
<213> ORGANISM: Artificial Sequence
<220> FEATURE:
<223> OTHER INFORMATION: Primer

<400> SEQUENCE: 700
catcccccac cccactagat                                               20

<210> SEQ ID NO 701
<211> LENGTH: 23
<212> TYPE: DNA
<213> ORGANISM: Artificial Sequence
<220> FEATURE:
<223> OTHER INFORMATION: Primer

<400> SEQUENCE: 701
acgtactgca actaactgca caa                                           23

<210> SEQ ID NO 702
<211> LENGTH: 22
<212> TYPE: DNA
<213> ORGANISM: Artificial Sequence
<220> FEATURE:

<223> OTHER INFORMATION: Primer

<400> SEQUENCE: 702
atcatgatgg ctgtatgtgc ca                                    22

<210> SEQ ID NO 703
<211> LENGTH: 29
<212> TYPE: DNA
<213> ORGANISM: Artificial Sequence
<220> FEATURE:
<223> OTHER INFORMATION: Primer

<400> SEQUENCE: 703
gtgcaggaga aaatactaga tctttacga                             29

<210> SEQ ID NO 704
<211> LENGTH: 22
<212> TYPE: DNA
<213> ORGANISM: Artificial Sequence
<220> FEATURE:
<223> OTHER INFORMATION: Primer

<400> SEQUENCE: 704
atcatgatgg ctgtatgtgc ca                                    22

<210> SEQ ID NO 705
<211> LENGTH: 28
<212> TYPE: DNA
<213> ORGANISM: Artificial Sequence
<220> FEATURE:
<223> OTHER INFORMATION: Primer

<400> SEQUENCE: 705
agcattggag acaactatac acaacatt                              28

<210> SEQ ID NO 706
<211> LENGTH: 28
<212> TYPE: DNA
<213> ORGANISM: Artificial Sequence
<220> FEATURE:
<223> OTHER INFORMATION: Primer

<400> SEQUENCE: 706
cgcaaacaca gtttacatat tccaaatg                              28

<210> SEQ ID NO 707
<211> LENGTH: 19
<212> TYPE: DNA
<213> ORGANISM: Artificial Sequence
<220> FEATURE:
<223> OTHER INFORMATION: Primer

<400> SEQUENCE: 707
gtgccctacc tgtgcacaa                                        19

<210> SEQ ID NO 708
<211> LENGTH: 18
<212> TYPE: DNA
<213> ORGANISM: Artificial Sequence
<220> FEATURE:
<223> OTHER INFORMATION: Primer

<400> SEQUENCE: 708
tctttgctcg cagctcgt                                         18

```
<210> SEQ ID NO 709
<211> LENGTH: 19
<212> TYPE: DNA
<213> ORGANISM: Artificial Sequence
<220> FEATURE:
<223> OTHER INFORMATION: Primer

<400> SEQUENCE: 709
gtgccctacc tgtgcacaa                                                  19

<210> SEQ ID NO 710
<211> LENGTH: 19
<212> TYPE: DNA
<213> ORGANISM: Artificial Sequence
<220> FEATURE:
<223> OTHER INFORMATION: Primer

<400> SEQUENCE: 710
aaatacggct gcaccgagt                                                  19

<210> SEQ ID NO 711
<211> LENGTH: 29
<212> TYPE: DNA
<213> ORGANISM: Artificial Sequence
<220> FEATURE:
<223> OTHER INFORMATION: Primer

<400> SEQUENCE: 711
gtgcaggaga aaatactaga tctttacga                                       29

<210> SEQ ID NO 712
<211> LENGTH: 24
<212> TYPE: DNA
<213> ORGANISM: Artificial Sequence
<220> FEATURE:
<223> OTHER INFORMATION: Primer

<400> SEQUENCE: 712
ggtgatccag actctgacct tttg                                            24

<210> SEQ ID NO 713
<211> LENGTH: 28
<212> TYPE: DNA
<213> ORGANISM: Artificial Sequence
<220> FEATURE:
<223> OTHER INFORMATION: Primer

<400> SEQUENCE: 713
agcattggag acaactatac acaacatt                                        28

<210> SEQ ID NO 714
<211> LENGTH: 28
<212> TYPE: DNA
<213> ORGANISM: Artificial Sequence
<220> FEATURE:
<223> OTHER INFORMATION: Primer

<400> SEQUENCE: 714
catacactgg gttaccattt tcatcaaa                                        28

<210> SEQ ID NO 715
<211> LENGTH: 29
<212> TYPE: DNA
<213> ORGANISM: Artificial Sequence
<220> FEATURE:
<223> OTHER INFORMATION: Primer
```

```
<400> SEQUENCE: 715
gtgcaggaga aaatactaga tctttacga                              29

<210> SEQ ID NO 716
<211> LENGTH: 21
<212> TYPE: DNA
<213> ORGANISM: Artificial Sequence
<220> FEATURE:
<223> OTHER INFORMATION: Primer

<400> SEQUENCE: 716
catggttcca ccagcgttat t                                      21

<210> SEQ ID NO 717
<211> LENGTH: 19
<212> TYPE: DNA
<213> ORGANISM: Artificial Sequence
<220> FEATURE:
<223> OTHER INFORMATION: Primer

<400> SEQUENCE: 717
gtgccctacc tgtgcacaa                                         19

<210> SEQ ID NO 718
<211> LENGTH: 28
<212> TYPE: DNA
<213> ORGANISM: Artificial Sequence
<220> FEATURE:
<223> OTHER INFORMATION: Primer

<400> SEQUENCE: 718
tgatatttcc tccatggttt tccttgtc                               28

<210> SEQ ID NO 719
<211> LENGTH: 28
<212> TYPE: DNA
<213> ORGANISM: Artificial Sequence
<220> FEATURE:
<223> OTHER INFORMATION: Primer

<400> SEQUENCE: 719
agcattggag acaactatac acaacatt                               28

<210> SEQ ID NO 720
<211> LENGTH: 21
<212> TYPE: DNA
<213> ORGANISM: Artificial Sequence
<220> FEATURE:
<223> OTHER INFORMATION: Primer

<400> SEQUENCE: 720
gtggtggtcg gttatcgttg t                                      21

<210> SEQ ID NO 721
<211> LENGTH: 25
<212> TYPE: DNA
<213> ORGANISM: Artificial Sequence
<220> FEATURE:
<223> OTHER INFORMATION: Primer

<400> SEQUENCE: 721
gatgagctag aagacagcgg atatg                                  25

<210> SEQ ID NO 722
<211> LENGTH: 28
```

```
<212> TYPE: DNA
<213> ORGANISM: Artificial Sequence
<220> FEATURE:
<223> OTHER INFORMATION: Primer

<400> SEQUENCE: 722
catacactgg gttaccattt tcatcaaa                                      28

<210> SEQ ID NO 723
<211> LENGTH: 19
<212> TYPE: DNA
<213> ORGANISM: Artificial Sequence
<220> FEATURE:
<223> OTHER INFORMATION: Primer

<400> SEQUENCE: 723
gtgccctacc tgtgcacaa                                                19

<210> SEQ ID NO 724
<211> LENGTH: 24
<212> TYPE: DNA
<213> ORGANISM: Artificial Sequence
<220> FEATURE:
<223> OTHER INFORMATION: Primer

<400> SEQUENCE: 724
ggtgatccag actctgacct tttg                                          24

<210> SEQ ID NO 725
<211> LENGTH: 29
<212> TYPE: DNA
<213> ORGANISM: Artificial Sequence
<220> FEATURE:
<223> OTHER INFORMATION: Primer

<400> SEQUENCE: 725
gtgcaggaga aaatactaga tctttacga                                     29

<210> SEQ ID NO 726
<211> LENGTH: 18
<212> TYPE: DNA
<213> ORGANISM: Artificial Sequence
<220> FEATURE:
<223> OTHER INFORMATION: Primer

<400> SEQUENCE: 726
tctttgctcg cagctcgt                                                 18

<210> SEQ ID NO 727
<211> LENGTH: 19
<212> TYPE: DNA
<213> ORGANISM: Artificial Sequence
<220> FEATURE:
<223> OTHER INFORMATION: Primer

<400> SEQUENCE: 727
gtgccctacc tgtgcacaa                                                19

<210> SEQ ID NO 728
<211> LENGTH: 21
<212> TYPE: DNA
<213> ORGANISM: Artificial Sequence
<220> FEATURE:
<223> OTHER INFORMATION: Primer

<400> SEQUENCE: 728
```

```
gtggtggtcg gttatcgttg t                                              21

<210> SEQ ID NO 729
<211> LENGTH: 19
<212> TYPE: DNA
<213> ORGANISM: Artificial Sequence
<220> FEATURE:
<223> OTHER INFORMATION: Primer

<400> SEQUENCE: 729
gtgccctacc tgtgcacaa                                                 19

<210> SEQ ID NO 730
<211> LENGTH: 21
<212> TYPE: DNA
<213> ORGANISM: Artificial Sequence
<220> FEATURE:
<223> OTHER INFORMATION: Primer

<400> SEQUENCE: 730
catggttcca ccagcgttat t                                              21

<210> SEQ ID NO 731
<211> LENGTH: 29
<212> TYPE: DNA
<213> ORGANISM: Artificial Sequence
<220> FEATURE:
<223> OTHER INFORMATION: Primer

<400> SEQUENCE: 731
gtgcaggaga aaatactaga tctttacga                                      29

<210> SEQ ID NO 732
<211> LENGTH: 19
<212> TYPE: DNA
<213> ORGANISM: Artificial Sequence
<220> FEATURE:
<223> OTHER INFORMATION: Primer

<400> SEQUENCE: 732
aaatacggct gcaccgagt                                                 19

<210> SEQ ID NO 733
<211> LENGTH: 25
<212> TYPE: DNA
<213> ORGANISM: Artificial Sequence
<220> FEATURE:
<223> OTHER INFORMATION: Primer

<400> SEQUENCE: 733
gatgagctag aagacagcgg atatg                                          25

<210> SEQ ID NO 734
<211> LENGTH: 28
<212> TYPE: DNA
<213> ORGANISM: Artificial Sequence
<220> FEATURE:
<223> OTHER INFORMATION: Primer

<400> SEQUENCE: 734
tgatatttcc tccatggttt tccttgtc                                       28

<210> SEQ ID NO 735
<211> LENGTH: 28
<212> TYPE: DNA
<213> ORGANISM: Artificial Sequence
```

```
<220> FEATURE:
<223> OTHER INFORMATION: Primer

<400> SEQUENCE: 735
ggatgctgca aagtattcta aaacacaa                                        28

<210> SEQ ID NO 736
<211> LENGTH: 21
<212> TYPE: DNA
<213> ORGANISM: Artificial Sequence
<220> FEATURE:
<223> OTHER INFORMATION: Primer

<400> SEQUENCE: 736
gtggtggtcg gttatcgttg t                                               21

<210> SEQ ID NO 737
<211> LENGTH: 27
<212> TYPE: DNA
<213> ORGANISM: Artificial Sequence
<220> FEATURE:
<223> OTHER INFORMATION: Primer

<400> SEQUENCE: 737
cgatttcata atatttcggg tcgttgg                                         27

<210> SEQ ID NO 738
<211> LENGTH: 26
<212> TYPE: DNA
<213> ORGANISM: Artificial Sequence
<220> FEATURE:
<223> OTHER INFORMATION: Primer

<400> SEQUENCE: 738
catattcctt taacgttggc ttgtgt                                          26

<210> SEQ ID NO 739
<211> LENGTH: 19
<212> TYPE: DNA
<213> ORGANISM: Artificial Sequence
<220> FEATURE:
<223> OTHER INFORMATION: Primer

<400> SEQUENCE: 739
gtgccctacc tgtgcacaa                                                  19

<210> SEQ ID NO 740
<211> LENGTH: 27
<212> TYPE: DNA
<213> ORGANISM: Artificial Sequence
<220> FEATURE:
<223> OTHER INFORMATION: Primer

<400> SEQUENCE: 740
atcagtgctg acaactttag atacagg                                         27

<210> SEQ ID NO 741
<211> LENGTH: 23
<212> TYPE: DNA
<213> ORGANISM: Artificial Sequence
<220> FEATURE:
<223> OTHER INFORMATION: Primer

<400> SEQUENCE: 741
acgtactgca actaactgca caa                                             23
```

```
<210> SEQ ID NO 742
<211> LENGTH: 27
<212> TYPE: DNA
<213> ORGANISM: Artificial Sequence
<220> FEATURE:
<223> OTHER INFORMATION: Primer

<400> SEQUENCE: 742
gccaggtgga tgacatagaa ctataca                                    27

<210> SEQ ID NO 743
<211> LENGTH: 23
<212> TYPE: DNA
<213> ORGANISM: Artificial Sequence
<220> FEATURE:
<223> OTHER INFORMATION: Primer

<400> SEQUENCE: 743
ttgttgtaga cggtgctgac ttt                                        23

<210> SEQ ID NO 744
<211> LENGTH: 27
<212> TYPE: DNA
<213> ORGANISM: Artificial Sequence
<220> FEATURE:
<223> OTHER INFORMATION: Primer

<400> SEQUENCE: 744
atcagtgctg acaactttag atacagg                                    27

<210> SEQ ID NO 745
<211> LENGTH: 19
<212> TYPE: DNA
<213> ORGANISM: Artificial Sequence
<220> FEATURE:
<223> OTHER INFORMATION: Primer

<400> SEQUENCE: 745
gtgccctacc tgtgcacaa                                             19

<210> SEQ ID NO 746
<211> LENGTH: 28
<212> TYPE: DNA
<213> ORGANISM: Artificial Sequence
<220> FEATURE:
<223> OTHER INFORMATION: Primer

<400> SEQUENCE: 746
catacactgg gttaccattt tcatcaaa                                   28

<210> SEQ ID NO 747
<211> LENGTH: 28
<212> TYPE: DNA
<213> ORGANISM: Artificial Sequence
<220> FEATURE:
<223> OTHER INFORMATION: Primer

<400> SEQUENCE: 747
agcattggag acaactatac acaacatt                                   28

<210> SEQ ID NO 748
<211> LENGTH: 28
<212> TYPE: DNA
<213> ORGANISM: Artificial Sequence
<220> FEATURE:
<223> OTHER INFORMATION: Primer
```

<400> SEQUENCE: 748
tgatatttcc tccatggttt tccttgtc                                      28

<210> SEQ ID NO 749
<211> LENGTH: 25
<212> TYPE: DNA
<213> ORGANISM: Artificial Sequence
<220> FEATURE:
<223> OTHER INFORMATION: Primer

<400> SEQUENCE: 749
ccatttctac ctatgcttgg ttgct                                         25

<210> SEQ ID NO 750
<211> LENGTH: 25
<212> TYPE: DNA
<213> ORGANISM: Artificial Sequence
<220> FEATURE:
<223> OTHER INFORMATION: Primer

<400> SEQUENCE: 750
gttgtgtcat atgctgtgca tgaaa                                         25

<210> SEQ ID NO 751
<211> LENGTH: 19
<212> TYPE: DNA
<213> ORGANISM: Artificial Sequence
<220> FEATURE:
<223> OTHER INFORMATION: Primer

<400> SEQUENCE: 751
cttgccctac cctgcattg                                                19

<210> SEQ ID NO 752
<211> LENGTH: 27
<212> TYPE: DNA
<213> ORGANISM: Artificial Sequence
<220> FEATURE:
<223> OTHER INFORMATION: Primer

<400> SEQUENCE: 752
cggttaggca tacaaaatgg aggaaat                                       27

<210> SEQ ID NO 753
<211> LENGTH: 21
<212> TYPE: DNA
<213> ORGANISM: Artificial Sequence
<220> FEATURE:
<223> OTHER INFORMATION: Primer

<400> SEQUENCE: 753
cggagccaaa catgtgcatt g                                             21

<210> SEQ ID NO 754
<211> LENGTH: 26
<212> TYPE: DNA
<213> ORGANISM: Artificial Sequence
<220> FEATURE:
<223> OTHER INFORMATION: Primer

<400> SEQUENCE: 754
cgttatcata tgcccactgt accatt                                        26

<210> SEQ ID NO 755

```
<211> LENGTH: 27
<212> TYPE: DNA
<213> ORGANISM: Artificial Sequence
<220> FEATURE:
<223> OTHER INFORMATION: Primer

<400> SEQUENCE: 755
catgtgtagg ccttgaaata ggtagag                                            27

<210> SEQ ID NO 756
<211> LENGTH: 22
<212> TYPE: DNA
<213> ORGANISM: Artificial Sequence
<220> FEATURE:
<223> OTHER INFORMATION: Primer

<400> SEQUENCE: 756
cctattatca gcacccggtt gt                                                 22

<210> SEQ ID NO 757
<211> LENGTH: 27
<212> TYPE: DNA
<213> ORGANISM: Artificial Sequence
<220> FEATURE:
<223> OTHER INFORMATION: Primer

<400> SEQUENCE: 757
cgaggtagaa gaaagcatcc atgaaat                                            27

<210> SEQ ID NO 758
<211> LENGTH: 23
<212> TYPE: DNA
<213> ORGANISM: Artificial Sequence
<220> FEATURE:
<223> OTHER INFORMATION: Primer

<400> SEQUENCE: 758
catactccat atggctggcc ttc                                                23

<210> SEQ ID NO 759
<211> LENGTH: 26
<212> TYPE: DNA
<213> ORGANISM: Artificial Sequence
<220> FEATURE:
<223> OTHER INFORMATION: Primer

<400> SEQUENCE: 759
tctacatctg actgcacaaa caaaga                                             26

<210> SEQ ID NO 760
<211> LENGTH: 27
<212> TYPE: DNA
<213> ORGANISM: Artificial Sequence
<220> FEATURE:
<223> OTHER INFORMATION: Primer

<400> SEQUENCE: 760
ccatctccat gtagatgaag catcttg                                            27

<210> SEQ ID NO 761
<211> LENGTH: 27
<212> TYPE: DNA
<213> ORGANISM: Artificial Sequence
<220> FEATURE:
<223> OTHER INFORMATION: Primer

<400> SEQUENCE: 761
```
cgaggtagaa gaaagcatcc atgaaat                                           27

<210> SEQ ID NO 762
<211> LENGTH: 26
<212> TYPE: DNA
<213> ORGANISM: Artificial Sequence
<220> FEATURE:
<223> OTHER INFORMATION: Primer

<400> SEQUENCE: 762
ggaaagcgtc tccatcattt tctttg                                            26

<210> SEQ ID NO 763
<211> LENGTH: 27
<212> TYPE: DNA
<213> ORGANISM: Artificial Sequence
<220> FEATURE:
<223> OTHER INFORMATION: Primer

<400> SEQUENCE: 763
attacgagac tgatagcaca tgtttgt                                           27

<210> SEQ ID NO 764
<211> LENGTH: 24
<212> TYPE: DNA
<213> ORGANISM: Artificial Sequence
<220> FEATURE:
<223> OTHER INFORMATION: Primer

<400> SEQUENCE: 764
ggtgatccag actctgacct tttg                                              24

<210> SEQ ID NO 765
<211> LENGTH: 26
<212> TYPE: DNA
<213> ORGANISM: Artificial Sequence
<220> FEATURE:
<223> OTHER INFORMATION: Primer

<400> SEQUENCE: 765
tctacatctg actgcacaaa caaaga                                            26

<210> SEQ ID NO 766
<211> LENGTH: 24
<212> TYPE: DNA
<213> ORGANISM: Artificial Sequence
<220> FEATURE:
<223> OTHER INFORMATION: Primer

<400> SEQUENCE: 766
ggtgatccag actctgacct tttg                                              24

<210> SEQ ID NO 767
<211> LENGTH: 23
<212> TYPE: DNA
<213> ORGANISM: Artificial Sequence
<220> FEATURE:
<223> OTHER INFORMATION: Primer

<400> SEQUENCE: 767
cggctgttca cagagagcat aat                                               23

<210> SEQ ID NO 768
<211> LENGTH: 19
<212> TYPE: DNA

```
<213> ORGANISM: Artificial Sequence
<220> FEATURE:
<223> OTHER INFORMATION: Primer

<400> SEQUENCE: 768
aaatacggct gcaccgagt                                                    19

<210> SEQ ID NO 769
<211> LENGTH: 27
<212> TYPE: DNA
<213> ORGANISM: Artificial Sequence
<220> FEATURE:
<223> OTHER INFORMATION: Primer

<400> SEQUENCE: 769
attacgagac tgatagcaca tgtttgt                                           27

<210> SEQ ID NO 770
<211> LENGTH: 21
<212> TYPE: DNA
<213> ORGANISM: Artificial Sequence
<220> FEATURE:
<223> OTHER INFORMATION: Primer

<400> SEQUENCE: 770
catggttcca ccagcgttat t                                                 21

<210> SEQ ID NO 771
<211> LENGTH: 26
<212> TYPE: DNA
<213> ORGANISM: Artificial Sequence
<220> FEATURE:
<223> OTHER INFORMATION: Primer

<400> SEQUENCE: 771
gggtgacttt tatttacacc ctagtt                                            26

<210> SEQ ID NO 772
<211> LENGTH: 26
<212> TYPE: DNA
<213> ORGANISM: Artificial Sequence
<220> FEATURE:
<223> OTHER INFORMATION: Primer

<400> SEQUENCE: 772
catcagtgct aacaacctta gacact                                            26

<210> SEQ ID NO 773
<211> LENGTH: 27
<212> TYPE: DNA
<213> ORGANISM: Artificial Sequence
<220> FEATURE:
<223> OTHER INFORMATION: Primer

<400> SEQUENCE: 773
attacgagac tgatagcaca tgtttgt                                           27

<210> SEQ ID NO 774
<211> LENGTH: 18
<212> TYPE: DNA
<213> ORGANISM: Artificial Sequence
<220> FEATURE:
<223> OTHER INFORMATION: Primer

<400> SEQUENCE: 774
tctttgctcg cagctcgt                                                     18
```

```
<210> SEQ ID NO 775
<211> LENGTH: 26
<212> TYPE: DNA
<213> ORGANISM: Artificial Sequence
<220> FEATURE:
<223> OTHER INFORMATION: Primer

<400> SEQUENCE: 775
tctacatctg actgcacaaa caaaga                                          26

<210> SEQ ID NO 776
<211> LENGTH: 26
<212> TYPE: DNA
<213> ORGANISM: Artificial Sequence
<220> FEATURE:
<223> OTHER INFORMATION: Primer

<400> SEQUENCE: 776
catcagtgct aacaaccttn gacact                                          26

<210> SEQ ID NO 777
<211> LENGTH: 23
<212> TYPE: DNA
<213> ORGANISM: Artificial Sequence
<220> FEATURE:
<223> OTHER INFORMATION: Primer

<400> SEQUENCE: 777
cggctgttca cagagagcat aat                                             23

<210> SEQ ID NO 778
<211> LENGTH: 26
<212> TYPE: DNA
<213> ORGANISM: Artificial Sequence
<220> FEATURE:
<223> OTHER INFORMATION: Primer

<400> SEQUENCE: 778
ggaaagcgtc tccatcattt tctttg                                          26

<210> SEQ ID NO 779
<211> LENGTH: 23
<212> TYPE: DNA
<213> ORGANISM: Artificial Sequence
<220> FEATURE:
<223> OTHER INFORMATION: Primer

<400> SEQUENCE: 779
cggctgttca cagagagcat aat                                             23

<210> SEQ ID NO 780
<211> LENGTH: 25
<212> TYPE: DNA
<213> ORGANISM: Artificial Sequence
<220> FEATURE:
<223> OTHER INFORMATION: Primer

<400> SEQUENCE: 780
cccgtacgtc tactaactac tgctt                                           25

<210> SEQ ID NO 781
<211> LENGTH: 27
<212> TYPE: DNA
<213> ORGANISM: Artificial Sequence
<220> FEATURE:
```

<223> OTHER INFORMATION: Primer

<400> SEQUENCE: 781
attacgagac tgatagcaca tgtttgt                              27

<210> SEQ ID NO 782
<211> LENGTH: 22
<212> TYPE: DNA
<213> ORGANISM: Artificial Sequence
<220> FEATURE:
<223> OTHER INFORMATION: Primer

<400> SEQUENCE: 782
atcatgatgg ctgtatgtgc ca                                   22

<210> SEQ ID NO 783
<211> LENGTH: 23
<212> TYPE: DNA
<213> ORGANISM: Artificial Sequence
<220> FEATURE:
<223> OTHER INFORMATION: Primer

<400> SEQUENCE: 783
cggctgttca cagagagcat aat                                  23

<210> SEQ ID NO 784
<211> LENGTH: 24
<212> TYPE: DNA
<213> ORGANISM: Artificial Sequence
<220> FEATURE:
<223> OTHER INFORMATION: Primer

<400> SEQUENCE: 784
ggtgatccag actctgacct tttg                                 24

<210> SEQ ID NO 785
<211> LENGTH: 23
<212> TYPE: DNA
<213> ORGANISM: Artificial Sequence
<220> FEATURE:
<223> OTHER INFORMATION: Primer

<400> SEQUENCE: 785
cggctgttca cagagagcat aat                                  23

<210> SEQ ID NO 786
<211> LENGTH: 26
<212> TYPE: DNA
<213> ORGANISM: Artificial Sequence
<220> FEATURE:
<223> OTHER INFORMATION: Primer

<400> SEQUENCE: 786
catcagtgct aacaacctta gacact                               26

<210> SEQ ID NO 787
<211> LENGTH: 23
<212> TYPE: DNA
<213> ORGANISM: Artificial Sequence
<220> FEATURE:
<223> OTHER INFORMATION: Primer

<400> SEQUENCE: 787
cggctgttca cagagagcat aat                                  23

```
<210> SEQ ID NO 788
<211> LENGTH: 19
<212> TYPE: DNA
<213> ORGANISM: Artificial Sequence
<220> FEATURE:
<223> OTHER INFORMATION: Primer

<400> SEQUENCE: 788
ctgagaagcc ctgcccttc                                              19

<210> SEQ ID NO 789
<211> LENGTH: 26
<212> TYPE: DNA
<213> ORGANISM: Artificial Sequence
<220> FEATURE:
<223> OTHER INFORMATION: Primer

<400> SEQUENCE: 789
tctacatctg actgcacaaa caaaga                                      26

<210> SEQ ID NO 790
<211> LENGTH: 18
<212> TYPE: DNA
<213> ORGANISM: Artificial Sequence
<220> FEATURE:
<223> OTHER INFORMATION: Primer

<400> SEQUENCE: 790
tctttgctcg cagctcgt                                               18

<210> SEQ ID NO 791
<211> LENGTH: 27
<212> TYPE: DNA
<213> ORGANISM: Artificial Sequence
<220> FEATURE:
<223> OTHER INFORMATION: Primer

<400> SEQUENCE: 791
attacgagac tgatagcaca tgtttgt                                     27

<210> SEQ ID NO 792
<211> LENGTH: 19
<212> TYPE: DNA
<213> ORGANISM: Artificial Sequence
<220> FEATURE:
<223> OTHER INFORMATION: Primer

<400> SEQUENCE: 792
aaatacggct gcaccgagt                                              19

<210> SEQ ID NO 793
<211> LENGTH: 27
<212> TYPE: DNA
<213> ORGANISM: Artificial Sequence
<220> FEATURE:
<223> OTHER INFORMATION: Primer

<400> SEQUENCE: 793
cgaggtagaa gaaagcatcc atgaaat                                     27

<210> SEQ ID NO 794
<211> LENGTH: 28
<212> TYPE: DNA
<213> ORGANISM: Artificial Sequence
<220> FEATURE:
<223> OTHER INFORMATION: Primer
```

<400> SEQUENCE: 794
tcattgtgaa atgtaaagac cactaccc                                      28

<210> SEQ ID NO 795
<211> LENGTH: 27
<212> TYPE: DNA
<213> ORGANISM: Artificial Sequence
<220> FEATURE:
<223> OTHER INFORMATION: Primer

<400> SEQUENCE: 795
attacgagac tgatagcaca tgtttgt                                       27

<210> SEQ ID NO 796
<211> LENGTH: 19
<212> TYPE: DNA
<213> ORGANISM: Artificial Sequence
<220> FEATURE:
<223> OTHER INFORMATION: Primer

<400> SEQUENCE: 796
ctgagaagcc ctgcccttc                                                19

<210> SEQ ID NO 797
<211> LENGTH: 25
<212> TYPE: DNA
<213> ORGANISM: Artificial Sequence
<220> FEATURE:
<223> OTHER INFORMATION: Primer

<400> SEQUENCE: 797
catctactat catgcaggca gttct                                         25

<210> SEQ ID NO 798
<211> LENGTH: 27
<212> TYPE: DNA
<213> ORGANISM: Artificial Sequence
<220> FEATURE:
<223> OTHER INFORMATION: Primer

<400> SEQUENCE: 798
actctgtatt gcaaaccaga taccttg                                       27

<210> SEQ ID NO 799
<211> LENGTH: 24
<212> TYPE: DNA
<213> ORGANISM: Artificial Sequence
<220> FEATURE:
<223> OTHER INFORMATION: Primer

<400> SEQUENCE: 799
ggaaacccag tgtatgggct taat                                          24

<210> SEQ ID NO 800
<211> LENGTH: 26
<212> TYPE: DNA
<213> ORGANISM: Artificial Sequence
<220> FEATURE:
<223> OTHER INFORMATION: Primer

<400> SEQUENCE: 800
ggaaagcgtc tccatcattt tctttg                                        26

<210> SEQ ID NO 801
<211> LENGTH: 23

```
<212> TYPE: DNA
<213> ORGANISM: Artificial Sequence
<220> FEATURE:
<223> OTHER INFORMATION: Primer

<400> SEQUENCE: 801
cggctgttca cagagagcat aat                                           23

<210> SEQ ID NO 802
<211> LENGTH: 22
<212> TYPE: DNA
<213> ORGANISM: Artificial Sequence
<220> FEATURE:
<223> OTHER INFORMATION: Primer

<400> SEQUENCE: 802
atcatgatgg ctgtatgtgc ca                                            22

<210> SEQ ID NO 803
<211> LENGTH: 26
<212> TYPE: DNA
<213> ORGANISM: Artificial Sequence
<220> FEATURE:
<223> OTHER INFORMATION: Primer

<400> SEQUENCE: 803
tctacatctg actgcacaaa caaaga                                        26

<210> SEQ ID NO 804
<211> LENGTH: 21
<212> TYPE: DNA
<213> ORGANISM: Artificial Sequence
<220> FEATURE:
<223> OTHER INFORMATION: Primer

<400> SEQUENCE: 804
catggttcca ccagcgttat t                                             21

<210> SEQ ID NO 805
<211> LENGTH: 26
<212> TYPE: DNA
<213> ORGANISM: Artificial Sequence
<220> FEATURE:
<223> OTHER INFORMATION: Primer

<400> SEQUENCE: 805
tctacatctg actgcacaaa caaaga                                        26

<210> SEQ ID NO 806
<211> LENGTH: 22
<212> TYPE: DNA
<213> ORGANISM: Artificial Sequence
<220> FEATURE:
<223> OTHER INFORMATION: Primer

<400> SEQUENCE: 806
atcatgatgg ctgtatgtgc ca                                            22

<210> SEQ ID NO 807
<211> LENGTH: 23
<212> TYPE: DNA
<213> ORGANISM: Artificial Sequence
<220> FEATURE:
<223> OTHER INFORMATION: Primer

<400> SEQUENCE: 807
```
cggctgttca cagagagcat aat                                              23

<210> SEQ ID NO 808
<211> LENGTH: 18
<212> TYPE: DNA
<213> ORGANISM: Artificial Sequence
<220> FEATURE:
<223> OTHER INFORMATION: Primer

<400> SEQUENCE: 808
tctttgctcg cagctcgt                                                    18

<210> SEQ ID NO 809
<211> LENGTH: 26
<212> TYPE: DNA
<213> ORGANISM: Artificial Sequence
<220> FEATURE:
<223> OTHER INFORMATION: Primer

<400> SEQUENCE: 809
tctacatctg actgcacaaa caaaga                                           26

<210> SEQ ID NO 810
<211> LENGTH: 19
<212> TYPE: DNA
<213> ORGANISM: Artificial Sequence
<220> FEATURE:
<223> OTHER INFORMATION: Primer

<400> SEQUENCE: 810
ctgagaagcc ctgcccttc                                                   19

<210> SEQ ID NO 811
<211> LENGTH: 23
<212> TYPE: DNA
<213> ORGANISM: Artificial Sequence
<220> FEATURE:
<223> OTHER INFORMATION: Primer

<400> SEQUENCE: 811
cggctgttca cagagagcat aat                                              23

<210> SEQ ID NO 812
<211> LENGTH: 20
<212> TYPE: DNA
<213> ORGANISM: Artificial Sequence
<220> FEATURE:
<223> OTHER INFORMATION: Primer

<400> SEQUENCE: 812
gctttggtat gggtctcggt                                                  20

<210> SEQ ID NO 813
<211> LENGTH: 26
<212> TYPE: DNA
<213> ORGANISM: Artificial Sequence
<220> FEATURE:
<223> OTHER INFORMATION: Primer

<400> SEQUENCE: 813
attatttgaa ctaccagaca gcggtt                                           26

<210> SEQ ID NO 814
<211> LENGTH: 20
<212> TYPE: DNA
<213> ORGANISM: Artificial Sequence

```
<220> FEATURE:
<223> OTHER INFORMATION: Primer

<400> SEQUENCE: 814
gctttggtat gggtctcggt                                                    20

<210> SEQ ID NO 815
<211> LENGTH: 23
<212> TYPE: DNA
<213> ORGANISM: Artificial Sequence
<220> FEATURE:
<223> OTHER INFORMATION: Primer

<400> SEQUENCE: 815
cggctgttca cagagagcat aat                                                23

<210> SEQ ID NO 816
<211> LENGTH: 28
<212> TYPE: DNA
<213> ORGANISM: Artificial Sequence
<220> FEATURE:
<223> OTHER INFORMATION: Primer

<400> SEQUENCE: 816
tcattgtgaa atgtaaagac cactaccc                                           28

<210> SEQ ID NO 817
<211> LENGTH: 26
<212> TYPE: DNA
<213> ORGANISM: Artificial Sequence
<220> FEATURE:
<223> OTHER INFORMATION: Primer

<400> SEQUENCE: 817
attatttgaa ctaccagaca gcggtt                                             26

<210> SEQ ID NO 818
<211> LENGTH: 26
<212> TYPE: DNA
<213> ORGANISM: Artificial Sequence
<220> FEATURE:
<223> OTHER INFORMATION: Primer

<400> SEQUENCE: 818
ggaaagcgtc tccatcattt tctttg                                             26

<210> SEQ ID NO 819
<211> LENGTH: 27
<212> TYPE: DNA
<213> ORGANISM: Artificial Sequence
<220> FEATURE:
<223> OTHER INFORMATION: Primer

<400> SEQUENCE: 819
cgaggtagaa gaaagcatcc atgaaat                                            27

<210> SEQ ID NO 820
<211> LENGTH: 25
<212> TYPE: DNA
<213> ORGANISM: Artificial Sequence
<220> FEATURE:
<223> OTHER INFORMATION: Primer

<400> SEQUENCE: 820
tccaccgatg ttatggaatc gtttt                                              25
```

```
<210> SEQ ID NO 821
<211> LENGTH: 26
<212> TYPE: DNA
<213> ORGANISM: Artificial Sequence
<220> FEATURE:
<223> OTHER INFORMATION: Primer

<400> SEQUENCE: 821
tctacatctg actgcacaaa caaaga                                         26

<210> SEQ ID NO 822
<211> LENGTH: 19
<212> TYPE: DNA
<213> ORGANISM: Artificial Sequence
<220> FEATURE:
<223> OTHER INFORMATION: Primer

<400> SEQUENCE: 822
aaatacggct gcaccgagt                                                 19

<210> SEQ ID NO 823
<211> LENGTH: 23
<212> TYPE: DNA
<213> ORGANISM: Artificial Sequence
<220> FEATURE:
<223> OTHER INFORMATION: Primer

<400> SEQUENCE: 823
cggctgttca cagagagcat aat                                            23

<210> SEQ ID NO 824
<211> LENGTH: 21
<212> TYPE: DNA
<213> ORGANISM: Artificial Sequence
<220> FEATURE:
<223> OTHER INFORMATION: Primer

<400> SEQUENCE: 824
catggttcca ccagcgttat t                                              21

<210> SEQ ID NO 825
<211> LENGTH: 28
<212> TYPE: DNA
<213> ORGANISM: Artificial Sequence
<220> FEATURE:
<223> OTHER INFORMATION: Primer

<400> SEQUENCE: 825
ggagaaacgt tagaaaaaca atgcaaca                                       28

<210> SEQ ID NO 826
<211> LENGTH: 25
<212> TYPE: DNA
<213> ORGANISM: Artificial Sequence
<220> FEATURE:
<223> OTHER INFORMATION: Primer

<400> SEQUENCE: 826
tccaccgatg ttatggaatc gtttt                                          25

<210> SEQ ID NO 827
<211> LENGTH: 27
<212> TYPE: DNA
<213> ORGANISM: Artificial Sequence
<220> FEATURE:
<223> OTHER INFORMATION: Primer
```

<400> SEQUENCE: 827
cgaggtagaa gaaagcatcc atgaaat                                27

<210> SEQ ID NO 828
<211> LENGTH: 20
<212> TYPE: DNA
<213> ORGANISM: Artificial Sequence
<220> FEATURE:
<223> OTHER INFORMATION: Primer

<400> SEQUENCE: 828
gctttggtat gggtctcggt                                        20

<210> SEQ ID NO 829
<211> LENGTH: 26
<212> TYPE: DNA
<213> ORGANISM: Artificial Sequence
<220> FEATURE:
<223> OTHER INFORMATION: Primer

<400> SEQUENCE: 829
attatttgaa ctaccagaca gcggtt                                 26

<210> SEQ ID NO 830
<211> LENGTH: 27
<212> TYPE: DNA
<213> ORGANISM: Artificial Sequence
<220> FEATURE:
<223> OTHER INFORMATION: Primer

<400> SEQUENCE: 830
gctactagag gttatactat ccccact                                27

<210> SEQ ID NO 831
<211> LENGTH: 23
<212> TYPE: DNA
<213> ORGANISM: Artificial Sequence
<220> FEATURE:
<223> OTHER INFORMATION: Primer

<400> SEQUENCE: 831
cggctgttca cagagagcat aat                                    23

<210> SEQ ID NO 832
<211> LENGTH: 27
<212> TYPE: DNA
<213> ORGANISM: Artificial Sequence
<220> FEATURE:
<223> OTHER INFORMATION: Primer

<400> SEQUENCE: 832
actctgtatt gcaaaccaga taccttg                                27

<210> SEQ ID NO 833
<211> LENGTH: 26
<212> TYPE: DNA
<213> ORGANISM: Artificial Sequence
<220> FEATURE:
<223> OTHER INFORMATION: Primer

<400> SEQUENCE: 833
attatttgaa ctaccagaca gcggtt                                 26

<210> SEQ ID NO 834

```
<211> LENGTH: 28
<212> TYPE: DNA
<213> ORGANISM: Artificial Sequence
<220> FEATURE:
<223> OTHER INFORMATION: Primer

<400> SEQUENCE: 834
tcattgtgaa atgtaaagac cactaccc                                28

<210> SEQ ID NO 835
<211> LENGTH: 27
<212> TYPE: DNA
<213> ORGANISM: Artificial Sequence
<220> FEATURE:
<223> OTHER INFORMATION: Primer

<400> SEQUENCE: 835
cattagtgca attaaaatgc ccacctt                                 27

<210> SEQ ID NO 836
<211> LENGTH: 28
<212> TYPE: DNA
<213> ORGANISM: Artificial Sequence
<220> FEATURE:
<223> OTHER INFORMATION: Primer

<400> SEQUENCE: 836
tcattgtgaa atgtaaagac cactaccc                                28

<210> SEQ ID NO 837
<211> LENGTH: 26
<212> TYPE: DNA
<213> ORGANISM: Artificial Sequence
<220> FEATURE:
<223> OTHER INFORMATION: Primer

<400> SEQUENCE: 837
tctacatctg actgcacaaa caaaga                                  26

<210> SEQ ID NO 838
<211> LENGTH: 27
<212> TYPE: DNA
<213> ORGANISM: Artificial Sequence
<220> FEATURE:
<223> OTHER INFORMATION: Primer

<400> SEQUENCE: 838
actctgtatt gcaaaccaga taccttg                                 27

<210> SEQ ID NO 839
<211> LENGTH: 26
<212> TYPE: DNA
<213> ORGANISM: Artificial Sequence
<220> FEATURE:
<223> OTHER INFORMATION: Primer

<400> SEQUENCE: 839
aaaatatatg ggaagtgcat gtgggt                                  26

<210> SEQ ID NO 840
<211> LENGTH: 20
<212> TYPE: DNA
<213> ORGANISM: Artificial Sequence
<220> FEATURE:
<223> OTHER INFORMATION: Primer

<400> SEQUENCE: 840
```

-continued gctttggtat gggtctcggt                                                  20

<210> SEQ ID NO 841
<211> LENGTH: 27
<212> TYPE: DNA
<213> ORGANISM: Artificial Sequence
<220> FEATURE:
<223> OTHER INFORMATION: Primer

<400> SEQUENCE: 841
cgttcgctat tgctatctgt gtcatta                                          27

<210> SEQ ID NO 842
<211> LENGTH: 27
<212> TYPE: DNA
<213> ORGANISM: Artificial Sequence
<220> FEATURE:
<223> OTHER INFORMATION: Primer

<400> SEQUENCE: 842
gccaaatatt gtgcatgagc gttaatc                                          27

<210> SEQ ID NO 843
<211> LENGTH: 24
<212> TYPE: DNA
<213> ORGANISM: Artificial Sequence
<220> FEATURE:
<223> OTHER INFORMATION: Primer

<400> SEQUENCE: 843
aacattccta cctcagcaga acac                                             24

<210> SEQ ID NO 844
<211> LENGTH: 23
<212> TYPE: DNA
<213> ORGANISM: Artificial Sequence
<220> FEATURE:
<223> OTHER INFORMATION: Primer

<400> SEQUENCE: 844
tgggtggacc acaagtatga aaa                                              23

<210> SEQ ID NO 845
<211> LENGTH: 27
<212> TYPE: DNA
<213> ORGANISM: Artificial Sequence
<220> FEATURE:
<223> OTHER INFORMATION: Primer

<400> SEQUENCE: 845
ggtacagata acagggaatg catttct                                          27

<210> SEQ ID NO 846
<211> LENGTH: 26
<212> TYPE: DNA
<213> ORGANISM: Artificial Sequence
<220> FEATURE:
<223> OTHER INFORMATION: Primer

<400> SEQUENCE: 846
gacattctcc tgcttttacc tggtta                                           26

<210> SEQ ID NO 847
<211> LENGTH: 27
<212> TYPE: DNA

<213> ORGANISM: Artificial Sequence
<220> FEATURE:
<223> OTHER INFORMATION: Primer

<400> SEQUENCE: 847
gctatgtatt tcagctgcaa gtatgct                      27

<210> SEQ ID NO 848
<211> LENGTH: 25
<212> TYPE: DNA
<213> ORGANISM: Artificial Sequence
<220> FEATURE:
<223> OTHER INFORMATION: Primer

<400> SEQUENCE: 848
cattctggtg tttctccatc aacct                        25

<210> SEQ ID NO 849
<211> LENGTH: 18
<212> TYPE: DNA
<213> ORGANISM: Artificial Sequence
<220> FEATURE:
<223> OTHER INFORMATION: Primer

<400> SEQUENCE: 849
cgtggtgtgc aactgcaa                                18

<210> SEQ ID NO 850
<211> LENGTH: 28
<212> TYPE: DNA
<213> ORGANISM: Artificial Sequence
<220> FEATURE:
<223> OTHER INFORMATION: Primer

<400> SEQUENCE: 850
ctgttttggt caaatggaaa tgcattag                     28

<210> SEQ ID NO 851
<211> LENGTH: 25
<212> TYPE: DNA
<213> ORGANISM: Artificial Sequence
<220> FEATURE:
<223> OTHER INFORMATION: Primer

<400> SEQUENCE: 851
gcaataacca ttcagggttc caatt                        25

<210> SEQ ID NO 852
<211> LENGTH: 22
<212> TYPE: DNA
<213> ORGANISM: Artificial Sequence
<220> FEATURE:
<223> OTHER INFORMATION: Primer

<400> SEQUENCE: 852
agtattgaca accttcgcca ca                           22

<210> SEQ ID NO 853
<211> LENGTH: 20
<212> TYPE: DNA
<213> ORGANISM: Artificial Sequence
<220> FEATURE:
<223> OTHER INFORMATION: Primer

<400> SEQUENCE: 853
ggtgtattcc gtgccagaca                              20

<210> SEQ ID NO 854
<211> LENGTH: 19
<212> TYPE: DNA
<213> ORGANISM: Artificial Sequence
<220> FEATURE:
<223> OTHER INFORMATION: Primer

<400> SEQUENCE: 854
gtacactgcc gccatgttc                                                  19

<210> SEQ ID NO 855
<211> LENGTH: 20
<212> TYPE: DNA
<213> ORGANISM: Artificial Sequence
<220> FEATURE:
<223> OTHER INFORMATION: Primer

<400> SEQUENCE: 855
ggtgtattcc gtgccagaca                                                 20

<210> SEQ ID NO 856
<211> LENGTH: 21
<212> TYPE: DNA
<213> ORGANISM: Artificial Sequence
<220> FEATURE:
<223> OTHER INFORMATION: Primer

<400> SEQUENCE: 856
ggtcgcggtg gtgtttgata a                                               21

<210> SEQ ID NO 857
<211> LENGTH: 25
<212> TYPE: DNA
<213> ORGANISM: Artificial Sequence
<220> FEATURE:
<223> OTHER INFORMATION: Primer

<400> SEQUENCE: 857
caccaccttg caggacatta caata                                           25

<210> SEQ ID NO 858
<211> LENGTH: 28
<212> TYPE: DNA
<213> ORGANISM: Artificial Sequence
<220> FEATURE:
<223> OTHER INFORMATION: CTGTTTTGGTCAAATGGAAATGCATTAG

<400> SEQUENCE: 858
ctgttttggt caaatggaaa tgcattag                                        28

<210> SEQ ID NO 859
<211> LENGTH: 22
<212> TYPE: DNA
<213> ORGANISM: Artificial Sequence
<220> FEATURE:
<223> OTHER INFORMATION: Primer

<400> SEQUENCE: 859
cacagtaaca gtacaggcca ca                                              22

<210> SEQ ID NO 860
<211> LENGTH: 21
<212> TYPE: DNA
<213> ORGANISM: Artificial Sequence
<220> FEATURE:

```
<223> OTHER INFORMATION: Primer

<400> SEQUENCE: 860
catggttcca ccagcgttat t                                          21

<210> SEQ ID NO 861
<211> LENGTH: 22
<212> TYPE: DNA
<213> ORGANISM: Artificial Sequence
<220> FEATURE:
<223> OTHER INFORMATION: Primer

<400> SEQUENCE: 861
cacagtaaca gtacaggcca ca                                         22

<210> SEQ ID NO 862
<211> LENGTH: 22
<212> TYPE: DNA
<213> ORGANISM: Artificial Sequence
<220> FEATURE:
<223> OTHER INFORMATION: Primer

<400> SEQUENCE: 862
atcatgatgg ctgtatgtgc ca                                         22

<210> SEQ ID NO 863
<211> LENGTH: 26
<212> TYPE: DNA
<213> ORGANISM: Artificial Sequence
<220> FEATURE:
<223> OTHER INFORMATION: Primer

<400> SEQUENCE: 863
catgcagtta atcaccaaca tcaact                                     26

<210> SEQ ID NO 864
<211> LENGTH: 23
<212> TYPE: DNA
<213> ORGANISM: Artificial Sequence
<220> FEATURE:
<223> OTHER INFORMATION: Primer

<400> SEQUENCE: 864
tgctgtagtt gtcgcagagt atc                                        23

<210> SEQ ID NO 865
<211> LENGTH: 25
<212> TYPE: DNA
<213> ORGANISM: Artificial Sequence
<220> FEATURE:
<223> OTHER INFORMATION: Primer

<400> SEQUENCE: 865
caccaccttg caggacatta caata                                      25

<210> SEQ ID NO 866
<211> LENGTH: 27
<212> TYPE: DNA
<213> ORGANISM: Artificial Sequence
<220> FEATURE:
<223> OTHER INFORMATION: Primer

<400> SEQUENCE: 866
ctgtcctgta tagcttcctg ctatttt                                    27
```

```
<210> SEQ ID NO 867
<211> LENGTH: 18
<212> TYPE: DNA
<213> ORGANISM: Artificial Sequence
<220> FEATURE:
<223> OTHER INFORMATION: Primer

<400> SEQUENCE: 867
cgtggtgtgc aactgcaa                                                 18

<210> SEQ ID NO 868
<211> LENGTH: 23
<212> TYPE: DNA
<213> ORGANISM: Artificial Sequence
<220> FEATURE:
<223> OTHER INFORMATION: Primer

<400> SEQUENCE: 868
cactgtgtcg cctgtttgtt tat                                           23

<210> SEQ ID NO 869
<211> LENGTH: 18
<212> TYPE: DNA
<213> ORGANISM: Artificial Sequence
<220> FEATURE:
<223> OTHER INFORMATION: Primer

<400> SEQUENCE: 869
cgtggtgtgc aactgcaa                                                 18

<210> SEQ ID NO 870
<211> LENGTH: 19
<212> TYPE: DNA
<213> ORGANISM: Artificial Sequence
<220> FEATURE:
<223> OTHER INFORMATION: Primer

<400> SEQUENCE: 870
aaatacggct gcaccgagt                                                19

<210> SEQ ID NO 871
<211> LENGTH: 31
<212> TYPE: DNA
<213> ORGANISM: Artificial Sequence
<220> FEATURE:
<223> OTHER INFORMATION: Primer

<400> SEQUENCE: 871
attagatggg tatgcaataa gtttagatag g                                  31

<210> SEQ ID NO 872
<211> LENGTH: 28
<212> TYPE: DNA
<213> ORGANISM: Artificial Sequence
<220> FEATURE:
<223> OTHER INFORMATION: Primer

<400> SEQUENCE: 872
ctgttttggt caaatggaaa tgcattag                                      28

<210> SEQ ID NO 873
<211> LENGTH: 26
<212> TYPE: DNA
<213> ORGANISM: Artificial Sequence
<220> FEATURE:
<223> OTHER INFORMATION: Primer
```

-continued

<400> SEQUENCE: 873
acaacgttta aatgtgttac aggaca                              26

<210> SEQ ID NO 874
<211> LENGTH: 19
<212> TYPE: DNA
<213> ORGANISM: Artificial Sequence
<220> FEATURE:
<223> OTHER INFORMATION: Primer

<400> SEQUENCE: 874
aaatacggct gcaccgagt                                      19

<210> SEQ ID NO 875
<211> LENGTH: 26
<212> TYPE: DNA
<213> ORGANISM: Artificial Sequence
<220> FEATURE:
<223> OTHER INFORMATION: Primer

<400> SEQUENCE: 875
acaacgttta aatgtgttac aggaca                              26

<210> SEQ ID NO 876
<211> LENGTH: 22
<212> TYPE: DNA
<213> ORGANISM: Artificial Sequence
<220> FEATURE:
<223> OTHER INFORMATION: Primer

<400> SEQUENCE: 876
atcatgatgg ctgtatgtgc ca                                  22

<210> SEQ ID NO 877
<211> LENGTH: 18
<212> TYPE: DNA
<213> ORGANISM: Artificial Sequence
<220> FEATURE:
<223> OTHER INFORMATION: Primer

<400> SEQUENCE: 877
cgtggtgtgc aactgcaa                                       18

<210> SEQ ID NO 878
<211> LENGTH: 22
<212> TYPE: DNA
<213> ORGANISM: Artificial Sequence
<220> FEATURE:
<223> OTHER INFORMATION: Primer

<400> SEQUENCE: 878
atcatgatgg ctgtatgtgc ca                                  22

<210> SEQ ID NO 879
<211> LENGTH: 18
<212> TYPE: DNA
<213> ORGANISM: Artificial Sequence
<220> FEATURE:
<223> OTHER INFORMATION: Primer

<400> SEQUENCE: 879
cgtggtgtgc aactgcaa                                       18

<210> SEQ ID NO 880
<211> LENGTH: 18

```
<212> TYPE: DNA
<213> ORGANISM: Artificial Sequence
<220> FEATURE:
<223> OTHER INFORMATION: Primer

<400> SEQUENCE: 880
tctttgctcg cagctcgt                                          18

<210> SEQ ID NO 881
<211> LENGTH: 18
<212> TYPE: DNA
<213> ORGANISM: Artificial Sequence
<220> FEATURE:
<223> OTHER INFORMATION: Primer

<400> SEQUENCE: 881
cgtggtgtgc aactgcaa                                          18

<210> SEQ ID NO 882
<211> LENGTH: 24
<212> TYPE: DNA
<213> ORGANISM: Artificial Sequence
<220> FEATURE:
<223> OTHER INFORMATION: Primer

<400> SEQUENCE: 882
ggtgatccag actctgacct tttg                                   24

<210> SEQ ID NO 883
<211> LENGTH: 26
<212> TYPE: DNA
<213> ORGANISM: Artificial Sequence
<220> FEATURE:
<223> OTHER INFORMATION: Primer

<400> SEQUENCE: 883
acaacgttta aatgtgttac aggaca                                 26

<210> SEQ ID NO 884
<211> LENGTH: 18
<212> TYPE: DNA
<213> ORGANISM: Artificial Sequence
<220> FEATURE:
<223> OTHER INFORMATION: Primer

<400> SEQUENCE: 884
tctttgctcg cagctcgt                                          18

<210> SEQ ID NO 885
<211> LENGTH: 18
<212> TYPE: DNA
<213> ORGANISM: Artificial Sequence
<220> FEATURE:
<223> OTHER INFORMATION: Primer

<400> SEQUENCE: 885
cgtggtgtgc aactgcaa                                          18

<210> SEQ ID NO 886
<211> LENGTH: 19
<212> TYPE: DNA
<213> ORGANISM: Artificial Sequence
<220> FEATURE:
<223> OTHER INFORMATION: Primer

<400> SEQUENCE: 886
```

```
ctgagaagcc ctgcccttc                                                    19

<210> SEQ ID NO 887
<211> LENGTH: 18
<212> TYPE: DNA
<213> ORGANISM: Artificial Sequence
<220> FEATURE:
<223> OTHER INFORMATION: Primer

<400> SEQUENCE: 887
cgtggtgtgc aactgcaa                                                     18

<210> SEQ ID NO 888
<211> LENGTH: 22
<212> TYPE: DNA
<213> ORGANISM: Artificial Sequence
<220> FEATURE:
<223> OTHER INFORMATION: Primer

<400> SEQUENCE: 888
agtattgaca accttcgcca ca                                                22

<210> SEQ ID NO 889
<211> LENGTH: 22
<212> TYPE: DNA
<213> ORGANISM: Artificial Sequence
<220> FEATURE:
<223> OTHER INFORMATION: Primer

<400> SEQUENCE: 889
cacagtaaca gtacaggcca ca                                                22

<210> SEQ ID NO 890
<211> LENGTH: 25
<212> TYPE: DNA
<213> ORGANISM: Artificial Sequence
<220> FEATURE:
<223> OTHER INFORMATION: Primer

<400> SEQUENCE: 890
cgtatccaat gccaggtaca tgaaa                                             25

<210> SEQ ID NO 891
<211> LENGTH: 22
<212> TYPE: DNA
<213> ORGANISM: Artificial Sequence
<220> FEATURE:
<223> OTHER INFORMATION: Primer

<400> SEQUENCE: 891
cacagtaaca gtacaggcca ca                                                22

<210> SEQ ID NO 892
<211> LENGTH: 22
<212> TYPE: DNA
<213> ORGANISM: Artificial Sequence
<220> FEATURE:
<223> OTHER INFORMATION: Primer

<400> SEQUENCE: 892
agtattgaca accttcgcca ca                                                22

<210> SEQ ID NO 893
<211> LENGTH: 22
<212> TYPE: DNA
<213> ORGANISM: Artificial Sequence
```

```
<220> FEATURE:
<223> OTHER INFORMATION: Primer

<400> SEQUENCE: 893
cacagtaaca gtacaggcca ca                                            22

<210> SEQ ID NO 894
<211> LENGTH: 18
<212> TYPE: DNA
<213> ORGANISM: Artificial Sequence
<220> FEATURE:
<223> OTHER INFORMATION: Primer

<400> SEQUENCE: 894
tctttgctcg cagctcgt                                                 18

<210> SEQ ID NO 895
<211> LENGTH: 20
<212> TYPE: DNA
<213> ORGANISM: Artificial Sequence
<220> FEATURE:
<223> OTHER INFORMATION: Primer

<400> SEQUENCE: 895
ctcggactcg gtgtatgcaa                                               20

<210> SEQ ID NO 896
<211> LENGTH: 27
<212> TYPE: DNA
<213> ORGANISM: Artificial Sequence
<220> FEATURE:
<223> OTHER INFORMATION: Primer

<400> SEQUENCE: 896
ctgtcctgta tagcttcctg ctatttt                                       27

<210> SEQ ID NO 897
<211> LENGTH: 18
<212> TYPE: DNA
<213> ORGANISM: Artificial Sequence
<220> FEATURE:
<223> OTHER INFORMATION: Primer

<400> SEQUENCE: 897
cgtggtgtgc aactgcaa                                                 18

<210> SEQ ID NO 898
<211> LENGTH: 21
<212> TYPE: DNA
<213> ORGANISM: Artificial Sequence
<220> FEATURE:
<223> OTHER INFORMATION: Primer

<400> SEQUENCE: 898
catggttcca ccagcgttat t                                             21

<210> SEQ ID NO 899
<211> LENGTH: 18
<212> TYPE: DNA
<213> ORGANISM: Artificial Sequence
<220> FEATURE:
<223> OTHER INFORMATION: Primer

<400> SEQUENCE: 899
cgtggtgtgc aactgcaa                                                 18
```

-continued

```
<210> SEQ ID NO 900
<211> LENGTH: 21
<212> TYPE: DNA
<213> ORGANISM: Artificial Sequence
<220> FEATURE:
<223> OTHER INFORMATION: Primer

<400> SEQUENCE: 900
ggtcgcggtg gtgtttgata a                                              21

<210> SEQ ID NO 901
<211> LENGTH: 25
<212> TYPE: DNA
<213> ORGANISM: Artificial Sequence
<220> FEATURE:
<223> OTHER INFORMATION: Primer

<400> SEQUENCE: 901
caccaccttg caggacatta caata                                          25

<210> SEQ ID NO 902
<211> LENGTH: 20
<212> TYPE: DNA
<213> ORGANISM: Artificial Sequence
<220> FEATURE:
<223> OTHER INFORMATION: Primer

<400> SEQUENCE: 902
gattggcatg cagctagtgg                                                20

<210> SEQ ID NO 903
<211> LENGTH: 25
<212> TYPE: DNA
<213> ORGANISM: Artificial Sequence
<220> FEATURE:
<223> OTHER INFORMATION: Primer

<400> SEQUENCE: 903
caccaccttg caggacatta caata                                          25

<210> SEQ ID NO 904
<211> LENGTH: 23
<212> TYPE: DNA
<213> ORGANISM: Artificial Sequence
<220> FEATURE:
<223> OTHER INFORMATION: Primer

<400> SEQUENCE: 904
tgctgtagtt gtcgcagagt atc                                            23

<210> SEQ ID NO 905
<211> LENGTH: 26
<212> TYPE: DNA
<213> ORGANISM: Artificial Sequence
<220> FEATURE:
<223> OTHER INFORMATION: Primer

<400> SEQUENCE: 905
acaacgttta aatgtgttac aggaca                                         26

<210> SEQ ID NO 906
<211> LENGTH: 24
<212> TYPE: DNA
<213> ORGANISM: Artificial Sequence
<220> FEATURE:
<223> OTHER INFORMATION: Primer
```

```
<400> SEQUENCE: 906
ggtgatccag actctgacct tttg                                          24

<210> SEQ ID NO 907
<211> LENGTH: 26
<212> TYPE: DNA
<213> ORGANISM: Artificial Sequence
<220> FEATURE:
<223> OTHER INFORMATION: Primer

<400> SEQUENCE: 907
acaacgttta aatgtgttac aggaca                                        26

<210> SEQ ID NO 908
<211> LENGTH: 19
<212> TYPE: DNA
<213> ORGANISM: Artificial Sequence
<220> FEATURE:
<223> OTHER INFORMATION: Primer

<400> SEQUENCE: 908
ctgagaagcc ctgcccttc                                                19

<210> SEQ ID NO 909
<211> LENGTH: 22
<212> TYPE: DNA
<213> ORGANISM: Artificial Sequence
<220> FEATURE:
<223> OTHER INFORMATION: Primer

<400> SEQUENCE: 909
cacagtaaca gtacaggcca ca                                            22

<210> SEQ ID NO 910
<211> LENGTH: 19
<212> TYPE: DNA
<213> ORGANISM: Artificial Sequence
<220> FEATURE:
<223> OTHER INFORMATION: Primer

<400> SEQUENCE: 910
aaatacggct gcaccgagt                                                19

<210> SEQ ID NO 911
<211> LENGTH: 20
<212> TYPE: DNA
<213> ORGANISM: Artificial Sequence
<220> FEATURE:
<223> OTHER INFORMATION: Primer

<400> SEQUENCE: 911
ggtgtattcc gtgccagaca                                               20

<210> SEQ ID NO 912
<211> LENGTH: 28
<212> TYPE: DNA
<213> ORGANISM: Artificial Sequence
<220> FEATURE:
<223> OTHER INFORMATION: Primer

<400> SEQUENCE: 912
ctgttttggt caaatggaaa tgcattag                                      28

<210> SEQ ID NO 913
```

```
<211> LENGTH: 22
<212> TYPE: DNA
<213> ORGANISM: Artificial Sequence
<220> FEATURE:
<223> OTHER INFORMATION: Primer

<400> SEQUENCE: 913
cacagtaaca gtacaggcca ca                                               22

<210> SEQ ID NO 914
<211> LENGTH: 19
<212> TYPE: DNA
<213> ORGANISM: Artificial Sequence
<220> FEATURE:
<223> OTHER INFORMATION: Primer

<400> SEQUENCE: 914
ctgagaagcc ctgcccttc                                                   19

<210> SEQ ID NO 915
<211> LENGTH: 26
<212> TYPE: DNA
<213> ORGANISM: Artificial Sequence
<220> FEATURE:
<223> OTHER INFORMATION: Primer

<400> SEQUENCE: 915
acaacgttta aatgtgttac aggaca                                           26

<210> SEQ ID NO 916
<211> LENGTH: 21
<212> TYPE: DNA
<213> ORGANISM: Artificial Sequence
<220> FEATURE:
<223> OTHER INFORMATION: Primer

<400> SEQUENCE: 916
catggttcca ccagcgttat t                                                21

<210> SEQ ID NO 917
<211> LENGTH: 22
<212> TYPE: DNA
<213> ORGANISM: Artificial Sequence
<220> FEATURE:
<223> OTHER INFORMATION: Primer

<400> SEQUENCE: 917
cacagtaaca gtacaggcca ca                                               22

<210> SEQ ID NO 918
<211> LENGTH: 24
<212> TYPE: DNA
<213> ORGANISM: Artificial Sequence
<220> FEATURE:
<223> OTHER INFORMATION: Primer

<400> SEQUENCE: 918
ggtgatccag actctgacct tttg                                             24

<210> SEQ ID NO 919
<211> LENGTH: 25
<212> TYPE: DNA
<213> ORGANISM: Artificial Sequence
<220> FEATURE:
<223> OTHER INFORMATION: Primer

<400> SEQUENCE: 919
```
caccaccttg caggacatta caata                                                 25

<210> SEQ ID NO 920
<211> LENGTH: 21
<212> TYPE: DNA
<213> ORGANISM: Artificial Sequence
<220> FEATURE:
<223> OTHER INFORMATION: Primer

<400> SEQUENCE: 920
ggtcgcggtg gtgtttgata a                                                     21

<210> SEQ ID NO 921
<211> LENGTH: 25
<212> TYPE: DNA
<213> ORGANISM: Artificial Sequence
<220> FEATURE:
<223> OTHER INFORMATION: Primer

<400> SEQUENCE: 921
ttggtgtggt ttggtgtgtg tatat                                                 25

<210> SEQ ID NO 922
<211> LENGTH: 26
<212> TYPE: DNA
<213> ORGANISM: Artificial Sequence
<220> FEATURE:
<223> OTHER INFORMATION: Primer

<400> SEQUENCE: 922
ctccaatggt gtggtacgta taagaa                                                26

<210> SEQ ID NO 923
<211> LENGTH: 20
<212> TYPE: DNA
<213> ORGANISM: Artificial Sequence
<220> FEATURE:
<223> OTHER INFORMATION: Primer

<400> SEQUENCE: 923
cattttgtgg cgaccgaagt                                                       20

<210> SEQ ID NO 924
<211> LENGTH: 26
<212> TYPE: DNA
<213> ORGANISM: Artificial Sequence
<220> FEATURE:
<223> OTHER INFORMATION: Primer

<400> SEQUENCE: 924
cctggacagg atgatgagta ataagg                                                26

<210> SEQ ID NO 925
<211> LENGTH: 27
<212> TYPE: DNA
<213> ORGANISM: Artificial Sequence
<220> FEATURE:
<223> OTHER INFORMATION: Primer

<400> SEQUENCE: 925
agggttactg taggaaaggg attaagt                                               27

<210> SEQ ID NO 926
<211> LENGTH: 28
<212> TYPE: DNA

```
<213> ORGANISM: Artificial Sequence
<220> FEATURE:
<223> OTHER INFORMATION: Primer

<400> SEQUENCE: 926
cgtatcccct gttaccacac taatattg                                28

<210> SEQ ID NO 927
<211> LENGTH: 20
<212> TYPE: DNA
<213> ORGANISM: Artificial Sequence
<220> FEATURE:
<223> OTHER INFORMATION: Primer

<400> SEQUENCE: 927
ccagccattg ggtgttggta                                         20

<210> SEQ ID NO 928
<211> LENGTH: 26
<212> TYPE: DNA
<213> ORGANISM: Artificial Sequence
<220> FEATURE:
<223> OTHER INFORMATION: Primer

<400> SEQUENCE: 928
gcctataatg cacaactgtg tctgtt                                  26

<210> SEQ ID NO 929
<211> LENGTH: 21
<212> TYPE: DNA
<213> ORGANISM: Artificial Sequence
<220> FEATURE:
<223> OTHER INFORMATION: Primer

<400> SEQUENCE: 929
agcaccttgt cctttgtgtg t                                       21

<210> SEQ ID NO 930
<211> LENGTH: 24
<212> TYPE: DNA
<213> ORGANISM: Artificial Sequence
<220> FEATURE:
<223> OTHER INFORMATION: Primer

<400> SEQUENCE: 930
ggtgatccag actctgacct tttg                                    24

<210> SEQ ID NO 931
<211> LENGTH: 28
<212> TYPE: DNA
<213> ORGANISM: Artificial Sequence
<220> FEATURE:
<223> OTHER INFORMATION: Primer

<400> SEQUENCE: 931
cgttacagga caaaatacta gaccacta                                28

<210> SEQ ID NO 932
<211> LENGTH: 21
<212> TYPE: DNA
<213> ORGANISM: Artificial Sequence
<220> FEATURE:
<223> OTHER INFORMATION: Primer

<400> SEQUENCE: 932
catggttcca ccagcgttat t                                       21
```

<210> SEQ ID NO 933
<211> LENGTH: 21
<212> TYPE: DNA
<213> ORGANISM: Artificial Sequence
<220> FEATURE:
<223> OTHER INFORMATION: Primer

<400> SEQUENCE: 933
agcaccttgt cctttgtgtg t                                              21

<210> SEQ ID NO 934
<211> LENGTH: 28
<212> TYPE: DNA
<213> ORGANISM: Artificial Sequence
<220> FEATURE:
<223> OTHER INFORMATION: Primer

<400> SEQUENCE: 934
gaaatgcatg tggaaatgta aataccgt                                       28

<210> SEQ ID NO 935
<211> LENGTH: 28
<212> TYPE: DNA
<213> ORGANISM: Artificial Sequence
<220> FEATURE:
<223> OTHER INFORMATION: Primer

<400> SEQUENCE: 935
tcctgtgttc aagtacaagt aacaacaa                                       28

<210> SEQ ID NO 936
<211> LENGTH: 19
<212> TYPE: DNA
<213> ORGANISM: Artificial Sequence
<220> FEATURE:
<223> OTHER INFORMATION: Primer

<400> SEQUENCE: 936
aaatacggct gcaccgagt                                                 19

<210> SEQ ID NO 937
<211> LENGTH: 24
<212> TYPE: DNA
<213> ORGANISM: Artificial Sequence
<220> FEATURE:
<223> OTHER INFORMATION: Primer

<400> SEQUENCE: 937
tcagatagtg gctatggctg ttct                                           24

<210> SEQ ID NO 938
<211> LENGTH: 28
<212> TYPE: DNA
<213> ORGANISM: Artificial Sequence
<220> FEATURE:
<223> OTHER INFORMATION: Primer

<400> SEQUENCE: 938
gaaatgcatg tggaaatgta aataccgt                                       28

<210> SEQ ID NO 939
<211> LENGTH: 28
<212> TYPE: DNA
<213> ORGANISM: Artificial Sequence
<220> FEATURE:

<223> OTHER INFORMATION: Primer

<400> SEQUENCE: 939
tcctgtgttc aagtacaagt aacaacaa                                    28

<210> SEQ ID NO 940
<211> LENGTH: 24
<212> TYPE: DNA
<213> ORGANISM: Artificial Sequence
<220> FEATURE:
<223> OTHER INFORMATION: Primer

<400> SEQUENCE: 940
ggtgatccag actctgacct tttg                                        24

<210> SEQ ID NO 941
<211> LENGTH: 26
<212> TYPE: DNA
<213> ORGANISM: Artificial Sequence
<220> FEATURE:
<223> OTHER INFORMATION: Primer

<400> SEQUENCE: 941
ctacaagacg tatctattgc ctgtgt                                      26

<210> SEQ ID NO 942
<211> LENGTH: 25
<212> TYPE: DNA
<213> ORGANISM: Artificial Sequence
<220> FEATURE:
<223> OTHER INFORMATION: Primer

<400> SEQUENCE: 942
tcaaaaacag ctgctgtagt gttct                                       25

<210> SEQ ID NO 943
<211> LENGTH: 21
<212> TYPE: DNA
<213> ORGANISM: Artificial Sequence
<220> FEATURE:
<223> OTHER INFORMATION: Primer

<400> SEQUENCE: 943
agcaccttgt cctttgtgtg t                                           21

<210> SEQ ID NO 944
<211> LENGTH: 18
<212> TYPE: DNA
<213> ORGANISM: Artificial Sequence
<220> FEATURE:
<223> OTHER INFORMATION: Primer

<400> SEQUENCE: 944
cccacggatg cggttttg                                               18

<210> SEQ ID NO 945
<211> LENGTH: 27
<212> TYPE: DNA
<213> ORGANISM: Artificial Sequence
<220> FEATURE:
<223> OTHER INFORMATION: Primer

<400> SEQUENCE: 945
aaactctgta tatggagaga cactgga                                     27

```
<210> SEQ ID NO 946
<211> LENGTH: 27
<212> TYPE: DNA
<213> ORGANISM: Artificial Sequence
<220> FEATURE:
<223> OTHER INFORMATION: Primer

<400> SEQUENCE: 946
cgtttgtcct taaggtgtct acgtttt                                            27

<210> SEQ ID NO 947
<211> LENGTH: 26
<212> TYPE: DNA
<213> ORGANISM: Artificial Sequence
<220> FEATURE:
<223> OTHER INFORMATION: Primer

<400> SEQUENCE: 947
ctacaagacg tatctattgc ctgtgt                                             26

<210> SEQ ID NO 948
<211> LENGTH: 27
<212> TYPE: DNA
<213> ORGANISM: Artificial Sequence
<220> FEATURE:
<223> OTHER INFORMATION: Primer

<400> SEQUENCE: 948
cgtttgtcct taaggtgtct acgtttt                                            27

<210> SEQ ID NO 949
<211> LENGTH: 26
<212> TYPE: DNA
<213> ORGANISM: Artificial Sequence
<220> FEATURE:
<223> OTHER INFORMATION: Primer

<400> SEQUENCE: 949
ctacaagacg tatctattgc ctgtgt                                             26

<210> SEQ ID NO 950
<211> LENGTH: 21
<212> TYPE: DNA
<213> ORGANISM: Artificial Sequence
<220> FEATURE:
<223> OTHER INFORMATION: Primer

<400> SEQUENCE: 950
ggattccttc ggtgtctgca t                                                  21

<210> SEQ ID NO 951
<211> LENGTH: 28
<212> TYPE: DNA
<213> ORGANISM: Artificial Sequence
<220> FEATURE:
<223> OTHER INFORMATION: Primer

<400> SEQUENCE: 951
cgttacagga caaaatacta gaccacta                                           28

<210> SEQ ID NO 952
<211> LENGTH: 19
<212> TYPE: DNA
<213> ORGANISM: Artificial Sequence
<220> FEATURE:
<223> OTHER INFORMATION: Primer
```

<400> SEQUENCE: 952
ctgagaagcc ctgcccttc                                                    19

<210> SEQ ID NO 953
<211> LENGTH: 26
<212> TYPE: DNA
<213> ORGANISM: Artificial Sequence
<220> FEATURE:
<223> OTHER INFORMATION: Primer

<400> SEQUENCE: 953
ctacaagacg tatctattgc ctgtgt                                            26

<210> SEQ ID NO 954
<211> LENGTH: 29
<212> TYPE: DNA
<213> ORGANISM: Artificial Sequence
<220> FEATURE:
<223> OTHER INFORMATION: Primer

<400> SEQUENCE: 954
aagtctatac atttatggca tgcagcata                                         29

<210> SEQ ID NO 955
<211> LENGTH: 21
<212> TYPE: DNA
<213> ORGANISM: Artificial Sequence
<220> FEATURE:
<223> OTHER INFORMATION: Primer

<400> SEQUENCE: 955
agcaccttgt cctttgtgtg t                                                 21

<210> SEQ ID NO 956
<211> LENGTH: 21
<212> TYPE: DNA
<213> ORGANISM: Artificial Sequence
<220> FEATURE:
<223> OTHER INFORMATION: Primer

<400> SEQUENCE: 956
catggttcca ccagcgttat t                                                 21

<210> SEQ ID NO 957
<211> LENGTH: 24
<212> TYPE: DNA
<213> ORGANISM: Artificial Sequence
<220> FEATURE:
<223> OTHER INFORMATION: Primer

<400> SEQUENCE: 957
tcagatagtg gctatggctg ttct                                              24

<210> SEQ ID NO 958
<211> LENGTH: 18
<212> TYPE: DNA
<213> ORGANISM: Artificial Sequence
<220> FEATURE:
<223> OTHER INFORMATION: Primer

<400> SEQUENCE: 958
cccacggatg cggttttg                                                     18

<210> SEQ ID NO 959
<211> LENGTH: 21

```
<212> TYPE: DNA
<213> ORGANISM: Artificial Sequence
<220> FEATURE:
<223> OTHER INFORMATION: Primer

<400> SEQUENCE: 959
agcaccttgt cctttgtgtg t                                          21

<210> SEQ ID NO 960
<211> LENGTH: 19
<212> TYPE: DNA
<213> ORGANISM: Artificial Sequence
<220> FEATURE:
<223> OTHER INFORMATION: Primer

<400> SEQUENCE: 960
aaatacggct gcaccgagt                                             19

<210> SEQ ID NO 961
<211> LENGTH: 21
<212> TYPE: DNA
<213> ORGANISM: Artificial Sequence
<220> FEATURE:
<223> OTHER INFORMATION: Primer

<400> SEQUENCE: 961
agcaccttgt cctttgtgtg t                                          21

<210> SEQ ID NO 962
<211> LENGTH: 18
<212> TYPE: DNA
<213> ORGANISM: Artificial Sequence
<220> FEATURE:
<223> OTHER INFORMATION: Primer

<400> SEQUENCE: 962
tctttgctcg cagctcgt                                              18

<210> SEQ ID NO 963
<211> LENGTH: 26
<212> TYPE: DNA
<213> ORGANISM: Artificial Sequence
<220> FEATURE:
<223> OTHER INFORMATION: Primer

<400> SEQUENCE: 963
ctacaagacg tatctattgc ctgtgt                                     26

<210> SEQ ID NO 964
<211> LENGTH: 18
<212> TYPE: DNA
<213> ORGANISM: Artificial Sequence
<220> FEATURE:
<223> OTHER INFORMATION: Primer

<400> SEQUENCE: 964
cccacggatg cggttttg                                              18

<210> SEQ ID NO 965
<211> LENGTH: 30
<212> TYPE: DNA
<213> ORGANISM: Artificial Sequence
<220> FEATURE:
<223> OTHER INFORMATION: Primer

<400> SEQUENCE: 965
```
cattattaca gctaaaatgt cctccaatcc                                    30

<210> SEQ ID NO 966
<211> LENGTH: 28
<212> TYPE: DNA
<213> ORGANISM: Artificial Sequence
<220> FEATURE:
<223> OTHER INFORMATION: Primer

<400> SEQUENCE: 966
gaaatgcatg tggaaatgta aataccgt                                      28

<210> SEQ ID NO 967
<211> LENGTH: 28
<212> TYPE: DNA
<213> ORGANISM: Artificial Sequence
<220> FEATURE:
<223> OTHER INFORMATION: Primer

<400> SEQUENCE: 967
tcctgtgttc aagtacaagt aacaacaa                                      28

<210> SEQ ID NO 968
<211> LENGTH: 22
<212> TYPE: DNA
<213> ORGANISM: Artificial Sequence
<220> FEATURE:
<223> OTHER INFORMATION: Primer

<400> SEQUENCE: 968
atcatgatgg ctgtatgtgc ca                                            22

<210> SEQ ID NO 969
<211> LENGTH: 28
<212> TYPE: DNA
<213> ORGANISM: Artificial Sequence
<220> FEATURE:
<223> OTHER INFORMATION: Primer

<400> SEQUENCE: 969
cgttacagga caaaatacta gaccacta                                      28

<210> SEQ ID NO 970
<211> LENGTH: 22
<212> TYPE: DNA
<213> ORGANISM: Artificial Sequence
<220> FEATURE:
<223> OTHER INFORMATION: Primer

<400> SEQUENCE: 970
atcatgatgg ctgtatgtgc ca                                            22

<210> SEQ ID NO 971
<211> LENGTH: 28
<212> TYPE: DNA
<213> ORGANISM: Artificial Sequence
<220> FEATURE:
<223> OTHER INFORMATION: Primer

<400> SEQUENCE: 971
cgttacagga caaaatacta gaccacta                                      28

<210> SEQ ID NO 972
<211> LENGTH: 19
<212> TYPE: DNA
<213> ORGANISM: Artificial Sequence
<220> FEATURE:
<223> OTHER INFORMATION: Primer

<400> SEQUENCE: 972
aaatacggct gcaccgagt                                                19

<210> SEQ ID NO 973
<211> LENGTH: 24
<212> TYPE: DNA
<213> ORGANISM: Artificial Sequence
<220> FEATURE:
<223> OTHER INFORMATION: Primer

<400> SEQUENCE: 973
ggagttagtc atgcacaact acca                                          24

<210> SEQ ID NO 974
<211> LENGTH: 25
<212> TYPE: DNA
<213> ORGANISM: Artificial Sequence
<220> FEATURE:
<223> OTHER INFORMATION: Primer

<400> SEQUENCE: 974
tcaaaaacag ctgctgtagt gttct                                         25

<210> SEQ ID NO 975
<211> LENGTH: 21
<212> TYPE: DNA
<213> ORGANISM: Artificial Sequence
<220> FEATURE:
<223> OTHER INFORMATION: Primer

<400> SEQUENCE: 975
agcaccttgt cctttgtgtg t                                             21

<210> SEQ ID NO 976
<211> LENGTH: 21
<212> TYPE: DNA
<213> ORGANISM: Artificial Sequence
<220> FEATURE:
<223> OTHER INFORMATION: Primer

<400> SEQUENCE: 976
ggattccttc ggtgtctgca t                                             21

<210> SEQ ID NO 977
<211> LENGTH: 28
<212> TYPE: DNA
<213> ORGANISM: Artificial Sequence
<220> FEATURE:
<223> OTHER INFORMATION: Primer

<400> SEQUENCE: 977
tcctgtgttc aagtacaagt aacaacaa                                      28

<210> SEQ ID NO 978
<211> LENGTH: 18
<212> TYPE: DNA
<213> ORGANISM: Artificial Sequence
<220> FEATURE:
<223> OTHER INFORMATION: Primer

<400> SEQUENCE: 978
tctttgctcg cagctcgt                                                 18

<210> SEQ ID NO 979
<211> LENGTH: 21
<212> TYPE: DNA
<213> ORGANISM: Artificial Sequence
<220> FEATURE:
<223> OTHER INFORMATION: Primer

<400> SEQUENCE: 979
agcaccttgt cctttgtgtg t                                           21

<210> SEQ ID NO 980
<211> LENGTH: 19
<212> TYPE: DNA
<213> ORGANISM: Artificial Sequence
<220> FEATURE:
<223> OTHER INFORMATION: Primer

<400> SEQUENCE: 980
gctgacaact ctggccaca                                              19

<210> SEQ ID NO 981
<211> LENGTH: 26
<212> TYPE: DNA
<213> ORGANISM: Artificial Sequence
<220> FEATURE:
<223> OTHER INFORMATION: Primer

<400> SEQUENCE: 981
ctacaagacg tatctattgc ctgtgt                                      26

<210> SEQ ID NO 982
<211> LENGTH: 28
<212> TYPE: DNA
<213> ORGANISM: Artificial Sequence
<220> FEATURE:
<223> OTHER INFORMATION: Primer

<400> SEQUENCE: 982
gaaatgcatg tggaaatgta aataccgt                                    28

<210> SEQ ID NO 983
<211> LENGTH: 28
<212> TYPE: DNA
<213> ORGANISM: Artificial Sequence
<220> FEATURE:
<223> OTHER INFORMATION: Primer

<400> SEQUENCE: 983
gcacacaata ttatttatgg ccatggta                                    28

<210> SEQ ID NO 984
<211> LENGTH: 19
<212> TYPE: DNA
<213> ORGANISM: Artificial Sequence
<220> FEATURE:
<223> OTHER INFORMATION: Primer

<400> SEQUENCE: 984
gctgacaact ctggccaca                                              19

<210> SEQ ID NO 985
<211> LENGTH: 28
<212> TYPE: DNA
<213> ORGANISM: Artificial Sequence
<220> FEATURE:
<223> OTHER INFORMATION: Primer -continued

<400> SEQUENCE: 985
cgttacagga caaaatacta gaccacta                                    28

<210> SEQ ID NO 986
<211> LENGTH: 18
<212> TYPE: DNA
<213> ORGANISM: Artificial Sequence
<220> FEATURE:
<223> OTHER INFORMATION: Primer

<400> SEQUENCE: 986
tctttgctcg cagctcgt                                               18

<210> SEQ ID NO 987
<211> LENGTH: 21
<212> TYPE: DNA
<213> ORGANISM: Artificial Sequence
<220> FEATURE:
<223> OTHER INFORMATION: Primer

<400> SEQUENCE: 987
agcaccttgt cctttgtgtg t                                           21

<210> SEQ ID NO 988
<211> LENGTH: 28
<212> TYPE: DNA
<213> ORGANISM: Artificial Sequence
<220> FEATURE:
<223> OTHER INFORMATION: Primer

<400> SEQUENCE: 988
caattgtttc tacaaagaac cagccatt                                    28

<210> SEQ ID NO 989
<211> LENGTH: 28
<212> TYPE: DNA
<213> ORGANISM: Artificial Sequence
<220> FEATURE:
<223> OTHER INFORMATION: Primer

<400> SEQUENCE: 989
cgttacagga caaaatacta gaccacta                                    28

<210> SEQ ID NO 990
<211> LENGTH: 24
<212> TYPE: DNA
<213> ORGANISM: Artificial Sequence
<220> FEATURE:
<223> OTHER INFORMATION: Primer

<400> SEQUENCE: 990
ggtgatccag actctgacct tttg                                        24

<210> SEQ ID NO 991
<211> LENGTH: 21
<212> TYPE: DNA
<213> ORGANISM: Artificial Sequence
<220> FEATURE:
<223> OTHER INFORMATION: Primer

<400> SEQUENCE: 991
agcaccttgt cctttgtgtg t                                           21

<210> SEQ ID NO 992

```
<211> LENGTH: 19
<212> TYPE: DNA
<213> ORGANISM: Artificial Sequence
<220> FEATURE:
<223> OTHER INFORMATION: Primer

<400> SEQUENCE: 992
ctgagaagcc ctgcccttc                                                    19

<210> SEQ ID NO 993
<211> LENGTH: 24
<212> TYPE: DNA
<213> ORGANISM: Artificial Sequence
<220> FEATURE:
<223> OTHER INFORMATION: Primer

<400> SEQUENCE: 993
tcagatagtg gctatggctg ttct                                              24

<210> SEQ ID NO 994
<211> LENGTH: 21
<212> TYPE: DNA
<213> ORGANISM: Artificial Sequence
<220> FEATURE:
<223> OTHER INFORMATION: Primer

<400> SEQUENCE: 994
ggattccttc ggtgtctgca t                                                 21

<210> SEQ ID NO 995
<211> LENGTH: 24
<212> TYPE: DNA
<213> ORGANISM: Artificial Sequence
<220> FEATURE:
<223> OTHER INFORMATION: Primer

<400> SEQUENCE: 995
tcagatagtg gctatggctg ttct                                              24

<210> SEQ ID NO 996
<211> LENGTH: 25
<212> TYPE: DNA
<213> ORGANISM: Artificial Sequence
<220> FEATURE:
<223> OTHER INFORMATION: Primer

<400> SEQUENCE: 996
actatcccca ccactactttt gtgta                                            25

<210> SEQ ID NO 997
<211> LENGTH: 28
<212> TYPE: DNA
<213> ORGANISM: Artificial Sequence
<220> FEATURE:
<223> OTHER INFORMATION: Primer

<400> SEQUENCE: 997
tcctgtgttc aagtacaagt aacaacaa                                          28

<210> SEQ ID NO 998
<211> LENGTH: 21
<212> TYPE: DNA
<213> ORGANISM: Artificial Sequence
<220> FEATURE:
<223> OTHER INFORMATION: Primer

<400> SEQUENCE: 998
```

```
catggttcca ccagcgttat t                                              21

<210> SEQ ID NO 999
<211> LENGTH: 28
<212> TYPE: DNA
<213> ORGANISM: Artificial Sequence
<220> FEATURE:
<223> OTHER INFORMATION: Primer

<400> SEQUENCE: 999
tcctgtgttc aagtacaagt aacaacaa                                       28

<210> SEQ ID NO 1000
<211> LENGTH: 19
<212> TYPE: DNA
<213> ORGANISM: Artificial Sequence
<220> FEATURE:
<223> OTHER INFORMATION: Primer

<400> SEQUENCE: 1000
gctgacaact ctggccaca                                                 19

<210> SEQ ID NO 1001
<211> LENGTH: 28
<212> TYPE: DNA
<213> ORGANISM: Artificial Sequence
<220> FEATURE:
<223> OTHER INFORMATION: Primer

<400> SEQUENCE: 1001
tcctgtgttc aagtacaagt aacaacaa                                       28

<210> SEQ ID NO 1002
<211> LENGTH: 19
<212> TYPE: DNA
<213> ORGANISM: Artificial Sequence
<220> FEATURE:
<223> OTHER INFORMATION: Primer

<400> SEQUENCE: 1002
ctgagaagcc ctgcccttc                                                 19

<210> SEQ ID NO 1003
<211> LENGTH: 21
<212> TYPE: DNA
<213> ORGANISM: Artificial Sequence
<220> FEATURE:
<223> OTHER INFORMATION: Primer

<400> SEQUENCE: 1003
agcaccttgt cctttgtgtg t                                              21

<210> SEQ ID NO 1004
<211> LENGTH: 22
<212> TYPE: DNA
<213> ORGANISM: Artificial Sequence
<220> FEATURE:
<223> OTHER INFORMATION: Primer

<400> SEQUENCE: 1004
atcatgatgg ctgtatgtgc ca                                             22

<210> SEQ ID NO 1005
<211> LENGTH: 21
<212> TYPE: DNA
```

```
<213> ORGANISM: Artificial Sequence
<220> FEATURE:
<223> OTHER INFORMATION: Primer

<400> SEQUENCE: 1005
tgcttttgct tggttgttgg t                                            21

<210> SEQ ID NO 1006
<211> LENGTH: 27
<212> TYPE: DNA
<213> ORGANISM: Artificial Sequence
<220> FEATURE:
<223> OTHER INFORMATION: Primer

<400> SEQUENCE: 1006
catcacaggt atgttacact gtactgt                                      27

<210> SEQ ID NO 1007
<211> LENGTH: 28
<212> TYPE: DNA
<213> ORGANISM: Artificial Sequence
<220> FEATURE:
<223> OTHER INFORMATION: Primer

<400> SEQUENCE: 1007
tcctgtgttc aagtacaagt aacaacaa                                     28

<210> SEQ ID NO 1008
<211> LENGTH: 25
<212> TYPE: DNA
<213> ORGANISM: Artificial Sequence
<220> FEATURE:
<223> OTHER INFORMATION: Primer

<400> SEQUENCE: 1008
ggtctgcata tttgcgtagc ctata                                        25

<210> SEQ ID NO 1009
<211> LENGTH: 23
<212> TYPE: DNA
<213> ORGANISM: Artificial Sequence
<220> FEATURE:
<223> OTHER INFORMATION: Primer

<400> SEQUENCE: 1009
atttcggttg cctgtggctt ata                                          23

<210> SEQ ID NO 1010
<211> LENGTH: 25
<212> TYPE: DNA
<213> ORGANISM: Artificial Sequence
<220> FEATURE:
<223> OTHER INFORMATION: Primer

<400> SEQUENCE: 1010
cagttgtgca agccattgtt ttagt                                        25

<210> SEQ ID NO 1011
<211> LENGTH: 27
<212> TYPE: DNA
<213> ORGANISM: Artificial Sequence
<220> FEATURE:
<223> OTHER INFORMATION: Primer

<400> SEQUENCE: 1011
cgcaaatatg cagaccatta ctcagaa                                      27
```

<210> SEQ ID NO 1012
<211> LENGTH: 19
<212> TYPE: DNA
<213> ORGANISM: Artificial Sequence
<220> FEATURE:
<223> OTHER INFORMATION: Primer

<400> SEQUENCE: 1012
gctgacaact ctggccaca                                            19

<210> SEQ ID NO 1013
<211> LENGTH: 25
<212> TYPE: DNA
<213> ORGANISM: Artificial Sequence
<220> FEATURE:
<223> OTHER INFORMATION: Primer

<400> SEQUENCE: 1013
gcaacgttat acgcccatat ccaat                                     25

<210> SEQ ID NO 1014
<211> LENGTH: 23
<212> TYPE: DNA
<213> ORGANISM: Artificial Sequence
<220> FEATURE:
<223> OTHER INFORMATION: Primer

<400> SEQUENCE: 1014
ggtacgtgca acaatgtgct taa                                       23

<210> SEQ ID NO 1015
<211> LENGTH: 27
<212> TYPE: DNA
<213> ORGANISM: Artificial Sequence
<220> FEATURE:
<223> OTHER INFORMATION: Primer

<400> SEQUENCE: 1015
cgcaaatatg cagaccatta ctcagaa                                   27

<210> SEQ ID NO 1016
<211> LENGTH: 24
<212> TYPE: DNA
<213> ORGANISM: Artificial Sequence
<220> FEATURE:
<223> OTHER INFORMATION: Primer

<400> SEQUENCE: 1016
cccaccgaga tttgtacact gtta                                      24

<210> SEQ ID NO 1017
<211> LENGTH: 25
<212> TYPE: DNA
<213> ORGANISM: Artificial Sequence
<220> FEATURE:
<223> OTHER INFORMATION: Primer

<400> SEQUENCE: 1017
ggcatgtgta ggtatggaaa ttggt                                     25

<210> SEQ ID NO 1018
<211> LENGTH: 25
<212> TYPE: DNA
<213> ORGANISM: Artificial Sequence
<220> FEATURE:

<223> OTHER INFORMATION: Primer

<400> SEQUENCE: 1018
acatcctgcg taataacagc tgtag                                              25

<210> SEQ ID NO 1019
<211> LENGTH: 20
<212> TYPE: DNA
<213> ORGANISM: Artificial Sequence
<220> FEATURE:
<223> OTHER INFORMATION: Primer

<400> SEQUENCE: 1019
tgacgacacg gtatccgcta                                                    20

<210> SEQ ID NO 1020
<211> LENGTH: 18
<212> TYPE: DNA
<213> ORGANISM: Artificial Sequence
<220> FEATURE:
<223> OTHER INFORMATION: Primer

<400> SEQUENCE: 1020
cccacggatg cggttttg                                                      18

<210> SEQ ID NO 1021
<211> LENGTH: 31
<212> TYPE: DNA
<213> ORGANISM: Artificial Sequence
<220> FEATURE:
<223> OTHER INFORMATION: Primer

<400> SEQUENCE: 1021
agtatgtcca ccattactaa taacgtcaaa c                                       31

<210> SEQ ID NO 1022
<211> LENGTH: 28
<212> TYPE: DNA
<213> ORGANISM: Artificial Sequence
<220> FEATURE:
<223> OTHER INFORMATION: Primer

<400> SEQUENCE: 1022
tcattcaatg tatacacagc attcccat                                           28

<210> SEQ ID NO 1023
<211> LENGTH: 21
<212> TYPE: DNA
<213> ORGANISM: Artificial Sequence
<220> FEATURE:
<223> OTHER INFORMATION: Primer

<400> SEQUENCE: 1023
ctaacactgg agggcaccaa a                                                  21

<210> SEQ ID NO 1024
<211> LENGTH: 19
<212> TYPE: DNA
<213> ORGANISM: Artificial Sequence
<220> FEATURE:
<223> OTHER INFORMATION: Primer

<400> SEQUENCE: 1024
aaatacggct gcaccgagt                                                     19

```
<210> SEQ ID NO 1025
<211> LENGTH: 20
<212> TYPE: DNA
<213> ORGANISM: Artificial Sequence
<220> FEATURE:
<223> OTHER INFORMATION: GGGCGAACTAAGCCTGGTTT

<400> SEQUENCE: 1025
gggcgaacta agcctggttt                                               20

<210> SEQ ID NO 1026
<211> LENGTH: 22
<212> TYPE: DNA
<213> ORGANISM: Artificial Sequence
<220> FEATURE:
<223> OTHER INFORMATION: Primer

<400> SEQUENCE: 1026
atcatgatgg ctgtatgtgc ca                                            22

<210> SEQ ID NO 1027
<211> LENGTH: 20
<212> TYPE: DNA
<213> ORGANISM: Artificial Sequence
<220> FEATURE:
<223> OTHER INFORMATION: Primer

<400> SEQUENCE: 1027
gggcgaacta agcctggttt                                               20

<210> SEQ ID NO 1028
<211> LENGTH: 19
<212> TYPE: DNA
<213> ORGANISM: Artificial Sequence
<220> FEATURE:
<223> OTHER INFORMATION: Primer

<400> SEQUENCE: 1028
aaatacggct gcaccgagt                                                19

<210> SEQ ID NO 1029
<211> LENGTH: 21
<212> TYPE: DNA
<213> ORGANISM: Artificial Sequence
<220> FEATURE:
<223> OTHER INFORMATION: CTAACACTGGAGGGCACCAAA

<400> SEQUENCE: 1029
ctaacactgg agggcaccaa a                                             21

<210> SEQ ID NO 1030
<211> LENGTH: 18
<212> TYPE: DNA
<213> ORGANISM: Artificial Sequence
<220> FEATURE:
<223> OTHER INFORMATION: Primer

<400> SEQUENCE: 1030
tctttgctcg cagctcgt                                                 18

<210> SEQ ID NO 1031
<211> LENGTH: 28
<212> TYPE: DNA
<213> ORGANISM: Artificial Sequence
<220> FEATURE:
<223> OTHER INFORMATION: Primer
```

```
<400> SEQUENCE: 1031
gtgccaggag aaaatactag actgttat                                28

<210> SEQ ID NO 1032
<211> LENGTH: 19
<212> TYPE: DNA
<213> ORGANISM: Artificial Sequence
<220> FEATURE:
<223> OTHER INFORMATION: Primer

<400> SEQUENCE: 1032
ctgagaagcc ctgcccttc                                          19

<210> SEQ ID NO 1033
<211> LENGTH: 21
<212> TYPE: DNA
<213> ORGANISM: Artificial Sequence
<220> FEATURE:
<223> OTHER INFORMATION: Primer

<400> SEQUENCE: 1033
ctaacactgg agggcaccaa a                                       21

<210> SEQ ID NO 1034
<211> LENGTH: 26
<212> TYPE: DNA
<213> ORGANISM: Artificial Sequence
<220> FEATURE:
<223> OTHER INFORMATION: Primer

<400> SEQUENCE: 1034
atgccaggtt gaggatacgt ttttat                                  26

<210> SEQ ID NO 1035
<211> LENGTH: 28
<212> TYPE: DNA
<213> ORGANISM: Artificial Sequence
<220> FEATURE:
<223> OTHER INFORMATION: Primer

<400> SEQUENCE: 1035
gtgccaggag aaaatactag actgttat                                28

<210> SEQ ID NO 1036
<211> LENGTH: 21
<212> TYPE: DNA
<213> ORGANISM: Artificial Sequence
<220> FEATURE:
<223> OTHER INFORMATION: Primer

<400> SEQUENCE: 1036
catggttcca ccagcgttat t                                       21

<210> SEQ ID NO 1037
<211> LENGTH: 21
<212> TYPE: DNA
<213> ORGANISM: Artificial Sequence
<220> FEATURE:
<223> OTHER INFORMATION: Primer

<400> SEQUENCE: 1037
cggacagcgg atatggcaat a                                       21

<210> SEQ ID NO 1038
<211> LENGTH: 26
```

<210> SEQ ID NO 1038
<211> LENGTH: 26 (implied)
<212> TYPE: DNA
<213> ORGANISM: Artificial Sequence
<220> FEATURE:
<223> OTHER INFORMATION: Primer

<400> SEQUENCE: 1038
tctgttgttt ccacatccat aacact                                          26

<210> SEQ ID NO 1039
<211> LENGTH: 21
<212> TYPE: DNA
<213> ORGANISM: Artificial Sequence
<220> FEATURE:
<223> OTHER INFORMATION: Primer

<400> SEQUENCE: 1039
ctaacactgg agggcaccaa a                                               21

<210> SEQ ID NO 1040
<211> LENGTH: 22
<212> TYPE: DNA
<213> ORGANISM: Artificial Sequence
<220> FEATURE:
<223> OTHER INFORMATION: Primer

<400> SEQUENCE: 1040
atcatgatgg ctgtatgtgc ca                                              22

<210> SEQ ID NO 1041
<211> LENGTH: 21
<212> TYPE: DNA
<213> ORGANISM: Artificial Sequence
<220> FEATURE:
<223> OTHER INFORMATION: Primer

<400> SEQUENCE: 1041
ctaacactgg agggcaccaa a                                               21

<210> SEQ ID NO 1042
<211> LENGTH: 21
<212> TYPE: DNA
<213> ORGANISM: Artificial Sequence
<220> FEATURE:
<223> OTHER INFORMATION: Primer

<400> SEQUENCE: 1042
caattcgaga cacaggtgca g                                               21

<210> SEQ ID NO 1043
<211> LENGTH: 28
<212> TYPE: DNA
<213> ORGANISM: Artificial Sequence
<220> FEATURE:
<223> OTHER INFORMATION: Primer

<400> SEQUENCE: 1043
gagagtatag acgttatagc aggtctgt                                        28

<210> SEQ ID NO 1044
<211> LENGTH: 24
<212> TYPE: DNA
<213> ORGANISM: Artificial Sequence
<220> FEATURE:
<223> OTHER INFORMATION: Primer

<400> SEQUENCE: 1044
tcccgctatt tcatggaacc tttt                                          24

<210> SEQ ID NO 1045
<211> LENGTH: 21
<212> TYPE: DNA
<213> ORGANISM: Artificial Sequence
<220> FEATURE:
<223> OTHER INFORMATION: Primer

<400> SEQUENCE: 1045
cggacagcgg atatggcaat a                                             21

<210> SEQ ID NO 1046
<211> LENGTH: 18
<212> TYPE: DNA
<213> ORGANISM: Artificial Sequence
<220> FEATURE:
<223> OTHER INFORMATION: Primer

<400> SEQUENCE: 1046
ccacgcaggt ggtaaggg                                                 18

<210> SEQ ID NO 1047
<211> LENGTH: 27
<212> TYPE: DNA
<213> ORGANISM: Artificial Sequence
<220> FEATURE:
<223> OTHER INFORMATION: Primer

<400> SEQUENCE: 1047
ctgcatgaat tatgtgaagc tttgaac                                       27

<210> SEQ ID NO 1048
<211> LENGTH: 21
<212> TYPE: DNA
<213> ORGANISM: Artificial Sequence
<220> FEATURE:
<223> OTHER INFORMATION: Primer

<400> SEQUENCE: 1048
catctgctgt acaacgcgaa g                                             21

<210> SEQ ID NO 1049
<211> LENGTH: 20
<212> TYPE: DNA
<213> ORGANISM: Artificial Sequence
<220> FEATURE:
<223> OTHER INFORMATION: Primer

<400> SEQUENCE: 1049
gggcgaacta agcctggttt                                               20

<210> SEQ ID NO 1050
<211> LENGTH: 24
<212> TYPE: DNA
<213> ORGANISM: Artificial Sequence
<220> FEATURE:
<223> OTHER INFORMATION: Primer

<400> SEQUENCE: 1050
ggtgatccag actctgacct tttg                                          24

<210> SEQ ID NO 1051
<211> LENGTH: 21
<212> TYPE: DNA
<213> ORGANISM: Artificial Sequence

```
<220> FEATURE:
<223> OTHER INFORMATION: Primer

<400> SEQUENCE: 1051
ctaacactgg agggcaccaa a                                              21

<210> SEQ ID NO 1052
<211> LENGTH: 21
<212> TYPE: DNA
<213> ORGANISM: Artificial Sequence
<220> FEATURE:
<223> OTHER INFORMATION: Primer

<400> SEQUENCE: 1052
catggttcca ccagcgttat t                                              21

<210> SEQ ID NO 1053
<211> LENGTH: 21
<212> TYPE: DNA
<213> ORGANISM: Artificial Sequence
<220> FEATURE:
<223> OTHER INFORMATION: Primer

<400> SEQUENCE: 1053
cggacagcgg atatggcaat a                                              21

<210> SEQ ID NO 1054
<211> LENGTH: 28
<212> TYPE: DNA
<213> ORGANISM: Artificial Sequence
<220> FEATURE:
<223> OTHER INFORMATION: Primer

<400> SEQUENCE: 1054
tcattcaatg tatacacagc attcccat                                       28

<210> SEQ ID NO 1055
<211> LENGTH: 20
<212> TYPE: DNA
<213> ORGANISM: Artificial Sequence
<220> FEATURE:
<223> OTHER INFORMATION: Primer

<400> SEQUENCE: 1055
gggcgaacta agcctggttt                                                20

<210> SEQ ID NO 1056
<211> LENGTH: 27
<212> TYPE: DNA
<213> ORGANISM: Artificial Sequence
<220> FEATURE:
<223> OTHER INFORMATION: Primer

<400> SEQUENCE: 1056
ctcatcatcc gaaacattat ctcctgt                                        27

<210> SEQ ID NO 1057
<211> LENGTH: 28
<212> TYPE: DNA
<213> ORGANISM: Artificial Sequence
<220> FEATURE:
<223> OTHER INFORMATION: Primer

<400> SEQUENCE: 1057
gtgccaggag aaaatactag actgttat                                       28
```

```
<210> SEQ ID NO 1058
<211> LENGTH: 22
<212> TYPE: DNA
<213> ORGANISM: Artificial Sequence
<220> FEATURE:
<223> OTHER INFORMATION: Primer

<400> SEQUENCE: 1058
atcatgatgg ctgtatgtgc ca                                              22

<210> SEQ ID NO 1059
<211> LENGTH: 24
<212> TYPE: DNA
<213> ORGANISM: Artificial Sequence
<220> FEATURE:
<223> OTHER INFORMATION: Primer

<400> SEQUENCE: 1059
gcacaacagt gggaggtcta tatg                                            24

<210> SEQ ID NO 1060
<211> LENGTH: 18
<212> TYPE: DNA
<213> ORGANISM: Artificial Sequence
<220> FEATURE:
<223> OTHER INFORMATION: Primer

<400> SEQUENCE: 1060
ccacgcaggt ggtaaggg                                                   18

<210> SEQ ID NO 1061
<211> LENGTH: 28
<212> TYPE: DNA
<213> ORGANISM: Artificial Sequence
<220> FEATURE:
<223> OTHER INFORMATION: Primer

<400> SEQUENCE: 1061
gtgccaggag aaaatactag actgttat                                        28

<210> SEQ ID NO 1062
<211> LENGTH: 19
<212> TYPE: DNA
<213> ORGANISM: Artificial Sequence
<220> FEATURE:
<223> OTHER INFORMATION: Primer

<400> SEQUENCE: 1062
aaatacggct gcaccgagt                                                  19

<210> SEQ ID NO 1063
<211> LENGTH: 20
<212> TYPE: DNA
<213> ORGANISM: Artificial Sequence
<220> FEATURE:
<223> OTHER INFORMATION: Primer

<400> SEQUENCE: 1063
gggcgaacta agcctggttt                                                 20

<210> SEQ ID NO 1064
<211> LENGTH: 21
<212> TYPE: DNA
<213> ORGANISM: Artificial Sequence
<220> FEATURE:
<223> OTHER INFORMATION: Primer
```

```
<400> SEQUENCE: 1064
caattcgaga cacaggtgca g                                                 21

<210> SEQ ID NO 1065
<211> LENGTH: 21
<212> TYPE: DNA
<213> ORGANISM: Artificial Sequence
<220> FEATURE:
<223> OTHER INFORMATION: Primer

<400> SEQUENCE: 1065
ctaacactgg agggcaccaa a                                                 21

<210> SEQ ID NO 1066
<211> LENGTH: 24
<212> TYPE: DNA
<213> ORGANISM: Artificial Sequence
<220> FEATURE:
<223> OTHER INFORMATION: Primer

<400> SEQUENCE: 1066
ggtgatccag actctgacct tttg                                              24

<210> SEQ ID NO 1067
<211> LENGTH: 27
<212> TYPE: DNA
<213> ORGANISM: Artificial Sequence
<220> FEATURE:
<223> OTHER INFORMATION: Primer

<400> SEQUENCE: 1067
ctgcatgaat tatgtgaagc tttgaac                                           27

<210> SEQ ID NO 1068
<211> LENGTH: 24
<212> TYPE: DNA
<213> ORGANISM: Artificial Sequence
<220> FEATURE:
<223> OTHER INFORMATION: Primer

<400> SEQUENCE: 1068
tcccgctatt tcatggaacc tttt                                              24

<210> SEQ ID NO 1069
<211> LENGTH: 20
<212> TYPE: DNA
<213> ORGANISM: Artificial Sequence
<220> FEATURE:
<223> OTHER INFORMATION: Primer

<400> SEQUENCE: 1069
gcgtgaccag ctaccagaaa                                                   20

<210> SEQ ID NO 1070
<211> LENGTH: 21
<212> TYPE: DNA
<213> ORGANISM: Artificial Sequence
<220> FEATURE:
<223> OTHER INFORMATION: Primer

<400> SEQUENCE: 1070
catctgctgt acaacgcgaa g                                                 21

<210> SEQ ID NO 1071
```

```
<211> LENGTH: 20
<212> TYPE: DNA
<213> ORGANISM: Artificial Sequence
<220> FEATURE:
<223> OTHER INFORMATION: Primer

<400> SEQUENCE: 1071
gggcgaacta agcctggttt                                              20

<210> SEQ ID NO 1072
<211> LENGTH: 21
<212> TYPE: DNA
<213> ORGANISM: Artificial Sequence
<220> FEATURE:
<223> OTHER INFORMATION: Primer

<400> SEQUENCE: 1072
catggttcca ccagcgttat t                                            21

<210> SEQ ID NO 1073
<211> LENGTH: 21
<212> TYPE: DNA
<213> ORGANISM: Artificial Sequence
<220> FEATURE:
<223> OTHER INFORMATION: Primer

<400> SEQUENCE: 1073
ctaacactgg agggcaccaa a                                            21

<210> SEQ ID NO 1074
<211> LENGTH: 19
<212> TYPE: DNA
<213> ORGANISM: Artificial Sequence
<220> FEATURE:
<223> OTHER INFORMATION: Primer

<400> SEQUENCE: 1074
ctgagaagcc ctgcccttc                                               19

<210> SEQ ID NO 1075
<211> LENGTH: 27
<212> TYPE: DNA
<213> ORGANISM: Artificial Sequence
<220> FEATURE:
<223> OTHER INFORMATION: Primer

<400> SEQUENCE: 1075
ctgcatgaat tatgtgaagc tttgaac                                      27

<210> SEQ ID NO 1076
<211> LENGTH: 29
<212> TYPE: DNA
<213> ORGANISM: Artificial Sequence
<220> FEATURE:
<223> OTHER INFORMATION: Primer

<400> SEQUENCE: 1076
gtaaacattg tttgcatact gcatatgga                                    29

<210> SEQ ID NO 1077
<211> LENGTH: 20
<212> TYPE: DNA
<213> ORGANISM: Artificial Sequence
<220> FEATURE:
<223> OTHER INFORMATION: Primer

<400> SEQUENCE: 1077
```

-continued gggcgaacta agcctggttt                                              20

<210> SEQ ID NO 1078
<211> LENGTH: 19
<212> TYPE: DNA
<213> ORGANISM: Artificial Sequence
<220> FEATURE:
<223> OTHER INFORMATION: Primer

<400> SEQUENCE: 1078
ctgagaagcc ctgcccttc                                               19

<210> SEQ ID NO 1079
<211> LENGTH: 20
<212> TYPE: DNA
<213> ORGANISM: Artificial Sequence
<220> FEATURE:
<223> OTHER INFORMATION: Primer

<400> SEQUENCE: 1079
gggcgaacta agcctggttt                                              20

<210> SEQ ID NO 1080
<211> LENGTH: 18
<212> TYPE: DNA
<213> ORGANISM: Artificial Sequence
<220> FEATURE:
<223> OTHER INFORMATION: Primer

<400> SEQUENCE: 1080
ccacgcaggt ggtaaggg                                                18

<210> SEQ ID NO 1081
<211> LENGTH: 28
<212> TYPE: DNA
<213> ORGANISM: Artificial Sequence
<220> FEATURE:
<223> OTHER INFORMATION: Primer

<400> SEQUENCE: 1081
gtgccaggag aaaatactag actgttat                                     28

<210> SEQ ID NO 1082
<211> LENGTH: 24
<212> TYPE: DNA
<213> ORGANISM: Artificial Sequence
<220> FEATURE:
<223> OTHER INFORMATION: Primer

<400> SEQUENCE: 1082
ggtgatccag actctgacct tttg                                         24

<210> SEQ ID NO 1083
<211> LENGTH: 28
<212> TYPE: DNA
<213> ORGANISM: Artificial Sequence
<220> FEATURE:
<223> OTHER INFORMATION: Primer

<400> SEQUENCE: 1083
gtgccaggag aaaatactag actgttat                                     28

<210> SEQ ID NO 1084
<211> LENGTH: 18
<212> TYPE: DNA

```
<213> ORGANISM: Artificial Sequence
<220> FEATURE:
<223> OTHER INFORMATION: Primer

<400> SEQUENCE: 1084
tctttgctcg cagctcgt                                              18

<210> SEQ ID NO 1085
<211> LENGTH: 20
<212> TYPE: DNA
<213> ORGANISM: Artificial Sequence
<220> FEATURE:
<223> OTHER INFORMATION: Primer

<400> SEQUENCE: 1085
gggcgaacta agcctggttt                                            20

<210> SEQ ID NO 1086
<211> LENGTH: 18
<212> TYPE: DNA
<213> ORGANISM: Artificial Sequence
<220> FEATURE:
<223> OTHER INFORMATION: Primer

<400> SEQUENCE: 1086
tctttgctcg cagctcgt                                              18

<210> SEQ ID NO 1087
<211> LENGTH: 26
<212> TYPE: DNA
<213> ORGANISM: Artificial Sequence
<220> FEATURE:
<223> OTHER INFORMATION: Primer

<400> SEQUENCE: 1087
ggccctatac acatttacta cgcaaa                                     26

<210> SEQ ID NO 1088
<211> LENGTH: 21
<212> TYPE: DNA
<213> ORGANISM: Artificial Sequence
<220> FEATURE:
<223> OTHER INFORMATION: Primer

<400> SEQUENCE: 1088
caattcgaga cacaggtgca g                                          21

<210> SEQ ID NO 1089
<211> LENGTH: 27
<212> TYPE: DNA
<213> ORGANISM: Artificial Sequence
<220> FEATURE:
<223> OTHER INFORMATION: Primer

<400> SEQUENCE: 1089
ctgcatgaat tatgtgaagc tttgaac                                    27

<210> SEQ ID NO 1090
<211> LENGTH: 18
<212> TYPE: DNA
<213> ORGANISM: Artificial Sequence
<220> FEATURE:
<223> OTHER INFORMATION: Primer

<400> SEQUENCE: 1090
ccacgcaggt ggtaaggg                                              18
```

<210> SEQ ID NO 1091
<211> LENGTH: 20
<212> TYPE: DNA
<213> ORGANISM: Artificial Sequence
<220> FEATURE:
<223> OTHER INFORMATION: Primer

<400> SEQUENCE: 1091
gggcgaacta agcctggttt                                               20

<210> SEQ ID NO 1092
<211> LENGTH: 28
<212> TYPE: DNA
<213> ORGANISM: Artificial Sequence
<220> FEATURE:
<223> OTHER INFORMATION: Primer

<400> SEQUENCE: 1092
tcattcaatg tatacacagc attcccat                                      28

<210> SEQ ID NO 1093
<211> LENGTH: 27
<212> TYPE: DNA
<213> ORGANISM: Artificial Sequence
<220> FEATURE:
<223> OTHER INFORMATION: Primer

<400> SEQUENCE: 1093
ctgcatgaat tatgtgaagc tttgaac                                       27

<210> SEQ ID NO 1094
<211> LENGTH: 28
<212> TYPE: DNA
<213> ORGANISM: Artificial Sequence
<220> FEATURE:
<223> OTHER INFORMATION: Primer

<400> SEQUENCE: 1094
tcattcaatg tatacacagc attcccat                                      28

<210> SEQ ID NO 1095
<211> LENGTH: 27
<212> TYPE: DNA
<213> ORGANISM: Artificial Sequence
<220> FEATURE:
<223> OTHER INFORMATION: Primer

<400> SEQUENCE: 1095
gggtattaca ttatccccgt aggtcaa                                       27

<210> SEQ ID NO 1096
<211> LENGTH: 23
<212> TYPE: DNA
<213> ORGANISM: Artificial Sequence
<220> FEATURE:
<223> OTHER INFORMATION: Primer

<400> SEQUENCE: 1096
gctgcagctg taacaaaatg gaa                                           23

<210> SEQ ID NO 1097
<211> LENGTH: 25
<212> TYPE: DNA
<213> ORGANISM: Artificial Sequence
<220> FEATURE:

<223> OTHER INFORMATION: Primer

<400> SEQUENCE: 1097
aagccaatat gtgctgctaa ttgta                                    25

<210> SEQ ID NO 1098
<211> LENGTH: 23
<212> TYPE: DNA
<213> ORGANISM: Artificial Sequence
<220> FEATURE:
<223> OTHER INFORMATION: Primer

<400> SEQUENCE: 1098
aacacgtatt gggacagcag tag                                      23

<210> SEQ ID NO 1099
<211> LENGTH: 24
<212> TYPE: DNA
<213> ORGANISM: Artificial Sequence
<220> FEATURE:
<223> OTHER INFORMATION: Primer

<400> SEQUENCE: 1099
gatggaggca actggagaga aatt                                     24

<210> SEQ ID NO 1100
<211> LENGTH: 26
<212> TYPE: DNA
<213> ORGANISM: Artificial Sequence
<220> FEATURE:
<223> OTHER INFORMATION: Primer

<400> SEQUENCE: 1100
gtgtttggtg ggccatatat gactat                                   26

<210> SEQ ID NO 1101
<211> LENGTH: 19
<212> TYPE: DNA
<213> ORGANISM: Artificial Sequence
<220> FEATURE:
<223> OTHER INFORMATION: Primer

<400> SEQUENCE: 1101
acacccctcc acaggctaa                                           19

<210> SEQ ID NO 1102
<211> LENGTH: 20
<212> TYPE: DNA
<213> ORGANISM: Artificial Sequence
<220> FEATURE:
<223> OTHER INFORMATION: Primer

<400> SEQUENCE: 1102
tgtacgccaa cctgcaacaa                                          20

<210> SEQ ID NO 1103
<211> LENGTH: 27
<212> TYPE: DNA
<213> ORGANISM: Artificial Sequence
<220> FEATURE:
<223> OTHER INFORMATION: Primer

<400> SEQUENCE: 1103
gacatgttaa tgcaaacaag cgatttc                                  27

```
<210> SEQ ID NO 1104
<211> LENGTH: 28
<212> TYPE: DNA
<213> ORGANISM: Artificial Sequence
<220> FEATURE:
<223> OTHER INFORMATION: Primer

<400> SEQUENCE: 1104
tcagttgttt caggttgcag atctaata                                        28

<210> SEQ ID NO 1105
<211> LENGTH: 22
<212> TYPE: DNA
<213> ORGANISM: Artificial Sequence
<220> FEATURE:
<223> OTHER INFORMATION: Primer

<400> SEQUENCE: 1105
gctgttgggc acattacaag tt                                              22

<210> SEQ ID NO 1106
<211> LENGTH: 19
<212> TYPE: DNA
<213> ORGANISM: Artificial Sequence
<220> FEATURE:
<223> OTHER INFORMATION: Primer

<400> SEQUENCE: 1106
ctgagaagcc ctgcccttc                                                  19

<210> SEQ ID NO 1107
<211> LENGTH: 28
<212> TYPE: DNA
<213> ORGANISM: Artificial Sequence
<220> FEATURE:
<223> OTHER INFORMATION: Primer

<400> SEQUENCE: 1107
gctgatagta atgacctaaa cgcacaaa                                        28

<210> SEQ ID NO 1108
<211> LENGTH: 18
<212> TYPE: DNA
<213> ORGANISM: Artificial Sequence
<220> FEATURE:
<223> OTHER INFORMATION: Primer

<400> SEQUENCE: 1108
tctttgctcg cagctcgt                                                   18

<210> SEQ ID NO 1109
<211> LENGTH: 22
<212> TYPE: DNA
<213> ORGANISM: Artificial Sequence
<220> FEATURE:
<223> OTHER INFORMATION: Primer

<400> SEQUENCE: 1109
gctgttgggc acattacaag tt                                              22

<210> SEQ ID NO 1110
<211> LENGTH: 21
<212> TYPE: DNA
<213> ORGANISM: Artificial Sequence
<220> FEATURE:
<223> OTHER INFORMATION: Primer
```

```
<400> SEQUENCE: 1110
catggttcca ccagcgttat t                                             21

<210> SEQ ID NO 1111
<211> LENGTH: 24
<212> TYPE: DNA
<213> ORGANISM: Artificial Sequence
<220> FEATURE:
<223> OTHER INFORMATION: Primer

<400> SEQUENCE: 1111
agaatcggtg catgaaataa ggct                                          24

<210> SEQ ID NO 1112
<211> LENGTH: 28
<212> TYPE: DNA
<213> ORGANISM: Artificial Sequence
<220> FEATURE:
<223> OTHER INFORMATION: Primer

<400> SEQUENCE: 1112
tcagttgttt caggttgcag atctaata                                      28

<210> SEQ ID NO 1113
<211> LENGTH: 21
<212> TYPE: DNA
<213> ORGANISM: Artificial Sequence
<220> FEATURE:
<223> OTHER INFORMATION: Primer

<400> SEQUENCE: 1113
tcactgcaac tgagtgcaca a                                             21

<210> SEQ ID NO 1114
<211> LENGTH: 26
<212> TYPE: DNA
<213> ORGANISM: Artificial Sequence
<220> FEATURE:
<223> OTHER INFORMATION: Primer

<400> SEQUENCE: 1114
tgcttacaac cttagagaca ggtaca                                        26

<210> SEQ ID NO 1115
<211> LENGTH: 21
<212> TYPE: DNA
<213> ORGANISM: Artificial Sequence
<220> FEATURE:
<223> OTHER INFORMATION: Primer

<400> SEQUENCE: 1115
tcactgcaac tgagtgcaca a                                             21

<210> SEQ ID NO 1116
<211> LENGTH: 18
<212> TYPE: DNA
<213> ORGANISM: Artificial Sequence
<220> FEATURE:
<223> OTHER INFORMATION: Primer

<400> SEQUENCE: 1116
tctttgctcg cagctcgt                                                 18

<210> SEQ ID NO 1117
<211> LENGTH: 22
```

```
<212> TYPE: DNA
<213> ORGANISM: Artificial Sequence
<220> FEATURE:
<223> OTHER INFORMATION: Primer

<400> SEQUENCE: 1117
ttttactacg tcgcaggcgt aa                                        22

<210> SEQ ID NO 1118
<211> LENGTH: 26
<212> TYPE: DNA
<213> ORGANISM: Artificial Sequence
<220> FEATURE:
<223> OTHER INFORMATION: Primer

<400> SEQUENCE: 1118
tgcttacaac cttagagaca ggtaca                                    26

<210> SEQ ID NO 1119
<211> LENGTH: 24
<212> TYPE: DNA
<213> ORGANISM: Artificial Sequence
<220> FEATURE:
<223> OTHER INFORMATION: Primer

<400> SEQUENCE: 1119
agaatcggtg catgaaataa ggct                                      24

<210> SEQ ID NO 1120
<211> LENGTH: 27
<212> TYPE: DNA
<213> ORGANISM: Artificial Sequence
<220> FEATURE:
<223> OTHER INFORMATION: Primer

<400> SEQUENCE: 1120
cgcttgtttg cattaacatg tctttct                                   27

<210> SEQ ID NO 1121
<211> LENGTH: 21
<212> TYPE: DNA
<213> ORGANISM: Artificial Sequence
<220> FEATURE:
<223> OTHER INFORMATION: Primer

<400> SEQUENCE: 1121
tcactgcaac tgagtgcaca a                                         21

<210> SEQ ID NO 1122
<211> LENGTH: 28
<212> TYPE: DNA
<213> ORGANISM: Artificial Sequence
<220> FEATURE:
<223> OTHER INFORMATION: Primer

<400> SEQUENCE: 1122
tgccaggtag atgaaatttg aacataca                                  28

<210> SEQ ID NO 1123
<211> LENGTH: 22
<212> TYPE: DNA
<213> ORGANISM: Artificial Sequence
<220> FEATURE:
<223> OTHER INFORMATION: Primer

<400> SEQUENCE: 1123
```

```
gctgttgggc acattacaag tt                                           22

<210> SEQ ID NO 1124
<211> LENGTH: 24
<212> TYPE: DNA
<213> ORGANISM: Artificial Sequence
<220> FEATURE:
<223> OTHER INFORMATION: Primer

<400> SEQUENCE: 1124
ggtgatccag actctgacct tttg                                         24

<210> SEQ ID NO 1125
<211> LENGTH: 22
<212> TYPE: DNA
<213> ORGANISM: Artificial Sequence
<220> FEATURE:
<223> OTHER INFORMATION: Primer

<400> SEQUENCE: 1125
gctgttgggc acattacaag tt                                           22

<210> SEQ ID NO 1126
<211> LENGTH: 19
<212> TYPE: DNA
<213> ORGANISM: Artificial Sequence
<220> FEATURE:
<223> OTHER INFORMATION: Primer

<400> SEQUENCE: 1126
aaatacggct gcaccgagt                                               19

<210> SEQ ID NO 1127
<211> LENGTH: 22
<212> TYPE: DNA
<213> ORGANISM: Artificial Sequence
<220> FEATURE:
<223> OTHER INFORMATION: Primer

<400> SEQUENCE: 1127
gctgttgggc acattacaag tt                                           22

<210> SEQ ID NO 1128
<211> LENGTH: 19
<212> TYPE: DNA
<213> ORGANISM: Artificial Sequence
<220> FEATURE:
<223> OTHER INFORMATION: Primer

<400> SEQUENCE: 1128
gcggaggtct tggaggttt                                               19

<210> SEQ ID NO 1129
<211> LENGTH: 21
<212> TYPE: DNA
<213> ORGANISM: Artificial Sequence
<220> FEATURE:
<223> OTHER INFORMATION: Primer

<400> SEQUENCE: 1129
tcactgcaac tgagtgcaca a                                            21

<210> SEQ ID NO 1130
<211> LENGTH: 22
<212> TYPE: DNA
<213> ORGANISM: Artificial Sequence
```

```
<220> FEATURE:
<223> OTHER INFORMATION: Primer

<400> SEQUENCE: 1130
atcatgatgg ctgtatgtgc ca                                              22

<210> SEQ ID NO 1131
<211> LENGTH: 28
<212> TYPE: DNA
<213> ORGANISM: Artificial Sequence
<220> FEATURE:
<223> OTHER INFORMATION: Primer

<400> SEQUENCE: 1131
gctgatagta atgacctaaa cgcacaaa                                        28

<210> SEQ ID NO 1132
<211> LENGTH: 24
<212> TYPE: DNA
<213> ORGANISM: Artificial Sequence
<220> FEATURE:
<223> OTHER INFORMATION: Primer

<400> SEQUENCE: 1132
ggtgatccag actctgacct tttg                                            24

<210> SEQ ID NO 1133
<211> LENGTH: 22
<212> TYPE: DNA
<213> ORGANISM: Artificial Sequence
<220> FEATURE:
<223> OTHER INFORMATION: Primer

<400> SEQUENCE: 1133
gctgtttggc acattacaag tt                                              22

<210> SEQ ID NO 1134
<211> LENGTH: 22
<212> TYPE: DNA
<213> ORGANISM: Artificial Sequence
<220> FEATURE:
<223> OTHER INFORMATION: Primer

<400> SEQUENCE: 1134
atcatgatgg ctgtatgtgc ca                                              22

<210> SEQ ID NO 1135
<211> LENGTH: 24
<212> TYPE: DNA
<213> ORGANISM: Artificial Sequence
<220> FEATURE:
<223> OTHER INFORMATION: Primer

<400> SEQUENCE: 1135
agaatcggtg catgaaataa ggct                                            24

<210> SEQ ID NO 1136
<211> LENGTH: 24
<212> TYPE: DNA
<213> ORGANISM: Artificial Sequence
<220> FEATURE:
<223> OTHER INFORMATION: Primer

<400> SEQUENCE: 1136
gcatttgctg tagagtacga aggt                                            24
```

<210> SEQ ID NO 1137
<211> LENGTH: 24
<212> TYPE: DNA
<213> ORGANISM: Artificial Sequence
<220> FEATURE:
<223> OTHER INFORMATION: Primer

<400> SEQUENCE: 1137
agaatcggtg catgaaataa ggct                          24

<210> SEQ ID NO 1138
<211> LENGTH: 19
<212> TYPE: DNA
<213> ORGANISM: Artificial Sequence
<220> FEATURE:
<223> OTHER INFORMATION: Primer

<400> SEQUENCE: 1138
gcggaggtct tggaggttt                                19

<210> SEQ ID NO 1139
<211> LENGTH: 24
<212> TYPE: DNA
<213> ORGANISM: Artificial Sequence
<220> FEATURE:
<223> OTHER INFORMATION: Primer

<400> SEQUENCE: 1139
caaaccatgt cacgtagaag acag                          24

<210> SEQ ID NO 1140
<211> LENGTH: 28
<212> TYPE: DNA
<213> ORGANISM: Artificial Sequence
<220> FEATURE:
<223> OTHER INFORMATION: Primer

<400> SEQUENCE: 1140
gggtttttga aatgaaacac aaccaatc                      28

<210> SEQ ID NO 1141
<211> LENGTH: 24
<212> TYPE: DNA
<213> ORGANISM: Artificial Sequence
<220> FEATURE:
<223> OTHER INFORMATION: Primer

<400> SEQUENCE: 1141
gatgaggagg atacagatgg tgtg                          24

<210> SEQ ID NO 1142
<211> LENGTH: 24
<212> TYPE: DNA
<213> ORGANISM: Artificial Sequence
<220> FEATURE:
<223> OTHER INFORMATION: Primer

<400> SEQUENCE: 1142
gcatttgctg tagagtacga aggt                          24

<210> SEQ ID NO 1143
<211> LENGTH: 24
<212> TYPE: DNA
<213> ORGANISM: Artificial Sequence
<220> FEATURE:
<223> OTHER INFORMATION: Primer

```
<400> SEQUENCE: 1143
caaaccatgt cacgtagaag acag                                        24

<210> SEQ ID NO 1144
<211> LENGTH: 19
<212> TYPE: DNA
<213> ORGANISM: Artificial Sequence
<220> FEATURE:
<223> OTHER INFORMATION: Primer

<400> SEQUENCE: 1144
ccccacccca cttgattga                                              19

<210> SEQ ID NO 1145
<211> LENGTH: 24
<212> TYPE: DNA
<213> ORGANISM: Artificial Sequence
<220> FEATURE:
<223> OTHER INFORMATION: Primer

<400> SEQUENCE: 1145
caaaccatgt cacgtagaag acag                                        24

<210> SEQ ID NO 1146
<211> LENGTH: 23
<212> TYPE: DNA
<213> ORGANISM: Artificial Sequence
<220> FEATURE:
<223> OTHER INFORMATION: Primer

<400> SEQUENCE: 1146
cggtatcgac tccatcgttt tcc                                         23

<210> SEQ ID NO 1147
<211> LENGTH: 28
<212> TYPE: DNA
<213> ORGANISM: Artificial Sequence
<220> FEATURE:
<223> OTHER INFORMATION: Primer

<400> SEQUENCE: 1147
gctgatagta atgacctaaa cgcacaaa                                    28

<210> SEQ ID NO 1148
<211> LENGTH: 19
<212> TYPE: DNA
<213> ORGANISM: Artificial Sequence
<220> FEATURE:
<223> OTHER INFORMATION: Primer

<400> SEQUENCE: 1148
ctgagaagcc ctgcccttc                                              19

<210> SEQ ID NO 1149
<211> LENGTH: 22
<212> TYPE: DNA
<213> ORGANISM: Artificial Sequence
<220> FEATURE:
<223> OTHER INFORMATION: Primer

<400> SEQUENCE: 1149
gctgttgggc acattacaag tt                                          22

<210> SEQ ID NO 1150
```

```
<211> LENGTH: 20
<212> TYPE: DNA
<213> ORGANISM: Artificial Sequence
<220> FEATURE:
<223> OTHER INFORMATION: Primer

<400> SEQUENCE: 1150
cctgtattgc aggccagaca                                              20

<210> SEQ ID NO 1151
<211> LENGTH: 24
<212> TYPE: DNA
<213> ORGANISM: Artificial Sequence
<220> FEATURE:
<223> OTHER INFORMATION: Primer

<400> SEQUENCE: 1151
agaatcggtg catgaaataa ggct                                         24

<210> SEQ ID NO 1152
<211> LENGTH: 27
<212> TYPE: DNA
<213> ORGANISM: Artificial Sequence
<220> FEATURE:
<223> OTHER INFORMATION: Primer

<400> SEQUENCE: 1152
cacacgccat atggattatt gtctcta                                      27

<210> SEQ ID NO 1153
<211> LENGTH: 22
<212> TYPE: DNA
<213> ORGANISM: Artificial Sequence
<220> FEATURE:
<223> OTHER INFORMATION: Primer

<400> SEQUENCE: 1153
gctgttgggc acattacaag tt                                           22

<210> SEQ ID NO 1154
<211> LENGTH: 23
<212> TYPE: DNA
<213> ORGANISM: Artificial Sequence
<220> FEATURE:
<223> OTHER INFORMATION: Primer

<400> SEQUENCE: 1154
cggtatcgac tccatcgttt tcc                                          23

<210> SEQ ID NO 1155
<211> LENGTH: 21
<212> TYPE: DNA
<213> ORGANISM: Artificial Sequence
<220> FEATURE:
<223> OTHER INFORMATION: Primer

<400> SEQUENCE: 1155
tcactgcaac tgagtgcaca a                                            21

<210> SEQ ID NO 1156
<211> LENGTH: 24
<212> TYPE: DNA
<213> ORGANISM: Artificial Sequence
<220> FEATURE:
<223> OTHER INFORMATION: Primer

<400> SEQUENCE: 1156
```

```
ggtgatccag actctgacct tttg                                         24

<210> SEQ ID NO 1157
<211> LENGTH: 22
<212> TYPE: DNA
<213> ORGANISM: Artificial Sequence
<220> FEATURE:
<223> OTHER INFORMATION: Primer

<400> SEQUENCE: 1157
gctgttgggc acattacaag tt                                           22

<210> SEQ ID NO 1158
<211> LENGTH: 28
<212> TYPE: DNA
<213> ORGANISM: Artificial Sequence
<220> FEATURE:
<223> OTHER INFORMATION: Primer

<400> SEQUENCE: 1158
tcctctgaaa tgttatctcc tgtttgtt                                     28

<210> SEQ ID NO 1159
<211> LENGTH: 27
<212> TYPE: DNA
<213> ORGANISM: Artificial Sequence
<220> FEATURE:
<223> OTHER INFORMATION: Primer

<400> SEQUENCE: 1159
ccttagtaca aataaaatgc ccaccat                                      27

<210> SEQ ID NO 1160
<211> LENGTH: 28
<212> TYPE: DNA
<213> ORGANISM: Artificial Sequence
<220> FEATURE:
<223> OTHER INFORMATION: Primer

<400> SEQUENCE: 1160
gggtttttga aatgaaacac aaccaatc                                     28

<210> SEQ ID NO 1161
<211> LENGTH: 28
<212> TYPE: DNA
<213> ORGANISM: Artificial Sequence
<220> FEATURE:
<223> OTHER INFORMATION: Primer

<400> SEQUENCE: 1161
gctgatagta atgacctaaa cgcacaaa                                     28

<210> SEQ ID NO 1162
<211> LENGTH: 22
<212> TYPE: DNA
<213> ORGANISM: Artificial Sequence
<220> FEATURE:
<223> OTHER INFORMATION: Primer

<400> SEQUENCE: 1162
atcatgatgg ctgtatgtgc ca                                           22

<210> SEQ ID NO 1163
<211> LENGTH: 24
<212> TYPE: DNA
```

```
<213> ORGANISM: Artificial Sequence
<220> FEATURE:
<223> OTHER INFORMATION: Primer

<400> SEQUENCE: 1163
agaatcggtg catgaaataa ggct                                    24

<210> SEQ ID NO 1164
<211> LENGTH: 23
<212> TYPE: DNA
<213> ORGANISM: Artificial Sequence
<220> FEATURE:
<223> OTHER INFORMATION: Primer

<400> SEQUENCE: 1164
cggtatcgac tccatcgttt tcc                                     23

<210> SEQ ID NO 1165
<211> LENGTH: 28
<212> TYPE: DNA
<213> ORGANISM: Artificial Sequence
<220> FEATURE:
<223> OTHER INFORMATION: Primer

<400> SEQUENCE: 1165
gctgatagta atgacctaaa cgcacaaa                                28

<210> SEQ ID NO 1166
<211> LENGTH: 19
<212> TYPE: DNA
<213> ORGANISM: Artificial Sequence
<220> FEATURE:
<223> OTHER INFORMATION: Primer

<400> SEQUENCE: 1166
aaatacggct gcaccgagt                                          19

<210> SEQ ID NO 1167
<211> LENGTH: 22
<212> TYPE: DNA
<213> ORGANISM: Artificial Sequence
<220> FEATURE:
<223> OTHER INFORMATION: Primer

<400> SEQUENCE: 1167
gctgttgggc acattacaag tt                                      22

<210> SEQ ID NO 1168
<211> LENGTH: 18
<212> TYPE: DNA
<213> ORGANISM: Artificial Sequence
<220> FEATURE:
<223> OTHER INFORMATION: Primer

<400> SEQUENCE: 1168
tctttgctcg cagctcgt                                           18

<210> SEQ ID NO 1169
<211> LENGTH: 27
<212> TYPE: DNA
<213> ORGANISM: Artificial Sequence
<220> FEATURE:
<223> OTHER INFORMATION: Primer

<400> SEQUENCE: 1169
gtaacaggag tatgggaagt acatgtg                                 27
```

<210> SEQ ID NO 1170
<211> LENGTH: 19
<212> TYPE: DNA
<213> ORGANISM: Artificial Sequence
<220> FEATURE:
<223> OTHER INFORMATION: Primer

<400> SEQUENCE: 1170
gcggaggtct tggaggttt                                            19

<210> SEQ ID NO 1171
<211> LENGTH: 27
<212> TYPE: DNA
<213> ORGANISM: Artificial Sequence
<220> FEATURE:
<223> OTHER INFORMATION: Primer

<400> SEQUENCE: 1171
gtatgggaaa acattagaag agagggt                                   27

<210> SEQ ID NO 1172
<211> LENGTH: 27
<212> TYPE: DNA
<213> ORGANISM: Artificial Sequence
<220> FEATURE:
<223> OTHER INFORMATION: Primer

<400> SEQUENCE: 1172
cgcttgtttg cattaacatg tctttct                                   27

<210> SEQ ID NO 1173
<211> LENGTH: 24
<212> TYPE: DNA
<213> ORGANISM: Artificial Sequence
<220> FEATURE:
<223> OTHER INFORMATION: Primer

<400> SEQUENCE: 1173
caaaccatgt cacgtagaag acag                                      24

<210> SEQ ID NO 1174
<211> LENGTH: 19
<212> TYPE: DNA
<213> ORGANISM: Artificial Sequence
<220> FEATURE:
<223> OTHER INFORMATION: Primer

<400> SEQUENCE: 1174
gcggaggtct tggaggttt                                            19

<210> SEQ ID NO 1175
<211> LENGTH: 21
<212> TYPE: DNA
<213> ORGANISM: Artificial Sequence
<220> FEATURE:
<223> OTHER INFORMATION: Primer

<400> SEQUENCE: 1175
tcactgcaac tgagtgcaca a                                         21

<210> SEQ ID NO 1176
<211> LENGTH: 19
<212> TYPE: DNA
<213> ORGANISM: Artificial Sequence
<220> FEATURE:

<223> OTHER INFORMATION: Primer

<400> SEQUENCE: 1176
aaatacggct gcaccgagt                                                    19

<210> SEQ ID NO 1177
<211> LENGTH: 22
<212> TYPE: DNA
<213> ORGANISM: Artificial Sequence
<220> FEATURE:
<223> OTHER INFORMATION: Primer

<400> SEQUENCE: 1177
gctgttgggc acattacaag tt                                                22

<210> SEQ ID NO 1178
<211> LENGTH: 28
<212> TYPE: DNA
<213> ORGANISM: Artificial Sequence
<220> FEATURE:
<223> OTHER INFORMATION: Primer

<400> SEQUENCE: 1178
gggtttttga aatgaaacac aaccaatc                                          28

<210> SEQ ID NO 1179
<211> LENGTH: 24
<212> TYPE: DNA
<213> ORGANISM: Artificial Sequence
<220> FEATURE:
<223> OTHER INFORMATION: Primer

<400> SEQUENCE: 1179
agaatcggtg catgaaataa ggct                                              24

<210> SEQ ID NO 1180
<211> LENGTH: 28
<212> TYPE: DNA
<213> ORGANISM: Artificial Sequence
<220> FEATURE:
<223> OTHER INFORMATION: Primer

<400> SEQUENCE: 1180
gggtttttga aatgaaacac aaccaatc                                          28

<210> SEQ ID NO 1181
<211> LENGTH: 21
<212> TYPE: DNA
<213> ORGANISM: Artificial Sequence
<220> FEATURE:
<223> OTHER INFORMATION: Primer

<400> SEQUENCE: 1181
tcactgcaac tgagtgcaca a                                                 21

<210> SEQ ID NO 1182
<211> LENGTH: 21
<212> TYPE: DNA
<213> ORGANISM: Artificial Sequence
<220> FEATURE:
<223> OTHER INFORMATION: Primer

<400> SEQUENCE: 1182
catggttcca ccagcgttat t                                                 21

<210> SEQ ID NO 1183
<211> LENGTH: 21
<212> TYPE: DNA
<213> ORGANISM: Artificial Sequence
<220> FEATURE:
<223> OTHER INFORMATION: Primer

<400> SEQUENCE: 1183
tcactgcaac tgagtgcaca a                                            21

<210> SEQ ID NO 1184
<211> LENGTH: 20
<212> TYPE: DNA
<213> ORGANISM: Artificial Sequence
<220> FEATURE:
<223> OTHER INFORMATION: Primer

<400> SEQUENCE: 1184
cctgtattgc aggccagaca                                              20

<210> SEQ ID NO 1185
<211> LENGTH: 22
<212> TYPE: DNA
<213> ORGANISM: Artificial Sequence
<220> FEATURE:
<223> OTHER INFORMATION: Primer

<400> SEQUENCE: 1185
gctgttgggc acattacaag tt                                           22

<210> SEQ ID NO 1186
<211> LENGTH: 26
<212> TYPE: DNA
<213> ORGANISM: Artificial Sequence
<220> FEATURE:
<223> OTHER INFORMATION: Primer

<400> SEQUENCE: 1186
tgcttacaac cttagagaca ggtaca                                       26

<210> SEQ ID NO 1187
<211> LENGTH: 28
<212> TYPE: DNA
<213> ORGANISM: Artificial Sequence
<220> FEATURE:
<223> OTHER INFORMATION: Primer

<400> SEQUENCE: 1187
aagcatctat tattatgcag gcagttct                                     28

<210> SEQ ID NO 1188
<211> LENGTH: 20
<212> TYPE: DNA
<213> ORGANISM: Artificial Sequence
<220> FEATURE:
<223> OTHER INFORMATION: Primer

<400> SEQUENCE: 1188
cctgtattgc aggccagaca                                              20

<210> SEQ ID NO 1189
<211> LENGTH: 21
<212> TYPE: DNA
<213> ORGANISM: Artificial Sequence
<220> FEATURE:
<223> OTHER INFORMATION: Primer

<400> SEQUENCE: 1189
tcactgcaac tgagtgcaca a                                              21

<210> SEQ ID NO 1190
<211> LENGTH: 19
<212> TYPE: DNA
<213> ORGANISM: Artificial Sequence
<220> FEATURE:
<223> OTHER INFORMATION: Primer

<400> SEQUENCE: 1190
ctgagaagcc ctgcccttc                                                 19

<210> SEQ ID NO 1191
<211> LENGTH: 28
<212> TYPE: DNA
<213> ORGANISM: Artificial Sequence
<220> FEATURE:
<223> OTHER INFORMATION: Primer

<400> SEQUENCE: 1191
gctgatagta atgacctaaa cgcacaaa                                       28

<210> SEQ ID NO 1192
<211> LENGTH: 21
<212> TYPE: DNA
<213> ORGANISM: Artificial Sequence
<220> FEATURE:
<223> OTHER INFORMATION: Primer

<400> SEQUENCE: 1192
catggttcca ccagcgttat t                                              21

<210> SEQ ID NO 1193
<211> LENGTH: 27
<212> TYPE: DNA
<213> ORGANISM: Artificial Sequence
<220> FEATURE:
<223> OTHER INFORMATION: Primer

<400> SEQUENCE: 1193
ggactatatg ttttgggagg tggattt                                        27

<210> SEQ ID NO 1194
<211> LENGTH: 22
<212> TYPE: DNA
<213> ORGANISM: Artificial Sequence
<220> FEATURE:
<223> OTHER INFORMATION: Primer

<400> SEQUENCE: 1194
gatgcagggc gttttagttt gg                                             22

<210> SEQ ID NO 1195
<211> LENGTH: 27
<212> TYPE: DNA
<213> ORGANISM: Artificial Sequence
<220> FEATURE:
<223> OTHER INFORMATION: Primer

<400> SEQUENCE: 1195
caccatcagt tgcagaagga ttaaaag                                        27

<210> SEQ ID NO 1196
<211> LENGTH: 25

```
<212> TYPE: DNA
<213> ORGANISM: Artificial Sequence
<220> FEATURE:
<223> OTHER INFORMATION: Primer

<400> SEQUENCE: 1196
ctgtgacatt agtttggaca ctgtt                                         25

<210> SEQ ID NO 1197
<211> LENGTH: 19
<212> TYPE: DNA
<213> ORGANISM: Artificial Sequence
<220> FEATURE:
<223> OTHER INFORMATION: Primer

<400> SEQUENCE: 1197
tcggttggtc ttggcacaa                                                19

<210> SEQ ID NO 1198
<211> LENGTH: 21
<212> TYPE: DNA
<213> ORGANISM: Artificial Sequence
<220> FEATURE:
<223> OTHER INFORMATION: Primer

<400> SEQUENCE: 1198
tttaggcggg acaacaagtg t                                             21

<210> SEQ ID NO 1199
<211> LENGTH: 24
<212> TYPE: DNA
<213> ORGANISM: Artificial Sequence
<220> FEATURE:
<223> OTHER INFORMATION: Primer

<400> SEQUENCE: 1199
caacacaagc caatattgct gcta                                          24

<210> SEQ ID NO 1200
<211> LENGTH: 23
<212> TYPE: DNA
<213> ORGANISM: Artificial Sequence
<220> FEATURE:
<223> OTHER INFORMATION: Primer

<400> SEQUENCE: 1200
cctgcgcata caccgatata gat                                           23

<210> SEQ ID NO 1201
<211> LENGTH: 23
<212> TYPE: DNA
<213> ORGANISM: Artificial Sequence
<220> FEATURE:
<223> OTHER INFORMATION: Primer

<400> SEQUENCE: 1201
gttaacagta acgtgcccac tct                                           23

<210> SEQ ID NO 1202
<211> LENGTH: 28
<212> TYPE: DNA
<213> ORGANISM: Artificial Sequence
<220> FEATURE:
<223> OTHER INFORMATION: Primer

<400> SEQUENCE: 1202
```

```
ttctacaatt gcctctactt caaaccat                                              28
```

<210> SEQ ID NO 1203
<211> LENGTH: 23
<212> TYPE: DNA
<213> ORGANISM: Artificial Sequence
<220> FEATURE:
<223> OTHER INFORMATION: Primer

<400> SEQUENCE: 1203

```
acaacaacca ccctggtgat aag                                                   23
```

<210> SEQ ID NO 1204
<211> LENGTH: 19
<212> TYPE: DNA
<213> ORGANISM: Artificial Sequence
<220> FEATURE:
<223> OTHER INFORMATION: Primer

<400> SEQUENCE: 1204

```
aaatacggct gcaccgagt                                                        19
```

<210> SEQ ID NO 1205
<211> LENGTH: 27
<212> TYPE: DNA
<213> ORGANISM: Artificial Sequence
<220> FEATURE:
<223> OTHER INFORMATION: Primer

<400> SEQUENCE: 1205

```
gtgccagaac aaaatactag actgttt                                               27
```

<210> SEQ ID NO 1206
<211> LENGTH: 22
<212> TYPE: DNA
<213> ORGANISM: Artificial Sequence
<220> FEATURE:
<223> OTHER INFORMATION: Primer

<400> SEQUENCE: 1206

```
atcatgatgg ctgtatgtgc ca                                                    22
```

<210> SEQ ID NO 1207
<211> LENGTH: 23
<212> TYPE: DNA
<213> ORGANISM: Artificial Sequence
<220> FEATURE:
<223> OTHER INFORMATION: Primer

<400> SEQUENCE: 1207

```
gttaacagta acgtgcccac tct                                                   23
```

<210> SEQ ID NO 1208
<211> LENGTH: 24
<212> TYPE: DNA
<213> ORGANISM: Artificial Sequence
<220> FEATURE:
<223> OTHER INFORMATION: Primer

<400> SEQUENCE: 1208

```
ggtgatccag actctgacct tttg                                                  24
```

<210> SEQ ID NO 1209
<211> LENGTH: 23
<212> TYPE: DNA
<213> ORGANISM: Artificial Sequence
<220> FEATURE:
<223> OTHER INFORMATION: Primer

<400> SEQUENCE: 1209
gttaacagta acgtgcccac tct        23

<210> SEQ ID NO 1210
<211> LENGTH: 30
<212> TYPE: DNA
<213> ORGANISM: Artificial Sequence
<220> FEATURE:
<223> OTHER INFORMATION: Primer

<400> SEQUENCE: 1210
tgaaactgaa acactaacat tctactgtgt        30

<210> SEQ ID NO 1211
<211> LENGTH: 27
<212> TYPE: DNA
<213> ORGANISM: Artificial Sequence
<220> FEATURE:
<223> OTHER INFORMATION: Primer

<400> SEQUENCE: 1211
gtgccagaac aaaatactag actgttt        27

<210> SEQ ID NO 1212
<211> LENGTH: 18
<212> TYPE: DNA
<213> ORGANISM: Artificial Sequence
<220> FEATURE:
<223> OTHER INFORMATION: Primer

<400> SEQUENCE: 1212
tctttgctcg cagctcgt        18

<210> SEQ ID NO 1213
<211> LENGTH: 27
<212> TYPE: DNA
<213> ORGANISM: Artificial Sequence
<220> FEATURE:
<223> OTHER INFORMATION: Primer

<400> SEQUENCE: 1213
gtgccagaac aaaatactag actgttt        27

<210> SEQ ID NO 1214
<211> LENGTH: 21
<212> TYPE: DNA
<213> ORGANISM: Artificial Sequence
<220> FEATURE:
<223> OTHER INFORMATION: Primer

<400> SEQUENCE: 1214
catggttcca ccagcgttat t        21

<210> SEQ ID NO 1215
<211> LENGTH: 23
<212> TYPE: DNA
<213> ORGANISM: Artificial Sequence
<220> FEATURE:
<223> OTHER INFORMATION: Primer

<400> SEQUENCE: 1215
acaacaacca ccctggtgat aag        23

```
<210> SEQ ID NO 1216
<211> LENGTH: 19
<212> TYPE: DNA
<213> ORGANISM: Artificial Sequence
<220> FEATURE:
<223> OTHER INFORMATION: Primer

<400> SEQUENCE: 1216
ctgagaagcc ctgcccttc                                                19

<210> SEQ ID NO 1217
<211> LENGTH: 23
<212> TYPE: DNA
<213> ORGANISM: Artificial Sequence
<220> FEATURE:
<223> OTHER INFORMATION: Primer

<400> SEQUENCE: 1217
acaacaacca ccctggtgat aag                                           23

<210> SEQ ID NO 1218
<211> LENGTH: 28
<212> TYPE: DNA
<213> ORGANISM: Artificial Sequence
<220> FEATURE:
<223> OTHER INFORMATION: Primer

<400> SEQUENCE: 1218
tattgtctgt acttgtccaa tgatatgt                                      28

<210> SEQ ID NO 1219
<211> LENGTH: 27
<212> TYPE: DNA
<213> ORGANISM: Artificial Sequence
<220> FEATURE:
<223> OTHER INFORMATION: Primer

<400> SEQUENCE: 1219
tgcattgtga cagaaaaga cgatttc                                        27

<210> SEQ ID NO 1220
<211> LENGTH: 19
<212> TYPE: DNA
<213> ORGANISM: Artificial Sequence
<220> FEATURE:
<223> OTHER INFORMATION: Primer

<400> SEQUENCE: 1220
acgtcttgca gcgttggta                                                19

<210> SEQ ID NO 1221
<211> LENGTH: 29
<212> TYPE: DNA
<213> ORGANISM: Artificial Sequence
<220> FEATURE:
<223> OTHER INFORMATION: Primer

<400> SEQUENCE: 1221
agaatgttag tgtttcagtt tcaaaatcc                                     29

<210> SEQ ID NO 1222
<211> LENGTH: 26
<212> TYPE: DNA
<213> ORGANISM: Artificial Sequence
<220> FEATURE:
<223> OTHER INFORMATION: Primer
```

```
<400> SEQUENCE: 1222 tttctttgt cctcgtcgtt atccaa                                          26

<210> SEQ ID NO 1223
<211> LENGTH: 23
<212> TYPE: DNA
<213> ORGANISM: Artificial Sequence
<220> FEATURE:
<223> OTHER INFORMATION: Primer

<400> SEQUENCE: 1223
acaacaacca ccctggtgat aag                                            23

<210> SEQ ID NO 1224
<211> LENGTH: 22
<212> TYPE: DNA
<213> ORGANISM: Artificial Sequence
<220> FEATURE:
<223> OTHER INFORMATION: Primer

<400> SEQUENCE: 1224
atcatgatgg ctgtatgtgc ca                                             22

<210> SEQ ID NO 1225
<211> LENGTH: 27
<212> TYPE: DNA
<213> ORGANISM: Artificial Sequence
<220> FEATURE:
<223> OTHER INFORMATION: Primer

<400> SEQUENCE: 1225
gtgccagaac aaaatactag actgttt                                        27

<210> SEQ ID NO 1226
<211> LENGTH: 19
<212> TYPE: DNA
<213> ORGANISM: Artificial Sequence
<220> FEATURE:
<223> OTHER INFORMATION: Primer

<400> SEQUENCE: 1226
ctgagaagcc ctgcccttc                                                 19

<210> SEQ ID NO 1227
<211> LENGTH: 25
<212> TYPE: DNA
<213> ORGANISM: Artificial Sequence
<220> FEATURE:
<223> OTHER INFORMATION: Primer

<400> SEQUENCE: 1227
gcaccacttg agtgaggtat tagaa                                          25

<210> SEQ ID NO 1228
<211> LENGTH: 30
<212> TYPE: DNA
<213> ORGANISM: Artificial Sequence
<220> FEATURE:
<223> OTHER INFORMATION: Primer

<400> SEQUENCE: 1228
tgaaactgaa acactaacat tctactgtgt                                     30

<210> SEQ ID NO 1229
```

```
<211> LENGTH: 25
<212> TYPE: DNA
<213> ORGANISM: Artificial Sequence
<220> FEATURE:
<223> OTHER INFORMATION: Primer

<400> SEQUENCE: 1229
acagcaagct agacaagcta aacaa                                           25

<210> SEQ ID NO 1230
<211> LENGTH: 20
<212> TYPE: DNA
<213> ORGANISM: Artificial Sequence
<220> FEATURE:
<223> OTHER INFORMATION: Primer

<400> SEQUENCE: 1230
tgtacaacac gcaggtcctc                                                 20

<210> SEQ ID NO 1231
<211> LENGTH: 23
<212> TYPE: DNA
<213> ORGANISM: Artificial Sequence
<220> FEATURE:
<223> OTHER INFORMATION: Primer

<400> SEQUENCE: 1231
gttaacagta acgtgcccac tct                                             23

<210> SEQ ID NO 1232
<211> LENGTH: 19
<212> TYPE: DNA
<213> ORGANISM: Artificial Sequence
<220> FEATURE:
<223> OTHER INFORMATION: Primer

<400> SEQUENCE: 1232
ctgagaagcc ctgcccttc                                                  19

<210> SEQ ID NO 1233
<211> LENGTH: 23
<212> TYPE: DNA
<213> ORGANISM: Artificial Sequence
<220> FEATURE:
<223> OTHER INFORMATION: Primer

<400> SEQUENCE: 1233
gttaacagta acgtgcccac tct                                             23

<210> SEQ ID NO 1234
<211> LENGTH: 24
<212> TYPE: DNA
<213> ORGANISM: Artificial Sequence
<220> FEATURE:
<223> OTHER INFORMATION: Primer

<400> SEQUENCE: 1234
acaacctttg aaacaggtgt tgga                                            24

<210> SEQ ID NO 1235
<211> LENGTH: 25
<212> TYPE: DNA
<213> ORGANISM: Artificial Sequence
<220> FEATURE:
<223> OTHER INFORMATION: Primer

<400> SEQUENCE: 1235
```
gcaccacttg agtgaggtat tagaa  25

<210> SEQ ID NO 1236
<211> LENGTH: 19
<212> TYPE: DNA
<213> ORGANISM: Artificial Sequence
<220> FEATURE:
<223> OTHER INFORMATION: Primer

<400> SEQUENCE: 1236
acgtcttgca gcgttggta  19

<210> SEQ ID NO 1237
<211> LENGTH: 27
<212> TYPE: DNA
<213> ORGANISM: Artificial Sequence
<220> FEATURE:
<223> OTHER INFORMATION: Primer

<400> SEQUENCE: 1237
gtgccagaac aaaatactag actgttt  27

<210> SEQ ID NO 1238
<211> LENGTH: 24
<212> TYPE: DNA
<213> ORGANISM: Artificial Sequence
<220> FEATURE:
<223> OTHER INFORMATION: Primer

<400> SEQUENCE: 1238
ggtgatccag actctgacct tttg  24

<210> SEQ ID NO 1239
<211> LENGTH: 20
<212> TYPE: DNA
<213> ORGANISM: Artificial Sequence
<220> FEATURE:
<223> OTHER INFORMATION: Primer

<400> SEQUENCE: 1239
atcatgcagg cagttcacga  20

<210> SEQ ID NO 1240
<211> LENGTH: 28
<212> TYPE: DNA
<213> ORGANISM: Artificial Sequence
<220> FEATURE:
<223> OTHER INFORMATION: Primer

<400> SEQUENCE: 1240
caaccgtacc ctaaataccc tatattga  28

<210> SEQ ID NO 1241
<211> LENGTH: 22
<212> TYPE: DNA
<213> ORGANISM: Artificial Sequence
<220> FEATURE:
<223> OTHER INFORMATION: Primer

<400> SEQUENCE: 1241
caagacagcg ggtatggcaa ta  22

<210> SEQ ID NO 1242
<211> LENGTH: 18
<212> TYPE: DNA

```
<213> ORGANISM: Artificial Sequence
<220> FEATURE:
<223> OTHER INFORMATION: Primer

<400> SEQUENCE: 1242
ggtggtggtg gtggtctt                                              18

<210> SEQ ID NO 1243
<211> LENGTH: 22
<212> TYPE: DNA
<213> ORGANISM: Artificial Sequence
<220> FEATURE:
<223> OTHER INFORMATION: Primer

<400> SEQUENCE: 1243
caagacagcg ggtatggcaa ta                                         22

<210> SEQ ID NO 1244
<211> LENGTH: 26
<212> TYPE: DNA
<213> ORGANISM: Artificial Sequence
<220> FEATURE:
<223> OTHER INFORMATION: Primer

<400> SEQUENCE: 1244
ttttctttgt cctcgtcgtt atccaa                                     26

<210> SEQ ID NO 1245
<211> LENGTH: 25
<212> TYPE: DNA
<213> ORGANISM: Artificial Sequence
<220> FEATURE:
<223> OTHER INFORMATION: Primer

<400> SEQUENCE: 1245
gcaccacttg agtgaggtat tagaa                                      25

<210> SEQ ID NO 1246
<211> LENGTH: 28
<212> TYPE: DNA
<213> ORGANISM: Artificial Sequence
<220> FEATURE:
<223> OTHER INFORMATION: Primer

<400> SEQUENCE: 1246
acaataaaca tactctgcac actgcata                                   28

<210> SEQ ID NO 1247
<211> LENGTH: 23
<212> TYPE: DNA
<213> ORGANISM: Artificial Sequence
<220> FEATURE:
<223> OTHER INFORMATION: Primer

<400> SEQUENCE: 1247
acaacaacca ccctggtgat aag                                        23

<210> SEQ ID NO 1248
<211> LENGTH: 24
<212> TYPE: DNA
<213> ORGANISM: Artificial Sequence
<220> FEATURE:
<223> OTHER INFORMATION: Primer

<400> SEQUENCE: 1248
acaacctttg aaacaggtgt tgga                                       24
```

<210> SEQ ID NO 1249
<211> LENGTH: 25
<212> TYPE: DNA
<213> ORGANISM: Artificial Sequence
<220> FEATURE:
<223> OTHER INFORMATION: Primer

<400> SEQUENCE: 1249
gcaccacttg agtgaggtat tagaa                                  25

<210> SEQ ID NO 1250
<211> LENGTH: 26
<212> TYPE: DNA
<213> ORGANISM: Artificial Sequence
<220> FEATURE:
<223> OTHER INFORMATION: Primer

<400> SEQUENCE: 1250
ttttctttgt cctcgtcgtt atccaa                                 26

<210> SEQ ID NO 1251
<211> LENGTH: 22
<212> TYPE: DNA
<213> ORGANISM: Artificial Sequence
<220> FEATURE:
<223> OTHER INFORMATION: Primer

<400> SEQUENCE: 1251
caagacagcg ggtatggcaa ta                                     22

<210> SEQ ID NO 1252
<211> LENGTH: 30
<212> TYPE: DNA
<213> ORGANISM: Artificial Sequence
<220> FEATURE:
<223> OTHER INFORMATION: Primer

<400> SEQUENCE: 1252
tgaaactgaa acactaacat tctactgtgt                             30

<210> SEQ ID NO 1253
<211> LENGTH: 23
<212> TYPE: DNA
<213> ORGANISM: Artificial Sequence
<220> FEATURE:
<223> OTHER INFORMATION: Primer

<400> SEQUENCE: 1253
gttaacagta acgtgcccac tct                                    23

<210> SEQ ID NO 1254
<211> LENGTH: 18
<212> TYPE: DNA
<213> ORGANISM: Artificial Sequence
<220> FEATURE:
<223> OTHER INFORMATION: Primer

<400> SEQUENCE: 1254
ggtggtggtg gtggtctt                                          18

<210> SEQ ID NO 1255
<211> LENGTH: 22
<212> TYPE: DNA
<213> ORGANISM: Artificial Sequence
<220> FEATURE:

<223> OTHER INFORMATION: Primer

<400> SEQUENCE: 1255
caagacagcg ggtatggcaa ta                                    22

<210> SEQ ID NO 1256
<211> LENGTH: 25
<212> TYPE: DNA
<213> ORGANISM: Artificial Sequence
<220> FEATURE:
<223> OTHER INFORMATION: Primer

<400> SEQUENCE: 1256
ggtactgttt tgtgagcctc cattt                                 25

<210> SEQ ID NO 1257
<211> LENGTH: 23
<212> TYPE: DNA
<213> ORGANISM: Artificial Sequence
<220> FEATURE:
<223> OTHER INFORMATION: Primer

<400> SEQUENCE: 1257
gttaacagta acgtgcccac tct                                   23

<210> SEQ ID NO 1258
<211> LENGTH: 19
<212> TYPE: DNA
<213> ORGANISM: Artificial Sequence
<220> FEATURE:
<223> OTHER INFORMATION: Primer

<400> SEQUENCE: 1258
aaatacggct gcaccgagt                                        19

<210> SEQ ID NO 1259
<211> LENGTH: 23
<212> TYPE: DNA
<213> ORGANISM: Artificial Sequence
<220> FEATURE:
<223> OTHER INFORMATION: Primer

<400> SEQUENCE: 1259
acaacaacca ccctggtgat aag                                   23

<210> SEQ ID NO 1260
<211> LENGTH: 24
<212> TYPE: DNA
<213> ORGANISM: Artificial Sequence
<220> FEATURE:
<223> OTHER INFORMATION: Primer

<400> SEQUENCE: 1260
ggtgatccag actctgacct tttg                                  24

<210> SEQ ID NO 1261
<211> LENGTH: 23
<212> TYPE: DNA
<213> ORGANISM: Artificial Sequence
<220> FEATURE:
<223> OTHER INFORMATION: Primer

<400> SEQUENCE: 1261
acaacaacca ccctggtgat aag                                   23

```
<210> SEQ ID NO 1262
<211> LENGTH: 21
<212> TYPE: DNA
<213> ORGANISM: Artificial Sequence
<220> FEATURE:
<223> OTHER INFORMATION: Primer

<400> SEQUENCE: 1262
catggttcca ccagcgttat t                                             21

<210> SEQ ID NO 1263
<211> LENGTH: 27
<212> TYPE: DNA
<213> ORGANISM: Artificial Sequence
<220> FEATURE:
<223> OTHER INFORMATION: Primer

<400> SEQUENCE: 1263
gtgccagaac aaaatactag actgttt                                       27

<210> SEQ ID NO 1264
<211> LENGTH: 19
<212> TYPE: DNA
<213> ORGANISM: Artificial Sequence
<220> FEATURE:
<223> OTHER INFORMATION: Primer

<400> SEQUENCE: 1264
aaatacggct gcaccgagt                                                19

<210> SEQ ID NO 1265
<211> LENGTH: 23
<212> TYPE: DNA
<213> ORGANISM: Artificial Sequence
<220> FEATURE:
<223> OTHER INFORMATION: Primer

<400> SEQUENCE: 1265
agggatcctc ctttgcatta tgg                                           23

<210> SEQ ID NO 1266
<211> LENGTH: 24
<212> TYPE: DNA
<213> ORGANISM: Artificial Sequence
<220> FEATURE:
<223> OTHER INFORMATION: Primer

<400> SEQUENCE: 1266
acaacctttg aaacaggtgt tgga                                          24

<210> SEQ ID NO 1267
<211> LENGTH: 25
<212> TYPE: DNA
<213> ORGANISM: Artificial Sequence
<220> FEATURE:
<223> OTHER INFORMATION: Primer

<400> SEQUENCE: 1267
gcaccacttg agtgaggtat tagaa                                         25

<210> SEQ ID NO 1268
<211> LENGTH: 24
<212> TYPE: DNA
<213> ORGANISM: Artificial Sequence
<220> FEATURE:
<223> OTHER INFORMATION: Primer
```

```
<400> SEQUENCE: 1268
caattgcttt tcctccggag ttaa                                    24

<210> SEQ ID NO 1269
<211> LENGTH: 23
<212> TYPE: DNA
<213> ORGANISM: Artificial Sequence
<220> FEATURE:
<223> OTHER INFORMATION: Primer

<400> SEQUENCE: 1269
gttaacagta acgtgcccac tct                                     23

<210> SEQ ID NO 1270
<211> LENGTH: 28
<212> TYPE: DNA
<213> ORGANISM: Artificial Sequence
<220> FEATURE:
<223> OTHER INFORMATION: Primer

<400> SEQUENCE: 1270
caaccgtacc ctaaataccc tatattga                                28

<210> SEQ ID NO 1271
<211> LENGTH: 23
<212> TYPE: DNA
<213> ORGANISM: Artificial Sequence
<220> FEATURE:
<223> OTHER INFORMATION: Primer

<400> SEQUENCE: 1271
gttaacagta acgtgcccac tct                                     23

<210> SEQ ID NO 1272
<211> LENGTH: 22
<212> TYPE: DNA
<213> ORGANISM: Artificial Sequence
<220> FEATURE:
<223> OTHER INFORMATION: Primer

<400> SEQUENCE: 1272
atcatgatgg ctgtatgtgc ca                                      22

<210> SEQ ID NO 1273
<211> LENGTH: 23
<212> TYPE: DNA
<213> ORGANISM: Artificial Sequence
<220> FEATURE:
<223> OTHER INFORMATION: Primer

<400> SEQUENCE: 1273
gttaacagta acgtgcccac tct                                     23

<210> SEQ ID NO 1274
<211> LENGTH: 26
<212> TYPE: DNA
<213> ORGANISM: Artificial Sequence
<220> FEATURE:
<223> OTHER INFORMATION: Primer

<400> SEQUENCE: 1274 tttctttgt cctcgtcgtt atccaa                                   26

<210> SEQ ID NO 1275
<211> LENGTH: 27
```

```
<212> TYPE: DNA
<213> ORGANISM: Artificial Sequence
<220> FEATURE:
<223> OTHER INFORMATION: Primer

<400> SEQUENCE: 1275
tcagtgtatg gagctacact agaaagt                                         27

<210> SEQ ID NO 1276
<211> LENGTH: 24
<212> TYPE: DNA
<213> ORGANISM: Artificial Sequence
<220> FEATURE:
<223> OTHER INFORMATION: Primer

<400> SEQUENCE: 1276
caattgcttt tcctccggag ttaa                                            24

<210> SEQ ID NO 1277
<211> LENGTH: 23
<212> TYPE: DNA
<213> ORGANISM: Artificial Sequence
<220> FEATURE:
<223> OTHER INFORMATION: Primer

<400> SEQUENCE: 1277
gttaacagta acgtgcccac tct                                             23

<210> SEQ ID NO 1278
<211> LENGTH: 18
<212> TYPE: DNA
<213> ORGANISM: Artificial Sequence
<220> FEATURE:
<223> OTHER INFORMATION: Primer

<400> SEQUENCE: 1278
tctttgctcg cagctcgt                                                   18

<210> SEQ ID NO 1279
<211> LENGTH: 23
<212> TYPE: DNA
<213> ORGANISM: Artificial Sequence
<220> FEATURE:
<223> OTHER INFORMATION: Primer

<400> SEQUENCE: 1279
acaacaacca ccctggtgat aag                                             23

<210> SEQ ID NO 1280
<211> LENGTH: 28
<212> TYPE: DNA
<213> ORGANISM: Artificial Sequence
<220> FEATURE:
<223> OTHER INFORMATION: Primer

<400> SEQUENCE: 1280
caaccgtacc ctaaataccc tatattga                                        28

<210> SEQ ID NO 1281
<211> LENGTH: 23
<212> TYPE: DNA
<213> ORGANISM: Artificial Sequence
<220> FEATURE:
<223> OTHER INFORMATION: Primer

<400> SEQUENCE: 1281
```
gttaacagta acgtgcccac tct                                            23

<210> SEQ ID NO 1282
<211> LENGTH: 21
<212> TYPE: DNA
<213> ORGANISM: Artificial Sequence
<220> FEATURE:
<223> OTHER INFORMATION: Primer

<400> SEQUENCE: 1282
catggttcca ccagcgttat t                                              21

<210> SEQ ID NO 1283
<211> LENGTH: 23
<212> TYPE: DNA
<213> ORGANISM: Artificial Sequence
<220> FEATURE:
<223> OTHER INFORMATION: Primer

<400> SEQUENCE: 1283
acaacaacca ccctggtgat aag                                            23

<210> SEQ ID NO 1284
<211> LENGTH: 18
<212> TYPE: DNA
<213> ORGANISM: Artificial Sequence
<220> FEATURE:
<223> OTHER INFORMATION: Primer

<400> SEQUENCE: 1284
tctttgctcg cagctcgt                                                  18

<210> SEQ ID NO 1285
<211> LENGTH: 25
<212> TYPE: DNA
<213> ORGANISM: Artificial Sequence
<220> FEATURE:
<223> OTHER INFORMATION: Primer

<400> SEQUENCE: 1285
gcaccacttg agtgaggtat tagaa                                          25

<210> SEQ ID NO 1286
<211> LENGTH: 18
<212> TYPE: DNA
<213> ORGANISM: Artificial Sequence
<220> FEATURE:
<223> OTHER INFORMATION: Primer

<400> SEQUENCE: 1286
ggtggtggtg gtggtctt                                                  18

<210> SEQ ID NO 1287
<211> LENGTH: 25
<212> TYPE: DNA
<213> ORGANISM: Artificial Sequence
<220> FEATURE:
<223> OTHER INFORMATION: Primer

<400> SEQUENCE: 1287
gcaccacttg agtgaggtat tagaa                                          25

<210> SEQ ID NO 1288
<211> LENGTH: 20
<212> TYPE: DNA
<213> ORGANISM: Artificial Sequence

```
<220> FEATURE:
<223> OTHER INFORMATION: Primer

<400> SEQUENCE: 1288
tgtacaacac gcaggtcctc                                                    20

<210> SEQ ID NO 1289
<211> LENGTH: 28
<212> TYPE: DNA
<213> ORGANISM: Artificial Sequence
<220> FEATURE:
<223> OTHER INFORMATION: Primer

<400> SEQUENCE: 1289
tgctacgcat atatattgca accattga                                           28

<210> SEQ ID NO 1290
<211> LENGTH: 28
<212> TYPE: DNA
<213> ORGANISM: Artificial Sequence
<220> FEATURE:
<223> OTHER INFORMATION: Primer

<400> SEQUENCE: 1290
ggatgtggct ataacaaacc aaaacaat                                           28

<210> SEQ ID NO 1291
<211> LENGTH: 21
<212> TYPE: DNA
<213> ORGANISM: Artificial Sequence
<220> FEATURE:
<223> OTHER INFORMATION: Primer

<400> SEQUENCE: 1291
aattcggttg catggcctag t                                                  21

<210> SEQ ID NO 1292
<211> LENGTH: 26
<212> TYPE: DNA
<213> ORGANISM: Artificial Sequence
<220> FEATURE:
<223> OTHER INFORMATION: Primer

<400> SEQUENCE: 1292
gggtgcggta ctgtacataa ttcaag                                             26

<210> SEQ ID NO 1293
<211> LENGTH: 21
<212> TYPE: DNA
<213> ORGANISM: Artificial Sequence
<220> FEATURE:
<223> OTHER INFORMATION: Primer

<400> SEQUENCE: 1293
tgtactcccg ctatgggtga a                                                  21

<210> SEQ ID NO 1294
<211> LENGTH: 25
<212> TYPE: DNA
<213> ORGANISM: Artificial Sequence
<220> FEATURE:
<223> OTHER INFORMATION: Primer

<400> SEQUENCE: 1294
gtgtctatca tgtccccatc ctcta                                              25
```

<210> SEQ ID NO 1295
<211> LENGTH: 25
<212> TYPE: DNA
<213> ORGANISM: Artificial Sequence
<220> FEATURE:
<223> OTHER INFORMATION: Primer

<400> SEQUENCE: 1295
cagatgatag ccaaattgcg tttca                                    25

<210> SEQ ID NO 1296
<211> LENGTH: 27
<212> TYPE: DNA
<213> ORGANISM: Artificial Sequence
<220> FEATURE:
<223> OTHER INFORMATION: Primer

<400> SEQUENCE: 1296
gctgttgtgc cctttataa tgtctac                                   27

<210> SEQ ID NO 1297
<211> LENGTH: 23
<212> TYPE: DNA
<213> ORGANISM: Artificial Sequence
<220> FEATURE:
<223> OTHER INFORMATION: Primer

<400> SEQUENCE: 1297
tgcttatggg cacatgtacc att                                      23

<210> SEQ ID NO 1298
<211> LENGTH: 23
<212> TYPE: DNA
<213> ORGANISM: Artificial Sequence
<220> FEATURE:
<223> OTHER INFORMATION: Primer

<400> SEQUENCE: 1298
gcttacaacc ttagacacag gca                                      23

<210> SEQ ID NO 1299
<211> LENGTH: 27
<212> TYPE: DNA
<213> ORGANISM: Artificial Sequence
<220> FEATURE:
<223> OTHER INFORMATION: Primer

<400> SEQUENCE: 1299
gaggaggact acacagtaca actaact                                  27

<210> SEQ ID NO 1300
<211> LENGTH: 22
<212> TYPE: DNA
<213> ORGANISM: Artificial Sequence
<220> FEATURE:
<223> OTHER INFORMATION: Primer

<400> SEQUENCE: 1300
atcatgatgg ctgtatgtgc ca                                       22

<210> SEQ ID NO 1301
<211> LENGTH: 23
<212> TYPE: DNA
<213> ORGANISM: Artificial Sequence
<220> FEATURE:
<223> OTHER INFORMATION: Primer

```
<400> SEQUENCE: 1301
tgcttatggg cacatgtacc att                                           23

<210> SEQ ID NO 1302
<211> LENGTH: 24
<212> TYPE: DNA
<213> ORGANISM: Artificial Sequence
<220> FEATURE:
<223> OTHER INFORMATION: Primer

<400> SEQUENCE: 1302
ggtgatccag actctgacct tttg                                          24

<210> SEQ ID NO 1303
<211> LENGTH: 28
<212> TYPE: DNA
<213> ORGANISM: Artificial Sequence
<220> FEATURE:
<223> OTHER INFORMATION: Primer

<400> SEQUENCE: 1303
aaaattattg agctagaaga cagcggat                                      28

<210> SEQ ID NO 1304
<211> LENGTH: 23
<212> TYPE: DNA
<213> ORGANISM: Artificial Sequence
<220> FEATURE:
<223> OTHER INFORMATION: Primer

<400> SEQUENCE: 1304
ccctgtgtac tttcgttgtt ggt                                           23

<210> SEQ ID NO 1305
<211> LENGTH: 28
<212> TYPE: DNA
<213> ORGANISM: Artificial Sequence
<220> FEATURE:
<223> OTHER INFORMATION: Primer

<400> SEQUENCE: 1305
aaaattattg agctagaaga cagcggat                                      28

<210> SEQ ID NO 1306
<211> LENGTH: 25
<212> TYPE: DNA
<213> ORGANISM: Artificial Sequence
<220> FEATURE:
<223> OTHER INFORMATION: Primer

<400> SEQUENCE: 1306
ccccactaga ctccgagtca tttaa                                         25

<210> SEQ ID NO 1307
<211> LENGTH: 27
<212> TYPE: DNA
<213> ORGANISM: Artificial Sequence
<220> FEATURE:
<223> OTHER INFORMATION: Primer

<400> SEQUENCE: 1307
gaggaggact acacagtaca actaact                                       27

<210> SEQ ID NO 1308
```

```
<211> LENGTH: 24
<212> TYPE: DNA
<213> ORGANISM: Artificial Sequence
<220> FEATURE:
<223> OTHER INFORMATION: Primer

<400> SEQUENCE: 1308
ggtgatccag actctgacct tttg                                              24

<210> SEQ ID NO 1309
<211> LENGTH: 28
<212> TYPE: DNA
<213> ORGANISM: Artificial Sequence
<220> FEATURE:
<223> OTHER INFORMATION: Primer

<400> SEQUENCE: 1309
gcaggacaaa atcctagaca tatacgaa                                          28

<210> SEQ ID NO 1310
<211> LENGTH: 18
<212> TYPE: DNA
<213> ORGANISM: Artificial Sequence
<220> FEATURE:
<223> OTHER INFORMATION: Primer

<400> SEQUENCE: 1310
tctttgctcg cagctcgt                                                     18

<210> SEQ ID NO 1311
<211> LENGTH: 27
<212> TYPE: DNA
<213> ORGANISM: Artificial Sequence
<220> FEATURE:
<223> OTHER INFORMATION: Primer

<400> SEQUENCE: 1311
gaggaggact acacagtaca actaact                                           27

<210> SEQ ID NO 1312
<211> LENGTH: 21
<212> TYPE: DNA
<213> ORGANISM: Artificial Sequence
<220> FEATURE:
<223> OTHER INFORMATION: Primer

<400> SEQUENCE: 1312
catggttcca ccagcgttat t                                                 21

<210> SEQ ID NO 1313
<211> LENGTH: 23
<212> TYPE: DNA
<213> ORGANISM: Artificial Sequence
<220> FEATURE:
<223> OTHER INFORMATION: Primer

<400> SEQUENCE: 1313
tgcttatggg cacatgtacc att                                               23

<210> SEQ ID NO 1314
<211> LENGTH: 27
<212> TYPE: DNA
<213> ORGANISM: Artificial Sequence
<220> FEATURE:
<223> OTHER INFORMATION: Primer

<400> SEQUENCE: 1314
```
ctgttcttcg ttctattacc gcttcta            27

<210> SEQ ID NO 1315
<211> LENGTH: 23
<212> TYPE: DNA
<213> ORGANISM: Artificial Sequence
<220> FEATURE:
<223> OTHER INFORMATION: Primer

<400> SEQUENCE: 1315
tgcttatggg cacatgtacc att            23

<210> SEQ ID NO 1316
<211> LENGTH: 22
<212> TYPE: DNA
<213> ORGANISM: Artificial Sequence
<220> FEATURE:
<223> OTHER INFORMATION: Primer

<400> SEQUENCE: 1316
atcatgatgg ctgtatgtgc ca            22

<210> SEQ ID NO 1317
<211> LENGTH: 30
<212> TYPE: DNA
<213> ORGANISM: Artificial Sequence
<220> FEATURE:
<223> OTHER INFORMATION: Primer

<400> SEQUENCE: 1317
attagatggt aacgacattt caatagatgt            30

<210> SEQ ID NO 1318
<211> LENGTH: 31
<212> TYPE: DNA
<213> ORGANISM: Artificial Sequence
<220> FEATURE:
<223> OTHER INFORMATION: Primer

<400> SEQUENCE: 1318
tgcatcaaat ggaaatggat tgttaaattc a            31

<210> SEQ ID NO 1319
<211> LENGTH: 20
<212> TYPE: DNA
<213> ORGANISM: Artificial Sequence
<220> FEATURE:
<223> OTHER INFORMATION: Primer

<400> SEQUENCE: 1319
gtcaggcgtt ggagacatct            20

<210> SEQ ID NO 1320
<211> LENGTH: 31
<212> TYPE: DNA
<213> ORGANISM: Artificial Sequence
<220> FEATURE:
<223> OTHER INFORMATION: Primer

<400> SEQUENCE: 1320
tgcatcaaat ggaaatggat tgttaaattc a            31

<210> SEQ ID NO 1321
<211> LENGTH: 28
<212> TYPE: DNA

```
<213> ORGANISM: Artificial Sequence
<220> FEATURE:
<223> OTHER INFORMATION: Primer

<400> SEQUENCE: 1321
gcaggacaaa atcctagaca tatacgaa                                         28

<210> SEQ ID NO 1322
<211> LENGTH: 24
<212> TYPE: DNA
<213> ORGANISM: Artificial Sequence
<220> FEATURE:
<223> OTHER INFORMATION: Primer

<400> SEQUENCE: 1322
ggtgatccag actctgacct tttg                                             24

<210> SEQ ID NO 1323
<211> LENGTH: 23
<212> TYPE: DNA
<213> ORGANISM: Artificial Sequence
<220> FEATURE:
<223> OTHER INFORMATION: Primer

<400> SEQUENCE: 1323
tgcttatggg cacatgtacc att                                              23

<210> SEQ ID NO 1324
<211> LENGTH: 19
<212> TYPE: DNA
<213> ORGANISM: Artificial Sequence
<220> FEATURE:
<223> OTHER INFORMATION: Primer

<400> SEQUENCE: 1324
aaatacggct gcaccgagt                                                   19

<210> SEQ ID NO 1325
<211> LENGTH: 20
<212> TYPE: DNA
<213> ORGANISM: Artificial Sequence
<220> FEATURE:
<223> OTHER INFORMATION: Primer

<400> SEQUENCE: 1325
gtcaggcgtt ggagacatct                                                  20

<210> SEQ ID NO 1326
<211> LENGTH: 28
<212> TYPE: DNA
<213> ORGANISM: Artificial Sequence
<220> FEATURE:
<223> OTHER INFORMATION: Primer

<400> SEQUENCE: 1326
cgacccgaaa tattatgaaa cctttgt                                          28

<210> SEQ ID NO 1327
<211> LENGTH: 23
<212> TYPE: DNA
<213> ORGANISM: Artificial Sequence
<220> FEATURE:
<223> OTHER INFORMATION: Primer

<400> SEQUENCE: 1327
tgcttatggg cacatgtacc att                                              23
```

<210> SEQ ID NO 1328
<211> LENGTH: 18
<212> TYPE: DNA
<213> ORGANISM: Artificial Sequence
<220> FEATURE:
<223> OTHER INFORMATION: Primer

<400> SEQUENCE: 1328
tctttgctcg cagctcgt                                             18

<210> SEQ ID NO 1329
<211> LENGTH: 20
<212> TYPE: DNA
<213> ORGANISM: Artificial Sequence
<220> FEATURE:
<223> OTHER INFORMATION: Primer

<400> SEQUENCE: 1329
gtcaggcgtt ggagacatct                                           20

<210> SEQ ID NO 1330
<211> LENGTH: 28
<212> TYPE: DNA
<213> ORGANISM: Artificial Sequence
<220> FEATURE:
<223> OTHER INFORMATION: Primer

<400> SEQUENCE: 1330
tgatatttcc tccatcgttt tccttgtc                                  28

<210> SEQ ID NO 1331
<211> LENGTH: 29
<212> TYPE: DNA
<213> ORGANISM: Artificial Sequence
<220> FEATURE:
<223> OTHER INFORMATION: Primer

<400> SEQUENCE: 1331
cgctatatgg agacacatta gaacaaaca                                 29

<210> SEQ ID NO 1332
<211> LENGTH: 28
<212> TYPE: DNA
<213> ORGANISM: Artificial Sequence
<220> FEATURE:
<223> OTHER INFORMATION: Primer

<400> SEQUENCE: 1332
cgacccgaaa tattatgaaa ccttttgt                                  28

<210> SEQ ID NO 1333
<211> LENGTH: 26
<212> TYPE: DNA
<213> ORGANISM: Artificial Sequence
<220> FEATURE:
<223> OTHER INFORMATION: Primer

<400> SEQUENCE: 1333
acaattatgg gaggtacatg tgggta                                    26

<210> SEQ ID NO 1334
<211> LENGTH: 23
<212> TYPE: DNA
<213> ORGANISM: Artificial Sequence
<220> FEATURE:

<223> OTHER INFORMATION: Primer

<400> SEQUENCE: 1334
ccctgtgtac tttcgttgtt ggt                                    23

<210> SEQ ID NO 1335
<211> LENGTH: 28
<212> TYPE: DNA
<213> ORGANISM: Artificial Sequence
<220> FEATURE:
<223> OTHER INFORMATION: Primer

<400> SEQUENCE: 1335
aaaattattg agctagaaga cagcggat                               28

<210> SEQ ID NO 1336
<211> LENGTH: 31
<212> TYPE: DNA
<213> ORGANISM: Artificial Sequence
<220> FEATURE:
<223> OTHER INFORMATION: Primer

<400> SEQUENCE: 1336
tgcatcaaat ggaaatggat tgttaaattc a                           31

<210> SEQ ID NO 1337
<211> LENGTH: 28
<212> TYPE: DNA
<213> ORGANISM: Artificial Sequence
<220> FEATURE:
<223> OTHER INFORMATION: Primer

<400> SEQUENCE: 1337
aaaattattg agctagaaga cagcggat                               28

<210> SEQ ID NO 1338
<211> LENGTH: 28
<212> TYPE: DNA
<213> ORGANISM: Artificial Sequence
<220> FEATURE:
<223> OTHER INFORMATION: Primer

<400> SEQUENCE: 1338
tgatatttcc tccatcgttt tccttgtc                               28

<210> SEQ ID NO 1339
<211> LENGTH: 28
<212> TYPE: DNA
<213> ORGANISM: Artificial Sequence
<220> FEATURE:
<223> OTHER INFORMATION: Primer

<400> SEQUENCE: 1339
gcaggacaaa atcctagaca tatacgaa                               28

<210> SEQ ID NO 1340
<211> LENGTH: 19
<212> TYPE: DNA
<213> ORGANISM: Artificial Sequence
<220> FEATURE:
<223> OTHER INFORMATION: Primer

<400> SEQUENCE: 1340
aaatacggct gcaccgagt                                         19

```
<210> SEQ ID NO 1341
<211> LENGTH: 20
<212> TYPE: DNA
<213> ORGANISM: Artificial Sequence
<220> FEATURE:
<223> OTHER INFORMATION: Primer

<400> SEQUENCE: 1341
gtcaggcgtt ggagacatct                                                  20

<210> SEQ ID NO 1342
<211> LENGTH: 21
<212> TYPE: DNA
<213> ORGANISM: Artificial Sequence
<220> FEATURE:
<223> OTHER INFORMATION: Primer

<400> SEQUENCE: 1342
gcgttgggtt gtttcctctc a                                                21

<210> SEQ ID NO 1343
<211> LENGTH: 23
<212> TYPE: DNA
<213> ORGANISM: Artificial Sequence
<220> FEATURE:
<223> OTHER INFORMATION: Primer

<400> SEQUENCE: 1343
tgcttatggg cacatgtacc att                                              23

<210> SEQ ID NO 1344
<211> LENGTH: 21
<212> TYPE: DNA
<213> ORGANISM: Artificial Sequence
<220> FEATURE:
<223> OTHER INFORMATION: Primer

<400> SEQUENCE: 1344
catggttcca ccagcgttat t                                                21

<210> SEQ ID NO 1345
<211> LENGTH: 23
<212> TYPE: DNA
<213> ORGANISM: Artificial Sequence
<220> FEATURE:
<223> OTHER INFORMATION: Primer

<400> SEQUENCE: 1345
tgcttatggg cacatgtacc att                                              23

<210> SEQ ID NO 1346
<211> LENGTH: 19
<212> TYPE: DNA
<213> ORGANISM: Artificial Sequence
<220> FEATURE:
<223> OTHER INFORMATION: Primer

<400> SEQUENCE: 1346
ctgagaagcc ctgcccttc                                                   19

<210> SEQ ID NO 1347
<211> LENGTH: 23
<212> TYPE: DNA
<213> ORGANISM: Artificial Sequence
<220> FEATURE:
<223> OTHER INFORMATION: Primer
```

```
<400> SEQUENCE: 1347
tgcttatggg cacatgtacc att                                          23

<210> SEQ ID NO 1348
<211> LENGTH: 28
<212> TYPE: DNA
<213> ORGANISM: Artificial Sequence
<220> FEATURE:
<223> OTHER INFORMATION: Primer

<400> SEQUENCE: 1348
tgatatttcc tccatcgttt tccttgtc                                     28

<210> SEQ ID NO 1349
<211> LENGTH: 27
<212> TYPE: DNA
<213> ORGANISM: Artificial Sequence
<220> FEATURE:
<223> OTHER INFORMATION: Primer

<400> SEQUENCE: 1349
gaggaggact acacagtaca actaact                                      27

<210> SEQ ID NO 1350
<211> LENGTH: 18
<212> TYPE: DNA
<213> ORGANISM: Artificial Sequence
<220> FEATURE:
<223> OTHER INFORMATION: Primer

<400> SEQUENCE: 1350
tctttgctcg cagctcgt                                                18

<210> SEQ ID NO 1351
<211> LENGTH: 28
<212> TYPE: DNA
<213> ORGANISM: Artificial Sequence
<220> FEATURE:
<223> OTHER INFORMATION: Primer

<400> SEQUENCE: 1351
gcaggacaaa atcctagaca tatacgaa                                     28

<210> SEQ ID NO 1352
<211> LENGTH: 21
<212> TYPE: DNA
<213> ORGANISM: Artificial Sequence
<220> FEATURE:
<223> OTHER INFORMATION: Primer

<400> SEQUENCE: 1352
catggttcca ccagcgttat t                                            21

<210> SEQ ID NO 1353
<211> LENGTH: 20
<212> TYPE: DNA
<213> ORGANISM: Artificial Sequence
<220> FEATURE:
<223> OTHER INFORMATION: Primer

<400> SEQUENCE: 1353
gtcaggcgtt ggagacatct                                              20

<210> SEQ ID NO 1354
<211> LENGTH: 23
```

```
<212> TYPE: DNA
<213> ORGANISM: Artificial Sequence
<220> FEATURE:
<223> OTHER INFORMATION: Primer

<400> SEQUENCE: 1354
ccctgtgtac tttcgttgtt ggt                                    23

<210> SEQ ID NO 1355
<211> LENGTH: 28
<212> TYPE: DNA
<213> ORGANISM: Artificial Sequence
<220> FEATURE:
<223> OTHER INFORMATION: Primer

<400> SEQUENCE: 1355
gcaggacaaa atcctagaca tatacgaa                                28

<210> SEQ ID NO 1356
<211> LENGTH: 22
<212> TYPE: DNA
<213> ORGANISM: Artificial Sequence
<220> FEATURE:
<223> OTHER INFORMATION: Primer

<400> SEQUENCE: 1356
atcatgatgg ctgtatgtgc ca                                     22

<210> SEQ ID NO 1357
<211> LENGTH: 27
<212> TYPE: DNA
<213> ORGANISM: Artificial Sequence
<220> FEATURE:
<223> OTHER INFORMATION: Primer

<400> SEQUENCE: 1357
gaggaggact acacagtaca actaact                                27

<210> SEQ ID NO 1358
<211> LENGTH: 19
<212> TYPE: DNA
<213> ORGANISM: Artificial Sequence
<220> FEATURE:
<223> OTHER INFORMATION: Primer

<400> SEQUENCE: 1358
aaatacggct gcaccgagt                                         19

<210> SEQ ID NO 1359
<211> LENGTH: 27
<212> TYPE: DNA
<213> ORGANISM: Artificial Sequence
<220> FEATURE:
<223> OTHER INFORMATION: Primer

<400> SEQUENCE: 1359
gaggaggact acacagtaca actaact                                27

<210> SEQ ID NO 1360
<211> LENGTH: 27
<212> TYPE: DNA
<213> ORGANISM: Artificial Sequence
<220> FEATURE:
<223> OTHER INFORMATION: Primer

<400> SEQUENCE: 1360
```
ccaatgccat gtggatgaca tattaca                                          27

<210> SEQ ID NO 1361
<211> LENGTH: 28
<212> TYPE: DNA
<213> ORGANISM: Artificial Sequence
<220> FEATURE:
<223> OTHER INFORMATION: Primer

<400> SEQUENCE: 1361
ctgattttat gttgcaccct agctatttt                                        28

<210> SEQ ID NO 1362
<211> LENGTH: 23
<212> TYPE: DNA
<213> ORGANISM: Artificial Sequence
<220> FEATURE:
<223> OTHER INFORMATION: Primer

<400> SEQUENCE: 1362
gcttacaacc ttagacacag gca                                              23

<210> SEQ ID NO 1363
<211> LENGTH: 27
<212> TYPE: DNA
<213> ORGANISM: Artificial Sequence
<220> FEATURE:
<223> OTHER INFORMATION: Primer

<400> SEQUENCE: 1363
gaggaggact acacagtaca actaact                                          27

<210> SEQ ID NO 1364
<211> LENGTH: 19
<212> TYPE: DNA
<213> ORGANISM: Artificial Sequence
<220> FEATURE:
<223> OTHER INFORMATION: Primer

<400> SEQUENCE: 1364
ctgagaagcc ctgcccttc                                                   19

<210> SEQ ID NO 1365
<211> LENGTH: 20
<212> TYPE: DNA
<213> ORGANISM: Artificial Sequence
<220> FEATURE:
<223> OTHER INFORMATION: Primer

<400> SEQUENCE: 1365
gtcaggcgtt ggagacatct                                                  20

<210> SEQ ID NO 1366
<211> LENGTH: 27
<212> TYPE: DNA
<213> ORGANISM: Artificial Sequence
<220> FEATURE:
<223> OTHER INFORMATION: Primer

<400> SEQUENCE: 1366
tcgtaagcac actttacata ctgcaaa                                          27

<210> SEQ ID NO 1367
<211> LENGTH: 23
<212> TYPE: DNA
<213> ORGANISM: Artificial Sequence

```
<220> FEATURE:
<223> OTHER INFORMATION: Primer

<400> SEQUENCE: 1367
tgcttatggg cacatgtacc att                                              23

<210> SEQ ID NO 1368
<211> LENGTH: 31
<212> TYPE: DNA
<213> ORGANISM: Artificial Sequence
<220> FEATURE:
<223> OTHER INFORMATION: Primer

<400> SEQUENCE: 1368
tgcatcaaat ggaaatggat tgttaaattc a                                     31

<210> SEQ ID NO 1369
<211> LENGTH: 23
<212> TYPE: DNA
<213> ORGANISM: Artificial Sequence
<220> FEATURE:
<223> OTHER INFORMATION: Primer

<400> SEQUENCE: 1369
tgcttatggg cacatgtacc att                                              23

<210> SEQ ID NO 1370
<211> LENGTH: 23
<212> TYPE: DNA
<213> ORGANISM: Artificial Sequence
<220> FEATURE:
<223> OTHER INFORMATION: Primer

<400> SEQUENCE: 1370
ccctgtgtac tttcgttgtt ggt                                              23

<210> SEQ ID NO 1371
<211> LENGTH: 27
<212> TYPE: DNA
<213> ORGANISM: Artificial Sequence
<220> FEATURE:
<223> OTHER INFORMATION: Primer

<400> SEQUENCE: 1371
gaggaggact acacagtaca actaact                                          27

<210> SEQ ID NO 1372
<211> LENGTH: 23
<212> TYPE: DNA
<213> ORGANISM: Artificial Sequence
<220> FEATURE:
<223> OTHER INFORMATION: Primer

<400> SEQUENCE: 1372
gcttacaacc ttagacacag gca                                              23

<210> SEQ ID NO 1373
<211> LENGTH: 28
<212> TYPE: DNA
<213> ORGANISM: Artificial Sequence
<220> FEATURE:
<223> OTHER INFORMATION: Primer

<400> SEQUENCE: 1373
gcaggacaaa atcctagaca tatacgaa                                         28
```

<210> SEQ ID NO 1374
<211> LENGTH: 19
<212> TYPE: DNA
<213> ORGANISM: Artificial Sequence
<220> FEATURE:
<223> OTHER INFORMATION: Primer

<400> SEQUENCE: 1374
ctgagaagcc ctgcccttc                                                    19

<210> SEQ ID NO 1375
<211> LENGTH: 21
<212> TYPE: DNA
<213> ORGANISM: Artificial Sequence
<220> FEATURE:
<223> OTHER INFORMATION: Primer

<400> SEQUENCE: 1375
cgtttggtct gggcatgtgt a                                                 21

<210> SEQ ID NO 1376
<211> LENGTH: 23
<212> TYPE: DNA
<213> ORGANISM: Artificial Sequence
<220> FEATURE:
<223> OTHER INFORMATION: Primer

<400> SEQUENCE: 1376
gctgtgcggg atatctgtta ctg                                               23

<210> SEQ ID NO 1377
<211> LENGTH: 27
<212> TYPE: DNA
<213> ORGANISM: Artificial Sequence
<220> FEATURE:
<223> OTHER INFORMATION: Primer

<400> SEQUENCE: 1377
tctatatatg cttggttgct ggtgttg                                           27

<210> SEQ ID NO 1378
<211> LENGTH: 27
<212> TYPE: DNA
<213> ORGANISM: Artificial Sequence
<220> FEATURE:
<223> OTHER INFORMATION: Primer

<400> SEQUENCE: 1378
catgtgcaga accagtatac agttagt                                           27

<210> SEQ ID NO 1379
<211> LENGTH: 27
<212> TYPE: DNA
<213> ORGANISM: Artificial Sequence
<220> FEATURE:
<223> OTHER INFORMATION: Primer

<400> SEQUENCE: 1379
caatgggaca atggatacaa agtaggt                                           27

<210> SEQ ID NO 1380
<211> LENGTH: 23
<212> TYPE: DNA
<213> ORGANISM: Artificial Sequence
<220> FEATURE:
<223> OTHER INFORMATION: Primer -continued

<400> SEQUENCE: 1380
gggccacaca gtaacataca act                                              23

<210> SEQ ID NO 1381
<211> LENGTH: 27
<212> TYPE: DNA
<213> ORGANISM: Artificial Sequence
<220> FEATURE:
<223> OTHER INFORMATION: Primer

<400> SEQUENCE: 1381
tctatgagta aggtgctgtc cctaaat                                          27

<210> SEQ ID NO 1382
<211> LENGTH: 26
<212> TYPE: DNA
<213> ORGANISM: Artificial Sequence
<220> FEATURE:
<223> OTHER INFORMATION: Primer

<400> SEQUENCE: 1382
ggaggtaaag taaaatggag gcagta                                           26

<210> SEQ ID NO 1383
<211> LENGTH: 19
<212> TYPE: DNA
<213> ORGANISM: Artificial Sequence
<220> FEATURE:
<223> OTHER INFORMATION: Primer

<400> SEQUENCE: 1383
tccgtttgca tccaggcaa                                                   19

<210> SEQ ID NO 1384
<211> LENGTH: 28
<212> TYPE: DNA
<213> ORGANISM: Artificial Sequence
<220> FEATURE:
<223> OTHER INFORMATION: Primer

<400> SEQUENCE: 1384
ccaatgccag gtagaggaaa tattttca                                         28

<210> SEQ ID NO 1385
<211> LENGTH: 27
<212> TYPE: DNA
<213> ORGANISM: Artificial Sequence
<220> FEATURE:
<223> OTHER INFORMATION: Primer

<400> SEQUENCE: 1385
gcgtttaagt gtgttacagg atcaaat                                          27

<210> SEQ ID NO 1386
<211> LENGTH: 19
<212> TYPE: DNA
<213> ORGANISM: Artificial Sequence
<220> FEATURE:
<223> OTHER INFORMATION: Primer

<400> SEQUENCE: 1386
ctgagaagcc ctgcccttc                                                   19

<210> SEQ ID NO 1387

```
<211> LENGTH: 27
<212> TYPE: DNA
<213> ORGANISM: Artificial Sequence
<220> FEATURE:
<223> OTHER INFORMATION: Primer

<400> SEQUENCE: 1387
aaagaaggtt aataacagtg ccagaca                                      27

<210> SEQ ID NO 1388
<211> LENGTH: 19
<212> TYPE: DNA
<213> ORGANISM: Artificial Sequence
<220> FEATURE:
<223> OTHER INFORMATION: Primer

<400> SEQUENCE: 1388
cccaagtacg tggcttcgg                                               19

<210> SEQ ID NO 1389
<211> LENGTH: 28
<212> TYPE: DNA
<213> ORGANISM: Artificial Sequence
<220> FEATURE:
<223> OTHER INFORMATION: Primer

<400> SEQUENCE: 1389
agatagaaag cataggcacc tagtacaa                                     28

<210> SEQ ID NO 1390
<211> LENGTH: 31
<212> TYPE: DNA
<213> ORGANISM: Artificial Sequence
<220> FEATURE:
<223> OTHER INFORMATION: Primer

<400> SEQUENCE: 1390
tctatttttg tcaaatggca atttgtttgg a                                 31

<210> SEQ ID NO 1391
<211> LENGTH: 28
<212> TYPE: DNA
<213> ORGANISM: Artificial Sequence
<220> FEATURE:
<223> OTHER INFORMATION: Primer

<400> SEQUENCE: 1391
cagatggagt taatcatcct ttgctact                                     28

<210> SEQ ID NO 1392
<211> LENGTH: 19
<212> TYPE: DNA
<213> ORGANISM: Artificial Sequence
<220> FEATURE:
<223> OTHER INFORMATION: Primer

<400> SEQUENCE: 1392
tgtaaggctc gcaatccgt                                               19

<210> SEQ ID NO 1393
<211> LENGTH: 25
<212> TYPE: DNA
<213> ORGANISM: Artificial Sequence
<220> FEATURE:
<223> OTHER INFORMATION: Primer

<400> SEQUENCE: 1393
```
actatccttt gtgtgtcctt tgtgt                                              25

<210> SEQ ID NO 1394
<211> LENGTH: 21
<212> TYPE: DNA
<213> ORGANISM: Artificial Sequence
<220> FEATURE:
<223> OTHER INFORMATION: Primer

<400> SEQUENCE: 1394
catggttcca ccagcgttat t                                                  21

<210> SEQ ID NO 1395
<211> LENGTH: 27
<212> TYPE: DNA
<213> ORGANISM: Artificial Sequence
<220> FEATURE:
<223> OTHER INFORMATION: Primer

<400> SEQUENCE: 1395
gcgtttaagt gtgttacagg atcaaat                                            27

<210> SEQ ID NO 1396
<211> LENGTH: 21
<212> TYPE: DNA
<213> ORGANISM: Artificial Sequence
<220> FEATURE:
<223> OTHER INFORMATION: Primer

<400> SEQUENCE: 1396
catggttcca ccagcgttat t                                                  21

<210> SEQ ID NO 1397
<211> LENGTH: 25
<212> TYPE: DNA
<213> ORGANISM: Artificial Sequence
<220> FEATURE:
<223> OTHER INFORMATION: Primer

<400> SEQUENCE: 1397
actatccttt gtgtgtcctt tgtgt                                              25

<210> SEQ ID NO 1398
<211> LENGTH: 22
<212> TYPE: DNA
<213> ORGANISM: Artificial Sequence
<220> FEATURE:
<223> OTHER INFORMATION: Primer

<400> SEQUENCE: 1398
atcatgatgg ctgtatgtgc ca                                                 22

<210> SEQ ID NO 1399
<211> LENGTH: 19
<212> TYPE: DNA
<213> ORGANISM: Artificial Sequence
<220> FEATURE:
<223> OTHER INFORMATION: Primer

<400> SEQUENCE: 1399
tccgtttgca tccaggcaa                                                     19

<210> SEQ ID NO 1400
<211> LENGTH: 19
<212> TYPE: DNA

```
<213> ORGANISM: Artificial Sequence
<220> FEATURE:
<223> OTHER INFORMATION: Primer

<400> SEQUENCE: 1400
ctgagaagcc ctgcccttc                                              19

<210> SEQ ID NO 1401
<211> LENGTH: 27
<212> TYPE: DNA
<213> ORGANISM: Artificial Sequence
<220> FEATURE:
<223> OTHER INFORMATION: Primer

<400> SEQUENCE: 1401
aaagaaggtt aataacagtg ccagaca                                     27

<210> SEQ ID NO 1402
<211> LENGTH: 21
<212> TYPE: DNA
<213> ORGANISM: Artificial Sequence
<220> FEATURE:
<223> OTHER INFORMATION: Primer

<400> SEQUENCE: 1402
ggtgtccatc actgtctgca t                                           21

<210> SEQ ID NO 1403
<211> LENGTH: 19
<212> TYPE: DNA
<213> ORGANISM: Artificial Sequence
<220> FEATURE:
<223> OTHER INFORMATION: Primer

<400> SEQUENCE: 1403
tccgtttgca tccaggcaa                                              19

<210> SEQ ID NO 1404
<211> LENGTH: 25
<212> TYPE: DNA
<213> ORGANISM: Artificial Sequence
<220> FEATURE:
<223> OTHER INFORMATION: Primer

<400> SEQUENCE: 1404
tgacatactc atcagtgctg acaac                                       25

<210> SEQ ID NO 1405
<211> LENGTH: 19
<212> TYPE: DNA
<213> ORGANISM: Artificial Sequence
<220> FEATURE:
<223> OTHER INFORMATION: Primer

<400> SEQUENCE: 1405
tccgtttgca tccaggcaa                                              19

<210> SEQ ID NO 1406
<211> LENGTH: 19
<212> TYPE: DNA
<213> ORGANISM: Artificial Sequence
<220> FEATURE:
<223> OTHER INFORMATION: Primer

<400> SEQUENCE: 1406
aaatacggct gcaccgagt                                              19
```

```
<210> SEQ ID NO 1407
<211> LENGTH: 27
<212> TYPE: DNA
<213> ORGANISM: Artificial Sequence
<220> FEATURE:
<223> OTHER INFORMATION: Primer

<400> SEQUENCE: 1407
gcgtttaagt gtgttacagg atcaaat                                         27

<210> SEQ ID NO 1408
<211> LENGTH: 24
<212> TYPE: DNA
<213> ORGANISM: Artificial Sequence
<220> FEATURE:
<223> OTHER INFORMATION: Primer

<400> SEQUENCE: 1408
ggtgatccag actctgacct tttg                                            24

<210> SEQ ID NO 1409
<211> LENGTH: 28
<212> TYPE: DNA
<213> ORGANISM: Artificial Sequence
<220> FEATURE:
<223> OTHER INFORMATION: Primer

<400> SEQUENCE: 1409
gtatgtcacc cgtaccagta ttttctac                                        28

<210> SEQ ID NO 1410
<211> LENGTH: 27
<212> TYPE: DNA
<213> ORGANISM: Artificial Sequence
<220> FEATURE:
<223> OTHER INFORMATION: Primer

<400> SEQUENCE: 1410
gccaaattta ttgggatcag gtaactt                                         27

<210> SEQ ID NO 1411
<211> LENGTH: 25
<212> TYPE: DNA
<213> ORGANISM: Artificial Sequence
<220> FEATURE:
<223> OTHER INFORMATION: Primer

<400> SEQUENCE: 1411
actatccttt gtgtgtcctt tgtgt                                           25

<210> SEQ ID NO 1412
<211> LENGTH: 19
<212> TYPE: DNA
<213> ORGANISM: Artificial Sequence
<220> FEATURE:
<223> OTHER INFORMATION: Primer

<400> SEQUENCE: 1412
cccaagtacg tggcttcgg                                                  19

<210> SEQ ID NO 1413
<211> LENGTH: 25
<212> TYPE: DNA
<213> ORGANISM: Artificial Sequence
<220> FEATURE:
```

<223> OTHER INFORMATION: Primer

<400> SEQUENCE: 1413
gcatcaattg tgtgttttgc aaagg                                    25

<210> SEQ ID NO 1414
<211> LENGTH: 31
<212> TYPE: DNA
<213> ORGANISM: Artificial Sequence
<220> FEATURE:
<223> OTHER INFORMATION: Primer

<400> SEQUENCE: 1414 tctattttg tcaaatggca atttgtttgg a                              31

<210> SEQ ID NO 1415
<211> LENGTH: 19
<212> TYPE: DNA
<213> ORGANISM: Artificial Sequence
<220> FEATURE:
<223> OTHER INFORMATION: Primer

<400> SEQUENCE: 1415
tccgtttgca tccaggcaa                                           19

<210> SEQ ID NO 1416
<211> LENGTH: 24
<212> TYPE: DNA
<213> ORGANISM: Artificial Sequence
<220> FEATURE:
<223> OTHER INFORMATION: Primer

<400> SEQUENCE: 1416
ggtgatccag actctgacct tttg                                     24

<210> SEQ ID NO 1417
<211> LENGTH: 25
<212> TYPE: DNA
<213> ORGANISM: Artificial Sequence
<220> FEATURE:
<223> OTHER INFORMATION: Primer

<400> SEQUENCE: 1417
actatccttt gtgtgtccttt tgtgt                                   25

<210> SEQ ID NO 1418
<211> LENGTH: 24
<212> TYPE: DNA
<213> ORGANISM: Artificial Sequence
<220> FEATURE:
<223> OTHER INFORMATION: Primer

<400> SEQUENCE: 1418
ggtgatccag actctgacct tttg                                     24

<210> SEQ ID NO 1419
<211> LENGTH: 19
<212> TYPE: DNA
<213> ORGANISM: Artificial Sequence
<220> FEATURE:
<223> OTHER INFORMATION: Primer

<400> SEQUENCE: 1419
tccgtttgca tccaggcaa                                           19

```
<210> SEQ ID NO 1420
<211> LENGTH: 18
<212> TYPE: DNA
<213> ORGANISM: Artificial Sequence
<220> FEATURE:
<223> OTHER INFORMATION: Primer

<400> SEQUENCE: 1420
tctttgctcg cagctcgt                                                    18

<210> SEQ ID NO 1421
<211> LENGTH: 27
<212> TYPE: DNA
<213> ORGANISM: Artificial Sequence
<220> FEATURE:
<223> OTHER INFORMATION: Primer

<400> SEQUENCE: 1421
gcgtttaagt gtgttacagg atcaaat                                          27

<210> SEQ ID NO 1422
<211> LENGTH: 19
<212> TYPE: DNA
<213> ORGANISM: Artificial Sequence
<220> FEATURE:
<223> OTHER INFORMATION: Primer

<400> SEQUENCE: 1422
aaatacggct gcaccgagt                                                   19

<210> SEQ ID NO 1423
<211> LENGTH: 25
<212> TYPE: DNA
<213> ORGANISM: Artificial Sequence
<220> FEATURE:
<223> OTHER INFORMATION: Primer

<400> SEQUENCE: 1423
actatccttt gtgtgtcctt tgtgt                                            25

<210> SEQ ID NO 1424
<211> LENGTH: 25
<212> TYPE: DNA
<213> ORGANISM: Artificial Sequence
<220> FEATURE:
<223> OTHER INFORMATION: Primer

<400> SEQUENCE: 1424
tgacatactc atcagtgctg acaac                                            25

<210> SEQ ID NO 1425
<211> LENGTH: 25
<212> TYPE: DNA
<213> ORGANISM: Artificial Sequence
<220> FEATURE:
<223> OTHER INFORMATION: Primer

<400> SEQUENCE: 1425
actatccttt gtgtgtcctt tgtgt                                            25

<210> SEQ ID NO 1426
<211> LENGTH: 19
<212> TYPE: DNA
<213> ORGANISM: Artificial Sequence
<220> FEATURE:
<223> OTHER INFORMATION: Primer
```

```
<400> SEQUENCE: 1426
aaatacggct gcaccgagt                                              19

<210> SEQ ID NO 1427
<211> LENGTH: 25
<212> TYPE: DNA
<213> ORGANISM: Artificial Sequence
<220> FEATURE:
<223> OTHER INFORMATION: Primer

<400> SEQUENCE: 1427
actatccttt gtgtgtcctt tgtgt                                       25

<210> SEQ ID NO 1428
<211> LENGTH: 27
<212> TYPE: DNA
<213> ORGANISM: Artificial Sequence
<220> FEATURE:
<223> OTHER INFORMATION: Primer

<400> SEQUENCE: 1428
gccaaattta ttgggatcag gtaactt                                     27

<210> SEQ ID NO 1429
<211> LENGTH: 25
<212> TYPE: DNA
<213> ORGANISM: Artificial Sequence
<220> FEATURE:
<223> OTHER INFORMATION: Primer

<400> SEQUENCE: 1429
actatccttt gtgtgtcctt tgtgt                                       25

<210> SEQ ID NO 1430
<211> LENGTH: 28
<212> TYPE: DNA
<213> ORGANISM: Artificial Sequence
<220> FEATURE:
<223> OTHER INFORMATION: Primer

<400> SEQUENCE: 1430
cgtcatctga aattttgtca cctgtttt                                    28

<210> SEQ ID NO 1431
<211> LENGTH: 27
<212> TYPE: DNA
<213> ORGANISM: Artificial Sequence
<220> FEATURE:
<223> OTHER INFORMATION: Primer

<400> SEQUENCE: 1431
gcgtttaagt gtgttacagg atcaaat                                     27

<210> SEQ ID NO 1432
<211> LENGTH: 22
<212> TYPE: DNA
<213> ORGANISM: Artificial Sequence
<220> FEATURE:
<223> OTHER INFORMATION: Primer

<400> SEQUENCE: 1432
atcatgatgg ctgtatgtgc ca                                          22

<210> SEQ ID NO 1433
<211> LENGTH: 19
```

```
<212> TYPE: DNA
<213> ORGANISM: Artificial Sequence
<220> FEATURE:
<223> OTHER INFORMATION: Primer

<400> SEQUENCE: 1433
tccgtttgca tccaggcaa                                              19

<210> SEQ ID NO 1434
<211> LENGTH: 27
<212> TYPE: DNA
<213> ORGANISM: Artificial Sequence
<220> FEATURE:
<223> OTHER INFORMATION: Primer

<400> SEQUENCE: 1434
gccaaattta ttgggatcag gtaactt                                     27

<210> SEQ ID NO 1435
<211> LENGTH: 27
<212> TYPE: DNA
<213> ORGANISM: Artificial Sequence
<220> FEATURE:
<223> OTHER INFORMATION: Primer

<400> SEQUENCE: 1435
aaagaaggtt aataacagtg ccagaca                                     27

<210> SEQ ID NO 1436
<211> LENGTH: 31
<212> TYPE: DNA
<213> ORGANISM: Artificial Sequence
<220> FEATURE:
<223> OTHER INFORMATION: Primer

<400> SEQUENCE: 1436
tctatttttg tcaaatggca atttgtttgg a                                31

<210> SEQ ID NO 1437
<211> LENGTH: 25
<212> TYPE: DNA
<213> ORGANISM: Artificial Sequence
<220> FEATURE:
<223> OTHER INFORMATION: Primer

<400> SEQUENCE: 1437
actatccttt gtgtgtcctt tgtgt                                       25

<210> SEQ ID NO 1438
<211> LENGTH: 31
<212> TYPE: DNA
<213> ORGANISM: Artificial Sequence
<220> FEATURE:
<223> OTHER INFORMATION: Primer

<400> SEQUENCE: 1438 tctattttig tcaaatggca atttgtttgg a                                31

<210> SEQ ID NO 1439
<211> LENGTH: 27
<212> TYPE: DNA
<213> ORGANISM: Artificial Sequence
<220> FEATURE:
<223> OTHER INFORMATION: Primer

<400> SEQUENCE: 1439
```
aaagaaggtt aataacagtg ccagaca                                    27

<210> SEQ ID NO 1440
<211> LENGTH: 26
<212> TYPE: DNA
<213> ORGANISM: Artificial Sequence
<220> FEATURE:
<223> OTHER INFORMATION: Primer

<400> SEQUENCE: 1440
gtctatttga ctgtcgctac aaacac                                    26

<210> SEQ ID NO 1441
<211> LENGTH: 23
<212> TYPE: DNA
<213> ORGANISM: Artificial Sequence
<220> FEATURE:
<223> OTHER INFORMATION: Primer

<400> SEQUENCE: 1441
cctcgtaaac gtaaacgtgt tcc                                       23

<210> SEQ ID NO 1442
<211> LENGTH: 25
<212> TYPE: DNA
<213> ORGANISM: Artificial Sequence
<220> FEATURE:
<223> OTHER INFORMATION: Primer

<400> SEQUENCE: 1442
tgacatactc atcagtgctg acaac                                     25

<210> SEQ ID NO 1443
<211> LENGTH: 19
<212> TYPE: DNA
<213> ORGANISM: Artificial Sequence
<220> FEATURE:
<223> OTHER INFORMATION: Primer

<400> SEQUENCE: 1443
tccgtttgca tccaggcaa                                            19

<210> SEQ ID NO 1444
<211> LENGTH: 22
<212> TYPE: DNA
<213> ORGANISM: Artificial Sequence
<220> FEATURE:
<223> OTHER INFORMATION: Primer

<400> SEQUENCE: 1444
atcatgatgg ctgtatgtgc ca                                        22

<210> SEQ ID NO 1445
<211> LENGTH: 19
<212> TYPE: DNA
<213> ORGANISM: Artificial Sequence
<220> FEATURE:
<223> OTHER INFORMATION: Primer

<400> SEQUENCE: 1445
tccgtttgca tccaggcaa                                            19

<210> SEQ ID NO 1446
<211> LENGTH: 21
<212> TYPE: DNA
<213> ORGANISM: Artificial Sequence

```
<220> FEATURE:
<223> OTHER INFORMATION: Primer

<400> SEQUENCE: 1446
catggttcca ccagcgttat t                                              21

<210> SEQ ID NO 1447
<211> LENGTH: 27
<212> TYPE: DNA
<213> ORGANISM: Artificial Sequence
<220> FEATURE:
<223> OTHER INFORMATION: Primer

<400> SEQUENCE: 1447
gcgtttaagt gtgttacagg atcaaat                                        27

<210> SEQ ID NO 1448
<211> LENGTH: 18
<212> TYPE: DNA
<213> ORGANISM: Artificial Sequence
<220> FEATURE:
<223> OTHER INFORMATION: Primer

<400> SEQUENCE: 1448
tctttgctcg cagctcgt                                                  18

<210> SEQ ID NO 1449
<211> LENGTH: 25
<212> TYPE: DNA
<213> ORGANISM: Artificial Sequence
<220> FEATURE:
<223> OTHER INFORMATION: Primer

<400> SEQUENCE: 1449
gcatcaattg tgtgttttgc aaagg                                          25

<210> SEQ ID NO 1450
<211> LENGTH: 19
<212> TYPE: DNA
<213> ORGANISM: Artificial Sequence
<220> FEATURE:
<223> OTHER INFORMATION: Primer

<400> SEQUENCE: 1450
cccaagtacg tggcttcgg                                                 19

<210> SEQ ID NO 1451
<211> LENGTH: 25
<212> TYPE: DNA
<213> ORGANISM: Artificial Sequence
<220> FEATURE:
<223> OTHER INFORMATION: Primer

<400> SEQUENCE: 1451
actatccttt gtgtgtcctt tgtgt                                          25

<210> SEQ ID NO 1452
<211> LENGTH: 21
<212> TYPE: DNA
<213> ORGANISM: Artificial Sequence
<220> FEATURE:
<223> OTHER INFORMATION: Primer

<400> SEQUENCE: 1452
ggtgtccatc actgtctgca t                                              21
```

<210> SEQ ID NO 1453
<211> LENGTH: 25
<212> TYPE: DNA
<213> ORGANISM: Artificial Sequence
<220> FEATURE:
<223> OTHER INFORMATION: Primer

<400> SEQUENCE: 1453
gcatcaattg tgtgttttgc aaagg                                       25

<210> SEQ ID NO 1454
<211> LENGTH: 21
<212> TYPE: DNA
<213> ORGANISM: Artificial Sequence
<220> FEATURE:
<223> OTHER INFORMATION: Primer

<400> SEQUENCE: 1454
ggtgtccatc actgtctgca t                                           21

<210> SEQ ID NO 1455
<211> LENGTH: 25
<212> TYPE: DNA
<213> ORGANISM: Artificial Sequence
<220> FEATURE:
<223> OTHER INFORMATION: Primer

<400> SEQUENCE: 1455
actatccttt gtgtgtcctt tgtgt                                       25

<210> SEQ ID NO 1456
<211> LENGTH: 19
<212> TYPE: DNA
<213> ORGANISM: Artificial Sequence
<220> FEATURE:
<223> OTHER INFORMATION: Primer

<400> SEQUENCE: 1456
ctgagaagcc ctgcccttc                                              19

<210> SEQ ID NO 1457
<211> LENGTH: 25
<212> TYPE: DNA
<213> ORGANISM: Artificial Sequence
<220> FEATURE:
<223> OTHER INFORMATION: Primer

<400> SEQUENCE: 1457
actatccttt gtgtgtcctt tgtgt                                       25

<210> SEQ ID NO 1458
<211> LENGTH: 18
<212> TYPE: DNA
<213> ORGANISM: Artificial Sequence
<220> FEATURE:
<223> OTHER INFORMATION: Primer

<400> SEQUENCE: 1458
tctttgctcg cagctcgt                                               18

<210> SEQ ID NO 1459
<211> LENGTH: 25
<212> TYPE: DNA
<213> ORGANISM: Artificial Sequence
<220> FEATURE:
<223> OTHER INFORMATION: Primer

<400> SEQUENCE: 1459
gcatcaattg tgtgttttgc aaagg  25

<210> SEQ ID NO 1460
<211> LENGTH: 19
<212> TYPE: DNA
<213> ORGANISM: Artificial Sequence
<220> FEATURE:
<223> OTHER INFORMATION: Primer

<400> SEQUENCE: 1460
tgtaaggctc gcaatccgt  19

<210> SEQ ID NO 1461
<211> LENGTH: 25
<212> TYPE: DNA
<213> ORGANISM: Artificial Sequence
<220> FEATURE:
<223> OTHER INFORMATION: Primer

<400> SEQUENCE: 1461
gcatcaattg tgtgttttgc aaagg  25

<210> SEQ ID NO 1462
<211> LENGTH: 22
<212> TYPE: DNA
<213> ORGANISM: Artificial Sequence
<220> FEATURE:
<223> OTHER INFORMATION: Primer

<400> SEQUENCE: 1462
gcatttcaga cacgctgcat ac  22

<210> SEQ ID NO 1463
<211> LENGTH: 20
<212> TYPE: DNA
<213> ORGANISM: Artificial Sequence
<220> FEATURE:
<223> OTHER INFORMATION: Primer

<400> SEQUENCE: 1463
gttgcaatgt cccgcttctg  20

<210> SEQ ID NO 1464
<211> LENGTH: 27
<212> TYPE: DNA
<213> ORGANISM: Artificial Sequence
<220> FEATURE:
<223> OTHER INFORMATION: Primer

<400> SEQUENCE: 1464
catgggcata tagtagtaac agtggaa  27

<210> SEQ ID NO 1465
<211> LENGTH: 23
<212> TYPE: DNA
<213> ORGANISM: Artificial Sequence
<220> FEATURE:
<223> OTHER INFORMATION: Primer

<400> SEQUENCE: 1465
ggttgcaccc aatgagtaag gta  23

<210> SEQ ID NO 1466

<211> LENGTH: 25
<212> TYPE: DNA
<213> ORGANISM: Artificial Sequence
<220> FEATURE:
<223> OTHER INFORMATION: Primer

<400> SEQUENCE: 1466
gcaaaactgg acattcagga caaaa                                            25

<210> SEQ ID NO 1467
<211> LENGTH: 20
<212> TYPE: DNA
<213> ORGANISM: Artificial Sequence
<220> FEATURE:
<223> OTHER INFORMATION: Primer

<400> SEQUENCE: 1467
gctgtgtacc tgccattgga                                                  20

<210> SEQ ID NO 1468
<211> LENGTH: 26
<212> TYPE: DNA
<213> ORGANISM: Artificial Sequence
<220> FEATURE:
<223> OTHER INFORMATION: Primer

<400> SEQUENCE: 1468
ctgtgtctac catatcacca tcttca                                           26

<210> SEQ ID NO 1469
<211> LENGTH: 25
<212> TYPE: DNA
<213> ORGANISM: Artificial Sequence
<220> FEATURE:
<223> OTHER INFORMATION: Primer

<400> SEQUENCE: 1469
gtgcatgtta attgaaccac ccaaa                                            25

<210> SEQ ID NO 1470
<211> LENGTH: 25
<212> TYPE: DNA
<213> ORGANISM: Artificial Sequence
<220> FEATURE:
<223> OTHER INFORMATION: Primer

<400> SEQUENCE: 1470
tcaaacacgc tatcatcaac tccat                                            25

<210> SEQ ID NO 1471
<211> LENGTH: 26
<212> TYPE: DNA
<213> ORGANISM: Artificial Sequence
<220> FEATURE:
<223> OTHER INFORMATION: Primer

<400> SEQUENCE: 1471
cgtgccagaa caaaatacta gactgt                                           26

<210> SEQ ID NO 1472
<211> LENGTH: 22
<212> TYPE: DNA
<213> ORGANISM: Artificial Sequence
<220> FEATURE:
<223> OTHER INFORMATION: Primer

<400> SEQUENCE: 1472
atcatgatgg ctgtatgtgc ca                                             22

<210> SEQ ID NO 1473
<211> LENGTH: 23
<212> TYPE: DNA
<213> ORGANISM: Artificial Sequence
<220> FEATURE:
<223> OTHER INFORMATION: Primer

<400> SEQUENCE: 1473
caccatctga gcgaggtatt aca                                            23

<210> SEQ ID NO 1474
<211> LENGTH: 21
<212> TYPE: DNA
<213> ORGANISM: Artificial Sequence
<220> FEATURE:
<223> OTHER INFORMATION: Primer

<400> SEQUENCE: 1474
tgtaccacac gtagctcctc t                                              21

<210> SEQ ID NO 1475
<211> LENGTH: 23
<212> TYPE: DNA
<213> ORGANISM: Artificial Sequence
<220> FEATURE:
<223> OTHER INFORMATION: Primer

<400> SEQUENCE: 1475
gttaacagta acgtgcccac tct                                            23

<210> SEQ ID NO 1476
<211> LENGTH: 19
<212> TYPE: DNA
<213> ORGANISM: Artificial Sequence
<220> FEATURE:
<223> OTHER INFORMATION: Primer

<400> SEQUENCE: 1476
ctgagaagcc ctgcccttc                                                 19

<210> SEQ ID NO 1477
<211> LENGTH: 23
<212> TYPE: DNA
<213> ORGANISM: Artificial Sequence
<220> FEATURE:
<223> OTHER INFORMATION: Primer

<400> SEQUENCE: 1477
caccatctga gcgaggtatt aca                                            23

<210> SEQ ID NO 1478
<211> LENGTH: 31
<212> TYPE: DNA
<213> ORGANISM: Artificial Sequence
<220> FEATURE:
<223> OTHER INFORMATION: Primer

<400> SEQUENCE: 1478
acaataaaca taccctacat actgcatatg g                                   31

<210> SEQ ID NO 1479
<211> LENGTH: 23
<212> TYPE: DNA

```
<213> ORGANISM: Artificial Sequence
<220> FEATURE:
<223> OTHER INFORMATION: Primer

<400> SEQUENCE: 1479
gttaacagta acgtgcccac tct                                           23

<210> SEQ ID NO 1480
<211> LENGTH: 24
<212> TYPE: DNA
<213> ORGANISM: Artificial Sequence
<220> FEATURE:
<223> OTHER INFORMATION: Primer

<400> SEQUENCE: 1480
ggtgatccag actctgacct tttg                                          24

<210> SEQ ID NO 1481
<211> LENGTH: 26
<212> TYPE: DNA
<213> ORGANISM: Artificial Sequence
<220> FEATURE:
<223> OTHER INFORMATION: Primer

<400> SEQUENCE: 1481
cgtgccagaa caaaatacta gactgt                                        26

<210> SEQ ID NO 1482
<211> LENGTH: 19
<212> TYPE: DNA
<213> ORGANISM: Artificial Sequence
<220> FEATURE:
<223> OTHER INFORMATION: Primer

<400> SEQUENCE: 1482
ctgagaagcc ctgcccttc                                                19

<210> SEQ ID NO 1483
<211> LENGTH: 22
<212> TYPE: DNA
<213> ORGANISM: Artificial Sequence
<220> FEATURE:
<223> OTHER INFORMATION: Primer

<400> SEQUENCE: 1483
gaagacagcg ggtatggcaa ta                                            22

<210> SEQ ID NO 1484
<211> LENGTH: 26
<212> TYPE: DNA
<213> ORGANISM: Artificial Sequence
<220> FEATURE:
<223> OTHER INFORMATION: Primer

<400> SEQUENCE: 1484
ttttctttgt cctcgtcgtt atccaa                                        26

<210> SEQ ID NO 1485
<211> LENGTH: 26
<212> TYPE: DNA
<213> ORGANISM: Artificial Sequence
<220> FEATURE:
<223> OTHER INFORMATION: Primer

<400> SEQUENCE: 1485
cgtgccagaa caaaatacta gactgt                                        26
```

<210> SEQ ID NO 1486
<211> LENGTH: 24
<212> TYPE: DNA
<213> ORGANISM: Artificial Sequence
<220> FEATURE:
<223> OTHER INFORMATION: Primer

<400> SEQUENCE: 1486
ggtgatccag actctgacct tttg                                              24

<210> SEQ ID NO 1487
<211> LENGTH: 22
<212> TYPE: DNA
<213> ORGANISM: Artificial Sequence
<220> FEATURE:
<223> OTHER INFORMATION: Primer

<400> SEQUENCE: 1487
gaagacagcg ggtatggcaa ta                                                22

<210> SEQ ID NO 1488
<211> LENGTH: 31
<212> TYPE: DNA
<213> ORGANISM: Artificial Sequence
<220> FEATURE:
<223> OTHER INFORMATION: Primer

<400> SEQUENCE: 1488
cattacttaa ttcatacaca ggattaccat t                                      31

<210> SEQ ID NO 1489
<211> LENGTH: 23
<212> TYPE: DNA
<213> ORGANISM: Artificial Sequence
<220> FEATURE:
<223> OTHER INFORMATION: Primer

<400> SEQUENCE: 1489
gtatcaacac acaaagccac tgt                                               23

<210> SEQ ID NO 1490
<211> LENGTH: 18
<212> TYPE: DNA
<213> ORGANISM: Artificial Sequence
<220> FEATURE:
<223> OTHER INFORMATION: Primer

<400> SEQUENCE: 1490
tctttgctcg cagctcgt                                                     18

<210> SEQ ID NO 1491
<211> LENGTH: 23
<212> TYPE: DNA
<213> ORGANISM: Artificial Sequence
<220> FEATURE:
<223> OTHER INFORMATION: Primer

<400> SEQUENCE: 1491
gttaacagta acgtgcccac tct                                               23

<210> SEQ ID NO 1492
<211> LENGTH: 24
<212> TYPE: DNA
<213> ORGANISM: Artificial Sequence
<220> FEATURE:

```
<223> OTHER INFORMATION: Primer

<400> SEQUENCE: 1492
acaacctttg aaacaggtgt tgga                                              24

<210> SEQ ID NO 1493
<211> LENGTH: 23
<212> TYPE: DNA
<213> ORGANISM: Artificial Sequence
<220> FEATURE:
<223> OTHER INFORMATION: Primer

<400> SEQUENCE: 1493
gtatcaacac acaaagccac tgt                                               23

<210> SEQ ID NO 1494
<211> LENGTH: 24
<212> TYPE: DNA
<213> ORGANISM: Artificial Sequence
<220> FEATURE:
<223> OTHER INFORMATION: Primer

<400> SEQUENCE: 1494
ggtgatccag actctgacct tttg                                              24

<210> SEQ ID NO 1495
<211> LENGTH: 23
<212> TYPE: DNA
<213> ORGANISM: Artificial Sequence
<220> FEATURE:
<223> OTHER INFORMATION: Primer

<400> SEQUENCE: 1495
gttaacagta acgtgcccac tct                                               23

<210> SEQ ID NO 1496
<211> LENGTH: 18
<212> TYPE: DNA
<213> ORGANISM: Artificial Sequence
<220> FEATURE:
<223> OTHER INFORMATION: Primer

<400> SEQUENCE: 1496
ggtggtggtg gtcctgtg                                                     18

<210> SEQ ID NO 1497
<211> LENGTH: 23
<212> TYPE: DNA
<213> ORGANISM: Artificial Sequence
<220> FEATURE:
<223> OTHER INFORMATION: Primer

<400> SEQUENCE: 1497
gtatcaacac acaaagccac tgt                                               23

<210> SEQ ID NO 1498
<211> LENGTH: 21
<212> TYPE: DNA
<213> ORGANISM: Artificial Sequence
<220> FEATURE:
<223> OTHER INFORMATION: Primer

<400> SEQUENCE: 1498
catggttcca ccagcgttat t                                                 21
```

```
<210> SEQ ID NO 1499
<211> LENGTH: 26
<212> TYPE: DNA
<213> ORGANISM: Artificial Sequence
<220> FEATURE:
<223> OTHER INFORMATION: Primer

<400> SEQUENCE: 1499
cgtgccagaa caaaatacta gactgt                                          26

<210> SEQ ID NO 1500
<211> LENGTH: 19
<212> TYPE: DNA
<213> ORGANISM: Artificial Sequence
<220> FEATURE:
<223> OTHER INFORMATION: Primer

<400> SEQUENCE: 1500
aaatacggct gcaccgagt                                                  19

<210> SEQ ID NO 1501
<211> LENGTH: 23
<212> TYPE: DNA
<213> ORGANISM: Artificial Sequence
<220> FEATURE:
<223> OTHER INFORMATION: Primer

<400> SEQUENCE: 1501
caccatctga gcgaggtatt aca                                             23

<210> SEQ ID NO 1502
<211> LENGTH: 26
<212> TYPE: DNA
<213> ORGANISM: Artificial Sequence
<220> FEATURE:
<223> OTHER INFORMATION: Primer

<400> SEQUENCE: 1502
ttttctttgt cctcgtcgtt atccaa                                          26

<210> SEQ ID NO 1503
<211> LENGTH: 23
<212> TYPE: DNA
<213> ORGANISM: Artificial Sequence
<220> FEATURE:
<223> OTHER INFORMATION: Primer

<400> SEQUENCE: 1503
caccatctga gcgaggtatt aca                                             23

<210> SEQ ID NO 1504
<211> LENGTH: 22
<212> TYPE: DNA
<213> ORGANISM: Artificial Sequence
<220> FEATURE:
<223> OTHER INFORMATION: Primer

<400> SEQUENCE: 1504
aacctcttgc aacgttggta ct                                              22

<210> SEQ ID NO 1505
<211> LENGTH: 22
<212> TYPE: DNA
<213> ORGANISM: Artificial Sequence
<220> FEATURE:
<223> OTHER INFORMATION: Primer
```

```
<400> SEQUENCE: 1505
acagcaagct agacaagctg aa                                          22

<210> SEQ ID NO 1506
<211> LENGTH: 21
<212> TYPE: DNA
<213> ORGANISM: Artificial Sequence
<220> FEATURE:
<223> OTHER INFORMATION: Primer

<400> SEQUENCE: 1506
tgtaccacac gtagctcctc t                                           21

<210> SEQ ID NO 1507
<211> LENGTH: 23
<212> TYPE: DNA
<213> ORGANISM: Artificial Sequence
<220> FEATURE:
<223> OTHER INFORMATION: Primer

<400> SEQUENCE: 1507
caccatctga gcgaggtatt aca                                         23

<210> SEQ ID NO 1508
<211> LENGTH: 28
<212> TYPE: DNA
<213> ORGANISM: Artificial Sequence
<220> FEATURE:
<223> OTHER INFORMATION: Primer

<400> SEQUENCE: 1508
gaaatcgtct tttatgttca cagtgcaa                                    28

<210> SEQ ID NO 1509
<211> LENGTH: 23
<212> TYPE: DNA
<213> ORGANISM: Artificial Sequence
<220> FEATURE:
<223> OTHER INFORMATION: Primer

<400> SEQUENCE: 1509
caccatctga gcgaggtatt aca                                         23

<210> SEQ ID NO 1510
<211> LENGTH: 31
<212> TYPE: DNA
<213> ORGANISM: Artificial Sequence
<220> FEATURE:
<223> OTHER INFORMATION: Primer

<400> SEQUENCE: 1510
cattacttaa ttcatacaca ggattaccat t                                31

<210> SEQ ID NO 1511
<211> LENGTH: 23
<212> TYPE: DNA
<213> ORGANISM: Artificial Sequence
<220> FEATURE:
<223> OTHER INFORMATION: Primer

<400> SEQUENCE: 1511
gtatcaacac acaaagccac tgt                                         23

<210> SEQ ID NO 1512
<211> LENGTH: 24
```

```
<212> TYPE: DNA
<213> ORGANISM: Artificial Sequence
<220> FEATURE:
<223> OTHER INFORMATION: Primer

<400> SEQUENCE: 1512
acaacctttg aaacaggtgt tgga                                          24

<210> SEQ ID NO 1513
<211> LENGTH: 26
<212> TYPE: DNA
<213> ORGANISM: Artificial Sequence
<220> FEATURE:
<223> OTHER INFORMATION: Primer

<400> SEQUENCE: 1513
cgtgccagaa caaaatacta gactgt                                        26

<210> SEQ ID NO 1514
<211> LENGTH: 21
<212> TYPE: DNA
<213> ORGANISM: Artificial Sequence
<220> FEATURE:
<223> OTHER INFORMATION: Primer

<400> SEQUENCE: 1514
catggttcca ccagcgttat t                                             21

<210> SEQ ID NO 1515
<211> LENGTH: 23
<212> TYPE: DNA
<213> ORGANISM: Artificial Sequence
<220> FEATURE:
<223> OTHER INFORMATION: Primer

<400> SEQUENCE: 1515
gttaacagta acgtgcccac tct                                           23

<210> SEQ ID NO 1516
<211> LENGTH: 22
<212> TYPE: DNA
<213> ORGANISM: Artificial Sequence
<220> FEATURE:
<223> OTHER INFORMATION: Primer

<400> SEQUENCE: 1516
atcatgatgg ctgtatgtgc ca                                            22

<210> SEQ ID NO 1517
<211> LENGTH: 23
<212> TYPE: DNA
<213> ORGANISM: Artificial Sequence
<220> FEATURE:
<223> OTHER INFORMATION: Primer

<400> SEQUENCE: 1517
gttaacagta acgtgcccac tct                                           23

<210> SEQ ID NO 1518
<211> LENGTH: 28
<212> TYPE: DNA
<213> ORGANISM: Artificial Sequence
<220> FEATURE:
<223> OTHER INFORMATION: Primer

<400> SEQUENCE: 1518
```
ttctacaatt gcttctacct gaaaccat 28

<210> SEQ ID NO 1519
<211> LENGTH: 23
<212> TYPE: DNA
<213> ORGANISM: Artificial Sequence
<220> FEATURE:
<223> OTHER INFORMATION: Primer

<400> SEQUENCE: 1519
caccatctga gcgaggtatt aca 23

<210> SEQ ID NO 1520
<211> LENGTH: 18
<212> TYPE: DNA
<213> ORGANISM: Artificial Sequence
<220> FEATURE:
<223> OTHER INFORMATION: Primer

<400> SEQUENCE: 1520
ggtggtggtg gtcctgtg 18

<210> SEQ ID NO 1521
<211> LENGTH: 23
<212> TYPE: DNA
<213> ORGANISM: Artificial Sequence
<220> FEATURE:
<223> OTHER INFORMATION: Primer

<400> SEQUENCE: 1521
gttaacagta acgtgcccac tct 23

<210> SEQ ID NO 1522
<211> LENGTH: 31
<212> TYPE: DNA
<213> ORGANISM: Artificial Sequence
<220> FEATURE:
<223> OTHER INFORMATION: Primer

<400> SEQUENCE: 1522
cattacttaa ttcatacaca ggattaccat t 31

<210> SEQ ID NO 1523
<211> LENGTH: 23
<212> TYPE: DNA
<213> ORGANISM: Artificial Sequence
<220> FEATURE:
<223> OTHER INFORMATION: Primer

<400> SEQUENCE: 1523
gtatcaacac acaaagccac tgt 23

<210> SEQ ID NO 1524
<211> LENGTH: 19
<212> TYPE: DNA
<213> ORGANISM: Artificial Sequence
<220> FEATURE:
<223> OTHER INFORMATION: Primer

<400> SEQUENCE: 1524
aaatacggct gcaccgagt 19

<210> SEQ ID NO 1525
<211> LENGTH: 26
<212> TYPE: DNA
<213> ORGANISM: Artificial Sequence

```
<220> FEATURE:
<223> OTHER INFORMATION: Primer

<400> SEQUENCE: 1525
cgtgccagaa caaaatacta gactgt                                          26

<210> SEQ ID NO 1526
<211> LENGTH: 18
<212> TYPE: DNA
<213> ORGANISM: Artificial Sequence
<220> FEATURE:
<223> OTHER INFORMATION: Primer

<400> SEQUENCE: 1526
tctttgctcg cagctcgt                                                   18

<210> SEQ ID NO 1527
<211> LENGTH: 23
<212> TYPE: DNA
<213> ORGANISM: Artificial Sequence
<220> FEATURE:
<223> OTHER INFORMATION: Primer

<400> SEQUENCE: 1527
gtatcaacac acaaagccac tgt                                             23

<210> SEQ ID NO 1528
<211> LENGTH: 22
<212> TYPE: DNA
<213> ORGANISM: Artificial Sequence
<220> FEATURE:
<223> OTHER INFORMATION: Primer

<400> SEQUENCE: 1528
atcatgatgg ctgtatgtgc ca                                              22

<210> SEQ ID NO 1529
<211> LENGTH: 22
<212> TYPE: DNA
<213> ORGANISM: Artificial Sequence
<220> FEATURE:
<223> OTHER INFORMATION: Primer

<400> SEQUENCE: 1529
gaagacagcg ggtatggcaa ta                                              22

<210> SEQ ID NO 1530
<211> LENGTH: 18
<212> TYPE: DNA
<213> ORGANISM: Artificial Sequence
<220> FEATURE:
<223> OTHER INFORMATION: Primer

<400> SEQUENCE: 1530
ggtggtggtg gtcctgtg                                                   18

<210> SEQ ID NO 1531
<211> LENGTH: 23
<212> TYPE: DNA
<213> ORGANISM: Artificial Sequence
<220> FEATURE:
<223> OTHER INFORMATION: Primer

<400> SEQUENCE: 1531
gttaacagta acgtgcccac tct                                             23
```

<210> SEQ ID NO 1532
<211> LENGTH: 26
<212> TYPE: DNA
<213> ORGANISM: Artificial Sequence
<220> FEATURE:
<223> OTHER INFORMATION: Primer

<400> SEQUENCE: 1532
ttttctttgt cctcgtcgtt atccaa                                          26

<210> SEQ ID NO 1533
<211> LENGTH: 23
<212> TYPE: DNA
<213> ORGANISM: Artificial Sequence
<220> FEATURE:
<223> OTHER INFORMATION: Primer

<400> SEQUENCE: 1533
gttaacagta acgtgcccac tct                                             23

<210> SEQ ID NO 1534
<211> LENGTH: 19
<212> TYPE: DNA
<213> ORGANISM: Artificial Sequence
<220> FEATURE:
<223> OTHER INFORMATION: Primer

<400> SEQUENCE: 1534
aaatacggct gcaccgagt                                                  19

<210> SEQ ID NO 1535
<211> LENGTH: 23
<212> TYPE: DNA
<213> ORGANISM: Artificial Sequence
<220> FEATURE:
<223> OTHER INFORMATION: Primer

<400> SEQUENCE: 1535
gtatcaacac acaaagccac tgt                                             23

<210> SEQ ID NO 1536
<211> LENGTH: 19
<212> TYPE: DNA
<213> ORGANISM: Artificial Sequence
<220> FEATURE:
<223> OTHER INFORMATION: Primer

<400> SEQUENCE: 1536
ctgagaagcc ctgcccttc                                                  19

<210> SEQ ID NO 1537
<211> LENGTH: 22
<212> TYPE: DNA
<213> ORGANISM: Artificial Sequence
<220> FEATURE:
<223> OTHER INFORMATION: Primer

<400> SEQUENCE: 1537
gaagacagcg ggtatggcaa ta                                              22

<210> SEQ ID NO 1538
<211> LENGTH: 27
<212> TYPE: DNA
<213> ORGANISM: Artificial Sequence
<220> FEATURE:
<223> OTHER INFORMATION: Primer

```
<400> SEQUENCE: 1538
gataccgagt gctcactaca attactg                                          27

<210> SEQ ID NO 1539
<211> LENGTH: 23
<212> TYPE: DNA
<213> ORGANISM: Artificial Sequence
<220> FEATURE:
<223> OTHER INFORMATION: Primer

<400> SEQUENCE: 1539
gttaacagta acgtgcccac tct                                              23

<210> SEQ ID NO 1540
<211> LENGTH: 21
<212> TYPE: DNA
<213> ORGANISM: Artificial Sequence
<220> FEATURE:
<223> OTHER INFORMATION: Primer

<400> SEQUENCE: 1540
catggttcca ccagcgttat t                                                21

<210> SEQ ID NO 1541
<211> LENGTH: 23
<212> TYPE: DNA
<213> ORGANISM: Artificial Sequence
<220> FEATURE:
<223> OTHER INFORMATION: Primer

<400> SEQUENCE: 1541
gttaacagta acgtgcccac tct                                              23

<210> SEQ ID NO 1542
<211> LENGTH: 18
<212> TYPE: DNA
<213> ORGANISM: Artificial Sequence
<220> FEATURE:
<223> OTHER INFORMATION: Primer

<400> SEQUENCE: 1542
tctttgctcg cagctcgt                                                    18

<210> SEQ ID NO 1543
<211> LENGTH: 23
<212> TYPE: DNA
<213> ORGANISM: Artificial Sequence
<220> FEATURE:
<223> OTHER INFORMATION: Primer

<400> SEQUENCE: 1543
gtatcaacac acaaagccac tgt                                              23

<210> SEQ ID NO 1544
<211> LENGTH: 29
<212> TYPE: DNA
<213> ORGANISM: Artificial Sequence
<220> FEATURE:
<223> OTHER INFORMATION: Primer

<400> SEQUENCE: 1544
tctgtacttg tccaatgata tgttgttgt                                        29

<210> SEQ ID NO 1545
```

```
<211> LENGTH: 24
<212> TYPE: DNA
<213> ORGANISM: Artificial Sequence
<220> FEATURE:
<223> OTHER INFORMATION: Primer

<400> SEQUENCE: 1545
gctacatttg cactatggcc tgta                                            24

<210> SEQ ID NO 1546
<211> LENGTH: 24
<212> TYPE: DNA
<213> ORGANISM: Artificial Sequence
<220> FEATURE:
<223> OTHER INFORMATION: Primer

<400> SEQUENCE: 1546
acaacctttg aaacaggtgt tgga                                            24

<210> SEQ ID NO 1547
<211> LENGTH: 31
<212> TYPE: DNA
<213> ORGANISM: Artificial Sequence
<220> FEATURE:
<223> OTHER INFORMATION: Primer

<400> SEQUENCE: 1547
gggcaacatt agaaagtata actaaaaaac a                                    31

<210> SEQ ID NO 1548
<211> LENGTH: 28
<212> TYPE: DNA
<213> ORGANISM: Artificial Sequence
<220> FEATURE:
<223> OTHER INFORMATION: Primer

<400> SEQUENCE: 1548
gaaatcgtct tttatgttca cagtgcaa                                        28

<210> SEQ ID NO 1549
<211> LENGTH: 26
<212> TYPE: DNA
<213> ORGANISM: Artificial Sequence
<220> FEATURE:
<223> OTHER INFORMATION: Primer

<400> SEQUENCE: 1549
ggttaggtgg tgttccttac tgttta                                          26

<210> SEQ ID NO 1550
<211> LENGTH: 22
<212> TYPE: DNA
<213> ORGANISM: Artificial Sequence
<220> FEATURE:
<223> OTHER INFORMATION: Primer

<400> SEQUENCE: 1550
caaaaggcta ggcaaccgaa tt                                              22

<210> SEQ ID NO 1551
<211> LENGTH: 25
<212> TYPE: DNA
<213> ORGANISM: Artificial Sequence
<220> FEATURE:
<223> OTHER INFORMATION: Primer

<400> SEQUENCE: 1551
```
agacatagat agcaatgcac aagca                                        25

<210> SEQ ID NO 1552
<211> LENGTH: 27
<212> TYPE: DNA
<213> ORGANISM: Artificial Sequence
<220> FEATURE:
<223> OTHER INFORMATION: Primer

<400> SEQUENCE: 1552
atcaccccct tcatctactt tactaca                                      27

<210> SEQ ID NO 1553
<211> LENGTH: 22
<212> TYPE: DNA
<213> ORGANISM: Artificial Sequence
<220> FEATURE:
<223> OTHER INFORMATION: Primer

<400> SEQUENCE: 1553
gtttgtctgt gtgtgtgcca tt                                           22

<210> SEQ ID NO 1554
<211> LENGTH: 27
<212> TYPE: DNA
<213> ORGANISM: Artificial Sequence
<220> FEATURE:
<223> OTHER INFORMATION: Primer

<400> SEQUENCE: 1554
gcatggcaat atatacacag tgtaggt                                      27

<210> SEQ ID NO 1555
<211> LENGTH: 21
<212> TYPE: DNA
<213> ORGANISM: Artificial Sequence
<220> FEATURE:
<223> OTHER INFORMATION: Primer

<400> SEQUENCE: 1555
gtaggccgag gtcaaccttt a                                            21

<210> SEQ ID NO 1556
<211> LENGTH: 25
<212> TYPE: DNA
<213> ORGANISM: Artificial Sequence
<220> FEATURE:
<223> OTHER INFORMATION: Primer

<400> SEQUENCE: 1556
gtgcacatcc cacaatacat aactg                                        25

<210> SEQ ID NO 1557
<211> LENGTH: 26
<212> TYPE: DNA
<213> ORGANISM: Artificial Sequence
<220> FEATURE:
<223> OTHER INFORMATION: Primer

<400> SEQUENCE: 1557
gacagggaga cagctcaaca attatt                                       26

<210> SEQ ID NO 1558
<211> LENGTH: 25
<212> TYPE: DNA

```
<213> ORGANISM: Artificial Sequence
<220> FEATURE:
<223> OTHER INFORMATION: Primer

<400> SEQUENCE: 1558
ctctcggtac acagtttgct gatta                                           25

<210> SEQ ID NO 1559
<211> LENGTH: 23
<212> TYPE: DNA
<213> ORGANISM: Artificial Sequence
<220> FEATURE:
<223> OTHER INFORMATION: Primer

<400> SEQUENCE: 1559
gtgggtggtg taaagtgtca tca                                             23

<210> SEQ ID NO 1560
<211> LENGTH: 26
<212> TYPE: DNA
<213> ORGANISM: Artificial Sequence
<220> FEATURE:
<223> OTHER INFORMATION: Primer

<400> SEQUENCE: 1560
ggacagtaaa tactctcggt ttccat                                          26

<210> SEQ ID NO 1561
<211> LENGTH: 25
<212> TYPE: DNA
<213> ORGANISM: Artificial Sequence
<220> FEATURE:
<223> OTHER INFORMATION: Primer

<400> SEQUENCE: 1561
gacattggac actacattgc atgac                                           25

<210> SEQ ID NO 1562
<211> LENGTH: 19
<212> TYPE: DNA
<213> ORGANISM: Artificial Sequence
<220> FEATURE:
<223> OTHER INFORMATION: Primer

<400> SEQUENCE: 1562
tcgcggtggt gttctgtag                                                  19

<210> SEQ ID NO 1563
<211> LENGTH: 25
<212> TYPE: DNA
<213> ORGANISM: Artificial Sequence
<220> FEATURE:
<223> OTHER INFORMATION: Primer

<400> SEQUENCE: 1563
gacattggac actacattgc atgac                                           25

<210> SEQ ID NO 1564
<211> LENGTH: 28
<212> TYPE: DNA
<213> ORGANISM: Artificial Sequence
<220> FEATURE:
<223> OTHER INFORMATION: Primer

<400> SEQUENCE: 1564
ctgttttggt caaatggaaa tgcattag                                        28
```

<210> SEQ ID NO 1565
<211> LENGTH: 28
<212> TYPE: DNA
<213> ORGANISM: Artificial Sequence
<220> FEATURE:
<223> OTHER INFORMATION: Primer

<400> SEQUENCE: 1565
acaggacagt aaatgtatac aggaccat                                      28

<210> SEQ ID NO 1566
<211> LENGTH: 19
<212> TYPE: DNA
<213> ORGANISM: Artificial Sequence
<220> FEATURE:
<223> OTHER INFORMATION: Primer

<400> SEQUENCE: 1566
ctgagaagcc ctgcccttc                                                19

<210> SEQ ID NO 1567
<211> LENGTH: 28
<212> TYPE: DNA
<213> ORGANISM: Artificial Sequence
<220> FEATURE:
<223> OTHER INFORMATION: Primer

<400> SEQUENCE: 1567
tacaaccttt gccataacta tatatggt                                      28

<210> SEQ ID NO 1568
<211> LENGTH: 21
<212> TYPE: DNA
<213> ORGANISM: Artificial Sequence
<220> FEATURE:
<223> OTHER INFORMATION: Primer

<400> SEQUENCE: 1568
attgacaacc ttcgccactg a                                             21

<210> SEQ ID NO 1569
<211> LENGTH: 23
<212> TYPE: DNA
<213> ORGANISM: Artificial Sequence
<220> FEATURE:
<223> OTHER INFORMATION: Primer

<400> SEQUENCE: 1569
agtagaagtg caggccaaaa caa                                           23

<210> SEQ ID NO 1570
<211> LENGTH: 21
<212> TYPE: DNA
<213> ORGANISM: Artificial Sequence
<220> FEATURE:
<223> OTHER INFORMATION: Primer

<400> SEQUENCE: 1570
catggttcca ccagcgttat t                                             21

<210> SEQ ID NO 1571
<211> LENGTH: 19
<212> TYPE: DNA
<213> ORGANISM: Artificial Sequence
<220> FEATURE:

<223> OTHER INFORMATION: Primer

<400> SEQUENCE: 1571
tccgtggtgt gcaactgaa                                           19

<210> SEQ ID NO 1572
<211> LENGTH: 19
<212> TYPE: DNA
<213> ORGANISM: Artificial Sequence
<220> FEATURE:
<223> OTHER INFORMATION: Primer

<400> SEQUENCE: 1572
ctgagaagcc ctgcccttc                                           19

<210> SEQ ID NO 1573
<211> LENGTH: 23
<212> TYPE: DNA
<213> ORGANISM: Artificial Sequence
<220> FEATURE:
<223> OTHER INFORMATION: Primer

<400> SEQUENCE: 1573
agtagaagtg caggccaaaa caa                                      23

<210> SEQ ID NO 1574
<211> LENGTH: 24
<212> TYPE: DNA
<213> ORGANISM: Artificial Sequence
<220> FEATURE:
<223> OTHER INFORMATION: Primer

<400> SEQUENCE: 1574
ggtgatccag actctgacct tttg                                     24

<210> SEQ ID NO 1575
<211> LENGTH: 28
<212> TYPE: DNA
<213> ORGANISM: Artificial Sequence
<220> FEATURE:
<223> OTHER INFORMATION: Primer

<400> SEQUENCE: 1575
acaggacagt aaatgtatac aggaccat                                 28

<210> SEQ ID NO 1576
<211> LENGTH: 22
<212> TYPE: DNA
<213> ORGANISM: Artificial Sequence
<220> FEATURE:
<223> OTHER INFORMATION: Primer

<400> SEQUENCE: 1576
atcatgatgg ctgtatgtgc ca                                       22

<210> SEQ ID NO 1577
<211> LENGTH: 28
<212> TYPE: DNA
<213> ORGANISM: Artificial Sequence
<220> FEATURE:
<223> OTHER INFORMATION: Primer

<400> SEQUENCE: 1577
acaggacagt aaatgtatac aggaccat                                 28

```
<210> SEQ ID NO 1578
<211> LENGTH: 19
<212> TYPE: DNA
<213> ORGANISM: Artificial Sequence
<220> FEATURE:
<223> OTHER INFORMATION: Primer

<400> SEQUENCE: 1578
aaatacggct gcaccgagt                                                19

<210> SEQ ID NO 1579
<211> LENGTH: 19
<212> TYPE: DNA
<213> ORGANISM: Artificial Sequence
<220> FEATURE:
<223> OTHER INFORMATION: Primer

<400> SEQUENCE: 1579
tccgtggtgt gcaactgaa                                                19

<210> SEQ ID NO 1580
<211> LENGTH: 21
<212> TYPE: DNA
<213> ORGANISM: Artificial Sequence
<220> FEATURE:
<223> OTHER INFORMATION: Primer

<400> SEQUENCE: 1580
catggttcca ccagcgttat t                                             21

<210> SEQ ID NO 1581
<211> LENGTH: 21
<212> TYPE: DNA
<213> ORGANISM: Artificial Sequence
<220> FEATURE:
<223> OTHER INFORMATION: Primer

<400> SEQUENCE: 1581
agacaaccgg cgtatacagt g                                             21

<210> SEQ ID NO 1582
<211> LENGTH: 24
<212> TYPE: DNA
<213> ORGANISM: Artificial Sequence
<220> FEATURE:
<223> OTHER INFORMATION: Primer

<400> SEQUENCE: 1582
cacactacta cagtcctccc gtat                                          24

<210> SEQ ID NO 1583
<211> LENGTH: 23
<212> TYPE: DNA
<213> ORGANISM: Artificial Sequence
<220> FEATURE:
<223> OTHER INFORMATION: Primer

<400> SEQUENCE: 1583
agtagaagtg caggccaaaa caa                                           23

<210> SEQ ID NO 1584
<211> LENGTH: 19
<212> TYPE: DNA
<213> ORGANISM: Artificial Sequence
<220> FEATURE:
<223> OTHER INFORMATION: Primer
```

<400> SEQUENCE: 1584
ctgagaagcc ctgcccttc                                                    19

<210> SEQ ID NO 1585
<211> LENGTH: 28
<212> TYPE: DNA
<213> ORGANISM: Artificial Sequence
<220> FEATURE:
<223> OTHER INFORMATION: Primer

<400> SEQUENCE: 1585
acaggacagt aaatgtatac aggaccat                                          28

<210> SEQ ID NO 1586
<211> LENGTH: 21
<212> TYPE: DNA
<213> ORGANISM: Artificial Sequence
<220> FEATURE:
<223> OTHER INFORMATION: Primer

<400> SEQUENCE: 1586
catggttcca ccagcgttat t                                                 21

<210> SEQ ID NO 1587
<211> LENGTH: 25
<212> TYPE: DNA
<213> ORGANISM: Artificial Sequence
<220> FEATURE:
<223> OTHER INFORMATION: Primer

<400> SEQUENCE: 1587
gacattggac actacattgc atgac                                             25

<210> SEQ ID NO 1588
<211> LENGTH: 22
<212> TYPE: DNA
<213> ORGANISM: Artificial Sequence
<220> FEATURE:
<223> OTHER INFORMATION: Primer

<400> SEQUENCE: 1588
gattggcatg cagcaaatgg ta                                                22

<210> SEQ ID NO 1589
<211> LENGTH: 28
<212> TYPE: DNA
<213> ORGANISM: Artificial Sequence
<220> FEATURE:
<223> OTHER INFORMATION: Primer

<400> SEQUENCE: 1589
acaggacagt aaatgtatac aggaccat                                          28

<210> SEQ ID NO 1590
<211> LENGTH: 24
<212> TYPE: DNA
<213> ORGANISM: Artificial Sequence
<220> FEATURE:
<223> OTHER INFORMATION: Primer

<400> SEQUENCE: 1590
ggtgatccag actctgacct tttg                                              24

<210> SEQ ID NO 1591
<211> LENGTH: 21

-continued

```
<212> TYPE: DNA
<213> ORGANISM: Artificial Sequence
<220> FEATURE:
<223> OTHER INFORMATION: Primer

<400> SEQUENCE: 1591
agacaaccgg cgtatacagt g                                        21

<210> SEQ ID NO 1592
<211> LENGTH: 28
<212> TYPE: DNA
<213> ORGANISM: Artificial Sequence
<220> FEATURE:
<223> OTHER INFORMATION: Primer

<400> SEQUENCE: 1592
ctgttttggt caaatggaaa tgcattag                                 28

<210> SEQ ID NO 1593
<211> LENGTH: 25
<212> TYPE: DNA
<213> ORGANISM: Artificial Sequence
<220> FEATURE:
<223> OTHER INFORMATION: Primer

<400> SEQUENCE: 1593
ccaccaacat ctactactag ccaga                                    25

<210> SEQ ID NO 1594
<211> LENGTH: 21
<212> TYPE: DNA
<213> ORGANISM: Artificial Sequence
<220> FEATURE:
<223> OTHER INFORMATION: Primer

<400> SEQUENCE: 1594
ctgttgtagt gtccgcaggt t                                        21

<210> SEQ ID NO 1595
<211> LENGTH: 30
<212> TYPE: DNA
<213> ORGANISM: Artificial Sequence
<220> FEATURE:
<223> OTHER INFORMATION: Primer

<400> SEQUENCE: 1595
cctaatacaa ataaagtgtc caccaatgct                               30

<210> SEQ ID NO 1596
<211> LENGTH: 28
<212> TYPE: DNA
<213> ORGANISM: Artificial Sequence
<220> FEATURE:
<223> OTHER INFORMATION: Primer

<400> SEQUENCE: 1596
ctgttttggt caaatggaaa tgcattag                                 28

<210> SEQ ID NO 1597
<211> LENGTH: 25
<212> TYPE: DNA
<213> ORGANISM: Artificial Sequence
<220> FEATURE:
<223> OTHER INFORMATION: Primer

<400> SEQUENCE: 1597
```
gacattggac actacattgc atgac                                        25

<210> SEQ ID NO 1598
<211> LENGTH: 26
<212> TYPE: DNA
<213> ORGANISM: Artificial Sequence
<220> FEATURE:
<223> OTHER INFORMATION: Primer

<400> SEQUENCE: 1598
cttcgttttg ttgttaggtg ccttag                                       26

<210> SEQ ID NO 1599
<211> LENGTH: 23
<212> TYPE: DNA
<213> ORGANISM: Artificial Sequence
<220> FEATURE:
<223> OTHER INFORMATION: Primer

<400> SEQUENCE: 1599
agtagaagtg caggccaaaa caa                                          23

<210> SEQ ID NO 1600
<211> LENGTH: 22
<212> TYPE: DNA
<213> ORGANISM: Artificial Sequence
<220> FEATURE:
<223> OTHER INFORMATION: Primer

<400> SEQUENCE: 1600
atcatgatgg ctgtatgtgc ca                                           22

<210> SEQ ID NO 1601
<211> LENGTH: 23
<212> TYPE: DNA
<213> ORGANISM: Artificial Sequence
<220> FEATURE:
<223> OTHER INFORMATION: Primer

<400> SEQUENCE: 1601
agtagaagtg caggccaaaa caa                                          23

<210> SEQ ID NO 1602
<211> LENGTH: 18
<212> TYPE: DNA
<213> ORGANISM: Artificial Sequence
<220> FEATURE:
<223> OTHER INFORMATION: Primer

<400> SEQUENCE: 1602
tctttgctcg cagctcgt                                                18

<210> SEQ ID NO 1603
<211> LENGTH: 19
<212> TYPE: DNA
<213> ORGANISM: Artificial Sequence
<220> FEATURE:
<223> OTHER INFORMATION: Primer

<400> SEQUENCE: 1603
tccgtggtgt gcaactgaa                                               19

<210> SEQ ID NO 1604
<211> LENGTH: 28
<212> TYPE: DNA
<213> ORGANISM: Artificial Sequence

```
<220> FEATURE:
<223> OTHER INFORMATION: Primer

<400> SEQUENCE: 1604
ctgttttggt caaatggaaa tgcattag                                      28

<210> SEQ ID NO 1605
<211> LENGTH: 19
<212> TYPE: DNA
<213> ORGANISM: Artificial Sequence
<220> FEATURE:
<223> OTHER INFORMATION: Primer

<400> SEQUENCE: 1605
tccgtggtgt gcaactgaa                                                19

<210> SEQ ID NO 1606
<211> LENGTH: 28
<212> TYPE: DNA
<213> ORGANISM: Artificial Sequence
<220> FEATURE:
<223> OTHER INFORMATION: Primer

<400> SEQUENCE: 1606
gactgtgtca cctgtttgtt tatctact                                      28

<210> SEQ ID NO 1607
<211> LENGTH: 19
<212> TYPE: DNA
<213> ORGANISM: Artificial Sequence
<220> FEATURE:
<223> OTHER INFORMATION: Primer

<400> SEQUENCE: 1607
tccgtggtgt gcaactgaa                                                19

<210> SEQ ID NO 1608
<211> LENGTH: 21
<212> TYPE: DNA
<213> ORGANISM: Artificial Sequence
<220> FEATURE:
<223> OTHER INFORMATION: Primer

<400> SEQUENCE: 1608
attgacaacc ttcgccactg a                                             21

<210> SEQ ID NO 1609
<211> LENGTH: 23
<212> TYPE: DNA
<213> ORGANISM: Artificial Sequence
<220> FEATURE:
<223> OTHER INFORMATION: Primer

<400> SEQUENCE: 1609
agtagaagtg caggccaaaa caa                                           23

<210> SEQ ID NO 1610
<211> LENGTH: 19
<212> TYPE: DNA
<213> ORGANISM: Artificial Sequence
<220> FEATURE:
<223> OTHER INFORMATION: Primer

<400> SEQUENCE: 1610
aaatacggct gcaccgagt                                                19
```

<210> SEQ ID NO 1611
<211> LENGTH: 19
<212> TYPE: DNA
<213> ORGANISM: Artificial Sequence
<220> FEATURE:
<223> OTHER INFORMATION: Primer

<400> SEQUENCE: 1611
tccgtggtgt gcaactgaa                                                    19

<210> SEQ ID NO 1612
<211> LENGTH: 22
<212> TYPE: DNA
<213> ORGANISM: Artificial Sequence
<220> FEATURE:
<223> OTHER INFORMATION: Primer

<400> SEQUENCE: 1612
atcatgatgg ctgtatgtgc ca                                                22

<210> SEQ ID NO 1613
<211> LENGTH: 19
<212> TYPE: DNA
<213> ORGANISM: Artificial Sequence
<220> FEATURE:
<223> OTHER INFORMATION: Primer

<400> SEQUENCE: 1613
tccgtggtgt gcaactgaa                                                    19

<210> SEQ ID NO 1614
<211> LENGTH: 18
<212> TYPE: DNA
<213> ORGANISM: Artificial Sequence
<220> FEATURE:
<223> OTHER INFORMATION: Primer

<400> SEQUENCE: 1614
tctttgctcg cagctcgt                                                     18

<210> SEQ ID NO 1615
<211> LENGTH: 19
<212> TYPE: DNA
<213> ORGANISM: Artificial Sequence
<220> FEATURE:
<223> OTHER INFORMATION: Primer

<400> SEQUENCE: 1615
tccgtggtgt gcaactgaa                                                    19

<210> SEQ ID NO 1616
<211> LENGTH: 19
<212> TYPE: DNA
<213> ORGANISM: Artificial Sequence
<220> FEATURE:
<223> OTHER INFORMATION: Primer

<400> SEQUENCE: 1616
tcgcggtggt gttctgtag                                                    19

<210> SEQ ID NO 1617
<211> LENGTH: 23
<212> TYPE: DNA
<213> ORGANISM: Artificial Sequence
<220> FEATURE:
<223> OTHER INFORMATION: Primer -continued

<400> SEQUENCE: 1617
agtagaagtg caggccaaaa caa                          23

<210> SEQ ID NO 1618
<211> LENGTH: 21
<212> TYPE: DNA
<213> ORGANISM: Artificial Sequence
<220> FEATURE:
<223> OTHER INFORMATION: Primer

<400> SEQUENCE: 1618
attgacaacc ttcgccactg a                            21

<210> SEQ ID NO 1619
<211> LENGTH: 19
<212> TYPE: DNA
<213> ORGANISM: Artificial Sequence
<220> FEATURE:
<223> OTHER INFORMATION: Primer

<400> SEQUENCE: 1619
tccgtggtgt gcaactgaa                               19

<210> SEQ ID NO 1620
<211> LENGTH: 19
<212> TYPE: DNA
<213> ORGANISM: Artificial Sequence
<220> FEATURE:
<223> OTHER INFORMATION: Primer

<400> SEQUENCE: 1620
aaatacggct gcaccgagt                               19

<210> SEQ ID NO 1621
<211> LENGTH: 25
<212> TYPE: DNA
<213> ORGANISM: Artificial Sequence
<220> FEATURE:
<223> OTHER INFORMATION: Primer

<400> SEQUENCE: 1621
gacattggac actacattgc atgac                        25

<210> SEQ ID NO 1622
<211> LENGTH: 21
<212> TYPE: DNA
<213> ORGANISM: Artificial Sequence
<220> FEATURE:
<223> OTHER INFORMATION: Primer

<400> SEQUENCE: 1622
ctgttgtagt gtccgcaggt t                            21

<210> SEQ ID NO 1623
<211> LENGTH: 27
<212> TYPE: DNA
<213> ORGANISM: Artificial Sequence
<220> FEATURE:
<223> OTHER INFORMATION: Primer

<400> SEQUENCE: 1623
ctagtggaaa atgggacgtg cattata                      27

<210> SEQ ID NO 1624

```
<211> LENGTH: 19
<212> TYPE: DNA
<213> ORGANISM: Artificial Sequence
<220> FEATURE:
<223> OTHER INFORMATION: Primer

<400> SEQUENCE: 1624
tcgcggtggt gttctgtag                                                  19

<210> SEQ ID NO 1625
<211> LENGTH: 23
<212> TYPE: DNA
<213> ORGANISM: Artificial Sequence
<220> FEATURE:
<223> OTHER INFORMATION: Primer

<400> SEQUENCE: 1625
agtagaagtg caggccaaaa caa                                             23

<210> SEQ ID NO 1626
<211> LENGTH: 27
<212> TYPE: DNA
<213> ORGANISM: Artificial Sequence
<220> FEATURE:
<223> OTHER INFORMATION: Primer

<400> SEQUENCE: 1626
aagcgttatg tttttgcaac ctatacc                                         27

<210> SEQ ID NO 1627
<211> LENGTH: 21
<212> TYPE: DNA
<213> ORGANISM: Artificial Sequence
<220> FEATURE:
<223> OTHER INFORMATION: Primer

<400> SEQUENCE: 1627
agacaaccgg cgtatacagt g                                               21

<210> SEQ ID NO 1628
<211> LENGTH: 19
<212> TYPE: DNA
<213> ORGANISM: Artificial Sequence
<220> FEATURE:
<223> OTHER INFORMATION: Primer

<400> SEQUENCE: 1628
tcgcggtggt gttctgtag                                                  19

<210> SEQ ID NO 1629
<211> LENGTH: 19
<212> TYPE: DNA
<213> ORGANISM: Artificial Sequence
<220> FEATURE:
<223> OTHER INFORMATION: Primer

<400> SEQUENCE: 1629
tccgtggtgt gcaactgaa                                                  19

<210> SEQ ID NO 1630
<211> LENGTH: 24
<212> TYPE: DNA
<213> ORGANISM: Artificial Sequence
<220> FEATURE:
<223> OTHER INFORMATION: Primer

<400> SEQUENCE: 1630
```
ggtgatccag actctgacct tttg                                          24

<210> SEQ ID NO 1631
<211> LENGTH: 28
<212> TYPE: DNA
<213> ORGANISM: Artificial Sequence
<220> FEATURE:
<223> OTHER INFORMATION: Primer

<400> SEQUENCE: 1631
acaggacagt aaatgtatac aggaccat                                      28

<210> SEQ ID NO 1632
<211> LENGTH: 18
<212> TYPE: DNA
<213> ORGANISM: Artificial Sequence
<220> FEATURE:
<223> OTHER INFORMATION: Primer

<400> SEQUENCE: 1632
tctttgctcg cagctcgt                                                 18

<210> SEQ ID NO 1633
<211> LENGTH: 28
<212> TYPE: DNA
<213> ORGANISM: Artificial Sequence
<220> FEATURE:
<223> OTHER INFORMATION: Primer

<400> SEQUENCE: 1633
ggaatcggtg tatgcaacta cattagaa                                      28

<210> SEQ ID NO 1634
<211> LENGTH: 26
<212> TYPE: DNA
<213> ORGANISM: Artificial Sequence
<220> FEATURE:
<223> OTHER INFORMATION: Primer

<400> SEQUENCE: 1634
cttcgttttg ttgttaggtg ccttag                                        26

<210> SEQ ID NO 1635
<211> LENGTH: 25
<212> TYPE: DNA
<213> ORGANISM: Artificial Sequence
<220> FEATURE:
<223> OTHER INFORMATION: Primer

<400> SEQUENCE: 1635
ccctgtgact aacatatgtc cttgt                                         25

<210> SEQ ID NO 1636
<211> LENGTH: 24
<212> TYPE: DNA
<213> ORGANISM: Artificial Sequence
<220> FEATURE:
<223> OTHER INFORMATION: Primer

<400> SEQUENCE: 1636
ccacacggta tagtttgcaa ccat                                          24

<210> SEQ ID NO 1637
<211> LENGTH: 25
<212> TYPE: DNA

```
<213> ORGANISM: Artificial Sequence
<220> FEATURE:
<223> OTHER INFORMATION: Primer

<400> SEQUENCE: 1637
gcctgtgttg gtgttgaaat aggta                                         25

<210> SEQ ID NO 1638
<211> LENGTH: 26
<212> TYPE: DNA
<213> ORGANISM: Artificial Sequence
<220> FEATURE:
<223> OTHER INFORMATION: Primer

<400> SEQUENCE: 1638
tgcaacattg tccctactgt ctttag                                        26

<210> SEQ ID NO 1639
<211> LENGTH: 23
<212> TYPE: DNA
<213> ORGANISM: Artificial Sequence
<220> FEATURE:
<223> OTHER INFORMATION: Primer

<400> SEQUENCE: 1639
ggtgtggttt tgtgtatgca tgt                                           23

<210> SEQ ID NO 1640
<211> LENGTH: 26
<212> TYPE: DNA
<213> ORGANISM: Artificial Sequence
<220> FEATURE:
<223> OTHER INFORMATION: Primer

<400> SEQUENCE: 1640
ggtatacagc aaacacctca aatggt                                        26

<210> SEQ ID NO 1641
<211> LENGTH: 20
<212> TYPE: DNA
<213> ORGANISM: Artificial Sequence
<220> FEATURE:
<223> OTHER INFORMATION: Primer

<400> SEQUENCE: 1641
cgacacgccg gaatggataa                                               20

<210> SEQ ID NO 1642
<211> LENGTH: 26
<212> TYPE: DNA
<213> ORGANISM: Artificial Sequence
<220> FEATURE:
<223> OTHER INFORMATION: Primer

<400> SEQUENCE: 1642
cgctgcagca ttactattac aatctg                                        26

<210> SEQ ID NO 1643
<211> LENGTH: 28
<212> TYPE: DNA
<213> ORGANISM: Artificial Sequence
<220> FEATURE:
<223> OTHER INFORMATION: Primer

<400> SEQUENCE: 1643
tgggtcaggt tttatattac accctagt                                      28
```

<210> SEQ ID NO 1644
<211> LENGTH: 25
<212> TYPE: DNA
<213> ORGANISM: Artificial Sequence
<220> FEATURE:
<223> OTHER INFORMATION: Primer

<400> SEQUENCE: 1644
gcttacaacc ttagacacag acaca                                         25

<210> SEQ ID NO 1645
<211> LENGTH: 26
<212> TYPE: DNA
<213> ORGANISM: Artificial Sequence
<220> FEATURE:
<223> OTHER INFORMATION: Primer

<400> SEQUENCE: 1645
gtatgaacgt gacagtgtac acctaa                                        26

<210> SEQ ID NO 1646
<211> LENGTH: 19
<212> TYPE: DNA
<213> ORGANISM: Artificial Sequence
<220> FEATURE:
<223> OTHER INFORMATION: Primer

<400> SEQUENCE: 1646
ctgagaagcc ctgcccttc                                                19

<210> SEQ ID NO 1647
<211> LENGTH: 23
<212> TYPE: DNA
<213> ORGANISM: Artificial Sequence
<220> FEATURE:
<223> OTHER INFORMATION: Primer

<400> SEQUENCE: 1647
aaacgaagac tgtttgagga gca                                           23

<210> SEQ ID NO 1648
<211> LENGTH: 19
<212> TYPE: DNA
<213> ORGANISM: Artificial Sequence
<220> FEATURE:
<223> OTHER INFORMATION: Primer

<400> SEQUENCE: 1648
tggtgttggt ggttgtggt                                                19

<210> SEQ ID NO 1649
<211> LENGTH: 21
<212> TYPE: DNA
<213> ORGANISM: Artificial Sequence
<220> FEATURE:
<223> OTHER INFORMATION: Primer

<400> SEQUENCE: 1649
acctacatcc caccacagag t                                             21

<210> SEQ ID NO 1650
<211> LENGTH: 19
<212> TYPE: DNA
<213> ORGANISM: Artificial Sequence
<220> FEATURE:

<223> OTHER INFORMATION: Primer

<400> SEQUENCE: 1650
aaatacggct gcaccgagt                                                    19

<210> SEQ ID NO 1651
<211> LENGTH: 27
<212> TYPE: DNA
<213> ORGANISM: Artificial Sequence
<220> FEATURE:
<223> OTHER INFORMATION: Primer

<400> SEQUENCE: 1651
tgcttatggg tacactaggt attgtgt                                           27

<210> SEQ ID NO 1652
<211> LENGTH: 24
<212> TYPE: DNA
<213> ORGANISM: Artificial Sequence
<220> FEATURE:
<223> OTHER INFORMATION: Primer

<400> SEQUENCE: 1652
gggttcccat tactgtcaaa tgga                                              24

<210> SEQ ID NO 1653
<211> LENGTH: 27
<212> TYPE: DNA
<213> ORGANISM: Artificial Sequence
<220> FEATURE:
<223> OTHER INFORMATION: Primer

<400> SEQUENCE: 1653
tgcttatggg tacactaggt attgtgt                                           27

<210> SEQ ID NO 1654
<211> LENGTH: 24
<212> TYPE: DNA
<213> ORGANISM: Artificial Sequence
<220> FEATURE:
<223> OTHER INFORMATION: Primer

<400> SEQUENCE: 1654
ggtgatccag actctgacct tttg                                              24

<210> SEQ ID NO 1655
<211> LENGTH: 28
<212> TYPE: DNA
<213> ORGANISM: Artificial Sequence
<220> FEATURE:
<223> OTHER INFORMATION: Primer

<400> SEQUENCE: 1655
agcgttatgt gacgaagtga atatttct                                          28

<210> SEQ ID NO 1656
<211> LENGTH: 28
<212> TYPE: DNA
<213> ORGANISM: Artificial Sequence
<220> FEATURE:
<223> OTHER INFORMATION: Primer

<400> SEQUENCE: 1656
ctgttctgct atttgatgaa accgtttt                                          28

```
<210> SEQ ID NO 1657
<211> LENGTH: 28
<212> TYPE: DNA
<213> ORGANISM: Artificial Sequence
<220> FEATURE:
<223> OTHER INFORMATION: Primer

<400> SEQUENCE: 1657
agcgttatgt gacgaagtga atatttct                                        28

<210> SEQ ID NO 1658
<211> LENGTH: 24
<212> TYPE: DNA
<213> ORGANISM: Artificial Sequence
<220> FEATURE:
<223> OTHER INFORMATION: Primer

<400> SEQUENCE: 1658
ttcggttgtt ggtttcaggt ctaa                                            24

<210> SEQ ID NO 1659
<211> LENGTH: 27
<212> TYPE: DNA
<213> ORGANISM: Artificial Sequence
<220> FEATURE:
<223> OTHER INFORMATION: Primer

<400> SEQUENCE: 1659
tgcttatggg tacactaggt attgtgt                                         27

<210> SEQ ID NO 1660
<211> LENGTH: 19
<212> TYPE: DNA
<213> ORGANISM: Artificial Sequence
<220> FEATURE:
<223> OTHER INFORMATION: Primer

<400> SEQUENCE: 1660
tggtgttggt ggttgtggt                                                  19

<210> SEQ ID NO 1661
<211> LENGTH: 26
<212> TYPE: DNA
<213> ORGANISM: Artificial Sequence
<220> FEATURE:
<223> OTHER INFORMATION: Primer

<400> SEQUENCE: 1661
gggtaaaagg catatgggaa gtacat                                          26

<210> SEQ ID NO 1662
<211> LENGTH: 19
<212> TYPE: DNA
<213> ORGANISM: Artificial Sequence
<220> FEATURE:
<223> OTHER INFORMATION: Primer

<400> SEQUENCE: 1662
tggtgttggt ggttgtggt                                                  19

<210> SEQ ID NO 1663
<211> LENGTH: 29
<212> TYPE: DNA
<213> ORGANISM: Artificial Sequence
<220> FEATURE:
<223> OTHER INFORMATION: Primer
```

<400> SEQUENCE: 1663
caagttaaat gccctccatt actgataac                                29

<210> SEQ ID NO 1664
<211> LENGTH: 24
<212> TYPE: DNA
<213> ORGANISM: Artificial Sequence
<220> FEATURE:
<223> OTHER INFORMATION: Primer

<400> SEQUENCE: 1664
gggttcccat tactgtcaaa tgga                                     24

<210> SEQ ID NO 1665
<211> LENGTH: 27
<212> TYPE: DNA
<213> ORGANISM: Artificial Sequence
<220> FEATURE:
<223> OTHER INFORMATION: Primer

<400> SEQUENCE: 1665
tgcttatggg tacactaggt attgtgt                                  27

<210> SEQ ID NO 1666
<211> LENGTH: 21
<212> TYPE: DNA
<213> ORGANISM: Artificial Sequence
<220> FEATURE:
<223> OTHER INFORMATION: Primer

<400> SEQUENCE: 1666
catggttcca ccagcgttat t                                        21

<210> SEQ ID NO 1667
<211> LENGTH: 21
<212> TYPE: DNA
<213> ORGANISM: Artificial Sequence
<220> FEATURE:
<223> OTHER INFORMATION: Primer

<400> SEQUENCE: 1667
acctacatcc caccacagag t                                        21

<210> SEQ ID NO 1668
<211> LENGTH: 24
<212> TYPE: DNA
<213> ORGANISM: Artificial Sequence
<220> FEATURE:
<223> OTHER INFORMATION: Primer

<400> SEQUENCE: 1668
gtccaatgcc atgttgttgt taca                                     24

<210> SEQ ID NO 1669
<211> LENGTH: 21
<212> TYPE: DNA
<213> ORGANISM: Artificial Sequence
<220> FEATURE:
<223> OTHER INFORMATION: Primer

<400> SEQUENCE: 1669
acctacatcc caccacagag t                                        21

<210> SEQ ID NO 1670
<211> LENGTH: 22

```
<212> TYPE: DNA
<213> ORGANISM: Artificial Sequence
<220> FEATURE:
<223> OTHER INFORMATION: Primer

<400> SEQUENCE: 1670
atcatgatgg ctgtatgtgc ca                                            22

<210> SEQ ID NO 1671
<211> LENGTH: 27
<212> TYPE: DNA
<213> ORGANISM: Artificial Sequence
<220> FEATURE:
<223> OTHER INFORMATION: Primer

<400> SEQUENCE: 1671
tgcttatggg tacactaggt attgtgt                                       27

<210> SEQ ID NO 1672
<211> LENGTH: 24
<212> TYPE: DNA
<213> ORGANISM: Artificial Sequence
<220> FEATURE:
<223> OTHER INFORMATION: Primer

<400> SEQUENCE: 1672
acgaagccta aacaccctgt attg                                          24

<210> SEQ ID NO 1673
<211> LENGTH: 26
<212> TYPE: DNA
<213> ORGANISM: Artificial Sequence
<220> FEATURE:
<223> OTHER INFORMATION: Primer

<400> SEQUENCE: 1673
gtatgaacgt gacagtgtac acctaa                                        26

<210> SEQ ID NO 1674
<211> LENGTH: 22
<212> TYPE: DNA
<213> ORGANISM: Artificial Sequence
<220> FEATURE:
<223> OTHER INFORMATION: Primer

<400> SEQUENCE: 1674
atcatgatgg ctgtatgtgc ca                                            22

<210> SEQ ID NO 1675
<211> LENGTH: 25
<212> TYPE: DNA
<213> ORGANISM: Artificial Sequence
<220> FEATURE:
<223> OTHER INFORMATION: Primer

<400> SEQUENCE: 1675
actcagagga tgaggatgaa acaga                                         25

<210> SEQ ID NO 1676
<211> LENGTH: 28
<212> TYPE: DNA
<213> ORGANISM: Artificial Sequence
<220> FEATURE:
<223> OTHER INFORMATION: Primer

<400> SEQUENCE: 1676
```
cctagtgtac ccataagcaa ctcttcta                                                28

<210> SEQ ID NO 1677
<211> LENGTH: 21
<212> TYPE: DNA
<213> ORGANISM: Artificial Sequence
<220> FEATURE:
<223> OTHER INFORMATION: Primer

<400> SEQUENCE: 1677
acctacatcc caccacagag t                                                       21

<210> SEQ ID NO 1678
<211> LENGTH: 25
<212> TYPE: DNA
<213> ORGANISM: Artificial Sequence
<220> FEATURE:
<223> OTHER INFORMATION: Primer

<400> SEQUENCE: 1678
gcttacaacc ttagacacag acaca                                                   25

<210> SEQ ID NO 1679
<211> LENGTH: 23
<212> TYPE: DNA
<213> ORGANISM: Artificial Sequence
<220> FEATURE:
<223> OTHER INFORMATION: Primer

<400> SEQUENCE: 1679
aaacgaagac tgtttgagga gca                                                     23

<210> SEQ ID NO 1680
<211> LENGTH: 28
<212> TYPE: DNA
<213> ORGANISM: Artificial Sequence
<220> FEATURE:
<223> OTHER INFORMATION: Primer

<400> SEQUENCE: 1680
gacacaattt ggttgccttc ttcattaa                                                28

<210> SEQ ID NO 1681
<211> LENGTH: 27
<212> TYPE: DNA
<213> ORGANISM: Artificial Sequence
<220> FEATURE:
<223> OTHER INFORMATION: Primer

<400> SEQUENCE: 1681
tgcttatggg tacactaggt attgtgt                                                 27

<210> SEQ ID NO 1682
<211> LENGTH: 19
<212> TYPE: DNA
<213> ORGANISM: Artificial Sequence
<220> FEATURE:
<223> OTHER INFORMATION: Primer

<400> SEQUENCE: 1682
aaatacggct gcaccgagt                                                          19

<210> SEQ ID NO 1683
<211> LENGTH: 20
<212> TYPE: DNA
<213> ORGANISM: Artificial Sequence

```
<220> FEATURE:
<223> OTHER INFORMATION: Primer

<400> SEQUENCE: 1683
tgcaggtagc acacgtttgt                                               20

<210> SEQ ID NO 1684
<211> LENGTH: 24
<212> TYPE: DNA
<213> ORGANISM: Artificial Sequence
<220> FEATURE:
<223> OTHER INFORMATION: Primer

<400> SEQUENCE: 1684
acgaagccta aacaccctgt attg                                          24

<210> SEQ ID NO 1685
<211> LENGTH: 21
<212> TYPE: DNA
<213> ORGANISM: Artificial Sequence
<220> FEATURE:
<223> OTHER INFORMATION: Primer

<400> SEQUENCE: 1685
acctacatcc caccacagag t                                             21

<210> SEQ ID NO 1686
<211> LENGTH: 18
<212> TYPE: DNA
<213> ORGANISM: Artificial Sequence
<220> FEATURE:
<223> OTHER INFORMATION: Primer

<400> SEQUENCE: 1686
tctttgctcg cagctcgt                                                 18

<210> SEQ ID NO 1687
<211> LENGTH: 27
<212> TYPE: DNA
<213> ORGANISM: Artificial Sequence
<220> FEATURE:
<223> OTHER INFORMATION: Primer

<400> SEQUENCE: 1687
tgcttatggg tacactaggt attgtgt                                       27

<210> SEQ ID NO 1688
<211> LENGTH: 26
<212> TYPE: DNA
<213> ORGANISM: Artificial Sequence
<220> FEATURE:
<223> OTHER INFORMATION: Primer

<400> SEQUENCE: 1688
tggaattgga tccctgttt ttcttt                                         26

<210> SEQ ID NO 1689
<211> LENGTH: 27
<212> TYPE: DNA
<213> ORGANISM: Artificial Sequence
<220> FEATURE:
<223> OTHER INFORMATION: Primer

<400> SEQUENCE: 1689
tgcttatggg tacactaggt attgtgt                                       27
```

-continued

<210> SEQ ID NO 1690
<211> LENGTH: 18
<212> TYPE: DNA
<213> ORGANISM: Artificial Sequence
<220> FEATURE:
<223> OTHER INFORMATION: Primer

<400> SEQUENCE: 1690
tctttgctcg cagctcgt                                              18

<210> SEQ ID NO 1691
<211> LENGTH: 27
<212> TYPE: DNA
<213> ORGANISM: Artificial Sequence
<220> FEATURE:
<223> OTHER INFORMATION: Primer

<400> SEQUENCE: 1691
tgcttatggg tacactaggt attgtgt                                    27

<210> SEQ ID NO 1692
<211> LENGTH: 19
<212> TYPE: DNA
<213> ORGANISM: Artificial Sequence
<220> FEATURE:
<223> OTHER INFORMATION: Primer

<400> SEQUENCE: 1692
ctgagaagcc ctgcccttc                                             19

<210> SEQ ID NO 1693
<211> LENGTH: 27
<212> TYPE: DNA
<213> ORGANISM: Artificial Sequence
<220> FEATURE:
<223> OTHER INFORMATION: Primer

<400> SEQUENCE: 1693
tgcttatggg tacactaggt attgtgt                                    27

<210> SEQ ID NO 1694
<211> LENGTH: 25
<212> TYPE: DNA
<213> ORGANISM: Artificial Sequence
<220> FEATURE:
<223> OTHER INFORMATION: Primer

<400> SEQUENCE: 1694
gcttacaacc ttagacacag acaca                                      25

<210> SEQ ID NO 1695
<211> LENGTH: 26
<212> TYPE: DNA
<213> ORGANISM: Artificial Sequence
<220> FEATURE:
<223> OTHER INFORMATION: Primer

<400> SEQUENCE: 1695
gtatgaacgt gacagtgtac acctaa                                     26

<210> SEQ ID NO 1696
<211> LENGTH: 21
<212> TYPE: DNA
<213> ORGANISM: Artificial Sequence
<220> FEATURE:
<223> OTHER INFORMATION: Primer

<400> SEQUENCE: 1696
catggttcca ccagcgttat t					21

<210> SEQ ID NO 1697
<211> LENGTH: 28
<212> TYPE: DNA
<213> ORGANISM: Artificial Sequence
<220> FEATURE:
<223> OTHER INFORMATION: Primer

<400> SEQUENCE: 1697
agcgttatgt gacgaagtga atatttct					28

<210> SEQ ID NO 1698
<211> LENGTH: 27
<212> TYPE: DNA
<213> ORGANISM: Artificial Sequence
<220> FEATURE:
<223> OTHER INFORMATION: Primer

<400> SEQUENCE: 1698
aaaattttaa acacggttga catacac					27

<210> SEQ ID NO 1699
<211> LENGTH: 26
<212> TYPE: DNA
<213> ORGANISM: Artificial Sequence
<220> FEATURE:
<223> OTHER INFORMATION: Primer

<400> SEQUENCE: 1699
gtatgaacgt gacagtgtac acctaa					26

<210> SEQ ID NO 1700
<211> LENGTH: 19
<212> TYPE: DNA
<213> ORGANISM: Artificial Sequence
<220> FEATURE:
<223> OTHER INFORMATION: Primer

<400> SEQUENCE: 1700
aaatacggct gcaccgagt					19

<210> SEQ ID NO 1701
<211> LENGTH: 26
<212> TYPE: DNA
<213> ORGANISM: Artificial Sequence
<220> FEATURE:
<223> OTHER INFORMATION: Primer

<400> SEQUENCE: 1701
gtatgaacgt gacagtgtac acctaa					26

<210> SEQ ID NO 1702
<211> LENGTH: 18
<212> TYPE: DNA
<213> ORGANISM: Artificial Sequence
<220> FEATURE:
<223> OTHER INFORMATION: Primer

<400> SEQUENCE: 1702
tctttgctcg cagctcgt					18

<210> SEQ ID NO 1703

```
<211> LENGTH: 27
<212> TYPE: DNA
<213> ORGANISM: Artificial Sequence
<220> FEATURE:
<223> OTHER INFORMATION: Primer

<400> SEQUENCE: 1703
tgcttatggg tacactaggt attgtgt                                          27

<210> SEQ ID NO 1704
<211> LENGTH: 22
<212> TYPE: DNA
<213> ORGANISM: Artificial Sequence
<220> FEATURE:
<223> OTHER INFORMATION: Primer

<400> SEQUENCE: 1704
atcatgatgg ctgtatgtgc ca                                               22

<210> SEQ ID NO 1705
<211> LENGTH: 29
<212> TYPE: DNA
<213> ORGANISM: Artificial Sequence
<220> FEATURE:
<223> OTHER INFORMATION: Primer

<400> SEQUENCE: 1705
agacaatcag tatatggcac tacgttaga                                        29

<210> SEQ ID NO 1706
<211> LENGTH: 28
<212> TYPE: DNA
<213> ORGANISM: Artificial Sequence
<220> FEATURE:
<223> OTHER INFORMATION: Primer

<400> SEQUENCE: 1706
ctgttctgct atttgatgaa accgtttt                                         28

<210> SEQ ID NO 1707
<211> LENGTH: 21
<212> TYPE: DNA
<213> ORGANISM: Artificial Sequence
<220> FEATURE:
<223> OTHER INFORMATION: Primer

<400> SEQUENCE: 1707
acctacatcc caccacagag t                                                21

<210> SEQ ID NO 1708
<211> LENGTH: 21
<212> TYPE: DNA
<213> ORGANISM: Artificial Sequence
<220> FEATURE:
<223> OTHER INFORMATION: Primer

<400> SEQUENCE: 1708
catggttcca ccagcgttat t                                                21

<210> SEQ ID NO 1709
<211> LENGTH: 28
<212> TYPE: DNA
<213> ORGANISM: Artificial Sequence
<220> FEATURE:
<223> OTHER INFORMATION: Primer

<400> SEQUENCE: 1709
```

-continued agcgttatgt gacgaagtga atatttct  28

<210> SEQ ID NO 1710
<211> LENGTH: 24
<212> TYPE: DNA
<213> ORGANISM: Artificial Sequence
<220> FEATURE:
<223> OTHER INFORMATION: Primer

<400> SEQUENCE: 1710
gggttcccat tactgtcaaa tgga  24

<210> SEQ ID NO 1711
<211> LENGTH: 21
<212> TYPE: DNA
<213> ORGANISM: Artificial Sequence
<220> FEATURE:
<223> OTHER INFORMATION: Primer

<400> SEQUENCE: 1711
acctacatcc caccacagag t  21

<210> SEQ ID NO 1712
<211> LENGTH: 19
<212> TYPE: DNA
<213> ORGANISM: Artificial Sequence
<220> FEATURE:
<223> OTHER INFORMATION: Primer

<400> SEQUENCE: 1712
ctgagaagcc ctgcccttc  19

<210> SEQ ID NO 1713
<211> LENGTH: 21
<212> TYPE: DNA
<213> ORGANISM: Artificial Sequence
<220> FEATURE:
<223> OTHER INFORMATION: Primer

<400> SEQUENCE: 1713
acctacatcc caccacagag t  21

<210> SEQ ID NO 1714
<211> LENGTH: 24
<212> TYPE: DNA
<213> ORGANISM: Artificial Sequence
<220> FEATURE:
<223> OTHER INFORMATION: Primer

<400> SEQUENCE: 1714
ggtgatccag actctgacct tttg  24

<210> SEQ ID NO 1715
<211> LENGTH: 23
<212> TYPE: DNA
<213> ORGANISM: Artificial Sequence
<220> FEATURE:
<223> OTHER INFORMATION: Primer

<400> SEQUENCE: 1715
aaacgaagac tgtttgagga gca  23

<210> SEQ ID NO 1716
<211> LENGTH: 24
<212> TYPE: DNA

```
<213> ORGANISM: Artificial Sequence
<220> FEATURE:
<223> OTHER INFORMATION: Primer

<400> SEQUENCE: 1716
gggttcccat tactgtcaaa tgga                                              24

<210> SEQ ID NO 1717
<211> LENGTH: 28
<212> TYPE: DNA
<213> ORGANISM: Artificial Sequence
<220> FEATURE:
<223> OTHER INFORMATION: Primer

<400> SEQUENCE: 1717
agcgttatgt gacgaagtga atatttct                                          28

<210> SEQ ID NO 1718
<211> LENGTH: 28
<212> TYPE: DNA
<213> ORGANISM: Artificial Sequence
<220> FEATURE:
<223> OTHER INFORMATION: Primer

<400> SEQUENCE: 1718
cctagtgtac ccataagcaa ctcttcta                                          28

<210> SEQ ID NO 1719
<211> LENGTH: 28
<212> TYPE: DNA
<213> ORGANISM: Artificial Sequence
<220> FEATURE:
<223> OTHER INFORMATION: Primer

<400> SEQUENCE: 1719
agcgttatgt gacgaagtga atatttct                                          28

<210> SEQ ID NO 1720
<211> LENGTH: 19
<212> TYPE: DNA
<213> ORGANISM: Artificial Sequence
<220> FEATURE:
<223> OTHER INFORMATION: Primer

<400> SEQUENCE: 1720
tggtgttggt ggttgtggt                                                    19

<210> SEQ ID NO 1721
<211> LENGTH: 26
<212> TYPE: DNA
<213> ORGANISM: Artificial Sequence
<220> FEATURE:
<223> OTHER INFORMATION: Primer

<400> SEQUENCE: 1721
gtatgaacgt gacagtgtac acctaa                                            26

<210> SEQ ID NO 1722
<211> LENGTH: 24
<212> TYPE: DNA
<213> ORGANISM: Artificial Sequence
<220> FEATURE:
<223> OTHER INFORMATION: Primer

<400> SEQUENCE: 1722
ggtgatccag actctgacct tttg                                              24
```

<210> SEQ ID NO 1723
<211> LENGTH: 21
<212> TYPE: DNA
<213> ORGANISM: Artificial Sequence
<220> FEATURE:
<223> OTHER INFORMATION: Primer

<400> SEQUENCE: 1723
acctacatcc caccacagag t                                             21

<210> SEQ ID NO 1724
<211> LENGTH: 24
<212> TYPE: DNA
<213> ORGANISM: Artificial Sequence
<220> FEATURE:
<223> OTHER INFORMATION: Primer

<400> SEQUENCE: 1724
acgaagccta aacaccctgt attg                                          24

<210> SEQ ID NO 1725
<211> LENGTH: 25
<212> TYPE: DNA
<213> ORGANISM: Artificial Sequence
<220> FEATURE:
<223> OTHER INFORMATION: Primer

<400> SEQUENCE: 1725
tcgcttgcag tgtctgtgta tattt                                         25

<210> SEQ ID NO 1726
<211> LENGTH: 26
<212> TYPE: DNA
<213> ORGANISM: Artificial Sequence
<220> FEATURE:
<223> OTHER INFORMATION: Primer

<400> SEQUENCE: 1726
catggtaatg tacaagtgcc atagga                                        26

<210> SEQ ID NO 1727
<211> LENGTH: 25
<212> TYPE: DNA
<213> ORGANISM: Artificial Sequence
<220> FEATURE:
<223> OTHER INFORMATION: Primer

<400> SEQUENCE: 1727
gaacgcatgt taattgaacc tccaa                                         25

<210> SEQ ID NO 1728
<211> LENGTH: 27
<212> TYPE: DNA
<213> ORGANISM: Artificial Sequence
<220> FEATURE:
<223> OTHER INFORMATION: Primer

<400> SEQUENCE: 1728
gctgcactaa cgtttgtctt ttaatcc                                       27

<210> SEQ ID NO 1729
<211> LENGTH: 27
<212> TYPE: DNA
<213> ORGANISM: Artificial Sequence
<220> FEATURE:

<223> OTHER INFORMATION: Primer

<400> SEQUENCE: 1729
tgtattttag gttgtaggcc tcccttta                                27

<210> SEQ ID NO 1730
<211> LENGTH: 27
<212> TYPE: DNA
<213> ORGANISM: Artificial Sequence
<220> FEATURE:
<223> OTHER INFORMATION: Primer

<400> SEQUENCE: 1730
ctccaaagcc aacatctatc atatcac                                 27

<210> SEQ ID NO 1731
<211> LENGTH: 25
<212> TYPE: DNA
<213> ORGANISM: Artificial Sequence
<220> FEATURE:
<223> OTHER INFORMATION: Primer

<400> SEQUENCE: 1731
gtcgccattt tacatgcatt aaggt                                   25

<210> SEQ ID NO 1732
<211> LENGTH: 22
<212> TYPE: DNA
<213> ORGANISM: Artificial Sequence
<220> FEATURE:
<223> OTHER INFORMATION: Primer

<400> SEQUENCE: 1732
aggaaacaaa ccctgccaag tt                                      22

<210> SEQ ID NO 1733
<211> LENGTH: 21
<212> TYPE: DNA
<213> ORGANISM: Artificial Sequence
<220> FEATURE:
<223> OTHER INFORMATION: Primer

<400> SEQUENCE: 1733
tgcgaccacc aaatacactg t                                       21

<210> SEQ ID NO 1734
<211> LENGTH: 21
<212> TYPE: DNA
<213> ORGANISM: Artificial Sequence
<220> FEATURE:
<223> OTHER INFORMATION: Primer

<400> SEQUENCE: 1734
gtgttgacaa tgcgtgacac t                                       21

<210> SEQ ID NO 1735
<211> LENGTH: 21
<212> TYPE: DNA
<213> ORGANISM: Artificial Sequence
<220> FEATURE:
<223> OTHER INFORMATION: Primer

<400> SEQUENCE: 1735
tgcgaccacc aaatacactg t                                       21

```
<210> SEQ ID NO 1736
<211> LENGTH: 19
<212> TYPE: DNA
<213> ORGANISM: Artificial Sequence
<220> FEATURE:
<223> OTHER INFORMATION: Primer

<400> SEQUENCE: 1736
ctgagaagcc ctgcccttc                                            19

<210> SEQ ID NO 1737
<211> LENGTH: 28
<212> TYPE: DNA
<213> ORGANISM: Artificial Sequence
<220> FEATURE:
<223> OTHER INFORMATION: Primer

<400> SEQUENCE: 1737
gtgccaggag aaaatactag actgttat                                  28

<210> SEQ ID NO 1738
<211> LENGTH: 24
<212> TYPE: DNA
<213> ORGANISM: Artificial Sequence
<220> FEATURE:
<223> OTHER INFORMATION: Primer

<400> SEQUENCE: 1738
ggtgatccag actctgacct tttg                                      24

<210> SEQ ID NO 1739
<211> LENGTH: 28
<212> TYPE: DNA
<213> ORGANISM: Artificial Sequence
<220> FEATURE:
<223> OTHER INFORMATION: Primer

<400> SEQUENCE: 1739
gtgccaggag aaaatactag actgttat                                  28

<210> SEQ ID NO 1740
<211> LENGTH: 18
<212> TYPE: DNA
<213> ORGANISM: Artificial Sequence
<220> FEATURE:
<223> OTHER INFORMATION: Primer

<400> SEQUENCE: 1740
tctttgctcg cagctcgt                                             18

<210> SEQ ID NO 1741
<211> LENGTH: 28
<212> TYPE: DNA
<213> ORGANISM: Artificial Sequence
<220> FEATURE:
<223> OTHER INFORMATION: Primer

<400> SEQUENCE: 1741
gtgccaggag aaaatactag actgttat                                  28

<210> SEQ ID NO 1742
<211> LENGTH: 19
<212> TYPE: DNA
<213> ORGANISM: Artificial Sequence
<220> FEATURE:
<223> OTHER INFORMATION: Primer
```

<400> SEQUENCE: 1742
ctgagaagcc ctgcccttc					19

<210> SEQ ID NO 1743
<211> LENGTH: 22
<212> TYPE: DNA
<213> ORGANISM: Artificial Sequence
<220> FEATURE:
<223> OTHER INFORMATION: Primer

<400> SEQUENCE: 1743
ccggacagtg gatatggcaa ta				22

<210> SEQ ID NO 1744
<211> LENGTH: 25
<212> TYPE: DNA
<213> ORGANISM: Artificial Sequence
<220> FEATURE:
<223> OTHER INFORMATION: Primer

<400> SEQUENCE: 1744
ggtctatctc tgtacttctg tcgct				25

<210> SEQ ID NO 1745
<211> LENGTH: 23
<212> TYPE: DNA
<213> ORGANISM: Artificial Sequence
<220> FEATURE:
<223> OTHER INFORMATION: Primer

<400> SEQUENCE: 1745
cctgcaatac gtctatgcac aat				23

<210> SEQ ID NO 1746
<211> LENGTH: 27
<212> TYPE: DNA
<213> ORGANISM: Artificial Sequence
<220> FEATURE:
<223> OTHER INFORMATION: Primer

<400> SEQUENCE: 1746
ccagtaacat ttgctgaaat atgcgaa			27

<210> SEQ ID NO 1747
<211> LENGTH: 28
<212> TYPE: DNA
<213> ORGANISM: Artificial Sequence
<220> FEATURE:
<223> OTHER INFORMATION: Primer

<400> SEQUENCE: 1747
ggaggatgaa gtagataata tgcgtgac			28

<210> SEQ ID NO 1748
<211> LENGTH: 27
<212> TYPE: DNA
<213> ORGANISM: Artificial Sequence
<220> FEATURE:
<223> OTHER INFORMATION: Primer

<400> SEQUENCE: 1748
ccagtaacat ttgctgaaat atgcgaa			27

<210> SEQ ID NO 1749
<211> LENGTH: 20

```
<212> TYPE: DNA
<213> ORGANISM: Artificial Sequence
<220> FEATURE:
<223> OTHER INFORMATION: Primer

<400> SEQUENCE: 1749
gggcacaaca atgggaggta                                              20

<210> SEQ ID NO 1750
<211> LENGTH: 21
<212> TYPE: DNA
<213> ORGANISM: Artificial Sequence
<220> FEATURE:
<223> OTHER INFORMATION: Primer

<400> SEQUENCE: 1750
gggtgttcga tagctgttca a                                            21

<210> SEQ ID NO 1751
<211> LENGTH: 21
<212> TYPE: DNA
<213> ORGANISM: Artificial Sequence
<220> FEATURE:
<223> OTHER INFORMATION: Primer

<400> SEQUENCE: 1751
tgcgaccacc aaatacactg t                                            21

<210> SEQ ID NO 1752
<211> LENGTH: 28
<212> TYPE: DNA
<213> ORGANISM: Artificial Sequence
<220> FEATURE:
<223> OTHER INFORMATION: Primer

<400> SEQUENCE: 1752
caatgccagg tagatgacac ttctttaa                                     28

<210> SEQ ID NO 1753
<211> LENGTH: 25
<212> TYPE: DNA
<213> ORGANISM: Artificial Sequence
<220> FEATURE:
<223> OTHER INFORMATION: Primer

<400> SEQUENCE: 1753
gggattacta ctttgtggcc gtata                                        25

<210> SEQ ID NO 1754
<211> LENGTH: 21
<212> TYPE: DNA
<213> ORGANISM: Artificial Sequence
<220> FEATURE:
<223> OTHER INFORMATION: Primer

<400> SEQUENCE: 1754
gtgttgacaa tgcgtgacac t                                            21

<210> SEQ ID NO 1755
<211> LENGTH: 23
<212> TYPE: DNA
<213> ORGANISM: Artificial Sequence
<220> FEATURE:
<223> OTHER INFORMATION: Primer

<400> SEQUENCE: 1755
```
cctgcaatac gtctatgcac aat                            23

<210> SEQ ID NO 1756
<211> LENGTH: 24
<212> TYPE: DNA
<213> ORGANISM: Artificial Sequence
<220> FEATURE:
<223> OTHER INFORMATION: Primer

<400> SEQUENCE: 1756 tttttgtcg tccaccacct tttg                            24

<210> SEQ ID NO 1757
<211> LENGTH: 21
<212> TYPE: DNA
<213> ORGANISM: Artificial Sequence
<220> FEATURE:
<223> OTHER INFORMATION: Primer

<400> SEQUENCE: 1757
tgcgaccacc aaatacactg t                              21

<210> SEQ ID NO 1758
<211> LENGTH: 24
<212> TYPE: DNA
<213> ORGANISM: Artificial Sequence
<220> FEATURE:
<223> OTHER INFORMATION: Primer

<400> SEQUENCE: 1758
ggtgatccag actctgacct tttg                           24

<210> SEQ ID NO 1759
<211> LENGTH: 20
<212> TYPE: DNA
<213> ORGANISM: Artificial Sequence
<220> FEATURE:
<223> OTHER INFORMATION: Primer

<400> SEQUENCE: 1759
cgtggtgtgc gaccaactaa                                20

<210> SEQ ID NO 1760
<211> LENGTH: 19
<212> TYPE: DNA
<213> ORGANISM: Artificial Sequence
<220> FEATURE:
<223> OTHER INFORMATION: Primer

<400> SEQUENCE: 1760
aaatacggct gcaccgagt                                 19

<210> SEQ ID NO 1761
<211> LENGTH: 20
<212> TYPE: DNA
<213> ORGANISM: Artificial Sequence
<220> FEATURE:
<223> OTHER INFORMATION: Primer

<400> SEQUENCE: 1761
cgtggtgtgc gaccaactaa                                20

<210> SEQ ID NO 1762
<211> LENGTH: 19
<212> TYPE: DNA
<213> ORGANISM: Artificial Sequence

```
<220> FEATURE:
<223> OTHER INFORMATION: Primer

<400> SEQUENCE: 1762
ctgagaagcc ctgcccttc                                              19

<210> SEQ ID NO 1763
<211> LENGTH: 23
<212> TYPE: DNA
<213> ORGANISM: Artificial Sequence
<220> FEATURE:
<223> OTHER INFORMATION: Primer

<400> SEQUENCE: 1763
cctgcaatac gtctatgcac aat                                         23

<210> SEQ ID NO 1764
<211> LENGTH: 21
<212> TYPE: DNA
<213> ORGANISM: Artificial Sequence
<220> FEATURE:
<223> OTHER INFORMATION: Primer

<400> SEQUENCE: 1764
gggtgttcga tagctgttca a                                           21

<210> SEQ ID NO 1765
<211> LENGTH: 23
<212> TYPE: DNA
<213> ORGANISM: Artificial Sequence
<220> FEATURE:
<223> OTHER INFORMATION: Primer

<400> SEQUENCE: 1765
cctgcaatac gtctatgcac aat                                         23

<210> SEQ ID NO 1766
<211> LENGTH: 23
<212> TYPE: DNA
<213> ORGANISM: Artificial Sequence
<220> FEATURE:
<223> OTHER INFORMATION: Primer

<400> SEQUENCE: 1766
catgctgcat atggcgtatt gtc                                         23

<210> SEQ ID NO 1767
<211> LENGTH: 25
<212> TYPE: DNA
<213> ORGANISM: Artificial Sequence
<220> FEATURE:
<223> OTHER INFORMATION: Primer

<400> SEQUENCE: 1767
gtaggtctgt gtatggtgct acatt                                       25

<210> SEQ ID NO 1768
<211> LENGTH: 24
<212> TYPE: DNA
<213> ORGANISM: Artificial Sequence
<220> FEATURE:
<223> OTHER INFORMATION: Primer

<400> SEQUENCE: 1768 tttttttgtcg tccaccacct tttg                                       24
```

```
<210> SEQ ID NO 1769
<211> LENGTH: 21
<212> TYPE: DNA
<213> ORGANISM: Artificial Sequence
<220> FEATURE:
<223> OTHER INFORMATION: Primer

<400> SEQUENCE: 1769
tgcgaccacc aaatacactg t                                              21

<210> SEQ ID NO 1770
<211> LENGTH: 22
<212> TYPE: DNA
<213> ORGANISM: Artificial Sequence
<220> FEATURE:
<223> OTHER INFORMATION: Primer

<400> SEQUENCE: 1770
atcatgatgg ctgtatgtgc ca                                             22

<210> SEQ ID NO 1771
<211> LENGTH: 21
<212> TYPE: DNA
<213> ORGANISM: Artificial Sequence
<220> FEATURE:
<223> OTHER INFORMATION: Primer

<400> SEQUENCE: 1771
tgcgaccacc aaatacactg t                                              21

<210> SEQ ID NO 1772
<211> LENGTH: 18
<212> TYPE: DNA
<213> ORGANISM: Artificial Sequence
<220> FEATURE:
<223> OTHER INFORMATION: Primer

<400> SEQUENCE: 1772
tctttgctcg cagctcgt                                                  18

<210> SEQ ID NO 1773
<211> LENGTH: 22
<212> TYPE: DNA
<213> ORGANISM: Artificial Sequence
<220> FEATURE:
<223> OTHER INFORMATION: Primer

<400> SEQUENCE: 1773
ccggacagtg gatatggcaa ta                                             22

<210> SEQ ID NO 1774
<211> LENGTH: 21
<212> TYPE: DNA
<213> ORGANISM: Artificial Sequence
<220> FEATURE:
<223> OTHER INFORMATION: Primer

<400> SEQUENCE: 1774
gggtgttcga tagctgttca a                                              21

<210> SEQ ID NO 1775
<211> LENGTH: 20
<212> TYPE: DNA
<213> ORGANISM: Artificial Sequence
<220> FEATURE:
<223> OTHER INFORMATION: Primer
```

-continued

<400> SEQUENCE: 1775
cgtggtgtgc gaccaactaa                                               20

<210> SEQ ID NO 1776
<211> LENGTH: 21
<212> TYPE: DNA
<213> ORGANISM: Artificial Sequence
<220> FEATURE:
<223> OTHER INFORMATION: Primer

<400> SEQUENCE: 1776
gtgttgacaa tgcgtgacac t                                             21

<210> SEQ ID NO 1777
<211> LENGTH: 20
<212> TYPE: DNA
<213> ORGANISM: Artificial Sequence
<220> FEATURE:
<223> OTHER INFORMATION: Primer

<400> SEQUENCE: 1777
cgtggtgtgc gaccaactaa                                               20

<210> SEQ ID NO 1778
<211> LENGTH: 21
<212> TYPE: DNA
<213> ORGANISM: Artificial Sequence
<220> FEATURE:
<223> OTHER INFORMATION: Primer

<400> SEQUENCE: 1778
catggttcca ccagcgttat t                                             21

<210> SEQ ID NO 1779
<211> LENGTH: 20
<212> TYPE: DNA
<213> ORGANISM: Artificial Sequence
<220> FEATURE:
<223> OTHER INFORMATION: Primer

<400> SEQUENCE: 1779
cgtggtgtgc gaccaactaa                                               20

<210> SEQ ID NO 1780
<211> LENGTH: 28
<212> TYPE: DNA
<213> ORGANISM: Artificial Sequence
<220> FEATURE:
<223> OTHER INFORMATION: Primer

<400> SEQUENCE: 1780
catcatttag tgcatataca ggattccc                                      28

<210> SEQ ID NO 1781
<211> LENGTH: 20
<212> TYPE: DNA
<213> ORGANISM: Artificial Sequence
<220> FEATURE:
<223> OTHER INFORMATION: Primer

<400> SEQUENCE: 1781
cgtggtgtgc gaccaactaa                                               20

<210> SEQ ID NO 1782

```
<211> LENGTH: 21
<212> TYPE: DNA
<213> ORGANISM: Artificial Sequence
<220> FEATURE:
<223> OTHER INFORMATION: Primer

<400> SEQUENCE: 1782
gggtgttcga tagctgttca a                                              21

<210> SEQ ID NO 1783
<211> LENGTH: 28
<212> TYPE: DNA
<213> ORGANISM: Artificial Sequence
<220> FEATURE:
<223> OTHER INFORMATION: Primer

<400> SEQUENCE: 1783
gtgccaggag aaaatactag actgttat                                       28

<210> SEQ ID NO 1784
<211> LENGTH: 21
<212> TYPE: DNA
<213> ORGANISM: Artificial Sequence
<220> FEATURE:
<223> OTHER INFORMATION: Primer

<400> SEQUENCE: 1784
catggttcca ccagcgttat t                                              21

<210> SEQ ID NO 1785
<211> LENGTH: 22
<212> TYPE: DNA
<213> ORGANISM: Artificial Sequence
<220> FEATURE:
<223> OTHER INFORMATION: Primer

<400> SEQUENCE: 1785
ccggacagtg gatatggcaa ta                                             22

<210> SEQ ID NO 1786
<211> LENGTH: 28
<212> TYPE: DNA
<213> ORGANISM: Artificial Sequence
<220> FEATURE:
<223> OTHER INFORMATION: Primer

<400> SEQUENCE: 1786
catcatttag tgcatataca ggattccc                                       28

<210> SEQ ID NO 1787
<211> LENGTH: 21
<212> TYPE: DNA
<213> ORGANISM: Artificial Sequence
<220> FEATURE:
<223> OTHER INFORMATION: Primer

<400> SEQUENCE: 1787
tgcgaccacc aaatacactg t                                              21

<210> SEQ ID NO 1788
<211> LENGTH: 21
<212> TYPE: DNA
<213> ORGANISM: Artificial Sequence
<220> FEATURE:
<223> OTHER INFORMATION: Primer

<400> SEQUENCE: 1788
```

```
catggttcca ccagcgttat t                                              21

<210> SEQ ID NO 1789
<211> LENGTH: 20
<212> TYPE: DNA
<213> ORGANISM: Artificial Sequence
<220> FEATURE:
<223> OTHER INFORMATION: Primer

<400> SEQUENCE: 1789
cgtggtgtgc gaccaactaa                                                20

<210> SEQ ID NO 1790
<211> LENGTH: 18
<212> TYPE: DNA
<213> ORGANISM: Artificial Sequence
<220> FEATURE:
<223> OTHER INFORMATION: Primer

<400> SEQUENCE: 1790
tctttgctcg cagctcgt                                                  18

<210> SEQ ID NO 1791
<211> LENGTH: 23
<212> TYPE: DNA
<213> ORGANISM: Artificial Sequence
<220> FEATURE:
<223> OTHER INFORMATION: Primer

<400> SEQUENCE: 1791
cctgcaatac gtctatgcac aat                                            23

<210> SEQ ID NO 1792
<211> LENGTH: 28
<212> TYPE: DNA
<213> ORGANISM: Artificial Sequence
<220> FEATURE:
<223> OTHER INFORMATION: Primer

<400> SEQUENCE: 1792
catcatttag tgcatataca ggattccc                                       28

<210> SEQ ID NO 1793
<211> LENGTH: 20
<212> TYPE: DNA
<213> ORGANISM: Artificial Sequence
<220> FEATURE:
<223> OTHER INFORMATION: Primer

<400> SEQUENCE: 1793
cgtggtgtgc gaccaactaa                                                20

<210> SEQ ID NO 1794
<211> LENGTH: 24
<212> TYPE: DNA
<213> ORGANISM: Artificial Sequence
<220> FEATURE:
<223> OTHER INFORMATION: Primer

<400> SEQUENCE: 1794
ggtgatccag actctgacct tttg                                           24

<210> SEQ ID NO 1795
<211> LENGTH: 20
<212> TYPE: DNA
```

<213> ORGANISM: Artificial Sequence
<220> FEATURE:
<223> OTHER INFORMATION: Primer

<400> SEQUENCE: 1795
cgtggtgtgc gaccaactaa                                           20

<210> SEQ ID NO 1796
<211> LENGTH: 26
<212> TYPE: DNA
<213> ORGANISM: Artificial Sequence
<220> FEATURE:
<223> OTHER INFORMATION: Primer

<400> SEQUENCE: 1796
ttgtcaacta ctgcctccac ataaaa                                    26

<210> SEQ ID NO 1797
<211> LENGTH: 23
<212> TYPE: DNA
<213> ORGANISM: Artificial Sequence
<220> FEATURE:
<223> OTHER INFORMATION: Primer

<400> SEQUENCE: 1797
cctgcaatac gtctatgcac aat                                       23

<210> SEQ ID NO 1798
<211> LENGTH: 27
<212> TYPE: DNA
<213> ORGANISM: Artificial Sequence
<220> FEATURE:
<223> OTHER INFORMATION: Primer

<400> SEQUENCE: 1798
tccaacacta tgtcctttaa ttgtggt                                   27

<210> SEQ ID NO 1799
<211> LENGTH: 21
<212> TYPE: DNA
<213> ORGANISM: Artificial Sequence
<220> FEATURE:
<223> OTHER INFORMATION: Primer

<400> SEQUENCE: 1799
tgcgaccacc aaatacactg t                                         21

<210> SEQ ID NO 1800
<211> LENGTH: 19
<212> TYPE: DNA
<213> ORGANISM: Artificial Sequence
<220> FEATURE:
<223> OTHER INFORMATION: Primer

<400> SEQUENCE: 1800
aaatacggct gcaccgagt                                            19

<210> SEQ ID NO 1801
<211> LENGTH: 28
<212> TYPE: DNA
<213> ORGANISM: Artificial Sequence
<220> FEATURE:
<223> OTHER INFORMATION: Primer

<400> SEQUENCE: 1801
gtgccaggag aaaatactag actgttat                                  28

<210> SEQ ID NO 1802
<211> LENGTH: 19
<212> TYPE: DNA
<213> ORGANISM: Artificial Sequence
<220> FEATURE:
<223> OTHER INFORMATION: Primer

<400> SEQUENCE: 1802
aaatacggct gcaccgagt                                                    19

<210> SEQ ID NO 1803
<211> LENGTH: 28
<212> TYPE: DNA
<213> ORGANISM: Artificial Sequence
<220> FEATURE:
<223> OTHER INFORMATION: Primer

<400> SEQUENCE: 1803
gtgccaggag aaaatactag actgttat                                          28

<210> SEQ ID NO 1804
<211> LENGTH: 22
<212> TYPE: DNA
<213> ORGANISM: Artificial Sequence
<220> FEATURE:
<223> OTHER INFORMATION: Primer

<400> SEQUENCE: 1804
atcatgatgg ctgtatgtgc ca                                                22

<210> SEQ ID NO 1805
<211> LENGTH: 20
<212> TYPE: DNA
<213> ORGANISM: Artificial Sequence
<220> FEATURE:
<223> OTHER INFORMATION: Primer

<400> SEQUENCE: 1805
cgtggtgtgc gaccaactaa                                                   20

<210> SEQ ID NO 1806
<211> LENGTH: 22
<212> TYPE: DNA
<213> ORGANISM: Artificial Sequence
<220> FEATURE:
<223> OTHER INFORMATION: Primer

<400> SEQUENCE: 1806
atcatgatgg ctgtatgtgc ca                                                22

<210> SEQ ID NO 1807
<211> LENGTH: 20
<212> TYPE: DNA
<213> ORGANISM: Artificial Sequence
<220> FEATURE:
<223> OTHER INFORMATION: Primer

<400> SEQUENCE: 1807
acacagaagc ctgctgcaaa                                                   20

<210> SEQ ID NO 1808
<211> LENGTH: 28
<212> TYPE: DNA
<213> ORGANISM: Artificial Sequence
<220> FEATURE:

<223> OTHER INFORMATION: Primer

<400> SEQUENCE: 1808
catcatttag tgcatataca ggattccc                                           28

<210> SEQ ID NO 1809
<211> LENGTH: 22
<212> TYPE: DNA
<213> ORGANISM: Artificial Sequence
<220> FEATURE:
<223> OTHER INFORMATION: Primer

<400> SEQUENCE: 1809
cctgtaggtt aagggtggtg tt                                                 22

<210> SEQ ID NO 1810
<211> LENGTH: 21
<212> TYPE: DNA
<213> ORGANISM: Artificial Sequence
<220> FEATURE:
<223> OTHER INFORMATION: Primer

<400> SEQUENCE: 1810
aaatcggtcg ccacaaaatg g                                                  21

<210> SEQ ID NO 1811
<211> LENGTH: 21
<212> TYPE: DNA
<213> ORGANISM: Artificial Sequence
<220> FEATURE:
<223> OTHER INFORMATION: Primer

<400> SEQUENCE: 1811
cgtagtacag ccgttgcatt g                                                  21

<210> SEQ ID NO 1812
<211> LENGTH: 24
<212> TYPE: DNA
<213> ORGANISM: Artificial Sequence
<220> FEATURE:
<223> OTHER INFORMATION: Primer

<400> SEQUENCE: 1812
cccattgtac catttgcgat agtt                                               24

<210> SEQ ID NO 1813
<211> LENGTH: 25
<212> TYPE: DNA
<213> ORGANISM: Artificial Sequence
<220> FEATURE:
<223> OTHER INFORMATION: Primer

<400> SEQUENCE: 1813
ggatgtgttg gtgttgaagt aggta                                              25

<210> SEQ ID NO 1814
<211> LENGTH: 20
<212> TYPE: DNA
<213> ORGANISM: Artificial Sequence
<220> FEATURE:
<223> OTHER INFORMATION: Primer

<400> SEQUENCE: 1814
tcctgttggt cgttgccatt                                                    20

```
<210> SEQ ID NO 1815
<211> LENGTH: 27
<212> TYPE: DNA
<213> ORGANISM: Artificial Sequence
<220> FEATURE:
<223> OTHER INFORMATION: Primer

<400> SEQUENCE: 1815
gctgctaagt gtatatagtt actcgca                                       27

<210> SEQ ID NO 1816
<211> LENGTH: 24
<212> TYPE: DNA
<213> ORGANISM: Artificial Sequence
<220> FEATURE:
<223> OTHER INFORMATION: Primer

<400> SEQUENCE: 1816
ctgctgcaaa cacatattgg gatt                                          24
```